US011426466B2

(12) United States Patent
Liu et al.

(10) Patent No.: US 11,426,466 B2
(45) Date of Patent: Aug. 30, 2022

(54) TOXIN-DERIVED DELIVERY CONSTRUCTS FOR PULMONARY DELIVERY

(71) Applicant: Applied Molecular Transport Inc., South San Francisco, CA (US)

(72) Inventors: Keyi Liu, Mountain View, CA (US); Julia Dawn Mackay, Bath (GB); Weijun Feng, Danville, CA (US); Thomas Carl Hunter, Mountain View, CA (US); Randall J. Mrsny, Los Altos Hills, CA (US)

(73) Assignee: Applied Molecular Transport Inc., South San Francisco, CA (US)

( * ) Notice: Subject to any disclaimer, the term of this patent is extended or adjusted under 35 U.S.C. 154(b) by 0 days.

(21) Appl. No.: 17/015,011

(22) Filed: Sep. 8, 2020

(65) Prior Publication Data

US 2021/0113704 A1 Apr. 22, 2021

Related U.S. Application Data

(63) Continuation of application No. PCT/US2019/021474, filed on Mar. 8, 2019.

(60) Provisional application No. 62/640,168, filed on Mar. 8, 2018, provisional application No. 62/640,188, filed on Mar. 8, 2018, provisional application No. 62/640,194, filed on Mar. 8, 2018, provisional application No. 62/756,889, filed on Nov. 7, 2018.

(51) Int. Cl.
| | |
|---|---|
| *A61K 47/64* | (2017.01) |
| *A61K 47/65* | (2017.01) |
| *A61K 9/00* | (2006.01) |
| *A61K 9/12* | (2006.01) |
| *A61K 38/21* | (2006.01) |
| *A61K 38/27* | (2006.01) |

(52) U.S. Cl.
CPC .......... *A61K 47/6415* (2017.08); *A61K 9/007* (2013.01); *A61K 9/0043* (2013.01); *A61K 38/21* (2013.01); *A61K 38/27* (2013.01); *A61K 47/65* (2017.08)

(58) Field of Classification Search
None
See application file for complete search history.

(56) References Cited

U.S. PATENT DOCUMENTS

| | | | |
|---|---|---|---|
| 5,328,984 A | 7/1994 | Pastan et al. | |
| 5,512,658 A | 4/1996 | Pastan et al. | |
| 5,589,384 A | 12/1996 | Lipscombe et al. | |
| 5,602,095 A | 2/1997 | Pastan et al. | |
| 5,668,255 A | 9/1997 | Murphy | |
| 5,696,237 A | 12/1997 | Fitzgerald et al. | |
| 5,807,832 A | 9/1998 | Russell-Jones et al. | |
| 5,817,633 A | 10/1998 | Heerze et al. | |
| 5,863,745 A | 1/1999 | Fitzgerald et al. | |
| 5,965,406 A | 10/1999 | Murphy | |
| 6,022,950 A | 2/2000 | Murphy | |
| 6,051,405 A | 4/2000 | Fitzgerald et al. | |
| 6,086,900 A | 7/2000 | Draper | |
| 6,086,918 A | 7/2000 | Stern et al. | |
| 6,251,392 B1 | 6/2001 | Hein et al. | |
| 6,565,856 B1 | 5/2003 | Skeiky et al. | |
| 6,673,574 B2 | 1/2004 | Stern et al. | |
| 6,838,553 B1 | 1/2005 | Hwang et al. | |
| 7,193,055 B2 | 3/2007 | Daugherty et al. | |
| 7,314,625 B2 | 1/2008 | Fitzgerald | |
| 7,314,632 B1 | 1/2008 | Fitzgerald | |
| 7,335,361 B2 | 2/2008 | Liao et al. | |
| 7,378,100 B2 | 5/2008 | Chang et al. | |
| 7,465,455 B2 | 12/2008 | Chang et al. | |
| 7,595,054 B2 | 9/2009 | Liao et al. | |
| 7,611,714 B2 | 11/2009 | Mrsny | |
| 7,618,635 B2 | 11/2009 | Chang et al. | |
| 7,666,991 B2 | 2/2010 | Mrsny | |
| 7,713,737 B2 | 5/2010 | Mrsny | |
| 7,727,538 B2 | 6/2010 | Quinn et al. | |
| 7,824,695 B1 | 11/2010 | Fitzgerald et al. | |
| 7,964,200 B2 | 6/2011 | Mrsny et al. | |
| 8,092,806 B2 | 1/2012 | Wallach et al. | |
| 8,092,809 B2 | 1/2012 | Fitzgerald | |
| 8,206,950 B2 | 6/2012 | Liao et al. | |
| 8,309,102 B2 | 11/2012 | Mrsny et al. | |
| 8,372,407 B2 | 2/2013 | Liao et al. | |

(Continued)

FOREIGN PATENT DOCUMENTS

| | | |
|---|---|---|
| EP | 0532090 A2 | 3/1993 |
| EP | 1522585 A1 | 4/2005 |

(Continued)

OTHER PUBLICATIONS

Groneberg, D.A., et al. 2003 Respiratory Medicine 97(4): 382-387. (Year: 2003).*
CA2,948,346 Office Action dated Jun. 2, 2021.
Challa et al. Bacterial Toxin Fusion Proteins Elicit Mucosal Immunity against a Foot-and-Mouth Disease Virus Antigen When Administered Intranasally to Guinea Pigs. Adv Virol, vol. 2011, Article ID 713769 (2011). 11 pages.
Challa et al. MARTs and MARylation in the Cytosol: Biological Functions, Mechanisms of Action, and Therapeutic Potential. Cells 10:313 (Feb. 3, 2021). 21 pages.

(Continued)

*Primary Examiner* — Marsha Tsay
(74) *Attorney, Agent, or Firm* — Wilson Sonsini Goodrich & Rosati

(57) ABSTRACT

The present disclosure relates to isolated non-naturally occurring delivery constructs comprising a bacterial toxin-derived delivery construct coupled to a biologically active therapeutic cargo; wherein the delivery construct is capable of delivering the biologically active cargo via transcytosis transport across an epithelial cell; and wherein the delivery construct does not comprise a bacterial toxin-derived translocation domain or a bacterial toxin-derived catalytic (cytotoxic) domain.

29 Claims, 33 Drawing Sheets

Specification includes a Sequence Listing.

(56) References Cited

U.S. PATENT DOCUMENTS

| | | |
|---|---|---|
| 8,790,897 B2 | 7/2014 | Quinn et al. |
| 9,090,691 B2 | 7/2015 | Mrsny et al. |
| 9,259,456 B2 | 2/2016 | Kidron |
| 9,481,714 B2 | 11/2016 | Wu et al. |
| 9,657,063 B2 | 5/2017 | Kuo et al. |
| 10,010,602 B2 | 7/2018 | Chien et al. |
| 10,130,688 B2 | 11/2018 | Mrsny et al. |
| 10,400,013 B2 | 9/2019 | Liao et al. |
| 10,617,741 B2 | 4/2020 | Mrsny et al. |
| 10,617,767 B2 | 4/2020 | Mrsny et al. |
| 10,624,955 B2 | 4/2020 | Mrsny et al. |
| 10,624,956 B2 | 4/2020 | Mrsny et al. |
| 10,624,957 B2 | 4/2020 | Mrsny et al. |
| 10,786,555 B2 | 9/2020 | Mrsny et al. |
| 10,786,556 B2 | 9/2020 | Mrsny et al. |
| 10,799,565 B2 | 10/2020 | Mrsny et al. |
| 11,027,020 B2 | 6/2021 | Mrsny et al. |
| 11,246,915 B2 | 2/2022 | Mrsny et al. |
| 11,324,833 B2 | 5/2022 | Mrsny et al. |
| 2003/0054012 A1 | 3/2003 | Fitzgerald et al. |
| 2004/0071736 A1 | 4/2004 | Quinn et al. |
| 2005/0079171 A1 | 4/2005 | Fitzgerald et al. |
| 2007/0003578 A1 | 1/2007 | Fitzgerald |
| 2007/0148131 A1 | 6/2007 | Mrsny |
| 2008/0085277 A1 | 4/2008 | Cho et al. |
| 2008/0317761 A1 | 12/2008 | Cines et al. |
| 2009/0081235 A1 | 3/2009 | Fitzgerald et al. |
| 2009/0092660 A1 | 4/2009 | Mrsny |
| 2009/0142341 A1 | 6/2009 | Pastan et al. |
| 2009/0148401 A1 | 6/2009 | Mrsny |
| 2009/0155297 A1 | 6/2009 | Mrsny |
| 2009/0285771 A1 | 11/2009 | Mrsny |
| 2009/0285848 A1 | 11/2009 | Mrsny |
| 2009/0304684 A1 | 12/2009 | Mrsny |
| 2009/0305978 A1 | 12/2009 | Zane |
| 2010/0151005 A1 | 6/2010 | Muro-Galindo et al. |
| 2011/0250199 A1 | 10/2011 | Fitzgerald et al. |
| 2012/0258104 A1 | 10/2012 | Echeverri et al. |
| 2014/0065172 A1 | 3/2014 | Echeverri et al. |
| 2015/0265718 A1 | 9/2015 | Mrsny et al. |
| 2015/0265719 A1 | 9/2015 | Mrsny et al. |
| 2016/0222362 A1 | 8/2016 | Zhang et al. |
| 2018/0353610 A1 | 12/2018 | Mrsny et al. |
| 2020/0140511 A1 | 5/2020 | Porat et al. |
| 2020/0354411 A1 | 11/2020 | Bard et al. |
| 2021/0100887 A1 | 4/2021 | Chen et al. |
| 2021/0154304 A1 | 5/2021 | Maclean et al. |
| 2022/0112259 A1 | 4/2022 | Maclean et al. |

FOREIGN PATENT DOCUMENTS

| | | |
|---|---|---|
| EP | 1000163 B1 | 10/2005 |
| EP | 1000162 B1 | 9/2006 |
| EP | 1749833 A1 | 2/2007 |
| EP | 1379550 B1 | 3/2009 |
| EP | 1242122 B1 | 9/2009 |
| EP | 1379273 B1 | 9/2009 |
| EP | 1757615 B1 | 8/2011 |
| EP | 1882478 B1 | 3/2012 |
| EP | 1871880 B1 | 8/2012 |
| EP | 2065392 B1 | 8/2012 |
| EP | 2237794 B1 | 4/2013 |
| EP | 3402810 A1 | 11/2018 |
| EP | 3302543 B1 | 4/2020 |
| WO | WO-2006044205 A2 | 4/2006 |
| WO | WO-2007109110 A2 | 9/2007 |
| WO | WO-2008021234 A2 | 2/2008 |
| WO | WO-2009014650 A2 | 1/2009 |
| WO | WO-2009026328 A2 | 2/2009 |
| WO | WO-2009115531 A2 | 9/2009 |
| WO | WO-2009149281 A1 | 12/2009 |
| WO | WO-2010046783 A2 | 4/2010 |
| WO | WO-2012036746 A1 | 3/2012 |
| WO | WO-2012110596 A1 | 8/2012 |
| WO | WO-2013003824 A1 | 1/2013 |
| WO | WO-2015113005 A1 | 7/2015 |
| WO | WO-2015171965 A2 | 11/2015 |
| WO | WO-2015171965 A3 | 3/2016 |
| WO | WO-2018067401 A1 | 4/2018 |
| WO | WO-2018106895 A1 | 6/2018 |
| WO | WO-2019036382 A1 | 2/2019 |
| WO | WO-2019133647 A1 | 7/2019 |
| WO | WO-2019173787 A1 | 9/2019 |
| WO | WO-2020096695 A1 | 5/2020 |

OTHER PUBLICATIONS

Challa et al. Non-toxic Pseudomonas aeruginosa exotoxin A expressing the FMDV VP1 G-H loop for mucosal vaccination of swine against foot and mouth disease virus. Vaccine 25 (2007) 3328-3337. Available online Jan. 12, 2007.

CN201580036678.8 Office Action dated Jul. 28, 2021 (w/ English translation).

EP19717013.7 Office Action dated May 20, 2021.

Gray et al. Cloning, nucleotide sequence, and expression in *Escherichia coli* of the exotoxin A structural gene of Pseudomonas aeruginosa. Proc Natl Acad Sci, vol. 81, pp. 2645-2649 (May 1984).

Kim et al. Induction of anti-inflammatory immune response by an adenovirus vector encoding 11 tandem repeats of Aβ1-6: Toward safer and effective vaccines against Alzheimer's disease. Biochemical and Biophysical Research Communications 336:84-92 (2005). Available online Aug. 19, 2005.

PCT/US2019/050708 International Preliminary Report on Patentability dated May 11, 2021.

PCT/US2021/032097 International Search Report and Written Opinion dated Jul. 30, 2021.

U.S. Appl. No. 17/004,686 Office Action dated Jul. 14, 2021.

U.S. Appl. No. 17/129,376 Office Action dated Jun. 29, 2021.

Co-pending U.S. Appl. No. 17/129,376, inventors Hunter; Thomas Carl et al., filed Dec. 21, 2020.

Aman et al. A mutant cholera toxin B subunit that binds GM1-ganglioside but lacks immunomodulatory or toxic activity. PNAS 98(15):8536-8541 (Jul. 17, 2001).

Anselmo et al. Non-invasive delivery strategies for biologies. Nature Reviews Drug Discovery 18:19-40 (Jan. 2019). Published online Nov. 30, 2018.

Apostolaki et al. Nasal Delivery of Antigen with the B Subunit of *Escherichia coli* Heat-Labile Enterotoxin Augments Antigen-Specific T-Cell Clonal Expansion and Differentiation. Infection and Immunity 72(7):4072-4080 (Jul. 2004). DOI: 10.1128/IAI.72.7.4072-4080.2004.

Arbit et al. Oral Insulin Delivery in a Physiologic Context: Review. J Diabetes Sci Technol 11(4):825-832 (Jul. 2017) Epub Feb. 2, 2017.

Arhewoh et al. An overview of site-specific delivery of orally administered proteins/peptides and modelling considerations. JMBR: A Peer-review Journal of Biomedical Sciences 3(1):7-20 (Jun. 2004).

Awasthi et al. Development of a PCR-restriction fragment length polymorphism assay for detection and subtyping of cholix toxin variant genes of Vibrio cholerae. Journal of Medical Microbiology 63(5):667-673 (May 1, 2014). DOI: 10.1099/jmm.0.070797-0.

Awasthi et al. Novel Cholix Toxin Variants, ADP-Ribosylating Toxins in Vibriocholerae Non-O1/Non-O139 Strains, and Their Pathogenicity. Infection and Immunity 81(2):531-541 (Feb. 2013). Published ahead of print Dec. 10, 2012.

Basset et al. Cholera-Like Enterotoxins and Regulatory T cells. Toxins 2:1774-1795 (Jul. 6, 2010). doi: 10.3390/toxins2071774.

Bishop-Lilly et al. Genome Sequencing of 15 Clinical Vibrio Isolates, Including 13 Non-O1/Non-O139 Serogroup Strains. Genome Announc 2(5):e00893-14 (Sep. 11, 2014). doi:10.1128/genomeA.00893-14.

Boirivant et al. Oral Administration of Recombinant Cholera Toxin Subunit B Inhibits IL-12-Mediated Murine Experimental (Trinitrobenzene Sulfonic Acid) Colitis. J Immunol 166:3522-3532 (2001). doi: 10.4049/jimmunol.166.5.3522.

(56) References Cited

OTHER PUBLICATIONS

Bonissone et al. N-terminal Protein Processing: A Comparative Proteogenomic Analysis. Molecular & Cellular Proteomics 12: 10.1074/mcp.M112.019075, 14-28 (2013).

Bourganis et al. Polyelectrolyte complexes as prospective carriers for the oral delivery of protein therapeutics. European Journal of Pharmaceutics and Biopharmaceutics 111:44-60 (2017). Available online Nov. 12, 2016.

Bublin et al. Use of a genetic cholera toxin B subunit/allergen fusion molecule as mucosal delivery system with immunosuppressive activity against Th2 immune responses. Vaccine 25(50):8395-8404 (Dec. 5, 2007). DOI: https://doi.org/10.1016/j.vaccine.2007.10.003. Available online Oct. 22, 2007.
Choonara et al. A review of advanced oral drug delivery technologies facilitating the protection and absorption of protein and peptide molecules. Biotechnology Advances 32:1269-1282 (2014). Available online Aug. 3, 2014.
Co-pending U.S. Appl. No. 16/779,350, inventors Liu; Keyi et al., filed Jan. 31, 2020.
Co-pending U.S. Appl. No. 16/884,456, inventors Mrsny; Randall J. et al., filed May 27, 2020.
Co-pending U.S. Appl. No. 16/997,781, inventors Mrsny; Randall J. et al., filed Aug. 19, 2020.
Co-pending U.S. Appl. No. 17/004,686, inventors Mrsny; Randall J. et al., filed Aug. 27, 2020.
Crowe et al. Oral delivery of the anti-tumor necrosis factor α domain antibody, V565, results in high intestinal and fecal concentrations with minimal systemic exposure in cynomolgus monkeys. Drug Development and Industrial Pharmacy 45(3):387-394 (2019). Accepted author version posted online Nov. 5, 2018. Published online Nov. 25, 2018.
Date et al. Nanoparticles for oral delivery: Design, evaluation and state-of-the-art. Journal of Controlled Release 240:504-526 (Oct. 28, 2016).
Delie et al. Polymeric Particulates to Improve Oral Bioavailability of Peptide Drugs. Molecules 10(1):65-80 (Jan. 31, 2005).
Donaldson et al. Mucosal administration of the B subunit of *E. coli* heat-labile enterotoxin promotes the development of Foxp3-expressing regulatory T cells. Mucosal Immunology 4(2):227-238 (Mar. 2011). Published online Oct. 13, 2010. doi: 10.1038/mi.2010.65.
Donaldson et al. The *Escherichia coli* heat-labile enterotoxin B subunit protects from allergic airway disease development by inducing CD4+ regulatory T cells. Mucosal Immunology 6(3):535-546 (May 2013). Published online Oct. 3, 2012. doi: 10.1038/mi.2012.93.
Fitzgerald, et al. Pseudomonas exotoxin-mediated selection yields cells with altered expression of low-density lipoprotein receptor-related protein. Journ of Cell Biology, 129.6 (1995): 1533-1541.
Fraser et al. Mutant *Escherichia coli* Heat-Labile Toxin B Subunit That Separates Toxoid-Mediated Signaling and Immunomodulatory Action from Trafficking and Delivery Functions. Infection and Immunity 71(3):1527-1537 (Mar. 2003). DOI: 10.1128/IAI.71.3.000-000.2003.
GenBank Accession No. AAW80252. Version No. AAW80252.1 hypothetical exotoxin A [Vibrio cholerae]. Record created Feb. 9, 2005. 2 pages. Retrieved Nov. 11, 2019 at URL: https://www.ncbi.nlm.nih.gov/protein/58615288?report=ipg.
GenBank Accession No. AKB06426. Version No. AKB06426.1. exotoxin A catalytic family protein [Vibrio cholerae]. Record created Apr. 6, 2015. 2 pages. Retrieved Aug. 30, 2019 at URL: https://www.ncbi.nlm.nih.gov/protein/AKB06426.
GenBank Accession No. ALH24940. Version No. ALH24940.1. cholix toxin [Vibrio cholerae]. Record created Oct. 11, 2015. 2 pages. Retrieved Sep. 6, 2019 at URL: https://www.ncbi.nlm.nih.gov/protein/ALH24940.1.
GenBank Accession No. ALI16365. Version No. ALI16365.1. truncated cholix toxin [Vibrio cholerae]. Record created Oct. 12, 2015. 2 pages. Retrieved Sep. 9, 2019 at URL: https://www.ncbi.nlm.nih.gov/protein/ALI16365.1.
GenBank Accession No. ALI16366. Version No. ALI16366.1. truncated cholix toxin [Vibrio cholerae]. Record created Oct. 12, 2015. 2 pages. Retrieved Sep. 9, 2019 at URL: https://www.ncbi.nlm.nih.gov/protein/ALI16366.1.
GenBank Accession No. ALI87044. Version No. ALI87044.1. cholix toxin [Vibrio cholerae]. Record created Oct. 14, 2015. 2 pages. Retrieved Aug. 30, 2019 at URL: https://www.ncbi.nlm.nih.gov/protein/ALI87044.1.
GenBank Accession No. ALJ02941. Version No. ALJ02941.1. cholix toxin [Vibrio cholerae]. Record created Oct. 18, 2015. 2 pages. Retrieved Sep. 6, 2019 at URL: https://www.ncbi.nlm.nih.gov/protein/ALJ02941.1.
GenBank Accession No. AUT32289. Version No. AUT32289.1. cholix toxin [Vibrio cholerae]. Record created Jan. 31, 2018. 2 pages. Retrieved Sep. 6, 2019 at URL: https://www.ncbi.nlm.nih.gov/protein/AUT32289.1.
GenBank Accession No. AUT32291. Version No. AUT32291.1. cholix toxin [Vibrio cholerae]. Record created Jan. 31, 2018. 2 pages. Retrieved Sep. 6, 2019 at URL: https://www.ncbi.nlm.nih.gov/protein/AUT32291.1.
GenBank Accession No. AUT32293. Version No. AUT32293.1. cholix toxin [Vibrio cholerae]. Record created Jan. 31, 2018. 2 pages. Retrieved Sep. 6, 2019 at URL: https://www.ncbi.nlm.nih.gov/protein/AUT32293.1.
GenBank Accession No. AUT32294. Version No. AUT32294.1. cholix toxin [Vibrio cholerae]. Record created Jan. 31, 2018. 2 pages. Retrieved Sep. 6, 2019 at URL: https://www.ncbi.nlm.nih.gov/protein/AUT32294.1.
GenBank Accession No. BAM72568. Version No. BAM72568.1. cholix toxin, partial [Vibrio cholerae]. Record created Dec. 14, 2012. 2 pages. Retrieved Sep. 9, 2019 at URL: https://www.ncbi.nlm.nih.gov/protein/BAM72568.1.
GenBank Accession No. BAM72569. Version No. BAM72569.1. cholix toxin, partial [Vibrio cholerae]. Record created Dec. 14, 2012. 2 pages. Retrieved Sep. 9, 2019 at URL: https://www.ncbi.nlm.nih.gov/protein/BAM72569.1.
GenBank Accession No. BAM72570. Version No. BAM72570.1. cholix toxin, partial [Vibrio cholerae]. Record created Dec. 14, 2012. 2 pages. Retrieved Sep. 9, 2019 at URL: https://www.ncbi.nlm.nih.gov/protein/BAM72570.1.
GenBank Accession No. BAM72571. Version No. BAM72571.1. cholix toxin, partial [Vibrio cholerae]. Record created Dec. 14, 2012. 2 pages. Retrieved Sep. 9, 2019 at URL: https://www.ncbi.nlm.nih.gov/protein/BAM72571.1.
GenBank Accession No. BAM72573. Version No. BAM72573.1. cholix toxin, partial [Vibrio cholerae]. Record created Dec. 14, 2012. 2 pages. Retrieved Sep. 6, 2019 at URL: https://www.ncbi.nlm.nih.gov/protein/BAM72573.1.
GenBank Accession No. BAM72574. Version No. BAM72574.1. cholix toxin, partial [Vibrio cholerae]. Record created Dec. 14, 2012. 2 pages. Retrieved Sep. 9, 2019 at URL: https://www.ncbi.nlm.nih.gov/protein/BAM72574.1.
GenBank Accession No. BAM72575. Version No. BAM72575.1. cholix toxin, partial [Vibrio cholerae]. Record created Dec. 14, 2012. 2 pages. Retrieved Sep. 6, 2019 at URL: https://www.ncbi.nlm.nih.gov/protein/BAM72575.1.
GenBank Accession No. BAM72576. Version No. BAM72576.1. cholix toxin, partial [Vibrio cholerae]. Record created Dec. 14, 2012. 2 pages. Retrieved Sep. 9, 2019 at URL: https://www.ncbi.nlm.nih.gov/protein/BAM72576.1.
GenBank Accession No. BAM72582. Version No. BAM72582.1. cholix toxin, partial [Vibrio cholerae]. Record created Dec. 14, 2012. 2 pages. Retrieved Sep. 9, 2019 at URL: https://www.ncbi.nlm.nih.gov/protein/BAM72582.1.
GenBank Accession No. BAM72585. Version No. BAM72585.1. cholix toxin, partial [Vibrio cholerae]. Record created Dec. 14, 2012. 2 pages. Retrieved Sep. 9, 2019 at URL: https://www.ncbi.nlm.nih.gov/protein/BAM72585.1.
GenBank Accession No. BAM72587. Version No. BAM72587.1. cholix toxin, partial [Vibrio cholerae]. Record created Dec. 14, 2012. 2 pages. Retrieved Sep. 9, 2019 at URL: https://www.ncbi.nlm.nih.gov/protein/BAM72587.1.

(56) References Cited

OTHER PUBLICATIONS

GenBank Accession No. BAM72590. Version No. BAM72590.1. cholix toxin, partial [Vibrio cholerae]. Record created Dec. 14, 2012. 2 pages. Retrieved Sep. 6, 2019 at URL: https://www.ncbi.nlm.nih.gov/protein/BAM72590.1.
GenBank Accession No. BAM72593. Version No. BAM72593.1. cholix toxin, partial [Vibrio cholerae]. Record created Dec. 14, 2012. 2 pages. Retrieved Sep. 6, 2019 at URL: https://www.ncbi.nlm.nih.gov/protein/BAM72593.1.
GenBank Accession No. BAM72594. Version No. BAM72594.1. cholix toxin, partial [Vibrio cholerae]. Record created Dec. 14, 2012. 2 pages. Retrieved Sep. 6, 2019 at URL: https://www.ncbi.nlm.nih.gov/protein/BAM72594.1.
GenBank Accession No. BAM72595. Version No. BAM72595.1. cholix toxin, partial [Vibrio cholerae]. Record created Dec. 14, 2012. 2 pages. Retrieved Sep. 6, 2019 at URL: https://www.ncbi.nlm.nih.gov/protein/BAM72595.1.
GenBank Accession No. BAM72596. Version No. BAM72596.1. cholix toxin, partial [Vibrio cholerae]. Record created Dec. 14, 2012. 2 pages. Retrieved Sep. 6, 2019 at URL: https://www.ncbi.nlm.nih.gov/protein/BAM72596.1.
GenBank Accession No. BAM72610. Version No. BAM72610.1. cholix toxin, partial [Vibrio cholerae]. Record created Dec. 14, 2012. 2 pages. Retrieved Sep. 9, 2019 at URL: https://www.ncbi.nlm.nih.gov/protein/BAM72610.1.
GenBank Accession No. BAM72611. Version No. BAM72611.1. cholix toxin, partial [Vibrio cholerae]. Record created Dec. 14, 2012. 2 pages. Retrieved Sep. 6, 2019 at URL: https://www.ncbi.nlm.nih.gov/protein/BAM72611.1.
GenBank Accession No. EFH75651. Version No. EFH75651.1. conserved hypothetical protein [Vibrio cholerae RC385]. Record created Jun. 4, 2010. 2 pages. Retrieved Sep. 6, 2019 at URL: https://www.ncbi.nlm.nih.gov/protein/EFH75651.1.
GenBank Accession No. KFD89501. Version No. KFD89501.1. exotoxin A binding family protein [Vibrio cholerae]. Record created Jul. 31, 2014. pages. Retrieved Sep. 6, 2019 at URL: https://www.ncbi.nlm.nih.gov/protein/KFD89501.1.
GenBank Accession No. KFD96741. Version No. KFD96741.1. exotoxin A binding family protein [Vibrio cholerae]. Record created Jul. 31, 2014. 2 pages. Retrieved Sep. 9, 2019 at URL: https://www.ncbi.nlm.nih.gov/protein/KFD96741.1.
GenBank Accession No. KFE28160. Version No. KFE28160.1. exotoxin A binding family protein [Vibrio cholerae]. Record created Jul. 31, 2014. 2 pages. Retrieved Sep. 6, 2019 at URL: https://www.ncbi.nlm.nih.gov/protein/KFE28160.1.
GenBank Accession No. KNH55243. Version No. KNH55243.1. hypothetical protein A59_2898 [Vibrio cholerae 623-39]. Record created Aug. 5, 2015. 2 pages. Retrieved Sep. 6, 2019 at URL: https://www.ncbi.nlm.nih.gov/protein/KNH55243.1.
GenBank Accession No. P01241. Somatotropin. Record created Jul. 21, 1986. 12 pages. Retrieved Aug. 29, 2019 at URL: https://www.ncbi.nlm.nih.gov/protein/P01241.
GenBank Accession No. Q5EK40. Version No. Q5EK40.1. Cholix toxin. Record created Feb. 9, 2005. 9 pages. Retrieved Aug. 30, 2019 at URL: https://www.ncbi.nlm.nih.gov/protein/Q5EK40.1.
GenBank Accession No. SYZ81493. Version No. SYZ81493.1. Cholix toxin precursor [Vibrio cholerae]. Record created Sep. 6, 2018. 1 page. Retrieved Sep. 9, 2019 at URL: https://www.ncbi.nlm.nih.gov/protein/SYZ81493.1.
GenBank Accession No. WP_000941100. Version No. WP_000941100.1. Multispecies: cholix toxin [Vibrio]. Record created Feb. 5, 2013. 1 page. Retrieved Sep. 9, 2019 at URL: https://www.ncbi.nlm.nih.gov/protein/WP_000941100.1.
GenBank Accession No. WP_002044040. Version No. WP_002044040.1. cholix toxin [Vibrio cholerae]. Record created May 4, 2013. 1 page. Retrieved Sep. 9, 2019 at URL: https://www.ncbi.nlm.nih.gov/protein/WP_002044040.1.
GenBank Accession No. WP_032467916. Version No. WP_032467916.1. cholix toxin [Vibrio cholerae]. Record created Oct. 4, 2014. 1 page. Retrieved Sep. 9, 2019 at URL: https://www.ncbi.nlm.nih.gov/protein/WP_032467916.1.
GenBank Accession No. WP_032482668. Version No. WP_032482668.1. cholix toxin [Vibrio cholerae]. Record created Oct. 4, 2014. 1 page. Retrieved Sep. 9, 2019 at URL: https://www.ncbi.nlm.nih.gov/protein/WP_032482668.1.
GenBank Accession No. WP_033932701. Version No. WP_033932701.1. cholix toxin [Vibrio cholerae]. Record created Dec. 5, 2014. 1 page. Retrieved Sep. 9, 2019 at URL: https://www.ncbi.nlm.nih.gov/protein/WP_033932701.1.
GenBank Accession No. WP_042988437. Version No. WP_042988437.1. cholix toxin [Vibrio cholerae]. Record created Feb. 17, 2015. 1 page. Retrieved Sep. 9, 2019 at URL: https://www.ncbi.nlm.nih.gov/protein/WP_042988437.1.
GenBank Accession No. WP_057552180. Version No. WP_057552180.1. cholix toxin [Vibrio cholerae]. Record created Nov. 10, 2015. 1 page. Retrieved Sep. 9, 2019 at URL: https://www.ncbi.nlm.nih.gov/protein/WP_057552180.1.
GenBank Accession No. WP_057557199. Version No. WP_057557199.1. cholix toxin [Vibrio cholerae]. Record created Nov. 10, 2015. 1 page. Retrieved Sep. 9, 2019 at URL: https://www.ncbi.nlm.nih.gov/protein/WP_057557199.1.
GenBank Accession No. WP_069648100. Version No. WP_069648100.1. cholix toxin [Vibrio cholerae]. Record created Sep. 20, 2016. 1 page. Retrieved Sep. 9, 2019 at URL: https://www.ncbi.nlm.nih.gov/protein/WP_069648100.1.
GenBank Accession No. WP_071178365. Version No. WP_071178365.1. cholix toxin [Vibrio cholerae]. Record created Nov. 2, 2016. 1 page. Retrieved Sep. 9, 2019 at URL: https://www.ncbi.nlm.nih.gov/protein/WP_071178365.1.
GenBank Accession No. WP_071186455. Version No. WP_071186455.1. cholix toxin [Vibrio cholerae]. Record created Nov. 2, 2016. 1 page. Retrieved Sep. 9, 2019 at URL: https://www.ncbi.nlm.nih.gov/protein/WP_071186455.1.
GenBank Accession No. WP_076008260. Version No. WP_076008260.1. cholix toxin [Vibrio cholerae]. Record created Jan. 19, 2017. 1 page. Retrieved Sep. 9, 2019 at URL: https://www.ncbi.nlm.nih.gov/protein/WP_076008260.1.
GenBank Accession No. WP_076025263. Version No. WP_076025263.1. cholix toxin [Vibrio cholerae]. Record created Jan. 19, 2017. 1 page. Retrieved Sep. 9, 2019 at URL: https://www.ncbi.nlm.nih.gov/protein/WP_076025263.1.
GenBank Accession No. WP_084980904. Version No. WP_084980904.1. cholix toxin [Vibrio cholerae]. Record created Apr. 21, 2017. 1 page. Retrieved Sep. 9, 2019 at URL: https://www.ncbi.nlm.nih.gov/protein/WP_084980904.1.
GenBank Accession No. WP_088131881. Version No. WP_088131881.1. cholix toxin [Vibrio cholerae]. Record created Jun. 19, 2017. 1 page. Retrieved Sep. 6, 2019 at URL: https://www.ncbi.nlm.nih.gov/protein/WP_088131881.1.
GenBank Accession No. WP_095461883. Version No. WP_095461883.1. cholix toxin [Vibrio cholerae]. Record created Sep. 2, 2017. 1 page. Retrieved Sep. 9, 2019 at URL: https://www.ncbi.nlm.nih.gov/protein/WP_095461883.1.
GenBank Accession No. WP_095463544. Version No. WP_095463544.1. cholix toxin [Vibrio cholerae]. Record created Sep. 2, 2017. 1 page. Retrieved Sep. 9, 2019 at URL: https://www.ncbi.nlm.nih.gov/protein/WP_095463544.1.
GenBank Accession No. WP_095466115. Version No. WP_095466115.1. cholix toxin [Vibrio cholerae]. Record created Sep. 2, 2017. 1 page. Retrieved Sep. 6, 2019 at URL: https://www.ncbi.nlm.nih.gov/protein/WP_095466115.1.
GenBank Accession No. WP_095473667. Version No. WP_095473667.1. cholix toxin [Vibrio cholerae]. Record created Sep. 2, 2017. 1 page. Retrieved Sep. 9, 2019 at URL: https://www.ncbi.nlm.nih.gov/protein/WP_095473667.1.
GenBank Accession No. WP_095477173. Version No. WP_095477173.1. cholix toxin [Vibrio cholerae]. Record created Sep. 2, 2017. 1 page. Retrieved Sep. 9, 2019 at URL: https://www.ncbi.nlm.nih.gov/protein/WP_095477173.1.

(56) References Cited

OTHER PUBLICATIONS

GenBank Accession No. WP_095490358. Version No. WP_095490358.1. cholix toxin [Vibrio cholerae]. Record created Sep. 2, 2017. 1 page. Retrieved Sep. 9, 2019 at URL: https://www.ncbi.nlm.nih.gov/protein/WP_095490358.1.
GenBank Accession No. WP_113605545. Version No. WP_113605545.1. cholix toxin [*Vibrio* sp. 2017V-1105]. Record created Jul. 15, 2018. 1 page. Retrieved Sep. 9, 2019 at URL: https://www.ncbi.nlm.nih.gov/protein/WP_113605545.1.
GenBank Accession No. WP_113620122. Version No. WP_113620122.1. cholix toxin [*Vibrio* sp. 2014V-1107]. Record created Jul. 15, 2018. 1 page. Retrieved Sep. 9, 2019 at URL: https://www.ncbi.nlm.nih.gov/protein/WP_113620122.1.
GenBank Accession No. WP_113628761. Version No. WP_113628761.1. cholix toxin [Vibrio cholerae]. Record created Jul. 15, 2018. 1 page. Retrieved Sep. 6, 2019 at URL: https://www.ncbi.nlm.nih.gov/protein/WP_113628761.1.
GenBank Accession No. WP_114707943. Version No. WP_114707943.1. cholix toxin [Vibrio cholerae]. Record created Aug. 2, 2018. 1 page. Retrieved Sep. 9, 2019 at URL: https://www.ncbi.nlm.nih.gov/protein/WP_114707943.1.
GenBank Accession No. WP_114708586. Version No. WP_114708586.1. cholix toxin [Vibrio cholerae]. Record created Aug. 2, 2018. 1 page. Retrieved Sep. 6, 2019 at URL: https://www.ncbi.nlm.nih.gov/protein/WP_114708586.1.
GenBank Accession No. WP_1 14711324. Version No. WP_114711324.1. cholix toxin [Vibrio cholerae]. Record created Aug. 2, 2018. 1 page. Retrieved Sep. 9, 2019 at URL: https://www.ncbi.nlm.nih.gov/protein/WP_114711324.1.
GenBank Accession No. WP_114718037. Version No. WP_114718037.1. cholix toxin [Vibrio cholerae]. Record created Aug. 2, 2018. 1 page. Retrieved Sep. 6, 2019 at URL: https://www.ncbi.nlm.nih.gov/protein/WP_114718037.1.
GenBank Accession No. WP_114728533. Version No. WP_114728533.1. cholix toxin [Vibrio cholerae]. Record created Aug. 2, 2018. 2 pages. Retrieved Sep. 6, 2019 at URL: https://www.ncbi.nlm.nih.gov/protein/WP_114728533.1.
GenBank Accession No. WP_114735885. Version No. WP_114735885.1. cholix toxin [Vibrio cholerae]. Record created Aug. 2, 2018. 1 page. Retrieved Sep. 6, 2019 at URL: https://www.ncbi.nlm.nih.gov/protein/WP_114735885.1.
GenBank Accession No. WP_114741531. Version No. WP_114741531.1. cholix toxin [Vibrio cholerae]. Record created Aug. 2, 2018. 1 page. Retrieved Sep. 6, 2019 at URL: https://www.ncbi.nlm.nih.gov/protein/WP_114741531.1.
GenBank Accession No. WP_114743333. Version No. WP_114743333.1. cholix toxin [Vibrio cholerae]. Record created Aug. 2, 2018. 1 page. Retrieved Sep. 9, 2019 at URL: https://www.ncbi.nlm.nih.gov/protein/WP_114743333.1.
GenBank Accession No. WP_114774300. Version No. WP_114774300.1. cholix toxin [Vibrio cholerae]. Record created Aug. 2, 2018. 1 page. Retrieved Sep. 6, 2019 at URL: https://www.ncbi.nlm.nih.gov/protein/WP_114774300.1.
GenBank Accession No. WP_114776277. Version No. WP_114776277.1. cholix toxin [Vibrio cholerae]. Record created Aug. 2, 2018. 1 page. Retrieved Sep. 6, 2019 at URL: https://www.ncbi.nlm.nih.gov/protein/WP_114776277.1.
GenBank Accession No. WP_114788528. Version No. WP_114788528.1. cholix toxin, partial [Vibrio cholerae]. Record created Aug. 2, 2018. 1 page. Retrieved Sep. 9, 2019 at URL: https://www.ncbi.nlm.nih.gov/protein/WP_114788528.1.
GenBank Accession No. WP_114794357. Version No. WP_114794357.1. cholix toxin [Vibrio cholerae]. Record created Aug. 2, 2018. 1 page. Retrieved Sep. 6, 2019 at URL: https://www.ncbi.nlm.nih.gov/protein/WP_114794357.1.
GenBank Accession No. WP_114808068. Version No. WP_114808068.1. cholix toxin [Vibrio cholerae]. Record created Aug. 2, 2018. 1 page. Retrieved Sep. 9, 2019 at URL: https://www.ncbi.nlm.nih.gov/protein/WP_114808068.1.
GenBank Accession No. WP_114967888. Version No. WP_114967888.1. cholix toxin [Vibrio cholerae]. Record created Aug. 3, 2018. 1 page. Retrieved Sep. 9, 2019 at URL: https://www.ncbi.nlm.nih.gov/protein/WP_114967888.1.
GenBank Accession No. WP_114974465. Version No. WP_114974465.1. cholix toxin [Vibrio cholerae]. Record created Aug. 3, 2018. 1 page. Retrieved Sep. 9, 2019 at URL: https://www.ncbi.nlm.nih.gov/protein/WP_114974465.1.
GenBank Accession No. WP_119788544. Version No. WP_119788544.1. cholix toxin [Vibrio cholerae]. Record created Sep. 26, 2018. 1 page. Retrieved Sep. 9, 2019 at URL: https://www.ncbi.nlm.nih.gov/protein/WP_119788544.1.
GenBank Accession No. WP_123013236. Version No. WP_123013236.1. cholix toxin [Vibrio cholerae]. Record created Nov. 10, 2018. 1 page. Retrieved Sep. 9, 2019 at URL: https://www.ncbi.nlm.nih.gov/protein/WP_123013236.1.
GenBank Accession No. WP_123162729. Version No. WP_123162729.1. cholix toxin [Vibrio cholerae]. Record created Nov. 14, 2018. 1 page. Retrieved Sep. 9, 2019 at URL: https://www.ncbi.nlm.nih.gov/protein/WP_123162729.1.
Ghosh et al. Peptides as drug delivery vehicles across biological barriers. Journal of Pharmaceutical Investigation 48:89-111 (Jan. 2018). Published online Dec. 12, 2017.
Gupta, et al. Permeation of insulin, calcitonin and exenatide across Caco-2 monolayers: measurement using a rapid, 3-day system. PloS one 8.2 (2013): e57136.
Hajishengallis et al. Type II Heat-labile Enterotoxins: Structure, Function, and Immunomodulatory Properties. Vet Immunol Immunopathol 152(1-2):68-77 (Mar. 15, 2013). doi:10.1016/j.vetimm.2012.09.034.
Hsu, et al. Vaccination against Gonadotropin-releasing Hormone (GnRH). Cancer Res. Jul. 15, 2000; 60:3701-3705.
Ji et al. The B subunit of *Escherichia coli* heat-labile toxin alters the development and antigen-presenting capacity of dendritic cells. J Cell Mol Med 19(8):2019-2031 (2015). doi: 10.1111/jcmm.12599.
Johnson et al. Complete Genome Assemblies for Two Single-Chromosome Vibrio cholerae Isolates, Strains 1154-74 (Serogroup O49) and 10432-62 (Serogroup O27). Genome Announc 3(3):e00462-15 (May 14, 2015). 2 pages. doi:10.1128/genomeA.00462-15.
Jørgensen, et al. Cholix toxin, a novel ADP-ribosylating factor from Vibrio cholerae. Journal of Biological Chemistry 283.16 (Apr. 18, 2008): 10671-10678.
Killeen, et al. Conformational integrity of a recombinant toxoid of Pseudomonas aeruginosa exotoxin A containing a deletion of glutamic acid-553. Biochimica et Biophysica Acta (BBA)-Molecular Basis of Disease 1138.2 (1992): 162-166.
Kondo et al. Activity of immunotoxins constructed with modified Pseudomonas exotoxin A lacking the cell recognition domain. J Biol Chem 263(19):9470-9475 (Jul. 5, 1988).
Kumar et al. Genome Sequence of Non-O1 Vibrio cholerae PS15. Genome Announcements 1(1):e00227-12 (Jan./Feb. 2013). 2 pages.
Laurent. Characterization of the trafficking pathway used by Pseudomonas aeruginosa Exotoxin A and application to oral drug delivery. Ph.D. Thesis. University of Bath. Dec. 2015. Retrieved Dec. 18, 2019 from URL: https://purehost.bath.ac.uk/ws/portalfiles/portal/187920618/Thesis_F.Laurent_Dec2015.pdf. 312 pages.
Lueben et al. Mucoadhesive Polymers in Peroral Peptide Drug Delivery. II. Carbomer and Polycarbophil Are Potent Inhibitors of the Intestinal Proteolytic Enzyme Trypsin. Pharmaceutical Research 12(9):1293-1298 (1995).
Lugo et al. The Father, Son and Cholix Toxin: The Third Member of the DT Group Mono-ADP-Ribosyltransferase Toxin Family. Toxins 7(8):2757-2772 (Jul. 24, 2015).
Luross et al. *Escherichia coli* Heat-Labile Enterotoxin B Subunit Prevents Autoimmune Arthritis Through Induction of Regulatory CD4+ T Cells. Arthritis & Rheumatism 46(6):1671-1682 (Jun. 6, 2002). DOI 10.1002/art. 10328.
Mahato et al. Emerging trends in oral delivery of peptide and protein drugs. Crit Rev Ther Drug Carrier Syst. 2003;20(2-3):153-214.
Mattoo et al. Interactions of bacterial effector proteins with host proteins. Curr Opin Immunol. Aug. 2007;19(4):392-401.
Mekalanos et al. Cholera toxin genes: nucleotide sequence, deletion analysis and vaccine development. Nature 306:551-557 (1983).

(56) References Cited

OTHER PUBLICATIONS

Merritt et al. Crystal structure of cholera toxin B-pentamer bound to receptor GM1 pentasaccharide. Protein Science 3:166-175 (1994).
Milling et al. Regulation of intestinal immunity: Effects of the oral adjuvant *Escherichia coli* heat-labile enterotoxin on heat-labile enterotoxin on migrating dendritic cells. Eur. J. Immunol. 37:87-99 (2007). DOI 10.1002/eji.200636199.
Moroz, et al. Oral delivery of macromolecular drugs: Where we are after almost 100years of attempts. Adv Drug Deliv Rev. Jun. 1, 2016;101:108-121.
Mrsny. Biotech Start-up—A Practical Guide. Bath, United Kingdom (Presentation.) (Nov. 19, 2018.) 18 pages.
Mrsny. Breaking Through the Biological Barriers that Limit Protein Drug Delivery. Bangor University, United Kingdom (Presentation.) (Aug. 6, 2015.) 26 pages.
Mrsny. Breaking Through the Biological Barriers that Limit Protein Drug Delivery. (Presentation.) Controlled Release Society, Florence, Italy (Nov. 8, 2014.) 43 pages.
Mrsny. Breaking Through the Biological Barriers that Limit Protein Drug Delivery. (Presentation.) Tours, France (Jul. 2, 2015.) 25 pages.
Mrsny. Employing endogenous pathways for the oral delivery of biopharmaceuticals. (Presentation.) Reading, United Kingdom (Jul. 18, 2018.) 35 pages.
Mrsny, et al. Bacterial toxins as tools for mucosal vaccination. Drug Discovery Today. 2002; 4:247-258.
Mrsny et al. Mucosal administration of a chimera composed of Pseudomonas exotoxin and the gp120 V3 loop sequence of HIV-1 induces both salivary and serum antibody responses. Vaccine 17(11-12):1425-1433 (Mar. 17, 1999).
Mrsny. Harnessing Mucosal Immunology for Health. Bath, United Kingdom (Presentation.) (Sep. 25, 2018.) 29 pages.
Mrsny. Harnessing Mucosal Immunology for Health. Ma'alot-Tarshiha, Israel (Presentation.) (Oct. 7, 2018.) 28 pages.
Mrsny, Lessons from nature: "Pathogen-Mimetic" systems for Mucosal Nano-medicines, Advanced Drug Delivery Reviews, vol. 61 :172-192 (online Dec. 24, 2008).
Mrsny. Molecular mechanisms of transcytosis pathways: Drug delivery thru epithelial and endothelial barriers. (Presentation.) (Dec. 3, 2010). 42 pages.
Mrsny. Molecular mechanisms of transcytosis pathways: Drug delivery thru epithelial and endothelial barriers. (Presentation.) Emory University, Atlanta, GA, United States. (Sep. 24, 2010). 51 pages.
Mrsny. Molecular mechanisms of transcytosis pathways: Drug delivery thru epithelial and endothelial barriers. (Presentation.) Nanomedicine and Drug Delivery Symposium (NanoDDS), University of Nebraska Omaha, Omaha, NE, United States. (Oct. 3, 2010.) 42 pages.
Mrsny. My Secondment(Gap Years?) at AMT. University of Bath, United Kingdom(Presentation.) (Oct. 6, 2017.) 20 pages.
Mrsny. Overcoming Barriers to Oral Protein Delivery. Boston, MA, United States (Presentation.) (Jul. 23, 2018.) 35 pages.
Mrsny. Overcoming Biological Barriers that Limit Peptide and Protein Drug Delivery. Berlin, Germany (Presentation.) (May 23, 2016.) 26 pages.
Mrsny. Overcoming Biological Barriers that Limit Peptide and Protein Drug Delivery. Denver, CO, United States (Presentation.) (Nov. 17, 2016.) 15 pages.
Mrsny. Overcoming Biological Barriers that Limit Peptide and Protein Drug Delivery. (Presentation.) (Jun. 14, 2016.) 36 pages.
Mrsny. Overcoming Biological Barriers that Limit Peptide and Protein Drug Delivery. University of California San Francisco, CA, United States (Presentation.) (Mar. 24, 2016.) 36 pages.
Mrsny. Paracellular and Transcellular Strategies to Enhance Oral Protein Delivery. (Presentation.) San Francisco, CA, United States (Mar. 15, 2013.) 41 pages.
Mrsny. Paracellular and Transcellular Strategies to Enhance Oral Protein Delivery. (Presentation.) Seoul, South Korea (Mar. 15, 2012.) 54 pages.
Mrsny. Paracellular and Transcellular Strategies to Enhance Oral Protein Delivery. (Presentation.) University of California, Santa Barbara, CA, United States. (Feb. 26, 2013.) 54 pages.
Mrsny. Permeation of barriers for GI and pulmonary drug delivery. (Presentation.) Gordon Research Conference, New Hampshire, United States. (Aug. 13, 2012.) 46 pages.
Mrsny. Prospects for Oral Delivery of Peptide and Protein Therapeutics. San Francisco, CA, United States (Presentation.) (May 21, 2018.) 29 pages.
Mrsny. Prospects for Oral Delivery of Peptide and Protein Therapeutics. University of Nottingham, United Kingdom(Presentation.) (Jun. 20, 2018.) 62 pages.
Mrsny. Strategies to Enhance the Oral Delivery of Therapeutic Proteins and Peptides. (Presentation.) Berlin, Germany. (Sep. 28, 2011.) 42 pages.
Mrsny. Strategies to Enhance the Oral Delivery of Therapeutic Proteins and Peptides. (Presentation.) Dunedin, New Zealand (Feb. 15, 2012). 42 pages.
Mrsny. Strategies to Enhance the Oral Delivery of Therapeutic Proteins and Peptides. (Presentation.) Nottingham, United Kingdom. (Sep. 2, 2011.) 42 pages.
Mrsny. Strategies to Enhance the Oral Delivery of Therapeutic Proteins and Peptides. (Presentation.) San Francisco, CA, United States. (Jun. 20, 2011.) 42 pages.
Mrsny. Strategies to Enhance the Oral Delivery of Therapeutic Proteins and Peptides. (Presentation.) The University of Sheffield, Sheffield, United Kingdom. (Jan. 16, 2012.) 42 pages.
Mrsny. TJ Regulation using Cell-Penetrating Peptides. (Presentation.) University of Copenhagen, Denmark (May 12, 2015.) 62 pages.
Mrsny. Understanding & Developing the Science Behind Oral Protein and Peptide Delivery. (Presentation.) Nottingham, United Kingdom (Jan. 22, 2014.) 48 pages.
Mrsny. Understanding & Developing the Science Behind Oral Protein Delivery: An Academic Case Study. (Presentation.) Berlin, Germany (Feb. 20, 2013.) 39 pages.
Mrsny. Understanding & Developing the Science Behind Oral Protein Delivery. (Presentation.) University of North Carolina at Chapel Hill, Chapel Hill, North Carolina, United States. (May 28, 2014.) 37 pages.
Mrsny. Understanding & Developing the Science Behind Oral Protein Delivery. (Presentation.) University of Westminster, London, United Kingdom. (Mar. 15, 2013). 40 pages.
Mrsny. Understanding & Developing the Science Behind Oral Protein Delivery. (Presentation.) Academy of Pharmaceutical Sciences, Edinburgh, United Kingdom.(Sep. 3, 2013). 40 pages.
Mrsny. Understanding & Developing the Science Behind Oral Protein Delivery. (Presentation.) University College Dublin, Dublin, Ireland(May 22, 2013). 44 pages.
Mrsny. Understanding & Developing the Science Behind Oral Protein Delivery. (Presentation.) University of East Anglia, Norwich, United Kingdom(Jun. 27, 2013). 43 pages.
Mrsny. Understanding Exotoxin Transcytosis for the Application of Oral Protein Delivery. Dresden, Germany (Presentation.) (Nov. 12, 2015.) 26 pages.
Mudrak et al. Heat-Labile Enterotoxin: Beyond GM1 Binding. Toxins 2:1445-1470 (Jun. 14, 2010). doi:10.3390/toxins2061445.
Pastan et al. Recombinant Toxins as Novel Therapeutic Agents. Annu Rev Biochem 61:331-54 (1992).
Plant et al. Modulation of the Immune Response by the Cholera-like Enterotoxins. Current Topics in Medicinal Chemistry 4:509-519 (2004).
Plant et al. The B subunit of *Escherichia coli* heat labile enterotoxin abrogates oral tolerance, promoting predominantly Th2-type immune responses. Eur J Immunol 33:3186-3195 (2003).
Porat. Accelerating Development of a Novel Chimera Protein through the Identification of a Two Column Purification Process Using NH2-750F and CaPure Resins. San Francisco, CA, United States.(Presentation.) (Nov. 7, 2018.) 30 pages.
Purdy et al. A Glimpse into the Expanded Genome Content of Vibrio cholerae through Identification of Genes Present in Environmental Strains. Journal of Bacteriology 187(9):2992-3001 (May 2005). DOI: 10.1128/JB.187.9.2992-3001.2005.

(56) References Cited

OTHER PUBLICATIONS

Purdy et al. Diversity and distribution of cholixtoxin, a novel ADP-ribosylating factor from Vibrio cholerae. Environmental Microbiology Reports 2(1):198-207 (Feb. 2010). First published Feb. 8, 2010. DOI: https://doi.org/10.1111/j.1758-2229.2010.00139.x.
Raveney et al. The B Subunit of *Escherichia coli* Heat-Labile Enterotoxin Inhibits Th1 but Not Th17 Cell Responses in Established Experimental Autoimmune Uveoretinitis. Investigative Ophthalmology & Visual Science 49(9):4008-4017 (Sep. 2008).
Rodighiero, et al. Structural Basis for the Differential Toxicity of Cholera Toxin and *Escherichia coli* Heat-labile Enterotoxin. The Journal of Biological Chemistry 274.77 (1999):3962-3969.
Rubas et al. Flux Measurements across Caco-2 Monolayers May Predict Transport in Human Large Intestinal Tissue. J Pharm Sci 85(2):165-169 (Feb. 1996).
Rubas et al. An integrated method to determine epithelial transport and bioactivity of oral drug candidates in vitro. Pharm Res 13(1):23-26 (Jan. 1996).
Rubas et al. Comparison of the permeability characteristics of a human colonic epithelial (Caco-2) cell line to colon of rabbit, monkey, and dog intestine and human drug absorption. Pharm Res.10(1):113-118 (1993).
Ruddock et al. Assembly of the B Subunit Pentamer of *Escherichia coli* Heat-labile Enterotoxin. J Biol Chem 271(32):19118-19123 (Aug. 9, 1996).
Ruddock et al. Kinetics of Acid-mediated Disassembly of the B Subunit Pentamer of *Escherichia coli* Heat-labile Enterotoxin. J Biol Chem 270(50):29953-29958 (Dec. 15, 1995).
Saidi et al. Prevalence of Vibrio cholerae O1 EI Tor variant in a cholera-endemic zone of Kenya. Journal of Medical Microbiology 63:415-420 (2014). First published online Mar. 1, 2014. doi:10.1099/jmm.0.068999-0.
Salmond et al. The B Subunit of *Escherichia coli* Heat-Labile Enterotoxin Induces Both Caspase-Dependent and -Independent Cell Death Pathways in CD8+ T Cells. Infection and Immunity 72(10):5850-5857 (Oct. 2004).
Sarnovsky, et al. Initial characterization of an immunotoxin constructed from domains II and III of cholera exotoxin. Cancer Immunol. Immunother., 59.5 2010 (published online Nov. 2009):737-746.
Schauer. AVX-470, an Orally-Delivered GI-Targeted anti-TNF for the Treatment of Pediatric IBD. Presentation. Avaxia Biologies (Oct. 26, 2015). 42 pages.
Shi et al. Oral delivery of human growth hormone: Preparation, characterization, and pharmacokinetics. J Biomater Appl 31(6):851-858 (Jan. 2017). Epub Oct. 14, 2016.
Shiraishi et al. Enhanced delivery of cell-penetrating peptide-peptide nucleic acid conjugates by endosomal disruption. Nat Protoc. 2006;1(2):633-6.Published online Jun. 29, 2006. doi: 10.1038/nprot.2006.92.
Siegall et al. Functional Analysis of Domains II, Ib, and III of Pseudomonas Exotoxin. J Biol Chem 264(24):14256-14261 (Aug. 25, 1989).
Simmons et al. Immunomodulation Using Bacterial Enterotoxins. Scand J Immunol 53:518-226 (2001).
Simon, et al. Novel bacterial ADP-ribosylating toxins: structure and function. Nature Reviews Microbiology 12.9 (2014): 599-611.
Song et al. Oral delivery system for low molecular weight protamine-dextran-poly(lactic-co-glycolic acid) carrying exenatide to overcome the mucus barrier and improve intestinal targeting efficiency. Nanomedicine (Lond.) 14(8):989-1009 (Apr. 2019). Published online Mar. 22, 2019.
Sun et al. Cholera toxin B subunit: An efficient transmucosal carrier-delivery system for induction of peripheral immunological tolerance. Proc Natl Acad Sci USA 91:10795-10799 (Nov. 1994).
Takeuchi et al. Mucoadhesive nanoparticulate systems for peptide drug delivery. Adv Drug Deliv Rev 47(1):39-54 (Mar. 23, 2001).
Taverner et al. Cholix protein domain I functions as a carrier element for efficient apical to basal epithelial transcytosis. Tissue Barriers, pp. 1710429-1 to 1710429-20 (Jan. 13, 2020). doi: 10.1080/21688370.2019.1710429.
Taverner, et al. Enhanced paracellular transport of insulin can be achieved via transient induction of myosin light chain phosphorylation. Journal of Controlled Release 210 (2015): 189-197.
Turcanu et al. Modulation of human monocytes by *Escherichia coli* heat-labile enterotoxin B-subunit; altered cytokine production and its functional consequences. Immunology 106:316-325 (2002).
U.S. Appl. No. 16/151,533 Notice of Allowance dated May 28, 2020.
U.S. Appl. No. 16/151,533 Notice of Allowance dated Sep. 8, 2020.
U.S. Appl. No. 16/207,655 Notice of Allowance dated Aug. 28, 2020.
U.S. Appl. No. 16/207,655 Notice of Allowance dated May 20, 2020.
U.S. Appl. No. 16/220,923 Notice of Allowance dated Aug. 27, 2020.
U.S. Appl. No. 16/220,923 Notice of Allowance dated May 20, 2020.
Wang et al. Methods to determine intestinal permeability and bacterial translocation during liver disease. J Immunol Methods 421:44-53 (Jun. 2015). Epub Jan. 13, 2015. doi:10.1016/j.jim.2014.12.015.
Wedekind et al. Refined crystallographic structure of Pseudomonas aeruginosa exotoxin A and its implications for the molecular mechanism of toxicity. J Mol Biol. Dec. 7, 2001;314(4):823-37.
Woodley, J.F. Enzymatic barriers for GI peptide and protein delivery. Crit Rev Ther Drug Carrier Syst. 1994;11(2-3):61-95.
Yahiro et al. Cholix toxin, an eukaryotic elongation factor 2 ADP-ribosyltransferase, interacts with Prohibitins and induces apoptosis with mitochondrial dysfunction in human hepatocytes. Cell Microbiol. Aug. 2019;21(8):e13033.doi: 10.1111/cmi.13033. Epub May 14, 2019.
Co-pending U.S. Appl. No. 17/558,418, inventors Mrsny; Randall J. et al., filed Dec. 21, 2021.
U.S. Appl. No. 16/884,456 Office Action dated Oct. 20, 2021.
U.S. Appl. No. 17/129,376 Office Action dated Oct. 6, 2021.
U.S. Appl. No. 16/884,456 Notice of Allowance dated Mar. 7, 2022.
Co-pending U.S. Appl. No. 17/684,619, inventors Mrsny; Randall J. et al., filed Mar. 2, 2022.
Co-pending U.S. Appl. No. 17/709,325, inventors Mrsny; Randall J. et al., filed Mar. 30, 2022.

\* cited by examiner

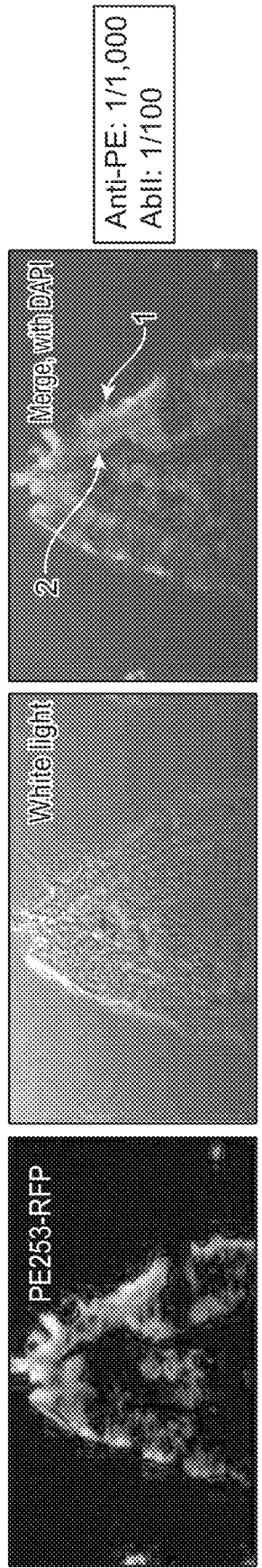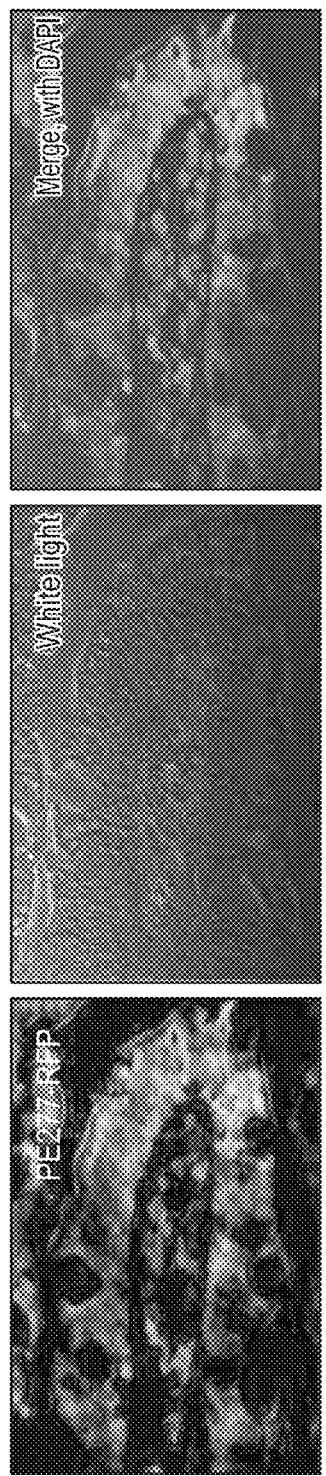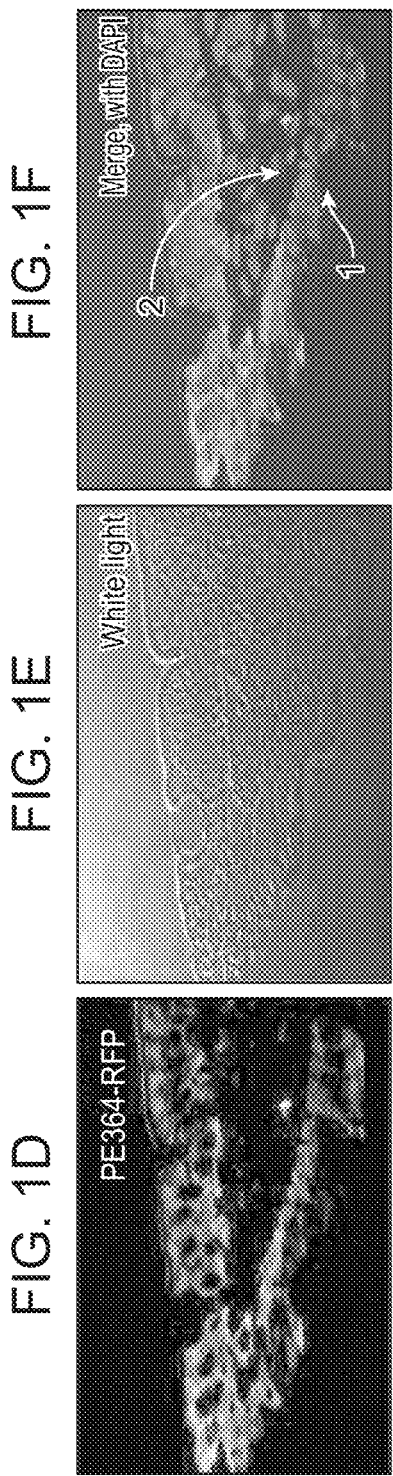

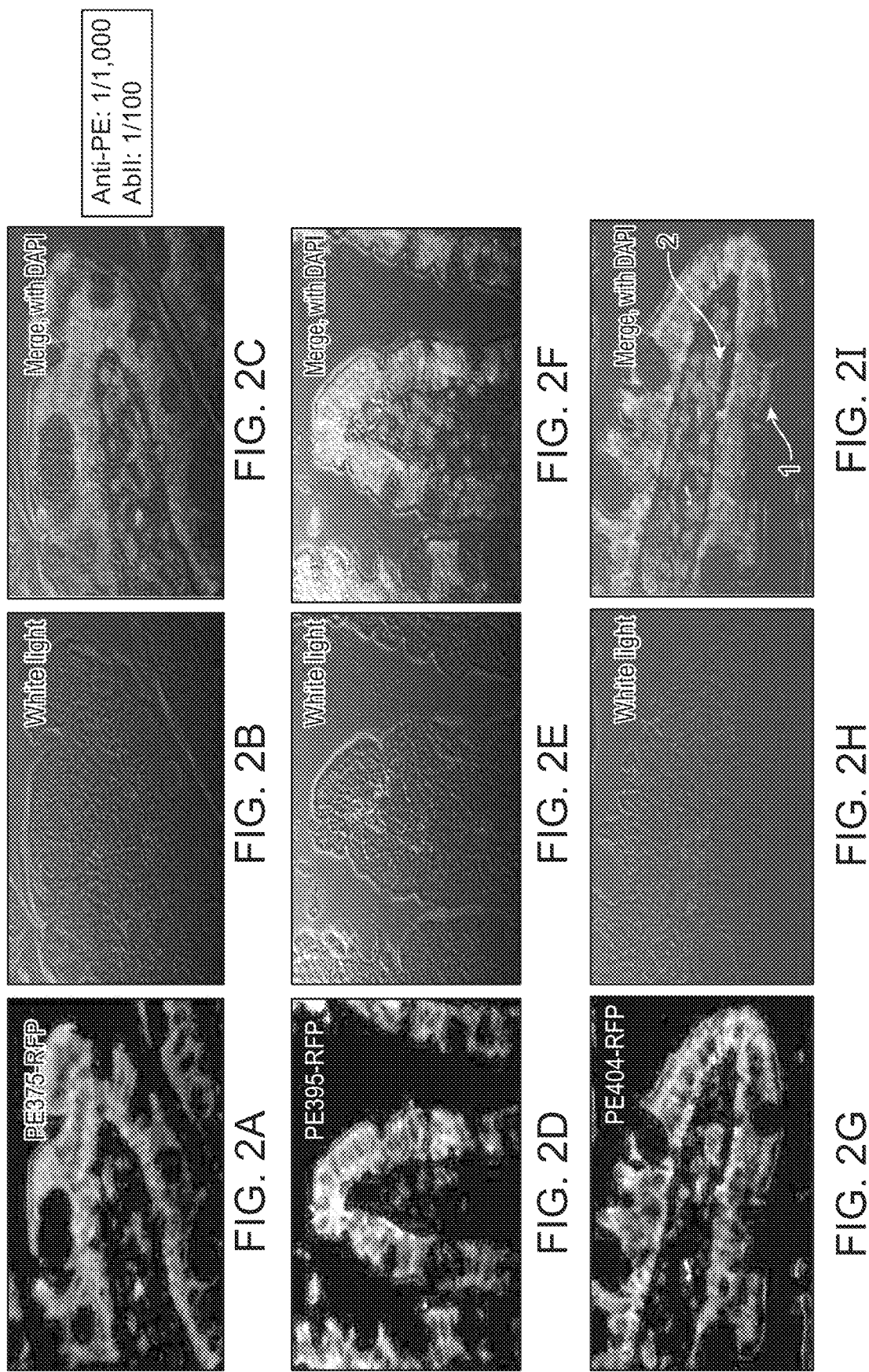

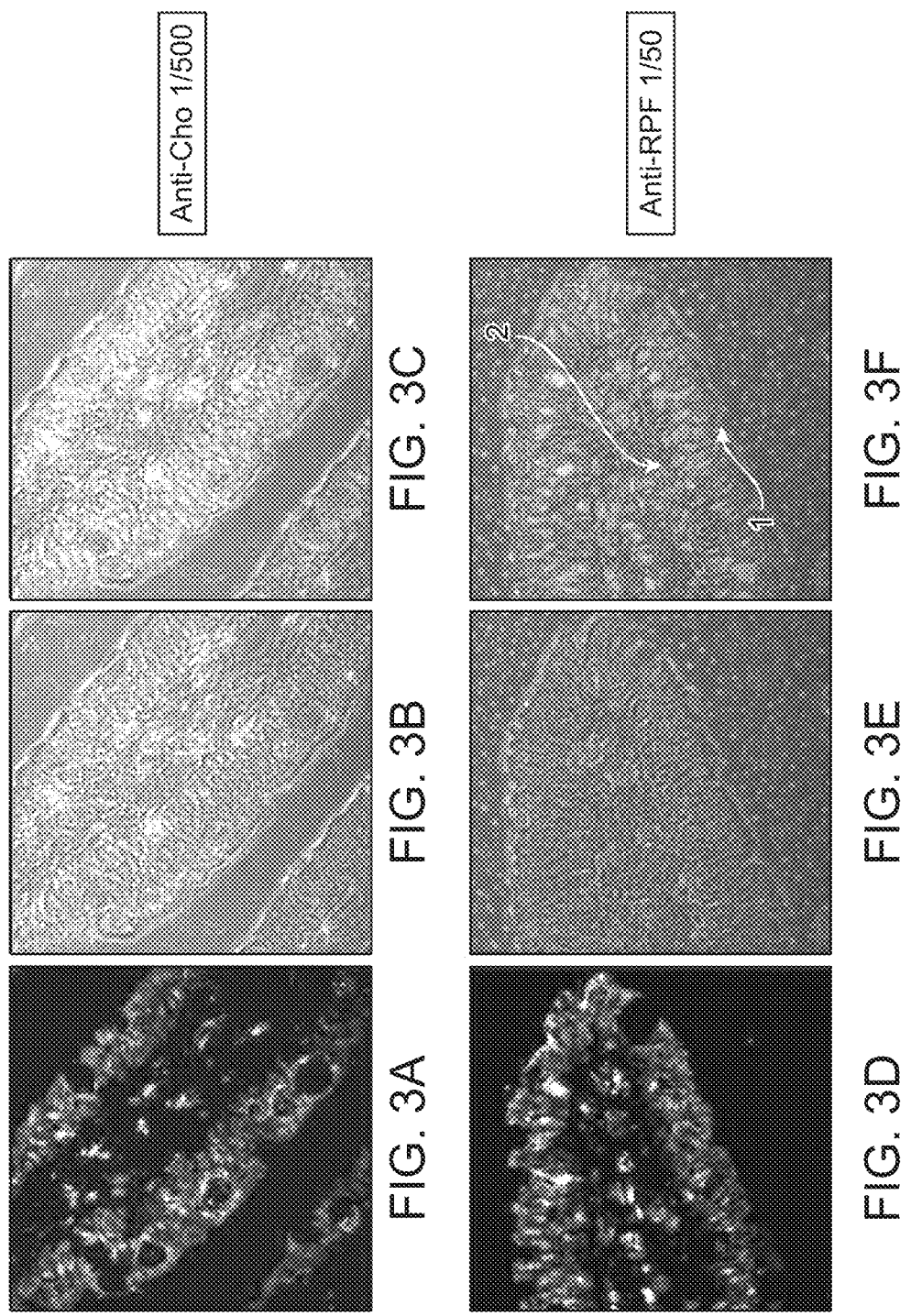

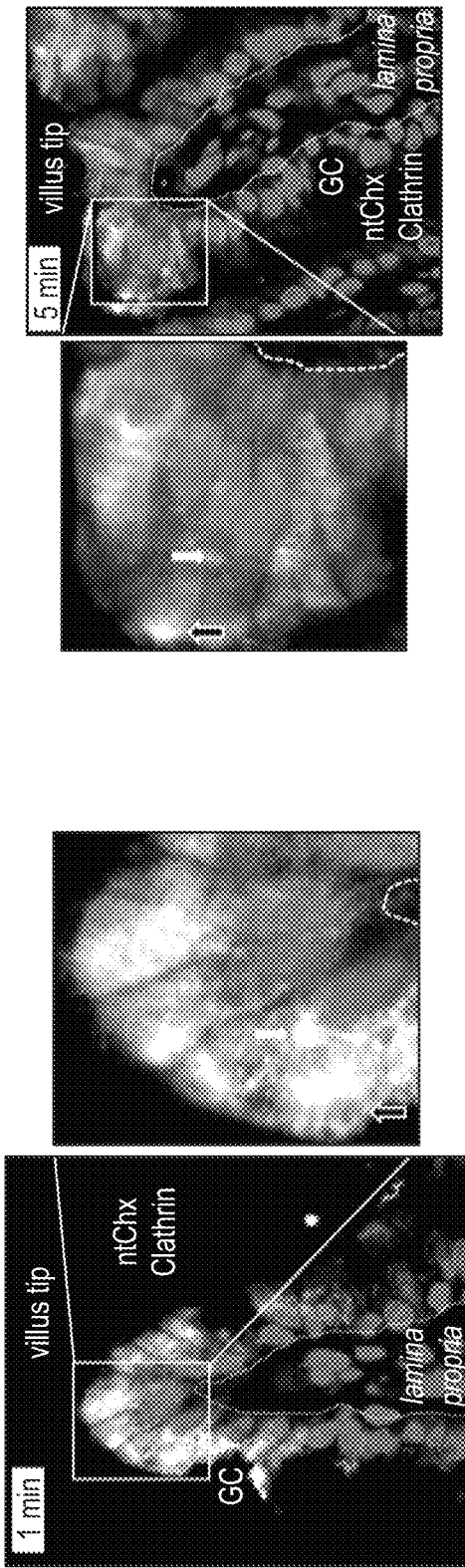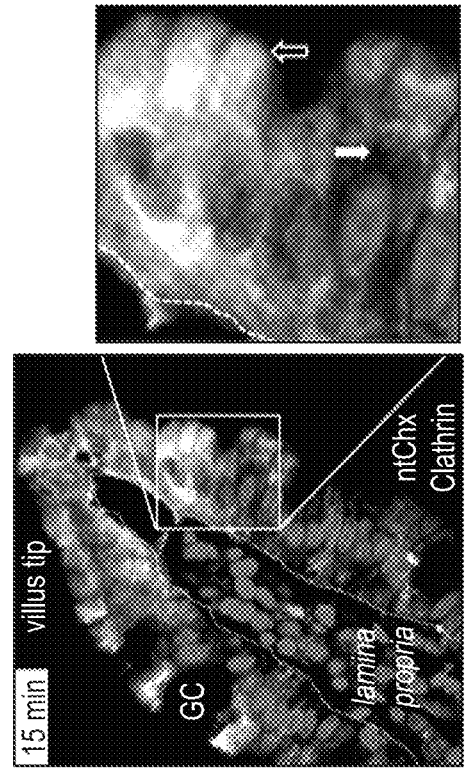
FIG. 12A
FIG. 12B
FIG. 12C

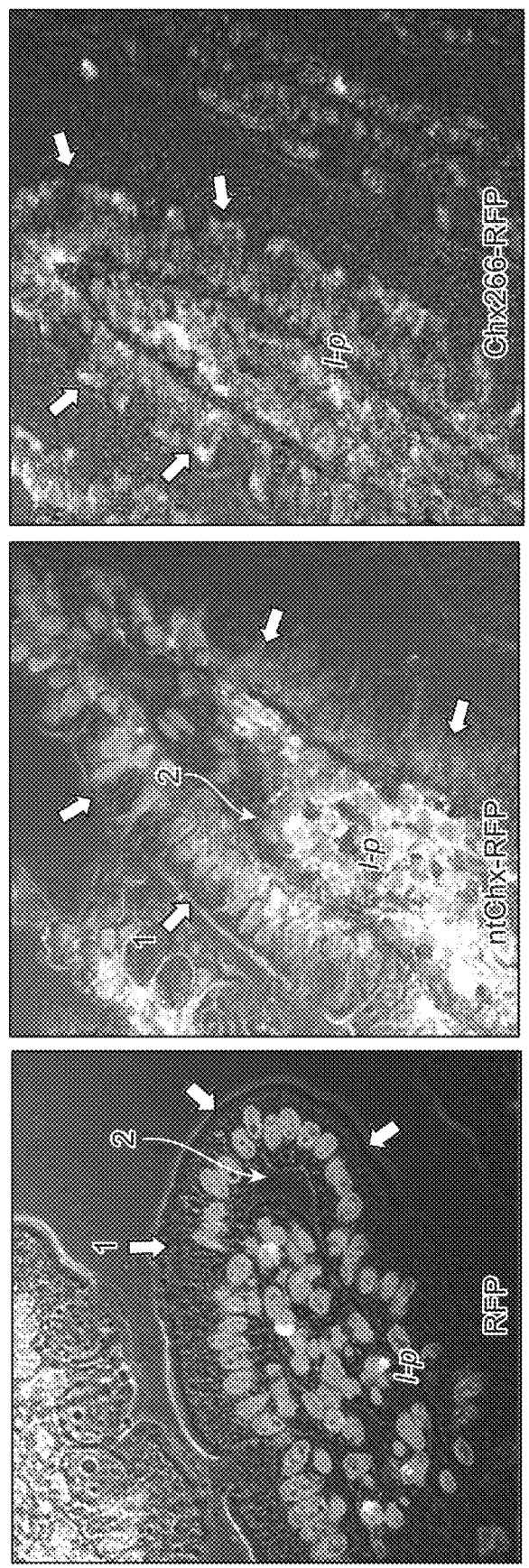

Numbered circles refer to specific proteins that were targeted for mass spectrometry analysis for identification. These represent those that were augmented in the carrier-bead analyte pool and a number of control proteins used to validate the methodology.

| Protein Candidate | Caco-2 vesicle | Caco-2 PD Cholix-His | Caco-2 PD Cholix-Biotin | Caco-2 IP anti-F4/80 | Rat jejunum PD Cholix-His | Rat jejunum PD Cholix-Biotin | MS confidence |
|---|---|---|---|---|---|---|---|
| Cytokeratin | ✓ | ✓ | ✓ | ✓ | ✓ | ✓ | High |
| Heparan sulfate proteoglycan | | ✓ | | | | | High |
| Heat shock protein | ✓ | ✓ | | | ✓ | ✓ | High |
| ATP synthase | ✓ | ✓ | | | ✓ | ✓ | High |
| Laminin | ✓ | ✓ | | ✓ | ✓ | ✓ | Low |
| Tubulin | ✓ | ✓ | | ✓ | ✓ | ✓ | Low |
| Actin | ✓ | ✓ | ✓ | | ✓ | ✓ | Low |
| 14-3-3 | ✓ | | | | ✓ | ✓ | High |
| Glial fibrillary acidic protein | ✓ | | | | | | |
| Dickkopf | | ✓ | | | | | ?? |

FIG. 25

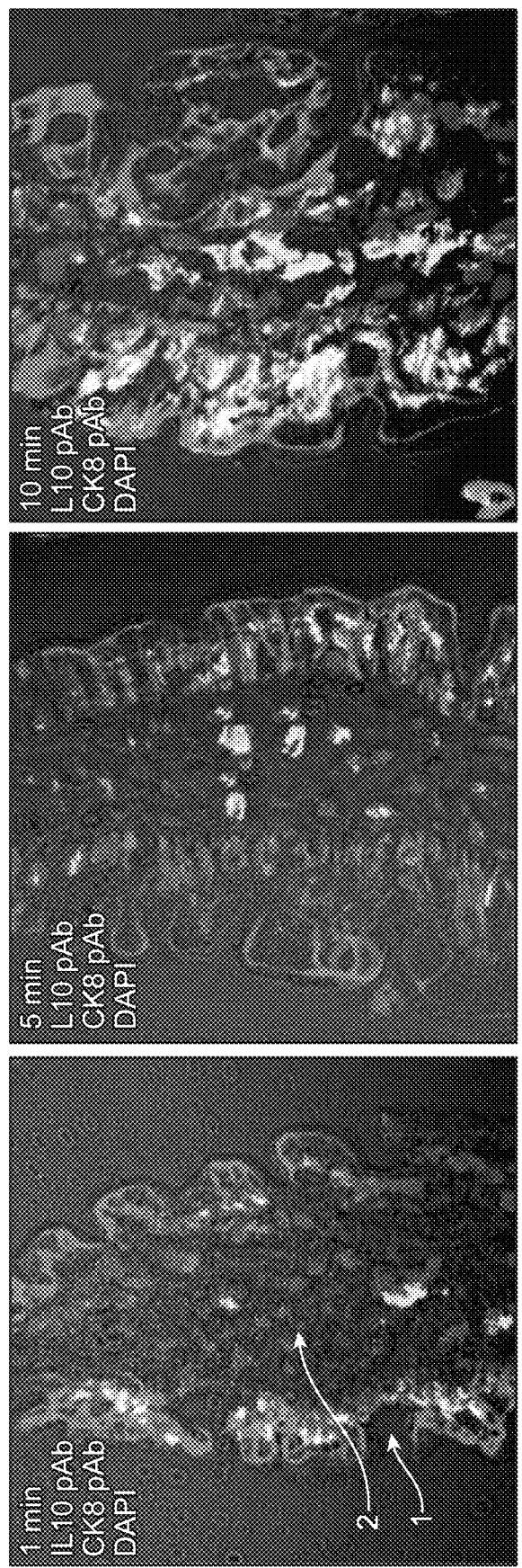

SEQUENCE LISTING

```
<160> NUMBER OF SEQ ID NOS: 221

<210> SEQ ID NO 1
<211> LENGTH: 634
<212> TYPE: PRT
<213> ORGANISM: Vibrio cholera

<400> SEQUENCE: 1

Val Glu Glu Ala Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
            20                  25                  30

Ser Asp Val Val Leu Asp Glu Gly Val Leu Tyr Tyr Ser Met Thr Ile
        35                  40                  45

Asn Asp Glu Gln Asn Asp Ile Lys Asp Glu Asp Lys Gly Glu Ser Ile
    50                  55                  60

Ile Thr Ile Gly Glu Phe Ala Thr Val Arg Ala Thr Arg His Tyr Val
65                  70                  75                  80

Asn Gln Asp Ala Pro Phe Gly Val Ile His Leu Asp Ile Thr Thr Glu
                85                  90                  95
```

-continued

```
Asn Gly Thr Lys Thr Tyr Ser Tyr Asn Arg Lys Glu Gly Glu Phe Ala
            100                 105                 110
Ile Asn Trp Leu Val Pro Ile Gly Glu Asp Ser Pro Ala Ser Ile Lys
            115                 120                 125
Ile Ser Val Asp Glu Leu Asp Gln Gln Arg Asn Ile Ile Glu Val Pro
130                 135                 140
Lys Leu Tyr Ser Ile Asp Leu Asp Asn Gln Thr Leu Glu Gln Trp Lys
145                 150                 155                 160
Thr Gln Gly Asn Val Ser Phe Ser Val Thr Arg Pro Glu His Asn Ile
            165                 170                 175
Ala Ile Ser Trp Pro Ser Val Ser Tyr Lys Ala Ala Gln Lys Glu Gly
            180                 185                 190
Ser Arg His Lys Arg Trp Ala His Trp His Thr Gly Leu Ala Leu Cys
            195                 200                 205
Trp Leu Val Pro Met Asp Ala Ile Tyr Asn Tyr Ile Thr Gln Gln Asn
            210                 215                 220
Cys Thr Leu Gly Asp Asn Trp Phe Gly Gly Ser Tyr Glu Thr Val Ala
225                 230                 235                 240
Gly Thr Pro Lys Val Ile Thr Val Lys Gln Gly Ile Glu Gln Lys Pro
            245                 250                 255
Val Glu Gln Arg Ile His Phe Ser Lys Gly Asn Ala Met Ser Ala Leu
            260                 265                 270
Ala Ala His Arg Val Cys Gly Val Pro Leu Glu Thr Leu Ala Arg Ser
            275                 280                 285
Arg Lys Pro Arg Asp Leu Thr Asp Asp Leu Ser Cys Ala Tyr Gln Ala
            290                 295                 300
Gln Asn Ile Val Ser Leu Phe Val Ala Thr Arg Ile Leu Phe Ser His
305                 310                 315                 320
Leu Asp Ser Val Phe Thr Leu Asn Leu Asp Glu Gln Glu Pro Glu Val
            325                 330                 335
Ala Glu Arg Leu Ser Asp Leu Arg Arg Ile Asn Glu Asn Asn Pro Gly
            340                 345                 350
Met Val Thr Gln Val Leu Thr Val Ala Arg Gln Ile Tyr Asn Asp Tyr
            355                 360                 365
Val Thr His His Pro Gly Leu Thr Pro Glu Gln Thr Ser Ala Gly Ala
370                 375                 380
Gln Ala Ala Asp Ile Leu Ser Leu Phe Cys Pro Asp Ala Asp Lys Ser
385                 390                 395                 400
Cys Val Ala Ser Asn Asn Asp Gln Ala Asn Ile Asn Ile Glu Ser Arg
            405                 410                 415
Ser Gly Arg Ser Tyr Leu Pro Gly Asn Arg Ala Val Ile Thr Pro Gln
            420                 425                 430
Gly Val Thr Asn Trp Thr Tyr Gln Glu Leu Glu Ala Thr His Gln Ala
            435                 440                 445
Leu Thr Arg Glu Gly Tyr Val Phe Val Gly Tyr His Gly Thr Asn His
            450                 455                 460
Val Ala Ala Gln Thr Ile Val Asn Arg Ile Ala Pro Val Pro Arg Gly
465                 470                 475                 480
Asn Asn Thr Glu Asn Glu Glu Lys Trp Gly Gly Leu Tyr Val Ala Thr
            485                 490                 495
His Ala Glu Val Ala His Gly Tyr Ala Arg Ile Lys Glu Gly Thr Gly
            500                 505                 510
```

```
Glu Tyr Gly Leu Pro Thr Arg Ala Glu Arg Asp Ala Arg Gly Val Met
            515                 520                 525

Leu Arg Val Tyr Ile Pro Arg Ala Ser Leu Glu Arg Phe Tyr Arg Thr
530                 535                 540

Asn Thr Pro Leu Glu Asn Ala Glu Glu His Ile Thr Gln Val Ile Gly
545                 550                 555                 560

His Ser Leu Pro Leu Arg Asn Glu Ala Phe Thr Gly Pro Glu Ser Ala
                565                 570                 575

Gly Gly Glu Asp Glu Thr Val Ile Gly Trp Asp Met Ala Ile His Ala
            580                 585                 590

Val Ala Ile Pro Ser Thr Ile Pro Gly Asn Ala Tyr Glu Glu Leu Ala
            595                 600                 605

Ile Asp Glu Glu Ala Val Ala Lys Glu Gln Ser Ile Ser Thr Lys Pro
610                 615                 620

Pro Tyr Lys Glu Arg Lys Asp Glu Leu Lys
625                 630

<210> SEQ ID NO 2
<211> LENGTH: 634
<212> TYPE: PRT
<213> ORGANISM: Vibrio cholera

<400> SEQUENCE: 2

Val Glu Asp Glu Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
            20                  25                  30

Ser Asp Val Val Leu Asp Glu Gly Val Leu Tyr Tyr Ser Met Thr Ile
        35                  40                  45

Asn Asp Glu Gln Asn Asp Ile Lys Asp Glu Asp Lys Gly Glu Ser Ile
50                  55                  60

Ile Thr Ile Gly Glu Phe Ala Thr Val Arg Ala Thr Arg His Tyr Val
65                  70                  75                  80

Asn Gln Asp Ala Pro Phe Gly Val Ile His Leu Asp Ile Thr Thr Glu
                85                  90                  95

Asn Gly Thr Lys Thr Tyr Ser Tyr Asn Arg Lys Glu Gly Glu Phe Ala
            100                 105                 110

Ile Asn Trp Leu Val Pro Ile Gly Glu Asp Ser Pro Ala Ser Ile Lys
        115                 120                 125

Ile Ser Val Asp Glu Leu Asp Gln Gln Arg Asn Ile Ile Glu Val Pro
130                 135                 140

Lys Leu Tyr Ser Ile Asp Leu Asp Asn Gln Thr Leu Glu Gln Trp Lys
145                 150                 155                 160

Thr Gln Gly Asn Val Ser Phe Ser Val Thr Arg Pro Glu His Asn Ile
                165                 170                 175

Ala Ile Ser Trp Pro Ser Val Ser Tyr Lys Ala Ala Gln Lys Glu Gly
            180                 185                 190

Ser Arg His Lys Arg Trp Ala His Trp His Thr Gly Leu Ala Leu Cys
        195                 200                 205

Trp Leu Val Pro Met Asp Ala Ile Tyr Asn Tyr Ile Thr Gln Gln Asn
210                 215                 220

Cys Thr Leu Gly Asp Asn Trp Phe Gly Ser Tyr Glu Thr Val Ala
225                 230                 235                 240

Gly Thr Pro Lys Val Ile Thr Val Lys Gln Gly Ile Glu Gln Lys Pro
                245                 250                 255
```

```
Val Glu Gln Arg Ile His Phe Ser Lys Gly Asn Ala Met Ser Ala Leu
            260                 265                 270

Ala Ala His Arg Val Cys Gly Val Pro Leu Glu Thr Leu Ala Arg Ser
        275                 280                 285

Arg Lys Pro Arg Asp Leu Thr Asp Asp Leu Ser Cys Ala Tyr Gln Ala
    290                 295                 300

Gln Asn Ile Val Ser Leu Phe Val Ala Thr Arg Ile Leu Phe Ser His
305                 310                 315                 320

Leu Asp Ser Val Phe Thr Leu Asn Leu Asp Glu Gln Glu Pro Glu Val
                325                 330                 335

Ala Glu Arg Leu Ser Asp Leu Arg Arg Ile Asn Glu Asn Asn Pro Gly
            340                 345                 350

Met Val Thr Gln Val Leu Thr Val Ala Arg Gln Ile Tyr Asn Asp Tyr
        355                 360                 365

Val Thr His His Pro Gly Leu Thr Pro Glu Gln Thr Ser Ala Gly Ala
    370                 375                 380

Gln Ala Ala Asp Ile Leu Ser Leu Phe Cys Pro Asp Ala Asp Lys Ser
385                 390                 395                 400

Cys Val Ala Ser Asn Asn Asp Gln Ala Asn Ile Asn Ile Glu Ser Arg
                405                 410                 415

Ser Gly Arg Ser Tyr Leu Pro Glu Asn Arg Ala Val Ile Thr Pro Gln
            420                 425                 430

Gly Val Thr Asn Trp Thr Tyr Gln Glu Leu Glu Ala Thr His Gln Ala
        435                 440                 445

Leu Thr Arg Glu Gly Tyr Val Phe Val Gly Tyr His Gly Thr Asn His
    450                 455                 460

Val Ala Ala Gln Thr Ile Val Asn Arg Ile Ala Pro Val Pro Arg Gly
465                 470                 475                 480

Asn Asn Thr Glu Asn Glu Glu Lys Trp Gly Gly Leu Tyr Val Ala Thr
                485                 490                 495

His Ala Glu Val Ala His Gly Tyr Ala Arg Ile Lys Glu Gly Thr Gly
            500                 505                 510

Glu Tyr Gly Leu Pro Thr Arg Ala Glu Arg Asp Ala Arg Gly Val Met
        515                 520                 525

Leu Arg Val Tyr Ile Pro Arg Ala Ser Leu Glu Arg Phe Tyr Arg Thr
    530                 535                 540

Asn Thr Pro Leu Glu Asn Ala Glu His Ile Thr Gln Val Ile Gly
545                 550                 555                 560

His Ser Leu Pro Leu Arg Asn Glu Ala Phe Thr Gly Pro Glu Ser Ala
                565                 570                 575

Gly Gly Glu Asp Glu Thr Val Ile Gly Trp Asp Met Ala Ile His Ala
            580                 585                 590

Val Ala Ile Pro Ser Thr Ile Pro Gly Asn Ala Tyr Glu Glu Leu Ala
        595                 600                 605

Ile Asp Glu Glu Ala Val Ala Lys Glu Gln Ser Ile Ser Thr Lys Pro
    610                 615                 620

Pro Tyr Lys Glu Arg Lys Asp Glu Leu Lys
625                 630

<210> SEQ ID NO 3
<211> LENGTH: 634
<212> TYPE: PRT
<213> ORGANISM: Vibrio cholera
```

```
<400> SEQUENCE: 3

Val Glu Asp Glu Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
            20                  25                  30

Ser Asp Val Val Leu Asp Glu Val Leu Tyr Tyr Ser Met Thr Ile
        35                  40                  45

Asn Asp Glu Gln Asn Asp Ile Lys Asp Glu Asp Lys Gly Glu Ser Ile
    50                  55                  60

Ile Thr Ile Gly Glu Phe Ala Thr Val Arg Ala Thr Arg His Tyr Val
65                  70                  75                  80

Asn Gln Asp Ala Pro Phe Gly Val Ile His Leu Asp Ile Thr Thr Glu
                85                  90                  95

Asn Gly Thr Lys Thr Tyr Ser Tyr Asn Arg Lys Glu Gly Glu Phe Ala
            100                 105                 110

Ile Asn Trp Leu Val Pro Ile Gly Glu Asp Ser Pro Ala Ser Ile Lys
        115                 120                 125

Ile Ser Val Asp Glu Leu Asp Gln Gln Arg Asn Ile Ile Glu Val Pro
    130                 135                 140

Lys Leu Tyr Ser Ile Asp Leu Asp Asn Gln Thr Leu Glu Gln Trp Lys
145                 150                 155                 160

Thr Gln Gly Asn Val Ser Phe Ser Val Thr Arg Pro Glu His Asn Ile
                165                 170                 175

Ala Ile Ser Trp Pro Ser Val Ser Tyr Lys Ala Ala Gln Lys Glu Gly
            180                 185                 190

Ser Arg His Lys Arg Trp Ala His Trp His Thr Gly Leu Ala Leu Cys
    195                 200                 205

Trp Leu Val Pro Met Asp Ala Ile Tyr Asn Tyr Ile Thr Gln Gln Asn
210                 215                 220

Cys Thr Leu Gly Asp Asn Trp Phe Gly Gly Ser Tyr Glu Thr Val Ala
225                 230                 235                 240

Gly Thr Pro Lys Val Ile Thr Val Lys Gln Gly Ile Glu Gln Lys Pro
                245                 250                 255

Val Glu Gln Arg Ile His Phe Ser Lys Gly Asn Ala Met Ser Ala Leu
            260                 265                 270

Ala Ala His Arg Val Cys Gly Val Pro Leu Glu Thr Leu Ala Arg Ser
    275                 280                 285

Arg Lys Pro Arg Asp Leu Thr Asp Asp Leu Ser Cys Ala Tyr Gln Ala
    290                 295                 300

Gln Asn Ile Val Ser Leu Phe Val Ala Thr Arg Ile Leu Phe Ser His
305                 310                 315                 320

Leu Asp Ser Val Phe Thr Leu Asn Leu Asp Glu Gln Glu Pro Glu Val
                325                 330                 335

Ala Glu Arg Leu Ser Asp Leu Arg Arg Ile Asn Glu Asn Asn Pro Gly
            340                 345                 350

Met Val Thr Gln Val Leu Thr Val Ala Arg Gln Ile Tyr Asn Asp Tyr
    355                 360                 365

Val Thr His His Pro Gly Leu Thr Pro Glu Gln Thr Ser Ala Gly Ala
    370                 375                 380

Gln Ala Ala Asp Ile Leu Ser Leu Phe Cys Pro Asp Ala Asp Lys Ser
385                 390                 395                 400

Cys Val Ala Ser Asn Asn Asp Gln Ala Asn Ile Asn Ile Glu Ser Arg
                405                 410                 415
```

```
Ser Gly Arg Ser Tyr Leu Pro Glu Asn Arg Ala Val Ile Thr Pro Gln
            420                 425                 430

Gly Val Thr Asn Trp Thr Tyr Gln Glu Leu Glu Ala Thr His Gln Ala
            435                 440                 445

Leu Thr Arg Glu Gly Tyr Val Phe Val Gly Tyr His Gly Thr Asn His
450                 455                 460

Val Ala Ala Gln Thr Ile Val Asn Arg Ile Ala Pro Val Pro Arg Gly
465                 470                 475                 480

Asn Asn Thr Glu Asn Glu Glu Lys Trp Gly Gly Leu Tyr Val Ala Thr
                485                 490                 495

His Ala Glu Val Ala His Gly Tyr Ala Arg Ile Lys Glu Gly Thr Gly
            500                 505                 510

Glu Tyr Gly Leu Pro Thr Arg Ala Glu Arg Asp Ala Arg Gly Val Met
            515                 520                 525

Leu Arg Val Tyr Ile Pro Arg Ala Ser Leu Glu Arg Phe Tyr Arg Thr
530                 535                 540

Asn Thr Pro Leu Glu Asn Ala Glu His Ile Thr Gln Val Ile Gly
545                 550                 555                 560

His Ser Leu Pro Leu Arg Asn Glu Ala Phe Thr Gly Pro Glu Ser Ala
                565                 570                 575

Gly Gly Glu Asp Ala Thr Val Ile Gly Trp Asp Met Ala Ile His Ala
            580                 585                 590

Val Ala Ile Pro Ser Thr Ile Pro Gly Asn Ala Tyr Glu Glu Leu Ala
            595                 600                 605

Ile Asp Glu Glu Ala Val Ala Lys Glu Gln Ser Ile Ser Thr Lys Pro
610                 615                 620

Pro Tyr Lys Glu Arg Lys Asp Glu Leu Lys
625                 630

<210> SEQ ID NO 4
<211> LENGTH: 265
<212> TYPE: PRT
<213> ORGANISM: Vibrio cholera

<400> SEQUENCE: 4

Val Glu Glu Ala Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
            20                  25                  30

Ser Asp Val Val Leu Asp Glu Gly Val Leu Tyr Tyr Ser Met Thr Ile
            35                  40                  45

Asn Asp Glu Gln Asn Asp Ile Lys Asp Glu Asp Lys Gly Glu Ser Ile
50                  55                  60

Ile Thr Ile Gly Glu Phe Ala Thr Val Arg Ala Thr Arg His Tyr Val
65                  70                  75                  80

Asn Gln Asp Ala Pro Phe Gly Val Ile His Leu Asp Ile Thr Thr Glu
            85                  90                  95

Asn Gly Thr Lys Thr Tyr Ser Tyr Asn Arg Lys Glu Gly Glu Phe Ala
            100                 105                 110

Ile Asn Trp Leu Val Pro Ile Gly Glu Asp Ser Pro Ala Ser Ile Lys
        115                 120                 125

Ile Ser Val Asp Glu Leu Asp Gln Gln Arg Asn Ile Ile Glu Val Pro
130                 135                 140
```

```
Lys Leu Tyr Ser Ile Asp Leu Asp Asn Gln Thr Leu Glu Gln Trp Lys
145                 150                 155                 160

Thr Gln Gly Asn Val Ser Phe Ser Val Thr Arg Pro Glu His Asn Ile
                165                 170                 175

Ala Ile Ser Trp Pro Ser Val Ser Tyr Lys Ala Ala Gln Lys Glu Gly
            180                 185                 190

Ser Arg His Lys Arg Trp Ala His Trp His Thr Gly Leu Ala Leu Cys
        195                 200                 205

Trp Leu Val Pro Met Asp Ala Ile Tyr Asn Tyr Ile Thr Gln Gln Asn
    210                 215                 220

Cys Thr Leu Gly Asp Asn Trp Phe Gly Gly Ser Tyr Glu Thr Val Ala
225                 230                 235                 240

Gly Thr Pro Lys Val Ile Thr Val Lys Gln Gly Ile Glu Gln Lys Pro
                245                 250                 255

Val Glu Gln Arg Ile His Phe Ser Lys
                260                 265

<210> SEQ ID NO 5
<211> LENGTH: 266
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 5

Met Val Glu Glu Ala Leu Asn Ile Phe Asp Glu Cys Arg Ser Pro Cys
1               5                   10                  15

Ser Leu Thr Pro Glu Pro Gly Lys Pro Ile Gln Ser Lys Leu Ser Ile
                20                  25                  30

Pro Ser Asp Val Val Leu Asp Glu Gly Val Leu Tyr Tyr Ser Met Thr
            35                  40                  45

Ile Asn Asp Glu Gln Asn Asp Ile Lys Asp Glu Asp Lys Gly Glu Ser
50                  55                  60

Ile Ile Thr Ile Gly Glu Phe Ala Thr Val Arg Ala Thr Arg His Tyr
65                  70                  75                  80

Val Asn Gln Asp Ala Pro Phe Gly Val Ile His Leu Asp Ile Thr Thr
                85                  90                  95

Glu Asn Gly Thr Lys Thr Tyr Ser Tyr Asn Arg Lys Glu Gly Glu Phe
                100                 105                 110

Ala Ile Asn Trp Leu Val Pro Ile Gly Glu Asp Ser Pro Ala Ser Ile
            115                 120                 125

Lys Ile Ser Val Asp Glu Leu Asp Gln Gln Arg Asn Ile Ile Glu Val
130                 135                 140

Pro Lys Leu Tyr Ser Ile Asp Leu Asp Asn Gln Thr Leu Glu Gln Trp
145                 150                 155                 160

Lys Thr Gln Gly Asn Val Ser Phe Ser Val Thr Arg Pro Glu His Asn
                165                 170                 175

Ile Ala Ile Ser Trp Pro Ser Val Ser Tyr Lys Ala Ala Gln Lys Glu
            180                 185                 190

Gly Ser Arg His Lys Arg Trp Ala His Trp His Thr Gly Leu Ala Leu
        195                 200                 205

Cys Trp Leu Val Pro Met Asp Ala Ile Tyr Asn Tyr Ile Thr Gln Gln
    210                 215                 220
```

```
Asn Cys Thr Leu Gly Asp Asn Trp Phe Gly Gly Ser Tyr Glu Thr Val
225                 230                 235                 240

Ala Gly Thr Pro Lys Val Ile Thr Val Lys Gln Gly Ile Glu Gln Lys
                245                 250                 255

Pro Val Glu Gln Arg Ile His Phe Ser Lys
            260                 265

<210> SEQ ID NO 6
<211> LENGTH: 250
<212> TYPE: PRT
<213> ORGANISM: Vibrio cholera

<400> SEQUENCE: 6

Val Glu Glu Ala Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
            20                  25                  30

Ser Asp Val Val Leu Asp Glu Gly Val Leu Tyr Tyr Ser Met Thr Ile
        35                  40                  45

Asn Asp Glu Gln Asn Asp Ile Lys Asp Glu Asp Lys Gly Glu Ser Ile
    50                  55                  60

Ile Thr Ile Gly Glu Phe Ala Thr Val Arg Ala Thr Arg His Tyr Val
65                  70                  75                  80

Asn Gln Asp Ala Pro Phe Gly Val Ile His Leu Asp Ile Thr Thr Glu
                85                  90                  95

Asn Gly Thr Lys Thr Tyr Ser Tyr Asn Arg Lys Glu Gly Glu Phe Ala
            100                 105                 110

Ile Asn Trp Leu Val Pro Ile Gly Glu Asp Ser Pro Ala Ser Ile Lys
        115                 120                 125

Ile Ser Val Asp Glu Leu Asp Gln Gln Arg Asn Ile Ile Glu Val Pro
    130                 135                 140

Lys Leu Tyr Ser Ile Asp Leu Asp Asn Gln Thr Leu Glu Gln Trp Lys
145                 150                 155                 160

Thr Gln Gly Asn Val Ser Phe Ser Val Thr Arg Pro Glu His Asn Ile
                165                 170                 175

Ala Ile Ser Trp Pro Ser Val Ser Tyr Lys Ala Ala Gln Lys Glu Gly
            180                 185                 190

Ser Arg His Lys Arg Trp Ala His Trp His Thr Gly Leu Ala Leu Cys
        195                 200                 205

Trp Leu Val Pro Met Asp Ala Ile Tyr Asn Tyr Ile Thr Gln Gln Asn
    210                 215                 220

Cys Thr Leu Gly Asp Asn Trp Phe Gly Gly Ser Tyr Glu Thr Val Ala
225                 230                 235                 240

Gly Thr Pro Lys Val Ile Thr Val Lys Gln
                245                 250

<210> SEQ ID NO 7
<211> LENGTH: 251
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 7

Met Val Glu Glu Ala Leu Asn Ile Phe Asp Glu Cys Arg Ser Pro Cys
1               5                   10                  15
```

Ser Leu Thr Pro Glu Pro Gly Lys Pro Ile Gln Ser Lys Leu Ser Ile
            20                  25                  30

Pro Ser Asp Val Val Leu Asp Glu Gly Val Leu Tyr Tyr Ser Met Thr
        35                  40                  45

Ile Asn Asp Glu Gln Asn Asp Ile Lys Asp Glu Asp Lys Gly Glu Ser
65                  55                  60

Ile Ile Thr Ile Gly Glu Phe Ala Thr Val Arg Ala Thr Arg His Tyr
65                  70                  75                  80

Val Asn Gln Asp Ala Pro Phe Gly Val Ile His Leu Asp Ile Thr Thr
                85                  90                  95

Glu Asn Gly Thr Lys Thr Tyr Ser Tyr Asn Arg Lys Glu Gly Glu Phe
            100                 105                 110

Ala Ile Asn Trp Leu Val Pro Ile Gly Glu Asp Ser Pro Ala Ser Ile
            115                 120                 125

Lys Ile Ser Val Asp Glu Leu Asp Gln Gln Arg Asn Ile Ile Glu Val
130                 135                 140

Pro Lys Leu Tyr Ser Ile Asp Leu Asp Asn Gln Thr Leu Glu Gln Trp
145                 150                 155                 160

Lys Thr Gln Gly Asn Val Ser Phe Ser Val Thr Arg Pro Glu His Asn
            165                 170                 175

Ile Ala Ile Ser Trp Pro Ser Val Ser Tyr Lys Ala Ala Gln Lys Glu
            180                 185                 190

Gly Ser Arg His Lys Arg Trp Ala His Trp His Thr Gly Leu Ala Leu
            195                 200                 205

Cys Trp Leu Val Pro Met Asp Ala Ile Tyr Asn Tyr Ile Thr Gln Gln
210                 215                 220

Asn Cys Thr Leu Gly Asp Asn Trp Phe Gly Gly Ser Tyr Glu Thr Val
225                 230                 235                 240

Ala Gly Thr Pro Lys Val Ile Thr Val Lys Gln
            245                 250

<210> SEQ ID NO 8
<211> LENGTH: 244
<212> TYPE: PRT
<213> ORGANISM: Vibrio cholera

<400> SEQUENCE: 8

Val Glu Glu Ala Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
            20                  25                  30

Ser Asp Val Val Leu Asp Glu Gly Val Leu Tyr Tyr Ser Met Thr Ile
        35                  40                  45

Asn Asp Glu Gln Asn Asp Ile Lys Asp Glu Asp Lys Gly Glu Ser Ile
    50                  55                  60

Ile Thr Ile Gly Glu Phe Ala Thr Val Arg Ala Thr Arg His Tyr Val
65                  70                  75                  80

Asn Gln Asp Ala Pro Phe Gly Val Ile His Leu Asp Ile Thr Thr Glu
                85                  90                  95

Asn Gly Thr Lys Thr Tyr Ser Tyr Asn Arg Lys Glu Gly Glu Phe Ala
            100                 105                 110

Ile Asn Trp Leu Val Pro Ile Gly Glu Asp Ser Pro Ala Ser Ile Lys
            115                 120                 125

Ile Ser Val Asp Glu Leu Asp Gln Gln Arg Asn Ile Ile Glu Val Pro
130                 135                 140

Lys Leu Tyr Ser Ile Asp Leu Asp Asn Gln Thr Leu Glu Gln Trp Lys
145                 150                 155                 160

Thr Gln Gly Asn Val Ser Phe Ser Val Thr Arg Pro Glu His Asn Ile
            165                 170                 175

Ala Ile Ser Trp Pro Ser Val Ser Tyr Lys Ala Ala Gln Lys Glu Gly
            180                 185                 190

Ser Arg His Lys Arg Trp Ala His Trp His Thr Gly Leu Ala Leu Cys
        195                 200                 205

Trp Leu Val Pro Met Asp Ala Ile Tyr Asn Tyr Ile Thr Gln Gln Asn
210                 215                 220

Cys Thr Leu Gly Asp Asn Trp Phe Gly Gly Ser Tyr Glu Thr Val Ala
225                 230                 235                 240

Gly Thr Pro Lys

<210> SEQ ID NO 9
<211> LENGTH: 245
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 9

Met Val Glu Glu Ala Leu Asn Ile Phe Asp Glu Cys Arg Ser Pro Cys
1               5                   10                  15

Ser Leu Thr Pro Glu Pro Gly Lys Pro Ile Gln Ser Lys Leu Ser Ile
            20                  25                  30

Pro Ser Asp Val Val Leu Asp Glu Gly Val Leu Tyr Tyr Ser Met Thr
        35                  40                  45

Ile Asn Asp Glu Gln Asn Asp Ile Lys Asp Glu Asp Lys Gly Glu Ser
50                  55                  60

Ile Ile Thr Ile Gly Glu Phe Ala Thr Val Arg Ala Thr Arg His Tyr
65                  70                  75                  80

Val Asn Gln Asp Ala Pro Phe Gly Val Ile His Leu Asp Ile Thr Thr
                85                  90                  95

Glu Asn Gly Thr Lys Thr Tyr Ser Tyr Asn Arg Lys Glu Gly Glu Phe
            100                 105                 110

Ala Ile Asn Trp Leu Val Pro Ile Gly Glu Asp Ser Pro Ala Ser Ile
        115                 120                 125

Lys Ile Ser Val Asp Glu Leu Asp Gln Gln Arg Asn Ile Ile Glu Val
    130                 135                 140

Pro Lys Leu Tyr Ser Ile Asp Leu Asp Asn Gln Thr Leu Glu Gln Trp
145                 150                 155                 160

Lys Thr Gln Gly Asn Val Ser Phe Ser Val Thr Arg Pro Glu His Asn
                165                 170                 175

Ile Ala Ile Ser Trp Pro Ser Val Ser Tyr Lys Ala Ala Gln Lys Glu
            180                 185                 190

Gly Ser Arg His Lys Arg Trp Ala His Trp His Thr Gly Leu Ala Leu
        195                 200                 205

Cys Trp Leu Val Pro Met Asp Ala Ile Tyr Asn Tyr Ile Thr Gln Gln
    210                 215                 220

-continued

```
Asn Cys Thr Leu Gly Asp Asn Trp Phe Gly Gly Ser Tyr Glu Thr Val
225                 230                 235                 240

Ala Gly Thr Pro Lys
                245

<210> SEQ ID NO 10
<211> LENGTH: 205
<212> TYPE: PRT
<213> ORGANISM: Vibrio cholera

<400> SEQUENCE: 10

Val Glu Glu Ala Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
                20                  25                  30

Ser Asp Val Val Leu Asp Glu Gly Val Leu Tyr Tyr Ser Met Thr Ile
            35                  40                  45

Asn Asp Glu Gln Asn Asp Ile Lys Asp Glu Asp Lys Gly Glu Ser Ile
        50                  55                  60

Ile Thr Ile Gly Glu Phe Ala Thr Val Arg Ala Thr Arg His Tyr Val
65                  70                  75                  80

Asn Gln Asp Ala Pro Phe Gly Val Ile His Leu Asp Ile Thr Thr Glu
                85                  90                  95

Asn Gly Thr Lys Thr Tyr Ser Tyr Asn Arg Lys Glu Gly Glu Phe Ala
            100                 105                 110

Ile Asn Trp Leu Val Pro Ile Gly Glu Asp Ser Pro Ala Ser Ile Lys
        115                 120                 125

Ile Ser Val Asp Glu Leu Asp Gln Gln Arg Asn Ile Ile Glu Val Pro
130                 135                 140

Lys Leu Tyr Ser Ile Asp Leu Asp Asn Gln Thr Leu Glu Gln Trp Lys
145                 150                 155                 160

Thr Gln Gly Asn Val Ser Phe Ser Val Thr Arg Pro Glu His Asn Ile
                165                 170                 175

Ala Ile Ser Trp Pro Ser Val Ser Tyr Lys Ala Ala Gln Lys Glu Gly
            180                 185                 190

Ser Arg His Lys Arg Trp Ala His Trp His Thr Gly Leu
        195                 200                 205

<210> SEQ ID NO 11
<211> LENGTH: 206
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 11

Met Val Glu Glu Ala Leu Asn Ile Phe Asp Glu Cys Arg Ser Pro Cys
1               5                   10                  15

Ser Leu Thr Pro Glu Pro Gly Lys Pro Ile Gln Ser Lys Leu Ser Ile
                20                  25                  30

Pro Ser Asp Val Val Leu Asp Glu Gly Val Leu Tyr Tyr Ser Met Thr
            35                  40                  45

Ile Asn Asp Glu Gln Asn Asp Ile Lys Asp Glu Asp Lys Gly Glu Ser
        50                  55                  60
```

-continued

```
Ile Ile Thr Ile Gly Glu Phe Ala Thr Val Arg Ala Thr Arg His Tyr
 65                  70                  75                  80

Val Asn Gln Asp Ala Pro Phe Gly Val Ile His Leu Asp Ile Thr Thr
                 85                  90                  95

Glu Asn Gly Thr Lys Thr Tyr Ser Tyr Asn Arg Lys Glu Gly Glu Phe
            100                 105                 110

Ala Ile Asn Trp Leu Val Pro Ile Gly Glu Asp Ser Pro Ala Ser Ile
        115                 120                 125

Lys Ile Ser Val Asp Glu Leu Asp Gln Gln Arg Asn Ile Ile Glu Val
130                 135                 140

Pro Lys Leu Tyr Ser Ile Asp Leu Asp Asn Gln Thr Leu Glu Gln Trp
145                 150                 155                 160

Lys Thr Gln Gly Asn Val Ser Phe Ser Val Thr Arg Pro Glu His Asn
                165                 170                 175

Ile Ala Ile Ser Trp Pro Ser Val Ser Tyr Lys Ala Ala Gln Lys Glu
            180                 185                 190

Gly Ser Arg His Lys Arg Trp Ala His Trp His Thr Gly Leu
        195                 200                 205
```

<210> SEQ ID NO 12
<211> LENGTH: 204
<212> TYPE: PRT
<213> ORGANISM: Vibrio cholera

<400> SEQUENCE: 12

```
Val Glu Glu Ala Leu Asn Ile Phe Asp Glu Cys Arg Ser Pro Cys Ser
 1               5                  10                  15

Leu Thr Pro Glu Pro Gly Lys Pro Ile Gln Ser Lys Leu Ser Ile Pro
                20                  25                  30

Ser Asp Val Val Leu Asp Glu Gly Val Leu Tyr Tyr Ser Met Thr Ile
            35                  40                  45

Asn Asp Glu Gln Asn Asp Ile Lys Asp Glu Asp Lys Gly Glu Ser Ile
        50                  55                  60

Ile Thr Ile Gly Glu Phe Ala Thr Val Arg Ala Thr Arg His Tyr Val
 65                  70                  75                  80

Asn Gln Asp Ala Pro Phe Gly Val Ile His Leu Asp Ile Thr Thr Glu
                 85                  90                  95

Asn Gly Thr Lys Thr Tyr Ser Tyr Asn Arg Lys Glu Gly Glu Phe Ala
            100                 105                 110

Ile Asn Trp Leu Val Pro Ile Gly Glu Asp Ser Pro Ala Ser Ile Lys
        115                 120                 125

Ile Ser Val Asp Glu Leu Asp Gln Gln Arg Asn Ile Ile Glu Val Pro
130                 135                 140

Lys Leu Tyr Ser Ile Asp Leu Asp Asn Gln Thr Leu Glu Gln Trp Lys
145                 150                 155                 160

Thr Gln Gly Asn Val Ser Phe Ser Val Thr Arg Pro Glu His Asn Ile
                165                 170                 175

Ala Ile Ser Trp Pro Ser Val Ser Tyr Lys Ala Ala Gln Lys Glu Gly
            180                 185                 190

Ser Arg His Lys Arg Trp Ala His Trp His Thr Gly
        195                 200
```

<210> SEQ ID NO 13
<211> LENGTH: 203
<212> TYPE: PRT

<213> ORGANISM: Vibrio cholera

<400> SEQUENCE: 13

Val Glu Glu Ala Leu Asn Ile Phe Asp Glu Cys Arg Ser Pro Cys Ser
1 5 10 15

Leu Thr Pro Glu Pro Gly Lys Pro Ile Gln Ser Lys Leu Ser Ile Pro
20 25 30

Ser Asp Val Val Leu Asp Glu Gly Val Leu Tyr Tyr Ser Met Thr Ile
35 40 45

Asn Asp Glu Gln Asn Asp Ile Lys Asp Glu Asp Lys Gly Glu Ser Ile
50 55 60

Ile Thr Ile Gly Glu Phe Ala Thr Val Arg Ala Thr Arg His Tyr Val
65 70 75 80

Asn Gln Asp Ala Pro Phe Gly Val Ile His Leu Asp Ile Thr Thr Glu
85 90 95

Asn Gly Thr Lys Thr Tyr Ser Tyr Asn Arg Lys Glu Gly Glu Phe Ala
100 105 110

Ile Asn Trp Leu Val Pro Ile Gly Glu Asp Ser Pro Ala Ser Ile Lys
115 120 125

Ile Ser Val Asp Glu Leu Asp Gln Gln Arg Asn Ile Ile Glu Val Pro
130 135 140

Lys Leu Tyr Ser Ile Asp Leu Asp Asn Gln Thr Leu Glu Gln Trp Lys
145 150 155 160

Thr Gln Gly Asn Val Ser Phe Ser Val Thr Arg Pro Glu His Asn Ile
165 170 175

Ala Ile Ser Trp Pro Ser Val Ser Tyr Lys Ala Ala Gln Lys Glu Gly
180 185 190

Ser Arg His Lys Arg Trp Ala His Trp His Thr
195 200

<210> SEQ ID NO 14
<211> LENGTH: 202
<212> TYPE: PRT
<213> ORGANISM: Vibrio cholera

<400> SEQUENCE: 14

Val Glu Glu Ala Leu Asn Ile Phe Asp Glu Cys Arg Ser Pro Cys Ser
1 5 10 15

Leu Thr Pro Glu Pro Gly Lys Pro Ile Gln Ser Lys Leu Ser Ile Pro
20 25 30

Ser Asp Val Val Leu Asp Glu Gly Val Leu Tyr Tyr Ser Met Thr Ile
35 40 45

Asn Asp Glu Gln Asn Asp Ile Lys Asp Glu Asp Lys Gly Glu Ser Ile
50 55 60

Ile Thr Ile Gly Glu Phe Ala Thr Val Arg Ala Thr Arg His Tyr Val
65 70 75 80

Asn Gln Asp Ala Pro Phe Gly Val Ile His Leu Asp Ile Thr Thr Glu
85 90 95

Asn Gly Thr Lys Thr Tyr Ser Tyr Asn Arg Lys Glu Gly Glu Phe Ala
100 105 110

Ile Asn Trp Leu Val Pro Ile Gly Glu Asp Ser Pro Ala Ser Ile Lys
115 120 125

Ile Ser Val Asp Glu Leu Asp Gln Gln Arg Asn Ile Ile Glu Val Pro
130 135 140

Lys Leu Tyr Ser Ile Asp Leu Asp Asn Gln Thr Leu Glu Gln Trp Lys
145                 150                 155                 160

Thr Gln Gly Asn Val Ser Phe Ser Val Thr Arg Pro Glu His Asn Ile
            165                 170                 175

Ala Ile Ser Trp Pro Ser Val Ser Tyr Lys Ala Ala Gln Lys Glu Gly
            180                 185                 190

Ser Arg His Lys Arg Trp Ala His Trp His
        195                 200

<210> SEQ ID NO 15
<211> LENGTH: 201
<212> TYPE: PRT
<213> ORGANISM: Vibrio cholera

<400> SEQUENCE: 15

Val Glu Glu Ala Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
            20                  25                  30

Ser Asp Val Val Leu Asp Glu Gly Val Leu Tyr Tyr Ser Met Thr Ile
        35                  40                  45

Asn Asp Glu Gln Asn Asp Ile Lys Asp Glu Asp Lys Gly Glu Ser Ile
    50                  55                  60

Ile Thr Ile Gly Glu Phe Ala Thr Val Arg Ala Thr Arg His Tyr Val
65                  70                  75                  80

Asn Gln Asp Ala Pro Phe Gly Val Ile His Leu Asp Ile Thr Thr Glu
                85                  90                  95

Asn Gly Thr Lys Thr Tyr Ser Tyr Asn Arg Lys Glu Gly Glu Phe Ala
            100                 105                 110

Ile Asn Trp Leu Val Pro Ile Gly Glu Asp Ser Pro Ala Ser Ile Lys
        115                 120                 125

Ile Ser Val Asp Glu Leu Asp Gln Gln Arg Asn Ile Ile Glu Val Pro
    130                 135                 140

Lys Leu Tyr Ser Ile Asp Leu Asp Asn Gln Thr Leu Glu Gln Trp Lys
145                 150                 155                 160

Thr Gln Gly Asn Val Ser Phe Ser Val Thr Arg Pro Glu His Asn Ile
            165                 170                 175

Ala Ile Ser Trp Pro Ser Val Ser Tyr Lys Ala Ala Gln Lys Glu Gly
            180                 185                 190

Ser Arg His Lys Arg Trp Ala His Trp
        195                 200

<210> SEQ ID NO 16
<211> LENGTH: 200
<212> TYPE: PRT
<213> ORGANISM: Vibrio cholera

<400> SEQUENCE: 16

Val Glu Glu Ala Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
            20                  25                  30

Ser Asp Val Val Leu Asp Glu Gly Val Leu Tyr Tyr Ser Met Thr Ile
        35                  40                  45

Asn Asp Glu Gln Asn Asp Ile Lys Asp Glu Asp Lys Gly Glu Ser Ile
    50                  55                  60

```
Ile Thr Ile Gly Glu Phe Ala Thr Val Arg Ala Thr Arg His Tyr Val
 65                  70                  75                  80

Asn Gln Asp Ala Pro Phe Gly Val Ile His Leu Asp Ile Thr Thr Glu
                 85                  90                  95

Asn Gly Thr Lys Thr Tyr Ser Tyr Asn Arg Lys Glu Gly Glu Phe Ala
            100                 105                 110

Ile Asn Trp Leu Val Pro Ile Gly Glu Asp Ser Pro Ala Ser Ile Lys
            115                 120                 125

Ile Ser Val Asp Glu Leu Asp Gln Gln Arg Asn Ile Ile Glu Val Pro
130                 135                 140

Lys Leu Tyr Ser Ile Asp Leu Asp Asn Gln Thr Leu Glu Gln Trp Lys
145                 150                 155                 160

Thr Gln Gly Asn Val Ser Phe Ser Val Thr Arg Pro Glu His Asn Ile
                165                 170                 175

Ala Ile Ser Trp Pro Ser Val Ser Tyr Lys Ala Ala Gln Lys Glu Gly
            180                 185                 190

Ser Arg His Lys Arg Trp Ala His
            195                 200

<210> SEQ ID NO 17
<211> LENGTH: 199
<212> TYPE: PRT
<213> ORGANISM: Vibrio cholera

<400> SEQUENCE: 17

Val Glu Glu Ala Leu Asn Ile Phe Asp Glu Cys Arg Ser Pro Cys Ser
  1               5                  10                  15

Leu Thr Pro Glu Pro Gly Lys Pro Ile Gln Ser Lys Leu Ser Ile Pro
                 20                  25                  30

Ser Asp Val Val Leu Asp Glu Gly Val Leu Tyr Tyr Ser Met Thr Ile
             35                  40                  45

Asn Asp Glu Gln Asn Asp Ile Lys Asp Glu Asp Lys Gly Glu Ser Ile
         50                  55                  60

Ile Thr Ile Gly Glu Phe Ala Thr Val Arg Ala Thr Arg His Tyr Val
 65                  70                  75                  80

Asn Gln Asp Ala Pro Phe Gly Val Ile His Leu Asp Ile Thr Thr Glu
                 85                  90                  95

Asn Gly Thr Lys Thr Tyr Ser Tyr Asn Arg Lys Glu Gly Glu Phe Ala
            100                 105                 110

Ile Asn Trp Leu Val Pro Ile Gly Glu Asp Ser Pro Ala Ser Ile Lys
            115                 120                 125

Ile Ser Val Asp Glu Leu Asp Gln Gln Arg Asn Ile Ile Glu Val Pro
130                 135                 140

Lys Leu Tyr Ser Ile Asp Leu Asp Asn Gln Thr Leu Glu Gln Trp Lys
145                 150                 155                 160

Thr Gln Gly Asn Val Ser Phe Ser Val Thr Arg Pro Glu His Asn Ile
                165                 170                 175

Ala Ile Ser Trp Pro Ser Val Ser Tyr Lys Ala Ala Gln Lys Glu Gly
            180                 185                 190

Ser Arg His Lys Arg Trp Ala
            195

<210> SEQ ID NO 18
<211> LENGTH: 198
<212> TYPE: PRT
```

<213> ORGANISM: Vibrio cholera

<400> SEQUENCE: 18

Val Glu Glu Ala Leu Asn Ile Phe Asp Glu Cys Arg Ser Pro Cys Ser
1 5 10 15

Leu Thr Pro Glu Pro Gly Lys Pro Ile Gln Ser Lys Leu Ser Ile Pro
20 25 30

Ser Asp Val Val Leu Asp Glu Gly Val Leu Tyr Tyr Ser Met Thr Ile
35 40 45

Asn Asp Glu Gln Asn Asp Ile Lys Asp Glu Asp Lys Gly Glu Ser Ile
50 55 60

Ile Thr Ile Gly Glu Phe Ala Thr Val Arg Ala Thr Arg His Tyr Val
65 70 75 80

Asn Gln Asp Ala Pro Phe Gly Val Ile His Leu Asp Ile Thr Thr Glu
85 90 95

Asn Gly Thr Lys Thr Tyr Ser Tyr Asn Arg Lys Glu Gly Glu Phe Ala
100 105 110

Ile Asn Trp Leu Val Pro Ile Gly Glu Asp Ser Pro Ala Ser Ile Lys
115 120 125

Ile Ser Val Asp Glu Leu Asp Gln Gln Arg Asn Ile Ile Glu Val Pro
130 135 140

Lys Leu Tyr Ser Ile Asp Leu Asp Asn Gln Thr Leu Glu Gln Trp Lys
145 150 155 160

Thr Gln Gly Asn Val Ser Phe Ser Val Thr Arg Pro Glu His Asn Ile
165 170 175

Ala Ile Ser Trp Pro Ser Val Ser Tyr Lys Ala Ala Gln Lys Glu Gly
180 185 190

Ser Arg His Lys Arg Trp
195

<210> SEQ ID NO 19
<211> LENGTH: 197
<212> TYPE: PRT
<213> ORGANISM: Vibrio cholera

<400> SEQUENCE: 19

Val Glu Glu Ala Leu Asn Ile Phe Asp Glu Cys Arg Ser Pro Cys Ser
1 5 10 15

Leu Thr Pro Glu Pro Gly Lys Pro Ile Gln Ser Lys Leu Ser Ile Pro
20 25 30

Ser Asp Val Val Leu Asp Glu Gly Val Leu Tyr Tyr Ser Met Thr Ile
35 40 45

Asn Asp Glu Gln Asn Asp Ile Lys Asp Glu Asp Lys Gly Glu Ser Ile
50 55 60

Ile Thr Ile Gly Glu Phe Ala Thr Val Arg Ala Thr Arg His Tyr Val
65 70 75 80

Asn Gln Asp Ala Pro Phe Gly Val Ile His Leu Asp Ile Thr Thr Glu
85 90 95

Asn Gly Thr Lys Thr Tyr Ser Tyr Asn Arg Lys Glu Gly Glu Phe Ala
100 105 110

Ile Asn Trp Leu Val Pro Ile Gly Glu Asp Ser Pro Ala Ser Ile Lys
115 120 125

Ile Ser Val Asp Glu Leu Asp Gln Gln Arg Asn Ile Ile Glu Val Pro
130 135 140

-continued

Lys Leu Tyr Ser Ile Asp Leu Asp Asn Gln Thr Leu Glu Gln Trp Lys
145                 150                 155                 160

Thr Gln Gly Asn Val Ser Phe Ser Val Thr Arg Pro Glu His Asn Ile
                165                 170                 175

Ala Ile Ser Trp Pro Ser Val Ser Tyr Lys Ala Ala Gln Lys Glu Gly
            180                 185                 190

Ser Arg His Lys Arg
        195

<210> SEQ ID NO 20
<211> LENGTH: 196
<212> TYPE: PRT
<213> ORGANISM: Vibrio cholera

<400> SEQUENCE: 20

Val Glu Glu Ala Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
                20                  25                  30

Ser Asp Val Val Leu Asp Glu Gly Val Leu Tyr Tyr Ser Met Thr Ile
            35                  40                  45

Asn Asp Glu Gln Asn Asp Ile Lys Asp Glu Asp Lys Gly Glu Ser Ile
50                  55                  60

Ile Thr Ile Gly Glu Phe Ala Thr Val Arg Ala Thr Arg His Tyr Val
65                  70                  75                  80

Asn Gln Asp Ala Pro Phe Gly Val Ile His Leu Asp Ile Thr Thr Glu
                85                  90                  95

Asn Gly Thr Lys Thr Tyr Ser Tyr Asn Arg Lys Glu Gly Glu Phe Ala
            100                 105                 110

Ile Asn Trp Leu Val Pro Ile Gly Glu Asp Ser Pro Ala Ser Ile Lys
        115                 120                 125

Ile Ser Val Asp Glu Leu Asp Gln Gln Arg Asn Ile Ile Glu Val Pro
    130                 135                 140

Lys Leu Tyr Ser Ile Asp Leu Asp Asn Gln Thr Leu Glu Gln Trp Lys
145                 150                 155                 160

Thr Gln Gly Asn Val Ser Phe Ser Val Thr Arg Pro Glu His Asn Ile
                165                 170                 175

Ala Ile Ser Trp Pro Ser Val Ser Tyr Lys Ala Ala Gln Lys Glu Gly
            180                 185                 190

Ser Arg His Lys
        195

<210> SEQ ID NO 21
<211> LENGTH: 195
<212> TYPE: PRT
<213> ORGANISM: Vibrio cholera

<400> SEQUENCE: 21

Val Glu Glu Ala Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
                20                  25                  30

Ser Asp Val Val Leu Asp Glu Gly Val Leu Tyr Tyr Ser Met Thr Ile
            35                  40                  45

Asn Asp Glu Gln Asn Asp Ile Lys Asp Glu Asp Lys Gly Glu Ser Ile
50                  55                  60

```
Ile Thr Ile Gly Glu Phe Ala Thr Val Arg Ala Thr Arg His Tyr Val
 65                  70                  75                  80

Asn Gln Asp Ala Pro Phe Gly Val Ile His Leu Asp Ile Thr Thr Glu
                 85                  90                  95

Asn Gly Thr Lys Thr Tyr Ser Tyr Asn Arg Lys Glu Gly Glu Phe Ala
                100                 105                 110

Ile Asn Trp Leu Val Pro Ile Gly Glu Asp Ser Pro Ala Ser Ile Lys
                115                 120                 125

Ile Ser Val Asp Glu Leu Asp Gln Gln Arg Asn Ile Ile Glu Val Pro
    130                 135                 140

Lys Leu Tyr Ser Ile Asp Leu Asp Asn Gln Thr Leu Glu Gln Trp Lys
145                 150                 155                 160

Thr Gln Gly Asn Val Ser Phe Ser Val Thr Arg Pro Glu His Asn Ile
                165                 170                 175

Ala Ile Ser Trp Pro Ser Val Ser Tyr Lys Ala Ala Gln Lys Glu Gly
                180                 185                 190

Ser Arg His
        195

<210> SEQ ID NO 22
<211> LENGTH: 194
<212> TYPE: PRT
<213> ORGANISM: Vibrio cholera

<400> SEQUENCE: 22

Val Glu Glu Ala Leu Asn Ile Phe Asp Glu Cys Arg Ser Pro Cys Ser
  1               5                  10                  15

Leu Thr Pro Glu Pro Gly Lys Pro Ile Gln Ser Lys Leu Ser Ile Pro
                 20                  25                  30

Ser Asp Val Val Leu Asp Glu Gly Val Leu Tyr Tyr Ser Met Thr Ile
                 35                  40                  45

Asn Asp Glu Gln Asn Asp Ile Lys Asp Glu Asp Lys Gly Glu Ser Ile
     50                  55                  60

Ile Thr Ile Gly Glu Phe Ala Thr Val Arg Ala Thr Arg His Tyr Val
 65                  70                  75                  80

Asn Gln Asp Ala Pro Phe Gly Val Ile His Leu Asp Ile Thr Thr Glu
                 85                  90                  95

Asn Gly Thr Lys Thr Tyr Ser Tyr Asn Arg Lys Glu Gly Glu Phe Ala
                100                 105                 110

Ile Asn Trp Leu Val Pro Ile Gly Glu Asp Ser Pro Ala Ser Ile Lys
                115                 120                 125

Ile Ser Val Asp Glu Leu Asp Gln Gln Arg Asn Ile Ile Glu Val Pro
    130                 135                 140

Lys Leu Tyr Ser Ile Asp Leu Asp Asn Gln Thr Leu Glu Gln Trp Lys
145                 150                 155                 160

Thr Gln Gly Asn Val Ser Phe Ser Val Thr Arg Pro Glu His Asn Ile
                165                 170                 175

Ala Ile Ser Trp Pro Ser Val Ser Tyr Lys Ala Ala Gln Lys Glu Gly
                180                 185                 190

Ser Arg

<210> SEQ ID NO 23
<211> LENGTH: 193
<212> TYPE: PRT
<213> ORGANISM: Vibrio cholera
```

<400> SEQUENCE: 23

```
Val Glu Glu Ala Leu Asn Ile Phe Asp Glu Cys Arg Ser Pro Cys Ser
 1               5                  10                  15

Leu Thr Pro Glu Pro Gly Lys Pro Ile Gln Ser Lys Leu Ser Ile Pro
            20                  25                  30

Ser Asp Val Val Leu Asp Glu Gly Val Leu Tyr Tyr Ser Met Thr Ile
        35                  40                  45

Asn Asp Glu Gln Asn Asp Ile Lys Asp Glu Asp Lys Gly Glu Ser Ile
 50                  55                  60

Ile Thr Ile Gly Glu Phe Ala Thr Val Arg Ala Thr Arg His Tyr Val
 65                  70                  75                  80

Asn Gln Asp Ala Pro Phe Gly Val Ile His Leu Asp Ile Thr Thr Glu
                85                  90                  95

Asn Gly Thr Lys Thr Tyr Ser Tyr Asn Arg Lys Glu Gly Glu Phe Ala
            100                 105                 110

Ile Asn Trp Leu Val Pro Ile Gly Glu Asp Ser Pro Ala Ser Ile Lys
        115                 120                 125

Ile Ser Val Asp Glu Leu Asp Gln Gln Arg Asn Ile Ile Glu Val Pro
130                 135                 140

Lys Leu Tyr Ser Ile Asp Leu Asp Asn Gln Thr Leu Glu Gln Trp Lys
145                 150                 155                 160

Thr Gln Gly Asn Val Ser Phe Ser Val Thr Arg Pro Glu His Asn Ile
                165                 170                 175

Ala Ile Ser Trp Pro Ser Val Ser Tyr Lys Ala Ala Gln Lys Glu Gly
            180                 185                 190

Ser
```

<210> SEQ ID NO 24
<211> LENGTH: 192
<212> TYPE: PRT
<213> ORGANISM: Vibrio cholera

<400> SEQUENCE: 24

```
Val Glu Glu Ala Leu Asn Ile Phe Asp Glu Cys Arg Ser Pro Cys Ser
 1               5                  10                  15

Leu Thr Pro Glu Pro Gly Lys Pro Ile Gln Ser Lys Leu Ser Ile Pro
            20                  25                  30

Ser Asp Val Val Leu Asp Glu Gly Val Leu Tyr Tyr Ser Met Thr Ile
        35                  40                  45

Asn Asp Glu Gln Asn Asp Ile Lys Asp Glu Asp Lys Gly Glu Ser Ile
 50                  55                  60

Ile Thr Ile Gly Glu Phe Ala Thr Val Arg Ala Thr Arg His Tyr Val
 65                  70                  75                  80

Asn Gln Asp Ala Pro Phe Gly Val Ile His Leu Asp Ile Thr Thr Glu
                85                  90                  95

Asn Gly Thr Lys Thr Tyr Ser Tyr Asn Arg Lys Glu Gly Glu Phe Ala
            100                 105                 110

Ile Asn Trp Leu Val Pro Ile Gly Glu Asp Ser Pro Ala Ser Ile Lys
        115                 120                 125

Ile Ser Val Asp Glu Leu Asp Gln Gln Arg Asn Ile Ile Glu Val Pro
130                 135                 140

Lys Leu Tyr Ser Ile Asp Leu Asp Asn Gln Thr Leu Glu Gln Trp Lys
145                 150                 155                 160
```

Thr Gln Gly Asn Val Ser Phe Ser Val Thr Arg Pro Glu His Asn Ile
            165                 170                 175

Ala Ile Ser Trp Pro Ser Val Ser Tyr Lys Ala Ala Gln Lys Glu Gly
            180                 185                 190

<210> SEQ ID NO 25
<211> LENGTH: 191
<212> TYPE: PRT
<213> ORGANISM: Vibrio cholera

<400> SEQUENCE: 25

Val Glu Glu Ala Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
            20                  25                  30

Ser Asp Val Val Leu Asp Glu Gly Val Leu Tyr Tyr Ser Met Thr Ile
        35                  40                  45

Asn Asp Glu Gln Asn Asp Ile Lys Asp Glu Asp Lys Gly Glu Ser Ile
    50                  55                  60

Ile Thr Ile Gly Glu Phe Ala Thr Val Arg Ala Thr Arg His Tyr Val
65                  70                  75                  80

Asn Gln Asp Ala Pro Phe Gly Val Ile His Leu Asp Ile Thr Thr Glu
                85                  90                  95

Asn Gly Thr Lys Thr Tyr Ser Tyr Asn Arg Lys Glu Gly Glu Phe Ala
            100                 105                 110

Ile Asn Trp Leu Val Pro Ile Gly Glu Asp Ser Pro Ala Ser Ile Lys
        115                 120                 125

Ile Ser Val Asp Glu Leu Asp Gln Gln Arg Asn Ile Ile Glu Val Pro
130                 135                 140

Lys Leu Tyr Ser Ile Asp Leu Asp Asn Gln Thr Leu Glu Gln Trp Lys
145                 150                 155                 160

Thr Gln Gly Asn Val Ser Phe Ser Val Thr Arg Pro Glu His Asn Ile
            165                 170                 175

Ala Ile Ser Trp Pro Ser Val Ser Tyr Lys Ala Ala Gln Lys Glu
            180                 185                 190

<210> SEQ ID NO 26
<211> LENGTH: 190
<212> TYPE: PRT
<213> ORGANISM: Vibrio cholera

<400> SEQUENCE: 26

Val Glu Glu Ala Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
            20                  25                  30

Ser Asp Val Val Leu Asp Glu Gly Val Leu Tyr Tyr Ser Met Thr Ile
        35                  40                  45

Asn Asp Glu Gln Asn Asp Ile Lys Asp Glu Asp Lys Gly Glu Ser Ile
    50                  55                  60

Ile Thr Ile Gly Glu Phe Ala Thr Val Arg Ala Thr Arg His Tyr Val
65                  70                  75                  80

Asn Gln Asp Ala Pro Phe Gly Val Ile His Leu Asp Ile Thr Thr Glu
                85                  90                  95

Asn Gly Thr Lys Thr Tyr Ser Tyr Asn Arg Lys Glu Gly Glu Phe Ala
            100                 105                 110

```
Ile Asn Trp Leu Val Pro Ile Gly Glu Asp Ser Pro Ala Ser Ile Lys
            115                 120                 125

Ile Ser Val Asp Glu Leu Asp Gln Gln Arg Asn Ile Ile Glu Val Pro
        130                 135                 140

Lys Leu Tyr Ser Ile Asp Leu Asp Asn Gln Thr Leu Glu Gln Trp Lys
145                 150                 155                 160

Thr Gln Gly Asn Val Ser Phe Ser Val Thr Arg Pro Glu His Asn Ile
                165                 170                 175

Ala Ile Ser Trp Pro Ser Val Ser Tyr Lys Ala Ala Gln Lys
            180                 185                 190
```

<210> SEQ ID NO 27
<211> LENGTH: 189
<212> TYPE: PRT
<213> ORGANISM: Vibrio cholera

<400> SEQUENCE: 27

```
Val Glu Glu Ala Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
            20                  25                  30

Ser Asp Val Val Leu Asp Glu Gly Val Leu Tyr Tyr Ser Met Thr Ile
        35                  40                  45

Asn Asp Glu Gln Asn Asp Ile Lys Asp Glu Asp Lys Gly Glu Ser Ile
50                  55                  60

Ile Thr Ile Gly Glu Phe Ala Thr Val Arg Ala Thr Arg His Tyr Val
65                  70                  75                  80

Asn Gln Asp Ala Pro Phe Gly Val Ile His Leu Asp Ile Thr Thr Glu
                85                  90                  95

Asn Gly Thr Lys Thr Tyr Ser Tyr Asn Arg Lys Glu Gly Glu Phe Ala
            100                 105                 110

Ile Asn Trp Leu Val Pro Ile Gly Glu Asp Ser Pro Ala Ser Ile Lys
            115                 120                 125

Ile Ser Val Asp Glu Leu Asp Gln Gln Arg Asn Ile Ile Glu Val Pro
        130                 135                 140

Lys Leu Tyr Ser Ile Asp Leu Asp Asn Gln Thr Leu Glu Gln Trp Lys
145                 150                 155                 160

Thr Gln Gly Asn Val Ser Phe Ser Val Thr Arg Pro Glu His Asn Ile
                165                 170                 175

Ala Ile Ser Trp Pro Ser Val Ser Tyr Lys Ala Ala Gln
            180                 185
```

<210> SEQ ID NO 28
<211> LENGTH: 188
<212> TYPE: PRT
<213> ORGANISM: Vibrio cholera

<400> SEQUENCE: 28

```
Val Glu Glu Ala Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
            20                  25                  30

Ser Asp Val Val Leu Asp Glu Gly Val Leu Tyr Tyr Ser Met Thr Ile
        35                  40                  45

Asn Asp Glu Gln Asn Asp Ile Lys Asp Glu Asp Lys Gly Glu Ser Ile
50                  55                  60
```

```
Ile Thr Ile Gly Glu Phe Ala Thr Val Arg Ala Thr Arg His Tyr Val
 65                  70                  75                  80

Asn Gln Asp Ala Pro Phe Gly Val Ile His Leu Asp Ile Thr Thr Glu
                 85                  90                  95

Asn Gly Thr Lys Thr Tyr Ser Tyr Asn Arg Lys Glu Gly Glu Phe Ala
            100                 105                 110

Ile Asn Trp Leu Val Pro Ile Gly Glu Asp Ser Pro Ala Ser Ile Lys
        115                 120                 125

Ile Ser Val Asp Glu Leu Asp Gln Gln Arg Asn Ile Ile Glu Val Pro
    130                 135                 140

Lys Leu Tyr Ser Ile Asp Leu Asp Asn Gln Thr Leu Glu Gln Trp Lys
145                 150                 155                 160

Thr Gln Gly Asn Val Ser Phe Ser Val Thr Arg Pro Glu His Asn Ile
                165                 170                 175

Ala Ile Ser Trp Pro Ser Val Ser Tyr Lys Ala Ala
                180                 185

<210> SEQ ID NO 29
<211> LENGTH: 187
<212> TYPE: PRT
<213> ORGANISM: Vibrio cholera

<400> SEQUENCE: 29

Val Glu Glu Ala Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
                20                  25                  30

Ser Asp Val Val Leu Asp Glu Gly Val Leu Tyr Tyr Ser Met Thr Ile
            35                  40                  45

Asn Asp Glu Gln Asn Asp Ile Lys Asp Glu Asp Lys Gly Glu Ser Ile
        50                  55                  60

Ile Thr Ile Gly Glu Phe Ala Thr Val Arg Ala Thr Arg His Tyr Val
 65                  70                  75                  80

Asn Gln Asp Ala Pro Phe Gly Val Ile His Leu Asp Ile Thr Thr Glu
                 85                  90                  95

Asn Gly Thr Lys Thr Tyr Ser Tyr Asn Arg Lys Glu Gly Glu Phe Ala
            100                 105                 110

Ile Asn Trp Leu Val Pro Ile Gly Glu Asp Ser Pro Ala Ser Ile Lys
        115                 120                 125

Ile Ser Val Asp Glu Leu Asp Gln Gln Arg Asn Ile Ile Glu Val Pro
    130                 135                 140

Lys Leu Tyr Ser Ile Asp Leu Asp Asn Gln Thr Leu Glu Gln Trp Lys
145                 150                 155                 160

Thr Gln Gly Asn Val Ser Phe Ser Val Thr Arg Pro Glu His Asn Ile
                165                 170                 175

Ala Ile Ser Trp Pro Ser Val Ser Tyr Lys Ala
                180                 185

<210> SEQ ID NO 30
<211> LENGTH: 186
<212> TYPE: PRT
<213> ORGANISM: Vibrio cholera

<400> SEQUENCE: 30

Val Glu Glu Ala Leu Asn Ile Phe Asp Glu Cys Arg Ser Pro Cys Ser
1               5                   10                  15
```

Leu Thr Pro Glu Pro Gly Lys Pro Ile Gln Ser Lys Leu Ser Ile Pro
            20                  25                  30

Ser Asp Val Val Leu Asp Glu Gly Val Leu Tyr Tyr Ser Met Thr Ile
        35                  40                  45

Asn Asp Glu Gln Asn Asp Ile Lys Asp Glu Lys Gly Glu Ser Ile
    50                  55                  60

Ile Thr Ile Gly Glu Phe Ala Thr Val Arg Ala Thr Arg His Tyr Val
65                  70                  75                  80

Asn Gln Asp Ala Pro Phe Gly Val Ile His Leu Asp Ile Thr Thr Glu
                85                  90                  95

Asn Gly Thr Lys Thr Tyr Ser Tyr Asn Arg Lys Glu Gly Glu Phe Ala
            100                 105                 110

Ile Asn Trp Leu Val Pro Ile Gly Glu Asp Ser Pro Ala Ser Ile Lys
        115                 120                 125

Ile Ser Val Asp Glu Leu Asp Gln Gln Arg Asn Ile Ile Glu Val Pro
130                 135                 140

Lys Leu Tyr Ser Ile Asp Leu Asp Asn Gln Thr Leu Glu Gln Trp Lys
145                 150                 155                 160

Thr Gln Gly Asn Val Ser Phe Ser Val Thr Arg Pro Glu His Asn Ile
                165                 170                 175

Ala Ile Ser Trp Pro Ser Val Ser Tyr Lys
            180                 185

<210> SEQ ID NO 31
<211> LENGTH: 187
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 31

Met Val Glu Glu Ala Leu Asn Ile Phe Asp Glu Cys Arg Ser Pro Cys
1               5                   10                  15

Ser Leu Thr Pro Glu Pro Gly Lys Pro Ile Gln Ser Lys Leu Ser Ile
            20                  25                  30

Pro Ser Asp Val Val Leu Asp Glu Gly Val Leu Tyr Tyr Ser Met Thr
        35                  40                  45

Ile Asn Asp Glu Gln Asn Asp Ile Lys Asp Glu Lys Gly Glu Ser
    50                  55                  60

Ile Ile Thr Ile Gly Glu Phe Ala Thr Val Arg Ala Thr Arg His Tyr
65                  70                  75                  80

Val Asn Gln Asp Ala Pro Phe Gly Val Ile His Leu Asp Ile Thr Thr
                85                  90                  95

Glu Asn Gly Thr Lys Thr Tyr Ser Tyr Asn Arg Lys Glu Gly Glu Phe
            100                 105                 110

Ala Ile Asn Trp Leu Val Pro Ile Gly Glu Asp Ser Pro Ala Ser Ile
        115                 120                 125

Lys Ile Ser Val Asp Glu Leu Asp Gln Gln Arg Asn Ile Ile Glu Val
    130                 135                 140

Pro Lys Leu Tyr Ser Ile Asp Leu Asp Asn Gln Thr Leu Glu Gln Trp
145                 150                 155                 160

Lys Thr Gln Gly Asn Val Ser Phe Ser Val Thr Arg Pro Glu His Asn
                165                 170                 175

```
Ile Ala Ile Ser Trp Pro Ser Val Ser Tyr Lys
            180                 185
```

<210> SEQ ID NO 32
<211> LENGTH: 185
<212> TYPE: PRT
<213> ORGANISM: Vibrio cholera

<400> SEQUENCE: 32

```
Glu Glu Ala Leu Asn Ile Phe Asp Glu Cys Arg Ser Pro Cys Ser Leu
1               5                   10                  15

Thr Pro Glu Pro Gly Lys Pro Ile Gln Ser Lys Leu Ser Ile Pro Ser
            20                  25                  30

Asp Val Val Leu Asp Glu Gly Val Leu Tyr Tyr Ser Met Thr Ile Asn
        35                  40                  45

Asp Glu Gln Asn Asp Ile Lys Asp Glu Asp Lys Gly Glu Ser Ile Ile
    50                  55                  60

Thr Ile Gly Glu Phe Ala Thr Val Arg Ala Thr Arg His Tyr Val Asn
65                  70                  75                  80

Gln Asp Ala Pro Phe Gly Val Ile His Leu Asp Ile Thr Thr Glu Asn
                85                  90                  95

Gly Thr Lys Thr Tyr Ser Tyr Asn Arg Lys Glu Gly Glu Phe Ala Ile
            100                 105                 110

Asn Trp Leu Val Pro Ile Gly Glu Asp Ser Pro Ala Ser Ile Lys Ile
        115                 120                 125

Ser Val Asp Glu Leu Asp Gln Gln Arg Asn Ile Ile Glu Val Pro Lys
    130                 135                 140

Leu Tyr Ser Ile Asp Leu Asp Asn Gln Thr Leu Glu Gln Trp Lys Thr
145                 150                 155                 160

Gln Gly Asn Val Ser Phe Ser Val Thr Arg Pro Glu His Asn Ile Ala
                165                 170                 175

Ile Ser Trp Pro Ser Val Ser Tyr Lys
            180                 185
```

<210> SEQ ID NO 33
<211> LENGTH: 184
<212> TYPE: PRT
<213> ORGANISM: Vibrio cholera

<400> SEQUENCE: 33

```
Glu Ala Leu Asn Ile Phe Asp Glu Cys Arg Ser Pro Cys Ser Leu Thr
1               5                   10                  15

Pro Glu Pro Gly Lys Pro Ile Gln Ser Lys Leu Ser Ile Pro Ser Asp
            20                  25                  30

Val Val Leu Asp Glu Gly Val Leu Tyr Tyr Ser Met Thr Ile Asn Asp
        35                  40                  45

Glu Gln Asn Asp Ile Lys Asp Glu Asp Lys Gly Glu Ser Ile Ile Thr
    50                  55                  60

Ile Gly Glu Phe Ala Thr Val Arg Ala Thr Arg His Tyr Val Asn Gln
65                  70                  75                  80

Asp Ala Pro Phe Gly Val Ile His Leu Asp Ile Thr Thr Glu Asn Gly
                85                  90                  95

Thr Lys Thr Tyr Ser Tyr Asn Arg Lys Glu Gly Glu Phe Ala Ile Asn
            100                 105                 110

Trp Leu Val Pro Ile Gly Glu Asp Ser Pro Ala Ser Ile Lys Ile Ser
        115                 120                 125
```

```
Val Asp Glu Leu Asp Gln Gln Arg Asn Ile Ile Glu Val Pro Lys Leu
    130                 135                 140

Tyr Ser Ile Asp Leu Asp Asn Gln Thr Leu Glu Gln Trp Lys Thr Gln
145                 150                 155                 160

Gly Asn Val Ser Phe Ser Val Thr Arg Pro Glu His Asn Ile Ala Ile
                165                 170                 175

Ser Trp Pro Ser Val Ser Tyr Lys
                180

<210> SEQ ID NO 34
<211> LENGTH: 183
<212> TYPE: PRT
<213> ORGANISM: Vibrio cholera

<400> SEQUENCE: 34

Ala Leu Asn Ile Phe Asp Glu Cys Arg Ser Pro Cys Ser Leu Thr Pro
1               5                   10                  15

Glu Pro Gly Lys Pro Ile Gln Ser Lys Leu Ser Ile Pro Ser Asp Val
                20                  25                  30

Val Leu Asp Glu Gly Val Leu Tyr Tyr Ser Met Thr Ile Asn Asp Glu
            35                  40                  45

Gln Asn Asp Ile Lys Asp Glu Asp Lys Gly Glu Ser Ile Ile Thr Ile
    50                  55                  60

Gly Glu Phe Ala Thr Val Arg Ala Thr Arg His Tyr Val Asn Gln Asp
65                  70                  75                  80

Ala Pro Phe Gly Val Ile His Leu Asp Ile Thr Thr Glu Asn Gly Thr
                85                  90                  95

Lys Thr Tyr Ser Tyr Asn Arg Lys Glu Gly Glu Phe Ala Ile Asn Trp
            100                 105                 110

Leu Val Pro Ile Gly Glu Asp Ser Pro Ala Ser Ile Lys Ile Ser Val
        115                 120                 125

Asp Glu Leu Asp Gln Gln Arg Asn Ile Ile Glu Val Pro Lys Leu Tyr
    130                 135                 140

Ser Ile Asp Leu Asp Asn Gln Thr Leu Glu Gln Trp Lys Thr Gln Gly
145                 150                 155                 160

Asn Val Ser Phe Ser Val Thr Arg Pro Glu His Asn Ile Ala Ile Ser
                165                 170                 175

Trp Pro Ser Val Ser Tyr Lys
            180

<210> SEQ ID NO 35
<211> LENGTH: 182
<212> TYPE: PRT
<213> ORGANISM: Vibrio cholera

<400> SEQUENCE: 35

Leu Asn Ile Phe Asp Glu Cys Arg Ser Pro Cys Ser Leu Thr Pro Glu
1               5                   10                  15

Pro Gly Lys Pro Ile Gln Ser Lys Leu Ser Ile Pro Ser Asp Val Val
                20                  25                  30

Leu Asp Glu Gly Val Leu Tyr Tyr Ser Met Thr Ile Asn Asp Glu Gln
            35                  40                  45

Asn Asp Ile Lys Asp Glu Asp Lys Gly Glu Ser Ile Ile Thr Ile Gly
    50                  55                  60

Glu Phe Ala Thr Val Arg Ala Thr Arg His Tyr Val Asn Gln Asp Ala
65                  70                  75                  80
```

```
Pro Phe Gly Val Ile His Leu Asp Ile Thr Thr Glu Asn Gly Thr Lys
                85                  90                  95

Thr Tyr Ser Tyr Asn Arg Lys Glu Gly Glu Phe Ala Ile Asn Trp Leu
            100                 105                 110

Val Pro Ile Gly Glu Asp Ser Pro Ala Ser Ile Lys Ile Ser Val Asp
        115                 120                 125

Glu Leu Asp Gln Gln Arg Asn Ile Ile Glu Val Pro Lys Leu Tyr Ser
    130                 135                 140

Ile Asp Leu Asp Asn Gln Thr Leu Glu Gln Trp Lys Thr Gln Gly Asn
145                 150                 155                 160

Val Ser Phe Ser Val Thr Arg Pro Glu His Asn Ile Ala Ile Ser Trp
                165                 170                 175

Pro Ser Val Ser Tyr Lys
            180

<210> SEQ ID NO 36
<211> LENGTH: 181
<212> TYPE: PRT
<213> ORGANISM: Vibrio cholera

<400> SEQUENCE: 36

Asn Ile Phe Asp Glu Cys Arg Ser Pro Cys Ser Leu Thr Pro Glu Pro
1               5                   10                  15

Gly Lys Pro Ile Gln Ser Lys Leu Ser Ile Pro Ser Asp Val Val Leu
            20                  25                  30

Asp Glu Gly Val Leu Tyr Tyr Ser Met Thr Ile Asn Asp Glu Gln Asn
        35                  40                  45

Asp Ile Lys Asp Glu Asp Lys Gly Glu Ser Ile Thr Ile Gly Glu
    50                  55                  60

Phe Ala Thr Val Arg Ala Thr Arg His Tyr Val Asn Gln Asp Ala Pro
65                  70                  75                  80

Phe Gly Val Ile His Leu Asp Ile Thr Thr Glu Asn Gly Thr Lys Thr
                85                  90                  95

Tyr Ser Tyr Asn Arg Lys Glu Gly Glu Phe Ala Ile Asn Trp Leu Val
            100                 105                 110

Pro Ile Gly Glu Asp Ser Pro Ala Ser Ile Lys Ile Ser Val Asp Glu
        115                 120                 125

Leu Asp Gln Gln Arg Asn Ile Ile Glu Val Pro Lys Leu Tyr Ser Ile
    130                 135                 140

Asp Leu Asp Asn Gln Thr Leu Glu Gln Trp Lys Thr Gln Gly Asn Val
145                 150                 155                 160

Ser Phe Ser Val Thr Arg Pro Glu His Asn Ile Ala Ile Ser Trp Pro
                165                 170                 175

Ser Val Ser Tyr Lys
            180

<210> SEQ ID NO 37
<211> LENGTH: 180
<212> TYPE: PRT
<213> ORGANISM: Vibrio cholera

<400> SEQUENCE: 37

Ile Phe Asp Glu Cys Arg Ser Pro Cys Ser Leu Thr Pro Glu Pro Gly
1               5                   10                  15

Lys Pro Ile Gln Ser Lys Leu Ser Ile Pro Ser Asp Val Val Leu Asp
            20                  25                  30
```

Glu Gly Val Leu Tyr Tyr Ser Met Thr Ile Asn Asp Glu Gln Asn Asp
          35                  40                  45

Ile Lys Asp Glu Asp Lys Gly Glu Ser Ile Ile Thr Ile Gly Glu Phe
 50                  55                  60

Ala Thr Val Arg Ala Thr Arg His Tyr Val Asn Gln Asp Ala Pro Phe
 65                  70                  75                  80

Gly Val Ile His Leu Asp Ile Thr Thr Glu Asn Gly Thr Lys Thr Tyr
              85                  90                  95

Ser Tyr Asn Arg Lys Glu Gly Glu Phe Ala Ile Asn Trp Leu Val Pro
             100                 105                 110

Ile Gly Glu Asp Ser Pro Ala Ser Ile Lys Ile Ser Val Asp Glu Leu
             115                 120                 125

Asp Gln Gln Arg Asn Ile Ile Glu Val Pro Lys Leu Tyr Ser Ile Asp
             130                 135                 140

Leu Asp Asn Gln Thr Leu Glu Gln Trp Lys Thr Gln Gly Asn Val Ser
145                 150                 155                 160

Phe Ser Val Thr Arg Pro Glu His Asn Ile Ala Ile Ser Trp Pro Ser
                165                 170                 175

Val Ser Tyr Lys
            180

<210> SEQ ID NO 38
<211> LENGTH: 179
<212> TYPE: PRT
<213> ORGANISM: Vibrio cholera

<400> SEQUENCE: 38

Phe Asp Glu Cys Arg Ser Pro Cys Ser Leu Thr Pro Glu Pro Gly Lys
1               5                   10                  15

Pro Ile Gln Ser Lys Leu Ser Ile Pro Ser Asp Val Val Leu Asp Glu
             20                  25                  30

Gly Val Leu Tyr Tyr Ser Met Thr Ile Asn Asp Glu Gln Asn Asp Ile
             35                  40                  45

Lys Asp Glu Asp Lys Gly Glu Ser Ile Ile Thr Ile Gly Glu Phe Ala
 50                  55                  60

Thr Val Arg Ala Thr Arg His Tyr Val Asn Gln Asp Ala Pro Phe Gly
 65                  70                  75                  80

Val Ile His Leu Asp Ile Thr Thr Glu Asn Gly Thr Lys Thr Tyr Ser
              85                  90                  95

Tyr Asn Arg Lys Glu Gly Glu Phe Ala Ile Asn Trp Leu Val Pro Ile
             100                 105                 110

Gly Glu Asp Ser Pro Ala Ser Ile Lys Ile Ser Val Asp Glu Leu Asp
             115                 120                 125

Gln Gln Arg Asn Ile Ile Glu Val Pro Lys Leu Tyr Ser Ile Asp Leu
             130                 135                 140

Asp Asn Gln Thr Leu Glu Gln Trp Lys Thr Gln Gly Asn Val Ser Phe
145                 150                 155                 160

Ser Val Thr Arg Pro Glu His Asn Ile Ala Ile Ser Trp Pro Ser Val
                165                 170                 175

Ser Tyr Lys

<210> SEQ ID NO 39
<211> LENGTH: 178
<212> TYPE: PRT
<213> ORGANISM: Vibrio cholera

<400> SEQUENCE: 39

Asp Glu Cys Arg Ser Pro Cys Ser Leu Thr Pro Glu Pro Gly Lys Pro
1               5                   10                  15

Ile Gln Ser Lys Leu Ser Ile Pro Ser Asp Val Val Leu Asp Glu Gly
            20                  25                  30

Val Leu Tyr Tyr Ser Met Thr Ile Asn Asp Glu Gln Asn Asp Ile Lys
        35                  40                  45

Asp Glu Asp Lys Gly Glu Ser Ile Ile Thr Ile Gly Glu Phe Ala Thr
    50                  55                  60

Val Arg Ala Thr Arg His Tyr Val Asn Gln Asp Ala Pro Phe Gly Val
65                  70                  75                  80

Ile His Leu Asp Ile Thr Thr Glu Asn Gly Thr Lys Thr Tyr Ser Tyr
                85                  90                  95

Asn Arg Lys Glu Gly Glu Phe Ala Ile Asn Trp Leu Val Pro Ile Gly
            100                 105                 110

Glu Asp Ser Pro Ala Ser Ile Lys Ile Ser Val Asp Glu Leu Asp Gln
        115                 120                 125

Gln Arg Asn Ile Ile Glu Val Pro Lys Leu Tyr Ser Ile Asp Leu Asp
    130                 135                 140

Asn Gln Thr Leu Glu Gln Trp Lys Thr Gln Gly Asn Val Ser Phe Ser
145                 150                 155                 160

Val Thr Arg Pro Glu His Asn Ile Ala Ile Ser Trp Pro Ser Val Ser
                165                 170                 175

Tyr Lys

<210> SEQ ID NO 40
<211> LENGTH: 177
<212> TYPE: PRT
<213> ORGANISM: Vibrio cholera

<400> SEQUENCE: 40

Glu Cys Arg Ser Pro Cys Ser Leu Thr Pro Glu Pro Gly Lys Pro Ile
1               5                   10                  15

Gln Ser Lys Leu Ser Ile Pro Ser Asp Val Val Leu Asp Glu Gly Val
            20                  25                  30

Leu Tyr Tyr Ser Met Thr Ile Asn Asp Glu Gln Asn Asp Ile Lys Asp
        35                  40                  45

Glu Asp Lys Gly Glu Ser Ile Ile Thr Ile Gly Glu Phe Ala Thr Val
    50                  55                  60

Arg Ala Thr Arg His Tyr Val Asn Gln Asp Ala Pro Phe Gly Val Ile
65                  70                  75                  80

His Leu Asp Ile Thr Thr Glu Asn Gly Thr Lys Thr Tyr Ser Tyr Asn
                85                  90                  95

Arg Lys Glu Gly Glu Phe Ala Ile Asn Trp Leu Val Pro Ile Gly Glu
            100                 105                 110

Asp Ser Pro Ala Ser Ile Lys Ile Ser Val Asp Glu Leu Asp Gln Gln
        115                 120                 125

Arg Asn Ile Ile Glu Val Pro Lys Leu Tyr Ser Ile Asp Leu Asp Asn
    130                 135                 140

Gln Thr Leu Glu Gln Trp Lys Thr Gln Gly Asn Val Ser Phe Ser Val
145                 150                 155                 160

```
Thr Arg Pro Glu His Asn Ile Ala Ile Ser Trp Pro Ser Val Ser Tyr
                165                 170                 175
Lys

<210> SEQ ID NO 41
<211> LENGTH: 176
<212> TYPE: PRT
<213> ORGANISM: Vibrio cholera

<400> SEQUENCE: 41

Cys Arg Ser Pro Cys Ser Leu Thr Pro Glu Pro Gly Lys Pro Ile Gln
1               5                   10                  15

Ser Lys Leu Ser Ile Pro Ser Asp Val Val Leu Asp Glu Gly Val Leu
                20                  25                  30

Tyr Tyr Ser Met Thr Ile Asn Asp Glu Gln Asn Asp Ile Lys Asp Glu
                35                  40                  45

Asp Lys Gly Glu Ser Ile Ile Thr Ile Gly Glu Phe Ala Thr Val Arg
    50                  55                  60

Ala Thr Arg His Tyr Val Asn Gln Asp Ala Pro Phe Gly Val Ile His
65                  70                  75                  80

Leu Asp Ile Thr Thr Glu Asn Gly Thr Lys Thr Tyr Ser Tyr Asn Arg
                85                  90                  95

Lys Glu Gly Glu Phe Ala Ile Asn Trp Leu Val Pro Ile Gly Glu Asp
                100                 105                 110

Ser Pro Ala Ser Ile Lys Ile Ser Val Asp Glu Leu Asp Gln Gln Arg
            115                 120                 125

Asn Ile Ile Glu Val Pro Lys Leu Tyr Ser Ile Asp Leu Asp Asn Gln
        130                 135                 140

Thr Leu Glu Gln Trp Lys Thr Gln Gly Asn Val Ser Phe Ser Val Thr
145                 150                 155                 160

Arg Pro Glu His Asn Ile Ala Ile Ser Trp Pro Ser Val Ser Tyr Lys
                165                 170                 175

<210> SEQ ID NO 42
<211> LENGTH: 175
<212> TYPE: PRT
<213> ORGANISM: Vibrio cholera

<400> SEQUENCE: 42

Arg Ser Pro Cys Ser Leu Thr Pro Glu Pro Gly Lys Pro Ile Gln Ser
1               5                   10                  15

Lys Leu Ser Ile Pro Ser Asp Val Val Leu Asp Glu Gly Val Leu Tyr
                20                  25                  30

Tyr Ser Met Thr Ile Asn Asp Glu Gln Asn Asp Ile Lys Asp Glu Asp
                35                  40                  45

Lys Gly Glu Ser Ile Ile Thr Ile Gly Glu Phe Ala Thr Val Arg Ala
    50                  55                  60

Thr Arg His Tyr Val Asn Gln Asp Ala Pro Phe Gly Val Ile His Leu
65                  70                  75                  80

Asp Ile Thr Thr Glu Asn Gly Thr Lys Thr Tyr Ser Tyr Asn Arg Lys
                85                  90                  95

Glu Gly Glu Phe Ala Ile Asn Trp Leu Val Pro Ile Gly Glu Asp Ser
                100                 105                 110

Pro Ala Ser Ile Lys Ile Ser Val Asp Glu Leu Asp Gln Gln Arg Asn
            115                 120                 125
```

```
Ile Ile Glu Val Pro Lys Leu Tyr Ser Ile Asp Leu Asp Asn Gln Thr
    130                 135                 140
Leu Glu Gln Trp Lys Thr Gln Gly Asn Val Ser Phe Ser Val Thr Arg
145                 150                 155                 160
Pro Glu His Asn Ile Ala Ile Ser Trp Pro Ser Val Ser Tyr Lys
                165                 170                 175
```

<210> SEQ ID NO 43
<211> LENGTH: 174
<212> TYPE: PRT
<213> ORGANISM: Vibrio cholera

<400> SEQUENCE: 43

```
Ser Pro Cys Ser Leu Thr Pro Glu Pro Gly Lys Pro Ile Gln Ser Lys
1               5                   10                  15
Leu Ser Ile Pro Ser Asp Val Val Leu Asp Glu Gly Val Leu Tyr Tyr
                20                  25                  30
Ser Met Thr Ile Asn Asp Glu Gln Asn Asp Ile Lys Asp Glu Asp Lys
            35                  40                  45
Gly Glu Ser Ile Ile Thr Ile Gly Glu Phe Ala Thr Val Arg Ala Thr
        50                  55                  60
Arg His Tyr Val Asn Gln Asp Ala Pro Phe Gly Val Ile His Leu Asp
65                  70                  75                  80
Ile Thr Thr Glu Asn Gly Thr Lys Thr Tyr Ser Tyr Asn Arg Lys Glu
                85                  90                  95
Gly Glu Phe Ala Ile Asn Trp Leu Val Pro Ile Gly Glu Asp Ser Pro
            100                 105                 110
Ala Ser Ile Lys Ile Ser Val Asp Glu Leu Asp Gln Gln Arg Asn Ile
        115                 120                 125
Ile Glu Val Pro Lys Leu Tyr Ser Ile Asp Leu Asp Asn Gln Thr Leu
    130                 135                 140
Glu Gln Trp Lys Thr Gln Gly Asn Val Ser Phe Ser Val Thr Arg Pro
145                 150                 155                 160
Glu His Asn Ile Ala Ile Ser Trp Pro Ser Val Ser Tyr Lys
                165                 170
```

<210> SEQ ID NO 44
<211> LENGTH: 173
<212> TYPE: PRT
<213> ORGANISM: Vibrio cholera

<400> SEQUENCE: 44

```
Pro Cys Ser Leu Thr Pro Glu Pro Gly Lys Pro Ile Gln Ser Lys Leu
1               5                   10                  15
Ser Ile Pro Ser Asp Val Val Leu Asp Glu Gly Val Leu Tyr Tyr Ser
                20                  25                  30
Met Thr Ile Asn Asp Glu Gln Asn Asp Ile Lys Asp Glu Asp Lys Gly
            35                  40                  45
Glu Ser Ile Ile Thr Ile Gly Glu Phe Ala Thr Val Arg Ala Thr Arg
        50                  55                  60
His Tyr Val Asn Gln Asp Ala Pro Phe Gly Val Ile His Leu Asp Ile
65                  70                  75                  80
Thr Thr Glu Asn Gly Thr Lys Thr Tyr Ser Tyr Asn Arg Lys Glu Gly
                85                  90                  95
Glu Phe Ala Ile Asn Trp Leu Val Pro Ile Gly Glu Asp Ser Pro Ala
            100                 105                 110
```

Ser Ile Lys Ile Ser Val Asp Glu Leu Asp Gln Gln Arg Asn Ile Ile
        115                 120                 125

Glu Val Pro Lys Leu Tyr Ser Ile Asp Leu Asp Asn Gln Thr Leu Glu
        130                 135                 140

Gln Trp Lys Thr Gln Gly Asn Val Ser Phe Ser Val Thr Arg Pro Glu
145                 150                 155                 160

His Asn Ile Ala Ile Ser Trp Pro Ser Val Ser Tyr Lys
            165                 170

<210> SEQ ID NO 45
<211> LENGTH: 172
<212> TYPE: PRT
<213> ORGANISM: Vibrio cholera

<400> SEQUENCE: 45

Cys Ser Leu Thr Pro Glu Pro Gly Lys Pro Ile Gln Ser Lys Leu Ser
1               5                   10                  15

Ile Pro Ser Asp Val Val Leu Asp Glu Gly Val Leu Tyr Tyr Ser Met
            20                  25                  30

Thr Ile Asn Asp Glu Gln Asn Asp Ile Lys Asp Glu Asp Lys Gly Glu
        35                  40                  45

Ser Ile Ile Thr Ile Gly Glu Phe Ala Thr Val Arg Ala Thr Arg His
    50                  55                  60

Tyr Val Asn Gln Asp Ala Pro Phe Gly Val Ile His Leu Asp Ile Thr
65                  70                  75                  80

Thr Glu Asn Gly Thr Lys Thr Tyr Ser Tyr Asn Arg Lys Glu Gly Glu
                85                  90                  95

Phe Ala Ile Asn Trp Leu Val Pro Ile Gly Glu Asp Ser Pro Ala Ser
            100                 105                 110

Ile Lys Ile Ser Val Asp Glu Leu Asp Gln Gln Arg Asn Ile Ile Glu
        115                 120                 125

Val Pro Lys Leu Tyr Ser Ile Asp Leu Asp Asn Gln Thr Leu Glu Gln
    130                 135                 140

Trp Lys Thr Gln Gly Asn Val Ser Phe Ser Val Thr Arg Pro Glu His
145                 150                 155                 160

Asn Ile Ala Ile Ser Trp Pro Ser Val Ser Tyr Lys
                165                 170

<210> SEQ ID NO 46
<211> LENGTH: 171
<212> TYPE: PRT
<213> ORGANISM: Vibrio cholera

<400> SEQUENCE: 46

Ser Leu Thr Pro Glu Pro Gly Lys Pro Ile Gln Ser Lys Leu Ser Ile
1               5                   10                  15

Pro Ser Asp Val Val Leu Asp Glu Gly Val Leu Tyr Tyr Ser Met Thr
            20                  25                  30

Ile Asn Asp Glu Gln Asn Asp Ile Lys Asp Glu Asp Lys Gly Glu Ser
        35                  40                  45

Ile Ile Thr Ile Gly Glu Phe Ala Thr Val Arg Ala Thr Arg His Tyr
    50                  55                  60

Val Asn Gln Asp Ala Pro Phe Gly Val Ile His Leu Asp Ile Thr Thr
65                  70                  75                  80

Glu Asn Gly Thr Lys Thr Tyr Ser Tyr Asn Arg Lys Glu Gly Glu Phe
                85                  90                  95

```
Ala Ile Asn Trp Leu Val Pro Ile Gly Glu Asp Ser Pro Ala Ser Ile
                100                 105                 110

Lys Ile Ser Val Asp Glu Leu Asp Gln Gln Arg Asn Ile Ile Glu Val
            115                 120                 125

Pro Lys Leu Tyr Ser Ile Asp Leu Asp Asn Gln Thr Leu Glu Gln Trp
        130                 135                 140

Lys Thr Gln Gly Asn Val Ser Phe Ser Val Thr Arg Pro Glu His Asn
145                 150                 155                 160

Ile Ala Ile Ser Trp Pro Ser Val Ser Tyr Lys
                165                 170
```

<210> SEQ ID NO 47
<211> LENGTH: 170
<212> TYPE: PRT
<213> ORGANISM: Vibrio cholera

<400> SEQUENCE: 47

```
Leu Thr Pro Glu Pro Gly Lys Pro Ile Gln Ser Lys Leu Ser Ile Pro
1               5                   10                  15

Ser Asp Val Val Leu Asp Glu Gly Val Leu Tyr Tyr Ser Met Thr Ile
            20                  25                  30

Asn Asp Glu Gln Asn Asp Ile Lys Asp Glu Lys Gly Glu Ser Ile
        35                  40                  45

Ile Thr Ile Gly Glu Phe Ala Thr Val Arg Ala Thr Arg His Tyr Val
    50                  55                  60

Asn Gln Asp Ala Pro Phe Gly Val Ile His Leu Asp Ile Thr Thr Glu
65                  70                  75                  80

Asn Gly Thr Lys Thr Tyr Ser Tyr Asn Arg Lys Glu Gly Glu Phe Ala
                85                  90                  95

Ile Asn Trp Leu Val Pro Ile Gly Glu Asp Ser Pro Ala Ser Ile Lys
                100                 105                 110

Ile Ser Val Asp Glu Leu Asp Gln Gln Arg Asn Ile Ile Glu Val Pro
            115                 120                 125

Lys Leu Tyr Ser Ile Asp Leu Asp Asn Gln Thr Leu Glu Gln Trp Lys
        130                 135                 140

Thr Gln Gly Asn Val Ser Phe Ser Val Thr Arg Pro Glu His Asn Ile
145                 150                 155                 160

Ala Ile Ser Trp Pro Ser Val Ser Tyr Lys
                165                 170
```

<210> SEQ ID NO 48
<211> LENGTH: 169
<212> TYPE: PRT
<213> ORGANISM: Vibrio cholera

<400> SEQUENCE: 48

```
Thr Pro Glu Pro Gly Lys Pro Ile Gln Ser Lys Leu Ser Ile Pro Ser
1               5                   10                  15

Asp Val Val Leu Asp Glu Gly Val Leu Tyr Tyr Ser Met Thr Ile Asn
            20                  25                  30

Asp Glu Gln Asn Asp Ile Lys Asp Glu Asp Lys Gly Glu Ser Ile Ile
        35                  40                  45

Thr Ile Gly Glu Phe Ala Thr Val Arg Ala Thr Arg His Tyr Val Asn
    50                  55                  60

Gln Asp Ala Pro Phe Gly Val Ile His Leu Asp Ile Thr Thr Glu Asn
65                  70                  75                  80
```

```
Gly Thr Lys Thr Tyr Ser Tyr Asn Arg Lys Glu Gly Glu Phe Ala Ile
                85                  90                  95

Asn Trp Leu Val Pro Ile Gly Glu Asp Ser Pro Ala Ser Ile Lys Ile
            100                 105                 110

Ser Val Asp Glu Leu Asp Gln Gln Arg Asn Ile Ile Glu Val Pro Lys
        115                 120                 125

Leu Tyr Ser Ile Asp Leu Asp Asn Gln Thr Leu Glu Gln Trp Lys Thr
    130                 135                 140

Gln Gly Asn Val Ser Phe Ser Val Thr Arg Pro Glu His Asn Ile Ala
145                 150                 155                 160

Ile Ser Trp Pro Ser Val Ser Tyr Lys
                165
```

<210> SEQ ID NO 49
<211> LENGTH: 168
<212> TYPE: PRT
<213> ORGANISM: Vibrio cholera

<400> SEQUENCE: 49

```
Pro Glu Pro Gly Lys Pro Ile Gln Ser Lys Leu Ser Ile Pro Ser Asp
1               5                   10                  15

Val Val Leu Asp Glu Gly Val Leu Tyr Tyr Ser Met Thr Ile Asn Asp
            20                  25                  30

Glu Gln Asn Asp Ile Lys Asp Glu Asp Lys Gly Glu Ser Ile Ile Thr
        35                  40                  45

Ile Gly Glu Phe Ala Thr Val Arg Ala Thr Arg His Tyr Val Asn Gln
    50                  55                  60

Asp Ala Pro Phe Gly Val Ile His Leu Asp Ile Thr Thr Glu Asn Gly
65                  70                  75                  80

Thr Lys Thr Tyr Ser Tyr Asn Arg Lys Glu Gly Glu Phe Ala Ile Asn
                85                  90                  95

Trp Leu Val Pro Ile Gly Glu Asp Ser Pro Ala Ser Ile Lys Ile Ser
            100                 105                 110

Val Asp Glu Leu Asp Gln Gln Arg Asn Ile Ile Glu Val Pro Lys Leu
        115                 120                 125

Tyr Ser Ile Asp Leu Asp Asn Gln Thr Leu Glu Gln Trp Lys Thr Gln
    130                 135                 140

Gly Asn Val Ser Phe Ser Val Thr Arg Pro Glu His Asn Ile Ala Ile
145                 150                 155                 160

Ser Trp Pro Ser Val Ser Tyr Lys
                165
```

<210> SEQ ID NO 50
<211> LENGTH: 167
<212> TYPE: PRT
<213> ORGANISM: Vibrio cholera

<400> SEQUENCE: 50

```
Glu Pro Gly Lys Pro Ile Gln Ser Lys Leu Ser Ile Pro Ser Asp Val
1               5                   10                  15

Val Leu Asp Glu Gly Val Leu Tyr Tyr Ser Met Thr Ile Asn Asp Glu
            20                  25                  30

Gln Asn Asp Ile Lys Asp Glu Asp Lys Gly Glu Ser Ile Ile Thr Ile
        35                  40                  45

Gly Glu Phe Ala Thr Val Arg Ala Thr Arg His Tyr Val Asn Gln Asp
    50                  55                  60
```

```
Ala Pro Phe Gly Val Ile His Leu Asp Ile Thr Thr Glu Asn Gly Thr
 65                  70                  75                  80

Lys Thr Tyr Ser Tyr Asn Arg Lys Glu Gly Glu Phe Ala Ile Asn Trp
                 85                  90                  95

Leu Val Pro Ile Gly Glu Asp Ser Pro Ala Ser Ile Lys Ile Ser Val
            100                 105                 110

Asp Glu Leu Asp Gln Gln Arg Asn Ile Ile Glu Val Pro Lys Leu Tyr
            115                 120                 125

Ser Ile Asp Leu Asp Asn Gln Thr Leu Glu Gln Trp Lys Thr Gln Gly
        130                 135                 140

Asn Val Ser Phe Ser Val Thr Arg Pro Glu His Asn Ile Ala Ile Ser
145                 150                 155                 160

Trp Pro Ser Val Ser Tyr Lys
                165

<210> SEQ ID NO 51
<211> LENGTH: 166
<212> TYPE: PRT
<213> ORGANISM: Vibrio cholera

<400> SEQUENCE: 51

Pro Gly Lys Pro Ile Gln Ser Lys Leu Ser Ile Pro Ser Asp Val Val
 1               5                  10                  15

Leu Asp Glu Gly Val Leu Tyr Tyr Ser Met Thr Ile Asn Asp Glu Gln
             20                  25                  30

Asn Asp Ile Lys Asp Glu Asp Lys Gly Glu Ser Ile Ile Thr Ile Gly
         35                  40                  45

Glu Phe Ala Thr Val Arg Ala Thr Arg His Tyr Val Asn Gln Asp Ala
 50                  55                  60

Pro Phe Gly Val Ile His Leu Asp Ile Thr Thr Glu Asn Gly Thr Lys
 65                  70                  75                  80

Thr Tyr Ser Tyr Asn Arg Lys Glu Gly Glu Phe Ala Ile Asn Trp Leu
                 85                  90                  95

Val Pro Ile Gly Glu Asp Ser Pro Ala Ser Ile Lys Ile Ser Val Asp
            100                 105                 110

Glu Leu Asp Gln Gln Arg Asn Ile Ile Glu Val Pro Lys Leu Tyr Ser
            115                 120                 125

Ile Asp Leu Asp Asn Gln Thr Leu Glu Gln Trp Lys Thr Gln Gly Asn
        130                 135                 140

Val Ser Phe Ser Val Thr Arg Pro Glu His Asn Ile Ala Ile Ser Trp
145                 150                 155                 160

Pro Ser Val Ser Tyr Lys
                165

<210> SEQ ID NO 52
<211> LENGTH: 165
<212> TYPE: PRT
<213> ORGANISM: Vibrio cholera

<400> SEQUENCE: 52

Gly Lys Pro Ile Gln Ser Lys Leu Ser Ile Pro Ser Asp Val Val Leu
 1               5                  10                  15

Asp Glu Gly Val Leu Tyr Tyr Ser Met Thr Ile Asn Asp Glu Gln Asn
             20                  25                  30

Asp Ile Lys Asp Glu Asp Lys Gly Glu Ser Ile Ile Thr Ile Gly Glu
         35                  40                  45
```

```
Phe Ala Thr Val Arg Ala Thr Arg His Tyr Val Asn Gln Asp Ala Pro
 50                  55                  60

Phe Gly Val Ile His Leu Asp Ile Thr Thr Glu Asn Gly Thr Lys Thr
 65                  70                  75                  80

Tyr Ser Tyr Asn Arg Lys Glu Gly Glu Phe Ala Ile Asn Trp Leu Val
                 85                  90                  95

Pro Ile Gly Glu Asp Ser Pro Ala Ser Ile Lys Ile Ser Val Asp Glu
                100                 105                 110

Leu Asp Gln Gln Arg Asn Ile Ile Glu Val Pro Lys Leu Tyr Ser Ile
            115                 120                 125

Asp Leu Asp Asn Gln Thr Leu Glu Gln Trp Lys Thr Gln Gly Asn Val
130                 135                 140

Ser Phe Ser Val Thr Arg Pro Glu His Asn Ile Ala Ile Ser Trp Pro
145                 150                 155                 160

Ser Val Ser Tyr Lys
                165
```

<210> SEQ ID NO 53
<211> LENGTH: 164
<212> TYPE: PRT
<213> ORGANISM: Vibrio cholera

<400> SEQUENCE: 53

```
Lys Pro Ile Gln Ser Lys Leu Ser Ile Pro Ser Asp Val Val Leu Asp
 1               5                  10                  15

Glu Gly Val Leu Tyr Tyr Ser Met Thr Ile Asn Asp Glu Gln Asn Asp
                 20                  25                  30

Ile Lys Asp Glu Asp Lys Gly Glu Ser Ile Ile Thr Ile Gly Glu Phe
             35                  40                  45

Ala Thr Val Arg Ala Thr Arg His Tyr Val Asn Gln Asp Ala Pro Phe
 50                  55                  60

Gly Val Ile His Leu Asp Ile Thr Thr Glu Asn Gly Thr Lys Thr Tyr
 65                  70                  75                  80

Ser Tyr Asn Arg Lys Glu Gly Glu Phe Ala Ile Asn Trp Leu Val Pro
                 85                  90                  95

Ile Gly Glu Asp Ser Pro Ala Ser Ile Lys Ile Ser Val Asp Glu Leu
                100                 105                 110

Asp Gln Gln Arg Asn Ile Ile Glu Val Pro Lys Leu Tyr Ser Ile Asp
            115                 120                 125

Leu Asp Asn Gln Thr Leu Glu Gln Trp Lys Thr Gln Gly Asn Val Ser
130                 135                 140

Phe Ser Val Thr Arg Pro Glu His Asn Ile Ala Ile Ser Trp Pro Ser
145                 150                 155                 160

Val Ser Tyr Lys
```

<210> SEQ ID NO 54
<211> LENGTH: 163
<212> TYPE: PRT
<213> ORGANISM: Vibrio cholera

<400> SEQUENCE: 54

```
Pro Ile Gln Ser Lys Leu Ser Ile Pro Ser Asp Val Val Leu Asp Glu
 1               5                  10                  15

Gly Val Leu Tyr Tyr Ser Met Thr Ile Asn Asp Glu Gln Asn Asp Ile
                 20                  25                  30
```

Lys Asp Glu Asp Lys Gly Glu Ser Ile Ile Thr Ile Gly Glu Phe Ala
            35                  40                  45

Thr Val Arg Ala Thr Arg His Tyr Val Asn Gln Asp Ala Pro Phe Gly
    50                  55                  60

Val Ile His Leu Asp Ile Thr Thr Glu Asn Gly Thr Lys Thr Tyr Ser
65                  70                  75                  80

Tyr Asn Arg Lys Glu Gly Glu Phe Ala Ile Asn Trp Leu Val Pro Ile
                85                  90                  95

Gly Glu Asp Ser Pro Ala Ser Ile Lys Ile Ser Val Asp Glu Leu Asp
                100                 105                 110

Gln Gln Arg Asn Ile Ile Glu Val Pro Lys Leu Tyr Ser Ile Asp Leu
            115                 120                 125

Asp Asn Gln Thr Leu Glu Gln Trp Lys Thr Gln Gly Asn Val Ser Phe
130                 135                 140

Ser Val Thr Arg Pro Glu His Asn Ile Ala Ile Ser Trp Pro Ser Val
145                 150                 155                 160

Ser Tyr Lys

<210> SEQ ID NO 55
<211> LENGTH: 162
<212> TYPE: PRT
<213> ORGANISM: Vibrio cholera

<400> SEQUENCE: 55

Ile Gln Ser Lys Leu Ser Ile Pro Ser Asp Val Val Leu Asp Glu Gly
1               5                   10                  15

Val Leu Tyr Tyr Ser Met Thr Ile Asn Asp Gln Asn Asp Ile Lys
                20                  25                  30

Asp Glu Asp Lys Gly Glu Ser Ile Ile Thr Ile Gly Glu Phe Ala Thr
            35                  40                  45

Val Arg Ala Thr Arg His Tyr Val Asn Gln Asp Ala Pro Phe Gly Val
    50                  55                  60

Ile His Leu Asp Ile Thr Thr Glu Asn Gly Thr Lys Thr Tyr Ser Tyr
65                  70                  75                  80

Asn Arg Lys Glu Gly Glu Phe Ala Ile Asn Trp Leu Val Pro Ile Gly
                85                  90                  95

Glu Asp Ser Pro Ala Ser Ile Lys Ile Ser Val Asp Glu Leu Asp Gln
            100                 105                 110

Gln Arg Asn Ile Ile Glu Val Pro Lys Leu Tyr Ser Ile Asp Leu Asp
        115                 120                 125

Asn Gln Thr Leu Glu Gln Trp Lys Thr Gln Gly Asn Val Ser Phe Ser
130                 135                 140

Val Thr Arg Pro Glu His Asn Ile Ala Ile Ser Trp Pro Ser Val Ser
145                 150                 155                 160

Tyr Lys

<210> SEQ ID NO 56
<211> LENGTH: 161
<212> TYPE: PRT
<213> ORGANISM: Vibrio cholera

<400> SEQUENCE: 56

Gln Ser Lys Leu Ser Ile Pro Ser Asp Val Val Leu Asp Glu Gly Val
1               5                   10                  15

-continued

```
Leu Tyr Tyr Ser Met Thr Ile Asn Asp Glu Gln Asn Asp Ile Lys Asp
            20                  25                  30

Glu Asp Lys Gly Glu Ser Ile Ile Thr Ile Gly Glu Phe Ala Thr Val
        35                  40                  45

Arg Ala Thr Arg His Tyr Val Asn Gln Asp Ala Pro Phe Gly Val Ile
    50                  55                  60

His Leu Asp Ile Thr Thr Glu Asn Gly Thr Lys Thr Tyr Ser Tyr Asn
65                  70                  75                  80

Arg Lys Glu Gly Glu Phe Ala Ile Asn Trp Leu Val Pro Ile Gly Glu
                85                  90                  95

Asp Ser Pro Ala Ser Ile Lys Ile Ser Val Asp Glu Leu Asp Gln Gln
            100                 105                 110

Arg Asn Ile Ile Glu Val Pro Lys Leu Tyr Ser Ile Asp Leu Asp Asn
        115                 120                 125

Gln Thr Leu Glu Gln Trp Lys Thr Gln Gly Asn Val Ser Phe Ser Val
    130                 135                 140

Thr Arg Pro Glu His Asn Ile Ala Ile Ser Trp Pro Ser Val Ser Tyr
145                 150                 155                 160

Lys
```

<210> SEQ ID NO 57
<211> LENGTH: 160
<212> TYPE: PRT
<213> ORGANISM: Vibrio cholera

<400> SEQUENCE: 57

```
Ser Lys Leu Ser Ile Pro Ser Asp Val Val Leu Asp Glu Gly Val Leu
1               5                   10                  15

Tyr Tyr Ser Met Thr Ile Asn Asp Glu Gln Asn Asp Ile Lys Asp Glu
            20                  25                  30

Asp Lys Gly Glu Ser Ile Ile Thr Ile Gly Glu Phe Ala Thr Val Arg
        35                  40                  45

Ala Thr Arg His Tyr Val Asn Gln Asp Ala Pro Phe Gly Val Ile His
    50                  55                  60

Leu Asp Ile Thr Thr Glu Asn Gly Thr Lys Thr Tyr Ser Tyr Asn Arg
65                  70                  75                  80

Lys Glu Gly Glu Phe Ala Ile Asn Trp Leu Val Pro Ile Gly Glu Asp
                85                  90                  95

Ser Pro Ala Ser Ile Lys Ile Ser Val Asp Glu Leu Asp Gln Gln Arg
            100                 105                 110

Asn Ile Ile Glu Val Pro Lys Leu Tyr Ser Ile Asp Leu Asp Asn Gln
        115                 120                 125

Thr Leu Glu Gln Trp Lys Thr Gln Gly Asn Val Ser Phe Ser Val Thr
    130                 135                 140

Arg Pro Glu His Asn Ile Ala Ile Ser Trp Pro Ser Val Ser Tyr Lys
145                 150                 155                 160
```

<210> SEQ ID NO 58
<211> LENGTH: 159
<212> TYPE: PRT
<213> ORGANISM: Vibrio cholera

<400> SEQUENCE: 58

```
Lys Leu Ser Ile Pro Ser Asp Val Val Leu Asp Glu Gly Val Leu Tyr
1               5                   10                  15
```

```
Tyr Ser Met Thr Ile Asn Asp Glu Gln Asn Asp Ile Lys Asp Glu Asp
            20                  25                  30

Lys Gly Glu Ser Ile Ile Thr Ile Gly Glu Phe Ala Thr Val Arg Ala
        35                  40                  45

Thr Arg His Tyr Val Asn Gln Asp Ala Pro Phe Gly Val Ile His Leu
    50                  55                  60

Asp Ile Thr Thr Glu Asn Gly Thr Lys Thr Tyr Ser Tyr Asn Arg Lys
65                  70                  75                  80

Glu Gly Glu Phe Ala Ile Asn Trp Leu Val Pro Ile Gly Glu Asp Ser
                85                  90                  95

Pro Ala Ser Ile Lys Ile Ser Val Asp Glu Leu Asp Gln Gln Arg Asn
            100                 105                 110

Ile Ile Glu Val Pro Lys Leu Tyr Ser Ile Asp Leu Asp Asn Gln Thr
        115                 120                 125

Leu Glu Gln Trp Lys Thr Gln Gly Asn Val Ser Phe Ser Val Thr Arg
130                 135                 140

Pro Glu His Asn Ile Ala Ile Ser Trp Pro Ser Val Ser Tyr Lys
145                 150                 155
```

<210> SEQ ID NO 59
<211> LENGTH: 158
<212> TYPE: PRT
<213> ORGANISM: Vibrio cholera

<400> SEQUENCE: 59

```
Leu Ser Ile Pro Ser Asp Val Val Leu Asp Glu Gly Val Leu Tyr Tyr
1               5                   10                  15

Ser Met Thr Ile Asn Asp Glu Gln Asn Asp Ile Lys Asp Glu Asp Lys
            20                  25                  30

Gly Glu Ser Ile Ile Thr Ile Gly Glu Phe Ala Thr Val Arg Ala Thr
        35                  40                  45

Arg His Tyr Val Asn Gln Asp Ala Pro Phe Gly Val Ile His Leu Asp
    50                  55                  60

Ile Thr Thr Glu Asn Gly Thr Lys Thr Tyr Ser Tyr Asn Arg Lys Glu
65                  70                  75                  80

Gly Glu Phe Ala Ile Asn Trp Leu Val Pro Ile Gly Glu Asp Ser Pro
                85                  90                  95

Ala Ser Ile Lys Ile Ser Val Asp Glu Leu Asp Gln Gln Arg Asn Ile
            100                 105                 110

Ile Glu Val Pro Lys Leu Tyr Ser Ile Asp Leu Asp Asn Gln Thr Leu
        115                 120                 125

Glu Gln Trp Lys Thr Gln Gly Asn Val Ser Phe Ser Val Thr Arg Pro
130                 135                 140

Glu His Asn Ile Ala Ile Ser Trp Pro Ser Val Ser Tyr Lys
145                 150                 155
```

<210> SEQ ID NO 60
<211> LENGTH: 157
<212> TYPE: PRT
<213> ORGANISM: Vibrio cholera

<400> SEQUENCE: 60

```
Ser Ile Pro Ser Asp Val Val Leu Asp Glu Gly Val Leu Tyr Tyr Ser
1               5                   10                  15

Met Thr Ile Asn Asp Glu Gln Asn Asp Ile Lys Asp Glu Asp Lys Gly
            20                  25                  30
```

```
Glu Ser Ile Ile Thr Ile Gly Glu Phe Ala Thr Val Arg Ala Thr Arg
        35                  40                  45

His Tyr Val Asn Gln Asp Ala Pro Phe Gly Val Ile His Leu Asp Ile
 50                  55                  60

Thr Thr Glu Asn Gly Thr Lys Thr Tyr Ser Tyr Asn Arg Lys Glu Gly
 65                  70                  75                  80

Glu Phe Ala Ile Asn Trp Leu Val Pro Ile Gly Glu Asp Ser Pro Ala
                 85                  90                  95

Ser Ile Lys Ile Ser Val Asp Glu Leu Asp Gln Gln Arg Asn Ile Ile
            100                 105                 110

Glu Val Pro Lys Leu Tyr Ser Ile Asp Leu Asp Asn Gln Thr Leu Glu
        115                 120                 125

Gln Trp Lys Thr Gln Gly Asn Val Ser Phe Ser Val Thr Arg Pro Glu
130                 135                 140

His Asn Ile Ala Ile Ser Trp Pro Ser Val Ser Tyr Lys
145                 150                 155

<210> SEQ ID NO 61
<211> LENGTH: 156
<212> TYPE: PRT
<213> ORGANISM: Vibrio cholera

<400> SEQUENCE: 61

Ile Pro Ser Asp Val Val Leu Asp Glu Gly Val Leu Tyr Tyr Ser Met
 1               5                  10                  15

Thr Ile Asn Asp Glu Gln Asn Asp Ile Lys Asp Glu Asp Lys Gly Glu
            20                  25                  30

Ser Ile Ile Thr Ile Gly Glu Phe Ala Thr Val Arg Ala Thr Arg His
        35                  40                  45

Tyr Val Asn Gln Asp Ala Pro Phe Gly Val Ile His Leu Asp Ile Thr
 50                  55                  60

Thr Glu Asn Gly Thr Lys Thr Tyr Ser Tyr Asn Arg Lys Glu Gly Glu
 65                  70                  75                  80

Phe Ala Ile Asn Trp Leu Val Pro Ile Gly Glu Asp Ser Pro Ala Ser
                 85                  90                  95

Ile Lys Ile Ser Val Asp Glu Leu Asp Gln Gln Arg Asn Ile Ile Glu
            100                 105                 110

Val Pro Lys Leu Tyr Ser Ile Asp Leu Asp Asn Gln Thr Leu Glu Gln
        115                 120                 125

Trp Lys Thr Gln Gly Asn Val Ser Phe Ser Val Thr Arg Pro Glu His
130                 135                 140

Asn Ile Ala Ile Ser Trp Pro Ser Val Ser Tyr Lys
145                 150                 155

<210> SEQ ID NO 62
<211> LENGTH: 155
<212> TYPE: PRT
<213> ORGANISM: Vibrio cholera

<400> SEQUENCE: 62

Pro Ser Asp Val Val Leu Asp Glu Gly Val Leu Tyr Tyr Ser Met Thr
 1               5                  10                  15

Ile Asn Asp Glu Gln Asn Asp Ile Lys Asp Glu Asp Lys Gly Glu Ser
            20                  25                  30

Ile Ile Thr Ile Gly Glu Phe Ala Thr Val Arg Ala Thr Arg His Tyr
        35                  40                  45
```

Val Asn Gln Asp Ala Pro Phe Gly Val Ile His Leu Asp Ile Thr Thr
 50                  55                  60

Glu Asn Gly Thr Lys Thr Tyr Ser Tyr Asn Arg Lys Glu Gly Glu Phe
 65                  70                  75                  80

Ala Ile Asn Trp Leu Val Pro Ile Gly Glu Asp Ser Pro Ala Ser Ile
                 85                  90                  95

Lys Ile Ser Val Asp Glu Leu Asp Gln Gln Arg Asn Ile Ile Glu Val
                100                 105                 110

Pro Lys Leu Tyr Ser Ile Asp Leu Asp Asn Gln Thr Leu Glu Gln Trp
            115                 120                 125

Lys Thr Gln Gly Asn Val Ser Phe Ser Val Thr Arg Pro Glu His Asn
130                 135                 140

Ile Ala Ile Ser Trp Pro Ser Val Ser Tyr Lys
145                 150                 155

<210> SEQ ID NO 63
<211> LENGTH: 154
<212> TYPE: PRT
<213> ORGANISM: Vibrio cholera

<400> SEQUENCE: 63

Ser Asp Val Val Leu Asp Glu Gly Val Leu Tyr Tyr Ser Met Thr Ile
1               5                   10                  15

Asn Asp Glu Gln Asn Asp Ile Lys Asp Glu Asp Lys Gly Glu Ser Ile
                20                  25                  30

Ile Thr Ile Gly Glu Phe Ala Thr Val Arg Ala Thr Arg His Tyr Val
            35                  40                  45

Asn Gln Asp Ala Pro Phe Gly Val Ile His Leu Asp Ile Thr Thr Glu
50                  55                  60

Asn Gly Thr Lys Thr Tyr Ser Tyr Asn Arg Lys Glu Gly Glu Phe Ala
65                  70                  75                  80

Ile Asn Trp Leu Val Pro Ile Gly Glu Asp Ser Pro Ala Ser Ile Lys
                85                  90                  95

Ile Ser Val Asp Glu Leu Asp Gln Gln Arg Asn Ile Ile Glu Val Pro
            100                 105                 110

Lys Leu Tyr Ser Ile Asp Leu Asp Asn Gln Thr Leu Glu Gln Trp Lys
        115                 120                 125

Thr Gln Gly Asn Val Ser Phe Ser Val Thr Arg Pro Glu His Asn Ile
    130                 135                 140

Ala Ile Ser Trp Pro Ser Val Ser Tyr Lys
145                 150

<210> SEQ ID NO 64
<211> LENGTH: 153
<212> TYPE: PRT
<213> ORGANISM: Vibrio cholera

<400> SEQUENCE: 64

Asp Val Val Leu Asp Glu Gly Val Leu Tyr Tyr Ser Met Thr Ile Asn
1               5                   10                  15

Asp Glu Gln Asn Asp Ile Lys Asp Glu Asp Lys Gly Glu Ser Ile Ile
                20                  25                  30

Thr Ile Gly Glu Phe Ala Thr Val Arg Ala Thr Arg His Tyr Val Asn
            35                  40                  45

Gln Asp Ala Pro Phe Gly Val Ile His Leu Asp Ile Thr Thr Glu Asn
50                  55                  60

```
Gly Thr Lys Thr Tyr Ser Tyr Asn Arg Lys Glu Gly Glu Phe Ala Ile
65                  70                  75                  80

Asn Trp Leu Val Pro Ile Gly Glu Asp Ser Pro Ala Ser Ile Lys Ile
                85                  90                  95

Ser Val Asp Glu Leu Asp Gln Gln Arg Asn Ile Ile Glu Val Pro Lys
                100                 105                 110

Leu Tyr Ser Ile Asp Leu Asp Asn Gln Thr Leu Glu Gln Trp Lys Thr
            115                 120                 125

Gln Gly Asn Val Ser Phe Ser Val Thr Arg Pro Glu His Asn Ile Ala
        130                 135                 140

Ile Ser Trp Pro Ser Val Ser Tyr Lys
145                 150
```

<210> SEQ ID NO 65
<211> LENGTH: 152
<212> TYPE: PRT
<213> ORGANISM: Vibrio cholera

<400> SEQUENCE: 65

```
Val Val Leu Asp Glu Gly Val Leu Tyr Tyr Ser Met Thr Ile Asn Asp
1               5                   10                  15

Glu Gln Asn Asp Ile Lys Asp Glu Asp Lys Gly Glu Ser Ile Ile Thr
                20                  25                  30

Ile Gly Glu Phe Ala Thr Val Arg Ala Thr Arg His Tyr Val Asn Gln
            35                  40                  45

Asp Ala Pro Phe Gly Val Ile His Leu Asp Ile Thr Thr Glu Asn Gly
        50                  55                  60

Thr Lys Thr Tyr Ser Tyr Asn Arg Lys Glu Gly Glu Phe Ala Ile Asn
65                  70                  75                  80

Trp Leu Val Pro Ile Gly Glu Asp Ser Pro Ala Ser Ile Lys Ile Ser
                85                  90                  95

Val Asp Glu Leu Asp Gln Gln Arg Asn Ile Ile Glu Val Pro Lys Leu
                100                 105                 110

Tyr Ser Ile Asp Leu Asp Asn Gln Thr Leu Glu Gln Trp Lys Thr Gln
            115                 120                 125

Gly Asn Val Ser Phe Ser Val Thr Arg Pro Glu His Asn Ile Ala Ile
        130                 135                 140

Ser Trp Pro Ser Val Ser Tyr Lys
145                 150
```

<210> SEQ ID NO 66
<211> LENGTH: 151
<212> TYPE: PRT
<213> ORGANISM: Vibrio cholera

<400> SEQUENCE: 66

```
Val Leu Asp Glu Gly Val Leu Tyr Tyr Ser Met Thr Ile Asn Asp Glu
1               5                   10                  15

Gln Asn Asp Ile Lys Asp Glu Asp Lys Gly Glu Ser Ile Ile Thr Ile
                20                  25                  30

Gly Glu Phe Ala Thr Val Arg Ala Thr Arg His Tyr Val Asn Gln Asp
            35                  40                  45

Ala Pro Phe Gly Val Ile His Leu Asp Ile Thr Thr Glu Asn Gly Thr
        50                  55                  60

Lys Thr Tyr Ser Tyr Asn Arg Lys Glu Gly Glu Phe Ala Ile Asn Trp
65                  70                  75                  80
```

-continued

Leu Val Pro Ile Gly Glu Asp Ser Pro Ala Ser Ile Lys Ile Ser Val
                85                  90                  95

Asp Glu Leu Asp Gln Gln Arg Asn Ile Ile Glu Val Pro Lys Leu Tyr
            100                 105                 110

Ser Ile Asp Leu Asp Asn Gln Thr Leu Glu Gln Trp Lys Thr Gln Gly
        115                 120                 125

Asn Val Ser Phe Ser Val Thr Arg Pro Glu His Asn Ile Ala Ile Ser
    130                 135                 140

Trp Pro Ser Val Ser Tyr Lys
145                 150

<210> SEQ ID NO 67
<211> LENGTH: 150
<212> TYPE: PRT
<213> ORGANISM: Vibrio cholera

<400> SEQUENCE: 67

Leu Asp Glu Gly Val Leu Tyr Tyr Ser Met Thr Ile Asn Asp Glu Gln
1               5                   10                  15

Asn Asp Ile Lys Asp Glu Asp Lys Gly Glu Ser Ile Ile Thr Ile Gly
            20                  25                  30

Glu Phe Ala Thr Val Arg Ala Thr Arg His Tyr Val Asn Gln Asp Ala
        35                  40                  45

Pro Phe Gly Val Ile His Leu Asp Ile Thr Thr Glu Asn Gly Thr Lys
    50                  55                  60

Thr Tyr Ser Tyr Asn Arg Lys Glu Gly Glu Phe Ala Ile Asn Trp Leu
65                  70                  75                  80

Val Pro Ile Gly Glu Asp Ser Pro Ala Ser Ile Lys Ile Ser Val Asp
                85                  90                  95

Glu Leu Asp Gln Gln Arg Asn Ile Ile Glu Val Pro Lys Leu Tyr Ser
            100                 105                 110

Ile Asp Leu Asp Asn Gln Thr Leu Glu Gln Trp Lys Thr Gln Gly Asn
        115                 120                 125

Val Ser Phe Ser Val Thr Arg Pro Glu His Asn Ile Ala Ile Ser Trp
    130                 135                 140

Pro Ser Val Ser Tyr Lys
145                 150

<210> SEQ ID NO 68
<211> LENGTH: 149
<212> TYPE: PRT
<213> ORGANISM: Vibrio cholera

<400> SEQUENCE: 68

Asp Glu Gly Val Leu Tyr Tyr Ser Met Thr Ile Asn Asp Glu Gln Asn
1               5                   10                  15

Asp Ile Lys Asp Glu Asp Lys Gly Glu Ser Ile Ile Thr Ile Gly Glu
            20                  25                  30

Phe Ala Thr Val Arg Ala Thr Arg His Tyr Val Asn Gln Asp Ala Pro
        35                  40                  45

Phe Gly Val Ile His Leu Asp Ile Thr Thr Glu Asn Gly Thr Lys Thr
    50                  55                  60

Tyr Ser Tyr Asn Arg Lys Glu Gly Glu Phe Ala Ile Asn Trp Leu Val
65                  70                  75                  80

Pro Ile Gly Glu Asp Ser Pro Ala Ser Ile Lys Ile Ser Val Asp Glu
                85                  90                  95

```
Leu Asp Gln Gln Arg Asn Ile Ile Glu Val Pro Lys Leu Tyr Ser Ile
            100                 105                 110

Asp Leu Asp Asn Gln Thr Leu Glu Gln Trp Lys Thr Gln Gly Asn Val
        115                 120                 125

Ser Phe Ser Val Thr Arg Pro Glu His Asn Ile Ala Ile Ser Trp Pro
130                 135                 140

Ser Val Ser Tyr Lys
145

<210> SEQ ID NO 69
<211> LENGTH: 148
<212> TYPE: PRT
<213> ORGANISM: Vibrio cholera

<400> SEQUENCE: 69

Glu Gly Val Leu Tyr Tyr Ser Met Thr Ile Asn Asp Glu Gln Asn Asp
1               5                   10                  15

Ile Lys Asp Glu Asp Lys Gly Glu Ser Ile Ile Thr Ile Gly Glu Phe
            20                  25                  30

Ala Thr Val Arg Ala Thr Arg His Tyr Val Asn Gln Asp Ala Pro Phe
        35                  40                  45

Gly Val Ile His Leu Asp Ile Thr Thr Glu Asn Gly Thr Lys Thr Tyr
    50                  55                  60

Ser Tyr Asn Arg Lys Glu Gly Glu Phe Ala Ile Asn Trp Leu Val Pro
65                  70                  75                  80

Ile Gly Glu Asp Ser Pro Ala Ser Ile Lys Ile Ser Val Asp Glu Leu
                85                  90                  95

Asp Gln Gln Arg Asn Ile Ile Glu Val Pro Lys Leu Tyr Ser Ile Asp
            100                 105                 110

Leu Asp Asn Gln Thr Leu Glu Gln Trp Lys Thr Gln Gly Asn Val Ser
        115                 120                 125

Phe Ser Val Thr Arg Pro Glu His Asn Ile Ala Ile Ser Trp Pro Ser
    130                 135                 140

Val Ser Tyr Lys
145

<210> SEQ ID NO 70
<211> LENGTH: 147
<212> TYPE: PRT
<213> ORGANISM: Vibrio cholera

<400> SEQUENCE: 70

Gly Val Leu Tyr Tyr Ser Met Thr Ile Asn Asp Glu Gln Asn Asp Ile
1               5                   10                  15

Lys Asp Glu Asp Lys Gly Glu Ser Ile Ile Thr Ile Gly Glu Phe Ala
            20                  25                  30

Thr Val Arg Ala Thr Arg His Tyr Val Asn Gln Asp Ala Pro Phe Gly
        35                  40                  45

Val Ile His Leu Asp Ile Thr Thr Glu Asn Gly Thr Lys Thr Tyr Ser
    50                  55                  60

Tyr Asn Arg Lys Glu Gly Glu Phe Ala Ile Asn Trp Leu Val Pro Ile
65                  70                  75                  80

Gly Glu Asp Ser Pro Ala Ser Ile Lys Ile Ser Val Asp Glu Leu Asp
                85                  90                  95

Gln Gln Arg Asn Ile Ile Glu Val Pro Lys Leu Tyr Ser Ile Asp Leu
            100                 105                 110
```

```
Asp Asn Gln Thr Leu Glu Gln Trp Lys Thr Gln Gly Asn Val Ser Phe
            115                 120                 125

Ser Val Thr Arg Pro Glu His Asn Ile Ala Ile Ser Trp Pro Ser Val
    130                 135                 140

Ser Tyr Lys
145

<210> SEQ ID NO 71
<211> LENGTH: 185
<212> TYPE: PRT
<213> ORGANISM: Vibrio cholera

<400> SEQUENCE: 71

Val Glu Glu Ala Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
            20                  25                  30

Ser Asp Val Val Leu Asp Glu Gly Val Leu Tyr Tyr Ser Met Thr Ile
        35                  40                  45

Asn Asp Glu Gln Asn Asp Ile Lys Asp Glu Asp Lys Gly Glu Ser Ile
    50                  55                  60

Ile Thr Ile Gly Glu Phe Ala Thr Val Arg Ala Thr Arg His Tyr Val
65                  70                  75                  80

Asn Gln Asp Ala Pro Phe Gly Val Ile His Leu Asp Ile Thr Thr Glu
                85                  90                  95

Asn Gly Thr Lys Thr Tyr Ser Tyr Asn Arg Lys Glu Gly Glu Phe Ala
            100                 105                 110

Ile Asn Trp Leu Val Pro Ile Gly Glu Asp Ser Pro Ala Ser Ile Lys
        115                 120                 125

Ile Ser Val Asp Glu Leu Asp Gln Gln Arg Asn Ile Ile Glu Val Pro
    130                 135                 140

Lys Leu Tyr Ser Ile Asp Leu Asp Asn Gln Thr Leu Glu Gln Trp Lys
145                 150                 155                 160

Thr Gln Gly Asn Val Ser Phe Ser Val Thr Arg Pro Glu His Asn Ile
                165                 170                 175

Ala Ile Ser Trp Pro Ser Val Ser Tyr
            180                 185

<210> SEQ ID NO 72
<211> LENGTH: 184
<212> TYPE: PRT
<213> ORGANISM: Vibrio cholera

<400> SEQUENCE: 72

Val Glu Glu Ala Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
            20                  25                  30

Ser Asp Val Val Leu Asp Glu Gly Val Leu Tyr Tyr Ser Met Thr Ile
        35                  40                  45

Asn Asp Glu Gln Asn Asp Ile Lys Asp Glu Asp Lys Gly Glu Ser Ile
    50                  55                  60

Ile Thr Ile Gly Glu Phe Ala Thr Val Arg Ala Thr Arg His Tyr Val
65                  70                  75                  80

Asn Gln Asp Ala Pro Phe Gly Val Ile His Leu Asp Ile Thr Thr Glu
                85                  90                  95
```

```
Asn Gly Thr Lys Thr Tyr Ser Tyr Asn Arg Lys Glu Gly Glu Phe Ala
            100                 105                 110

Ile Asn Trp Leu Val Pro Ile Gly Glu Asp Ser Pro Ala Ser Ile Lys
        115                 120                 125

Ile Ser Val Asp Glu Leu Asp Gln Gln Arg Asn Ile Ile Glu Val Pro
    130                 135                 140

Lys Leu Tyr Ser Ile Asp Leu Asp Asn Gln Thr Leu Glu Gln Trp Lys
145                 150                 155                 160

Thr Gln Gly Asn Val Ser Phe Ser Val Thr Arg Pro Glu His Asn Ile
                165                 170                 175

Ala Ile Ser Trp Pro Ser Val Ser
            180
```

<210> SEQ ID NO 73
<211> LENGTH: 183
<212> TYPE: PRT
<213> ORGANISM: Vibrio cholera

<400> SEQUENCE: 73

```
Val Glu Glu Ala Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
            20                  25                  30

Ser Asp Val Val Leu Asp Glu Gly Val Leu Tyr Tyr Ser Met Thr Ile
        35                  40                  45

Asn Asp Glu Gln Asn Asp Ile Lys Asp Glu Lys Gly Glu Ser Ile
    50                  55                  60

Ile Thr Ile Gly Glu Phe Ala Thr Val Arg Ala Thr Arg His Tyr Val
65                  70                  75                  80

Asn Gln Asp Ala Pro Phe Gly Val Ile His Leu Asp Ile Thr Thr Glu
                85                  90                  95

Asn Gly Thr Lys Thr Tyr Ser Tyr Asn Arg Lys Glu Gly Glu Phe Ala
            100                 105                 110

Ile Asn Trp Leu Val Pro Ile Gly Glu Asp Ser Pro Ala Ser Ile Lys
        115                 120                 125

Ile Ser Val Asp Glu Leu Asp Gln Gln Arg Asn Ile Ile Glu Val Pro
    130                 135                 140

Lys Leu Tyr Ser Ile Asp Leu Asp Asn Gln Thr Leu Glu Gln Trp Lys
145                 150                 155                 160

Thr Gln Gly Asn Val Ser Phe Ser Val Thr Arg Pro Glu His Asn Ile
                165                 170                 175

Ala Ile Ser Trp Pro Ser Val
            180
```

<210> SEQ ID NO 74
<211> LENGTH: 182
<212> TYPE: PRT
<213> ORGANISM: Vibrio cholera

<400> SEQUENCE: 74

```
Val Glu Glu Ala Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
            20                  25                  30

Ser Asp Val Val Leu Asp Glu Gly Val Leu Tyr Tyr Ser Met Thr Ile
        35                  40                  45
```

Asn Asp Glu Gln Asn Asp Ile Lys Asp Glu Asp Lys Gly Glu Ser Ile
    50                  55                  60

Ile Thr Ile Gly Glu Phe Ala Thr Val Arg Ala Thr Arg His Tyr Val
 65                  70                  75                  80

Asn Gln Asp Ala Pro Phe Gly Val Ile His Leu Asp Ile Thr Thr Glu
                 85                  90                  95

Asn Gly Thr Lys Thr Tyr Ser Tyr Asn Arg Lys Glu Gly Glu Phe Ala
            100                 105                 110

Ile Asn Trp Leu Val Pro Ile Gly Glu Asp Ser Pro Ala Ser Ile Lys
        115                 120                 125

Ile Ser Val Asp Glu Leu Asp Gln Gln Arg Asn Ile Ile Glu Val Pro
130                 135                 140

Lys Leu Tyr Ser Ile Asp Leu Asp Asn Gln Thr Leu Glu Gln Trp Lys
145                 150                 155                 160

Thr Gln Gly Asn Val Ser Phe Ser Val Thr Arg Pro Glu His Asn Ile
                165                 170                 175

Ala Ile Ser Trp Pro Ser
            180

<210> SEQ ID NO 75
<211> LENGTH: 181
<212> TYPE: PRT
<213> ORGANISM: Vibrio cholera

<400> SEQUENCE: 75

Val Glu Glu Ala Leu Asn Ile Phe Asp Glu Cys Arg Ser Pro Cys Ser
1               5                  10                  15

Leu Thr Pro Glu Pro Gly Lys Pro Ile Gln Ser Lys Leu Ser Ile Pro
            20                  25                  30

Ser Asp Val Val Leu Asp Glu Gly Val Leu Tyr Tyr Ser Met Thr Ile
        35                  40                  45

Asn As

<400> SEQUENCE: 76

```
Val Glu Glu Ala Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
            20                  25                  30

Ser Asp Val Val Leu Asp Glu Gly Val Leu Tyr Tyr Ser Met Thr Ile
        35                  40                  45

Asn Asp Glu Gln Asn Asp Ile Lys Asp Glu Asp Lys Gly Glu Ser Ile
    50                  55                  60

Ile Thr Ile Gly Glu Phe Ala Thr Val Arg Ala Thr Arg His Tyr Val
65                  70                  75                  80

Asn Gln Asp Ala Pro Phe Gly Val Ile His Leu Asp Ile Thr Thr Glu
                85                  90                  95

Asn Gly Thr Lys Thr Tyr Ser Tyr Asn Arg Lys Glu Gly Glu Phe Ala
            100                 105                 110

Ile Asn Trp Leu Val Pro Ile Gly Glu Asp Ser Pro Ala Ser Ile Lys
        115                 120                 125

Ile Ser Val Asp Glu Leu Asp Gln Gln Arg Asn Ile Ile Glu Val Pro
    130                 135                 140

Lys Leu Tyr Ser Ile Asp Leu Asp Asn Gln Thr Leu Glu Gln Trp Lys
145                 150                 155                 160

Thr Gln Gly Asn Val Ser Phe Ser Val Thr Arg Pro Glu His Asn Ile
                165                 170                 175

Ala Ile Ser Trp
            180
```

<210> SEQ ID NO 77
<211> LENGTH: 179
<212> TYPE: PRT
<213> ORGANISM: Vibrio cholera

<400> SEQUENCE: 77

```
Val Glu Glu Ala Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
            20                  25                  30

Ser Asp Val Val Leu Asp Glu Gly Val Leu Tyr Tyr Ser Met Thr Ile
        35                  40                  45

Asn Asp Glu Gln Asn Asp Ile Lys Asp Glu Asp Lys Gly Glu Ser Ile
    50                  55                  60

Ile Thr Ile Gly Glu Phe Ala Thr Val Arg Ala Thr Arg His Tyr Val
65                  70                  75                  80

Asn Gln Asp Ala Pro Phe Gly Val Ile His Leu Asp Ile Thr Thr Glu
                85                  90                  95

Asn Gly Thr Lys Thr Tyr Ser Tyr Asn Arg Lys Glu Gly Glu Phe Ala
            100                 105                 110

Ile Asn Trp Leu Val Pro Ile Gly Glu Asp Ser Pro Ala Ser Ile Lys
        115                 120                 125

Ile Ser Val Asp Glu Leu Asp Gln Gln Arg Asn Ile Ile Glu Val Pro
    130                 135                 140

Lys Leu Tyr Ser Ile Asp Leu Asp Asn Gln Thr Leu Glu Gln Trp Lys
145                 150                 155                 160
```

```
Thr Gln Gly Asn Val Ser Phe Ser Val Thr Arg Pro Glu His Asn Ile
                165                 170                 175

Ala Ile Ser

<210> SEQ ID NO 78
<211> LENGTH: 178
<212> TYPE: PRT
<213> ORGANISM: Vibrio cholera

<400> SEQUENCE: 78

Val Glu Glu Ala Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
                20                  25                  30

Ser Asp Val Val Leu Asp Glu Gly Val Leu Tyr Tyr Ser Met Thr Ile
                35                  40                  45

Asn Asp Glu Gln Asn Asp Ile Lys Asp Glu Asp Lys Gly Glu Ser Ile
            50                  55                  60

Ile Thr Ile Gly Glu Phe Ala Thr Val Arg Ala Thr Arg His Tyr Val
65                  70                  75                  80

Asn Gln Asp Ala Pro Phe Gly Val Ile His Leu Asp Ile Thr Thr Glu
                85                  90                  95

Asn Gly Thr Lys Thr Tyr Ser Tyr Asn Arg Lys Glu Gly Glu Phe Ala
                100                 105                 110

Ile Asn Trp Leu Val Pro Ile Gly Glu Asp Ser Pro Ala Ser Ile Lys
            115                 120                 125

Ile Ser Val Asp Glu Leu Asp Gln Gln Arg Asn Ile Ile Glu Val Pro
130                 135                 140

Lys Leu Tyr Ser Ile Asp Leu Asp Asn Gln Thr Leu Glu Gln Trp Lys
145                 150                 155                 160

Thr Gln Gly Asn Val Ser Phe Ser Val Thr Arg Pro Glu His Asn Ile
                165                 170                 175

Ala Ile

<210> SEQ ID NO 79
<211> LENGTH: 177
<212> TYPE: PRT
<213> ORGANISM: Vibrio cholera

<400> SEQUENCE: 79

Val Glu Glu Ala Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
                20                  25                  30

Ser Asp Val Val Leu Asp Glu Gly Val Leu Tyr Tyr Ser Met Thr Ile
                35                  40                  45

Asn Asp Glu Gln Asn Asp Ile Lys Asp Glu Asp Lys Gly Glu Ser Ile
            50                  55                  60

Ile Thr Ile Gly Glu Phe Ala Thr Val Arg Ala Thr Arg His Tyr Val
65                  70                  75                  80

Asn Gln Asp Ala Pro Phe Gly Val Ile His Leu Asp Ile Thr Thr Glu
                85                  90                  95

Asn Gly Thr Lys Thr Tyr Ser Tyr Asn Arg Lys Glu Gly Glu Phe Ala
                100                 105                 110
```

```
Ile Asn Trp Leu Val Pro Ile Gly Glu Asp Ser Pro Ala Ser Ile Lys
        115                 120                 125

Ile Ser Val Asp Glu Leu Asp Gln Gln Arg Asn Ile Ile Glu Val Pro
    130                 135                 140

Lys Leu Tyr Ser Ile Asp Leu Asp Asn Gln Thr Leu Glu Gln Trp Lys
145                 150                 155                 160

Thr Gln Gly Asn Val Ser Phe Ser Val Thr Arg Pro Glu His Asn Ile
                165                 170                 175

Ala

<210> SEQ ID NO 80
<211> LENGTH: 176
<212> TYPE: PRT
<213> ORGANISM: Vibrio cholera

<400> SEQUENCE: 80

Val Glu Glu Ala Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
            20                  25                  30

Ser Asp Val Val Leu Asp Glu Gly Val Leu Tyr Tyr Ser Met Thr Ile
        35                  40                  45

Asn Asp Glu Gln Asn Asp Ile Lys Asp Glu Asp Lys Gly Glu Ser Ile
    50                  55                  60

Ile Thr Ile Gly Glu Phe Ala Thr Val Arg Ala Thr Arg His Tyr Val
65                  70                  75                  80

Asn Gln Asp Ala Pro Phe Gly Val Ile His Leu Asp Ile Thr Thr Glu
                85                  90                  95

Asn Gly Thr Lys Thr Tyr Ser Tyr Asn Arg Lys Glu Gly Glu Phe Ala
            100                 105                 110

Ile Asn Trp Leu Val Pro Ile Gly Glu Asp Ser Pro Ala Ser Ile Lys
        115                 120                 125

Ile Ser Val Asp Glu Leu Asp Gln Gln Arg Asn Ile Ile Glu Val Pro
    130                 135                 140

Lys Leu Tyr Ser Ile Asp Leu Asp Asn Gln Thr Leu Glu Gln Trp Lys
145                 150                 155                 160

Thr Gln Gly Asn Val Ser Phe Ser Val Thr Arg Pro Glu His Asn Ile
                165                 170                 175

<210> SEQ ID NO 81
<211> LENGTH: 175
<212> TYPE: PRT
<213> ORGANISM: Vibrio cholera

<400> SEQUENCE: 81

Val Glu Glu Ala Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
            20                  25                  30

Ser Asp Val Val Leu Asp Glu Gly Val Leu Tyr Tyr Ser Met Thr Ile
        35                  40                  45

Asn Asp Glu Gln Asn Asp Ile Lys Asp Glu Asp Lys Gly Glu Ser Ile
    50                  55                  60

Ile Thr Ile Gly Glu Phe Ala Thr Val Arg Ala Thr Arg His Tyr Val
65                  70                  75                  80
```

Asn Gln Asp Ala Pro Phe Gly Val Ile His Leu Asp Ile Thr Thr Glu
                85                  90                  95

Asn Gly Thr Lys Thr Tyr Ser Tyr Asn Arg Lys Glu Gly Glu Phe Ala
            100                 105                 110

Ile Asn Trp Leu Val Pro Ile Gly Glu Asp Ser Pro Ala Ser Ile Lys
        115                 120                 125

Ile Ser Val Asp Glu Leu Asp Gln Gln Arg Asn Ile Ile Glu Val Pro
    130                 135                 140

Lys Leu Tyr Ser Ile Asp Leu Asp Asn Gln Thr Leu Glu Gln Trp Lys
145                 150                 155                 160

Thr Gln Gly Asn Val Ser Phe Ser Val Thr Arg Pro Glu His Asn
                165                 170                 175

<210> SEQ ID NO 82
<211> LENGTH: 174
<212> TYPE: PRT
<213> ORGANISM: Vibrio cholera

<400> SEQUENCE: 82

Val Glu Glu Ala Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
            20                  25                  30

Ser Asp Val Val Leu Asp Glu Gly Val Leu Tyr Tyr Ser Met Thr Ile
        35                  40                  45

Asn Asp Glu Gln Asn Asp Ile Lys Asp Glu Asp Lys Gly Glu Ser Ile
    50                  55                  60

Ile Thr Ile Gly Glu Phe Ala Thr Val Arg Ala Thr Arg His Tyr Val
65                  70                  75                  80

Asn Gln Asp Ala Pro Phe Gly Val Ile His Leu Asp Ile Thr Thr Glu
                85                  90                  95

Asn Gly Thr Lys Thr Tyr Ser Tyr Asn Arg Lys Glu Gly Glu Phe Ala
            100                 105                 110

Ile Asn Trp Leu Val Pro Ile Gly Glu Asp Ser Pro Ala Ser Ile Lys
        115                 120                 125

Ile Ser Val Asp Glu Leu Asp Gln Gln Arg Asn Ile Ile Glu Val Pro
    130                 135                 140

Lys Leu Tyr Ser Ile Asp Leu Asp Asn Gln Thr Leu Glu Gln Trp Lys
145                 150                 155                 160

Thr Gln Gly Asn Val Ser Phe Ser Val Thr Arg Pro Glu His
                165                 170

<210> SEQ ID NO 83
<211> LENGTH: 173
<212> TYPE: PRT
<213> ORGANISM: Vibrio cholera

<400> SEQUENCE: 83

Val Glu Glu Ala Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
            20                  25                  30

Ser Asp Val Val Leu Asp Glu Gly Val Leu Tyr Tyr Ser Met Thr Ile
        35                  40                  45

Asn Asp Glu Gln Asn Asp Ile Lys Asp Glu Asp Lys Gly Glu Ser Ile
    50                  55                  60

```
Ile Thr Ile Gly Glu Phe Ala Thr Val Arg Ala Thr Arg His Tyr Val
 65                  70                  75                  80

Asn Gln Asp Ala Pro Phe Gly Val Ile His Leu Asp Ile Thr Thr Glu
                 85                  90                  95

Asn Gly Thr Lys Thr Tyr Ser Tyr Asn Arg Lys Glu Gly Glu Phe Ala
            100                 105                 110

Ile Asn Trp Leu Val Pro Ile Gly Glu Asp Ser Pro Ala Ser Ile Lys
        115                 120                 125

Ile Ser Val Asp Glu Leu Asp Gln Gln Arg Asn Ile Ile Glu Val Pro
    130                 135                 140

Lys Leu Tyr Ser Ile Asp Leu Asp Asn Gln Thr Leu Glu Gln Trp Lys
145                 150                 155                 160

Thr Gln Gly Asn Val Ser Phe Ser Val Thr Arg Pro Glu
                165                 170
```

<210> SEQ ID NO 84
<211> LENGTH: 172
<212> TYPE: PRT
<213> ORGANISM: Vibrio cholera

<400> SEQUENCE: 84

```
Val Glu Glu Ala Leu Asn Ile Phe Asp Glu Cys Arg Ser Pro Cys Ser
  1               5                  10                  15

Leu Thr Pro Glu Pro Gly Lys Pro Ile Gln Ser Lys Leu Ser Ile Pro
             20                  25                  30

Ser Asp Val Val Leu Asp Glu Gly Val Leu Tyr Tyr Ser Met Thr Ile
         35                  40                  45

Asn Asp Glu Gln Asn Asp Ile Lys Asp Glu Asp Lys Gly Glu Ser Ile
 50                  55                  60

Ile Thr Ile Gly Glu Phe Ala Thr Val Arg Ala Thr Arg His Tyr Val
 65                  70                  75                  80

Asn Gln Asp Ala Pro Phe Gly Val Ile His Leu Asp Ile Thr Thr Glu
                 85                  90                  95

Asn Gly Thr Lys Thr Tyr Ser Tyr Asn Arg Lys Glu Gly Glu Phe Ala
            100                 105                 110

Ile Asn Trp Leu Val Pro Ile Gly Glu Asp Ser Pro Ala Ser Ile Lys
        115                 120                 125

Ile Ser Val Asp Glu Leu Asp Gln Gln Arg Asn Ile Ile Glu Val Pro
    130                 135                 140

Lys Leu Tyr Ser Ile Asp Leu Asp Asn Gln Thr Leu Glu Gln Trp Lys
145                 150                 155                 160

Thr Gln Gly Asn Val Ser Phe Ser Val Thr Arg Pro
                165                 170
```

<210> SEQ ID NO 85
<211> LENGTH: 171
<212> TYPE: PRT
<213> ORGANISM: Vibrio cholera

<400> SEQUENCE: 85

```
Val Glu Glu Ala Leu Asn Ile Phe Asp Glu Cys Arg Ser Pro Cys Ser
  1               5                  10                  15

Leu Thr Pro Glu Pro Gly Lys Pro Ile Gln Ser Lys Leu Ser Ile Pro
             20                  25                  30

Ser Asp Val Val Leu Asp Glu Gly Val Leu Tyr Tyr Ser Met Thr Ile
         35                  40                  45
```

Asn Asp Glu Gln Asn Asp Ile Lys Asp Glu Asp Lys Gly Glu Ser Ile
    50                  55                  60

Ile Thr Ile Gly Glu Phe Ala Thr Val Arg Ala Thr Arg His Tyr Val
65                  70                  75                  80

Asn Gln Asp Ala Pro Phe Gly Val Ile His Leu Asp Ile Thr Thr Glu
                85                  90                  95

Asn Gly Thr Lys Thr Tyr Ser Tyr Asn Arg Lys Glu Gly Glu Phe Ala
                100                 105                 110

Ile Asn Trp Leu Val Pro Ile Gly Glu Asp Ser Pro Ala Ser Ile Lys
            115                 120                 125

Ile Ser Val Asp Glu Leu Asp Gln Gln Arg Asn Ile Ile Glu Val Pro
        130                 135                 140

Lys Leu Tyr Ser Ile Asp Leu Asp Asn Gln Thr Leu Glu Gln Trp Lys
145                 150                 155                 160

Thr Gln Gly Asn Val Ser Phe Ser Val Thr Arg
                165                 170

<210> SEQ ID NO 86
<211> LENGTH: 170
<212> TYPE: PRT
<213> ORGANISM: Vibrio cholera

<400> SEQUENCE: 86

Val Glu Glu Ala Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
                20                  25                  30

Ser Asp Val Val Leu Asp Glu Gly Val Leu Tyr Tyr Ser Met Thr Ile
            35                  40                  45

Asn Asp Glu Gln Asn Asp Ile Lys Asp Glu Asp Lys Gly Glu Ser Ile
    50                  55                  60

Ile Thr Ile Gly Glu Phe Ala Thr Val Arg Ala Thr Arg His Tyr Val
65                  70                  75                  80

Asn Gln Asp Ala Pro Phe Gly Val Ile His Leu Asp Ile Thr Thr Glu
                85                  90                  95

Asn Gly Thr Lys Thr Tyr Ser Tyr Asn Arg Lys Glu Gly Glu Phe Ala
                100                 105                 110

Ile Asn Trp Leu Val Pro Ile Gly Glu Asp Ser Pro Ala Ser Ile Lys
            115                 120                 125

Ile Ser Val Asp Glu Leu Asp Gln Gln Arg Asn Ile Ile Glu Val Pro
        130                 135                 140

Lys Leu Tyr Ser Ile Asp Leu Asp Asn Gln Thr Leu Glu Gln Trp Lys
145                 150                 155                 160

Thr Gln Gly Asn Val Ser Phe Ser Val Thr
                165                 170

<210> SEQ ID NO 87
<211> LENGTH: 169
<212> TYPE: PRT
<213> ORGANISM: Vibrio cholera

<400> SEQUENCE: 87

Val Glu Glu Ala Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
                20                  25                  30

Ser Asp Val Leu Asp Glu Gly Val Leu Tyr Tyr Ser Met Thr Ile
       35                 40                 45

Asn Asp Glu Gln Asn Asp Ile Lys Asp Glu Asp Lys Gly Glu Ser Ile
 50                 55                 60

Ile Thr Ile Gly Glu Phe Ala Thr Val Arg Ala Thr Arg His Tyr Val
65                 70                 75                 80

Asn Gln Asp Ala Pro Phe Gly Val Ile His Leu Asp Ile Thr Thr Glu
               85                 90                 95

Asn Gly Thr Lys Thr Tyr Ser Tyr Asn Arg Lys Glu Gly Glu Phe Ala
           100                105              110

Ile Asn Trp Leu Val Pro Ile Gly Glu Asp Ser Pro Ala Ser Ile Lys
       115                120              125

Ile Ser Val Asp Glu Leu Asp Gln Gln Arg Asn Ile Ile Glu Val Pro
   130                135                140

Lys Leu Tyr Ser Ile Asp Leu Asp Asn Gln Thr Leu Glu Gln Trp Lys
145                150                155              160

Thr Gln Gly Asn Val Ser Phe Ser Val
           165

<210> SEQ ID NO 88
<211> LENGTH: 168
<212> TYPE: PRT
<213> ORGANISM: Vibrio cholera

<400> SEQUENCE: 88

Val Glu Glu Ala Leu Asn Ile Phe Asp Glu Cys Arg Ser Pro Cys Ser
1               5                 10                 15

Leu Thr Pro Glu Pro Gly Lys Pro Ile Gln Ser Lys Leu Ser Ile Pro
            20                25                 30

Ser Asp Val Leu Asp Glu Gly Val Leu Tyr Tyr Ser Met Thr Ile
       35                 40                 45

Asn Asp Glu Gln Asn Asp Ile Lys Asp Glu Asp Lys Gly Glu Ser Ile
 50                 55                 60

Ile Thr Ile Gly Glu Phe Ala Thr Val Arg Ala Thr Arg His Tyr Val
65                 70                 75                 80

Asn Gln Asp Ala Pro Phe Gly Val Ile His Leu Asp Ile Thr Thr Glu
               85                 90                 95

Asn Gly Thr Lys Thr Tyr Ser Tyr Asn Arg Lys Glu Gly Glu Phe Ala
           100                105              110

Ile Asn Trp Leu Val Pro Ile Gly Glu Asp Ser Pro Ala Ser Ile Lys
       115                120              125

Ile Ser Val Asp Glu Leu Asp Gln Gln Arg Asn Ile Ile Glu Val Pro
   130                135                140

Lys Leu Tyr Ser Ile Asp Leu Asp Asn Gln Thr Leu Glu Gln Trp Lys
145                150                155              160

Thr Gln Gly Asn Val Ser Phe Ser
           165

<210> SEQ ID NO 89
<211> LENGTH: 167
<212> TYPE: PRT
<213> ORGANISM: Vibrio cholera

<400> SEQUENCE: 89

Val Glu Glu Ala Leu Asn Ile Phe Asp Glu Cys Arg Ser Pro Cys Ser
1               5                 10                 15

```
Leu Thr Pro Glu Pro Gly Lys Pro Ile Gln Ser Lys Leu Ser Ile Pro
             20                  25                  30

Ser Asp Val Val Leu Asp Glu Gly Val Leu Tyr Tyr Ser Met Thr Ile
         35                  40                  45

Asn Asp Glu Gln Asn Asp Ile Lys Asp Glu Asp Lys Gly Glu Ser Ile
     50                  55                  60

Ile Thr Ile Gly Glu Phe Ala Thr Val Arg Ala Thr Arg His Tyr Val
 65                  70                  75                  80

Asn Gln Asp Ala Pro Phe Gly Val Ile His Leu Asp Ile Thr Thr Glu
                 85                  90                  95

Asn Gly Thr Lys Thr Tyr Ser Tyr Asn Arg Lys Glu Gly Glu Phe Ala
            100                 105                 110

Ile Asn Trp Leu Val Pro Ile Gly Glu Asp Ser Pro Ala Ser Ile Lys
        115                 120                 125

Ile Ser Val Asp Glu Leu Asp Gln Gln Arg Asn Ile Ile Glu Val Pro
    130                 135                 140

Lys Leu Tyr Ser Ile Asp Leu Asp Asn Gln Thr Leu Glu Gln Trp Lys
145                 150                 155                 160

Thr Gln Gly Asn Val Ser Phe
            165
```

<210> SEQ ID NO 90
<211> LENGTH: 166
<212> TYPE: PRT
<213> ORGANISM: Vibrio cholera

<400> SEQUENCE: 90

```
Val Glu Glu Ala Leu Asn Ile Phe Asp Glu Cys Arg Ser Pro Cys Ser
 1               5                  10                  15

Leu Thr Pro Glu Pro Gly Lys Pro Ile Gln Ser Lys Leu Ser Ile Pro
             20                  25                  30

Ser Asp Val Val Leu Asp Glu Gly Val Leu Tyr Tyr Ser Met Thr Ile
         35                  40                  45

Asn Asp Glu Gln Asn Asp Ile Lys Asp Glu Asp Lys Gly Glu Ser Ile
     50                  55                  60

Ile Thr Ile Gly Glu Phe Ala Thr Val Arg Ala Thr Arg His Tyr Val
 65                  70                  75                  80

Asn Gln Asp Ala Pro Phe Gly Val Ile His Leu Asp Ile Thr Thr Glu
                 85                  90                  95

Asn Gly Thr Lys Thr Tyr Ser Tyr Asn Arg Lys Glu Gly Glu Phe Ala
            100                 105                 110

Ile Asn Trp Leu Val Pro Ile Gly Glu Asp Ser Pro Ala Ser Ile Lys
        115                 120                 125

Ile Ser Val Asp Glu Leu Asp Gln Gln Arg Asn Ile Ile Glu Val Pro
    130                 135                 140

Lys Leu Tyr Ser Ile Asp Leu Asp Asn Gln Thr Leu Glu Gln Trp Lys
145                 150                 155                 160

Thr Gln Gly Asn Val Ser
            165
```

<210> SEQ ID NO 91
<211> LENGTH: 165
<212> TYPE: PRT
<213> ORGANISM: Vibrio cholera

<400> SEQUENCE: 91

```
Val Glu Glu Ala Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
            20                  25                  30

Ser Asp Val Val Leu Asp Glu Gly Val Leu Tyr Tyr Ser Met Thr Ile
        35                  40                  45

Asn Asp Glu Gln Asn Asp Ile Lys Asp Glu Asp Lys Gly Glu Ser Ile
    50                  55                  60

Ile Thr Ile Gly Glu Phe Ala Thr Val Arg Ala Thr Arg His Tyr Val
65                  70                  75                  80

Asn Gln Asp Ala Pro Phe Gly Val Ile His Leu Asp Ile Thr Thr Glu
                85                  90                  95

Asn Gly Thr Lys Thr Tyr Ser Tyr Asn Arg Lys Glu Gly Glu Phe Ala
            100                 105                 110

Ile Asn Trp Leu Val Pro Ile Gly Glu Asp Ser Pro Ala Ser Ile Lys
        115                 120                 125

Ile Ser Val Asp Glu Leu Asp Gln Gln Arg Asn Ile Ile Glu Val Pro
    130                 135                 140

Lys Leu Tyr Ser Ile Asp Leu Asp Asn Gln Thr Leu Glu Gln Trp Lys
145                 150                 155                 160

Thr Gln Gly Asn Val
                165
```

<210> SEQ ID NO 92
<211> LENGTH: 164
<212> TYPE: PRT
<213> ORGANISM: Vibrio cholera

<400> SEQUENCE: 92

```
Val Glu Glu Ala Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
            20                  25                  30

Ser Asp Val Val Leu Asp Glu Gly Val Leu Tyr Tyr Ser Met Thr Ile
        35                  40                  45

Asn Asp Glu Gln Asn Asp Ile Lys Asp Glu Asp Lys Gly Glu Ser Ile
    50                  55                  60

Ile Thr Ile Gly Glu Phe Ala Thr Val Arg Ala Thr Arg His Tyr Val
65                  70                  75                  80

Asn Gln Asp Ala Pro Phe Gly Val Ile His Leu Asp Ile Thr Thr Glu
                85                  90                  95

Asn Gly Thr Lys Thr Tyr Ser Tyr Asn Arg Lys Glu Gly Glu Phe Ala
            100                 105                 110

Ile Asn Trp Leu Val Pro Ile Gly Glu Asp Ser Pro Ala Ser Ile Lys
        115                 120                 125

Ile Ser Val Asp Glu Leu Asp Gln Gln Arg Asn Ile Ile Glu Val Pro
    130                 135                 140

Lys Leu Tyr Ser Ile Asp Leu Asp Asn Gln Thr Leu Glu Gln Trp Lys
145                 150                 155                 160

Thr Gln Gly Asn
```

<210> SEQ ID NO 93
<211> LENGTH: 163

```
<212> TYPE: PRT
<213> ORGANISM: Vibrio cholera

<400> SEQUENCE: 93

Val Glu Glu Ala Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
            20                  25                  30

Ser Asp Val Val Leu Asp Glu Gly Val Leu Tyr Tyr Ser Met Thr Ile
        35                  40                  45

Asn Asp Glu Gln Asn Asp Ile Lys Asp Glu Asp Lys Gly Glu Ser Ile
    50                  55                  60

Ile Thr Ile Gly Glu Phe Ala Thr Val Arg Ala Thr Arg His Tyr Val
65                  70                  75                  80

Asn Gln Asp Ala Pro Phe Gly Val Ile His Leu Asp Ile Thr Thr Glu
                85                  90                  95

Asn Gly Thr Lys Thr Tyr Ser Tyr Asn Arg Lys Glu Gly Glu Phe Ala
            100                 105                 110

Ile Asn Trp Leu Val Pro Ile Gly Glu Asp Ser Pro Ala Ser Ile Lys
        115                 120                 125

Ile Ser Val Asp Glu Leu Asp Gln Gln Arg Asn Ile Ile Glu Val Pro
    130                 135                 140

Lys Leu Tyr Ser Ile Asp Leu Asp Asn Gln Thr Leu Glu Gln Trp Lys
145                 150                 155                 160

Thr Gln Gly

<210> SEQ ID NO 94
<211> LENGTH: 162
<212> TYPE: PRT
<213> ORGANISM: Vibrio cholera

<400> SEQUENCE: 94

Val Glu Glu Ala Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
            20                  25                  30

Ser Asp Val Val Leu Asp Glu Gly Val Leu Tyr Tyr Ser Met Thr Ile
        35                  40                  45

Asn Asp Glu Gln Asn Asp Ile Lys Asp Glu Asp Lys Gly Glu Ser Ile
    50                  55                  60

Ile Thr Ile Gly Glu Phe Ala Thr Val Arg Ala Thr Arg His Tyr Val
65                  70                  75                  80

Asn Gln Asp Ala Pro Phe Gly Val Ile His Leu Asp Ile Thr Thr Glu
                85                  90                  95

Asn Gly Thr Lys Thr Tyr Ser Tyr Asn Arg Lys Glu Gly Glu Phe Ala
            100                 105                 110

Ile Asn Trp Leu Val Pro Ile Gly Glu Asp Ser Pro Ala Ser Ile Lys
        115                 120                 125

Ile Ser Val Asp Glu Leu Asp Gln Gln Arg Asn Ile Ile Glu Val Pro
    130                 135                 140

Lys Leu Tyr Ser Ile Asp Leu Asp Asn Gln Thr Leu Glu Gln Trp Lys
145                 150                 155                 160

Thr Gln

<210> SEQ ID NO 95
```

<211> LENGTH: 161
<212> TYPE: PRT
<213> ORGANISM: Vibrio cholera

<400> SEQUENCE: 95

```
Val Glu Glu Ala Leu Asn Ile Phe Asp Glu Cys Arg Ser Pro Cys Ser
1               5                   10                  15
Leu Thr Pro Glu Pro Gly Lys Pro Ile Gln Ser Lys Leu Ser Ile Pro
            20                  25                  30
Ser Asp Val Val Leu Asp Glu Gly Val Leu Tyr Tyr Ser Met Thr Ile
        35                  40                  45
Asn Asp Glu Gln Asn Asp Ile Lys Asp Glu Asp Lys Gly Glu Ser Ile
    50                  55                  60
Ile Thr Ile Gly Glu Phe Ala Thr Val Arg Ala Thr Arg His Tyr Val
65                  70                  75                  80
Asn Gln Asp Ala Pro Phe Gly Val Ile His Leu Asp Ile Thr Thr Glu
                85                  90                  95
Asn Gly Thr Lys Thr Tyr Ser Tyr Asn Arg Lys Glu Gly Glu Phe Ala
            100                 105                 110
Ile Asn Trp Leu Val Pro Ile Gly Glu Asp Ser Pro Ala Ser Ile Lys
        115                 120                 125
Ile Ser Val Asp Glu Leu Asp Gln Gln Arg Asn Ile Ile Glu Val Pro
    130                 135                 140
Lys Leu Tyr Ser Ile Asp Leu Asp Asn Gln Thr Leu Glu Gln Trp Lys
145                 150                 155                 160
Thr
```

<210> SEQ ID NO 96
<211> LENGTH: 160
<212> TYPE: PRT
<213> ORGANISM: Vibrio cholera

<400> SEQUENCE: 96

```
Val Glu Glu Ala Leu Asn Ile Phe Asp Glu Cys Arg Ser Pro Cys Ser
1               5                   10                  15
Leu Thr Pro Glu Pro Gly Lys Pro Ile Gln Ser Lys Leu Ser Ile Pro
            20                  25                  30
Ser Asp Val Val Leu Asp Glu Gly Val Leu Tyr Tyr Ser Met Thr Ile
        35                  40                  45
Asn Asp Glu Gln Asn Asp Ile Lys Asp Glu Asp Lys Gly Glu Ser Ile
    50                  55                  60
Ile Thr Ile Gly Glu Phe Ala Thr Val Arg Ala Thr Arg His Tyr Val
65                  70                  75                  80
Asn Gln Asp Ala Pro Phe Gly Val Ile His Leu Asp Ile Thr Thr Glu
                85                  90                  95
Asn Gly Thr Lys Thr Tyr Ser Tyr Asn Arg Lys Glu Gly Glu Phe Ala
            100                 105                 110
Ile Asn Trp Leu Val Pro Ile Gly Glu Asp Ser Pro Ala Ser Ile Lys
        115                 120                 125
Ile Ser Val Asp Glu Leu Asp Gln Gln Arg Asn Ile Ile Glu Val Pro
    130                 135                 140
Lys Leu Tyr Ser Ile Asp Leu Asp Asn Gln Thr Leu Glu Gln Trp Lys
145                 150                 155                 160
```

<210> SEQ ID NO 97
<211> LENGTH: 159

```
<212> TYPE: PRT
<213> ORGANISM: Vibrio cholera

<400> SEQUENCE: 97

Val Glu Glu Ala Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
            20                  25                  30

Ser Asp Val Val Leu Asp Glu Gly Val Leu Tyr Tyr Ser Met Thr Ile
        35                  40                  45

Asn Asp Glu Gln Asn Asp Ile Lys Asp Glu Asp Lys Gly Glu Ser Ile
    50                  55                  60

Ile Thr Ile Gly Glu Phe Ala Thr Val Arg Ala Thr Arg His Tyr Val
65                  70                  75                  80

Asn Gln Asp Ala Pro Phe Gly Val Ile His Leu Asp Ile Thr Thr Glu
                85                  90                  95

Asn Gly Thr Lys Thr Tyr Ser Tyr Asn Arg Lys Glu Gly Glu Phe Ala
            100                 105                 110

Ile Asn Trp Leu Val Pro Ile Gly Glu Asp Ser Pro Ala Ser Ile Lys
        115                 120                 125

Ile Ser Val Asp Glu Leu Asp Gln Gln Arg Asn Ile Ile Glu Val Pro
    130                 135                 140

Lys Leu Tyr Ser Ile Asp Leu Asp Asn Gln Thr Leu Glu Gln Trp
145                 150                 155

<210> SEQ ID NO 98
<211> LENGTH: 158
<212> TYPE: PRT
<213> ORGANISM: Vibrio cholera

<400> SEQUENCE: 98

Val Glu Glu Ala Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
            20                  25                  30

Ser Asp Val Val Leu Asp Glu Gly Val Leu Tyr Tyr Ser Met Thr Ile
        35                  40                  45

Asn Asp Glu Gln Asn Asp Ile Lys Asp Glu Asp Lys Gly Glu Ser Ile
    50                  55                  60

Ile Thr Ile Gly Glu Phe Ala Thr Val Arg Ala Thr Arg His Tyr Val
65                  70                  75                  80

Asn Gln Asp Ala Pro Phe Gly Val Ile His Leu Asp Ile Thr Thr Glu
                85                  90                  95

Asn Gly Thr Lys Thr Tyr Ser Tyr Asn Arg Lys Glu Gly Glu Phe Ala
            100                 105                 110

Ile Asn Trp Leu Val Pro Ile Gly Glu Asp Ser Pro Ala Ser Ile Lys
        115                 120                 125

Ile Ser Val Asp Glu Leu Asp Gln Gln Arg Asn Ile Ile Glu Val Pro
    130                 135                 140

Lys Leu Tyr Ser Ile Asp Leu Asp Asn Gln Thr Leu Glu Gln
145                 150                 155

<210> SEQ ID NO 99
<211> LENGTH: 157
<212> TYPE: PRT
<213> ORGANISM: Vibrio cholera
```

<400> SEQUENCE: 99

```
Val Glu Glu Ala Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
            20                  25                  30

Ser Asp Val Val Leu Asp Glu Gly Val Leu Tyr Tyr Ser Met Thr Ile
        35                  40                  45

Asn Asp Glu Gln Asn Asp Ile Lys Asp Glu Asp Lys Gly Glu Ser Ile
    50                  55                  60

Ile Thr Ile Gly Glu Phe Ala Thr Val Arg Ala Thr Arg His Tyr Val
65                  70                  75                  80

Asn Gln Asp Ala Pro Phe Gly Val Ile His Leu Asp Ile Thr Thr Glu
                85                  90                  95

Asn Gly Thr Lys Thr Tyr Ser Tyr Asn Arg Lys Glu Gly Glu Phe Ala
            100                 105                 110

Ile Asn Trp Leu Val Pro Ile Gly Glu Asp Ser Pro Ala Ser Ile Lys
        115                 120                 125

Ile Ser Val Asp Glu Leu Asp Gln Gln Arg Asn Ile Ile Glu Val Pro
    130                 135                 140

Lys Leu Tyr Ser Ile Asp Leu Asp Asn Gln Thr Leu Glu
145                 150                 155
```

<210> SEQ ID NO 100
<211> LENGTH: 156
<212> TYPE: PRT
<213> ORGANISM: Vibrio cholera

<400> SEQUENCE: 100

```
Val Glu Glu Ala Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
            20                  25                  30

Ser Asp Val Val Leu Asp Glu Gly Val Leu Tyr Tyr Ser Met Thr Ile
        35                  40                  45

Asn Asp Glu Gln Asn Asp Ile Lys Asp Glu Asp Lys Gly Glu Ser Ile
    50                  55                  60

Ile Thr Ile Gly Glu Phe Ala Thr Val Arg Ala Thr Arg His Tyr Val
65                  70                  75                  80

Asn Gln Asp Ala Pro Phe Gly Val Ile His Leu Asp Ile Thr Thr Glu
                85                  90                  95

Asn Gly Thr Lys Thr Tyr Ser Tyr Asn Arg Lys Glu Gly Glu Phe Ala
            100                 105                 110

Ile Asn Trp Leu Val Pro Ile Gly Glu Asp Ser Pro Ala Ser Ile Lys
        115                 120                 125

Ile Ser Val Asp Glu Leu Asp Gln Gln Arg Asn Ile Ile Glu Val Pro
    130                 135                 140

Lys Leu Tyr Ser Ile Asp Leu Asp Asn Gln Thr Leu
145                 150                 155
```

<210> SEQ ID NO 101
<211> LENGTH: 155
<212> TYPE: PRT
<213> ORGANISM: Vibrio cholera

<400> SEQUENCE: 101

```
Val Glu Glu Ala Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
            20                  25                  30

Ser Asp Val Val Leu Asp Glu Gly Val Leu Tyr Tyr Ser Met Thr Ile
        35                  40                  45

Asn Asp Glu Gln Asn Asp Ile Lys Asp Glu Asp Lys Gly Glu Ser Ile
    50                  55                  60

Ile Thr Ile Gly Glu Phe Ala Thr Val Arg Ala Thr Arg His Tyr Val
65                  70                  75                  80

Asn Gln Asp Ala Pro Phe Gly Val Ile His Leu Asp Ile Thr Thr Glu
                85                  90                  95

Asn Gly Thr Lys Thr Tyr Ser Tyr Asn Arg Lys Glu Gly Glu Phe Ala
            100                 105                 110

Ile Asn Trp Leu Val Pro Ile Gly Glu Asp Ser Pro Ala Ser Ile Lys
                115                 120                 125

Ile Ser Val Asp Glu Leu Asp Gln Gln Arg Asn Ile Ile Glu Val Pro
    130                 135                 140

Lys Leu Tyr Ser Ile Asp Leu Asp Asn Gln Thr
145                 150                 155
```

<210> SEQ ID NO 102
<211> LENGTH: 154
<212> TYPE: PRT
<213> ORGANISM: Vibrio cholera

<400> SEQUENCE: 102

```
Val Glu Glu Ala Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
            20                  25                  30

Ser Asp Val Val Leu Asp Glu Gly Val Leu Tyr Tyr Ser Met Thr Ile
        35                  40                  45

Asn Asp Glu Gln Asn Asp Ile Lys Asp Glu Asp Lys Gly Glu Ser Ile
    50                  55                  60

Ile Thr Ile Gly Glu Phe Ala Thr Val Arg Ala Thr Arg His Tyr Val
65                  70                  75                  80

Asn Gln Asp Ala Pro Phe Gly Val Ile His Leu Asp Ile Thr Thr Glu
                85                  90                  95

Asn Gly Thr Lys Thr Tyr Ser Tyr Asn Arg Lys Glu Gly Glu Phe Ala
            100                 105                 110

Ile Asn Trp Leu Val Pro Ile Gly Glu Asp Ser Pro Ala Ser Ile Lys
                115                 120                 125

Ile Ser Val Asp Glu Leu Asp Gln Gln Arg Asn Ile Ile Glu Val Pro
    130                 135                 140

Lys Leu Tyr Ser Ile Asp Leu Asp Asn Gln
145                 150
```

<210> SEQ ID NO 103
<211> LENGTH: 153
<212> TYPE: PRT
<213> ORGANISM: Vibrio cholera -continued

<400> SEQUENCE: 103

| Val | Glu | Glu | Ala | Leu | Asn | Ile | Phe | Asp | Glu | Cys | Arg | Ser | Pro | Cys | Ser |
| 1 | | | | 5 | | | | | 10 | | | | | 15 | |

| Leu | Thr | Pro | Glu | Pro | Gly | Lys | Pro | Ile | Gln | Ser | Lys | Leu | Ser | Ile | Pro |
| | | | 20 | | | | | 25 | | | | | 30 | | |

| Ser | Asp | Val | Val | Leu | Asp | Glu | Gly | Val | Leu | Tyr | Tyr | Ser | Met | Thr | Ile |
| | | | 35 | | | | | 40 | | | | | 45 | | |

| Asn | Asp | Glu | Gln | Asn | Asp | Ile | Lys | Asp | Glu | Asp | Lys | Gly | Glu | Ser | Ile |
| | 50 | | | | | 55 | | | | | 60 | | | | |

| Ile | Thr | Ile | Gly | Glu | Phe | Ala | Thr | Val | Arg | Ala | Thr | Arg | His | Tyr | Val |
| 65 | | | | | 70 | | | | | 75 | | | | | 80 |

| Asn | Gln | Asp | Ala | Pro | Phe | Gly | Val | Ile | His | Leu | Asp | Ile | Thr | Thr | Glu |
| | | | | 85 | | | | | 90 | | | | | 95 | |

| Asn | Gly | Thr | Lys | Thr | Tyr | Ser | Tyr | Asn | Arg | Lys | Glu | Gly | Glu | Phe | Ala |
| | | | 100 | | | | | 105 | | | | | 110 | | |

| Ile | Asn | Trp | Leu | Val | Pro | Ile | Gly | Glu | Asp | Ser | Pro | Ala | Ser | Ile | Lys |
| | | | 115 | | | | | 120 | | | | | 125 | | |

| Ile | Ser | Val | Asp | Glu | Leu | Asp | Gln | Gln | Arg | Asn | Ile | Ile | Glu | Val | Pro |
| | 130 | | | | | 135 | | | | | 140 | | | | |

| Lys | Leu | Tyr | Ser | Ile | Asp | Leu | Asp | Asn |
| 145 | | | | | 150 | | | |

<210> SEQ ID NO 104
<211> LENGTH: 152
<212> TYPE: PRT
<213> ORGANISM: Vibrio cholera

<400> SEQUENCE: 104

| Val | Glu | Glu | Ala | Leu | Asn | Ile | Phe | Asp | Glu | Cys | Arg | Ser | Pro | Cys | Ser |
| 1 | | | | 5 | | | | | 10 | | | | | 15 | |

| Leu | Thr | Pro | Glu | Pro | Gly | Lys | Pro | Ile | Gln | Ser | Lys | Leu | Ser | Ile | Pro |
| | | | 20 | | | | | 25 | | | | | 30 | | |

| Ser | Asp | Val | Val | Leu | Asp | Glu | Gly | Val | Leu | Tyr | Tyr | Ser | Met | Thr | Ile |
| | | | 35 | | | | | 40 | | | | | 45 | | |

| Asn | Asp | Glu | Gln | Asn | Asp | Ile | Lys | Asp | Glu | Asp | Lys | Gly | Glu | Ser | Ile |
| | 50 | | | | | 55 | | | | | 60 | | | | |

| Ile | Thr | Ile | Gly | Glu | Phe | Ala | Thr | Val | Arg | Ala | Thr | Arg | His | Tyr | Val |
| 65 | | | | | 70 | | | | | 75 | | | | | 80 |

| Asn | Gln | Asp | Ala | Pro | Phe | Gly | Val | Ile | His | Leu | Asp | Ile | Thr | Thr | Glu |
| | | | | 85 | | | | | 90 | | | | | 95 | |

| Asn | Gly | Thr | Lys | Thr | Tyr | Ser | Tyr | Asn | Arg | Lys | Glu | Gly | Glu | Phe | Ala |
| | | | 100 | | | | | 105 | | | | | 110 | | |

| Ile | Asn | Trp | Leu | Val | Pro | Ile | Gly | Glu | Asp | Ser | Pro | Ala | Ser | Ile | Lys |
| | | | 115 | | | | | 120 | | | | | 125 | | |

| Ile | Ser | Val | Asp | Glu | Leu | Asp | Gln | Gln | Arg | Asn | Ile | Ile | Glu | Val | Pro |
| | 130 | | | | | 135 | | | | | 140 | | | | |

| Lys | Leu | Tyr | Ser | Ile | Asp | Leu | Asp |
| 145 | | | | | 150 | | |

<210> SEQ ID NO 105
<211> LENGTH: 151
<212> TYPE: PRT
<213> ORGANISM: Vibrio cholera

<400> SEQUENCE: 105

Val Glu Glu Ala Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
            20                  25                  30

Ser Asp Val Val Leu Asp Glu Gly Val Leu Tyr Tyr Ser Met Thr Ile
        35                  40                  45

Asn Asp Glu Gln Asn Asp Ile Lys Asp Glu Asp Lys Gly Glu Ser Ile
    50                  55                  60

Ile Thr Ile Gly Glu Phe Ala Thr Val Arg Ala Thr Arg His Tyr Val
65                  70                  75                  80

Asn Gln Asp Ala Pro Phe Gly Val Ile His Leu Asp Ile Thr Thr Glu
                85                  90                  95

Asn Gly Thr Lys Thr Tyr Ser Tyr Asn Arg Lys Glu Gly Glu Phe Ala
            100                 105                 110

Ile Asn Trp Leu Val Pro Ile Gly Glu Asp Ser Pro Ala Ser Ile Lys
        115                 120                 125

Ile Ser Val Asp Glu Leu Asp Gln Gln Arg Asn Ile Ile Glu Val Pro
    130                 135                 140

Lys Leu Tyr Ser Ile Asp Leu
145                 150

<210> SEQ ID NO 106
<211> LENGTH: 150
<212> TYPE: PRT
<213> ORGANISM: Vibrio cholera

<400> SEQUENCE: 106

Val Glu Glu Ala Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
            20                  25                  30

Ser Asp Val Val Leu Asp Glu Gly Val Leu Tyr Tyr Ser Met Thr Ile
        35                  40                  45

Asn Asp Glu Gln Asn Asp Ile Lys Asp Glu Asp Lys Gly Glu Ser Ile
    50                  55                  60

Ile Thr Ile Gly Glu Phe Ala Thr Val Arg Ala Thr Arg His Tyr Val
65                  70                  75                  80

Asn Gln Asp Ala Pro Phe Gly Val Ile His Leu Asp Ile Thr Thr Glu
                85                  90                  95

Asn Gly Thr Lys Thr Tyr Ser Tyr Asn Arg Lys Glu Gly Glu Phe Ala
            100                 105                 110

Ile Asn Trp Leu Val Pro Ile Gly Glu Asp Ser Pro Ala Ser Ile Lys
        115                 120                 125

Ile Ser Val Asp Glu Leu Asp Gln Gln Arg Asn Ile Ile Glu Val Pro
    130                 135                 140

Lys Leu Tyr Ser Ile Asp
145                 150

<210> SEQ ID NO 107
<211> LENGTH: 151
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 107

Met Val Glu Glu Ala Leu Asn Ile Phe Asp Glu Cys Arg Ser Pro Cys
1               5                   10                  15

Ser Leu Thr Pro Glu Pro Gly Lys Pro Ile Gln Ser Lys Leu Ser Ile
            20                  25                  30

Pro Ser Asp Val Val Leu Asp Glu Gly Val Leu Tyr Tyr Ser Met Thr
        35                  40                  45

Ile Asn Asp Glu Gln Asn Asp Ile Lys Asp Glu Asp Lys Gly Glu Ser
50                  55                  60

Ile Ile Thr Ile Gly Glu Phe Ala Thr Val Arg Ala Thr Arg His Tyr
65                  70                  75                  80

Val Asn Gln Asp Ala Pro Phe Gly Val Ile His Leu Asp Ile Thr Thr
                85                  90                  95

Glu Asn Gly Thr Lys Thr Tyr Ser Tyr Asn Arg Lys Glu Gly Glu Phe
            100                 105                 110

Ala Ile Asn Trp Leu Val Pro Ile Gly Glu Asp Ser Pro Ala Ser Ile
        115                 120                 125

Lys Ile Ser Val Asp Glu Leu Asp Gln Gln Arg Asn Ile Ile Glu Val
130                 135                 140

Pro Lys Leu Tyr Ser Ile Asp
145                 150

<210> SEQ ID NO 108
<211> LENGTH: 149
<212> TYPE: PRT
<213> ORGANISM: Vibrio cholera

<400> SEQUENCE: 108

Val Glu Glu Ala Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
            20                  25                  30

Ser Asp Val Val Leu Asp Glu Gly Val Leu Tyr Tyr Ser Met Thr Ile
        35                  40                  45

Asn Asp Glu Gln Asn Asp Ile Lys Asp Glu Asp Lys Gly Glu Ser Ile
50                  55                  60

Ile Thr Ile Gly Glu Phe Ala Thr Val Arg Ala Thr Arg His Tyr Val
65                  70                  75                  80

Asn Gln Asp Ala Pro Phe Gly Val Ile His Leu Asp Ile Thr Thr Glu
                85                  90                  95

Asn Gly Thr Lys Thr Tyr Ser Tyr Asn Arg Lys Glu Gly Glu Phe Ala
            100                 105                 110

Ile Asn Trp Leu Val Pro Ile Gly Glu Asp Ser Pro Ala Ser Ile Lys
        115                 120                 125

Ile Ser Val Asp Glu Leu Asp Gln Gln Arg Asn Ile Ile Glu Val Pro
130                 135                 140

Lys Leu Tyr Ser Ile
145

<210> SEQ ID NO 109
<211> LENGTH: 148
<212> TYPE: PRT
<213> ORGANISM: Vibrio cholera

<400> SEQUENCE: 109

Val Glu Glu Ala Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
            20                  25                  30

Ser Asp Val Val Leu Asp Glu Gly Val Leu Tyr Tyr Ser Met Thr Ile
        35                  40                  45

Asn Asp Glu Gln Asn Asp Ile Lys Asp Glu Asp Lys Gly Glu Ser Ile
    50                  55                  60

Ile Thr Ile Gly Glu Phe Ala Thr Val Arg Ala Thr Arg His Tyr Val
65                  70                  75                  80

Asn Gln Asp Ala Pro Phe Gly Val Ile His Leu Asp Ile Thr Thr Glu
                85                  90                  95

Asn Gly Thr Lys Thr Tyr Ser Tyr Asn Arg Lys Glu Gly Glu Phe Ala
            100                 105                 110

Ile Asn Trp Leu Val Pro Ile Gly Glu Asp Ser Pro Ala Ser Ile Lys
        115                 120                 125

Ile Ser Val Asp Glu Leu Asp Gln Gln Arg Asn Ile Ile Glu Val Pro
    130                 135                 140

Lys Leu Tyr Ser
145

<210> SEQ ID NO 110
<211> LENGTH: 147
<212> TYPE: PRT
<213> ORGANISM: Vibrio cholera

<400> SEQUENCE: 110

Val Glu Glu Ala Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
            20                  25                  30

Ser Asp Val Val Leu Asp Glu Gly Val Leu Tyr Tyr Ser Met Thr Ile
        35                  40                  45

Asn Asp Glu Gln Asn Asp Ile Lys Asp Glu Asp Lys Gly Glu Ser Ile
    50                  55                  60

Ile Thr Ile Gly Glu Phe Ala Thr Val Arg Ala Thr Arg His Tyr Val
65                  70                  75                  80

Asn Gln Asp Ala Pro Phe Gly Val Ile His Leu Asp Ile Thr Thr Glu
                85                  90                  95

Asn Gly Thr Lys Thr Tyr Ser Tyr Asn Arg Lys Glu Gly Glu Phe Ala
            100                 105                 110

Ile Asn Trp Leu Val Pro Ile Gly Glu Asp Ser Pro Ala Ser Ile Lys
        115                 120                 125

Ile Ser Val Asp Glu Leu Asp Gln Gln Arg Asn Ile Ile Glu Val Pro
    130                 135                 140

Lys Leu Tyr
145

<210> SEQ ID NO 111
<211> LENGTH: 146
<212> TYPE: PRT
<213> ORGANISM: Vibrio cholera

<400> SEQUENCE: 111

```
Val Glu Glu Ala Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
            20                  25                  30

Ser Asp Val Val Leu Asp Glu Gly Val Leu Tyr Tyr Ser Met Thr Ile
        35                  40                  45

Asn Asp Glu Gln Asn Asp Ile Lys Asp Glu Asp Lys Gly Glu Ser Ile
    50                  55                  60

Ile Thr Ile Gly Glu Phe Ala Thr Val Arg Ala Thr Arg His Tyr Val
65                  70                  75                  80

Asn Gln Asp Ala Pro Phe Gly Val Ile His Leu Asp Ile Thr Thr Glu
                85                  90                  95

Asn Gly Thr Lys Thr Tyr Ser Tyr Asn Arg Lys Glu Gly Glu Phe Ala
            100                 105                 110

Ile Asn Trp Leu Val Pro Ile Gly Glu Asp Ser Pro Ala Ser Ile Lys
        115                 120                 125

Ile Ser Val Asp Glu Leu Asp Gln Gln Arg Asn Ile Ile Glu Val Pro
    130                 135                 140

Lys Leu
145
```

<210> SEQ ID NO 112
<211> LENGTH: 145
<212> TYPE: PRT
<213> ORGANISM: Vibrio cholera

<400> SEQUENCE: 112

```
Val Glu Glu Ala Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
            20                  25                  30

Ser Asp Val Val Leu Asp Glu Gly Val Leu Tyr Tyr Ser Met Thr Ile
        35                  40                  45

Asn Asp Glu Gln Asn Asp Ile Lys Asp Glu Asp Lys Gly Glu Ser Ile
    50                  55                  60

Ile Thr Ile Gly Glu Phe Ala Thr Val Arg Ala Thr Arg His Tyr Val
65                  70                  75                  80

Asn Gln Asp Ala Pro Phe Gly Val Ile His Leu Asp Ile Thr Thr Glu
                85                  90                  95

Asn Gly Thr Lys Thr Tyr Ser Tyr Asn Arg Lys Glu Gly Glu Phe Ala
            100                 105                 110

Ile Asn Trp Leu Val Pro Ile Gly Glu Asp Ser Pro Ala Ser Ile Lys
        115                 120                 125

Ile Ser Val Asp Glu Leu Asp Gln Gln Arg Asn Ile Ile Glu Val Pro
    130                 135                 140

Lys
145
```

<210> SEQ ID NO 113
<211> LENGTH: 144
<212> TYPE: PRT
<213> ORGANISM: Vibrio cholera

<400> SEQUENCE: 113

Val Glu Glu Ala Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
            20                  25                  30

Ser Asp Val Val Leu Asp Glu Gly Val Leu Tyr Tyr Ser Met Thr Ile
        35                  40                  45

Asn Asp Glu Gln Asn Asp Ile Lys Asp Glu Asp Lys Gly Glu Ser Ile
    50                  55                  60

Ile Thr Ile Gly Glu Phe Ala Thr Val Arg Ala Thr Arg His Tyr Val
65                  70                  75                  80

Asn Gln Asp Ala Pro Phe Gly Val Ile His Leu Asp Ile Thr Thr Glu
                85                  90                  95

Asn Gly Thr Lys Thr Tyr Ser Tyr Asn Arg Lys Glu Gly Glu Phe Ala
            100                 105                 110

Ile Asn Trp Leu Val Pro Ile Gly Glu Asp Ser Pro Ala Ser Ile Lys
        115                 120                 125

Ile Ser Val Asp Glu Leu Asp Gln Gln Arg Asn Ile Ile Glu Val Pro
    130                 135                 140

<210> SEQ ID NO 114
<211> LENGTH: 143
<212> TYPE: PRT
<213> ORGANISM: Vibrio cholera

<400> SEQUENCE: 114

Val Glu Glu Ala Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
            20                  25                  30

Ser Asp Val Val Leu Asp Glu Gly Val Leu Tyr Tyr Ser Met Thr Ile
        35                  40                  45

Asn Asp Glu Gln Asn Asp Ile Lys Asp Glu Asp Lys Gly Glu Ser Ile
    50                  55                  60

Ile Thr Ile Gly Glu Phe Ala Thr Val Arg Ala Thr Arg His Tyr Val
65                  70                  75                  80

Asn Gln Asp Ala Pro Phe Gly Val Ile His Leu Asp Ile Thr Thr Glu
                85                  90                  95

Asn Gly Thr Lys Thr Tyr Ser Tyr Asn Arg Lys Glu Gly Glu Phe Ala
            100                 105                 110

Ile Asn Trp Leu Val Pro Ile Gly Glu Asp Ser Pro Ala Ser Ile Lys
        115                 120                 125

Ile Ser Val Asp Glu Leu Asp Gln Gln Arg Asn Ile Ile Glu Val
    130                 135                 140

<210> SEQ ID NO 115
<211> LENGTH: 142
<212> TYPE: PRT
<213> ORGANISM: Vibrio cholera

<400> SEQUENCE: 115

Val Glu Glu Ala Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
            20                  25                  30

Ser Asp Val Val Leu Asp Glu Gly Val Leu Tyr Tyr Ser Met Thr Ile
        35                  40                   45

Asn Asp Glu Gln Asn Asp Ile Lys Asp Glu Asp Lys Gly Glu Ser Ile
  50                      55                   60

Ile Thr Ile Gly Glu Phe Ala Thr Val Arg Ala Thr Arg His Tyr Val
65                  70                   75                   80

Asn Gln Asp Ala Pro Phe Gly Val Ile His Leu Asp Ile Thr Thr Glu
                  85                   90                   95

Asn Gly Thr Lys Thr Tyr Ser Tyr Asn Arg Lys Glu Gly Glu Phe Ala
            100                 105                110

Ile Asn Trp Leu Val Pro Ile Gly Glu Asp Ser Pro Ala Ser Ile Lys
            115                 120                125

Ile Ser Val Asp Glu Leu Asp Gln Gln Arg Asn Ile Ile Glu
130                 135                 140

<210> SEQ ID NO 116
<211> LENGTH: 141
<212> TYPE: PRT
<213> ORGANISM: Vibrio cholera

<400> SEQUENCE: 116

Val Glu Glu Ala Leu Asn Ile Phe Asp Glu Cys Arg Ser Pro Cys Ser
1                5                   10                   15

Leu Thr Pro Glu Pro Gly Lys Pro Ile Gln Ser Lys Leu Ser Ile Pro
            20                   25                  30

Ser Asp Val Val Leu Asp Glu Gly Val Leu Tyr Tyr Ser Met Thr Ile
        35                  40                   45

Asn Asp Glu Gln Asn Asp Ile Lys Asp Glu Asp Lys Gly Glu Ser Ile
  50                      55                   60

Ile Thr Ile Gly Glu Phe Ala Thr Val Arg Ala Thr Arg His Tyr Val
65                  70                   75                   80

Asn Gln Asp Ala Pro Phe Gly Val Ile His Leu Asp Ile Thr Thr Glu
                  85                   90                   95

Asn Gly Thr Lys Thr Tyr Ser Tyr Asn Arg Lys Glu Gly Glu Phe Ala
            100                 105                110

Ile Asn Trp Leu Val Pro Ile Gly Glu Asp Ser Pro Ala Ser Ile Lys
            115                 120                125

Ile Ser Val Asp Glu Leu Asp Gln Gln Arg Asn Ile Ile
130                 135                 140

<210> SEQ ID NO 117
<211> LENGTH: 140
<212> TYPE: PRT
<213> ORGANISM: Vibrio cholera

<400> SEQUENCE: 117

Val Glu Glu Ala Leu Asn Ile Phe Asp Glu Cys Arg Ser Pro Cys Ser
1                5                   10                   15

Leu Thr Pro Glu Pro Gly Lys Pro Ile Gln Ser Lys Leu Ser Ile Pro
            20                   25                  30

Ser Asp Val Val Leu Asp Glu Gly Val Leu Tyr Tyr Ser Met Thr Ile
        35                  40                   45

Asn Asp Glu Gln Asn Asp Ile Lys Asp Glu Asp Lys Gly Glu Ser Ile
  50                      55                   60

Ile Thr Ile Gly Glu Phe Ala Thr Val Arg Ala Thr Arg His Tyr Val
65                  70                   75                   80

```
Asn Gln Asp Ala Pro Phe Gly Val Ile His Leu Asp Ile Thr Thr Glu
                85                  90                  95

Asn Gly Thr Lys Thr Tyr Ser Tyr Asn Arg Lys Glu Gly Glu Phe Ala
            100                 105                 110

Ile Asn Trp Leu Val Pro Ile Gly Glu Asp Ser Pro Ala Ser Ile Lys
        115                 120                 125

Ile Ser Val Asp Glu Leu Asp Gln Gln Arg Asn Ile
    130                 135                 140
```

<210> SEQ ID NO 118
<211> LENGTH: 139
<212> TYPE: PRT
<213> ORGANISM: Vibrio cholera

<400> SEQUENCE: 118

```
Val Glu Glu Ala Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
            20                  25                  30

Ser Asp Val Val Leu Asp Glu Gly Val Leu Tyr Tyr Ser Met Thr Ile
        35                  40                  45

Asn Asp Glu Gln Asn Asp Ile Lys Asp Glu Asp Lys Gly Glu Ser Ile
    50                  55                  60

Ile Thr Ile Gly Glu Phe Ala Thr Val Arg Ala Thr Arg His Tyr Val
65                  70                  75                  80

Asn Gln Asp Ala Pro Phe Gly Val Ile His Leu Asp Ile Thr Thr Glu
                85                  90                  95

Asn Gly Thr Lys Thr Tyr Ser Tyr Asn Arg Lys Glu Gly Glu Phe Ala
            100                 105                 110

Ile Asn Trp Leu Val Pro Ile Gly Glu Asp Ser Pro Ala Ser Ile Lys
        115                 120                 125

Ile Ser Val Asp Glu Leu Asp Gln Gln Arg Asn
    130                 135
```

<210> SEQ ID NO 119
<211> LENGTH: 138
<212> TYPE: PRT
<213> ORGANISM: Vibrio cholera

<400> SEQUENCE: 119

```
Val Glu Glu Ala Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
            20                  25                  30

Ser Asp Val Val Leu Asp Glu Gly Val Leu Tyr Tyr Ser Met Thr Ile
        35                  40                  45

Asn Asp Glu Gln Asn Asp Ile Lys Asp Glu Asp Lys Gly Glu Ser Ile
    50                  55                  60

Ile Thr Ile Gly Glu Phe Ala Thr Val Arg Ala Thr Arg His Tyr Val
65                  70                  75                  80

Asn Gln Asp Ala Pro Phe Gly Val Ile His Leu Asp Ile Thr Thr Glu
                85                  90                  95

Asn Gly Thr Lys Thr Tyr Ser Tyr Asn Arg Lys Glu Gly Glu Phe Ala
            100                 105                 110

Ile Asn Trp Leu Val Pro Ile Gly Glu Asp Ser Pro Ala Ser Ile Lys
        115                 120                 125
```

Ile Ser Val Asp Glu Leu Asp Gln Gln Arg
    130                 135

<210> SEQ ID NO 120
<211> LENGTH: 137
<212> TYPE: PRT
<213> ORGANISM: Vibrio cholera

<400> SEQUENCE: 120

Val Glu Glu Ala Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
            20                  25                  30

Ser Asp Val Val Leu Asp Glu Gly Val Leu Tyr Tyr Ser Met Thr Ile
        35                  40                  45

Asn Asp Glu Gln Asn Asp Ile Lys Asp Glu Asp Lys Gly Glu Ser Ile
    50                  55                  60

Ile Thr Ile Gly Glu Phe Ala Thr Val Arg Ala Thr Arg His Tyr Val
65                  70                  75                  80

Asn Gln Asp Ala Pro Phe Gly Val Ile His Leu Asp Ile Thr Thr Glu
                85                  90                  95

Asn Gly Thr Lys Thr Tyr Ser Tyr Asn Arg Lys Glu Gly Glu Phe Ala
            100                 105                 110

Ile Asn Trp Leu Val Pro Ile Gly Glu Asp Ser Pro Ala Ser Ile Lys
        115                 120                 125

Ile Ser Val Asp Glu Leu Asp Gln Gln
    130                 135

<210> SEQ ID NO 121
<211> LENGTH: 136
<212> TYPE: PRT
<213> ORGANISM: Vibrio cholera

<400> SEQUENCE: 121

Val Glu Glu Ala Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
            20                  25                  30

Ser Asp Val Val Leu Asp Glu Gly Val Leu Tyr Tyr Ser Met Thr Ile
        35                  40                  45

Asn Asp Glu Gln Asn Asp Ile Lys Asp Glu Asp Lys Gly Glu Ser Ile
    50                  55                  60

Ile Thr Ile Gly Glu Phe Ala Thr Val Arg Ala Thr Arg His Tyr Val
65                  70                  75                  80

Asn Gln Asp Ala Pro Phe Gly Val Ile His Leu Asp Ile Thr Thr Glu
                85                  90                  95

Asn Gly Thr Lys Thr Tyr Ser Tyr Asn Arg Lys Glu Gly Glu Phe Ala
            100                 105                 110

Ile Asn Trp Leu Val Pro Ile Gly Glu Asp Ser Pro Ala Ser Ile Lys
        115                 120                 125

Ile Ser Val Asp Glu Leu Asp Gln
    130                 135

<210> SEQ ID NO 122
<211> LENGTH: 135
<212> TYPE: PRT
<213> ORGANISM: Vibrio cholera

<400> SEQUENCE: 122

Val Glu Glu Ala Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
            20                  25                  30

Ser Asp Val Val Leu Asp Glu Gly Val Leu Tyr Tyr Ser Met Thr Ile
        35                  40                  45

Asn Asp Glu Gln Asn Asp Ile Lys Asp Glu Lys Gly Glu Ser Ile
    50                  55                  60

Ile Thr Ile Gly Glu Phe Ala Thr Val Arg Ala Thr Arg His Tyr Val
65                  70                  75                  80

Asn Gln Asp Ala Pro Phe Gly Val Ile His Leu Asp Ile Thr Thr Glu
                85                  90                  95

Asn Gly Thr Lys Thr Tyr Ser Tyr Asn Arg Lys Glu Gly Glu Phe Ala
            100                 105                 110

Ile Asn Trp Leu Val Pro Ile Gly Glu Asp Ser Pro Ala Ser Ile Lys
        115                 120                 125

Ile Ser Val Asp Glu Leu Asp
    130                 135

<210> SEQ ID NO 123
<211> LENGTH: 134
<212> TYPE: PRT
<213> ORGANISM: Vibrio cholera

<400> SEQUENCE: 123

Val Glu Glu Ala Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
            20                  25                  30

Ser Asp Val Val Leu Asp Glu Gly Val Leu Tyr Tyr Ser Met Thr Ile
        35                  40                  45

Asn Asp Glu Gln Asn Asp Ile Lys Asp Glu Lys Gly Glu Ser Ile
    50                  55                  60

Ile Thr Ile Gly Glu Phe Ala Thr Val Arg Ala Thr Arg His Tyr Val
65                  70                  75                  80

Asn Gln Asp Ala Pro Phe Gly Val Ile His Leu Asp Ile Thr Thr Glu
                85                  90                  95

Asn Gly Thr Lys Thr Tyr Ser Tyr Asn Arg Lys Glu Gly Glu Phe Ala
            100                 105                 110

Ile Asn Trp Leu Val Pro Ile Gly Glu Asp Ser Pro Ala Ser Ile Lys
        115                 120                 125

Ile Ser Val Asp Glu Leu
    130

<210> SEQ ID NO 124
<211> LENGTH: 133
<212> TYPE: PRT
<213> ORGANISM: Vibrio cholera

<400> SEQUENCE: 124

Val Glu Glu Ala Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
            20                  25                  30

```
Ser Asp Val Val Leu Asp Glu Gly Val Leu Tyr Tyr Ser Met Thr Ile
            35                  40                  45

Asn Asp Glu Gln Asn Asp Ile Lys Asp Glu Asp Lys Gly Glu Ser Ile
 50                  55                  60

Ile Thr Ile Gly Glu Phe Ala Thr Val Arg Ala Thr Arg His Tyr Val
 65                  70                  75                  80

Asn Gln Asp Ala Pro Phe Gly Val Ile His Leu Asp Ile Thr Thr Glu
                85                  90                  95

Asn Gly Thr Lys Thr Tyr Ser Tyr Asn Arg Lys Glu Gly Glu Phe Ala
            100                 105                 110

Ile Asn Trp Leu Val Pro Ile Gly Glu Asp Ser Pro Ala Ser Ile Lys
            115                 120                 125

Ile Ser Val Asp Glu
        130

<210> SEQ ID NO 125
<211> LENGTH: 134
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 125

Met Val Glu Glu Ala Leu Asn Ile Phe Asp Glu Cys Arg Ser Pro Cys
 1               5                  10                  15

Ser Leu Thr Pro Glu Pro Gly Lys Pro Ile Gln Ser Lys Leu Ser Ile
            20                  25                  30

Pro Ser Asp Val Val Leu Asp Glu Gly Val Leu Tyr Tyr Ser Met Thr
            35                  40                  45

Ile Asn Asp Glu Gln Asn Asp Ile Lys Asp Glu Asp Lys Gly Glu Ser
         50                  55                  60

Ile Ile Thr Ile Gly Glu Phe Ala Thr Val Arg Ala Thr Arg His Tyr
 65                  70                  75                  80

Val Asn Gln Asp Ala Pro Phe Gly Val Ile His Leu Asp Ile Thr Thr
                85                  90                  95

Glu Asn Gly Thr Lys Thr Tyr Ser Tyr Asn Arg Lys Glu Gly Glu Phe
            100                 105                 110

Ala Ile Asn Trp Leu Val Pro Ile Gly Glu Asp Ser Pro Ala Ser Ile
            115                 120                 125

Lys Ile Ser Val Asp Glu
        130

<210> SEQ ID NO 126
<211> LENGTH: 121
<212> TYPE: PRT
<213> ORGANISM: Vibrio cholera

<400> SEQUENCE: 126

Gly Asn Ala Met Ser Ala Leu Ala Ala His Arg Val Cys Gly Val Pro
 1               5                  10                  15

Leu Glu Thr Leu Ala Arg Ser Arg Lys Pro Arg Asp Leu Thr Asp Asp
            20                  25                  30

Leu Ser Cys Ala Tyr Gln Ala Gln Asn Ile Val Ser Leu Phe Val Ala
            35                  40                  45
```

Thr Arg Ile Leu Phe Ser His Leu Asp Ser Val Phe Thr Leu Asn Leu
    50                  55                  60

Asp Glu Gln Glu Pro Glu Val Ala Glu Arg Leu Ser Asp Leu Arg Arg
65                  70                  75                  80

Ile Asn Glu Asn Asn Pro Gly Met Val Thr Gln Val Leu Thr Val Ala
                85                  90                  95

Arg Gln Ile Tyr Asn Asp Tyr Val Thr His His Pro Gly Leu Thr Pro
            100                 105                 110

Glu Gln Thr Ser Ala Gly Ala Gln Ala
            115                 120

<210> SEQ ID NO 127
<211> LENGTH: 39
<212> TYPE: PRT
<213> ORGANISM: Vibrio cholera

<400> SEQUENCE: 127

Ala Asp Ile Leu Ser Leu Phe Cys Pro Asp Ala Asp Lys Ser Cys Val
1               5                   10                  15

Ala Ser Asn Asn Asp Gln Ala Asn Ile Asn Ile Glu Ser Arg Ser Gly
            20                  25                  30

Arg Ser Tyr Leu Pro Glu Asn
        35

<210> SEQ ID NO 128
<211> LENGTH: 209
<212> TYPE: PRT
<213> ORGANISM: Vibrio cholera

<400> SEQUENCE: 128

Arg Ala Val Ile Thr Pro Gln Gly Val Thr Asn Trp Thr Tyr Gln Glu
1               5                   10                  15

Leu Glu Ala Thr His Gln Ala Leu Thr Arg Glu Gly Tyr Val Phe Val
            20                  25                  30

Gly Tyr His Gly Thr Asn His Val Ala Ala Gln Thr Ile Val Asn Arg
        35                  40                  45

Ile Ala Pro Val Pro Arg Gly Asn Asn Thr Glu Asn Glu Glu Lys Trp
    50                  55                  60

Gly Gly Leu Tyr Val Ala Thr His Ala Glu Val Ala His Gly Tyr Ala
65                  70                  75                  80

Arg Ile Lys Glu Gly Thr Gly Glu Tyr Gly Leu Pro Thr Arg Ala Glu
                85                  90                  95

Arg Asp Ala Arg Gly Val Met Leu Arg Val Tyr Ile Pro Arg Ala Ser
            100                 105                 110

Leu Glu Arg Phe Tyr Arg Thr Asn Thr Pro Leu Glu Asn Ala Glu Glu
        115                 120                 125

His Ile Thr Gln Val Ile Gly His Ser Leu Pro Leu Arg Asn Glu Ala
    130                 135                 140

Phe Thr Gly Pro Glu Ser Ala Gly Gly Glu Asp Glu Thr Val Ile Gly
145                 150                 155                 160

Trp Asp Met Ala Ile His Ala Val Ala Ile Pro Ser Thr Ile Pro Gly
                165                 170                 175

Asn Ala Tyr Glu Glu Leu Ala Ile Asp Glu Glu Ala Val Ala Lys Glu
            180                 185                 190

Gln Ser Ile Ser Thr Lys Pro Pro Tyr Lys Glu Arg Lys Asp Glu Leu
            195                 200                 205

Lys

<210> SEQ ID NO 129
<211> LENGTH: 425
<212> TYPE: PRT
<213> ORGANISM: Vibrio cholera

<400> SEQUENCE: 129

Val Glu Glu Ala Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
            20                  25                  30

Ser Asp Val Val Leu Asp Glu Gly Val Leu Tyr Tyr Ser Met Thr Ile
        35                  40                  45

Asn Asp Glu Gln Asn Asp Ile Lys Asp Glu Asp Lys Gly Glu Ser Ile
    50                  55                  60

Ile Thr Ile Gly Glu Phe Ala Thr Val Arg Ala Thr Arg His Tyr Val
65                  70                  75                  80

Asn Gln Asp Ala Pro Phe Gly Val Ile His Leu Asp Ile Thr Thr Glu
                85                  90                  95

Asn Gly Thr Lys Thr Tyr Ser Tyr Asn Arg Lys Glu Gly Glu Phe Ala
            100                 105                 110

Ile Asn Trp Leu Val Pro Ile Gly Glu Asp Ser Pro Ala Ser Ile Lys
        115                 120                 125

Ile Ser Val Asp Glu Leu Asp Gln Gln Arg Asn Ile Ile Glu Val Pro
    130                 135                 140

Lys Leu Tyr Ser Ile Asp Leu Asp Asn Gln Thr Leu Glu Gln Trp Lys
145                 150                 155                 160

Thr Gln Gly Asn Val Ser Phe Ser Val Thr Arg Pro Glu His Asn Ile
                165                 170                 175

Ala Ile Ser Trp Pro Ser Val Ser Tyr Lys Ala Ala Gln Lys Glu Gly
            180                 185                 190

Ser Arg His Lys Arg Trp Ala His Trp His Thr Gly Leu Ala Leu Cys
        195                 200                 205

Trp Leu Val Pro Met Asp Ala Ile Tyr Asn Tyr Ile Thr Gln Gln Asn
    210                 215                 220

Cys Thr Leu Gly Asp Asn Trp Phe Gly Gly Ser Tyr Glu Thr Val Ala
225                 230                 235                 240

Gly Thr Pro Lys Val Ile Thr Val Lys Gln Gly Ile Glu Gln Lys Pro
                245                 250                 255

Val Glu Gln Arg Ile His Phe Ser Lys Gly Asn Ala Met Ser Ala Leu
            260                 265                 270

Ala Ala His Arg Val Cys Gly Val Pro Leu Glu Thr Leu Ala Arg Ser
        275                 280                 285

Arg Lys Pro Arg Asp Leu Thr Asp Asp Leu Ser Cys Ala Tyr Gln Ala
    290                 295                 300

Gln Asn Ile Val Ser Leu Phe Val Ala Thr Arg Ile Leu Phe Ser His
305                 310                 315                 320

Leu Asp Ser Val Phe Thr Leu Asn Leu Asp Glu Gln Glu Pro Glu Val
                325                 330                 335

Ala Glu Arg Leu Ser Asp Leu Arg Arg Ile Asn Glu Asn Asn Pro Gly
            340                 345                 350

Met Val Thr Gln Val Leu Thr Val Ala Arg Gln Ile Tyr Asn Asp Tyr
            355                 360                 365

Val Thr His His Pro Gly Leu Thr Pro Glu Gln Thr Ser Ala Gly Ala
        370                 375                 380

Gln Ala Ala Asp Ile Leu Ser Leu Phe Cys Pro Asp Ala Asp Lys Ser
385                 390                 395                 400

Cys Val Ala Ser Asn Asn Asp Gln Ala Asn Ile Asn Ile Glu Ser Arg
                405                 410                 415

Ser Gly Arg Ser Tyr Leu Pro Glu Asn
            420                 425

<210> SEQ ID NO 130
<211> LENGTH: 415
<212> TYPE: PRT
<213> ORGANISM: Vibrio cholera

<400> SEQUENCE: 130

Val Glu Glu Ala Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
            20                  25                  30

Ser Asp Val Val Leu Asp Glu Gly Val Leu Tyr Tyr Ser Met Thr Ile
        35                  40                  45

Asn Asp Glu Gln Asn Asp Ile Lys Asp Glu Asp Lys Gly Glu Ser Ile
    50                  55                  60

Ile Thr Ile Gly Glu Phe Ala Thr Val Arg Ala Thr Arg His Tyr Val
65                  70                  75                  80

Asn Gln Asp Ala Pro Phe Gly Val Ile His Leu Asp Ile Thr Thr Glu
                85                  90                  95

Asn Gly Thr Lys Thr Tyr Ser Tyr Asn Arg Lys Glu Gly Glu Phe Ala
            100                 105                 110

Ile Asn Trp Leu Val Pro Ile Gly Glu Asp Ser Pro Ala Ser Ile Lys
        115                 120                 125

Ile Ser Val Asp Glu Leu Asp Gln Gln Arg Asn Ile Ile Glu Val Pro
    130                 135                 140

Lys Leu Tyr Ser Ile Asp Leu Asp Asn Gln Thr Leu Glu Gln Trp Lys
145                 150                 155                 160

Thr Gln Gly Asn Val Ser Phe Ser Val Thr Arg Pro Glu His Asn Ile
                165                 170                 175

Ala Ile Ser Trp Pro Ser Val Ser Tyr Lys Ala Ala Gln Lys Glu Gly
            180                 185                 190

Ser Arg His Lys Arg Trp Ala His Trp His Thr Gly Leu Ala Leu Cys
        195                 200                 205

Trp Leu Val Pro Met Asp Ala Ile Tyr Asn Tyr Ile Thr Gln Gln Asn
    210                 215                 220

Cys Thr Leu Gly Asp Asn Trp Phe Gly Gly Ser Tyr Glu Thr Val Ala
225                 230                 235                 240

Gly Thr Pro Lys Val Ile Thr Val Lys Gln Gly Ile Glu Gln Lys Pro
                245                 250                 255

Val Glu Gln Arg Ile His Phe Ser Lys Gly Asn Ala Met Ser Ala Leu
            260                 265                 270

Ala Ala His Arg Val Cys Gly Val Pro Leu Glu Thr Leu Ala Arg Ser
        275                 280                 285

-continued

```
Arg Lys Pro Arg Asp Leu Thr Asp Asp Leu Ser Cys Ala Tyr Gln Ala
    290                 295                 300

Gln Asn Ile Val Ser Leu Phe Val Ala Thr Arg Ile Leu Phe Ser His
305                 310                 315                 320

Leu Asp Ser Val Phe Thr Leu Asn Leu Asp Glu Gln Glu Pro Glu Val
                325                 330                 335

Ala Glu Arg Leu Ser Asp Leu Arg Arg Ile Asn Glu Asn Asn Pro Gly
            340                 345                 350

Met Val Thr Gln Val Leu Thr Val Ala Arg Gln Ile Tyr Asn Asp Tyr
        355                 360                 365

Val Thr His His Pro Gly Leu Thr Pro Glu Gln Thr Ser Ala Gly Ala
    370                 375                 380

Gln Ala Ala Asp Ile Leu Ser Leu Phe Cys Pro Asp Ala Asp Lys Ser
385                 390                 395                 400

Cys Val Ala Ser Asn Asn Asp Gln Ala Asn Ile Asn Ile Glu Ser
                405                 410                 415

<210> SEQ ID NO 131
<211> LENGTH: 397
<212> TYPE: PRT
<213> ORGANISM: Vibrio cholera

<400> SEQUENCE: 131

Val Glu Glu Ala Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
                20                  25                  30

Ser Asp Val Val Leu Asp Glu Gly Val Leu Tyr Tyr Ser Met Thr Ile
            35                  40                  45

Asn Asp Glu Gln Asn Asp Ile Lys Asp Glu Asp Lys Gly Glu Ser Ile
        50                  55                  60

Ile Thr Ile Gly Glu Phe Ala Thr Val Arg Ala Thr Arg His Tyr Val
65                  70                  75                  80

Asn Gln Asp Ala Pro Phe Gly Val Ile His Leu Asp Ile Thr Thr Glu
                85                  90                  95

Asn Gly Thr Lys Thr Tyr Ser Tyr Asn Arg Lys Glu Gly Glu Phe Ala
            100                 105                 110

Ile Asn Trp Leu Val Pro Ile Gly Glu Asp Ser Pro Ala Ser Ile Lys
        115                 120                 125

Ile Ser Val Asp Glu Leu Asp Gln Gln Arg Asn Ile Ile Glu Val Pro
    130                 135                 140

Lys Leu Tyr Ser Ile Asp Leu Asp Asn Gln Thr Leu Glu Gln Trp Lys
145                 150                 155                 160

Thr Gln Gly Asn Val Ser Phe Ser Val Thr Arg Pro Glu His Asn Ile
                165                 170                 175

Ala Ile Ser Trp Pro Ser Val Ser Tyr Lys Ala Ala Gln Lys Glu Gly
            180                 185                 190

Ser Arg His Lys Arg Trp Ala His Trp His Thr Gly Leu Ala Leu Cys
        195                 200                 205

Trp Leu Val Pro Met Asp Ala Ile Tyr Asn Tyr Ile Thr Gln Gln Asn
    210                 215                 220

Cys Thr Leu Gly Asp Asn Trp Phe Gly Gly Ser Tyr Glu Thr Val Ala
225                 230                 235                 240
```

```
Gly Thr Pro Lys Val Ile Thr Val Lys Gln Gly Ile Glu Gln Lys Pro
            245                 250                 255

Val Glu Gln Arg Ile His Phe Ser Lys Gly Asn Ala Met Ser Ala Leu
            260                 265                 270

Ala Ala His Arg Val Cys Gly Val Pro Leu Glu Thr Leu Ala Arg Ser
            275                 280                 285

Arg Lys Pro Arg Asp Leu Thr Asp Asp Leu Ser Cys Ala Tyr Gln Ala
            290                 295                 300

Gln Asn Ile Val Ser Leu Phe Val Ala Thr Arg Ile Leu Phe Ser His
305                 310                 315                 320

Leu Asp Ser Val Phe Thr Leu Asn Leu Asp Glu Gln Glu Pro Glu Val
                    325                 330                 335

Ala Glu Arg Leu Ser Asp Leu Arg Arg Ile Asn Glu Asn Asn Pro Gly
                340                 345                 350

Met Val Thr Gln Val Leu Thr Val Ala Arg Gln Ile Tyr Asn Asp Tyr
            355                 360                 365

Val Thr His His Pro Gly Leu Thr Pro Glu Gln Thr Ser Ala Gly Ala
            370                 375                 380

Gln Ala Ala Asp Ile Leu Ser Leu Phe Cys Pro Asp Ala
385                 390                 395

<210> SEQ ID NO 132
<211> LENGTH: 386
<212> TYPE: PRT
<213> ORGANISM: Vibrio cholera

<400> SEQUENCE: 132

Val Glu Glu Ala Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
            20                  25                  30

Ser Asp Val Val Leu Asp Glu Gly Val Leu Tyr Tyr Ser Met Thr Ile
            35                  40                  45

Asn Asp Glu Gln Asn Asp Ile Lys Asp Glu Asp Lys Gly Glu Ser Ile
    50                  55                  60

Ile Thr Ile Gly Glu Phe Ala Thr Val Arg Ala Thr Arg His Tyr Val
65              70                  75                  80

Asn Gln Asp Ala Pro Phe Gly Val Ile His Leu Asp Ile Thr Thr Glu
                85                  90                  95

Asn Gly Thr Lys Thr Tyr Ser Tyr Asn Arg Lys Glu Gly Glu Phe Ala
            100                 105                 110

Ile Asn Trp Leu Val Pro Ile Gly Glu Asp Ser Pro Ala Ser Ile Lys
            115                 120                 125

Ile Ser Val Asp Glu Leu Asp Gln Gln Arg Asn Ile Ile Glu Val Pro
    130                 135                 140

Lys Leu Tyr Ser Ile Asp Leu Asp Asn Gln Thr Leu Glu Gln Trp Lys
145                 150                 155                 160

Thr Gln Gly Asn Val Ser Phe Ser Val Thr Arg Pro Glu His Asn Ile
                165                 170                 175

Ala Ile Ser Trp Pro Ser Val Ser Tyr Lys Ala Ala Gln Lys Glu Gly
            180                 185                 190

Ser Arg His Lys Arg Trp Ala His Trp His Thr Gly Leu Ala Leu Cys
            195                 200                 205
```

```
Trp Leu Val Pro Met Asp Ala Ile Tyr Asn Tyr Ile Thr Gln Gln Asn
    210                 215                 220

Cys Thr Leu Gly Asp Asn Trp Phe Gly Gly Ser Tyr Glu Thr Val Ala
225                 230                 235                 240

Gly Thr Pro Lys Val Ile Thr Val Lys Gln Gly Ile Glu Gln Lys Pro
                245                 250                 255

Val Glu Gln Arg Ile His Phe Ser Lys Gly Asn Ala Met Ser Ala Leu
                260                 265                 270

Ala Ala His Arg Val Cys Gly Val Pro Leu Glu Thr Leu Ala Arg Ser
            275                 280                 285

Arg Lys Pro Arg Asp Leu Thr Asp Asp Leu Ser Cys Ala Tyr Gln Ala
290                 295                 300

Gln Asn Ile Val Ser Leu Phe Val Ala Thr Arg Ile Leu Phe Ser His
305                 310                 315                 320

Leu Asp Ser Val Phe Thr Leu Asn Leu Asp Glu Gln Glu Pro Glu Val
                325                 330                 335

Ala Glu Arg Leu Ser Asp Leu Arg Arg Ile Asn Glu Asn Asn Pro Gly
            340                 345                 350

Met Val Thr Gln Val Leu Thr Val Ala Arg Gln Ile Tyr Asn Asp Tyr
            355                 360                 365

Val Thr His His Pro Gly Leu Thr Pro Glu Gln Thr Ser Ala Gly Ala
370                 375                 380

Gln Ala
385

<210> SEQ ID NO 133
<211> LENGTH: 291
<212> TYPE: PRT
<213> ORGANISM: Vibrio cholera

<400> SEQUENCE: 133

Val Glu Glu Ala Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
                20                  25                  30

Ser Asp Val Val Leu Asp Glu Gly Val Leu Tyr Tyr Ser Met Thr Ile
            35                  40                  45

Asn Asp Glu Gln Asn Asp Ile Lys Asp Glu Asp Lys Gly Glu Ser Ile
        50                  55                  60

Ile Thr Ile Gly Glu Phe Ala Thr Val Arg Ala Thr Arg His Tyr Val
65                  70                  75                  80

Asn Gln Asp Ala Pro Phe Gly Val Ile His Leu Asp Ile Thr Thr Glu
                85                  90                  95

Asn Gly Thr Lys Thr Tyr Ser Tyr Asn Arg Lys Glu Gly Glu Phe Ala
            100                 105                 110

Ile Asn Trp Leu Val Pro Ile Gly Glu Asp Ser Pro Ala Ser Ile Lys
        115                 120                 125

Ile Ser Val Asp Glu Leu Asp Gln Gln Arg Asn Ile Ile Glu Val Pro
130                 135                 140

Lys Leu Tyr Ser Ile Asp Leu Asp Asn Gln Thr Leu Glu Gln Trp Lys
145                 150                 155                 160

Thr Gln Gly Asn Val Ser Phe Ser Val Thr Arg Pro Glu His Asn Ile
                165                 170                 175
```

Ala Ile Ser Trp Pro Ser Val Ser Tyr Lys Ala Ala Gln Lys Glu Gly
            180                 185                 190

Ser Arg His Lys Arg Trp Ala His Trp His Thr Gly Leu Ala Leu Cys
        195                 200                 205

Trp Leu Val Pro Met Asp Ala Ile Tyr Asn Tyr Ile Thr Gln Gln Asn
210                 215                 220

Cys Thr Leu Gly Asp Asn Trp Phe Gly Gly Ser Tyr Glu Thr Val Ala
225                 230                 235                 240

Gly Thr Pro Lys Val Ile Thr Val Lys Gln Gly Ile Glu Gln Lys Pro
                245                 250                 255

Val Glu Gln Arg Ile His Phe Ser Lys Gly Asn Ala Met Ser Ala Leu
            260                 265                 270

Ala Ala His Arg Val Cys Gly Val Pro Leu Glu Thr Leu Ala Arg Ser
        275                 280                 285

Arg Lys Pro
    290

<210> SEQ ID NO 134
<211> LENGTH: 1902
<212> TYPE: DNA
<213> ORGANISM: Vibrio cholera

<400> SEQUENCE: 134

| | |
|---|---|
| gtcgaagaag ctttaaacat cttttgatgaa tgccgttcgc catgttcgtt gaccccggaa | 60 |
| ccgggtaagc cgattcaatc aaaactgtct atccctagtg atgttgttct ggatgaaggt | 120 |
| gttctgtatt actcgatgac gattaatgat gagcagaatg atattaagga tgaggacaaa | 180 |
| ggcgagtcca ttatcactat tggtgaattt gccacagtac gcgcgactag acattatgtt | 240 |
| aatcaagatg cgccttttgg tgtcatccat ttagatatta cgacagaaaa tggtacaaaa | 300 |
| acgtactctt ataaccgcaa agagggtgaa tttgcaatca attggttagt gcctattggt | 360 |
| gaagattctc ctgcaagcat caaaatctcc gttgatgagc tcgatcagca acgcaatatc | 420 |
| atcgaggtgc ctaaactgta tagtattgat ctcgataacc aaacgttaga gcagtggaaa | 480 |
| acccaaggta atgtttcttt tcggtaacg cgtcctgaac ataatatcgc tatctcttgg | 540 |
| ccaagcgtga gttacaaagc agcgcagaaa gagggttcac gccataagcg ttgggctcat | 600 |
| tggcatacag gcttagcact gtgttggctt gtgccaatgg atgctatcta aactatatc | 660 |
| acccagcaaa attgtacttt aggggataat tggtttggtg gctcttatga gactgttgca | 720 |
| ggcactccga aggtgattac ggttaagcaa gggattgaac aaaagccagt tgagcagcgc | 780 |
| atccatttct ccaaggggaa tgcgatgagc gcacttgctg ctcatcgcgt ctgtggtgtg | 840 |
| ccattagaaa ctttggcgcg cagtcgcaaa cctcgtgatc tgacggatga tttatcatgt | 900 |
| gcctatcaag cgcagaatat cgtgagttta tttgtcgcga cgcgtatcct gttctctcat | 960 |
| ctggatagcg tatttactct gaatcttgac gaacaagaac cagaggtggc tgaacgtcta | 1020 |
| agtgatcttc gccgtatcaa tgaaaataac ccgggcatgg ttacacaggt tttaaccgtt | 1080 |
| gctcgtcaga tctataacga ttatgtcact caccatccgg gcttaactcc tgagcaaacc | 1140 |
| agtgcgggtg cacaagctgc cgatatcctc tctttatttt gcccagatgc tgataagtct | 1200 |
| tgtgtggctt caaacaacga tcaagccaat atcaacatcg agtctcgttc tggccgttca | 1260 |
| tatttgcctg aaaaccgtgc ggtaatcacc cctcaaggcg tcacaaattg gacttaccag | 1320 |
| gaactcgaag caacacatca agctctgact cgtgagggtt atgtgttcgt gggttaccat | 1380 |

-continued

```
ggtacgaatc atgtcgctgc gcaaaccatc gtgaatcgca ttgccctgt tccgcgcggc    1440 aacaacactg aaaacgagga aaagtggggc gggttatatg ttgcaactca cgctgaagtt    1500
gcccatggtt atgctcgcat caaagaaggg acagggagt atggccttcc gacccgtgct    1560
gagcgcgacg ctcgtggggt aatgctgcgc gtgtatatcc ctcgtgcttc attagaacgt    1620
ttttatcgca cgaatacacc tttggaaaat gctgaggagc atatcacgca agtgattggt    1680
cattctttgc cattacgcaa tgaagcattt actggtccag aaagtgcggg cggggaagac    1740
gaaactgtca ttggctggga tatggcgatt catgcagttg cgatcccttc gactatccca    1800
gggaacgctt acgaagaatt ggcgattgat gaggaggctg ttgcaaaaga gcaatcgatt    1860
agcacaaaac caccttataa agagcgcaaa gatgaactta ag    1902
```

<210> SEQ ID NO 135
<211> LENGTH: 613
<212> TYPE: PRT
<213> ORGANISM: Pseudomonas aeruginosa

<400> SEQUENCE: 135

```
Ala Glu Glu Ala Phe Asp Leu Trp Asn Glu Cys Ala Lys Ala Cys Val
1               5                   10                  15

Leu Asp Leu Lys Asp Gly Val Arg Ser Ser Arg Met Ser Val Asp Pro
            20                  25                  30

Ala Ile Ala Asp Thr Asn Gly Gln Gly Val Leu His Tyr Ser Met Val
        35                  40                  45

Leu Glu Gly Gly Asn Asp Ala Leu Lys Leu Ala Ile Asp Asn Ala Leu
    50                  55                  60

Ser Ile Thr Ser Asp Gly Leu Thr Ile Arg Leu Glu Gly Gly Val Glu
65                  70                  75                  80

Pro Asn Lys Pro Val Arg Tyr Ser Tyr Thr Arg Gln Ala Arg Gly Ser
                85                  90                  95

Trp Ser Leu Asn Trp Leu Val Pro Ile Gly His Glu Lys Pro Ser Asn
            100                 105                 110

Ile Lys Val Phe Ile His Glu Leu Asn Ala Gly Asn Gln Leu Ser His
        115                 120                 125

Met Ser Pro Ile Tyr Thr Ile Glu Met Gly Asp Glu Leu Leu Ala Lys
    130                 135                 140

Leu Ala Arg Asp Ala Thr Phe Phe Val Arg Ala His Glu Ser Asn Glu
145                 150                 155                 160

Met Gln Pro Thr Leu Ala Ile Ser His Ala Gly Val Ser Val Met
                165                 170                 175

Ala Gln Ala Gln Pro Arg Arg Glu Lys Arg Trp Ser Glu Trp Ala Ser
            180                 185                 190

Gly Lys Val Leu Cys Leu Leu Asp Pro Leu Asp Gly Val Tyr Asn Tyr
        195                 200                 205

Leu Ala Gln Gln Arg Cys Asn Leu Asp Asp Thr Trp Glu Gly Lys Ile
    210                 215                 220

Tyr Arg Val Leu Ala Gly Asn Pro Ala Lys His Asp Leu Asp Ile Lys
225                 230                 235                 240

Pro Thr Val Ile Ser His Arg Leu His Phe Pro Glu Gly Gly Ser Leu
                245                 250                 255

Ala Ala Leu Thr Ala His Gln Ala Cys His Leu Pro Leu Glu Thr Phe
            260                 265                 270

Thr Arg His Arg Gln Pro Arg Gly Trp Glu Gln Leu Glu Gln Cys Gly
        275                 280                 285
```

| Tyr | Pro | Val | Gln | Arg | Leu | Val | Ala | Leu | Tyr | Leu | Ala | Ala | Arg | Leu | Ser |
|---|---|---|---|---|---|---|---|---|---|---|---|---|---|---|---|
| | 290 | | | | 295 | | | | | 300 | | | | | |

Trp Asn Gln Val Asp Gln Val Ile Arg Asn Ala Leu Ala Ser Pro Gly
305                 310                 315                 320

Ser Gly Gly Asp Leu Gly Glu Ala Ile Arg Glu Gln Pro Glu Gln Ala
            325                 330                 335

Arg Leu Ala Leu Thr Leu Ala Ala Ala Glu Ser Glu Arg Phe Val Arg
        340                 345                 350

Gln Gly Thr Gly Asn Asp Glu Ala Gly Ala Ser Ala Asp Val Val
    355                 360                 365

Ser Leu Thr Cys Pro Val Ala Ala Gly Glu Cys Ala Gly Pro Ala Asp
370                 375                 380

Ser Gly Asp Ala Leu Leu Glu Arg Asn Tyr Pro Thr Gly Ala Glu Phe
385                 390                 395                 400

Leu Gly Asp Gly Gly Asp Val Ser Phe Ser Thr Arg Gly Thr Gln Asn
            405                 410                 415

Trp Thr Val Glu Arg Leu Leu Gln Ala His Arg Gln Leu Glu Glu Arg
        420                 425                 430

Gly Tyr Val Phe Val Gly Tyr His Gly Thr Phe Leu Glu Ala Ala Gln
    435                 440                 445

Ser Ile Val Phe Gly Gly Val Arg Ala Arg Ser Gln Asp Leu Asp Ala
450                 455                 460

Ile Trp Arg Gly Phe Tyr Ile Ala Gly Asp Pro Ala Leu Ala Tyr Gly
465                 470                 475                 480

Tyr Ala Gln Asp Gln Glu Pro Asp Ala Arg Gly Arg Ile Arg Asn Gly
            485                 490                 495

Ala Leu Leu Arg Val Tyr Val Pro Arg Ser Ser Leu Pro Gly Phe Tyr
        500                 505                 510

Arg Thr Gly Leu Thr Leu Ala Ala Pro Glu Ala Ala Gly Glu Val Glu
    515                 520                 525

Arg Leu Ile Gly His Pro Leu Pro Leu Arg Leu Asp Ala Ile Thr Gly
530                 535                 540

Pro Glu Glu Glu Gly Gly Arg Leu Glu Thr Ile Leu Gly Trp Pro Leu
545                 550                 555                 560

Ala Glu Arg Thr Val Val Ile Pro Ser Ala Ile Pro Thr Asp Pro Arg
            565                 570                 575

Asn Val Gly Gly Asp Leu Asp Pro Ser Ser Ile Pro Asp Lys Glu Gln
        580                 585                 590

Ala Ile Ser Ala Leu Pro Asp Tyr Ala Ser Gln Pro Gly Lys Pro Pro
    595                 600                 605

Arg Glu Asp Leu Lys
    610

<210> SEQ ID NO 136
<211> LENGTH: 1839
<212> TYPE: DNA
<213> ORGANISM: Pseudomonas aeruginosa

<400> SEQUENCE: 136
gccgaggaag ccttcgacct ctggaacgaa tgcgccaagg cctgcgtgct cgacctcaag     60
gacggcgtgc gttccagccg catgagcgtc gacccggcca tcgccgacac caacggccag    120
ggcgtgctgc actactccat ggtcctggag ggcggcaacg acgcgctcaa gctggccatc    180
gacaacgccc tcagcatcac cagcgacggc ctgaccatcc gcctcgaagg tggcgtcgag    240

```
ccgaacaagc cggtgcgcta cagctacacg cgccaggcgc gcggcagttg gtcgctgaac       300
tggctggtgc cgatcggcca cgagaagcct tcgaacatca aggtgttcat ccacgaactg       360
aacgccggta accagctcag ccacatgtcg ccgatctaca ccatcgagat gggcgacgag       420
ttgctggcga agctggcgcg cgatgccacc ttcttcgtca gggcgcacga gagcaacgag       480
atgcagccga cgctcgccat cagccatgcc ggggtcagcg tggtcatggc ccaggcccag       540
ccgcgccggg aaaagcgctg gagcgaatgg gccagcggca aggtgttgtg cctgctcgac       600
ccgctggacg gggtctacaa ctacctcgcc cagcagcgct gcaacctcga cgatacctgg       660
gaaggcaaga tctaccgggt gctcgccggc aacccggcga agcatgacct ggacatcaag       720
cccacggtca tcagtcatcg cctgcatttc cccgagggcg gcagcctggc cgcgctgacc       780
gcgcaccagg cctgccacct gccgctggag accttcaccc gtcatcgcca gccgcgcggc       840
tgggaacaac tggagcagtg cggctatccg gtgcagcggc tggtcgccct ctacctggcg       900
gcgcggctgt cgtggaacca ggtcgaccag gtgatccgca acgccctggc cagccccggc       960
agcggcggcg acctgggcga agcgatccgc gagcagccgg agcaggcccg tctggccctg      1020
accctggccg ccgccgagag cgagcgcttc gtccggcagg gcacaggcaa cgacgaggcc      1080
ggcgcggcca gcgccgacgt ggtgagcctg acctgcccgg tcgccgccgg tgaatgcgcg      1140
ggcccggcgg acagcggcga cgccctgctg gagcgcaact atcccactgg cgcggagttc      1200
ctcggcgacg gcgcgacat cagcttcagc acccgcggca cgcagaactg gacggtggag      1260
cggctgctcc aggcgcaccg ccaactggag gagcgcggct atgtgttcgt cggctaccac      1320
ggcaccttcc tcgaagcggc gcaaagcatc gtcttcggcg gggtgcgcgc gcgcagccag      1380
gacctcgacg cgatctggcg cggtttctat atcgccggcg atccggcgct ggcctacggc      1440
tacgcccagg accaggaacc cgacgcgcgc ggccggatcc gcaacggtgc cctgctgcgg      1500
gtctatgtgc cgcgctcgag tctgccgggc ttctaccgca ccggcctgac cctggccgcg      1560
ccggaggcgg cgggcgaggt cgaacggctg atcgccatcc gctgccgct cgcgcctggac      1620 gccatcaccg ccccgagga ggaaggcggg cgcctggaaa ccattctcgg ctggccgctg      1680
gccgagcgca ccgtggtgat ccctcggcg atccccaccg acccgcgcaa cgtcggcggc      1740
gacctcgacc cgtccagcat ccccgacaag gaacaggcga tcagcgccct gccggactac      1800
gccagccagc ccggcaaacc gccgcgcgag gacctgaag                             1839
```

<210> SEQ ID NO 137
<211> LENGTH: 252
<212> TYPE: PRT
<213> ORGANISM: Pseudomonas aeruginosa

<400> SEQUENCE: 137

Ala Glu Glu Ala Phe Asp Leu Trp Asn Glu Cys Ala Lys Ala Cys Val
1               5                   10                  15

Leu Asp Leu Lys Asp Gly Val Arg Ser Ser Arg Met Ser Val Asp Pro
            20                  25                  30

Ala Ile Ala Asp Thr Asn Gly Gln Gly Val Leu His Tyr Ser Met Val
        35                  40                  45

Leu Glu Gly Gly Asn Asp Ala Leu Lys Leu Ala Ile Asp Asn Ala Leu
    50                  55                  60

Ser Ile Thr Ser Asp Gly Leu Thr Ile Arg Leu Glu Gly Gly Val Glu
65                  70                  75                  80

```
Pro Asn Lys Pro Val Arg Tyr Ser Tyr Thr Arg Gln Ala Arg Gly Ser
                85                  90                  95

Trp Ser Leu Asn Trp Leu Val Pro Ile Gly His Glu Lys Pro Ser Asn
            100                 105                 110

Ile Lys Val Phe Ile His Glu Leu Asn Ala Gly Asn Gln Leu Ser His
        115                 120                 125

Met Ser Pro Ile Tyr Thr Ile Glu Met Gly Asp Glu Leu Leu Ala Lys
    130                 135                 140

Leu Ala Arg Asp Ala Thr Phe Phe Val Arg Ala His Glu Ser Asn Glu
145                 150                 155                 160

Met Gln Pro Thr Leu Ala Ile Ser His Ala Gly Val Ser Val Val Met
                165                 170                 175

Ala Gln Ala Gln Pro Arg Arg Glu Lys Arg Trp Ser Glu Trp Ala Ser
            180                 185                 190

Gly Lys Val Leu Cys Leu Leu Asp Pro Leu Asp Gly Val Tyr Asn Tyr
        195                 200                 205

Leu Ala Gln Gln Arg Cys Asn Leu Asp Asp Thr Trp Glu Gly Lys Ile
210                 215                 220

Tyr Arg Val Leu Ala Gly Asn Pro Ala Lys His Asp Leu Asp Ile Lys
225                 230                 235                 240

Pro Thr Val Ile Ser His Arg Leu His Phe Pro Glu
                245                 250

<210> SEQ ID NO 138
<211> LENGTH: 112
<212> TYPE: PRT
<213> ORGANISM: Pseudomonas aeruginosa

<400> SEQUENCE: 138

Gly Gly Ser Leu Ala Ala Leu Thr Ala His Gln Ala Cys His Leu Pro
1               5                   10                  15

Leu Glu Thr Phe Thr Arg His Arg Gln Pro Arg Gly Trp Glu Gln Leu
                20                  25                  30

Glu Gln Cys Gly Tyr Pro Val Gln Arg Leu Val Ala Leu Tyr Leu Ala
            35                  40                  45

Ala Arg Leu Ser Trp Asn Gln Val Asp Gln Val Ile Arg Asn Ala Leu
        50                  55                  60

Ala Ser Pro Gly Ser Gly Asp Leu Gly Glu Ala Ile Arg Glu Gln
65                  70                  75                  80

Pro Glu Gln Ala Arg Leu Ala Leu Thr Leu Ala Ala Glu Ser Glu
                85                  90                  95

Arg Phe Val Arg Gln Gly Thr Gly Asn Asp Glu Ala Gly Ala Ala Ser
            100                 105                 110

<210> SEQ ID NO 139
<211> LENGTH: 40
<212> TYPE: PRT
<213> ORGANISM: Pseudomonas aeruginosa

<400> SEQUENCE: 139

Ala Asp Val Val Ser Leu Thr Cys Pro Val Ala Gly Glu Cys Ala
1               5                   10                  15

Gly Pro Ala Asp Ser Gly Asp Ala Leu Leu Glu Arg Asn Tyr Pro Thr
                20                  25                  30

Gly Ala Glu Phe Leu Gly Asp Gly
            35                  40
```

<210> SEQ ID NO 140
<211> LENGTH: 209
<212> TYPE: PRT
<213> ORGANISM: Pseudomonas aeruginosa

<400> SEQUENCE: 140

Gly Asp Val Ser Phe Ser Thr Arg Gly Thr Gln Asn Trp Thr Val Glu
1               5                   10                  15

Arg Leu Leu Gln Ala His Arg Gln Leu Glu Arg Gly Tyr Val Phe
            20                  25                  30

Val Gly Tyr His Gly Thr Phe Leu Glu Ala Ala Gln Ser Ile Val Phe
            35                  40                  45

Gly Gly Val Arg Ala Arg Ser Gln Asp Leu Asp Ala Ile Trp Arg Gly
        50                  55                  60

Phe Tyr Ile Ala Gly Asp Pro Ala Leu Ala Tyr Gly Tyr Ala Gln Asp
65                  70                  75                  80

Gln Glu Pro Asp Ala Arg Gly Arg Ile Arg Asn Gly Ala Leu Leu Arg
                85                  90                  95

Val Tyr Val Pro Arg Ser Ser Leu Pro Gly Phe Tyr Arg Thr Gly Leu
            100                 105                 110

Thr Leu Ala Ala Pro Glu Ala Ala Gly Glu Val Glu Arg Leu Ile Gly
        115                 120                 125

His Pro Leu Pro Leu Arg Leu Asp Ala Ile Thr Gly Pro Glu Glu Glu
    130                 135                 140

Gly Gly Arg Leu Glu Thr Ile Leu Gly Trp Pro Leu Ala Glu Arg Thr
145                 150                 155                 160

Val Val Ile Pro Ser Ala Ile Pro Thr Asp Pro Arg Asn Val Gly Gly
                165                 170                 175

Asp Leu Asp Pro Ser Ser Ile Pro Asp Lys Glu Gln Ala Ile Ser Ala
            180                 185                 190

Leu Pro Asp Tyr Ala Ser Gln Pro Gly Lys Pro Pro Arg Glu Asp Leu
        195                 200                 205

Lys

<210> SEQ ID NO 141
<211> LENGTH: 404
<212> TYPE: PRT
<213> ORGANISM: Pseudomonas aeruginosa

<400> SEQUENCE: 141

Ala Glu Glu Ala Phe Asp Leu Trp Asn Glu Cys Ala Lys Ala Cys Val
1               5                   10                  15

Leu Asp Leu Lys Asp Gly Val Arg Ser Ser Arg Met Ser Val Asp Pro
            20                  25                  30

Ala Ile Ala Asp Thr Asn Gly Gln Gly Val Leu His Tyr Ser Met Val
        35                  40                  45

Leu Glu Gly Gly Asn Asp Ala Leu Lys Leu Ala Ile Asp Asn Ala Leu
    50                  55                  60

Ser Ile Thr Ser Asp Gly Leu Thr Ile Arg Leu Glu Gly Gly Val Glu
65                  70                  75                  80

Pro Asn Lys Pro Val Arg Tyr Ser Tyr Thr Arg Gln Ala Arg Gly Ser
                85                  90                  95

Trp Ser Leu Asn Trp Leu Val Pro Ile Gly His Glu Lys Pro Ser Asn
            100                 105                 110

Ile Lys Val Phe Ile His Glu Leu Asn Ala Gly Asn Gln Leu Ser His
            115                 120                 125

Met Ser Pro Ile Tyr Thr Ile Glu Met Gly Asp Glu Leu Leu Ala Lys
130                 135                 140

Leu Ala Arg Asp Ala Thr Phe Phe Val Arg Ala His Glu Ser Asn Glu
145                 150                 155                 160

Met Gln Pro Thr Leu Ala Ile Ser His Ala Gly Val Ser Val Val Met
                165                 170                 175

Ala Gln Ala Gln Pro Arg Arg Glu Lys Arg Trp Ser Glu Trp Ala Ser
            180                 185                 190

Gly Lys Val Leu Cys Leu Leu Asp Pro Leu Asp Gly Val Tyr Asn Tyr
        195                 200                 205

Leu Ala Gln Gln Arg Cys Asn Leu Asp Asp Thr Trp Glu Gly Lys Ile
210                 215                 220

Tyr Arg Val Leu Ala Gly Asn Pro Ala Lys His Asp Leu Asp Ile Lys
225                 230                 235                 240

Pro Thr Val Ile Ser His Arg Leu His Phe Pro Glu Gly Gly Ser Leu
                245                 250                 255

Ala Ala Leu Thr Ala His Gln Ala Cys His Leu Pro Leu Glu Thr Phe
            260                 265                 270

Thr Arg His Arg Gln Pro Arg Gly Trp Glu Gln Leu Glu Gln Cys Gly
        275                 280                 285

Tyr Pro Val Gln Arg Leu Val Ala Leu Tyr Leu Ala Ala Arg Leu Ser
290                 295                 300

Trp Asn Gln Val Asp Gln Val Ile Arg Asn Ala Leu Ala Ser Pro Gly
305                 310                 315                 320

Ser Gly Gly Asp Leu Gly Glu Ala Ile Arg Glu Gln Pro Glu Gln Ala
                325                 330                 335

Arg Leu Ala Leu Thr Leu Ala Ala Glu Ser Glu Arg Phe Val Arg
            340                 345                 350

Gln Gly Thr Gly Asn Asp Glu Ala Gly Ala Ala Ser Ala Asp Val Val
        355                 360                 365

Ser Leu Thr Cys Pro Val Ala Ala Gly Glu Cys Ala Gly Pro Ala Asp
370                 375                 380

Ser Gly Asp Ala Leu Leu Glu Arg Asn Tyr Pro Thr Gly Ala Glu Phe
385                 390                 395                 400

Leu Gly Asp Gly

<210> SEQ ID NO 142
<211> LENGTH: 395
<212> TYPE: PRT
<213> ORGANISM: Pseudomonas aeruginosa

<400> SEQUENCE: 142

Ala Glu Glu Ala Phe Asp Leu Trp Asn Glu Cys Ala Lys Ala Cys Val
1               5                   10                  15

Leu Asp Leu Lys Asp Gly Val Arg Ser Ser Arg Met Ser Val Asp Pro
            20                  25                  30

Ala Ile Ala Asp Thr Asn Gly Gln Gly Val Leu His Tyr Ser Met Val
        35                  40                  45

Leu Glu Gly Gly Asn Asp Ala Leu Lys Leu Ala Ile Asp Asn Ala Leu
    50                  55                  60

Ser Ile Thr Ser Asp Gly Leu Thr Ile Arg Leu Glu Gly Gly Val Glu
65                  70                  75                  80

```
Pro Asn Lys Pro Val Arg Tyr Ser Tyr Thr Arg Gln Ala Arg Gly Ser
                85                  90                  95

Trp Ser Leu Asn Trp Leu Val Pro Ile Gly His Glu Lys Pro Ser Asn
            100                 105                 110

Ile Lys Val Phe Ile His Glu Leu Asn Ala Gly Asn Gln Leu Ser His
            115                 120                 125

Met Ser Pro Ile Tyr Thr Ile Glu Met Gly Asp Glu Leu Leu Ala Lys
            130                 135                 140

Leu Ala Arg Asp Ala Thr Phe Phe Val Arg Ala His Glu Ser Asn Glu
145                 150                 155                 160

Met Gln Pro Thr Leu Ala Ile Ser His Ala Gly Val Ser Val Val Met
                165                 170                 175

Ala Gln Ala Gln Pro Arg Arg Glu Lys Arg Trp Ser Glu Trp Ala Ser
                180                 185                 190

Gly Lys Val Leu Cys Leu Leu Asp Pro Leu Asp Gly Val Tyr Asn Tyr
                195                 200                 205

Leu Ala Gln Gln Arg Cys Asn Leu Asp Asp Thr Trp Glu Gly Lys Ile
210                 215                 220

Tyr Arg Val Leu Ala Gly Asn Pro Ala Lys His Asp Leu Asp Ile Lys
225                 230                 235                 240

Pro Thr Val Ile Ser His Arg Leu His Phe Pro Glu Gly Gly Ser Leu
                245                 250                 255

Ala Ala Leu Thr Ala His Gln Ala Cys His Leu Pro Leu Glu Thr Phe
                260                 265                 270

Thr Arg His Arg Gln Pro Arg Gly Trp Glu Gln Leu Glu Gln Cys Gly
                275                 280                 285

Tyr Pro Val Gln Arg Leu Val Ala Leu Tyr Leu Ala Ala Arg Leu Ser
                290                 295                 300

Trp Asn Gln Val Asp Gln Val Ile Arg Asn Ala Leu Ala Ser Pro Gly
305                 310                 315                 320

Ser Gly Gly Asp Leu Gly Glu Ala Ile Arg Glu Gln Pro Glu Gln Ala
                325                 330                 335

Arg Leu Ala Leu Thr Leu Ala Ala Ala Glu Ser Glu Arg Phe Val Arg
                340                 345                 350

Gln Gly Thr Gly Asn Asp Glu Ala Gly Ala Ala Ser Ala Asp Val Val
                355                 360                 365

Ser Leu Thr Cys Pro Val Ala Ala Gly Glu Cys Ala Gly Pro Ala Asp
                370                 375                 380

Ser Gly Asp Ala Leu Leu Glu Arg Asn Tyr Pro
385                 390                 395

<210> SEQ ID NO 143
<211> LENGTH: 375
<212> TYPE: PRT
<213> ORGANISM: Pseudomonas aeruginosa

<400> SEQUENCE: 143

Ala Glu Glu Ala Phe Asp Leu Trp Asn Glu Cys Ala Lys Ala Cys Val
1               5                   10                  15

Leu Asp Leu Lys Asp Gly Val Arg Ser Ser Arg Met Ser Val Asp Pro
                20                  25                  30

Ala Ile Ala Asp Thr Asn Gly Gln Gly Val Leu His Tyr Ser Met Val
            35                  40                  45

Leu Glu Gly Gly Asn Asp Ala Leu Lys Leu Ala Ile Asp Asn Ala Leu
50                  55                  60
```

```
Ser Ile Thr Ser Asp Gly Leu Thr Ile Arg Leu Glu Gly Gly Val Glu
 65                  70                  75                  80

Pro Asn Lys Pro Val Arg Tyr Ser Tyr Thr Arg Gln Ala Arg Gly Ser
                 85                  90                  95

Trp Ser Leu Asn Trp Leu Val Pro Ile Gly His Glu Lys Pro Ser Asn
            100                 105                 110

Ile Lys Val Phe Ile His Glu Leu Asn Ala Gly Asn Gln Leu Ser His
        115                 120                 125

Met Ser Pro Ile Tyr Thr Ile Glu Met Gly Asp Glu Leu Leu Ala Lys
    130                 135                 140

Leu Ala Arg Asp Ala Thr Phe Phe Val Arg Ala His Glu Ser Asn Glu
145                 150                 155                 160

Met Gln Pro Thr Leu Ala Ile Ser His Ala Gly Val Ser Val Val Met
                165                 170                 175

Ala Gln Ala Gln Pro Arg Arg Glu Lys Arg Trp Ser Glu Trp Ala Ser
            180                 185                 190

Gly Lys Val Leu Cys Leu Leu Asp Pro Leu Asp Gly Val Tyr Asn Tyr
        195                 200                 205

Leu Ala Gln Gln Arg Cys Asn Leu Asp Asp Thr Trp Glu Gly Lys Ile
    210                 215                 220

Tyr Arg Val Leu Ala Gly Asn Pro Ala Lys His Asp Leu Asp Ile Lys
225                 230                 235                 240

Pro Thr Val Ile Ser His Arg Leu His Phe Pro Glu Gly Gly Ser Leu
                245                 250                 255

Ala Ala Leu Thr Ala His Gln Ala Cys His Leu Pro Leu Glu Thr Phe
            260                 265                 270

Thr Arg His Arg Gln Pro Arg Gly Trp Glu Gln Leu Glu Gln Cys Gly
    275                 280                 285

Tyr Pro Val Gln Arg Leu Val Ala Leu Tyr Leu Ala Ala Arg Leu Ser
                295                 300

Trp Asn Gln Val Asp Gln Val Ile Arg Asn Ala Leu Ala Ser Pro Gly
305                 310                 315                 320

Ser Gly Gly Asp Leu Gly Glu Ala Ile Arg Glu Gln Pro Glu Gln Ala
                325                 330                 335

Arg Leu Ala Leu Thr Leu Ala Ala Glu Ser Glu Arg Phe Val Arg
            340                 345                 350

Gln Gly Thr Gly Asn Asp Glu Ala Gly Ala Ala Ser Ala Asp Val Val
                355                 360                 365

Ser Leu Thr Cys Pro Val Ala
    370                 375

<210> SEQ ID NO 144
<211> LENGTH: 364
<212> TYPE: PRT
<213> ORGANISM: Pseudomonas aeruginosa

<400> SEQUENCE: 144

Ala Glu Glu Ala Phe Asp Leu Trp Asn Glu Cys Ala Lys Ala Cys Val
1               5                   10                  15

Leu Asp Leu Lys Asp Gly Val Arg Ser Ser Arg Met Ser Val Asp Pro
                20                  25                  30

Ala Ile Ala Asp Thr Asn Gly Gln Gly Val Leu His Tyr Ser Met Val
            35                  40                  45
```

Leu Glu Gly Gly Asn Asp Ala Leu Lys Leu Ala Ile Asp Asn Ala Leu
 50                  55                  60

Ser Ile Thr Ser Asp Gly Leu Thr Ile Arg Leu Glu Gly Gly Val Glu
 65                  70                  75                  80

Pro Asn Lys Pro Val Arg Tyr Ser Tyr Thr Arg Gln Ala Arg Gly Ser
                 85                  90                  95

Trp Ser Leu Asn Trp Leu Val Pro Ile Gly His Glu Lys Pro Ser Asn
             100                 105                 110

Ile Lys Val Phe Ile His Glu Leu Asn Ala Gly Asn Gln Leu Ser His
         115                 120                 125

Met Ser Pro Ile Tyr Thr Ile Glu Met Gly Asp Glu Leu Leu Ala Lys
 130                 135                 140

Leu Ala Arg Asp Ala Thr Phe Phe Val Arg Ala His Glu Ser Asn Glu
145                 150                 155                 160

Met Gln Pro Thr Leu Ala Ile Ser His Ala Gly Val Ser Val Val Met
                 165                 170                 175

Ala Gln Ala Gln Pro Arg Arg Glu Lys Arg Trp Ser Glu Trp Ala Ser
             180                 185                 190

Gly Lys Val Leu Cys Leu Leu Asp Pro Leu Asp Gly Val Tyr Asn Tyr
         195                 200                 205

Leu Ala Gln Gln Arg Cys Asn Leu Asp Asp Thr Trp Glu Gly Lys Ile
 210                 215                 220

Tyr Arg Val Leu Ala Gly Asn Pro Ala Lys His Asp Leu Asp Ile Lys
225                 230                 235                 240

Pro Thr Val Ile Ser His Arg Leu His Phe Pro Glu Gly Gly Ser Leu
                 245                 250                 255

Ala Ala Leu Thr Ala His Gln Ala Cys His Leu Pro Leu Glu Thr Phe
             260                 265                 270

Thr Arg His Arg Gln Pro Arg Gly Trp Glu Gln Leu Glu Gln Cys Gly
         275                 280                 285

Tyr Pro Val Gln Arg Leu Val Ala Leu Tyr Leu Ala Ala Arg Leu Ser
 290                 295                 300

Trp Asn Gln Val Asp Gln Val Ile Arg Asn Ala Leu Ala Ser Pro Gly
305                 310                 315                 320

Ser Gly Gly Asp Leu Gly Glu Ala Ile Arg Glu Gln Pro Glu Gln Ala
                 325                 330                 335

Arg Leu Ala Leu Thr Leu Ala Ala Glu Ser Glu Arg Phe Val Arg
             340                 345                 350

Gln Gly Thr Gly Asn Asp Glu Ala Gly Ala Ala Ser
         355                 360

<210> SEQ ID NO 145
<211> LENGTH: 277
<212> TYPE: PRT
<213> ORGANISM: Pseudomonas aeruginosa

<400> SEQUENCE: 145

Ala Glu Glu Ala Phe Asp Leu Trp Asn Glu Cys Ala Lys Ala Cys Val
 1               5                  10                  15

Leu Asp Leu Lys Asp Gly Val Arg Ser Ser Arg Met Ser Val Asp Pro
             20                  25                  30

Ala Ile Ala Asp Thr Asn Gly Gln Gly Val Leu His Tyr Ser Met Val
         35                  40                  45

```
Leu Glu Gly Gly Asn Asp Ala Leu Lys Leu Ala Ile Asp Asn Ala Leu
 50                  55                  60

Ser Ile Thr Ser Asp Gly Leu Thr Ile Arg Leu Glu Gly Gly Val Glu
 65                  70                  75                  80

Pro Asn Lys Pro Val Arg Tyr Ser Tyr Thr Arg Gln Ala Arg Gly Ser
                 85                  90                  95

Trp Ser Leu Asn Trp Leu Val Pro Ile Gly His Glu Lys Pro Ser Asn
            100                 105                 110

Ile Lys Val Phe Ile His Glu Leu Asn Ala Gly Asn Gln Leu Ser His
        115                 120                 125

Met Ser Pro Ile Tyr Thr Ile Glu Met Gly Asp Glu Leu Leu Ala Lys
130                 135                 140

Leu Ala Arg Asp Ala Thr Phe Phe Val Arg Ala His Glu Ser Asn Glu
145                 150                 155                 160

Met Gln Pro Thr Leu Ala Ile Ser His Ala Gly Val Ser Val Val Met
                165                 170                 175

Ala Gln Ala Gln Pro Arg Arg Glu Lys Arg Trp Ser Glu Trp Ala Ser
            180                 185                 190

Gly Lys Val Leu Cys Leu Leu Asp Pro Leu Asp Gly Val Tyr Asn Tyr
        195                 200                 205

Leu Ala Gln Gln Arg Cys Asn Leu Asp Asp Thr Trp Glu Gly Lys Ile
210                 215                 220

Tyr Arg Val Leu Ala Gly Asn Pro Ala Lys His Asp Leu Asp Ile Lys
225                 230                 235                 240

Pro Thr Val Ile Ser His Arg Leu His Phe Pro Glu Gly Gly Ser Leu
                245                 250                 255

Ala Ala Leu Thr Ala His Gln Ala Cys His Leu Pro Leu Glu Thr Phe
            260                 265                 270

Thr Arg His Arg Gln
        275

<210> SEQ ID NO 146
<211> LENGTH: 627
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 146

Met Val Glu Glu Ala Leu Asn Ile Phe Asp Glu Cys Arg Ser Pro Cys
1               5                  10                  15

Ser Leu Thr Pro Glu Pro Gly Lys Pro Ile Gln Ser Lys Leu Ser Ile
            20                  25                  30

Pro Ser Asp Val Val Leu Asp Glu Gly Val Leu Tyr Tyr Ser Met Thr
        35                  40                  45

Ile Asn Asp Glu Gln Asn Asp Ile Lys Asp Glu Asp Lys Gly Glu Ser
 50                  55                  60

Ile Ile Thr Ile Gly Glu Phe Ala Thr Val Arg Ala Thr Arg His Tyr
 65                  70                  75                  80

Val Asn Gln Asp Ala Pro Phe Gly Val Ile His Leu Asp Ile Thr Thr
                 85                  90                  95

Glu Asn Gly Thr Lys Thr Tyr Ser Tyr Asn Arg Lys Glu Gly Glu Phe
            100                 105                 110
```

```
Ala Ile Asn Trp Leu Val Pro Ile Gly Glu Asp Ser Pro Ala Ser Ile
            115                 120                 125

Lys Ile Ser Val Asp Glu Leu Asp Gln Gln Arg Asn Ile Ile Glu Val
        130                 135                 140

Pro Lys Leu Tyr Ser Ile Asp Leu Asp Asn Gln Thr Leu Glu Gln Trp
145                 150                 155                 160

Lys Thr Gln Gly Asn Val Ser Phe Ser Val Thr Arg Pro Glu His Asn
                165                 170                 175

Ile Ala Ile Ser Trp Pro Ser Val Ser Tyr Lys Ala Ala Gln Lys Glu
            180                 185                 190

Gly Ser Arg His Lys Arg Trp Ala His Trp His Thr Gly Leu Ala Leu
        195                 200                 205

Cys Trp Leu Val Pro Met Asp Ala Ile Tyr Asn Tyr Ile Thr Gln Gln
210                 215                 220

Asn Cys Thr Leu Gly Asp Asn Trp Phe Gly Ser Tyr Glu Thr Val
225                 230                 235                 240

Ala Gly Thr Pro Lys Val Ile Thr Val Lys Gln Gly Ile Glu Gln Lys
                245                 250                 255

Pro Val Glu Gln Arg Ile His Phe Ser Lys Gly Gly Ser Leu Ala
            260                 265                 270

Ala Leu Thr Ala His Gln Ala Cys His Leu Pro Leu Glu Thr Phe Thr
        275                 280                 285

Arg His Arg Gln Pro Arg Gly Trp Glu Gln Leu Glu Cys Gly Tyr
290                 295                 300

Pro Val Gln Arg Leu Val Ala Leu Tyr Leu Ala Ala Arg Leu Ser Trp
305                 310                 315                 320

Asn Gln Val Asp Gln Val Ile Arg Asn Ala Leu Ala Ser Pro Gly Ser
                325                 330                 335

Gly Gly Asp Leu Gly Glu Ala Ile Arg Glu Gln Pro Glu Gln Ala Arg
            340                 345                 350

Leu Ala Leu Thr Leu Ala Ala Ala Glu Ser Glu Arg Phe Val Arg Gln
        355                 360                 365

Gly Thr Gly Asn Asp Glu Ala Gly Ala Ala Ser Ala Asp Val Val Ser
370                 375                 380

Leu Thr Cys Pro Val Ala Ala Gly Glu Cys Ala Gly Pro Ala Asp Ser
385                 390                 395                 400

Gly Asp Ala Leu Leu Glu Arg Asn Tyr Pro Thr Gly Ala Glu Phe Leu
                405                 410                 415

Gly Asp Gly Gly Asp Val Ser Phe Ser Thr Arg Gly Thr Gln Asn Trp
            420                 425                 430

Thr Val Glu Arg Leu Leu Gln Ala His Arg Gln Leu Glu Glu Arg Gly
        435                 440                 445

Tyr Val Phe Val Gly Tyr His Gly Thr Phe Leu Glu Ala Ala Gln Ser
450                 455                 460

Ile Val Phe Gly Gly Val Arg Ala Arg Ser Gln Asp Leu Asp Ala Ile
465                 470                 475                 480

Trp Arg Gly Phe Tyr Ile Ala Gly Asp Pro Ala Leu Ala Tyr Gly Tyr
                485                 490                 495

Ala Gln Asp Gln Glu Pro Asp Ala Arg Gly Arg Ile Arg Asn Gly Ala
            500                 505                 510

Leu Leu Arg Val Tyr Val Pro Arg Ser Ser Leu Pro Gly Phe Tyr Arg
        515                 520                 525
```

```
Thr Ser Leu Thr Leu Ala Ala Pro Glu Ala Ala Gly Glu Val Glu Arg
    530                 535                 540

Leu Ile Gly His Pro Leu Pro Leu Arg Leu Asp Ala Ile Thr Gly Pro
545                 550                 555                 560

Glu Glu Glu Gly Gly Arg Leu Thr Ile Leu Gly Trp Pro Leu Ala Glu
                565                 570                 575

Arg Thr Val Val Ile Pro Ser Ala Ile Pro Thr Asp Pro Arg Asn Val
            580                 585                 590

Gly Gly Asp Leu Asp Pro Ser Ser Ile Pro Asp Lys Glu Gln Ala Ile
        595                 600                 605

Ser Ala Leu Pro Asp Tyr Ala Ser Gln Pro Gly Lys Pro Pro Arg Glu
    610                 615                 620

Asp Leu Lys
625

<210> SEQ ID NO 147
<211> LENGTH: 620
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 147

Met Ala Glu Glu Ala Phe Asp Leu Trp Asn Glu Cys Ala Lys Ala Cys
1               5                   10                  15

Val Leu Asp Leu Lys Asp Gly Val Arg Ser Ser Arg Met Ser Val Asp
                20                  25                  30

Pro Ala Ile Ala Asp Thr Asn Gly Gln Gly Val Leu His Tyr Ser Met
            35                  40                  45

Val Leu Glu Gly Gly Asn Asp Ala Leu Lys Leu Ala Ile Asp Asn Ala
        50                  55                  60

Leu Ser Ile Thr Ser Asp Gly Leu Thr Ile Arg Leu Glu Gly Gly Val
65                  70                  75                  80

Glu Pro Asn Lys Pro Val Arg Tyr Ser Tyr Thr Arg Gln Ala Arg Gly
                85                  90                  95

Ser Trp Ser Leu Asn Trp Leu Val Pro Ile Gly His Glu Lys Pro Ser
            100                 105                 110

Asn Ile Lys Val Phe Ile His Glu Leu Asn Ala Gly Asn Gln Leu Ser
        115                 120                 125

His Met Ser Pro Ile Tyr Thr Ile Glu Met Gly Asp Glu Leu Leu Ala
    130                 135                 140

Lys Leu Ala Arg Asp Ala Thr Phe Phe Val Arg Ala His Glu Ser Asn
145                 150                 155                 160

Glu Met Gln Pro Thr Leu Ala Ile Ser His Ala Gly Val Ser Val Val
                165                 170                 175

Met Ala Gln Thr Gln Pro Arg Arg Glu Lys Arg Trp Ser Glu Trp Ala
            180                 185                 190

Ser Gly Lys Val Leu Cys Leu Leu Asp Pro Leu Asp Gly Val Tyr Asn
        195                 200                 205

Tyr Leu Ala Gln Gln Arg Cys Asn Leu Asp Asp Thr Trp Glu Gly Lys
    210                 215                 220

Ile Tyr Arg Val Leu Ala Gly Asn Pro Ala Lys His Asp Leu Asp Ile
225                 230                 235                 240
```

```
Lys Pro Thr Val Ile Ser His Arg Leu His Phe Pro Glu Gly Gly Asn
                245                 250                 255

Ala Met Ser Ala Leu Ala Ala His Arg Val Cys Gly Val Pro Leu Glu
            260                 265                 270

Thr Leu Ala Arg Ser Arg Lys Pro Arg Asp Leu Thr Asp Asp Leu Ser
        275                 280                 285

Cys Ala Tyr Gln Ala Gln Asn Ile Val Ser Leu Phe Val Ala Thr Arg
290                 295                 300

Ile Leu Phe Ser His Leu Asp Ser Val Phe Thr Leu Asn Leu Asp Glu
305                 310                 315                 320

Gln Glu Pro Glu Val Ala Glu Arg Leu Ser Asp Leu Arg Arg Ile Asn
                325                 330                 335

Glu Asn Asn Pro Gly Met Val Thr Gln Val Leu Thr Val Ala Arg Gln
            340                 345                 350

Ile Tyr Asn Asp Tyr Val Thr His His Pro Gly Leu Thr Pro Glu Gln
        355                 360                 365

Thr Ser Ala Gly Ala Gln Ala Ala Glu Ile Leu Ser Leu Phe Cys Pro
    370                 375                 380

Asp Ala Asp Lys Ser Cys Val Ala Thr Asn Asn Asp Gln Ala Asn Ile
385                 390                 395                 400

Asn Ile Glu Ser Arg Ser Gly Arg Ser Tyr Leu Pro Glu Asn Arg Ala
                405                 410                 415

Val Ile Thr Pro Gln Gly Val Thr Asn Trp Thr Tyr Gln Glu Leu Glu
            420                 425                 430

Ala Thr His Gln Ala Leu Thr Arg Glu Gly Tyr Val Phe Val Gly Tyr
        435                 440                 445

Thr Asn His Val Ala Ala Gln Thr Ile Val Asn Arg Ile Ala Pro Val
    450                 455                 460

Pro Arg Gly Asn Asn Thr Glu Asn Glu Glu Lys Trp Gly Gly Leu Tyr
465                 470                 475                 480

Val Ala Thr His Ala Glu Val Ala His Gly Tyr Ala Arg Ile Lys Glu
                485                 490                 495

Gly Thr Gly Glu Tyr Gly Leu Pro Thr Arg Ala Glu Arg Asp Ala Arg
            500                 505                 510

Gly Val Met Leu Arg Val Tyr Ile Pro Arg Ala Ser Leu Glu Arg Phe
        515                 520                 525

Tyr Arg Thr Asn Thr Pro Leu Glu Asn Ala Glu His Ile Thr Gln
    530                 535                 540

Val Ile Gly His Ser Leu Pro Leu Arg Asn Glu Ala Phe Thr Gly Pro
545                 550                 555                 560

Glu Ser Ala Gly Gly Glu Asp Thr Val Ile Gly Trp Asp Met Ala Ile
                565                 570                 575

His Ala Val Ala Ile Pro Ser Thr Ile Pro Gly Asn Ala Tyr Glu Glu
            580                 585                 590

Leu Ala Ile Asp Glu Glu Ala Val Ala Lys Glu Gln Ser Ile Ser Thr
        595                 600                 605

Lys Pro Pro Tyr Lys Glu Arg Lys Asp Glu Leu Lys
    610                 615                 620

<210> SEQ ID NO 148
<211> LENGTH: 18
<212> TYPE: PRT
<213> ORGANISM: Vibrio cholera
```

<400> SEQUENCE: 148

Glu Leu Asp Gln Gln Arg Asn Ile Ile Glu Val Pro Lys Leu Tyr Ser
1               5                   10                  15

Ile Asp

<210> SEQ ID NO 149
<211> LENGTH: 39
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 149

Met Val Glu Glu Ala Leu Asn Ile Phe Asp Glu Cys Arg Ser Pro Cys
1               5                   10                  15

Ser Leu Thr Pro Glu Pro Gly Lys Pro Ile Gln Ser Lys Leu Ser Ile
            20                  25                  30

Pro Ser Asp Val Val Leu Asp
        35

<210> SEQ ID NO 150
<211> LENGTH: 38
<212> TYPE: PRT
<213> ORGANISM: Vibrio cholera

<400> SEQUENCE: 150

Val Glu Glu Ala Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
            20                  25                  30

Ser Asp Val Val Leu Asp
        35

<210> SEQ ID NO 151
<211> LENGTH: 37
<212> TYPE: PRT
<213> ORGANISM: Vibrio cholera

<400> SEQUENCE: 151

Asp Leu Asp Asn Gln Thr Leu Glu Gln Trp Lys Thr Gln Gly Asn Val
1               5                   10                  15

Ser Phe Ser Val Thr Arg Pro Glu His Asn Ile Ala Ile Ser Trp Pro
            20                  25                  30

Ser Val Ser Tyr Lys
        35

<210> SEQ ID NO 152
<211> LENGTH: 22
<212> TYPE: PRT
<213> ORGANISM: Vibrio cholera

<400> SEQUENCE: 152

Lys Ala Ala Gln Lys Glu Gly Ser Arg His Lys Arg Trp Ala His Trp
1               5                   10                  15

His Thr Gly Leu Ala Leu
            20

<210> SEQ ID NO 153

```
<211> LENGTH: 593
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 153

Met Val Glu Glu Ala Leu Asn Ile Phe Asp Glu Cys Arg Ser Pro Cys
1               5                   10                  15

Ser Leu Thr Pro Glu Pro Gly Lys Pro Ile Gln Ser Lys Leu Ser Ile
            20                  25                  30

Pro Ser Asp Val Val Leu Asp Glu Gly Val Leu Tyr Tyr Ser Met Thr
        35                  40                  45

Ile Asn Asp Glu Gln Asn Asp Ile Lys Asp Glu Asp Lys Gly Glu Ser
    50                  55                  60

Ile Ile Thr Ile Gly Glu Phe Ala Thr Val Arg Ala Thr Arg His Tyr
65                  70                  75                  80

Val Asn Gln Asp Ala Pro Phe Gly Val Ile His Leu Asp Ile Thr Thr
                85                  90                  95

Glu Asn Gly Thr Lys Thr Tyr Ser Tyr Asn Arg Lys Glu Gly Glu Phe
            100                 105                 110

Ala Ile Asn Trp Leu Val Pro Ile Gly Glu Asp Ser Pro Ala Ser Ile
        115                 120                 125

Lys Ile Ser Val Asp Glu Leu Asp Gln Gln Arg Asn Ile Ile Glu Val
    130                 135                 140

Pro Lys Leu Tyr Ser Ile Asp Leu Asp Asn Gln Thr Leu Glu Gln Trp
145                 150                 155                 160

Lys Thr Gln Gly Asn Val Ser Phe Ser Val Thr Arg Pro Glu His Asn
                165                 170                 175

Ile Ala Ile Ser Trp Pro Ser Val Ser Tyr Lys Ala Ala Gln Lys Glu
            180                 185                 190

Gly Ser Arg His Lys Arg Trp Ala His Trp His Thr Gly Leu Ala Leu
        195                 200                 205

Cys Trp Leu Val Pro Met Asp Ala Ile Tyr Asn Tyr Ile Thr Gln Gln
    210                 215                 220

Asn Cys Thr Leu Gly Asp Asn Trp Phe Gly Gly Ser Tyr Glu Thr Val
225                 230                 235                 240

Ala Gly Thr Pro Lys Val Ile Thr Val Lys Gln Gly Ile Glu Gln Lys
                245                 250                 255

Pro Val Glu Gln Arg Ile His Phe Ser Lys Gly Asn Ala Met Ser Ala
            260                 265                 270

Leu Ala Ala His Arg Val Cys Gly Val Pro Leu Glu Thr Leu Ala Arg
        275                 280                 285

Ser Arg Lys Pro Arg Asp Leu Thr Asp Asp Leu Ser Cys Ala Tyr Gln
    290                 295                 300

Ala Gln Asn Ile Val Ser Leu Phe Val Ala Thr Arg Ile Leu Phe Ser
305                 310                 315                 320

His Leu Asp Ser Val Phe Thr Leu Asn Leu Asp Glu Gln Glu Pro Glu
                325                 330                 335

Val Ala Glu Arg Leu Ser Asp Leu Arg Arg Ile Asn Glu Asn Asn Pro
            340                 345                 350

Gly Met Val Thr Gln Val Leu Thr Val Ala Arg Gln Ile Tyr Asn Asp
        355                 360                 365
```

```
Tyr Val Thr His His Pro Gly Leu Thr Pro Glu Gln Thr Ser Ala Gly
    370                 375                 380

Ala Gln Ala Gly Gly Gly Ser Gly Gly Gly Ser Gly Gly Gly
385                 390                 395                 400

Gly Ser Phe Pro Thr Ile Pro Leu Ser Arg Leu Phe Asp Asn Ala Met
                405                 410                 415

Leu Arg Ala His Arg Leu His Gln Leu Ala Phe Asp Thr Tyr Gln Glu
                420                 425                 430

Phe Glu Glu Ala Tyr Ile Pro Lys Glu Gln Lys Tyr Ser Phe Leu Gln
                435                 440                 445

Asn Pro Gln Thr Ser Leu Cys Phe Ser Glu Ser Ile Pro Thr Pro Ser
450                 455                 460

Asn Arg Glu Glu Thr Gln Gln Lys Ser Asn Leu Glu Leu Leu Arg Ile
465                 470                 475                 480

Ser Leu Leu Leu Ile Gln Ser Trp Leu Glu Pro Val Gln Phe Leu Arg
                485                 490                 495

Ser Val Phe Ala Asn Ser Leu Val Tyr Gly Ala Ser Asp Ser Asn Val
                500                 505                 510

Tyr Asp Leu Leu Lys Asp Leu Glu Glu Gly Ile Gln Thr Leu Met Gly
                515                 520                 525

Arg Leu Glu Asp Gly Ser Pro Arg Thr Gly Gln Ile Phe Lys Gln Thr
530                 535                 540

Tyr Ser Lys Phe Asp Thr Asn Ser His Asn Asp Asp Ala Leu Leu Lys
545                 550                 555                 560

Asn Tyr Gly Leu Leu Tyr Cys Phe Arg Lys Asp Met Asp Lys Val Glu
                565                 570                 575

Thr Phe Leu Arg Ile Val Gln Cys Arg Ser Val Glu Gly Ser Cys Gly
                580                 585                 590

Phe

<210> SEQ ID NO 154
<211> LENGTH: 580
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 154

Met Val Glu Glu Ala Leu Asn Ile Phe Asp Glu Cys Arg Ser Pro Cys
1               5                   10                  15

Ser Leu Thr Pro Glu Pro Gly Lys Pro Ile Gln Ser Lys Leu Ser Ile
                20                  25                  30

Pro Ser Asp Val Val Leu Asp Glu Gly Val Leu Tyr Tyr Ser Met Thr
                35                  40                  45

Ile Asn Asp Glu Gln Asn Asp Ile Lys Asp Glu Asp Lys Gly Glu Ser
                50                  55                  60

Ile Ile Thr Ile Gly Glu Phe Ala Thr Val Arg Ala Thr Arg His Tyr
65              70                  75                  80

Val Asn Gln Asp Ala Pro Phe Gly Val Ile His Leu Asp Ile Thr Thr
                85                  90                  95

Glu Asn Gly Thr Lys Thr Tyr Ser Tyr Asn Arg Lys Glu Gly Glu Phe
                100                 105                 110

Ala Ile Asn Trp Leu Val Pro Ile Gly Glu Asp Ser Pro Ala Ser Ile
                115                 120                 125
```

```
Lys Ile Ser Val Asp Glu Leu Asp Gln Gln Arg Asn Ile Ile Glu Val
        130                 135                 140
Pro Lys Leu Tyr Ser Ile Asp Leu Asp Asn Gln Thr Leu Glu Gln Trp
145                 150                 155                 160
Lys Thr Gln Gly Asn Val Ser Phe Ser Val Thr Arg Pro Glu His Asn
                165                 170                 175
Ile Ala Ile Ser Trp Pro Ser Val Ser Tyr Lys Ala Ala Gln Lys Glu
                180                 185                 190
Gly Ser Arg His Lys Arg Trp Ala His Trp His Thr Gly Leu Ala Leu
                195                 200                 205
Cys Trp Leu Val Pro Met Asp Ala Ile Tyr Asn Tyr Ile Thr Gln Gln
210                 215                 220
Asn Cys Thr Leu Gly Asp Asn Trp Phe Gly Gly Ser Tyr Glu Thr Val
225                 230                 235                 240
Ala Gly Thr Pro Lys Val Ile Thr Val Lys Gln Gly Ile Glu Gln Lys
                245                 250                 255
Pro Val Glu Gln Arg Ile His Phe Ser Lys Gly Asn Ala Met Ser Ala
                260                 265                 270
Leu Ala Ala His Arg Val Cys Gly Val Pro Leu Glu Thr Leu Ala Arg
                275                 280                 285
Ser Arg Lys Pro Arg Asp Leu Thr Asp Asp Leu Ser Cys Ala Tyr Gln
            290                 295                 300
Ala Gln Asn Ile Val Ser Leu Phe Val Ala Thr Arg Ile Leu Phe Ser
305                 310                 315                 320
His Leu Asp Ser Val Phe Thr Leu Asn Leu Asp Glu Gln Glu Pro Glu
                325                 330                 335
Val Ala Glu Arg Leu Ser Asp Leu Arg Arg Ile Asn Glu Asn Asn Pro
            340                 345                 350
Gly Met Val Thr Gln Val Leu Thr Val Ala Arg Gln Ile Tyr Asn Asp
                355                 360                 365
Tyr Val Thr His His Pro Gly Leu Thr Pro Glu Gln Thr Ser Ala Gly
        370                 375                 380
Ala Gln Ala Gly Gly Gly Ser Gly Gly Gly Ser Gly Gly Gly
385                 390                 395                 400
Gly Ser Met His Ser Ser Ala Leu Leu Cys Cys Leu Val Leu Leu Thr
                405                 410                 415
Gly Val Arg Ala Ser Pro Gly Gln Gly Thr Gln Ser Glu Asn Ser Cys
            420                 425                 430
Thr His Phe Pro Gly Asn Leu Pro Asn Met Leu Arg Asp Leu Arg Asp
        435                 440                 445
Ala Phe Ser Arg Val Lys Thr Phe Phe Gln Met Lys Asp Gln Leu Asp
450                 455                 460
Asn Leu Leu Leu Lys Glu Ser Leu Leu Glu Asp Phe Lys Gly Tyr Leu
465                 470                 475                 480
Gly Cys Gln Ala Leu Ser Glu Met Ile Gln Phe Tyr Leu Glu Glu Val
                485                 490                 495
Met Pro Gln Ala Glu Asn Gln Asp Pro Asp Ile Lys Ala His Val Asn
            500                 505                 510
Ser Leu Gly Glu Asn Leu Lys Thr Leu Arg Leu Arg Leu Arg Arg Cys
        515                 520                 525
His Arg Phe Leu Pro Cys Glu Asn Lys Ser Lys Ala Val Glu Gln Val
530                 535                 540
```

```
Lys Asn Ala Phe Asn Lys Leu Gln Glu Lys Gly Ile Tyr Lys Ala Met
545                 550                 555                 560

Ser Glu Phe Asp Ile Phe Ile Asn Tyr Ile Glu Ala Tyr Met Thr Met
                565                 570                 575

Lys Ile Arg Asn
            580

<210> SEQ ID NO 155
<211> LENGTH: 460
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 155

Met Val Glu Glu Ala Leu Asn Ile Phe Asp Glu Cys Arg Ser Pro Cys
1               5                   10                  15

Ser Leu Thr Pro Glu Pro Gly Lys Pro Ile Gln Ser Lys Leu Ser Ile
            20                  25                  30

Pro Ser Asp Val Val Leu Asp Glu Gly Val Leu Tyr Tyr Ser Met Thr
        35                  40                  45

Ile Asn Asp Glu Gln Asn Asp Ile Lys Asp Glu Asp Lys Gly Glu Ser
50                  55                  60

Ile Ile Thr Ile Gly Glu Phe Ala Thr Val Arg Ala Thr Arg His Tyr
65                  70                  75                  80

Val Asn Gln Asp Ala Pro Phe Gly Val Ile His Leu Asp Ile Thr Thr
                85                  90                  95

Glu Asn Gly Thr Lys Thr Tyr Ser Tyr Asn Arg Lys Glu Gly Glu Phe
            100                 105                 110

Ala Ile Asn Trp Leu Val Pro Ile Gly Glu Asp Ser Pro Ala Ser Ile
        115                 120                 125

Lys Ile Ser Val Asp Glu Leu Asp Gln Gln Arg Asn Ile Ile Glu Val
130                 135                 140

Pro Lys Leu Tyr Ser Ile Asp Leu Asp Asn Gln Thr Leu Glu Gln Trp
145                 150                 155                 160

Lys Thr Gln Gly Asn Val Ser Phe Ser Val Thr Arg Pro Glu His Asn
                165                 170                 175

Ile Ala Ile Ser Trp Pro Ser Val Ser Tyr Lys Ala Ala Gln Lys Glu
            180                 185                 190

Gly Ser Arg His Lys Arg Trp Ala His Trp His Thr Gly Leu Ala Leu
        195                 200                 205

Cys Trp Leu Val Pro Met Asp Ala Ile Tyr Asn Tyr Ile Thr Gln Gln
210                 215                 220

Asn Cys Thr Leu Gly Asp Asn Trp Phe Gly Gly Ser Tyr Glu Thr Val
225                 230                 235                 240

Ala Gly Thr Pro Lys Val Ile Thr Val Lys Gln Gly Ile Glu Gln Lys
                245                 250                 255

Pro Val Glu Gln Arg Ile His Phe Ser Lys Gly Gly Gly Gly Ser Gly
            260                 265                 270

Gly Gly Gly Ser Gly Gly Gly Gly Ser Met Ala Ala Leu Gln Lys Ser
        275                 280                 285

Val Ser Ser Phe Leu Met Gly Thr Leu Ala Thr Ser Cys Leu Leu Leu
290                 295                 300
```

```
Leu Ala Leu Leu Val Gln Gly Gly Ala Ala Pro Ile Ser Ser His
305                 310                 315                 320

Cys Arg Leu Asp Lys Ser Asn Phe Gln Gln Pro Tyr Ile Thr Asn Arg
            325                 330                 335

Thr Phe Met Leu Ala Lys Glu Ala Ser Leu Ala Asp Asn Asn Thr Asp
        340                 345                 350

Val Arg Leu Ile Gly Glu Lys Leu Phe His Gly Val Ser Met Ser Glu
    355                 360                 365

Arg Cys Tyr Leu Met Lys Gln Val Leu Asn Phe Thr Leu Glu Glu Val
    370                 375                 380

Leu Phe Pro Gln Ser Asp Arg Phe Gln Pro Tyr Met Gln Glu Val Val
385                 390                 395                 400

Pro Phe Leu Ala Arg Leu Ser Asn Arg Leu Ser Thr Cys His Ile Glu
            405                 410                 415

Gly Asp Asp Leu His Ile Gln Arg Asn Val Gln Lys Leu Lys Asp Thr
        420                 425                 430

Val Lys Lys Leu Gly Glu Ser Gly Glu Ile Lys Ala Ile Gly Glu Leu
    435                 440                 445

Asp Leu Leu Phe Met Ser Leu Arg Asn Ala Cys Ile
450                 455                 460

<210> SEQ ID NO 156
<211> LENGTH: 491
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 156

Met Val Glu Glu Ala Leu Asn Ile Phe Asp Glu Cys Arg Ser Pro Cys
1               5                   10                  15

Ser Leu Thr Pro Glu Pro Gly Lys Pro Ile Gln Ser Lys Leu Ser Ile
            20                  25                  30

Pro Ser Asp Val Val Leu Asp Glu Gly Val Leu Tyr Tyr Ser Met Thr
        35                  40                  45

Ile Asn Asp Glu Gln Asn Asp Ile Lys Asp Glu Asp Lys Gly Glu Ser
    50                  55                  60

Ile Ile Thr Ile Gly Glu Phe Ala Thr Val Arg Ala Thr Arg His Tyr
65                  70                  75                  80

Val Asn Gln Asp Ala Pro Phe Gly Val Ile His Leu Asp Ile Thr Thr
                85                  90                  95

Glu Asn Gly Thr Lys Thr Tyr Ser Tyr Asn Arg Lys Glu Gly Glu Phe
            100                 105                 110

Ala Ile Asn Trp Leu Val Pro Ile Gly Glu Asp Ser Pro Ala Ser Ile
        115                 120                 125

Lys Ile Ser Val Asp Glu Leu Asp Gln Gln Arg Asn Ile Ile Glu Val
    130                 135                 140

Pro Lys Leu Tyr Ser Ile Asp Leu Asp Asn Gln Thr Leu Glu Gln Trp
145                 150                 155                 160

Lys Thr Gln Gly Asn Val Ser Phe Ser Val Thr Arg Pro Glu His Asn
                165                 170                 175

Ile Ala Ile Ser Trp Pro Ser Val Ser Tyr Lys Ala Ala Gln Lys Glu
            180                 185                 190
```

```
Gly Ser Arg His Lys Arg Trp Ala His Trp His Thr Gly Leu Ala Leu
            195                 200                 205

Cys Trp Leu Val Pro Met Asp Ala Ile Tyr Asn Tyr Ile Thr Gln Gln
210                 215                 220

Asn Cys Thr Leu Gly Asp Asn Trp Phe Gly Gly Ser Tyr Glu Thr Val
225                 230                 235                 240

Ala Gly Thr Pro Lys Val Ile Thr Val Lys Gln Gly Ile Glu Gln Lys
            245                 250                 255

Pro Val Glu Gln Arg Ile His Phe Ser Lys Met Arg Ser Ser Lys Asn
            260                 265                 270

Val Ile Lys Glu Phe Met Arg Phe Lys Val Arg Met Glu Gly Thr Val
            275                 280                 285

Asn Gly His Glu Phe Glu Ile Glu Gly Glu Gly Glu Gly Arg Pro Tyr
            290                 295                 300

Glu Gly His Asn Thr Val Lys Leu Lys Val Thr Lys Gly Gly Pro Leu
305                 310                 315                 320

Pro Phe Ala Trp Asp Ile Leu Ser Pro Gln Phe Gln Tyr Gly Ser Lys
            325                 330                 335

Val Tyr Val Lys His Pro Ala Asp Ile Pro Asp Tyr Lys Lys Leu Ser
            340                 345                 350

Phe Pro Glu Gly Phe Lys Trp Glu Arg Val Met Asn Phe Glu Asp Gly
            355                 360                 365

Gly Val Val Thr Val Thr Gln Asp Ser Ser Leu Gln Asp Gly Cys Phe
            370                 375                 380

Ile Tyr Lys Val Lys Phe Ile Gly Val Asn Phe Pro Ser Asp Gly Pro
385                 390                 395                 400

Val Met Gln Lys Lys Thr Met Gly Trp Glu Ala Ser Thr Glu Arg Leu
            405                 410                 415

Tyr Pro Arg Asp Gly Val Leu Lys Gly Glu Ile His Lys Ala Leu Lys
            420                 425                 430

Leu Lys Asp Gly Gly His Tyr Leu Val Glu Phe Lys Ser Ile Tyr Met
            435                 440                 445

Ala Lys Lys Pro Val Gln Leu Pro Gly Tyr Tyr Tyr Val Asp Ser Lys
            450                 455                 460

Leu Asp Ile Thr Ser His Asn Glu Asp Tyr Thr Ile Val Glu Gln Tyr
465                 470                 475                 480

Glu Arg Thr Glu Gly Arg His His Leu Phe Leu
            485                 490

<210> SEQ ID NO 157
<211> LENGTH: 859
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 157

Val Glu Asp Glu Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
            20                  25                  30

Ser Asp Val Val Leu Asp Glu Gly Val Leu Tyr Tyr Ser Met Thr Ile
        35                  40                  45
```

```
Asn Asp Glu Gln Asn Asp Ile Lys Asp Glu Asp Lys Gly Glu Ser Ile
    50                  55                  60
Ile Thr Ile Gly Glu Phe Ala Thr Val Arg Ala Thr Arg His Tyr Val
65                  70                  75                  80
Asn Gln Asp Ala Pro Phe Gly Val Ile His Leu Asp Ile Thr Thr Glu
                85                  90                  95
Asn Gly Thr Lys Thr Tyr Ser Tyr Asn Arg Lys Glu Gly Glu Phe Ala
            100                 105                 110
Ile Asn Trp Leu Val Pro Ile Gly Glu Asp Ser Pro Ala Ser Ile Lys
        115                 120                 125
Ile Ser Val Asp Glu Leu Asp Gln Gln Arg Asn Ile Ile Glu Val Pro
    130                 135                 140
Lys Leu Tyr Ser Ile Asp Leu Asp Asn Gln Thr Leu Glu Gln Trp Lys
145                 150                 155                 160
Thr Gln Gly Asn Val Ser Phe Ser Val Thr Arg Pro Glu His Asn Ile
                165                 170                 175
Ala Ile Ser Trp Pro Ser Val Ser Tyr Lys Ala Ala Gln Lys Glu Gly
            180                 185                 190
Ser Arg His Lys Arg Trp Ala His Trp His Thr Gly Leu Ala Leu Cys
        195                 200                 205
Trp Leu Val Pro Met Asp Ala Ile Tyr Asn Tyr Ile Thr Gln Gln Asn
    210                 215                 220
Cys Thr Leu Gly Asp Asn Trp Phe Gly Gly Ser Tyr Glu Thr Val Ala
225                 230                 235                 240
Gly Thr Pro Lys Val Ile Thr Val Lys Gln Gly Ile Glu Gln Lys Pro
                245                 250                 255
Val Glu Gln Arg Ile His Phe Ser Lys Gly Asn Ala Met Ser Ala Leu
            260                 265                 270
Ala Ala His Arg Val Cys Gly Val Pro Leu Glu Thr Leu Ala Arg Ser
        275                 280                 285
Arg Lys Pro Arg Asp Leu Thr Asp Asp Leu Ser Cys Ala Tyr Gln Ala
    290                 295                 300
Gln Asn Ile Val Ser Leu Phe Val Ala Thr Arg Ile Leu Phe Ser His
305                 310                 315                 320
Leu Asp Ser Val Phe Thr Leu Asn Leu Asp Glu Gln Glu Pro Glu Val
                325                 330                 335
Ala Glu Arg Leu Ser Asp Leu Arg Arg Ile Asn Glu Asn Asn Pro Gly
            340                 345                 350
Met Val Thr Gln Val Leu Thr Val Ala Arg Gln Ile Tyr Asn Asp Tyr
        355                 360                 365
Val Thr His His Pro Gly Leu Thr Pro Glu Gln Thr Ser Ala Gly Ala
    370                 375                 380
Gln Ala Ala Asp Ile Leu Ser Leu Phe Cys Pro Asp Ala Asp Lys Ser
385                 390                 395                 400
Cys Val Ala Ser Asn Asn Asp Gln Ala Asn Ile Asn Ile Glu Ser Arg
                405                 410                 415
Ser Gly Arg Ser Tyr Leu Pro Glu Asn Arg Ala Val Ile Thr Pro Gln
            420                 425                 430
Gly Val Thr Asn Trp Thr Tyr Gln Glu Leu Glu Ala Thr His Gln Ala
        435                 440                 445
Leu Thr Arg Glu Gly Tyr Val Phe Val Gly Tyr His Gly Thr Asn His
    450                 455                 460
```

Val Ala Ala Gln Thr Ile Val Asn Arg Ile Ala Pro Val Pro Arg Gly
465                 470                 475                 480

Asn Asn Thr Glu Asn Glu Glu Lys Trp Gly Gly Leu Tyr Val Ala Thr
            485                 490                 495

His Ala Glu Val Ala His Gly Tyr Ala Arg Ile Lys Glu Gly Thr Gly
        500                 505                 510

Glu Tyr Gly Leu Pro Thr Arg Ala Glu Arg Asp Ala Arg Gly Val Met
    515                 520                 525

Leu Arg Val Tyr Ile Pro Arg Ala Ser Leu Glu Arg Phe Tyr Arg Thr
530                 535                 540

Asn Thr Pro Leu Glu Asn Ala Glu Glu His Ile Thr Gln Val Ile Gly
545                 550                 555                 560

His Ser Leu Pro Leu Arg Asn Glu Ala Phe Thr Gly Pro Glu Ser Ala
                565                 570                 575

Gly Gly Glu Asp Ala Thr Val Ile Gly Trp Asp Met Ala Ile His Ala
            580                 585                 590

Val Ala Ile Pro Ser Thr Ile Pro Gly Asn Ala Tyr Glu Glu Leu Ala
        595                 600                 605

Ile Asp Glu Glu Ala Val Ala Lys Glu Gln Ser Ile Ser Thr Lys Pro
610                 615                 620

Pro Tyr Lys Glu Arg Lys Asp Glu Leu Lys Met Arg Ser Ser Lys Asn
625                 630                 635                 640

Val Ile Lys Glu Phe Met Arg Phe Lys Val Arg Met Glu Gly Thr Val
                645                 650                 655

Asn Gly His Glu Phe Glu Ile Glu Gly Glu Gly Glu Gly Arg Pro Tyr
            660                 665                 670

Glu Gly His Asn Thr Val Lys Leu Lys Val Thr Lys Gly Gly Pro Leu
        675                 680                 685

Pro Phe Ala Trp Asp Ile Leu Ser Pro Gln Phe Gln Tyr Gly Ser Lys
690                 695                 700

Val Tyr Val Lys His Pro Ala Asp Ile Pro Asp Tyr Lys Lys Leu Ser
705                 710                 715                 720

Phe Pro Glu Gly Phe Lys Trp Glu Arg Val Met Asn Phe Glu Asp Gly
                725                 730                 735

Gly Val Val Thr Val Thr Gln Asp Ser Ser Leu Gln Asp Gly Cys Phe
            740                 745                 750

Ile Tyr Lys Val Lys Phe Ile Gly Val Asn Phe Pro Ser Asp Gly Pro
        755                 760                 765

Val Met Gln Lys Lys Thr Met Gly Trp Glu Ala Ser Thr Glu Arg Leu
770                 775                 780

Tyr Pro Arg Asp Gly Val Leu Lys Gly Glu Ile His Lys Ala Leu Lys
785                 790                 795                 800

Leu Lys Asp Gly Gly His Tyr Leu Val Glu Phe Lys Ser Ile Tyr Met
                805                 810                 815

Ala Lys Lys Pro Val Gln Leu Pro Gly Tyr Tyr Val Asp Ser Lys
            820                 825                 830

Leu Asp Ile Thr Ser His Asn Glu Asp Tyr Thr Ile Val Glu Gln Tyr
        835                 840                 845

Glu Arg Thr Glu Gly Arg His His Leu Phe Leu
    850                 855

<210> SEQ ID NO 158
<211> LENGTH: 340
<212> TYPE: PRT

<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 158

```
Met Val Glu Glu Ala Leu Asn Ile Phe Asp Glu Cys Arg Ser Pro Cys
1               5                   10                  15

Ser Leu Thr Pro Glu Pro Gly Lys Pro Ile Gln Ser Lys Leu Ser Ile
            20                  25                  30

Pro Ser Asp Val Val Leu Asp Glu Gly Val Leu Tyr Tyr Ser Met Thr
        35                  40                  45

Ile Asn Asp Glu Gln Asn Asp Ile Lys Asp Glu Asp Lys Gly Glu Ser
50                  55                  60

Ile Ile Thr Ile Gly Glu Phe Ala Thr Val Arg Ala Thr Arg His Tyr
65                  70                  75                  80

Val Asn Gln Asp Ala Pro Phe Gly Val Ile His Leu Asp Ile Thr Thr
                85                  90                  95

Glu Asn Gly Thr Lys Thr Tyr Ser Tyr Asn Arg Lys Glu Gly Glu Phe
            100                 105                 110

Ala Ile Asn Trp Leu Val Pro Ile Gly Glu Asp Ser Pro Ala Ser Ile
        115                 120                 125

Lys Ile Ser Val Asp Gly Gly Gly Ser Gly Gly Gly Ser
130                 135                 140

Gly Gly Gly Gly Ser Phe Pro Thr Ile Pro Leu Ser Arg Leu Phe Asp
145                 150                 155                 160

Asn Ala Met Leu Arg Ala His Arg Leu His Gln Leu Ala Phe Asp Thr
                165                 170                 175

Tyr Gln Glu Phe Glu Glu Ala Tyr Ile Pro Lys Glu Gln Lys Tyr Ser
            180                 185                 190

Phe Leu Gln Asn Pro Gln Thr Ser Leu Cys Phe Ser Glu Ser Ile Pro
        195                 200                 205

Thr Pro Ser Asn Arg Glu Glu Thr Gln Gln Lys Ser Asn Leu Glu Leu
210                 215                 220

Leu Arg Ile Ser Leu Leu Leu Ile Gln Ser Trp Leu Glu Pro Val Gln
225                 230                 235                 240

Phe Leu Arg Ser Val Phe Ala Asn Ser Leu Val Tyr Gly Ala Ser Asp
                245                 250                 255

Ser Asn Val Tyr Asp Leu Leu Lys Asp Leu Glu Glu Gly Ile Gln Thr
            260                 265                 270

Leu Met Gly Arg Leu Glu Asp Gly Ser Pro Arg Thr Gly Gln Ile Phe
        275                 280                 285

Lys Gln Thr Tyr Ser Lys Phe Asp Thr Asn Ser His Asn Asp Asp Ala
290                 295                 300

Leu Leu Lys Asn Tyr Gly Leu Leu Tyr Cys Phe Arg Lys Asp Met Asp
305                 310                 315                 320

Lys Val Glu Thr Phe Leu Arg Ile Val Gln Cys Arg Ser Val Glu Gly
                325                 330                 335

Ser Cys Gly Phe
            340
```

<210> SEQ ID NO 159
<211> LENGTH: 357
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 159

Met Val Glu Glu Ala Leu Asn Ile Phe Asp Glu Cys Arg Ser Pro Cys
1               5                   10                  15

Ser Leu Thr Pro Glu Pro Gly Lys Pro Ile Gln Ser Lys Leu Ser Ile
            20                  25                  30

Pro Ser Asp Val Val Leu Asp Glu Gly Val Leu Tyr Tyr Ser Met Thr
        35                  40                  45

Ile Asn Asp Glu Gln Asn Asp Ile Lys Asp Glu Asp Lys Gly Glu Ser
    50                  55                  60

Ile Ile Thr Ile Gly Glu Phe Ala Thr Val Arg Ala Thr Arg His Tyr
65                  70                  75                  80

Val Asn Gln Asp Ala Pro Phe Gly Val Ile His Leu Asp Ile Thr Thr
                85                  90                  95

Glu Asn Gly Thr Lys Thr Tyr Ser Tyr Asn Arg Lys Glu Gly Glu Phe
            100                 105                 110

Ala Ile Asn Trp Leu Val Pro Ile Gly Glu Asp Ser Pro Ala Ser Ile
        115                 120                 125

Lys Ile Ser Val Asp Glu Leu Asp Gln Gln Arg Asn Ile Ile Glu Val
130                 135                 140

Pro Lys Leu Tyr Ser Ile Asp Gly Gly Gly Ser Gly Gly Gly Gly
145                 150                 155                 160

Ser Gly Gly Gly Gly Ser Phe Pro Thr Ile Pro Leu Ser Arg Leu Phe
                165                 170                 175

Asp Asn Ala Met Leu Arg Ala His Arg Leu His Gln Leu Ala Phe Asp
            180                 185                 190

Thr Tyr Gln Glu Phe Glu Glu Ala Tyr Ile Pro Lys Glu Gln Lys Tyr
        195                 200                 205

Ser Phe Leu Gln Asn Pro Gln Thr Ser Leu Cys Phe Ser Glu Ser Ile
    210                 215                 220

Pro Thr Pro Ser Asn Arg Glu Glu Thr Gln Gln Lys Ser Asn Leu Glu
225                 230                 235                 240

Leu Leu Arg Ile Ser Leu Leu Leu Ile Gln Ser Trp Leu Glu Pro Val
                245                 250                 255

Gln Phe Leu Arg Ser Val Phe Ala Asn Ser Leu Val Tyr Gly Ala Ser
            260                 265                 270

Asp Ser Asn Val Tyr Asp Leu Leu Lys Asp Leu Glu Glu Gly Ile Gln
        275                 280                 285

Thr Leu Met Gly Arg Leu Glu Asp Gly Ser Pro Arg Thr Gly Gln Ile
    290                 295                 300

Phe Lys Gln Thr Tyr Ser Lys Phe Asp Thr Asn Ser His Asn Asp Asp
305                 310                 315                 320

Ala Leu Leu Lys Asn Tyr Gly Leu Leu Tyr Cys Phe Arg Lys Asp Met
                325                 330                 335

Asp Lys Val Glu Thr Phe Leu Arg Ile Val Gln Cys Arg Ser Val Glu
            340                 345                 350

Gly Ser Cys Gly Phe
            355

<210> SEQ ID NO 160
<211> LENGTH: 393

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 160

Met Val Glu Glu Ala Leu Asn Ile Phe Asp Glu Cys Arg Ser Pro Cys
1               5                   10                  15

Ser Leu Thr Pro Glu Pro Gly Lys Pro Ile Gln Ser Lys Leu Ser Ile
            20                  25                  30

Pro Ser Asp Val Val Leu Asp Glu Gly Val Leu Tyr Tyr Ser Met Thr
        35                  40                  45

Ile Asn Asp Glu Gln Asn Asp Ile Lys Asp Glu Asp Lys Gly Glu Ser
50                  55                  60

Ile Ile Thr Ile Gly Glu Phe Ala Thr Val Arg Ala Thr Arg His Tyr
65                  70                  75                  80

Val Asn Gln Asp Ala Pro Phe Gly Val Ile His Leu Asp Ile Thr Thr
                85                  90                  95

Glu Asn Gly Thr Lys Thr Tyr Ser Tyr Asn Arg Lys Glu Gly Glu Phe
            100                 105                 110

Ala Ile Asn Trp Leu Val Pro Ile Gly Glu Asp Ser Pro Ala Ser Ile
        115                 120                 125

Lys Ile Ser Val Asp Glu Leu Asp Gln Gln Arg Asn Ile Ile Glu Val
130                 135                 140

Pro Lys Leu Tyr Ser Ile Asp Leu Asp Asn Gln Thr Leu Glu Gln Trp
145                 150                 155                 160

Lys Thr Gln Gly Asn Val Ser Phe Ser Val Thr Arg Pro Glu His Asn
                165                 170                 175

Ile Ala Ile Ser Trp Pro Ser Val Ser Tyr Lys Gly Gly Gly Gly Ser
            180                 185                 190

Gly Gly Gly Gly Ser Gly Gly Gly Ser Phe Pro Thr Ile Pro Leu
        195                 200                 205

Ser Arg Leu Phe Asp Asn Ala Met Leu Arg Ala His Arg Leu His Gln
210                 215                 220

Leu Ala Phe Asp Thr Tyr Gln Glu Phe Glu Glu Ala Tyr Ile Pro Lys
225                 230                 235                 240

Glu Gln Lys Tyr Ser Phe Leu Gln Asn Pro Gln Thr Ser Leu Cys Phe
                245                 250                 255

Ser Glu Ser Ile Pro Thr Pro Ser Asn Arg Glu Glu Thr Gln Gln Lys
            260                 265                 270

Ser Asn Leu Glu Leu Leu Arg Ile Ser Leu Leu Leu Ile Gln Ser Trp
        275                 280                 285

Leu Glu Pro Val Gln Phe Leu Arg Ser Val Phe Ala Asn Ser Leu Val
290                 295                 300

Tyr Gly Ala Ser Asp Ser Asn Val Tyr Asp Leu Leu Lys Asp Leu Glu
305                 310                 315                 320

Glu Gly Ile Gln Thr Leu Met Gly Arg Leu Glu Asp Gly Ser Pro Arg
                325                 330                 335

Thr Gly Gln Ile Phe Lys Gln Thr Tyr Ser Lys Phe Asp Thr Asn Ser
            340                 345                 350

His Asn Asp Asp Ala Leu Leu Lys Asn Tyr Gly Leu Leu Tyr Cys Phe
        355                 360                 365
```

Arg Lys Asp Met Asp Lys Val Glu Thr Phe Leu Arg Ile Val Gln Cys
            370                 375                 380

Arg Ser Val Glu Gly Ser Cys Gly Phe
385                 390

<210> SEQ ID NO 161
<211> LENGTH: 412
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 161

Met Val Glu Glu Ala Leu Asn Ile Phe Asp Glu Cys Arg Ser Pro Cys
1               5                   10                  15

Ser Leu Thr Pro Glu Pro Gly Lys Pro Ile Gln Ser Lys Leu Ser Ile
            20                  25                  30

Pro Ser Asp Val Val Leu Asp Glu Gly Val Leu Tyr Tyr Ser Met Thr
        35                  40                  45

Ile Asn Asp Glu Gln Asn Asp Ile Lys Asp Glu Asp Lys Gly Glu Ser
    50                  55                  60

Ile Ile Thr Ile Gly Glu Phe Ala Thr Val Arg Ala Thr Arg His Tyr
65                  70                  75                  80

Val Asn Gln Asp Ala Pro Phe Gly Val Ile His Leu Asp Ile Thr Thr
                85                  90                  95

Glu Asn Gly Thr Lys Thr Tyr Ser Tyr Asn Arg Lys Glu Gly Glu Phe
            100                 105                 110

Ala Ile Asn Trp Leu Val Pro Ile Gly Glu Asp Ser Pro Ala Ser Ile
        115                 120                 125

Lys Ile Ser Val Asp Glu Leu Asp Gln Gln Arg Asn Ile Ile Glu Val
    130                 135                 140

Pro Lys Leu Tyr Ser Ile Asp Leu Asp Asn Gln Thr Leu Glu Gln Trp
145                 150                 155                 160

Lys Thr Gln Gly Asn Val Ser Phe Ser Val Thr Arg Pro Glu His Asn
                165                 170                 175

Ile Ala Ile Ser Trp Pro Ser Val Ser Tyr Lys Ala Ala Gln Lys Glu
            180                 185                 190

Gly Ser Arg His Lys Arg Trp Ala His Trp His Thr Gly Leu Gly Gly
        195                 200                 205

Gly Gly Ser Gly Gly Gly Ser Gly Gly Gly Ser Phe Pro Thr
    210                 215                 220

Ile Pro Leu Ser Arg Leu Phe Asp Asn Ala Met Leu Arg Ala His Arg
225                 230                 235                 240

Leu His Gln Leu Ala Phe Asp Thr Tyr Gln Glu Phe Glu Glu Ala Tyr
                245                 250                 255

Ile Pro Lys Glu Gln Lys Tyr Ser Phe Leu Gln Asn Pro Gln Thr Ser
            260                 265                 270

Leu Cys Phe Ser Glu Ser Ile Pro Thr Pro Ser Asn Arg Glu Glu Thr
        275                 280                 285

Gln Gln Lys Ser Asn Leu Glu Leu Leu Arg Ile Ser Leu Leu Leu Ile
    290                 295                 300

Gln Ser Trp Leu Glu Pro Val Gln Phe Leu Arg Ser Val Phe Ala Asn
305                 310                 315                 320

```
Ser Leu Val Tyr Gly Ala Ser Asp Ser Asn Val Tyr Asp Leu Leu Lys
            325                 330                 335

Asp Leu Glu Glu Gly Ile Gln Thr Leu Met Gly Arg Leu Glu Asp Gly
        340                 345                 350

Ser Pro Arg Thr Gly Gln Ile Phe Lys Gln Thr Tyr Ser Lys Phe Asp
        355                 360                 365

Thr Asn Ser His Asn Asp Asp Ala Leu Leu Lys Asn Tyr Gly Leu Leu
        370                 375                 380

Tyr Cys Phe Arg Lys Asp Met Asp Lys Val Glu Thr Phe Leu Arg Ile
385                 390                 395                 400

Val Gln Cys Arg Ser Val Glu Gly Ser Cys Gly Phe
                405                 410

<210> SEQ ID NO 162
<211> LENGTH: 451
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 162

Met Val Glu Glu Ala Leu Asn Ile Phe Asp Glu Cys Arg Ser Pro Cys
1               5                   10                  15

Ser Leu Thr Pro Glu Pro Gly Lys Pro Ile Gln Ser Lys Leu Ser Ile
            20                  25                  30

Pro Ser Asp Val Val Leu Asp Glu Gly Val Leu Tyr Tyr Ser Met Thr
        35                  40                  45

Ile Asn Asp Glu Gln Asn Asp Ile Lys Asp Glu Asp Lys Gly Glu Ser
50                  55                  60

Ile Ile Thr Ile Gly Glu Phe Ala Thr Val Arg Ala Thr Arg His Tyr
65                  70                  75                  80

Val Asn Gln Asp Ala Pro Phe Gly Val Ile His Leu Asp Ile Thr Thr
                85                  90                  95

Glu Asn Gly Thr Lys Thr Tyr Ser Tyr Asn Arg Lys Glu Gly Glu Phe
            100                 105                 110

Ala Ile Asn Trp Leu Val Pro Ile Gly Glu Asp Ser Pro Ala Ser Ile
        115                 120                 125

Lys Ile Ser Val Asp Glu Leu Asp Gln Gln Arg Asn Ile Ile Glu Val
    130                 135                 140

Pro Lys Leu Tyr Ser Ile Asp Leu Asp Asn Gln Thr Leu Glu Gln Trp
145                 150                 155                 160

Lys Thr Gln Gly Asn Val Ser Phe Ser Val Thr Arg Pro Glu His Asn
                165                 170                 175

Ile Ala Ile Ser Trp Pro Ser Val Ser Tyr Lys Ala Ala Gln Lys Glu
            180                 185                 190

Gly Ser Arg His Lys Arg Trp Ala His Trp His Thr Gly Leu Ala Leu
        195                 200                 205

Cys Trp Leu Val Pro Met Asp Ala Ile Tyr Asn Tyr Ile Thr Gln Gln
    210                 215                 220

Asn Cys Thr Leu Gly Asp Asn Trp Phe Gly Gly Ser Tyr Glu Thr Val
225                 230                 235                 240

Ala Gly Thr Pro Lys Gly Gly Gly Ser Gly Gly Gly Ser Gly
                245                 250                 255
```

```
Gly Gly Gly Ser Phe Pro Thr Ile Pro Leu Ser Arg Leu Phe Asp Asn
            260                 265                 270

Ala Met Leu Arg Ala His Arg Leu His Gln Leu Ala Phe Asp Thr Tyr
        275                 280                 285

Gln Glu Phe Glu Glu Ala Tyr Ile Pro Lys Gln Lys Tyr Ser Phe
290                 295                 300

Leu Gln Asn Pro Gln Thr Ser Leu Cys Phe Ser Glu Ser Ile Pro Thr
305                 310                 315                 320

Pro Ser Asn Arg Glu Glu Thr Gln Gln Lys Ser Asn Leu Glu Leu Leu
                325                 330                 335

Arg Ile Ser Leu Leu Ile Gln Ser Trp Leu Glu Pro Val Gln Phe
            340                 345                 350

Leu Arg Ser Val Phe Ala Asn Ser Leu Val Tyr Gly Ala Ser Asp Ser
        355                 360                 365

Asn Val Tyr Asp Leu Leu Lys Asp Leu Glu Glu Gly Ile Gln Thr Leu
    370                 375                 380

Met Gly Arg Leu Glu Asp Gly Ser Pro Arg Thr Gly Gln Ile Phe Lys
385                 390                 395                 400

Gln Thr Tyr Ser Lys Phe Asp Thr Asn Ser His Asn Asp Asp Ala Leu
                405                 410                 415

Leu Lys Asn Tyr Gly Leu Leu Tyr Cys Phe Arg Lys Asp Met Asp Lys
            420                 425                 430

Val Glu Thr Phe Leu Arg Ile Val Gln Cys Arg Ser Val Glu Gly Ser
        435                 440                 445

Cys Gly Phe
    450

<210> SEQ ID NO 163
<211> LENGTH: 457
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 163

Met Val Glu Glu Ala Leu Asn Ile Phe Asp Glu Cys Arg Ser Pro Cys
1               5                   10                  15

Ser Leu Thr Pro Glu Pro Gly Lys Pro Ile Gln Ser Lys Leu Ser Ile
            20                  25                  30

Pro Ser Asp Val Val Leu Asp Glu Gly Val Leu Tyr Tyr Ser Met Thr
        35                  40                  45

Ile Asn Asp Glu Gln Asn Asp Ile Lys Asp Glu Asp Lys Gly Glu Ser
    50                  55                  60

Ile Ile Thr Ile Gly Glu Phe Ala Thr Val Arg Ala Thr Arg His Tyr
65                  70                  75                  80

Val Asn Gln Asp Ala Pro Phe Gly Val Ile His Leu Asp Ile Thr Thr
                85                  90                  95

Glu Asn Gly Thr Lys Thr Tyr Ser Tyr Asn Arg Lys Glu Gly Glu Phe
            100                 105                 110

Ala Ile Asn Trp Leu Val Pro Ile Gly Glu Asp Ser Pro Ala Ser Ile
        115                 120                 125

Lys Ile Ser Val Asp Glu Leu Asp Gln Gln Arg Asn Ile Ile Glu Val
    130                 135                 140
```

```
Pro Lys Leu Tyr Ser Ile Asp Leu Asp Asn Gln Thr Leu Glu Gln Trp
145                 150                 155                 160

Lys Thr Gln Gly Asn Val Ser Phe Ser Val Thr Arg Pro Glu His Asn
            165                 170                 175

Ile Ala Ile Ser Trp Pro Ser Val Ser Tyr Lys Ala Ala Gln Lys Glu
                180                 185                 190

Gly Ser Arg His Lys Arg Trp Ala His Trp His Thr Gly Leu Ala Leu
            195                 200                 205

Cys Trp Leu Val Pro Met Asp Ala Ile Tyr Asn Tyr Ile Thr Gln Gln
210                 215                 220

Asn Cys Thr Leu Gly Asp Asn Trp Phe Gly Gly Ser Tyr Glu Thr Val
225                 230                 235                 240

Ala Gly Thr Pro Lys Val Ile Thr Val Lys Gln Gly Gly Gly Gly Ser
                245                 250                 255

Gly Gly Gly Gly Ser Gly Gly Gly Ser Phe Pro Thr Ile Pro Leu
            260                 265                 270

Ser Arg Leu Phe Asp Asn Ala Met Leu Arg Ala His Arg Leu His Gln
            275                 280                 285

Leu Ala Phe Asp Thr Tyr Gln Glu Phe Glu Glu Ala Tyr Ile Pro Lys
290                 295                 300

Glu Gln Lys Tyr Ser Phe Leu Gln Asn Pro Gln Thr Ser Leu Cys Phe
305                 310                 315                 320

Ser Glu Ser Ile Pro Thr Pro Ser Asn Arg Glu Glu Thr Gln Gln Lys
                325                 330                 335

Ser Asn Leu Glu Leu Leu Arg Ile Ser Leu Leu Leu Ile Gln Ser Trp
            340                 345                 350

Leu Glu Pro Val Gln Phe Leu Arg Ser Val Phe Ala Asn Ser Leu Val
            355                 360                 365

Tyr Gly Ala Ser Asp Ser Asn Val Tyr Asp Leu Leu Lys Asp Leu Glu
370                 375                 380

Glu Gly Ile Gln Thr Leu Met Gly Arg Leu Glu Asp Gly Ser Pro Arg
385                 390                 395                 400

Thr Gly Gln Ile Phe Lys Gln Thr Tyr Ser Lys Phe Asp Thr Asn Ser
                405                 410                 415

His Asn Asp Asp Ala Leu Leu Lys Asn Tyr Gly Leu Leu Tyr Cys Phe
            420                 425                 430

Arg Lys Asp Met Asp Lys Val Glu Thr Phe Leu Arg Ile Val Gln Cys
            435                 440                 445

Arg Ser Val Glu Gly Ser Cys Gly Phe
450                 455

<210> SEQ ID NO 164
<211> LENGTH: 472
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 164

Met Val Glu Glu Ala Leu Asn Ile Phe Asp Glu Cys Arg Ser Pro Cys
1               5                   10                  15

Ser Leu Thr Pro Glu Pro Gly Lys Pro Ile Gln Ser Lys Leu Ser Ile
            20                  25                  30
```

```
Pro Ser Asp Val Val Leu Asp Glu Gly Val Leu Tyr Tyr Ser Met Thr
        35                  40                  45
Ile Asn Asp Glu Gln Asn Asp Ile Lys Asp Glu Asp Lys Gly Glu Ser
50                  55                  60
Ile Ile Thr Ile Gly Glu Phe Ala Thr Val Arg Ala Thr Arg His Tyr
65                  70                  75                  80
Val Asn Gln Asp Ala Pro Phe Gly Val Ile His Leu Asp Ile Thr Thr
                85                  90                  95
Glu Asn Gly Thr Lys Thr Tyr Ser Tyr Asn Arg Lys Glu Gly Glu Phe
                100                 105                 110
Ala Ile Asn Trp Leu Val Pro Ile Gly Glu Asp Ser Pro Ala Ser Ile
                115                 120                 125
Lys Ile Ser Val Asp Glu Leu Asp Gln Gln Arg Asn Ile Ile Glu Val
                130                 135                 140
Pro Lys Leu Tyr Ser Ile Asp Leu Asp Asn Gln Thr Leu Glu Gln Trp
145                 150                 155                 160
Lys Thr Gln Gly Asn Val Ser Phe Ser Val Thr Arg Pro Glu His Asn
                165                 170                 175
Ile Ala Ile Ser Trp Pro Ser Val Ser Tyr Lys Ala Ala Gln Lys Glu
                180                 185                 190
Gly Ser Arg His Lys Arg Trp Ala His Trp His Thr Gly Leu Ala Leu
                195                 200                 205
Cys Trp Leu Val Pro Met Asp Ala Ile Tyr Asn Tyr Ile Thr Gln Gln
                210                 215                 220
Asn Cys Thr Leu Gly Asp Asn Trp Phe Gly Ser Tyr Glu Thr Val
225                 230                 235                 240
Ala Gly Thr Pro Lys Val Ile Thr Val Lys Gln Gly Ile Glu Gln Lys
                245                 250                 255
Pro Val Glu Gln Arg Ile His Phe Ser Lys Gly Gly Gly Ser Gly
                260                 265                 270
Gly Gly Gly Ser Gly Gly Gly Ser Phe Pro Thr Ile Pro Leu Ser
                275                 280                 285
Arg Leu Phe Asp Asn Ala Met Leu Arg Ala His Arg Leu His Gln Leu
                290                 295                 300
Ala Phe Asp Thr Tyr Gln Glu Phe Glu Glu Ala Tyr Ile Pro Lys Glu
305                 310                 315                 320
Gln Lys Tyr Ser Phe Leu Gln Asn Pro Gln Thr Ser Leu Cys Phe Ser
                325                 330                 335
Glu Ser Ile Pro Thr Pro Ser Asn Arg Glu Glu Thr Gln Gln Lys Ser
                340                 345                 350
Asn Leu Glu Leu Leu Arg Ile Ser Leu Leu Leu Ile Gln Ser Trp Leu
                355                 360                 365
Glu Pro Val Gln Phe Leu Arg Ser Val Phe Ala Asn Ser Leu Val Tyr
370                 375                 380
Gly Ala Ser Asp Ser Asn Val Tyr Asp Leu Leu Lys Asp Leu Glu Glu
385                 390                 395                 400
Gly Ile Gln Thr Leu Met Gly Arg Leu Glu Asp Gly Ser Pro Arg Thr
                405                 410                 415
Gly Gln Ile Phe Lys Gln Thr Tyr Ser Lys Phe Asp Thr Asn Ser His
                420                 425                 430
Asn Asp Asp Ala Leu Leu Lys Asn Tyr Gly Leu Leu Tyr Cys Phe Arg
435                 440                 445
```

```
Lys Asp Met Asp Lys Val Glu Thr Phe Leu Arg Ile Val Gln Cys Arg
    450                 455                 460

Ser Val Glu Gly Ser Cys Gly Phe
465                 470

<210> SEQ ID NO 165
<211> LENGTH: 354
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 165

Gly Val Leu Tyr Tyr Ser Met Thr Ile Asn Asp Glu Gln Asn Asp Ile
1               5                   10                  15

Lys Asp Glu Asp Lys Gly Glu Ser Ile Ile Thr Ile Gly Glu Phe Ala
            20                  25                  30

Thr Val Arg Ala Thr Arg His Tyr Val Asn Gln Asp Ala Pro Phe Gly
        35                  40                  45

Val Ile His Leu Asp Ile Thr Thr Glu Asn Gly Thr Lys Thr Tyr Ser
50                  55                  60

Tyr Asn Arg Lys Glu Gly Glu Phe Ala Ile Asn Trp Leu Val Pro Ile
65                  70                  75                  80

Gly Glu Asp Ser Pro Ala Ser Ile Lys Ile Ser Val Asp Glu Leu Asp
                85                  90                  95

Gln Gln Arg Asn Ile Ile Glu Val Pro Lys Leu Tyr Ser Ile Asp Leu
            100                 105                 110

Asp Asn Gln Thr Leu Glu Gln Trp Lys Thr Gln Gly Asn Val Ser Phe
        115                 120                 125

Ser Val Thr Arg Pro Glu His Asn Ile Ala Ile Ser Trp Pro Ser Val
130                 135                 140

Ser Tyr Lys Ala Gly Gly Gly Ser Gly Gly Gly Ser Gly Gly
145                 150                 155                 160

Gly Gly Ser Phe Pro Thr Ile Pro Leu Ser Arg Leu Phe Asp Asn Ala
                165                 170                 175

Met Leu Arg Ala His Arg Leu His Gln Leu Ala Phe Asp Thr Tyr Gln
            180                 185                 190

Glu Phe Glu Glu Ala Tyr Ile Pro Lys Glu Gln Lys Tyr Ser Phe Leu
        195                 200                 205

Gln Asn Pro Gln Thr Ser Leu Cys Phe Ser Glu Ser Ile Pro Thr Pro
210                 215                 220

Ser Asn Arg Glu Glu Thr Gln Gln Lys Ser Asn Leu Glu Leu Leu Arg
225                 230                 235                 240

Ile Ser Leu Leu Leu Ile Gln Ser Trp Leu Glu Pro Val Gln Phe Leu
                245                 250                 255

Arg Ser Val Phe Ala Asn Ser Leu Val Tyr Gly Ala Ser Asp Ser Asn
            260                 265                 270

Val Tyr Asp Leu Leu Lys Asp Leu Glu Glu Gly Ile Gln Thr Leu Met
        275                 280                 285

Gly Arg Leu Glu Asp Gly Ser Pro Arg Thr Gly Gln Ile Phe Lys Gln
290                 295                 300

Thr Tyr Ser Lys Phe Asp Thr Asn Ser His Asn Asp Asp Ala Leu Leu
305                 310                 315                 320
```

```
Lys Asn Tyr Gly Leu Leu Tyr Cys Phe Arg Lys Asp Met Asp Lys Val
                325                 330                 335

Glu Thr Phe Leu Arg Ile Val Gln Cys Arg Ser Val Glu Gly Ser Cys
            340                 345                 350

Gly Phe

<210> SEQ ID NO 166
<211> LENGTH: 4
<212> TYPE: PRT
<213> ORGANISM: Unknown
<220> FEATURE:
<221> NAME/KEY: source
<223> OTHER INFORMATION: /note="Description of Unknown:
      Peptidase cleavage sequence"

<400> SEQUENCE: 166

Ala Ala Pro Phe
1

<210> SEQ ID NO 167
<211> LENGTH: 3
<212> TYPE: PRT
<213> ORGANISM: Unknown
<220> FEATURE:
<221> NAME/KEY: source
<223> OTHER INFORMATION: /note="Description of Unknown:
      Peptidase cleavage sequence"

<400> SEQUENCE: 167

Gly Gly Phe
1

<210> SEQ ID NO 168
<211> LENGTH: 4
<212> TYPE: PRT
<213> ORGANISM: Unknown
<220> FEATURE:
<221> NAME/KEY: source
<223> OTHER INFORMATION: /note="Description of Unknown:
      Peptidase cleavage sequence"

<400> SEQUENCE: 168

Ala Ala Pro Val
1

<210> SEQ ID NO 169
<211> LENGTH: 3
<212> TYPE: PRT
<213> ORGANISM: Unknown
<220> FEATURE:
<221> NAME/KEY: source
<223> OTHER INFORMATION: /note="Description of Unknown:
      Peptidase cleavage sequence"

<400> SEQUENCE: 169

Gly Gly Leu
1

<210> SEQ ID NO 170
<211> LENGTH: 3
<212> TYPE: PRT
<213> ORGANISM: Unknown
<220> FEATURE:
<221> NAME/KEY: source
<223> OTHER INFORMATION: /note="Description of Unknown:
      Peptidase cleavage sequence"
```

```
<400> SEQUENCE: 170

Ala Ala Leu
1

<210> SEQ ID NO 171
<211> LENGTH: 3
<212> TYPE: PRT
<213> ORGANISM: Unknown
<220> FEATURE:
<221> NAME/KEY: source
<223> OTHER INFORMATION: /note="Description of Unknown:
      Peptidase cleavage sequence"

<400> SEQUENCE: 171

Phe Val Arg
1

<210> SEQ ID NO 172
<211> LENGTH: 3
<212> TYPE: PRT
<213> ORGANISM: Unknown
<220> FEATURE:
<221> NAME/KEY: source
<223> OTHER INFORMATION: /note="Description of Unknown:
      Peptidase cleavage sequence"

<400> SEQUENCE: 172

Val Gly Arg
1

<210> SEQ ID NO 173
<211> LENGTH: 4
<212> TYPE: PRT
<213> ORGANISM: Unknown
<220> FEATURE:
<221> NAME/KEY: source
<223> OTHER INFORMATION: /note="Description of Unknown:
      Peptidase cleavage sequence"

<400> SEQUENCE: 173

Arg Gln Pro Arg
1

<210> SEQ ID NO 174
<211> LENGTH: 5
<212> TYPE: PRT
<213> ORGANISM: Unknown
<220> FEATURE:
<221> NAME/KEY: source
<223> OTHER INFORMATION: /note="Description of Unknown:
      Peptidase cleavage sequence"
<220> FEATURE:
<221> NAME/KEY: MOD_RES
<222> LOCATION: (5)..(5)
<223> OTHER INFORMATION: Any amino acid

<400> SEQUENCE: 174

Tyr Val Ala Asp Xaa
1               5

<210> SEQ ID NO 175
<211> LENGTH: 5
<212> TYPE: PRT
<213> ORGANISM: Unknown
<220> FEATURE:
<221> NAME/KEY: source
<223> OTHER INFORMATION: /note="Description of Unknown:
      Peptidase cleavage sequence"
<220> FEATURE:
```

```
<221> NAME/KEY: MOD_RES
<222> LOCATION: (2)..(3)
<223> OTHER INFORMATION: Any amino acid
<220> FEATURE:
<221> NAME/KEY: MOD_RES
<222> LOCATION: (5)..(5)
<223> OTHER INFORMATION: Any amino acid

<400> SEQUENCE: 175

Asp Xaa Xaa Asp Xaa
1               5

<210> SEQ ID NO 176
<211> LENGTH: 9
<212> TYPE: PRT
<213> ORGANISM: Unknown
<220> FEATURE:
<221> NAME/KEY: source
<223> OTHER INFORMATION: /note="Description of Unknown:
      Peptidase cleavage sequence"
<220> FEATURE:
<221> NAME/KEY: MOD_RES
<222> LOCATION: (2)..(7)
<223> OTHER INFORMATION: Any amino acid
<220> FEATURE:
<221> NAME/KEY: SITE
<222> LOCATION: (2)..(7)
<223> OTHER INFORMATION: /note="This region may encompass 0, 2, 4 or 6
      residues"
<220> FEATURE:
<221> NAME/KEY: MOD_RES
<222> LOCATION: (9)..(9)
<223> OTHER INFORMATION: Any amino acid

<400> SEQUENCE: 176

Arg Xaa Xaa Xaa Xaa Xaa Xaa Arg Xaa
1               5

<210> SEQ ID NO 177
<211> LENGTH: 9
<212> TYPE: PRT
<213> ORGANISM: Unknown
<220> FEATURE:
<221> NAME/KEY: source
<223> OTHER INFORMATION: /note="Description of Unknown:
      Peptidase cleavage sequence"
<220> FEATURE:
<221> NAME/KEY: MOD_RES
<222> LOCATION: (2)..(7)
<223> OTHER INFORMATION: Any amino acid
<220> FEATURE:
<221> NAME/KEY: SITE
<222> LOCATION: (2)..(7)
<223> OTHER INFORMATION: /note="This region may encompass 0, 2, 4 or 6
      residues"
<220> FEATURE:
<221> NAME/KEY: MOD_RES
<222> LOCATION: (9)..(9)
<223> OTHER INFORMATION: Any amino acid

<400> SEQUENCE: 177

Lys Xaa Xaa Xaa Xaa Xaa Xaa Arg Xaa
1               5

<210> SEQ ID NO 178
<211> LENGTH: 6
<212> TYPE: PRT
<213> ORGANISM: Unknown
<220> FEATURE:
<221> NAME/KEY: source
<223> OTHER INFORMATION: /note="Description of Unknown:
      Peptidase cleavage sequence"
<220> FEATURE:
```

```
<221> NAME/KEY: MOD_RES
<222> LOCATION: (6)..(6)
<223> OTHER INFORMATION: Any amino acid

<400> SEQUENCE: 178

Glu Arg Thr Lys Arg Xaa
1               5

<210> SEQ ID NO 179
<211> LENGTH: 5
<212> TYPE: PRT
<213> ORGANISM: Unknown
<220> FEATURE:
<221> NAME/KEY: source
<223> OTHER INFORMATION: /note="Description of Unknown:
      Peptidase cleavage sequence"
<220> FEATURE:
<221> NAME/KEY: MOD_RES
<222> LOCATION: (5)..(5)
<223> OTHER INFORMATION: Any amino acid

<400> SEQUENCE: 179

Arg Val Arg Arg Xaa
1               5

<210> SEQ ID NO 180
<211> LENGTH: 5
<212> TYPE: PRT
<213> ORGANISM: Unknown
<220> FEATURE:
<221> NAME/KEY: source
<223> OTHER INFORMATION: /note="Description of Unknown:
      Peptidase cleavage sequence"
<220> FEATURE:
<221> NAME/KEY: MOD_RES
<222> LOCATION: (5)..(5)
<223> OTHER INFORMATION: Any amino acid

<400> SEQUENCE: 180

Arg Val Arg Arg Xaa
1               5

<210> SEQ ID NO 181
<211> LENGTH: 6
<212> TYPE: PRT
<213> ORGANISM: Unknown
<220> FEATURE:
<221> NAME/KEY: source
<223> OTHER INFORMATION: /note="Description of Unknown:
      Peptidase cleavage sequence"
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (6)..(6)
<223> OTHER INFORMATION: Any amino acid

<400> SEQUENCE: 181

Pro Xaa Trp Val Pro Xaa
1               5

<210> SEQ ID NO 182
<211> LENGTH: 4
<212> TYPE: PRT
<213> ORGANISM: Unknown
<220> FEATURE:
<221> NAME/KEY: source
<223> OTHER INFORMATION: /note="Description of Unknown:
      Peptidase cleavage sequence"
```

```
<220> FEATURE:
<221> NAME/KEY: MOD_RES
<222> LOCATION: (4)..(4)
<223> OTHER INFORMATION: Any amino acid

<400> SEQUENCE: 182

Trp Val Ala Xaa
1

<210> SEQ ID NO 183
<211> LENGTH: 4
<212> TYPE: PRT
<213> ORGANISM: Unknown
<220> FEATURE:
<221> NAME/KEY: source
<223> OTHER INFORMATION: /note="Description of Unknown:
      Peptidase cleavage sequence"
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (3)..(4)
<223> OTHER INFORMATION: Any amino acid

<400> SEQUENCE: 183

Xaa Phe Xaa Xaa
1

<210> SEQ ID NO 184
<211> LENGTH: 4
<212> TYPE: PRT
<213> ORGANISM: Unknown
<220> FEATURE:
<221> NAME/KEY: source
<223> OTHER INFORMATION: /note="Description of Unknown:
      Peptidase cleavage sequence"
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (3)..(4)
<223> OTHER INFORMATION: Any amino acid

<400> SEQUENCE: 184

Xaa Tyr Xaa Xaa
1

<210> SEQ ID NO 185
<211> LENGTH: 4
<212> TYPE: PRT
<213> ORGANISM: Unknown
<220> FEATURE:
<221> NAME/KEY: source
<223> OTHER INFORMATION: /note="Description of Unknown:
      Peptidase cleavage sequence"
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (3)..(4)
<223> OTHER INFORMATION: Any amino acid

<400> SEQUENCE: 185

Xaa Trp Xaa Xaa
1
```

```
<210> SEQ ID NO 186
<211> LENGTH: 12
<212> TYPE: PRT
<213> ORGANISM: Unknown
<220> FEATURE:
<221> NAME/KEY: source
<223> OTHER INFORMATION: /note="Description of Unknown:
      Peptidase cleavage sequence"
<220> FEATURE:
<221> NAME/KEY: VARIANT
<222> LOCATION: (10)..(10)
<223> OTHER INFORMATION: /replace="Ala" or "Pro"
<220> FEATURE:
<221> NAME/KEY: VARIANT
<222> LOCATION: (12)..(12)
<223> OTHER INFORMATION: /replace="Pro" or "Ala"
<220> FEATURE:
<221> NAME/KEY: SITE
<222> LOCATION: (1)..(12)
<223> OTHER INFORMATION: /note="Variant residues given in the sequence
      have no preference with respect to those in the annotations
      for variant positions"

<400> SEQUENCE: 186

Asp Arg Tyr Ile Pro Phe His Leu Leu Val Tyr Ser
1               5                   10

<210> SEQ ID NO 187
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 187

Ser Gly Gly Gly Gly Ser Gly Lys Ala Gly Ser Arg Gly Leu Thr
1               5                   10                  15

<210> SEQ ID NO 188
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 188

Ser Gly Gly Gly Gly Ser Gly Gly Gly Leu Arg Gln Pro Arg
1               5                   10                  15

<210> SEQ ID NO 189
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 189

Ser Gly Gly Gly Gly Ser Gly Lys Lys Val Glu Arg Phe Arg Tyr
1               5                   10                  15

<210> SEQ ID NO 190
<211> LENGTH: 15
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"

<400> SEQUENCE: 190

Ser Gly Gly Gly Gly Ser Gly Gly Gly Leu Met Thr Pro Arg
1               5                   10                  15

<210> SEQ ID NO 191
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 191

Ser Gly Gly Gly Gly Ser Gly Lys Ala Gly Ser Phe Ser Glu Gly
1               5                   10                  15

<210> SEQ ID NO 192
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 192

Ser Gly Gly Gly Gly Ser Gly Lys Ala Gly Ser Ala Ala Pro Phe
1               5                   10                  15

<210> SEQ ID NO 193
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 193

Gly Gly Gly Gly Ser Gly Gly Gly Glu Asn Leu Tyr Phe Gln Ser
1               5                   10                  15

<210> SEQ ID NO 194
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 194

Val Ser Trp Lys Thr Trp Phe Pro Asn Leu Ala Val
1               5                   10

<210> SEQ ID NO 195
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

<400> SEQUENCE: 195

Tyr Ser Pro Phe His Lys Trp Phe Pro Ser Met His
1               5                   10

<210> SEQ ID NO 196
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 196

Ile Pro Gln Val Trp Arg Asp Trp Phe Lys Leu Pro
1               5                   10

<210> SEQ ID NO 197
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 197

Phe Pro Ala Trp Phe Thr Lys Leu Tyr Pro Arg Thr
1               5                   10

<210> SEQ ID NO 198
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 198

Gln Ile Asn Thr Ala Lys Trp Trp Lys Thr His Phe
1               5                   10

<210> SEQ ID NO 199
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 199

Asp Ala Ser Lys Ala Leu Arg Ser Ser Gly Met Pro
1               5                   10

<210> SEQ ID NO 200
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

```
<400> SEQUENCE: 200

Trp Lys Thr Trp Phe Pro
1               5

<210> SEQ ID NO 201
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 201

Ser Gly Gly Gly Gly Trp Lys Thr Trp Phe Pro Arg Gly Leu Thr
1               5                   10                  15

<210> SEQ ID NO 202
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 202

Ser Gly Gly Gly Gly Trp Lys Thr Trp Phe Pro Arg Gln Pro Arg
1               5                   10                  15

<210> SEQ ID NO 203
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 203

Ser Gly Gly Gly Gly Trp Lys Thr Trp Phe Pro Arg Phe Arg Tyr
1               5                   10                  15

<210> SEQ ID NO 204
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 204

Ser Gly Gly Gly Gly Trp Lys Thr Trp Phe Pro Met Thr Pro Arg
1               5                   10                  15

<210> SEQ ID NO 205
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 205

Ser Gly Gly Gly Gly Trp Lys Thr Trp Phe Pro Phe Ser Glu Gly
1               5                   10                  15

<210> SEQ ID NO 206
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 206

Ser Gly Gly Gly Gly Trp Lys Thr Trp Phe Pro Ala Ala Pro Phe
1               5                   10                  15

<210> SEQ ID NO 207
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 207

Gly Thr Gly Gly Ser
1               5

<210> SEQ ID NO 208
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 208

Gly Gly Gly Gly Ser
1               5

<210> SEQ ID NO 209
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 209

Gly Gly Gly Gly Ser Gly Gly Gly Gly Ser
1               5                   10

<210> SEQ ID NO 210
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 210

Gly Gly Gly Gly Ser Gly Gly Gly Gly Ser Gly Gly Gly Gly Ser
1               5                   10                  15

<210> SEQ ID NO 211
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 211

Gly Gly Gly Gly Ser Gly Gly Gly
1               5

<210> SEQ ID NO 212
<211> LENGTH: 50
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: SITE
<222> LOCATION: (1)..(50)
<223> OTHER INFORMATION: /note="This sequence may encompass 1-10 'Gly
      Gly Gly Gly Ser' repeating units"

<400> SEQUENCE: 212

Gly Gly Gly Gly Ser Gly Gly Gly Ser Gly Gly Gly Gly Ser Gly
1               5                   10                  15

Gly Gly Gly Ser Gly Gly Gly Ser Gly Gly Gly Gly Ser Gly Gly
                20                  25                  30

Gly Gly Ser Gly Gly Gly Gly Ser Gly Gly Gly Gly Ser Gly Gly
            35                  40                  45

Gly Ser
    50

<210> SEQ ID NO 213
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: SITE
<222> LOCATION: (1)..(20)
<223> OTHER INFORMATION: /note="This sequence may encompass 1-10
      'Gly Ser' repeating units"

<400> SEQUENCE: 213

Gly Ser Gly Ser Gly Ser Gly Ser Gly Ser Gly Ser Gly Ser Gly Ser
1               5                   10                  15

Gly Ser Gly Ser
        20

<210> SEQ ID NO 214
<211> LENGTH: 191
<212> TYPE: PRT
<213> ORGANISM: Homo sapiens
```

<400> SEQUENCE: 214

Phe Pro Thr Ile Pro Leu Ser Arg Leu Phe Asp Asn Ala Met Leu Arg
1               5                   10                  15

Ala His Arg Leu His Gln Leu Ala Phe Asp Thr Tyr Gln Glu Phe Glu
            20                  25                  30

Glu Ala Tyr Ile Pro Lys Glu Gln Lys Tyr Ser Phe Leu Gln Asn Pro
        35                  40                  45

Gln Thr Ser Leu Cys Phe Ser Glu Ser Ile Pro Thr Pro Ser Asn Arg
    50                  55                  60

Glu Glu Thr Gln Gln Lys Ser Asn Leu Glu Leu Leu Arg Ile Ser Leu
65                  70                  75                  80

Leu Leu Ile Gln Ser Trp Leu Glu Pro Val Gln Phe Leu Arg Ser Val
                85                  90                  95

Phe Ala Asn Ser Leu Val Tyr Gly Ala Ser Asp Ser Asn Val Tyr Asp
            100                 105                 110

Leu Leu Lys Asp Leu Glu Glu Gly Ile Gln Thr Leu Met Gly Arg Leu
        115                 120                 125

Glu Asp Gly Ser Pro Arg Thr Gly Gln Ile Phe Lys Gln Thr Tyr Ser
130                 135                 140

Lys Phe Asp Thr Asn Ser His Asn Asp Asp Ala Leu Leu Lys Asn Tyr
145                 150                 155                 160

Gly Leu Leu Tyr Cys Phe Arg Lys Asp Met Asp Lys Val Glu Thr Phe
                165                 170                 175

Leu Arg Ile Val Gln Cys Arg Ser Val Glu Gly Ser Cys Gly Phe
            180                 185                 190

<210> SEQ ID NO 215
<211> LENGTH: 87
<212> TYPE: PRT
<213> ORGANISM: Unknown
<220> FEATURE:
<221> NAME/KEY: source
<223> OTHER INFORMATION: /note="Description of Unknown:
    GPL-1 agonist peptide"

<400> SEQUENCE: 215

Met Lys Ile Ile Leu Trp Leu Cys Val Phe Gly Leu Phe Leu Ala Thr
1               5                   10                  15

Leu Phe Pro Ile Ser Trp Gln Met Pro Val Glu Ser Gly Leu Ser Ser
            20                  25                  30

Glu Asp Ser Ala Ser Ser Glu Ser Phe Ala Ser Lys Ile Lys Arg His
        35                  40                  45

Gly Glu Gly Thr Phe Thr Ser Asp Leu Ser Lys Gln Met Glu Glu Glu
    50                  55                  60

Ala Val Arg Leu Phe Ile Glu Trp Leu Lys Asn Gly Gly Pro Ser Ser
65                  70                  75                  80

Gly Ala Pro Pro Pro Ser Gly
                85

<210> SEQ ID NO 216
<211> LENGTH: 110
<212> TYPE: PRT
<213> ORGANISM: Unknown
<220> FEATURE:
<221> NAME/KEY: source
<223> OTHER INFORMATION: /note="Description of Unknown:
    Insulin peptide"

```
<400> SEQUENCE: 216

Met Ala Leu Trp Met Arg Leu Leu Pro Leu Leu Ala Leu Leu Ala Leu
1               5                   10                  15

Trp Gly Pro Asp Pro Ala Ala Ala Phe Val Asn Gln His Leu Cys Gly
                20                  25                  30

Ser His Leu Val Glu Ala Leu Tyr Leu Val Cys Gly Glu Arg Gly Phe
            35                  40                  45

Phe Tyr Thr Pro Lys Thr Arg Arg Glu Ala Glu Asp Leu Gln Val Gly
        50                  55                  60

Gln Val Glu Leu Gly Gly Gly Pro Gly Ala Gly Ser Leu Gln Pro Leu
65                  70                  75                  80

Ala Leu Glu Gly Ser Leu Gln Lys Arg Gly Ile Val Glu Gln Cys Cys
                85                  90                  95

Thr Ser Ile Cys Ser Leu Tyr Gln Leu Glu Asn Tyr Cys Asn
            100                 105                 110

<210> SEQ ID NO 217
<211> LENGTH: 178
<212> TYPE: PRT
<213> ORGANISM: Homo sapiens

<400> SEQUENCE: 217

Met His Ser Ser Ala Leu Leu Cys Cys Leu Val Leu Leu Thr Gly Val
1               5                   10                  15

Arg Ala Ser Pro Gly Gln Gly Thr Gln Ser Glu Asn Ser Cys Thr His
                20                  25                  30

Phe Pro Gly Asn Leu Pro Asn Met Leu Arg Asp Leu Arg Asp Ala Phe
            35                  40                  45

Ser Arg Val Lys Thr Phe Phe Gln Met Lys Asp Gln Leu Asp Asn Leu
        50                  55                  60

Leu Leu Lys Glu Ser Leu Leu Glu Asp Phe Lys Gly Tyr Leu Gly Cys
65                  70                  75                  80

Gln Ala Leu Ser Glu Met Ile Gln Phe Tyr Leu Glu Glu Val Met Pro
                85                  90                  95

Gln Ala Glu Asn Gln Asp Pro Asp Ile Lys Ala His Val Asn Ser Leu
            100                 105                 110

Gly Glu Asn Leu Lys Thr Leu Arg Leu Arg Leu Arg Arg Cys His Arg
        115                 120                 125

Phe Leu Pro Cys Glu Asn Lys Ser Lys Ala Val Glu Gln Val Lys Asn
130                 135                 140

Ala Phe Asn Lys Leu Gln Glu Lys Gly Ile Tyr Lys Ala Met Ser Glu
145                 150                 155                 160

Phe Asp Ile Phe Ile Asn Tyr Ile Glu Ala Tyr Met Thr Met Lys Ile
                165                 170                 175

Arg Asn

<210> SEQ ID NO 218
<211> LENGTH: 179
<212> TYPE: PRT
<213> ORGANISM: Homo sapiens

<400> SEQUENCE: 218

Met Ala Ala Leu Gln Lys Ser Val Ser Ser Phe Leu Met Gly Thr Leu
1               5                   10                  15
```

-continued

```
Ala Thr Ser Cys Leu Leu Leu Ala Leu Leu Val Gln Gly Gly Ala
             20                  25                  30

Ala Ala Pro Ile Ser Ser His Cys Arg Leu Asp Lys Ser Asn Phe Gln
         35                  40                  45

Gln Pro Tyr Ile Thr Asn Arg Thr Phe Met Leu Ala Lys Glu Ala Ser
     50                  55                  60

Leu Ala Asp Asn Asn Thr Asp Val Arg Leu Ile Gly Glu Lys Leu Phe
 65                  70                  75                  80

His Gly Val Ser Met Ser Glu Arg Cys Tyr Leu Met Lys Gln Val Leu
                 85                  90                  95

Asn Phe Thr Leu Glu Glu Val Leu Phe Pro Gln Ser Asp Arg Phe Gln
            100                 105                 110

Pro Tyr Met Gln Glu Val Val Pro Phe Leu Ala Arg Leu Ser Asn Arg
        115                 120                 125

Leu Ser Thr Cys His Ile Glu Gly Asp Asp Leu His Ile Gln Arg Asn
130                 135                 140

Val Gln Lys Leu Lys Asp Thr Val Lys Leu Gly Glu Ser Gly Glu
145                 150                 155                 160

Ile Lys Ala Ile Gly Glu Leu Asp Leu Leu Phe Met Ser Leu Arg Asn
                165                 170                 175

Ala Cys Ile

<210> SEQ ID NO 219
<211> LENGTH: 71
<212> TYPE: PRT
<213> ORGANISM: Unknown
<220> FEATURE:
<221> NAME/KEY: source
<223> OTHER INFORMATION: /note="Description of Unknown:
      ExtB polypeptide"

<400> SEQUENCE: 219

Met Lys Lys Asn Ile Ala Phe Leu Leu Ala Ser Met Phe Val Phe Ser
1               5                   10                  15

Ile Ala Thr Asn Ala Tyr Ala Ser Thr Gln Ser Asn Lys Lys Asp Leu
            20                  25                  30

Cys Glu His Tyr Arg Gln Ile Ala Lys Glu Ser Cys Lys Lys Gly Phe
        35                  40                  45

Leu Gly Val Arg Asp Gly Thr Ala Gly Ala Cys Phe Gly Ala Gln Ile
    50                  55                  60

Met Val Ala Ala Lys Gly Cys
65                  70

<210> SEQ ID NO 220
<211> LENGTH: 225
<212> TYPE: PRT
<213> ORGANISM: Unknown
<220> FEATURE:
<221> NAME/KEY: source
<223> OTHER INFORMATION: /note="Description of Unknown:
      Red Fluorescent Protein (RFP) sequence"

<400> SEQUENCE: 220

Met Arg Ser Ser Lys Asn Val Ile Lys Glu Phe Met Arg Phe Lys Val
1               5                   10                  15

Arg Met Glu Gly Thr Val Asn Gly His Glu Phe Glu Ile Glu Gly Glu
            20                  25                  30
```

```
Gly Glu Gly Arg Pro Tyr Gly His Asn Thr Val Lys Leu Lys Val
            35                  40                  45

Thr Lys Gly Gly Pro Leu Pro Phe Ala Trp Asp Ile Leu Ser Pro Gln
 50                  55                  60

Phe Gln Tyr Gly Ser Lys Val Tyr Val Lys His Pro Ala Asp Ile Pro
 65                  70                  75                  80

Asp Tyr Lys Lys Leu Ser Phe Pro Glu Gly Phe Lys Trp Glu Arg Val
                 85                  90                  95

Met Asn Phe Glu Asp Gly Gly Val Val Thr Val Thr Gln Asp Ser Ser
                100                 105                 110

Leu Gln Asp Gly Cys Phe Ile Tyr Lys Val Lys Phe Ile Gly Val Asn
                115                 120                 125

Phe Pro Ser Asp Gly Pro Val Met Gln Lys Lys Thr Met Gly Trp Glu
130                 135                 140

Ala Ser Thr Glu Arg Leu Tyr Pro Arg Asp Gly Val Leu Lys Gly Glu
145                 150                 155                 160

Ile His Lys Ala Leu Lys Leu Lys Asp Gly Gly His Tyr Leu Val Glu
                165                 170                 175

Phe Lys Ser Ile Tyr Met Ala Lys Lys Pro Val Gln Leu Pro Gly Tyr
                180                 185                 190

Tyr Tyr Val Asp Ser Lys Leu Asp Ile Thr Ser His Asn Glu Asp Tyr
                195                 200                 205

Thr Ile Val Glu Gln Tyr Glu Arg Thr Glu Gly Arg His His Leu Phe
    210                 215                 220

Leu
225

<210> SEQ ID NO 221
<211> LENGTH: 281
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 221

Met Val Glu Glu Ala Leu Asn Ile Phe Asp Glu Cys Arg Ser Pro Cys
 1               5                  10                  15

Ser Leu Thr Pro Glu Pro Gly Lys Pro Ile Gln Ser Lys Leu Ser Ile
                20                  25                  30

Pro Ser Asp Val Val Leu Asp Glu Gly Val Leu Tyr Tyr Ser Met Thr
            35                  40                  45

Ile Asn Asp Glu Gln Asn Asp Ile Lys Asp Glu Asp Lys Gly Glu Ser
 50                  55                  60

Ile Ile Thr Ile Gly Glu Phe Ala Thr Val Arg Ala Thr Arg His Tyr
 65                  70                  75                  80

Val Asn Gln Asp Ala Pro Phe Gly Val Ile His Leu Asp Ile Thr Thr
                 85                  90                  95

Glu Asn Gly Thr Lys Thr Tyr Ser Tyr Asn Arg Lys Glu Gly Glu Phe
                100                 105                 110

Ala Ile Asn Trp Leu Val Pro Ile Gly Glu Asp Ser Pro Ala Ser Ile
            115                 120                 125

Lys Ile Ser Val Asp Glu Leu Asp Gln Gln Arg Asn Ile Ile Glu Val
130                 135                 140
```

-continued

```
Pro Lys Leu Tyr Ser Ile Asp Leu Asp Asn Gln Thr Leu Glu Gln Trp
145                 150                 155                 160

Lys Thr Gln Gly Asn Val Ser Phe Ser Val Thr Arg Pro Glu His Asn
            165                 170                 175

Ile Ala Ile Ser Trp Pro Ser Val Ser Tyr Lys Ala Ala Gln Lys Glu
            180                 185                 190

Gly Ser Arg His Lys Arg Trp Ala His Trp His Thr Gly Leu Ala Leu
        195                 200                 205

Cys Trp Leu Val Pro Met Asp Ala Ile Tyr Asn Tyr Ile Thr Gln Gln
    210                 215                 220

Asn Cys Thr Leu Gly Asp Asn Trp Phe Gly Gly Ser Tyr Glu Thr Val
225                 230                 235                 240

Ala Gly Thr Pro Lys Val Ile Thr Val Lys Gln Gly Ile Glu Gln Lys
            245                 250                 255

Pro Val Glu Gln Arg Ile His Phe Ser Lys Gly Gly Gly Gly Ser Gly
            260                 265                 270

Gly Gly Gly Ser Gly Gly Gly Gly Ser
        275                 280
```

TOXIN-DERIVED DELIVERY CONSTRUCTS FOR PULMONARY DELIVERY

CROSS-REFERENCE

This application is a continuation of PCT/US2019/021474, filed Mar. 8, 2019, which claims the benefit of U.S. Provisional Application Nos. 62/640,168 filed Mar. 8, 2018; 62/640,188 filed Mar. 8, 2018; 62/640,194 filed Mar. 8, 2018, and 62/756,889, filed Nov. 7, 2018 which applications are incorporated herein by reference in their entirety for all purposes.

SEQUENCE LISTING

The instant application contains a Sequence Listing in the form of a "paper copy" (PDF File) and a file containing the referenced sequences (SEQ ID NO: 1-SEQ ID NO: 221) in computer readable form (ST25 format text file) which is submitted herein. The Sequence Listing is shown using standard three letter code for amino acids, as defined in 37 C.F.R. 1.822. Said ASCII copy, created on Mar. 8, 2019, is named 40566-711_601_SL.txt and is 350,816 bytes in size.

BACKGROUND

The gut epithelium has thwarted efforts to orally administer large molecule biologics because proteins cannot diffuse across the barrier or sneak through the tight junctions. When they are taken up by endocytosis—the only route left to them—they are typically degraded in lysosomes rather than being transported into the body. This inability to be readily absorbed across the intestinal epithelium continues to be a limiting factor in developing commercially viable oral formulations of these agents. The most common solution is to use systemic administration, but that can often create considerable side effects and reduce patient convenience that negatively affects compliance.

INCORPORATION BY REFERENCE

All references disclosed herein are hereby incorporated by reference in their entirety for all purposes.

SUMMARY

The present disclosure provides methods and composition for transport and/or delivery of a cargo molecule to certain location(s) within a cell (e.g., a supranuclear location) or across a cell (e.g., epithelial cell), either in vitro or in vivo (e.g., in a rodent or a human). Such cargo can be directed to a set of location(s) by coupling it to a carrier molecule. Such carrier molecule can interact with unique receptors both on the cell surface and intracellularly for the targeted delivery of the cargo. Various such carrier, cargos, and uses thereof are described herein.

The disclosure provides an isolated delivery construct that can comprise: a carrier derived from a domain I of an exotoxin and lacking a domain II, a domain Ib and a domain III of the exotoxin; coupled to a heterologous cargo. The carrier can consist essentially of the domain I of the exotoxin. The delivery construct can deliver the heterologous cargo according to one or more of the following: across an epithelial cell via transcytosis; to the basal side of the epithelial cell; to a supranuclear region within the epithelial cell; or to the interior of the epithelial cell via endocytosis. In some aspects, the carrier is configured to deliver a heterologous cargo to the basal side of an epithelial cell.

The disclosure provides an isolated delivery construct that can comprise: a chimeric carrier comprising an intracellular epithelial targeting domain; coupled to a heterologous cargo.

The disclosure provides an isolated delivery construct that can comprise: a chimeric carrier comprising a supranuclear epithelial targeting domain; coupled to the heterologous cargo.

The disclosure provides an isolated delivery construct that can comprise: a carrier coupled to a heterologous cargo, wherein the carrier interacts with one or more of ribophilin 1, SEC24, CK-8, TMEM132, GRP75, ERGIC-53, or perlecan, and does not display interaction with one or more of a clathrin or GPR78, or a combination thereof. The interaction can be a selective interaction. The interaction can be a pH-dependent interaction. The interaction of the carrier with the one or more of ribophilin 1, SEC24, CK-8, TMEM132, GRP75, ERGIC-53, or perlecan can occur on a surface of the epithelial cell, in the interior of an epithelial cell, or a combination thereof. The delivery of the heterologous cargo across the epithelial cell can occur in vitro from the apical surface of the epithelial cell to a basolateral compartment. The delivery of the heterologous cargo can occur in vitro from the apical surface of the epithelial cell to the interior of the epithelial cell. The delivery of the heterologous cargo can occur in vitro from the apical surface of the epithelial cell to the supranuclear region within the epithelial cell. The interaction of the carrier with the one or more of ribophilin 1, SEC24, CK-8, TMEM132, GRP75, ERGIC-53, or perlecan, or the combination thereof can occur in vitro on the apical surface of the epithelial cell, in the interior of the epithelial cell, or a combination thereof. The epithelial cell can be a polarized epithelial cell. The polarized epithelial cell can be part of a monolayer of polarized epithelial cells. The polarized epithelial cell can be from a rodent or a human. The polarized epithelial cell can be from a human. The human polarized epithelial cell can be a human polarized gut epithelial cell. The human polarized gut epithelial cell can be a Caco-2 cell. The delivery of the heterologous cargo across the epithelial cell can occur in vivo from a gut of a subject to a basolateral compartment of a subject. The delivery of the heterologous cargo can occur in vivo from a gut of a subject to the interior of the epithelial cell of a subject. The delivery of the heterologous cargo can occur in vivo from a gut of a subject to the supranuclear region within the epithelial cell of a subject. The interaction of the carrier with the one or more of ribophilin 1, SEC24, CK-8, TMEM132, GRP75, ERGIC-53, and perlecan, or the combination thereof, can occur in vivo on the apical surface of the epithelial cell of a subject, in the interior of the epithelial cell of the subject, or a combination thereof. The subject can be a rodent or a human. The subject can be a human and affected by one or more of the following: inflammatory bowel disease, psoriasis, bacterial sepsis, systemic lupus erythematosus (SLE), pemphigus vulgaris, myasthenia gravis, hemolytic anemia, thrombocytopenia purpura, Grave's disease, Sjogren's disease, dermatomyositis, Hashimoto's disease, polymyositis, inflammatory bowel disease, multiple sclerosis (MS), diabetes mellitus, rheumatoid arthritis, scleroderma, non-Hodgkin's lymphomas, Hodgkin's lymphoma, chronic lymphocytic leukemia, hairy cell leukemia, acute lymphoblastic leukemia, multiple myeloma, carcinomas of the bladder, kidney ovary, cervix, breast, lung, nasopharynx, malignant melanoma, rituximab resistant NHL or leukemia, diabetes, obesity, diabetes as a consequence of obesity, hyperglycemia, dyslipidemia, hypertriglyceridemia, syndrome X, insulin resistance, impaired glucose tolerance (IGT), diabetic dyslipidemia, hyperlipidemia, growth hormone deficiency (GHD), Turner syndrome (TS), Noonan syndrome, Prader-Willi syndrome, short stature homeobox-containing gene (SHOX) deficiency, chronic renal insufficiency, or idiopathic short stature short bowel syndrome. The epithelial cell can be a polarized epithelial cell. The polarized epithelial cell can be a polarized gut epithelial cell. The carrier can be a small molecule, a polypeptide, an aptamer, or a combination thereof. The carrier can be a small molecule. The carrier can be a polypeptide. The polypeptide can be an antibody or a functional fragment thereof. The carrier can be an aptamer. The carrier can be derived from an exotoxin. The carrier can be derived from a domain I of the exotoxin and lacks a domain II, a domain Ib and a domain III of the exotoxin The carrier that can be derived from a domain I of an exotoxin comprises an amino acid sequence that has at least 80% sequence identity to the amino acid sequence of the domain I of the exotoxin, or at least 80% sequence identity to a functional fragment thereof, wherein the exotoxin is a Cholix toxin or a *Pseudomonas* exotoxin A. In some aspects, the carrier comprises at least 110 amino acid residues of the domain I of the exotoxin. In some aspects, the carrier comprises at least 50 contiguous amino acid residues of the domain I of the exotoxin. The carrier that lacks the domain II, the domain Ib and the domain III of the exotoxin can comprise a portion of the domain II, the domain Ib or the domain III of the exotoxin, or a combination thereof. The portion can comprise no more than 70% of the amino acid residues of the domain II, the domain Ib or the domain III of the exotoxin. The exotoxin can be a Cholix toxin. The carrier can comprise: an amino acid sequence having at least 80% sequence identity to the amino acid sequence of SEQ ID NO: 4 or SEQ ID NO: 5 or at least 80% sequence identity to a functional fragment thereof, and no more than 347 contiguous amino acid residues from SEQ ID NO: 1. The carrier can comprise a deletion or mutation in one or more of the amino acid residues of the amino acid sequence set forth in SEQ ID NO: 4 or SEQ ID NO: 5. The carrier can comprise: an amino acid sequence having at least 90% sequence identity to the amino acid sequence of SEQ ID NO: 4 or SEQ ID NO: 5 or at least 90% sequence identity to a functional fragment thereof, and no more than 347 contiguous amino acid residues from SEQ ID NO: 1. The carrier can comprise: an amino acid sequence having at least 95% sequence identity to the amino acid sequence of SEQ ID NO: 4 or SEQ ID NO: 5 or at least 95% sequence identity to a functional fragment thereof, and no more than 347 contiguous amino acid residues from SEQ ID NO: 1. The carrier can comprise: an amino acid sequence having at least 99% sequence identity to the amino acid sequence of SEQ ID NO: 4 or SEQ ID NO: 5 or at least 99% sequence identity to a functional fragment thereof, and no more than 347 contiguous amino acid residues from SEQ ID NO: 1. The carrier can comprise: an amino acid sequence having 100% sequence identity to the amino acid sequence of SEQ ID NO: 4 or SEQ ID NO: 5 or 100% sequence identity to a functional fragment thereof, and no more than 347 contiguous amino acid residues from SEQ ID NO: 1. The carrier can comprise the amino acid sequence set forth in SEQ ID NO: 4 or SEQ ID NO: 5 or a functional fragment thereof. The carrier can comprise the amino acid sequence set forth in SEQ ID NO: 6 or SEQ ID NO: 7 or a functional fragment thereof. The carrier can comprise the amino acid sequence set forth in SEQ ID NO: 8 or SEQ ID NO: 9 or a functional fragment thereof. The carrier can comprise an amino acid sequence having at least 80% sequence identity to any one of the amino acid sequences set forth in SEQ ID NO: 148, SEQ ID NO: 149, SEQ ID NO: 150, SEQ ID NO: 151, SEQ ID NO: 152, a functional fragment thereof, or any combination thereof. The carrier can comprise a spatial structure in which one or more amino acid residues of SEQ ID NO: 148 or SEQ ID NO: 149 are in close proximity to one or more amino acid residues of SEQ ID NO: 151, and one or more amino acid residues of SEQ ID NO: 148 or SEQ ID NO: 149 are in close proximity to one or more amino acid residues of SEQ ID NO: 152. The carrier can comprise an amino acid sequence having at least 80% sequence identity to the amino acid sequence set forth in SEQ ID NO: 30 or SEQ ID NO: 31 or the amino acid sequence set forth in SEQ ID NO: 10 or SEQ ID NO: 11 or at least 80% sequence identity to a functional fragment thereof. The carrier can comprise a deletion or mutation in one or more of amino acid residues 1-187 or 1-206 of SEQ ID NO: 11 or 1-186 or 1-205 of SEQ ID NO: 10. The carrier can comprise residues 1-187 of SEQ ID NO: 30 or 1-186 of SEQ ID NO: 31 and no more than 206 contiguous amino acid residues of SEQ ID NO: 1. The carrier can comprise an amino acid sequence having at least 80% sequence identity to the amino acid sequence set forth in any one of SEQ ID NO: 10-SEQ ID NO: 31 or at least 80% sequence identity to a functional fragment thereof. The carrier can comprise the amino acid sequence set forth in SEQ ID NO: 10 or SEQ ID NO: 11 or a functional fragment thereof. The carrier can comprise an amino acid sequence having at least 80% sequence identity to the amino acid sequence set forth in SEQ ID NO: 106 or SEQ ID NO: 107 or the amino acid sequence set forth in SEQ ID NO: 30 or SEQ ID NO: 31 or at least 80% sequence identity to a functional fragment thereof. The carrier can comprise a deletion or mutation in one or more of amino acid residues 1-151 or 1-187 of SEQ ID NO: 4 or SEQ ID NO: 5. The carrier can lack any one or more of the amino acid residues 1-39 of SEQ ID NO: 5 or amino acid residues 1-38 of SEQ ID NO: 4. The carrier can comprise an amino acid sequence having at least 80% sequence identity to the amino acid sequence set forth in SEQ ID NO: 69 or SEQ ID NO: 70 or 80% sequence identity to a functional fragment thereof. The carrier can comprise residues 1-151 of SEQ ID NO: 5 or residues 1-150 of SEQ ID NO: 4 and no more than 187 contiguous amino acid residues of SEQ ID NO: 1 The carrier can comprise an amino acid sequence having at least 80% sequence identity to the amino acid sequence set forth in any one of SEQ ID NO: 30-SEQ ID NO: 107 or at least 80% sequence identity to a functional fragment thereof. The carrier can comprise the amino acid sequence set forth in SEQ ID NO: 30 or SEQ ID NO: 31 or a functional fragment thereof. The carrier can comprise an amino acid sequence having at least 80% sequence identity to the amino acid sequence set forth in SEQ ID NO: 106 or SEQ ID NO: 107 or the amino acid sequence set forth in SEQ ID NO: 124 or SEQ ID NO: 125 or at least 80% sequence identity to a functional fragment thereof. The carrier can comprise a deletion or mutation in one or more of amino acid residues 1-150 of SEQ ID NO: 6 or in one or more of amino acid residues 1-151 of SEQ ID NO: 7. The carrier can comprise residues 1-134 of SEQ ID NO: 5 or residues 1-133 of SEQ ID NO: 4 and no more than 151 contiguous amino acid residues of SEQ ID NO: 1. The carrier can comprise an amino acid sequence having at least 80% sequence identity to the amino acid sequence set forth in any of SEQ ID NO: 106-SEQ ID NO: 125 or at least 80% sequence identity to a functional fragment thereof The carrier can comprise the amino acid sequence set forth in SEQ ID NO: 106 or SEQ ID NO: 107 or a functional fragment thereof. The carrier or isolated delivery construct can comprise at least one but no more than 20 beta strands. The exotoxin can be a *Pseudomonas* exotoxin A. The carrier can comprise an amino acid sequence having at least 80% identity to the amino acid sequence of SEQ ID NO: 137 or at least 80% identity to a functional fragment thereof. The carrier can comprise a deletion or mutation in one or more of amino acid residues 1-252 of SEQ ID NO: 137. The carrier can comprise an amino acid sequence having at least 90% sequence identity to the amino acid sequence of 1-252 of SEQ ID NO: 137 or at least 90% sequence identity to a functional fragment thereof. The carrier can comprise an amino acid sequence having at least 95% sequence identity to the amino acid sequence of 1-252 of SEQ ID NO: 137 or at least 95% sequence identity to a functional fragment thereof. The carrier can comprise an amino acid sequence having at least 99% sequence identity to the amino acid sequence of 1-252 of SEQ ID NO: 137 or at least 99% sequence identity to a functional fragment thereof. The carrier can comprise an amino acid sequence having 100% sequence identity to the amino acid sequence of 1-252 of SEQ ID NO: 137 or 100% sequence identity to a functional fragment thereof. The carrier can comprise no more than 252 contiguous amino acid residues from SEQ ID NO: 134. In some aspects, the carrier comprises residues 1-252 of SEQ ID NO: 134. The carrier can comprise at least one N-terminal methionine residue. The carrier can comprise an amino acid sequence having at least 80% sequence identity to an amino acid sequence set forth in any one of SEQ ID NO: 5, SEQ ID NO: 7, SEQ ID NO: 9, SEQ ID NO: 11, SEQ ID NO: 31, SEQ ID NO: 107, SEQ ID NO: 125, or 80% sequence identity to a functional fragment thereof. The delivery construct can form a multimer. The multimer can be formed by multimerization of the heterologous cargo. The multimer can be a heteromer or a homomer The homomer can be a homodimer. The homodimer can be formed by dimerization of the heterologous cargo.

The present disclosure provides an isolated delivery construct that can comprise: a carrier comprising a first portion and a second portion, wherein the first portion is derived from a first exotoxin and the second portion is derived from a second exotoxin; coupled to a heterologous cargo. The first exotoxin can be Cholix. The second exotoxin can be PE. The first portion can be derived from a domain I, a domain II, a domain Ib, or a domain III of Cholix, or any combination thereof. The first portion can comprise an amino acid sequence having at least 80% sequence identity to any one of the amino acid sequences set forth in SEQ ID NO: 1-SEQ ID NO: 125 or SEQ ID NO: 133, a functional fragment thereof, or any combination thereof. The first portion can comprise an amino acid sequence having at least 80% sequence identity to any one of the amino acid sequences set forth in SEQ ID NO: 148-SEQ ID NO: 152, a functional fragment thereof, or any combination thereof. The first portion can comprise an amino acid sequence having at least 80% sequence identity to any one of the amino acid sequences set forth in SEQ ID NO: 4, SEQ ID NO: 5, SEQ ID NO: 10, or SEQ ID NO: 11, a functional fragment thereof, or any combination thereof. The second portion can be derived from a domain I, a domain II, a domain Ib, or a domain III of PE, or any combination thereof. The second portion can comprise an amino acid sequence having at least 80% sequence identity to any one of the amino acid sequences set forth in SEQ ID NO: 137-SEQ ID NO: 145, a functional fragment thereof, or any combination thereof. The first portion can be chemically coupled or recombinantly coupled to the second portion. The first portion can be directly or indirectly coupled to the second portion. The carrier can comprise an amino acid sequence having at least 80% sequence identity to the amino acid sequence SEQ ID NO: 146 or SEQ ID NO: 147. The carrier can be chemically coupled or recombinantly coupled to the heterologous cargo. The carrier can be covalently coupled to the heterologous cargo. The heterologous cargo can be coupled to the C-terminus of the carrier. The heterologous cargo can be coupled to the N-terminus of the carrier. The carrier can be coupled directly to the heterologous cargo. The carrier can be coupled indirectly to the heterologous cargo. The carrier can be coupled to the heterologous cargo via a spacer. The spacer can comprise an amino acid spacer. The amino acid spacer can be between 1 and 50 amino acid residues in length. The amino acid spacer can comprise one or more glycine residues and one or more serine residues. The spacer can be a cleavable spacer. The cleavable spacer can comprise an amino acid sequence set forth in any one of SEQ ID NO: 174-SEQ ID NO: 206. The spacer can be a non-cleavable spacer. The non-cleavable spacer can comprise one or more of the amino acid sequences GTGGS (SEQ ID NO: 207), GGGGS (SEQ ID NO: 208), GGGGSGGGGS (SEQ ID NO: 209), GGGGSGGGGSGGGGS (SEQ ID NO: 210), or GGGGSGGG (SEQ ID NO: 211). The non-cleavable spacer can comprise one or more of (GGGGS)$_x$ (SEQ ID NO: 212), wherein x=1, 2, 3, 4, 5, 6, 7, 8, 9, or 10. The non-cleavable spacer can comprise one or more of (GS)$_x$ (SEQ ID NO: 213), wherein x=1, 2, 3, 4, 5, 6, 7, 8, 9, or 10. The spacer can comprise one or more fragments of the domain II, the domain Ib or the domain III of the exotoxin, or a combination thereof. The spacer can comprise at most 80 amino acid residues of the domain II, 80 amino acid residues of the domain III, or a combination thereof. The heterologous cargo can be a macromolecule, a small molecule, a polypeptide, a nucleic acid, a mRNA, a miRNA, a shRNA, a siRNA, an antisense molecule, an antibody, a DNA, a plasmid, a vaccine, a polymer a nanoparticle, or a catalytically-active material. The heterologous cargo can be a biologically active cargo. The biologically active cargo can be a cytokine, a hormone, a therapeutic antibody, a functional fragment thereof, or any combination thereof. The cytokine can be IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, or IL-30. The cytokine can have the amino acid sequence set forth in SEQ ID NO: 217 or SEQ ID NO: 218. The hormone can have the amino acid sequence set forth in SEQ ID NO: 215 or SEQ ID NO: 216. The therapeutic antibody can be an anti-TNFa antibody. The anti-TNFa antibody can be adalimumab or infliximab. The heterologous cargo can be a detectable agent. The detectable agent can be a fluorophore, a contrast agent, an X-ray contrast agent, a PET agent, a nanoparticle, or a radioisotope. The fluorophore can be a red fluorescent protein (RFP). The RFP can have the amino acid sequence set forth in SEQ ID NO: 220.

A delivery construct of the present disclosure can comprise an amino acid sequence having at least 80% sequence identity to the amino acid sequence set forth in any one of SEQ ID NO: 155, SEQ ID NO: 156, or SEQ ID NO: 158-SEQ ID NO: 165, or at least 80% sequence identity to a functional fragment thereof. A delivery construct of the present disclosure can comprise an amino acid sequence having at least 90% sequence identity to the amino acid sequence set forth in any one of SEQ ID NO: 155, SEQ ID NO: 156, or SEQ ID NO: 158-SEQ ID NO: 165, or at least 90% sequence identity to a functional fragment thereof. A delivery construct of the present disclosure can comprise an amino acid sequence having at least 95% sequence identity to the amino acid sequence set forth in any one of SEQ ID NO: 155, SEQ ID NO: 156, or SEQ ID NO: 158-SEQ ID NO: 165, or at least 95% sequence identity to a functional fragment thereof. A delivery construct of the present disclosure can comprise an amino acid sequence having at least 99% sequence identity to the amino acid sequence set forth in any one of SEQ ID NO: 155, SEQ ID NO: 156, or SEQ ID NO: 158-SEQ ID NO: 165, or at least 99% sequence identity to a functional fragment thereof. A delivery construct of the present disclosure can comprise an amino acid sequence having 100% sequence identity to the amino acid sequence set forth in any one of SEQ ID NO: 155, SEQ ID NO: 156, or SEQ ID NO: 158-SEQ ID NO: 165, or 100% sequence identity to a functional fragment thereof.

The present disclosure provides a pharmaceutical composition comprising: an isolated delivery construct as described herein; and a pharmaceutically acceptable carrier. The composition can be formulated for oral administration, topical administration, pulmonary administration, intra-nasal administration, buccal administration, sublingual administration or ocular administration. The composition can be formulated for oral administration. The composition can be formulated in a capsule or tablet.

The present disclosure provides a polynucleotide that can encode an isolated delivery construct as described herein.

In various aspects, the present disclosure provides a vector comprising a polynucleotide encoding an isolated delivery construct as described herein.

The present disclosure provides a host cell that can comprise a vector that expresses a delivery construct, wherein the host cell comprises a vector comprising a polynucleotide encoding an isolated delivery construct as described herein.

The present disclosure provides a method of delivering a heterologous cargo across an epithelial cell, the method can comprise: applying a delivery construct to the apical surface of the epithelial cell; and delivering the delivery construct to the basal side of the epithelial cell at a rate greater than $10^{-6}$ cm/sec, wherein the delivery construct comprises: a carrier; coupled to the heterologous cargo. In some aspects, the method further comprises releasing the delivery construct from the basal side of the epithelial cell following delivery across the epithelial cell. In some aspects, the carrier is configured to deliver a heterologous cargo to the basal side of an epithelial cell.

The present disclosure provides a method of delivering a heterologous cargo to the interior of an epithelial cell via endocytosis, the method can comprise: applying a delivery construct to the apical surface of the epithelial cell; and delivering the delivery construct to the interior of the epithelial cell via endocytosis, wherein the delivery construct comprises: a carrier; coupled to the heterologous cargo.

The present disclosure provides a method of delivering a heterologous cargo to a supranuclear region within an epithelial cell via endocytosis, the method can comprise: applying a delivery construct to the apical surface of an epithelial cell; and delivering the delivery construct to the supranuclear region within the epithelial cell via endocytosis, wherein the delivery construct comprises: a carrier; coupled to the heterologous cargo.

The present disclosure provides a method of interacting with ribophilin 1, SEC24, CK-8, TMEM132, GRP75, ERGIC-53, or perlecan, or a combination thereof, the method can comprise: applying a delivery construct to the apical surface of the epithelial cell; and interacting the delivery construct with the ribophilin 1, SEC24, CK-8, TMEM132, GRP75, ERGIC-53, or perlecan, or the combination thereof, wherein the delivery construct comprises: a carrier; coupled to a heterologous cargo. The carrier can interact with one or more of ribophilin 1, SEC24, CK-8, TMEM132, GRP75, ERGIC-53, or perlecan, or the combination thereof, and does not display interaction with one or more of a clathrin or GPR78, or a combination thereof. The interaction can be a selective interaction or a pH-dependent interaction, or a combination thereof. The interaction of the carrier with the one or more of ribophilin 1, SEC24, CK-8, TMEM132, GRP75, ERGIC-53, or perlecan can occur on a surface of an epithelial cell, in the interior of an epithelial cell, or a combination thereof.

The present disclosure provides a method of treating a disease in a subject in need thereof, the method can comprise administering to the subject a delivery construct comprising: a carrier; coupled to a heterologous cargo; wherein the delivery construct is capable of delivering the heterologous cargo to the interior of an epithelial cell.

The present disclosure provides a method of treating a disease in a subject in need thereof, the method can comprise administering to the subject a delivery construct comprising: a carrier; coupled to a heterologous cargo; wherein the delivery construct is capable of delivering the heterologous cargo to a supranuclear region within an epithelial cell.

The present disclosure provides a method of diagnosing a disease in a subject in need thereof, the method can comprise administering to the subject a delivery construct comprising: a carrier; coupled to a heterologous cargo; wherein the delivery construct is capable of delivering the heterologous cargo to the interior of an epithelial cell.

The present disclosure provides a method of diagnosing a disease in a subject in need thereof, the method can comprise administering to the subject a delivery construct comprising: a carrier; coupled to a heterologous cargo; wherein the delivery construct is capable of delivering the heterologous cargo to a supranuclear region within an epithelial cell.

The present disclosure provides a method of treating a disease in a subject in need thereof, the method can comprise administering to the subject a delivery construct comprising: a carrier derived from a domain I of an exotoxin and lacking a domain II, a domain Ib and a domain III of the exotoxin; coupled to a heterologous cargo; wherein the delivery construct is capable of delivering the heterologous cargo via transcytosis across an epithelial cell.

The present disclosure provides a method of diagnosing a disease in a subject in need thereof, the method can comprise administering to the subject a delivery construct comprising: a carrier derived from a domain I of an exotoxin and lacking a domain II, a domain Ib and a domain III of the exotoxin; coupled to a heterologous cargo; wherein the delivery construct is capable of delivering the heterologous cargo via transcytosis across an epithelial cell. The delivery of the heterologous cargo across the epithelial cell can occur in vitro from the apical surface of the epithelial cell to a basolateral compartment. The delivery of the heterologous cargo can occur in vitro from the apical surface of the epithelial cell to the interior of the epithelial cell. The delivery of the heterologous cargo can occur in vitro from the apical surface of the epithelial cell to the supranuclear region within the epithelial cell. The interaction of the carrier with the one or more of ribophilin 1, SEC24, CK-8, TMEM132, GRP75, ERGIC-53, or perlecan, or the combination thereof, can occur in vitro on the apical surface of the epithelial cell, in the interior of the epithelial cell, or a combination thereof. The epithelial cell can be a polarized epithelial cell. The polarized epithelial cell can be part of a monolayer of polarized epithelial cells. The polarized epithelial cell can be from a rodent. The polarized epithelial cell can be from a human. The human polarized epithelial cell can be a human polarized gut epithelial cell. The human polarized gut epithelial cell can be a Caco-2 cell. The delivery of the heterologous cargo across the epithelial cell can occur in vivo from a gut of a subject to a basolateral compartment of the subject. The delivery of the heterologous cargo can occur in vivo from a gut of a subject to the interior of the epithelial cell of the subject. The delivery of the heterologous cargo can occur in vivo from a gut of a subject to the supranuclear region within the epithelial cell of the subject. The interaction of the carrier with the one or more of ribophilin 1, SEC24, CK-8, TMEM132, GRP75, ERGIC-53, and perlecan, or the combination thereof, can occur in vivo on the apical surface of the epithelial cell of a subject, in the interior of the epithelial cell of the subject, or a combination thereof. The subject can be a rodent or a human. The epithelial cell can be a polarized epithelial cell. The polarized epithelial cell can be a polarized gut epithelial cell. The method further can comprise formulating the delivery construct for administration to the subject. The formulation can comprise one or more pharmaceutically acceptable carriers. The delivery construct can be formulated for oral administration, topical administration, pulmonary administration, intra-nasal administration, buccal administration, sublingual administration or ocular administration. The composition can be formulated for oral administration. The disease can be an inflammatory disease, an autoimmune disease, a cancer, a metabolic disease, a fatty liver disease, or a growth hormone deficient growth disorder. The inflammatory disease can be an inflammatory bowel disease, psoriasis or bacterial sepsis. The inflammatory bowel disease can be Crohn's disease, ulcerative colitis, collagenous colitis, lymphocytic colitis, ischemic colitis, diversion colitis, Behcet's syndrome or indeterminate colitis. The autoimmune disease can be systemic lupus erythematosus (SLE), pemphigus vulgaris, myasthenia gravis, hemolytic anemia, thrombocytopenia purpura, Grave's disease, Sjogren's disease, dermatomyositis, Hashimoto's disease, polymyositis, inflammatory bowel disease, multiple sclerosis (MS), diabetes mellitus, rheumatoid arthritis, or scleroderma. The cancer can be a non-Hodgkin's lymphoma, Hodgkin's lymphoma, chronic lymphocytic leukemia, hairy cell leukemia, acute lymphoblastic leukemia, multiple myeloma, carcinomas of the bladder, kidney ovary, cervix, breast, lung, nasopharynx, malignant melanoma, rituximab resistant NHL, or leukemia. The metabolic disease can be diabetes, obesity, diabetes as a consequence of obesity, hyperglycemia, dyslipidemia, hypertriglyceridemia, syndrome X, insulin resistance, impaired glucose tolerance (IGT), diabetic dyslipidemia, or hyperlipidemia. The carrier can be a small molecule. The carrier can be a polypeptide. The polypeptide can be an antibody or a functional fragment thereof. The carrier can be an aptamer. The carrier can be derived from an exotoxin. The carrier can be derived from a domain I of the exotoxin and lacks a domain II, a domain Ib and a domain III of the exotoxin. The carrier can be derived from a domain I of an exotoxin comprises an amino acid sequence that has at least 80% sequence identity to the amino acid sequence of the domain I of the exotoxin, or at least 80% sequence identity to a functional fragment thereof, wherein the exotoxin is a Cholix toxin or a *Pseudomonas* exotoxin A. The carrier can comprise at least 130 amino acid residues of the domain I of the exotoxin. The carrier can comprise at least 150 contiguous amino acid residues of the domain I of the exotoxin. The carrier that lacks the domain II and domain III of the exotoxin can comprise a portion of the domain II or the domain III of the exotoxin, or a combination thereof. The portion comprises no more than 82 of the amino acid residues of the domain II or the domain III of the exotoxin. The exotoxin can be a Cholix toxin. The carrier can comprise: an amino acid sequence having at least 80% sequence identity to the amino acid sequence of SEQ ID NO: 4 or SEQ ID NO: 5 or at least 80% sequence identity to a functional fragment thereof, and no more than 347 contiguous amino acid residues from SEQ ID NO: 1. The carrier can comprise a deletion or mutation in one or more of amino acid residues of the amino acid sequence set forth in SEQ ID NO: 4 or SEQ ID NO: 5. The carrier can comprise: an amino acid sequence having at least 90% sequence identity to the amino acid sequence of SEQ ID NO: 4 or SEQ ID NO: 5 or at least 90% sequence identity to a functional fragment thereof, and no more than 347 contiguous amino acid residues from SEQ ID NO: 1. The carrier can comprise: an amino acid sequence having at least 95% sequence identity to the amino acid sequence of SEQ ID NO: 4 or SEQ ID NO: 5 or at least 95% sequence identity to a functional fragment thereof, and no more than 347 contiguous amino acid residues from SEQ ID NO: 1. The carrier can comprise: an amino acid sequence having at least 99% sequence identity to the amino acid sequence of SEQ ID NO: 4 or SEQ ID NO: 5 or at least 99% sequence identity to a functional fragment thereof, and no more than 347 contiguous amino acid residues from SEQ ID NO: 1. The carrier can comprise: an amino acid sequence having 100% sequence identity to the amino acid sequence of SEQ ID NO: 4 or SEQ ID NO: 5 or 100% sequence identity to a functional fragment thereof, and no more than 347 contiguous amino acid residues from SEQ ID NO: 1. The carrier can comprise the amino acid sequence set forth in SEQ ID NO: 4 or SEQ ID NO: 5 or a functional fragment thereof. In some aspects, the carrier comprises the amino acid sequence set forth in SEQ ID NO: 6 or SEQ ID NO: 7 or a functional fragment thereof. The carrier can comprise the amino acid sequence set forth in SEQ ID NO: 8 or SEQ ID NO: 9 or a functional fragment thereof. The carrier can comprise an amino acid sequence having at least 80% sequence identity to any one of the amino acid sequences set forth in SEQ ID NO: 148, SEQ ID NO: 149, SEQ ID NO: 150, SEQ ID NO: 151, SEQ ID NO: 152, a functional fragment thereof, or any combination thereof. The carrier can comprise an amino acid sequence having at least 80% sequence identity to the amino acid sequence set forth in SEQ ID NO: 30 or SEQ ID NO: 31 or the amino acid sequence set forth in SEQ ID NO: 10 or SEQ ID NO: 11 or at least 80% sequence identity to a functional fragment thereof. The carrier can comprise a deletion or mutation in one or more of amino acid residues 1-187 or 1-206 of SEQ ID NO: 5 or one or more of amino acid residues 1-186 or 1-205 of SEQ ID NO: 4. The carrier can comprise residues 1-187 of SEQ ID NO: 5 or residues 1-186 of SEQ ID NO: 4 and no more than 206 contiguous amino acid residues of SEQ ID NO: 1. The carrier can comprise an amino acid sequence having at least 80% sequence identity to the amino acid sequence set forth in any one of SEQ ID NO: 1-SEQ ID NO: 31 or at least 80% sequence identity to a functional fragment thereof. The carrier can comprise the amino acid sequence set forth in SEQ ID NO: 10 or SEQ ID NO: 11 or a functional fragment thereof. The carrier can comprise an amino acid sequence having at least 80% sequence identity to the amino acid sequence set forth in SEQ ID NO: 106 or SEQ ID NO: 107 or the amino acid sequence set forth in SEQ ID NO: 30 or SEQ ID NO: 31 or at least 80% sequence identity to a functional fragment thereof. The carrier can comprise a deletion or mutation in one or more of amino acid residues 1-151 or 1-187 of SEQ ID NO: 5 or in one or more of amino acid residues 1-150 or 1-186 of SEQ ID NO: 4. The carrier can lack any one or more of the amino acid residues 1-39 of SEQ ID NO: 5 or residues 1-38 of SEQ ID NO: 4. The carrier can comprise an amino acid sequence having at least 80% sequence identity to the amino acid sequence set forth in SEQ ID NO: 69 or SEQ ID NO: 70 or 80% sequence identity to a functional fragment thereof. The carrier can comprise residues 1-151 of SEQ ID NO: 5 or residues 1-150 of SEQ ID NO: 4 and no more than 187 contiguous amino acid residues of SEQ ID NO: 1. The carrier can comprise an amino acid sequence having at least 80% sequence identity to the amino acid sequence set forth in any of SEQ ID NO: 30-SEQ ID NO: 107 or at least 80% sequence identity to a functional fragment thereof. The carrier can comprise the amino acid sequence set forth in SEQ ID NO: 30 or SEQ ID NO: 31 or a functional fragment thereof. The carrier can comprise an amino acid sequence having at least 80% sequence identity to the amino acid sequence set forth in SEQ ID NO: 124 or SEQ ID NO: 125 or the amino acid sequence set forth in SEQ ID NO: 106 or SEQ ID NO: 107 or at least 80% sequence identity to a functional fragment thereof. The carrier can comprise a deletion or mutation in one or more of amino acid residues 1-151 of SEQ ID NO: 5 or in one or more of amino acid residues 1-150 of SEQ ID NO: 4. The carrier can comprise residues 1-134 of SEQ ID NO: 5 or residues 1-133 of SEQ ID NO: 4 and no more than 151 contiguous amino acid residues of SEQ ID NO: 1. The carrier can comprise an amino acid sequence having at least 80% sequence identity to the amino acid sequence set forth in any one of SEQ ID NO: 106-SEQ ID NO: 125 or at least 80% sequence identity to a functional fragment thereof. The carrier can comprise the amino acid sequence set forth in SEQ ID NO: 106 or SEQ ID NO: 107 or a functional fragment thereof. The carrier can comprise at least one but no more than 20 beta strands. The exotoxin can be a *Pseudomonas* exotoxin A. The carrier can comprise an amino acid sequence having at least 80% identity to the amino acid sequence of SEQ ID NO: 137 or at least 80% identity to a functional fragment thereof. The carrier can comprise a deletion or mutation in one or more of amino acid residues 1-252 of SEQ ID NO: 137. The carrier can comprise an amino acid sequence having at least 90% sequence identity to the amino acid sequence of 1-252 of SEQ ID NO: 137 or at least 90% sequence identity to a functional fragment thereof. The carrier can comprise an amino acid sequence having at least 95% sequence identity to the amino acid sequence of 1-252 of SEQ ID NO: 137 or at least 95% sequence identity to a functional fragment thereof. The carrier can comprise an amino acid sequence having at least 99% sequence identity to the amino acid sequence of 1-252 of SEQ ID NO: 137 or at least 99% sequence identity to a functional fragment thereof. The carrier can comprise an amino acid sequence having 100% sequence identity to the amino acid sequence of 1-252 of SEQ ID NO: 137 or 100% sequence identity to a functional fragment thereof. The carrier can comprise residues 1-252 of SEQ ID NO: 135. The carrier can comprise a first portion and a second portion, wherein the first portion is derived from a first exotoxin and the second portion is derived from a second exotoxin. The first exotoxin can be Cholix and the second exotoxin can be PE. The first portion can be derived from a domain I, a domain II, a domain Ib, or a domain III of Cholix, or any combination thereof. The first portion can comprise an amino acid sequence having at least 80% sequence identity to any one of the amino acid sequences set forth in SEQ ID NO: 1-SEQ ID NO: 125, a functional fragment thereof, or any combination thereof. The first portion can comprise an amino acid sequence having at least 80% sequence identity to any one of the amino acid sequences set forth in SEQ ID NO: 148-SEQ ID NO: 152, a functional fragment thereof, or any combination thereof. The first portion can comprise an amino acid sequence having at least 80% sequence identity to any one of the amino acid sequences set forth in SEQ ID NO: 4, SEQ ID NO: 5, SEQ ID NO: 10, or SEQ ID NO: 11, a functional fragment thereof, or any combination thereof. The second portion can be derived from a domain I, a domain II, a domain Ib, or a domain III of PE, or any combination thereof. The second portion can comprise an amino acid sequence having at least 80% sequence identity to any one of the amino acid sequences set forth in SEQ ID NO: 137-SEQ ID NO: 145, a functional fragment thereof, or any combination thereof. The first portion can be chemically coupled or recombinantly coupled to the second portion. The first portion can be directly or indirectly coupled to the second portion. The carrier can comprise an amino acid sequence having at least 80% sequence identity to the amino acid sequence SEQ ID NO: 146 or SEQ ID NO: 147. The carrier can further comprise at least one N-terminal methionine residue. The carrier can comprise an amino acid sequence having at least 80% sequence identity to an amino acid sequence set forth in any one of SEQ ID NO: 5, SEQ ID NO: 7, SEQ ID NO: 9, SEQ ID NO: 11, SEQ ID NO: 31, SEQ ID NO: 107, SEQ ID NO: 125, or 80% sequence identity to a functional fragment thereof. The delivery construct can form a multimer. The multimer can be formed by multimerization of the heterologous cargo. The multimer can be a heteromer or a homomer. The homomer can be a homodimer. The homodimer can be formed by dimerization of the heterologous cargo. The carrier can be chemically coupled or recombinantly coupled to the heterologous cargo. The carrier can be covalently coupled to the heterologous cargo. The heterologous cargo can be coupled to the C-terminus of the carrier. The heterologous cargo can be coupled to the N-terminus of the carrier. The carrier can be coupled directly to the heterologous cargo. The carrier can be coupled indirectly to the heterologous cargo. The carrier can be coupled to the heterologous cargo via a spacer. The spacer can comprise an amino acid spacer. The amino acid spacer can comprise one or more glycine residues and one or more serine residues. The amino acid spacer can be between 1 and 50 amino acid residues in length. The spacer can be a cleavable spacer. The cleavable spacer can comprise an amino acid sequence selected from the group consisting of the amino acid sequences set forth in SEQ ID NO: 174-SEQ ID NO: 206. The spacer can be a non-cleavable spacer. The non-cleavable spacer can comprise one or more of the amino acid sequences GTGGS (SEQ ID NO: 207), GGGGS (SEQ ID NO: 208), GGGGSGGGGS (SEQ ID NO: 209), GGGGSGGGGSGGGGS (SEQ ID NO: 210), or GGGGSGGG (SEQ ID NO: 211). The non-cleavable spacer can comprises one or more of $(GGGGS)_x$ (SEQ ID NO: 212), wherein x=1, 2, 3, 4, 5, 6, 7, 8, 9, or 10. The non-cleavable spacer can comprise one or more of $(GS)_x$ (SEQ ID NO: 213), wherein x=1, 2, 3, 4, 5, 6, 7, 8, 9, or 10. The spacer can comprise one or more fragments of the domain II, a domain Ib or the domain III of the exotoxin, or a combination thereof. The spacer can comprise at most 82 amino acid residues of the domain II, 82 amino acid residues of the domain III, or a combination thereof. The heterologous cargo can be a macromolecule, a small molecule, a polypeptide, a nucleic acid, a mRNA, a miRNA, a shRNA, a siRNA, an antisense molecule, an antibody, a DNA, a plasmid, a vaccine, a polymer a nanoparticle, or a catalytically-active material. The heterologous cargo can be a biologically active cargo. The biologically active cargo can be a cytokine, a hormone, a therapeutic antibody, a functional fragment thereof, or any combination thereof. The cytokine can be IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, or IL-30. The cytokine can have the amino acid sequence set forth in SEQ ID NO: 217 or SEQ ID NO: 218. The hormone can have the amino acid sequence set forth in SEQ ID NO: 215 or SEQ ID NO: 216. The therapeutic antibody can be an anti-TNFa antibody. The anti-TNFa antibody can be adalimumab or infliximab. The heterologous cargo can be a detectable agent. The detectable agent can be a fluorophore, a contrast agent, an X-ray contrast agent, a PET agent, a nanoparticle, or a radioisotope. The fluorophore can be a red fluorescent protein (RFP). The RFP can have the amino acid sequence set forth in SEQ ID NO: 220.

The present disclosure relates to novel non-naturally occurring delivery constructs that can comprise a bacterial toxin-derived chimeric carrier coupled to a biologically active cargo; wherein the chimeric carrier is derived from a domain I but does not comprise a domain II, a domain Ib, or a domain III of the bacterial toxin (e.g., an exotoxin); and wherein the delivery construct is capable of delivering a heterologous (e.g., a biologically active) cargo via transcytosis transport across an epithelial cell (e.g., an intestinal epithelial cell).

The carrier can be derived from a domain I of an exotoxin and is capable of recognizing and interacting with one or more receptors on the luminal (e.g., apical) surface of intestinal epithelial cells. The receptor can be selective or non-selective. In some aspects, the receptor that a carrier interacts with is a non-selective scavenger receptor or a transmembrane receptor 132 (TMEM132) receptor. Interaction of the delivery constructs with a cell surface receptor that is present on the apical membrane of a polarized epithelial cell can occur with sufficient affinity to allow endocytosis of the delivery construct. The carrier that a delivery construct of the present disclosure is comprised of can bind to receptor(s) known to be present on the apical membrane of an epithelial cell by one of skill in the art without limitation. In various embodiments, the receptor binding domain of the delivery construct can bind to low density lipoprotein receptor-related protein 1 (LRP1) or TMEM132 receptor.

A delivery construct as described herein can be capable of delivering a heterologous (e.g., a biologically active) cargo across an epithelial cell from the apical side to a basolateral compartment and/or the *Lamina propria*. A delivery construct as described herein can be capable of delivering a heterologous (e.g., a biologically active) cargo into an epithelial cell (e.g., a polarized gut epithelial cell), such as an intracellular vesicle or compartment or the cytosol of the epithelial cell, thereby allowing for accumulation of the heterologous (e.g., biologically active) cargo in the epithelial cell. The carrier can be derived from the domain I of an exotoxin selected from the group consisting of cholix carrier (Cholix) and *Pseudomonas* exotoxin A (PE).

The carrier can be a polypeptide derived from Cholix and/or PE and having: at most 5 amino acid residues; at most 10 amino acid residues; at most 15 amino acid residues; at most 20 amino acid residues; at most 30 amino acid residues; at most 40 amino acid residues; at most 50 amino acid residues; at most 60 amino acid residues; at most 70 amino acid residues; at most 80 amino acid residues; at most 90 amino acid residues; at most 100 amino acid residues; at most 110 amino acid residues; at most 120 amino acid residues; at most 130 amino acid residues; at most 140 amino acid residues; at most 150 amino acid residues; at most 160 amino acid residues; at most 170 amino acid residues; at most 180 amino acid residues; at most 190 amino acid residues; at most 200 amino acid residues; at most 210 amino acid residues; at most 220 amino acid residues; at most 230 amino acid residues; at most 240 amino acid residues; at most 250 amino acid residues; at most 260 amino acid residues; and at most 265 amino acid residues.

The carrier can be derived from a domain I of a Cholix exotoxin and can comprise an amino acid sequence selected from the group consisting of an amino acid sequence having greater than 50% homology to SEQ ID NO: 4, having greater than 60% homology to SEQ ID NO: 4, having greater than 70% homology to SEQ ID NO: 4, having greater than 80% homology to SEQ ID NO: 4, having greater than 85% homology to SEQ ID NO: 4, having greater than 90% homology to SEQ ID NO: 4, and having greater than 95% homology to SEQ ID NO: 4. In some cases, the delivery construct is derived from cholix exotoxin (Cholix) and comprises the receptor binding domain polypeptide having the amino acid sequence set forth in SEQ ID NO: 4. The carrier can comprise an amino acid sequence with greater than 90% homology to SEQ ID NO: 4. The carrier can comprise an amino acid sequence with greater than 95% homology to SEQ ID NO: 4. The carrier can comprise a receptor binding domain polypeptide wherein one or more amino residues of SEQ ID NO: 4 is substituted with another amino acid. The carrier can comprise a receptor binding domain polypeptide that is a truncated portion of the amino acid sequence set forth in SEQ ID NO: 4.

The carrier can be derived from a domain I of a *Pseudomonas* exotoxin A (PE) and can comprise a polypeptide having the amino acid sequence set forth in SEQ ID NO: 137. The delivery construct can comprise an amino acid sequence with greater than 90% homology to SEQ ID NO: 137. The carrier can comprise an amino acid sequence with greater than 95% homology to SEQ ID NO: 137. The carrier can comprise a receptor binding domain polypeptide wherein one or more amino residues of SEQ ID NO: 137 is substituted with another amino acid. The carrier can comprise a receptor binding domain polypeptide that is a truncated portion of the amino acid sequence set forth in SEQ ID NO: 137.

A delivery construct can comprise a carrier, wherein the carrier comprises one or more amino acid residues of one exotoxin domain I (e.g., a Cholix or PE domain I) is replaced by one or more amino acid residues of a second exotoxin domain I (e.g., a Cholix or PE domain I), (also referred to hereinafter as a hybrid or chimeric carrier). The carrier can comprise an amino acid sequence wherein one or more amino acid residues of SEQ ID NO: 4 is replaced by one or more amino acid residues of SEQ ID NO: 137. The carrier can comprise an amino acid sequence wherein one or more amino acid residues of SEQ ID NO: 137 is replaced by one or more amino acid residues of SEQ ID NO: 4. The carrier can comprise an amino acid sequence wherein amino acid residues 77-87 of SEQ ID NO: 4 are replaced by amino acid residues of a second bacterial carrier receptor binding domain polypeptide. The carrier can comprise an amino acid sequence wherein amino acid residues 188-236 of SEQ ID NO: 4 are replaced by amino acid residues of a second bacterial carrier receptor binding domain polypeptide. The carrier can comprise an amino acid sequence wherein amino acid residues 69-71 of SEQ ID NO: 137 are replaced by amino acid residues of a second bacterial carrier receptor binding domain polypeptide. The carrier can comprise an amino acid sequence wherein amino acid residues 177-228 of SEQ ID NO: 137 are replaced by amino acid residues of a second bacterial carrier receptor binding domain polypeptide.

A carrier of the present disclosure that can be derived from a domain I of an exotoxin and can further comprise a portion of a domain II, a portion of a domain Ib, and/or a portion of a domain III of the same or another exotoxin. Thus, a carrier can comprise a domain I of an exotoxin, or a truncated and/or modified version thereof, and one or more portions derived from a domain II, domain Ib, and/or domain III of the same or a different exotoxin. The domain II, or modified domain II, and domain III, or modified domain III, can be derived from the same bacterial toxin. The domain II, or modified domain II, and domain III, or modified domain III, can be derived from a bacterial carrier selected from the group consisting of cholix carrier (Cholix) and *Pseudomonas* exotoxin A (PE), botulinum toxin, diptheria toxin, pertussis toxin, cholera toxin, heat-labile *E. coli* entero-toxin, shiga toxin, and shiga-like toxin. Toxicity of the bacterial carrier (e.g., Cholix or PE) may not be required for transport across epithelial layers such as the gut epithelium. For example, a delivery construct as described herein can comprise a carrier coupled to a heterologous cargo, and wherein the carrier is derived from a Cholix domain I (e.g., having an amino acid sequence set forth in any one of SEQ ID NO: 4-SEQ ID NO: 125) and further comprising portions of a domain II (e.g., SEQ ID NO: 126 or SEQ ID NO: 138), a domain Ib (e.g., SEQ ID NO: 127 or SEQ ID NO: 139), and/or a domain III (e.g., SEQ ID NO: 128 or SEQ ID NO: 140) of an exotoxin (e.g., Cholix and/or PE).

A delivery construct can comprise a carrier having the amino acid sequence derived from the sequence set forth in SEQ ID NO: 4, a translocation domain having the amino acid sequence derived from the sequence set forth in SEQ ID NO: 126, and a non-toxic catalytic domain having the amino acid sequence derived from the sequence set forth in SEQ ID NO: 128. A delivery constructs can comprise a receptor binding domain polypeptide having the amino acid sequence derived from the sequence set forth in SEQ ID NO: 136, a translocation domain having the amino acid sequence derived from the sequence set forth in SEQ ID NO: 137, and a non-toxic catalytic domain having the amino acid sequence derived from the sequence set forth in SEQ ID NO: 139. The delivery construct can comprises the amino acid sequence set forth in SEQ ID NO: 146. In various embodiments, the delivery construct comprises the amino acid sequence set forth in SEQ ID NO: 147.

The delivery constructs of the present disclosure can comprise a carrier coupled to a heterologous cargo. The heterologous cargo can be a biologically active cargo. The heterologous cargo can be a detectable agent. The carrier can be coupled to a biologically active cargo to produce a delivery construct that is capable of delivering the biologically active cargo via transcytosis transport across an intestinal epithelium. The biologically active cargo can be selected from e.g., a macromolecule, small molecule, peptide, polypeptide, nucleic acid, mRNA, miRNA, shRNA, siRNA, antisense molecule, antibody, DNA, plasmid, vaccine, polymer nanoparticle, or catalytically-active material. The biologically active cargo can be an enzyme selected from hyaluronidase, streptokinase, tissue plasminogen activator, urokinase, or PGE-adenosine deaminase. The biologically active cargo can comprises an amino acid sequence selected from the group consisting of the amino acid sequences set forth in SEQ ID NO: 214, SEQ ID NO: 215, SEQ ID NO: 216, SEQ ID NO: 217, SEQ ID NO: 218, and SEQ ID NO: 219, or any combination thereof.

The delivery constructs can comprise a carrier directly coupled to a heterologous (e.g., a biologically active) cargo. The heterologous (e.g., a biologically active) cargo can be directly coupled to the C-terminus of the delivery construct. The heterologous (e.g., a biologically active) cargo can be directly coupled to the N-terminus of the delivery construct.

The delivery constructs can comprise a carrier chemically coupled to a heterologous (e.g., a biologically active) cargo. The delivery constructs can comprise a carrier recombinantly coupled to a heterologous (e.g., a biologically active) cargo. A delivery construct of the present disclosure can be produced partly synthetically (e.g., via solid-phase synthesis) or recombinantly (e.g., bacterially expressed (e.g., *E. coli*) or in a mammalian cell (e.g., CHO cell)). A delivery construct of the present disclosure can be produced partly synthetic and partly recombinant.

The delivery constructs can comprise a delivery construct coupled to a biologically active cargo by a cleavable spacer. The spacer can be cleavable by an enzyme that is present at a basolateral membrane of a polarized epithelial cell. The spacer can be cleavable by an enzyme that is present in the plasma. The cleavable spacer can comprise the amino acid sequence set forth in any one of SEQ ID NO: 174-SEQ ID NO: 206. The cleavable spacer can be a spacer that comprises an amino acid sequence that can be a known substrate for the tobacco etch virus (TEV) protease. The cleavable spacer comprises the amino acid sequence set in forth in SEQ ID NO: 193. The spacer can be cleavable by an enzyme that is present at a basal-lateral membrane of a polarized epithelial cell. The spacer can be cleavable by an enzyme that is present in the plasma of a subject.

The cleavable spacers can comprise a peptide sequence (or like domain), which serves to inhibit, interfere with, or block the ability of the biologically active cargo to bind to receptors at the surface of epithelial cells, but wherein the delivery construct retains the ability of the cargo to activate it's receptor after the delivery construct is transported across the epithelial barrier and the cargo is released from the delivery construct and spacer components of the construct. The cleavable spacer can comprise the amino acid sequence set forth in, e.g., SEQ ID NO: 194-SEQ ID NO: 206.

The present disclosure also relates to pharmaceutical compositions that can comprise a novel non-naturally occurring delivery construct of the present disclosure and one or more pharmaceutically acceptable carriers, formulated for oral administration, topical administration, pulmonary administration, intra-nasal administration, buccal administration, sublingual administration or ocular administration.

The present disclosure provides a method of treating an inflammatory disease in a subject that can comprise administering a pharmaceutical composition of the present disclosure to the subject. In various embodiments, the inflammatory disease is selected from an inflammatory bowel disease, psoriasis or bacterial sepsis. In various embodiments, the inflammatory bowel disease is Crohn's disease, ulcerative colitis, collagenous colitis, lymphocytic colitis, ischemic colitis, diversion colitis, Behcet's syndrome or indeterminate colitis.

The present disclosure provides a method of treating an autoimmune disease in a subject that can comprise administering a pharmaceutical composition of the present disclosure to the subject. In various embodiments, the autoimmune disease is systemic lupus erythematosus (SLE), pemphigus vulgaris, myasthenia gravis, hemolytic anemia, thrombocytopenia purpura, Grave's disease, Sjogren's disease, dermatomyositis, Hashimoto's disease, polymyositis, inflammatory bowel disease, multiple sclerosis (MS), diabetes mellitus, rheumatoid arthritis, or scleroderma.

The present disclosure provides a method of treating a cancer in a subject that can comprise administering a pharmaceutical composition of the present disclosure to the subject. In various embodiments, the cancer to be treated includes, but is not limited to, non-Hodgkin's lymphomas, Hodgkin's lymphoma, chronic lymphocytic leukemia, hairy cell leukemia, acute lymphoblastic leukemia, multiple myeloma, carcinomas of the bladder, kidney ovary, cervix, breast, lung, nasopharynx, malignant melanoma and rituximab resistant NHL and leukemia.

The present disclosure provides a method of treating a subject having a metabolic disorder, said method can comprise administering a pharmaceutical composition of the present disclosure in an amount sufficient to treat said disorder, wherein said metabolic disorder is diabetes, obesity, diabetes as a consequence of obesity, hyperglycemia, dyslipidemia, hypertriglyceridemia, syndrome X, insulin resistance, impaired glucose tolerance (IGT), diabetic dyslipidemia, or hyperlipidemia.

The present disclosure provides a method of treating a subject having a fatty liver disease (e.g., nonalcoholic fatty liver disease (NAFLD); nonalcoholic steatohepatitis (NASH)), a gastrointestinal disease, or a neurodegenerative disease, said method comprising orally administering a pharmaceutical composition of the present disclosure in an amount sufficient to treat said disease.

The present disclosure provides a method of treating a subject having a GH deficient growth disorder, said method can comprise administering a pharmaceutical composition of the present disclosure in an amount sufficient to treat said disorder, wherein said disorder is growth hormone deficiency (GHD), Turner syndrome (TS), Noonan syndrome, Prader-Willi syndrome, short stature homeobox-containing gene (SHOX) deficiency, chronic renal insufficiency, and idiopathic short stature short bowel syndrome, GH deficiency due to rare pituitary tumors or their treatment, and muscle-wasting disease associated with HIV/AIDS.

A delivery construct can comprise a carrier comprising an amino acid sequence having at least 80% sequence identity to any one or more of the amino acid sequences set forth in SEQ ID NO: 1-SEQ ID NO: 133 or SEQ ID NO: 137-SEQ ID NO: 147. A delivery construct can comprise a carrier comprising an amino acid sequence having at least 90% sequence identity to any one or more of the amino acid sequences set forth in SEQ ID NO: 1-SEQ ID NO: 133 or SEQ ID NO: 137-SEQ ID NO: 147. A delivery construct can comprise a carrier comprising an amino acid sequence having at least 95% sequence identity to any one or more of the amino acid sequences set forth in SEQ ID NO: 1-SEQ ID NO: 133 or SEQ ID NO: 137-SEQ ID NO: 147. A delivery construct can comprise a carrier comprising an amino acid sequence having at least 99% sequence identity to any one or more of the amino acid sequences set forth in SEQ ID NO: 1-SEQ ID NO: 133 or SEQ ID NO: 137-SEQ ID NO: 147. The carrier can be derived from a Cholix domain I and can comprise an amino acid sequence having at least 80% sequence identity to any one or more of the amino acid sequences set forth in SEQ ID NO: 4-SEQ ID NO: 125 and/or SEQ ID NO: 148-SEQ ID NO: 152. The carrier can be derived from a Cholix domain I and can comprise an amino acid sequence having at least 90% sequence identity to any one or more of the amino acid sequences set forth in SEQ ID NO: 4-SEQ ID NO: 125 and/or SEQ ID NO: 148-SEQ ID NO: 152. The carrier can be derived from a Cholix domain I and can comprise an amino acid sequence having at least 95% sequence identity to any one or more of the amino acid sequences set forth in SEQ ID NO: 4-SEQ ID NO: 125 and/or SEQ ID NO: 148-SEQ ID NO: 152. The carrier can be derived from a Cholix domain I and can comprise an amino acid sequence having at least 99% sequence identity to any one or more of the amino acid sequences set forth in SEQ ID NO: 4-SEQ ID NO: 125 and/or SEQ ID NO: 148-SEQ ID NO: 152. Any one of these carriers can be combined with any heterologous cargo described and disclosed herein, e.g., those having at least 80% sequence identity to an amino acid sequence set forth in any one of SEQ ID NO: 214-SEQ ID NO: 220. Any one of these carriers can be combined with any heterologous cargo described and disclosed herein, e.g., those having at least 90% sequence identity to an amino acid sequence set forth in any one of SEQ ID NO: 214-SEQ ID NO: 220. Any one of these carriers can be combined with any heterologous cargo described and disclosed herein, e.g., those having at least 95% sequence identity to an amino acid sequence set forth in any one of SEQ ID NO: 214-SEQ ID NO: 220. Any one of these carriers can be combined with any heterologous cargo described and disclosed herein, e.g., those having at least 99% sequence identity to an amino acid sequence set forth in any one of SEQ ID NO: 214-SEQ ID NO: 220. A delivery construct described herein can comprise an amino acid sequence having at least 80% sequence identity to an amino acid sequence set forth in any one of SEQ ID NO: 153-SEQ ID NO: 165. A delivery construct described herein can comprise an amino acid sequence having at least 90% sequence identity to an amino acid sequence set forth in any one of SEQ ID NO: 153-SEQ ID NO: 165. A delivery construct described herein can comprise an amino acid sequence having at least 95% sequence identity to an amino acid sequence set forth in any one of SEQ ID NO: 153-SEQ ID NO: 165. A delivery construct described herein can comprise an amino acid sequence having at least 99% sequence identity to an amino acid sequence set forth in any one of SEQ ID NO: 153-SEQ ID NO: 165. A construct can be capable of endocytosis (e.g., apical endocytosis). A construct can be capable of apical-to-basal transcytosis.

The present disclosure provides isolated delivery constructs that can be capable of binding a receptor on the luminal surface of intestinal epithelial cells with sufficient affinity to allow endocytosis; wherein the domain is a polypeptide comprising an amino acid sequence wherein one or more amino acid residues of one bacterial toxin domain I polypeptide is replaced by one or more amino acid residues of a second bacterial toxin (e.g., an exotoxin) domain I polypeptide. The domain I of a first exotoxin can comprise a polypeptide which comprises an amino acid sequence wherein one or more amino acid residues of SEQ ID NO: 4 can be replaced by one or more amino acid residues of a second bacterial toxin (e.g., an exotoxin) receptor binding domain polypeptide. The receptor binding domain can be a polypeptide which comprises an amino acid sequence wherein one or more amino acid residues of SEQ ID NO: 4 is replaced by one or more amino acid residues of SEQ ID NO: 137. The receptor binding domain can be a polypeptide which comprises an amino acid sequence wherein one or more amino acid residues of SEQ ID NO: 137 is replaced by one or more amino acid residues a second bacterial toxin receptor binding domain polypeptide. The receptor binding domain can be a polypeptide which comprises an amino acid sequence wherein one or more amino acid residues of SEQ ID NO: 136 is replaced by one or more amino acid residues of SEQ ID NO: 4. A chimeric carrier can comprise a biologically active cargo coupled to the polypeptide to produce a chimeric construct; wherein the chimeric construct is capable of delivering the biologically active cargo.

The present disclosure provides a chimeric construct comprising a bacterial toxin-derived delivery construct; and a biologically active cargo; wherein the delivery construct is capable of delivering the biologically active cargo into an epithelial cell; and wherein the delivery construct does not comprise a bacterial toxin-derived translocation domain or a bacterial toxin-derived catalytic (cytotoxic) domain. The present disclosure provides a chimeric construct consisting of a receptor binding domain of a bacterial toxin; and a biologically active cargo; wherein the delivery construct is capable of delivering the biologically active cargo into an epithelial cell, and wherein the chimeric construct is capable of binding a receptor on the luminal surface of intestinal epithelial cells.

The present disclosure further provides polynucleotides that encode the non-naturally occurring delivery constructs and/or delivery constructs of the present disclosure; vectors comprising polynucleotides encoding the non-naturally occurring delivery constructs and/or delivery constructs of the present disclosure; optionally, operably-linked to control sequences recognized by a host cell transformed with the vector; host cells comprising vectors comprising polynucleotides encoding the non-naturally occurring delivery constructs and/or delivery constructs of the present disclosure; a process for producing the non-naturally occurring delivery constructs and/or delivery constructs of the present disclosure comprising culturing host cells comprising vectors comprising polynucleotides encoding the non-naturally occurring delivery constructs and/or delivery constructs of the present disclosure such that the polynucleotide is expressed; and, optionally, recovering the non-naturally occurring delivery constructs and/or delivery constructs from host cell culture medium.

Disclosed herein is a use of a non-naturally occurring delivery construct of the present disclosure for the preparation of a medicament for treatment, prophylaxis and/or prevention of an inflammatory disease in a subject in need thereof.

Disclosed herein is a use of a non-naturally occurring delivery construct of the present disclosure for the preparation of a medicament for treatment, prophylaxis and/or prevention of an autoimmune disease in a subject in need thereof.

Disclosed herein is a use of a non-naturally occurring delivery construct of the present disclosure for the preparation of a medicament for treatment, prophylaxis and/or prevention of a cancer in a subject in need thereof.

Disclosed herein is a use of a non-naturally occurring delivery construct of the present disclosure for the preparation of a medicament for treatment, prophylaxis and/or prevention of a metabolic disorder in a subject in need thereof.

Disclosed herein is a use of a non-naturally occurring delivery construct of the present disclosure for the preparation of a medicament for treatment, prophylaxis and/or prevention of a fatty liver disease in a subject in need thereof.

Disclosed herein is a use of a non-naturally occurring delivery construct of the present disclosure for the preparation of a medicament for treatment, prophylaxis and/or prevention of GH deficient growth disorder in a subject in need thereof.

BRIEF DESCRIPTION OF THE DRAWINGS

The novel features of the present disclosure are set forth with particularity in the appended claims. A better understanding of the features and advantages of the present disclosure will be obtained by reference to the following detailed description that sets forth illustrative aspects, in which the principles of the disclosure are utilized, and the accompanying drawings (also “Figure” and “FIG.” herein), of which:

FIG. 1 and FIG. 2 depict fluorescence microscopic detection of Constructs 7-12 (prepared as described in EXAMPLE 1 herein) observed 20 min after intra-luminal injection using a rat intra-luminal injection model. FIG. 1 depicts (top to bottom) localization of Constructs 12, 11 and 10. FIG. 2 depicts (top to bottom) Constructs 9, 8 and 7. Left to right: fluorescence image, dark field illumination, composite of fluorescence image and dark field illumination (white arrow #1 highlights the apical surface, and white arrow #2 highlights the basal surface).

FIG. 1A shows localization (fluorescence image) of construct 12 observed 20 min after intra-luminal injection using a rat intra-luminal injection model.

FIG. 1B shows localization (white light image) of construct 12 observed 20 min after intra-luminal injection using a rat intra-luminal injection model.

FIG. 1C shows localization (merge image, with DAPI) of construct 12 observed 20 min after intra-luminal injection using a rat intra-luminal injection model.

FIG. 1D shows localization (fluorescence image) of construct 11 observed 20 min after intra-luminal injection using a rat intra-luminal injection model.

FIG. 1E shows localization (white light image) of construct 11 observed 20 min after intra-luminal injection using a rat intra-luminal injection model.

FIG. 1F shows localization (merge image, with DAPI) of construct 11 observed 20 min after intra-luminal injection using a rat intra-luminal injection model.

FIG. 1G shows localization (fluorescence image) of construct 10 observed 20 min after intra-luminal injection using a rat intra-luminal injection model.

FIG. 111 shows localization (white light image) of construct 10 observed 20 min after intra-luminal injection using a rat intra-luminal injection model.

FIG. 1I shows localization (merge image, with DAPI) of construct 10 observed 20 min after intra-luminal injection using a rat intra-luminal injection model.

FIG. 2A shows localization (fluorescence image) of construct 9 observed 20 min after intra-luminal injection using a rat intra-luminal injection model.

FIG. 2B shows localization (white light image) of construct 9 observed 20 min after intra-luminal injection using a rat intra-luminal injection model.

FIG. 2C shows localization (merge image, with DAPI) of construct 9 observed 20 min after intra-luminal injection using a rat intra-luminal injection model.

FIG. 2D shows localization (fluorescence image) of construct 8 observed 20 min after intra-luminal injection using a rat intra-luminal injection model.

FIG. 2E shows localization (white light image) of construct 8 observed 20 min after intra-luminal injection using a rat intra-luminal injection model.

FIG. 2F shows localization (merge image, with DAPI) of construct 8 observed 20 min after intra-luminal injection using a rat intra-luminal injection model.

FIG. 2G shows localization (fluorescence image) of construct 7 observed 20 min after intra-luminal injection using a rat intra-luminal injection model.

FIG. 2H shows localization (white light image) of construct 7 observed 20 min after intra-luminal injection using a rat intra-luminal injection model.

FIG. 2I shows localization (merge image, with DAPI) of construct 7 observed 20 min after intra-luminal injection using a rat intra-luminal injection model.

FIG. 3 depicts fluorescence microscopic detection of Construct 6 (prepared as described in EXAMPLE 1 herein) observed 20 min after intra-luminal injection using a rat intra-luminal injection model. Left to right: fluorescence image, dark field illumination, composite of fluorescence image and dark field illumination (white arrow #1 highlights the apical surface, and white arrow #2 highlights the basal surface).

FIG. 3A depicts fluorescence microscopic detection of Construct 6 (anti-Cho, 1/500).

FIG. 3B depicts dark field illumination detection of Construct 6 (anti-Cho, 1/500).

FIG. 3C depicts a composite of fluorescence image and dark field illumination detection of Construct 6 (anti-Cho, 1/500).

FIG. 3D depicts fluorescence microscopic detection of Construct 6 (anti-RPF, 1/50).

FIG. 3E depicts dark field illumination detection of Construct 6 (anti-RPF, 1/50).

FIG. 3F depicts a composite of fluorescence image and dark field illumination detection of Construct 6 (anti-RPF, 1/50).

FIG. 4 and FIG. 5 depict fluorescence microscopic detection of Construct 13 (SEQ ID NO: 146, prepared as described in EXAMPLE 5 herein) observed after 1 min (FIG. 4) and 20 min (FIG. 5) after intra-luminal injection using a rat intra-luminal injection model.

Figure 4A:
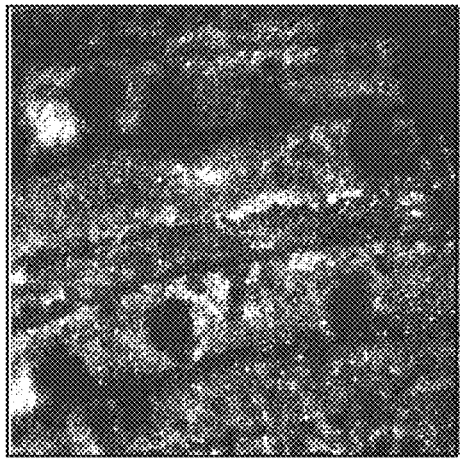

FIG. 4A shows fluorescence microscopic detection of Construct 13 after 1 min.

Figure 4B:
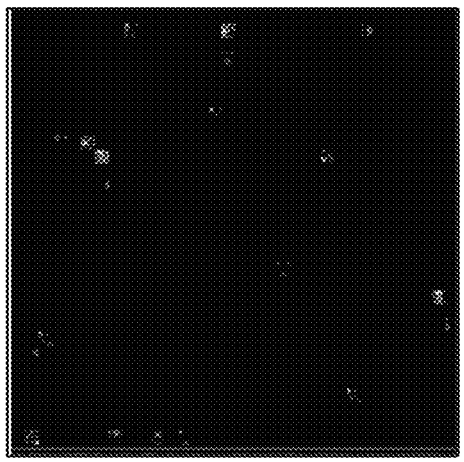

FIG. 4B shows fluorescence microscopic detection of Construct 13 after 1 min.

Figure 4C:
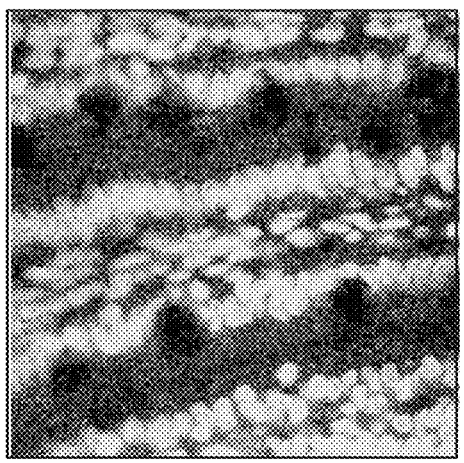

FIG. 4C shows fluorescence microscopic detection of Construct 13 after 1 min.

Figure 4D:
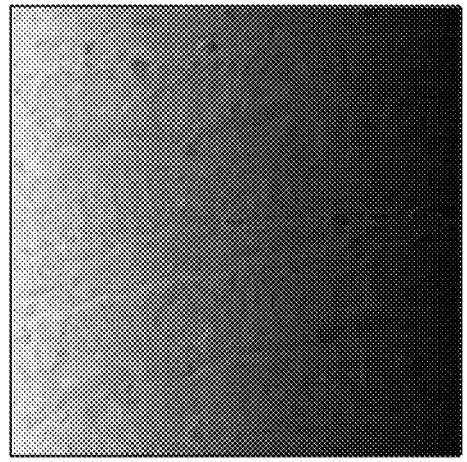

FIG. 4D shows fluorescence microscopic detection of Construct 13 after 1 min.

Figure 4E:
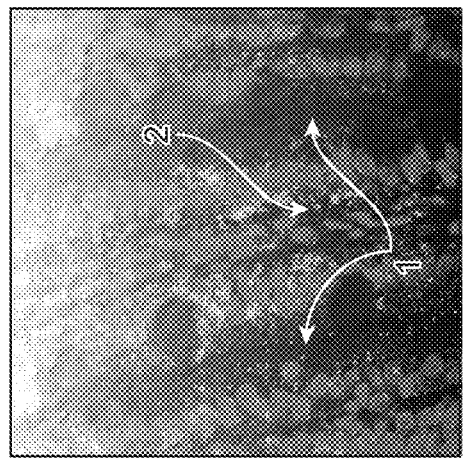

FIG. 4E shows fluorescence microscopic detection of Construct 13 after 1 min (white arrow #1 highlights the apical surface, and white arrow #2 highlights the basal surface).

Figure 5C:
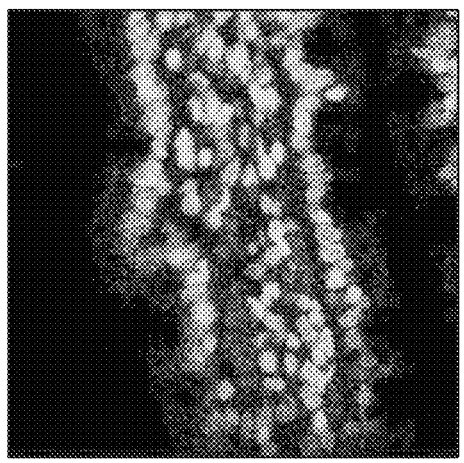
Figure 5B:
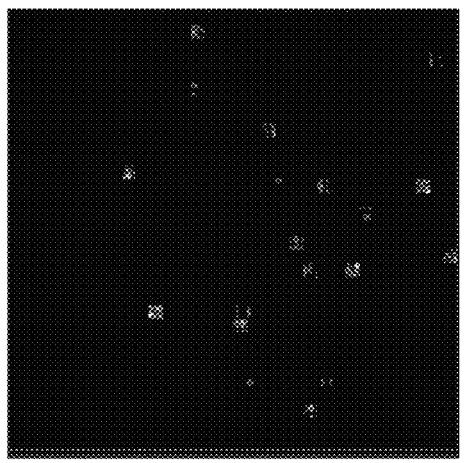
Figure 5A:
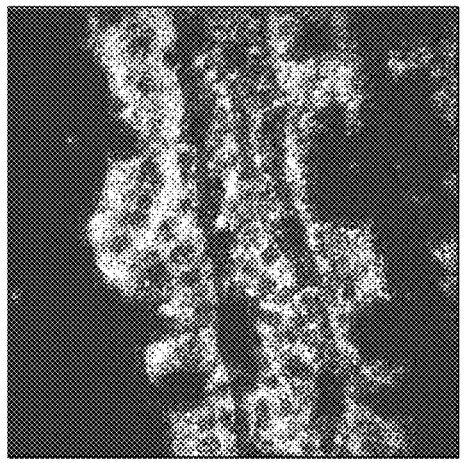

FIG. 5A shows fluorescence microscopic detection of Construct 13 after 20 min.

FIG. 5B shows fluorescence microscopic detection of Construct 13 after 20 min.

FIG. 5C shows fluorescence microscopic detection of Construct 13 after 20 min.

Figure 5E:
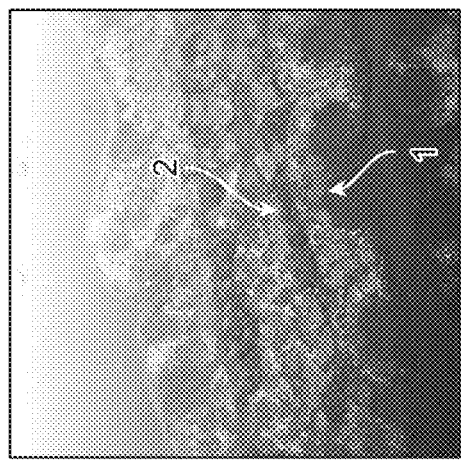
Figure 5D:
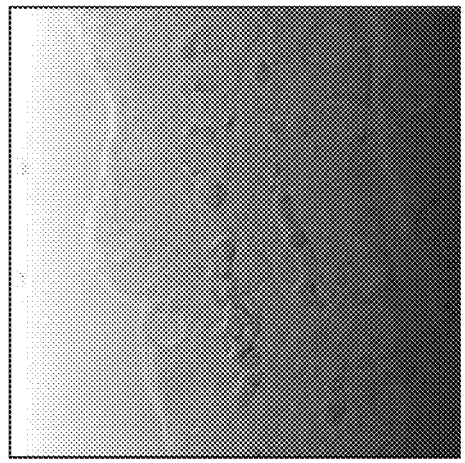

FIG. 5D shows fluorescence microscopic detection of Construct 13 after 20 min.

FIG. 5E shows fluorescence microscopic detection of Construct 13 after 20 min (white arrow #1 highlights the apical surface, and white arrow #2 highlights the basal surface).

FIG. 6 and FIG. 7 depict fluorescence microscopic detection of Construct 14 (SEQ ID NO: 147, prepared as described in EXAMPLE 5 herein) observed after 1 min (FIG. 6) and 20 min (FIG. 7) after intra-luminal injection using a rat intra-luminal injection model (white arrow #1 highlights the apical surface, and white arrow #2 highlights the basal surface).

Figure 6C:
Figure 6B:
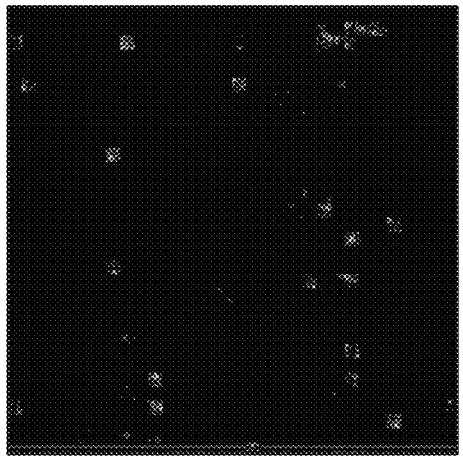
Figure 6A:

FIG. 6A shows fluorescence microscopic detection of Construct 14 after 1 min.

FIG. 6B shows fluorescence microscopic detection of Construct 14 after 1 min.

FIG. 6C shows fluorescence microscopic detection of Construct 14 after 1 min.

Figure 6E:
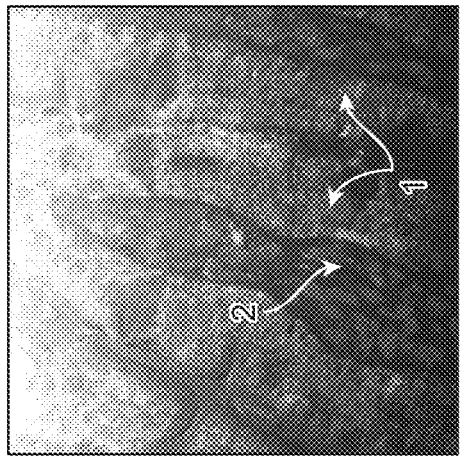
Figure 6D:
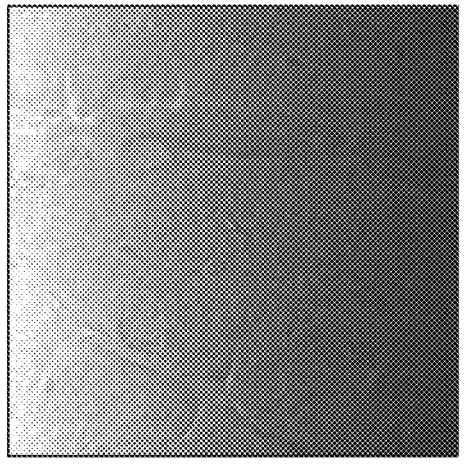

FIG. 6D shows fluorescence microscopic detection of Construct 14 after 1 min.

FIG. 6E shows fluorescence microscopic detection of Construct 14 after 1 min (white arrow #1 highlights the apical surface, and white arrow #2 highlights the basal surface).

Figure 7C:
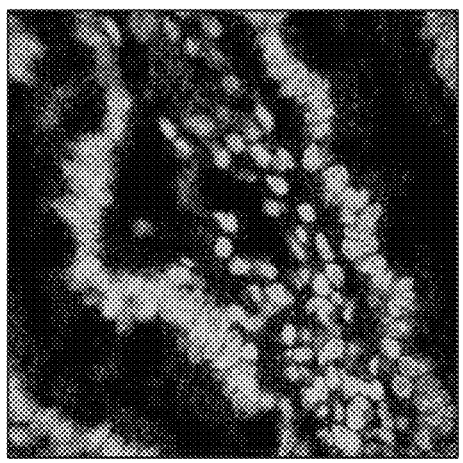
Figure 7B:
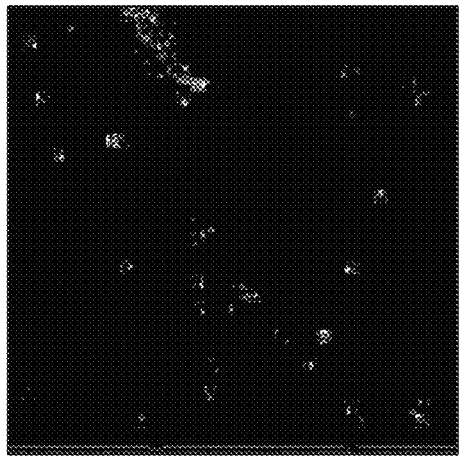
Figure 7E:
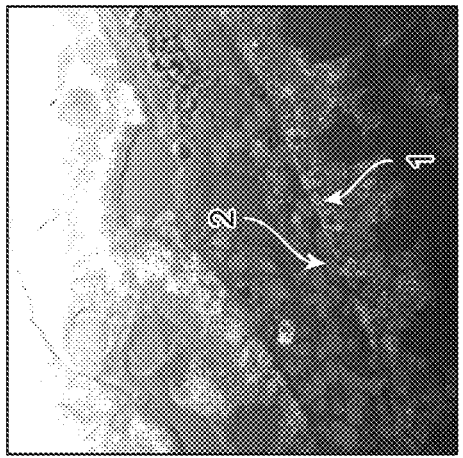
Figure 7A:
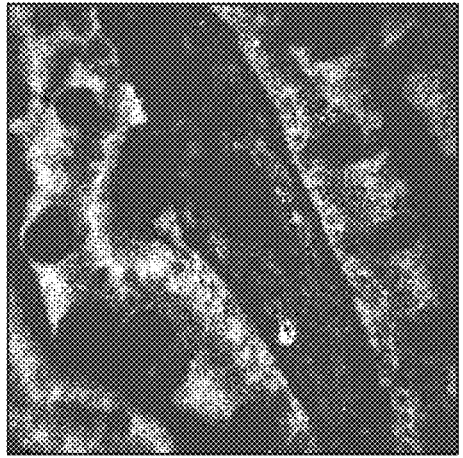

FIG. 7A shows fluorescence microscopic detection of Construct 14 after 20 min.

FIG. 7B shows fluorescence microscopic detection of Construct 14 after 20 min.

FIG. 7C shows fluorescence microscopic detection of Construct 14 after 20 min.

Figure 7D:
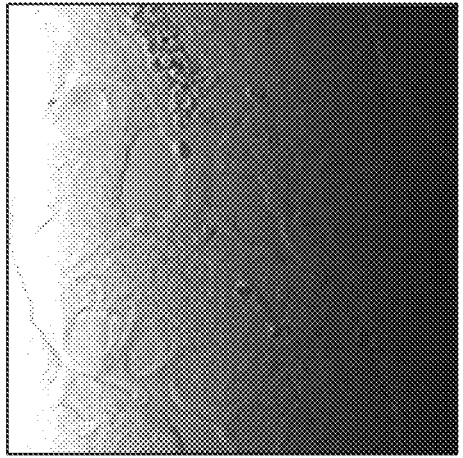

FIG. 7D shows fluorescence microscopic detection of Construct 14 after 20 min.

FIG. 7E shows fluorescence microscopic detection of Construct 14 after 20 min (white arrow #1 highlights the apical surface, and white arrow #2 highlights the basal surface).

Figures 8A, 8B, 8C:
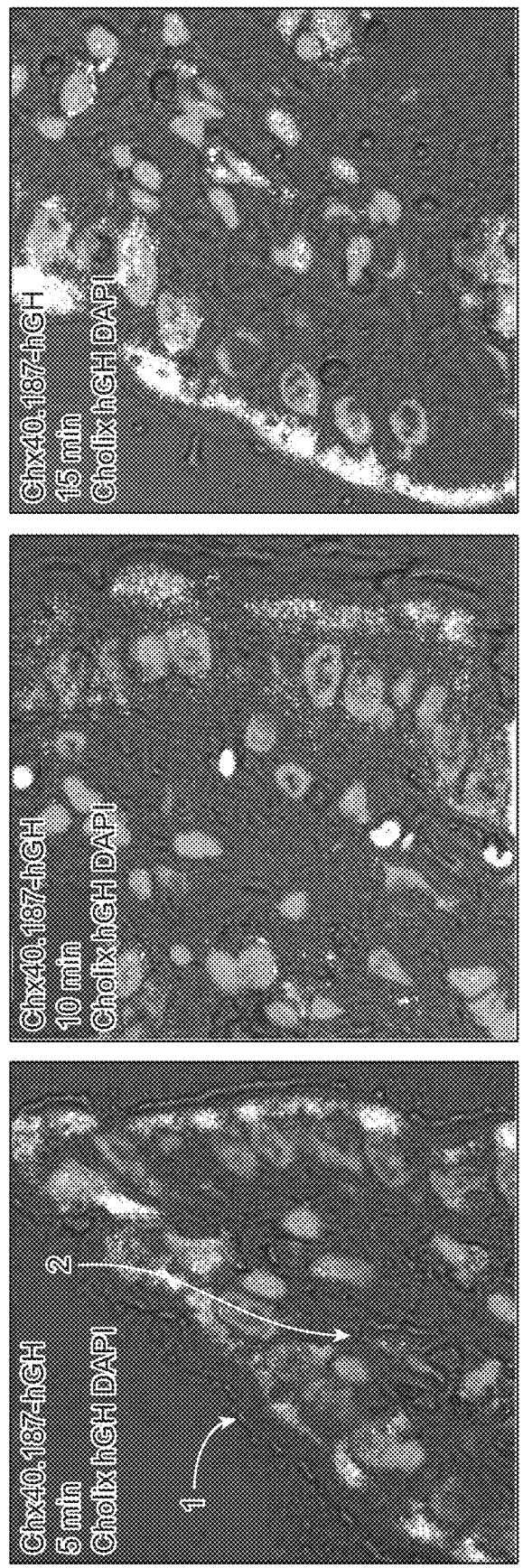

FIG. 8A depicts fluorescence microscopic detection of the construct comprising an amino acid sequence set forth in SEQ ID NO: 165 (M+Cholix$^{39-186}$-(spacer with SEQ ID NO: 210)-HGH) observed 5 min after intra-luminal injection using a rat intra-luminal injection model (white arrow #1 highlights the apical surface, and white arrow #2 highlights the basal surface).

FIG. 8B depicts fluorescence microscopic detection of the construct comprising an amino acid sequence set forth in SEQ ID NO: 165 (M+Cholix$^{39-186}$-(spacer with SEQ ID NO: 210)-HGH) observed 10 min after intra-luminal injection using a rat intra-luminal injection model.

FIG. 8C depicts fluorescence microscopic detection of the construct comprising an amino acid sequence set forth in SEQ ID NO: 165 (M+Cholix$^{39-186}$-(spacer with SEQ ID NO: 210)-HGH) observed 15 min after intra-luminal injection using a rat intra-luminal injection model.

Figure 9C:
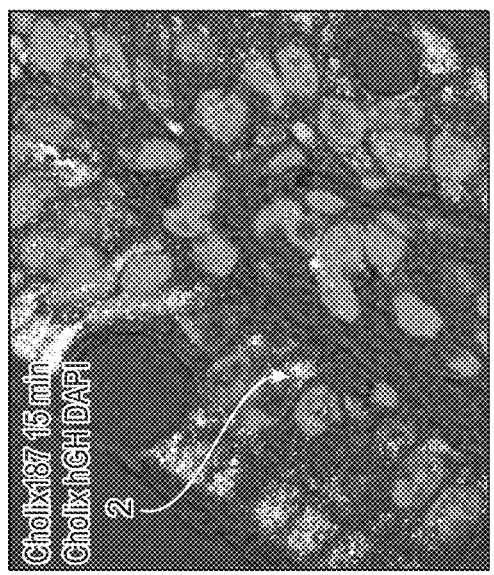
Figure 9B:
Figure 9A:
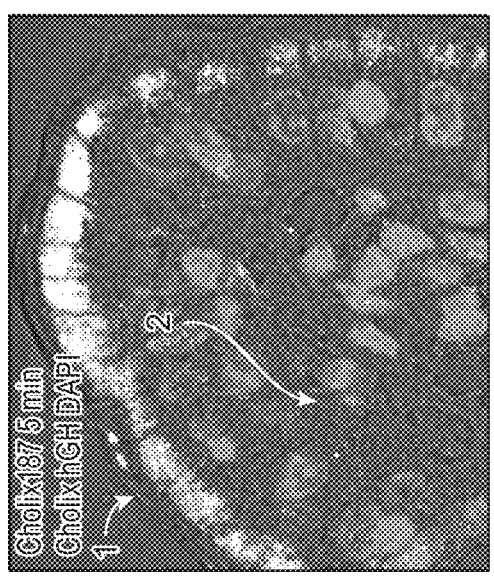

FIG. 9A depicts fluorescence microscopic detection of the construct comprising an amino acid sequence set forth in SEQ ID NO: 160 (Cholix$^{1-187}$-(spacer with SEQ ID NO: 210)-HGH) observed 5 min after intra-luminal injection using a rat intra-luminal injection model (white arrow #1 highlights the apical surface, and white arrow #2 highlights the basal surface).

FIG. 9B depicts fluorescence microscopic detection of the construct comprising an amino acid sequence set forth in SEQ ID NO: 160 (Cholix$^{1-187}$-(spacer with SEQ ID NO: 210)-HGH) observed 10 min after intra-luminal injection using a rat intra-luminal injection model.

FIG. 9C depicts fluorescence microscopic detection of the construct comprising an amino acid sequence set forth in SEQ ID NO: 160 (Cholix$^{1-187}$-(spacer with SEQ ID NO:

210)-HGH) observed 15 min after intra-luminal injection using a rat intra-luminal injection model (white arrow #2 highlights the basal surface).

Figure 10B:
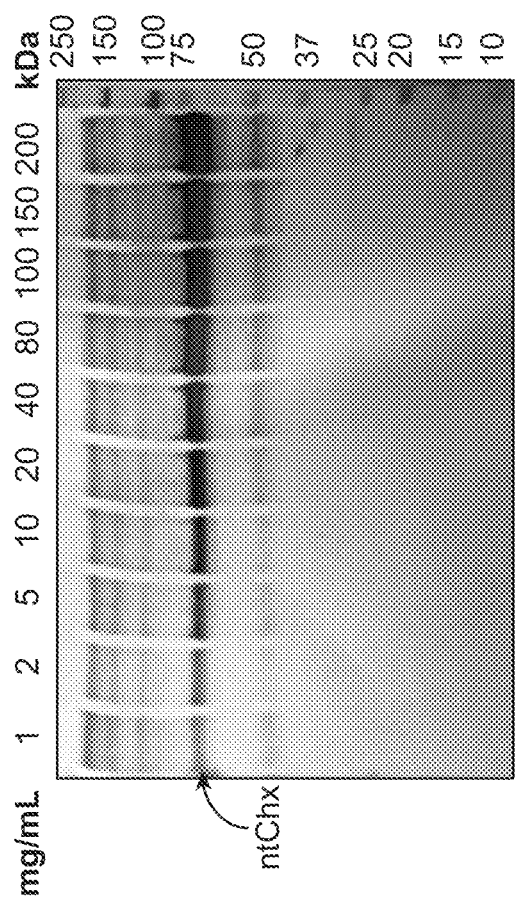
Figure 10A:
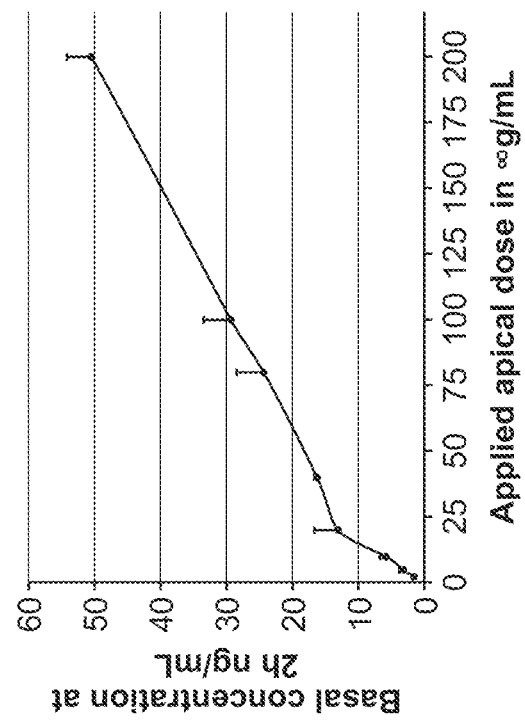

FIG. 10A shows Non-toxic Cholix (ntChx) transcytosis across human polarized intestinal epithelium in vitro. FIG. 10A depicts the amount of non-toxic Cholix (ntChx, SEQ ID NO: 3) detected in the basal compartment by ELISA at 2 h after an apical application of 2.5-200 mg/mL ntChx (N=2; mean±S.E., white arrow #1 highlights the apical surface, and white arrow #2 highlights the basal surface).

FIG. 10B depicts a Western blot analysis of basal compartment contents 2 h after an apical application of 2.5-200 mg/mL ntChx that were concentrated approximately 10-fold prior to analysis showing that the ntChx that transported was not significantly altered (e.g., chemically altered) during transport.

Figure 10C:
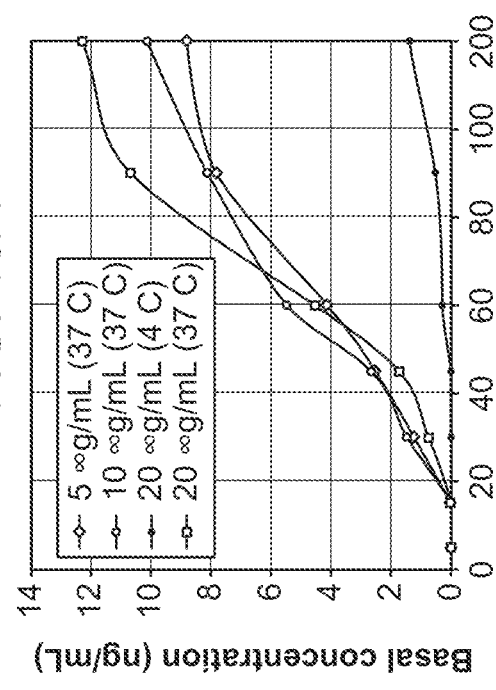

FIG. 10C depicts basal quantities of ntChx detected over a time course of 2 h by ELISA. The graph shows a delay of ~20-25 min in detectable quantities and comparable rates of transport for apical applications of 5-20 mg/mL at 37° C., and a significant reduction in transport rate at 4° C.

Figure 11:
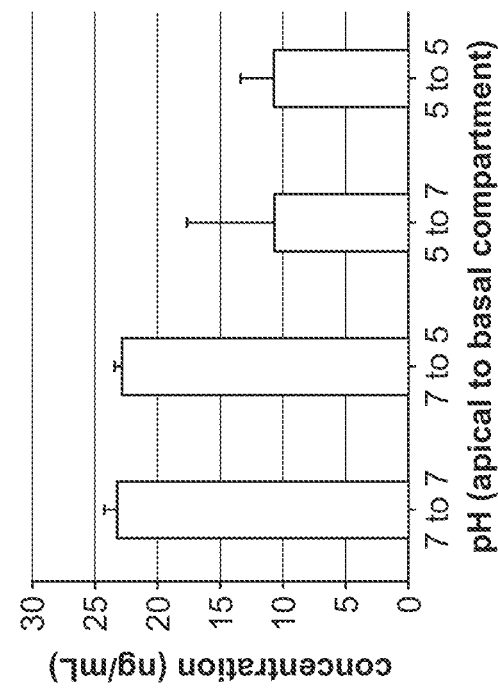

FIG. 11 shows that apical to basal transport of 5-20 mg/mL ntChx (SEQ ID NO: 3), as measured by ELISA, was more efficient with apical compartment at pH 7 compared to pH 5 (N=2; mean±S.E).

FIG. 12A depicts transcytosis of non-toxic Cholix (ntChx, SEQ ID NO: 3) in vivo after 1 minutes following intraluminal injection (ILI) into rat jejunum visualized by immunofluorescence microscopy. Open arrow=apical enterocyte domain; solid arrow=peri-nuclear region of cell; dashed line=epithelial cell-basement membrane demarcation; GC=goblet cell.

FIG. 12B depicts transcytosis of non-toxic Cholix (ntChx, SEQ ID NO: 3) in vivo after 5 minutes following ILI into rat jejunum visualized by immunofluorescence microscopy. Open arrow=apical enterocyte domain; solid arrow=peri-nuclear region of cell; dashed line=epithelial cell-basement membrane demarcation; GC=goblet cell.

FIG. 12C depicts transcytosis of non-toxic Cholix (ntChx, SEQ ID NO: 3) in vivo after 15 minutes following ILI into rat jejunum visualized by immunofluorescence microscopy. Co-localization with clathrin shows the villus tip area. Open arrow=apical enterocyte domain; solid arrow=peri-nuclear region of cell; dashed line=epithelial cell-basement membrane demarcation; GC=goblet cell.

Figure 13C:
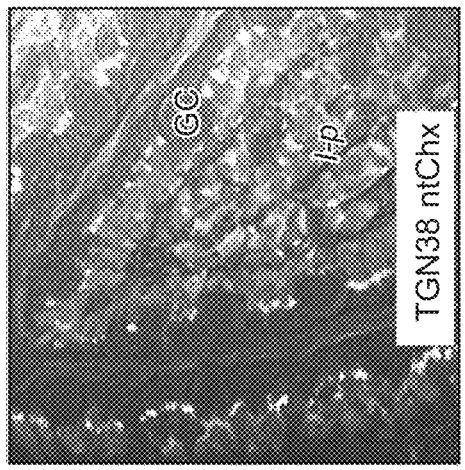
Figure 13F:
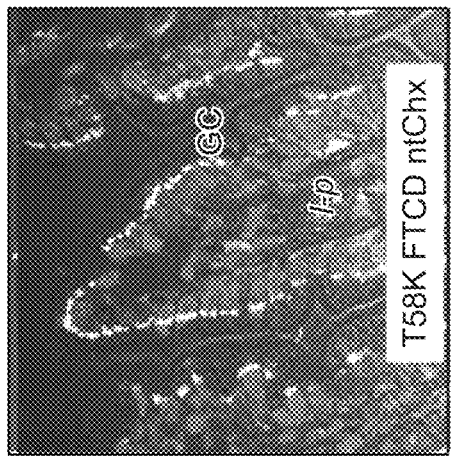
Figure 13B:
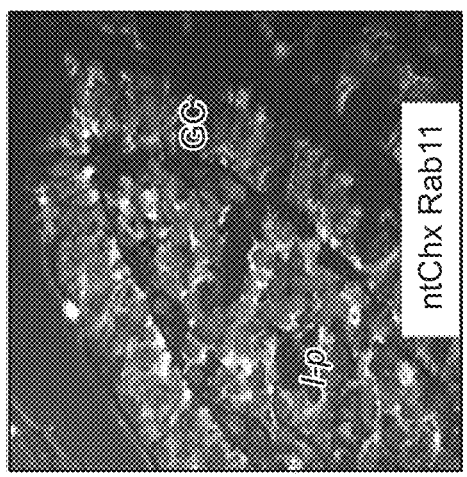
Figure 13E:
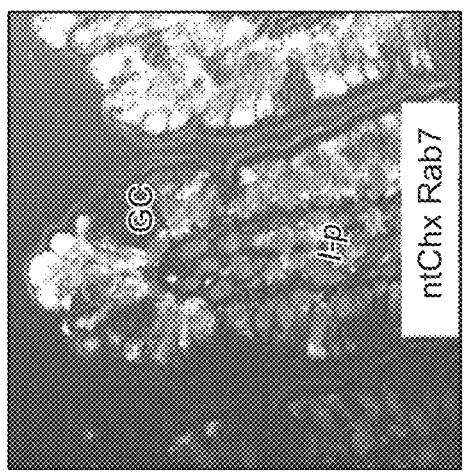
Figure 13A:
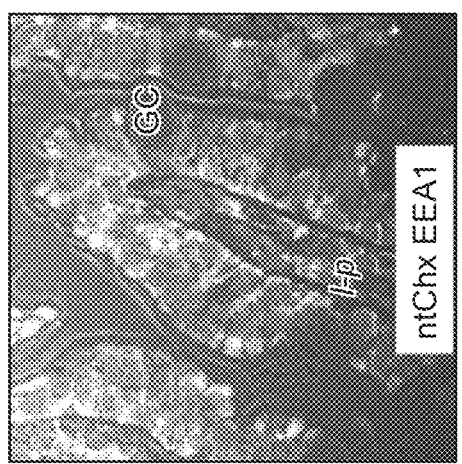

FIG. 13A shows in vivo ntChx transcytosis at 15 min after ILI of ntChx (SEQ ID NO: 3) into rat jejunum with simultaneous staining of early endosomal antigen 1 (EEA1) (white arrow #1 highlights the apical surface, and white arrow #2 highlights the basal surface). GC=goblet cell; l-p=*Lamina propria*.

FIG. 13B shows in vivo ntChx transcytosis at 15 min after ILI of ntChx (SEQ ID NO: 3) into rat jejunum with simultaneous staining of Ras-related protein Rab 11a (white arrow #1 highlights the apical surface, and white arrow #2 highlights the basal surface). GC=goblet cell; l-p=*Lamina propria*.

FIG. 13C shows in vivo ntChx transcytosis at 15 min after ILI of ntChx (SEQ ID NO: 3) into rat jejunum with simultaneous staining of trans-Golgi network (TGN)-38 protein.

Figure 13D:
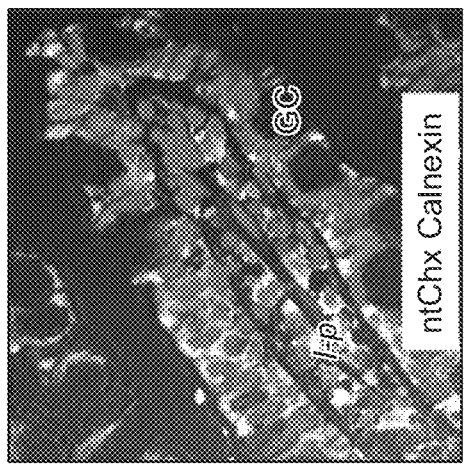

FIG. 13D shows in vivo ntChx transcytosis at 15 min after ILI of ntChx (SEQ ID NO: 3) into rat jejunum with simultaneous staining of calnexin (white arrow #1 highlights the apical surface, and white arrow #2 highlights the basal surface). GC=goblet cell; l-p=*Lamina propria*.

FIG. 13E shows in vivo ntChx transcytosis at 15 min after ILI of ntChx (SEQ ID NO: 3) into rat jejunum with simultaneous staining of Ras-related protein Rab 7 (white arrow #1 highlights the apical surface, and white arrow #2 highlights the basal surface). GC=goblet cell; l-p=*Lamina propria*.

FIG. 13F shows in vivo ntChx transcytosis at 15 min after ILI of ntChx (SEQ ID NO: 3) into rat jejunum with simultaneous staining of Golgi-associated 58 kDa formiminotransferase cyclodeaminase protein (FTCD). GC=goblet cell; l-p=*Lamina propria*.

FIG. 14A shows small amounts of RFP (negative control) reaching cells within the *Lamina propria* (l-p) with no detectable RFP in the villus epithelium (solid arrows point to apical surface of epithelium) at 30 min post ILI. A polyclonal antibody to RFP demonstrates small amounts of RFP can reach cells within the *Lamina propria* (l-p) with no detectable RFP in the villus epithelium; (solid arrows point to apical surface of epithelium) at 30 min post ILI. Solid arrow (#1)=luminal (apical) membrane; white arrow #2=basal membrane; GC=goblet cell; l-p=*Lamina propria*.

FIG. 14B shows that a construct comprising an amino acid sequence set forth in SEQ ID NO: 157 comprising full-length of non-toxic Cholix (ntChx, SEQ ID NO: 3) genetically fused to or conjugated to red fluorescent protein (RFP, SEQ ID NO: 220) is capable of efficient apical-to-basal transcytosis. Solid arrow (#1)=luminal (apical) membrane; white arrow #2=basal membrane; GC=goblet cell; l-p=*Lamina propria*. Full-length of non-toxic Cholix (ntChx, SEQ ID NO: 3) was genetically conjoined to the red fluorescent protein (RFP, SEQ ID NO: 220).

FIG. 14C shows that Cholix domain I is sufficient for apical to basal transcytosis after intraluminal injection (ILI) into rat jejunum in vivo. FIG. 14C shows that a Cholix truncated at the termination of domain I (amino acid residue 265 of SEQ ID NO: 1, plus an N-terminal methionine residue resulting in SEQ ID NO: 5) and that is genetically fused to RFP (e.g., thus having an amino acid sequence set forth in SEQ ID NO: 156) is capable of efficient apical-to-basal transcytosis, suggesting that Cholix domain I may be sufficient for apical to basal transcytosis after intraluminal injection (ILI) into rat jejunum in vivo. Solid white arrows #1 indicate the apical epithelial surface, and white arrow #2 highlights the basal surface. Cholix domain I (SEQ ID NO: 5) was genetically conjoined to the red fluorescent protein (RFP, SEQ ID NO: 220).

FIG. 15 depicts apical-to-basal transport of human growth hormone (HGH, SEQ ID NO: 214) compared to chimeras of Cholix domain I and truncated elements of this domain (designated by amino acids) that were genetically conjoined to HGH. Western blotting for HGH qualitatively assessed the capacity of these proteins to undergo apical-to-basal transport across polarized monolayers of primary human small intestinal epithelial cells in vitro after 2 h. The amounts of apically-applied materials were equivalent on a molar basis for HGH content and basal collections were concentrated ~10-fold prior to analysis.

Figure 15A:
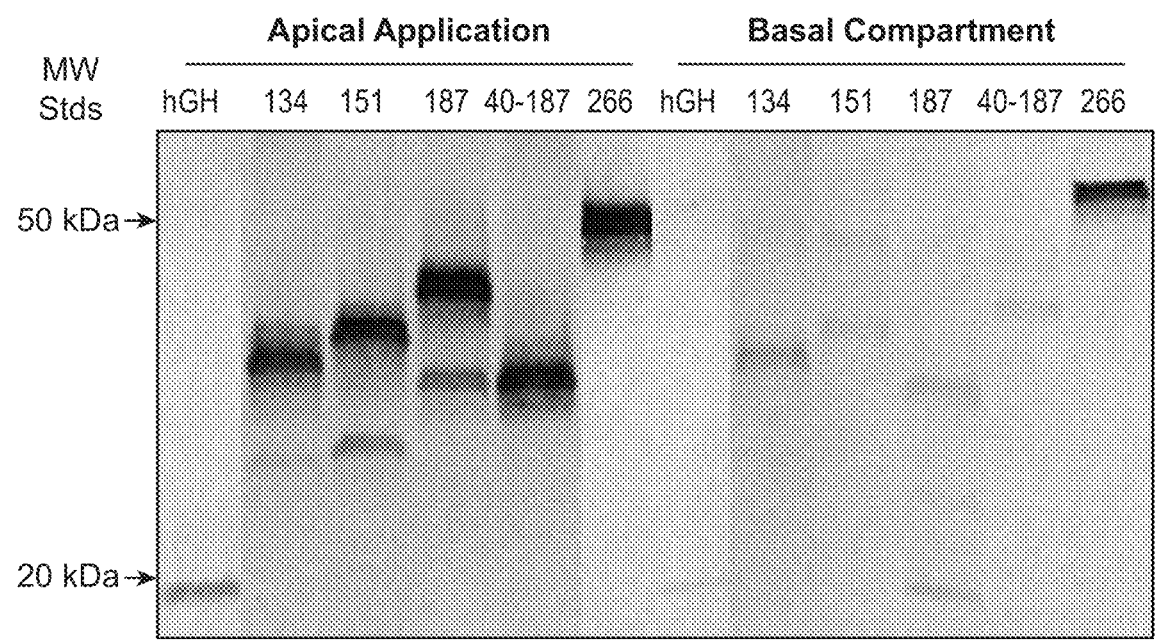

FIG. 15A shows that background apical-to-basal transport of HGH alone in this model was minimal compared to that observed for the delivery construct comprising the amino acid sequence set forth in SEQ ID NO: 164, comprising a Cholix domain I (SEQ ID NO: 5), a spacer (SEQ ID NO: 210), and HGH (SEQ ID NO: 214). Cholix domain I (SEQ ID NO: 5) truncations at positions 134, 151, 187 or at 40-187 of SEQ ID NO: 5 were incapable of facilitating apical-to-basal transport of conjoined HGH.

Figure 15B:
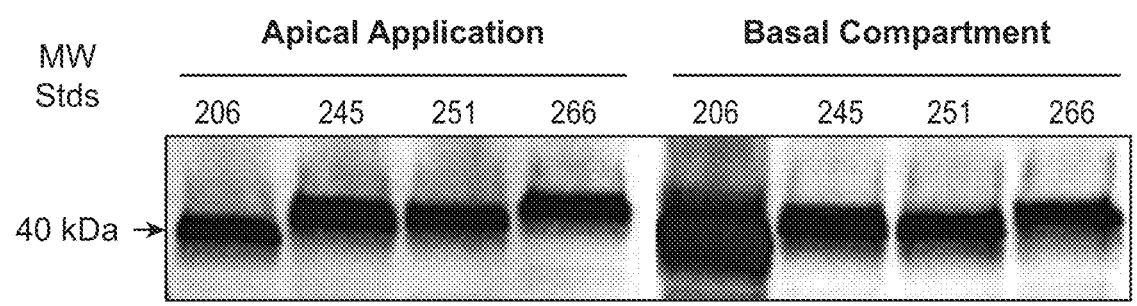

FIG. 15B shows that truncations of Cholix domain I (SEQ ID NO: 5) at positions 206, 245, or 251 demonstrated apical-to-basal transport of conjoined HGH. While truncations as positions 245 and 251 resulted in apical-to-basal transport comparable to that of the construct comprising the carrier with SEQ ID NO: 5, the chimera where Cholix domain I is truncated at position 206 showed a significant enhancement of apical-to-basal transport.

Figure 16A:
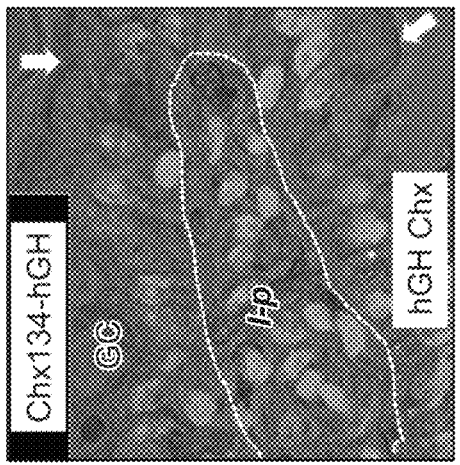

FIG. 16A shows the assessment of Cholix domain I truncation-human growth hormone (HGH) chimera transport across rat jejunum epithelia monolayers in vivo 15 min after intraluminal injection as demonstrated by immunofluorescence microscopy. FIG. 16A shows that the Cholix-HGH construct with SEQ ID NO: 211 (comprises Cholix$^{1-133}$+N-term. methionine) did not enter epithelial cells, suggesting that the functional peptide fragment having an amino acid sequence set forth in SEQ ID NO: 148 may be required for endocytosis.

Figure 16B:
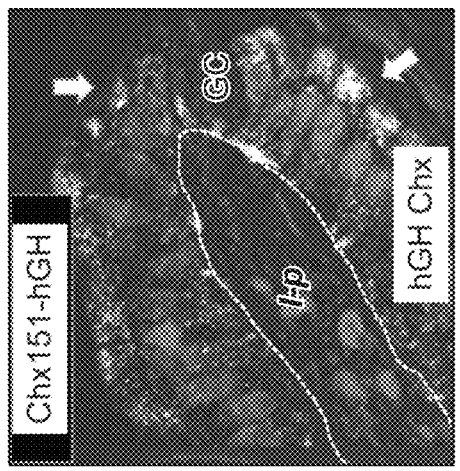

FIG. 16B shows the assessment of Cholix domain I truncation-human growth hormone (HGH) chimera transport across rat jejunum epithelia monolayers in vivo 15 min after intraluminal injection as demonstrated by immunofluorescence microscopy. FIG. 16B shows that the Cholix-HGH construct with SEQ ID NO: 212 (comprises Cholix$^{1-150}$+N-term. methionine) did enter epithelial cells (as opposed to protein with SEQ ID NO: 211) but remained in apical and basal vesicular pools and did not enter the *Lamina propria*, thus enabling delivery the interior of an epithelial cell (e.g., a compartment at the basal side of the epithelial cell).

Figure 16C:
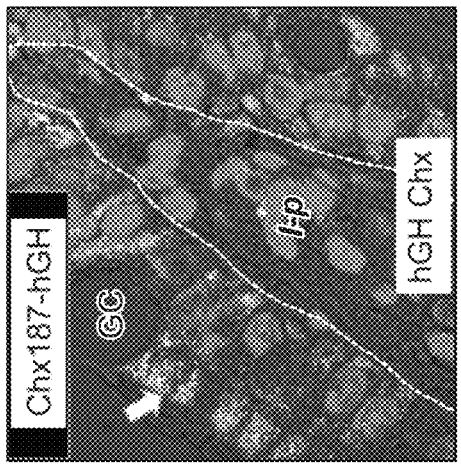

FIG. 16C shows the assessment of Cholix domain I truncation-human growth hormone (HGH) chimera transport across rat jejunum epithelia monolayers in vivo 15 min after intraluminal injection as demonstrated by immunofluorescence microscopy. FIG. 16C shows that the Cholix-HGH construct with SEQ ID NO: 213 (comprises Cholix$^{1-186}$+N-term. methionine) entered epithelial cells, reached apical and basal compartments and, significantly, also a supra-nuclear region of the cell, yet still remained inside the epithelial cell, suggesting that the functional peptide fragment having an amino acid sequence set forth in SEQ ID NO: 151 may allow access and delivery to supranuclear regions, yet does not allow release of the construct into a basolateral compartment (e.g., *Lamina propria*).

Figure 16D:
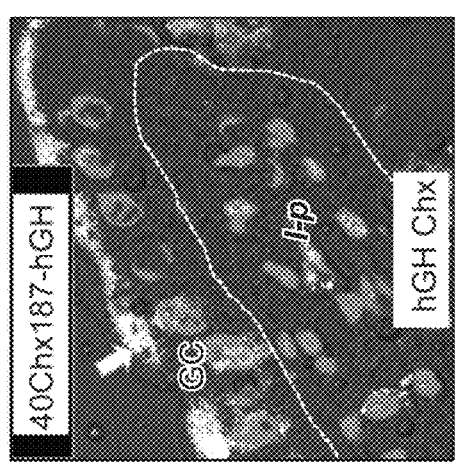

FIG. 16D shows the assessment of Cholix domain I truncation-human growth hormone (HGH) chimera transport across rat jejunum epithelia monolayers in vivo 15 min after intraluminal injection as demonstrated by immunofluorescence microscopy. FIG. 16D shows that the Cholix-HGH construct with SEQ ID NO: 218 (comprises Cholix$^{39-186}$+N-term. Methionine) entered epithelial cells but remained in the apical compartment and did not appear to reach the basal or supra-nuclear compartments.

Figure 16E:
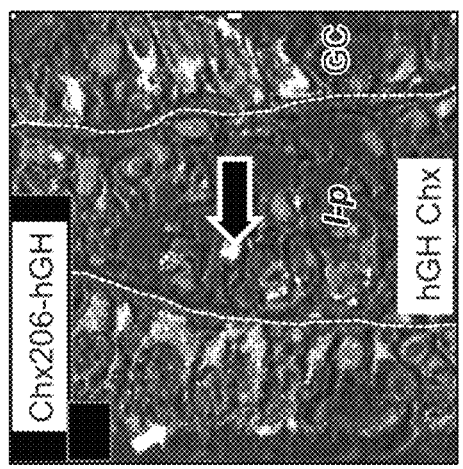

FIG. 16E shows the assessment of Cholix domain I truncation-human growth hormone (HGH) chimera transport across rat jejunum epithelia monolayers in vivo 15 min after intraluminal injection as demonstrated by immunofluorescence microscopy. FIG. 16E shows that the Cholix-HGH construct with SEQ ID NO: 161 (comprises Cholix$^{1-205}$+N-term. methionine) completed the transcytosis process as indicated by delivery of the chimera to cells within the *Lamina propria*, suggesting that the functional peptide fragment having an amino acid sequence set forth in SEQ ID NO: 152 (e.g., amino acid residues 187-206 of SEQ ID NO: 5) may allow release of the construct from the epithelium into a basolateral compartment (e.g., *Lamina propria*).

Figure 16F:
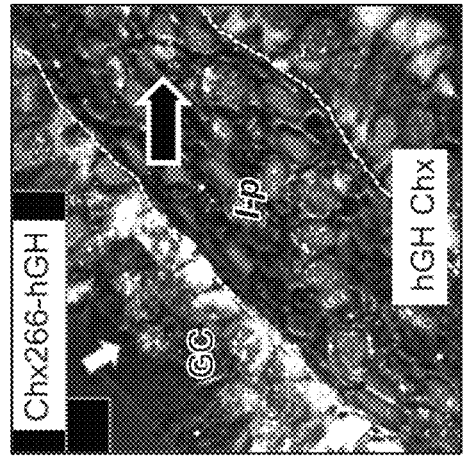

FIG. 16F shows the assessment of Cholix domain I truncation-human growth hormone (HGH) chimera transport across rat jejunum epithelia monolayers in vivo 15 min after intraluminal injection as demonstrated by immunofluorescence microscopy. FIG. 16F shows that the Cholix-HGH construct with SEQ ID NO: 164 (comprises Cholix$^{1-265}$+N-term. Methionine, SEQ ID NO: 5) completed the transcytosis process as indicated by delivery of the chimera to cells within the *Lamina propria* similar to the Cholix-HGH construct with SEQ ID NO: 164.

FIG. 17 shows that selected amino acid fragments of Cholix domain I achieve apical to basal transcytosis in vitro and in vivo. A polymer framework containing peptide sequences of amino acids from positions 1-39, 134-151, 151-178, and 178-206 of Cholix domain I with SEQ ID NO: 5 in various combinations were labeled with different forms of quantum dots (e.g., cadmium sulfide, lead sulfide, etc.).

Figure 17A:
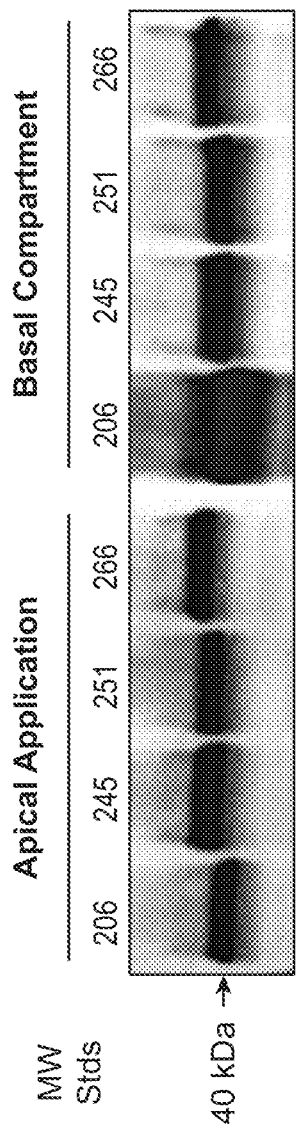

FIG. 17A shows transcytosis of various truncated Cholix (Chx) constructs across polarized intestinal epithelium in vitro after 2 h. The amount of transported material is reported as the florescence-fold increase relative to polymer-quantum dot preparation lacking any Chx peptides. (N=2; mean±S.E.).

Figure 17C:
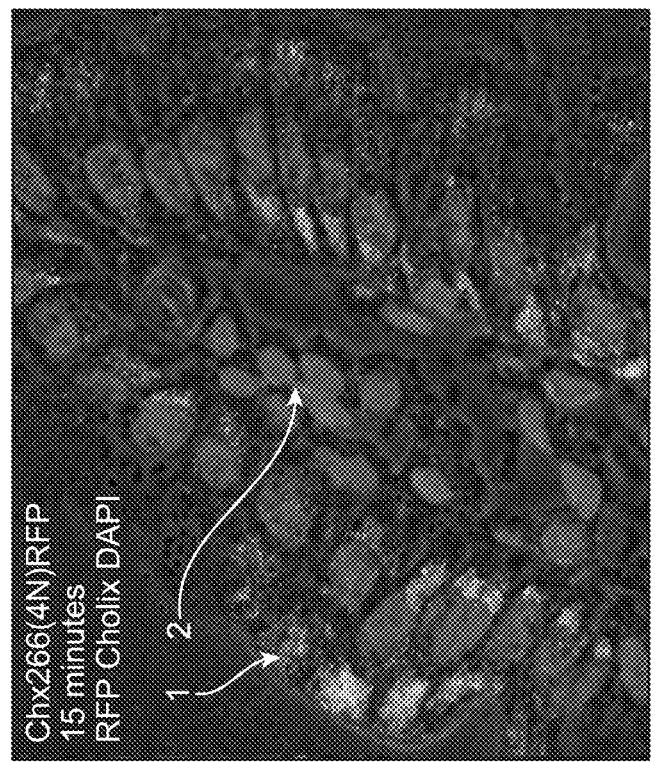
Figure 17B:
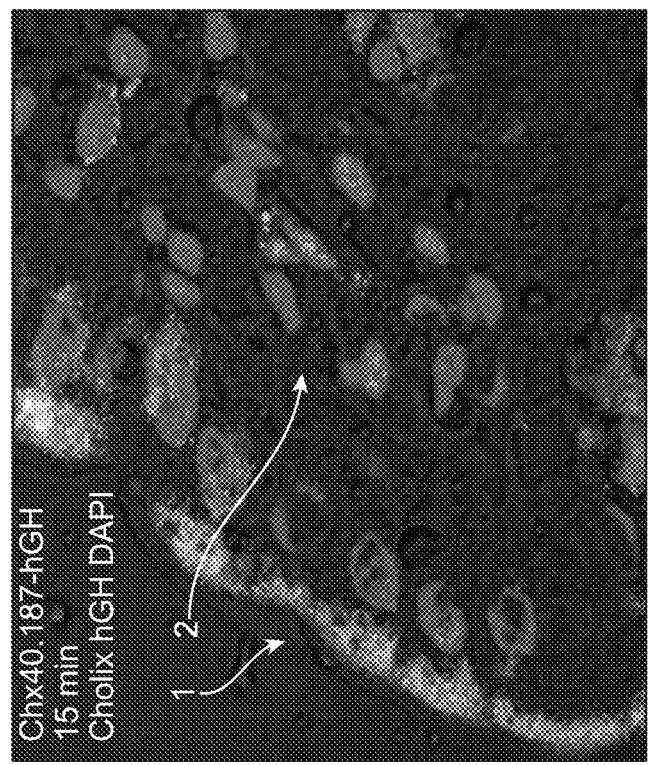

FIG. 17B shows in vivo transcytosis at 15 min of the Cholix$^{39-186}$-HGH construct (SEQ ID NO: 218) (white arrow #1 highlights the apical surface, and white arrow #2 highlights the basal surface).

FIG. 17C shows in vivo transcytosis at 15 min of the (SEQ ID NO: 5)-(4N)-RFP construct labeled with quantum dots (white arrow #1 highlights the apical surface, and white arrow #2 highlights the basal surface).

Figure 18:
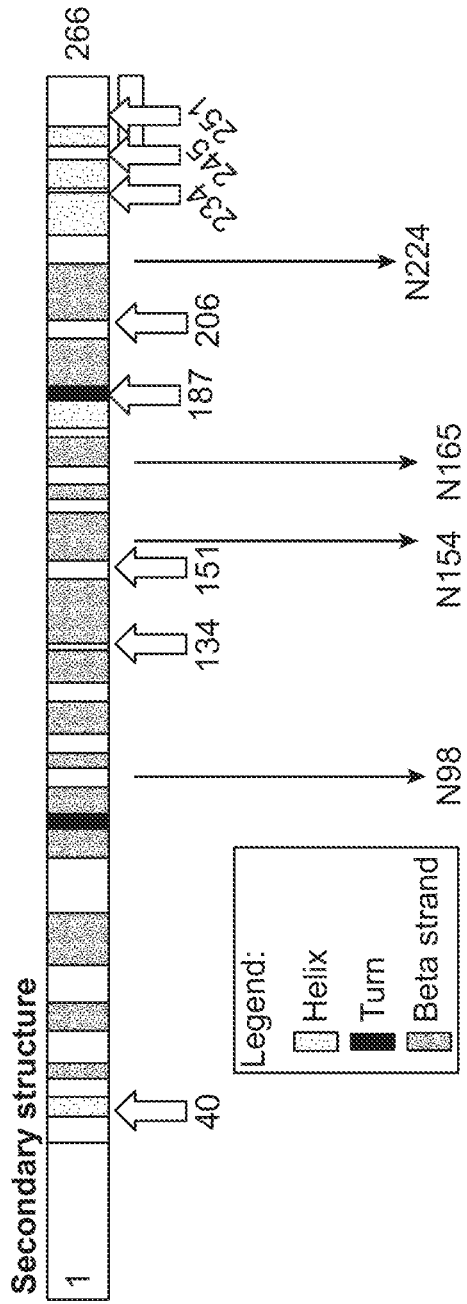

FIG. 18 shows the amino acid sequence set forth in SEQ ID NO: 221 of a Cholix domain 1 (incl. and N-terminal methionine) having a spacer with an amino acid sequence set forth in SEQ ID NO: 210 attached to its C-terminus. This spacer can be used to attach cargo moieties (e.g., therapeutic agents) to the Cholix carrier for transport across epithelial layers (e.g., the gut epithelium). The highlighted amino acid fragments can provide certain functionalities in relation to transcytosis across epithelial layers. For example, the fragment with the amino acid residues of positions 134-151 of the sequence set forth in SEQ ID NO: 5 can promote apical entry of Cholix constructs into epithelial cells. The highlighted fragment with amino acid residues 151-187 (e.g., of SEQ ID NO: 5) can promote early endosomal sorting. The highlighted fragment with amino acid residues 187-206 (e.g., of SEQ ID NO: 5) can promote complete transcytosis of a Chx construct as described herein.

Figure 19:
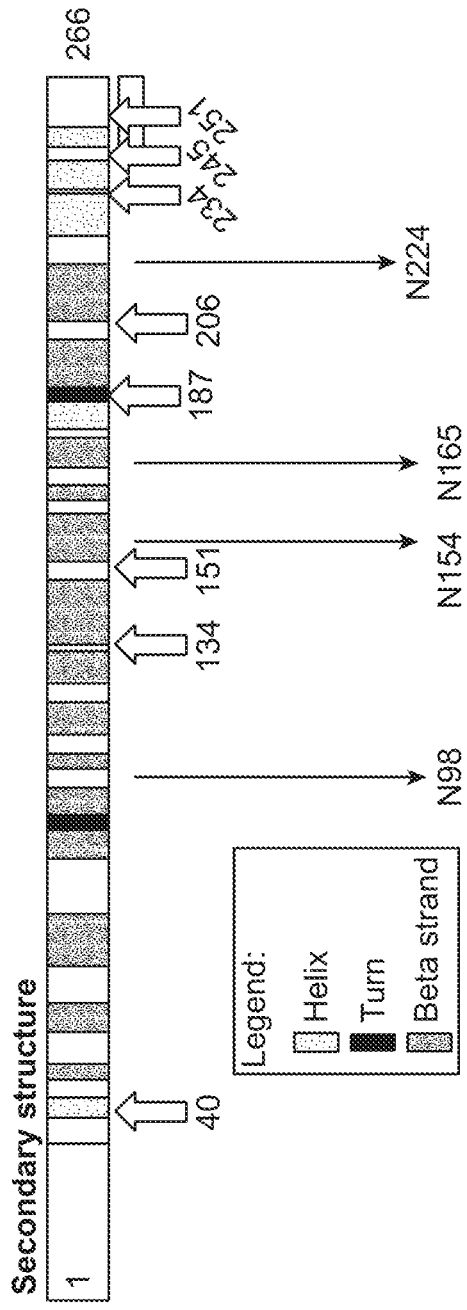

FIG. 19 shows potential glycosylation sites of the asparagine residues located at positions N98, N154, N165, and N224 of Cholix domain I having an amino acid sequence set forth in SEQ ID NO: 221.

FIG. 20 shows a general 3D structure of Cholix domain I (SEQ ID NO: 5) with highlighted functional fragments.

Figure 20C:
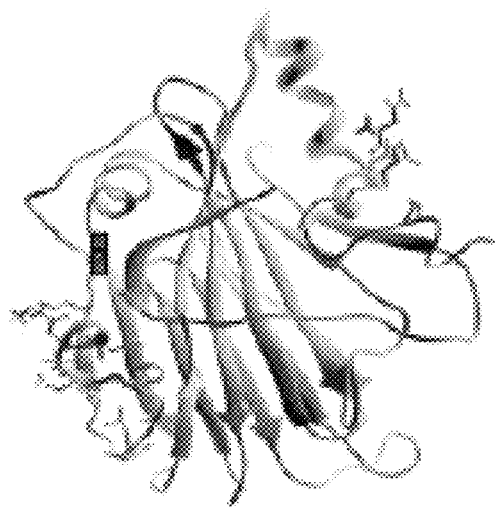
Figure 20B:
Figure 20A:
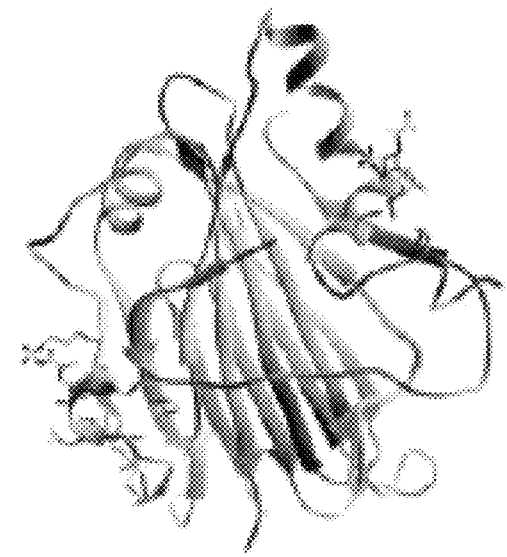

FIG. 20A shows a general 3D structure of Cholix domain I (SEQ ID NO: 5) with the highlighted functional fragment having an amino acid sequence of SEQ ID NO: 148 (residues 134-151 of SEQ ID NO: 5).

FIG. 20B shows a general 3D structure of Cholix domain I (SEQ ID NO: 5) with the highlighted functional fragment having an amino acid sequence of SEQ ID NO: 149 (e.g., residues 151-187 of SEQ ID NO: 5).

FIG. 20C shows a general 3D structure of Cholix domain I (SEQ ID NO: 5) with the highlighted functional fragment having an amino acid sequence of SEQ ID NO: 152 (e.g., residues 187-206 of SEQ ID NO: 5).

FIG. 21 illustrates a trafficking pathway analysis for the Cholix derived delivery construct having the amino acid sequence set forth in SEQ ID NO: 154 (the delivery construct is M+Cholix$^{386}$-GGGGSGGGGSGGGGS (SEQ ID NO: 210)-IL-10, from N- to C-terminus). The delivery construct comprising Cholix domain (SEQ ID NO: 5) and human growth hormone (HGH) as cargo could also be used to show similar results as shown for the construct comprising M+Cholix$^{386}$.

Figure 21A:
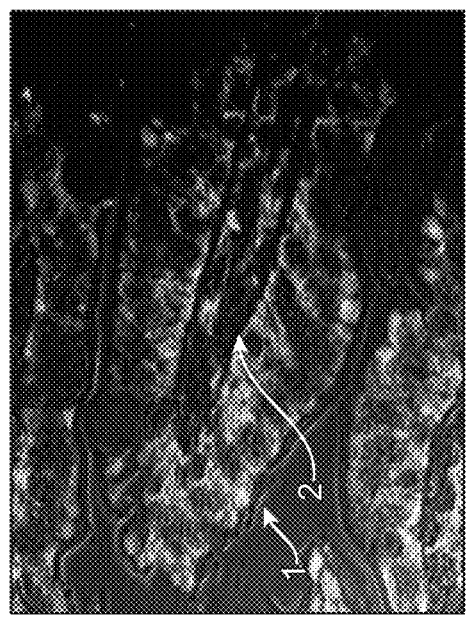

FIG. 21A shows that M+Cholix$^{386}$-IL-10 (SEQ ID NO: 154) delivery construct strongly co-localized with the EEA1 antigen in cellular locations consistent with trafficking at both the apical and basal domains of enterocytes, suggesting the presence of the Cholix derived delivery constructs in early endosome compartments (white arrow #1 highlights the apical surface, and white arrow #2 highlights the basal surface).

Figure 21B:
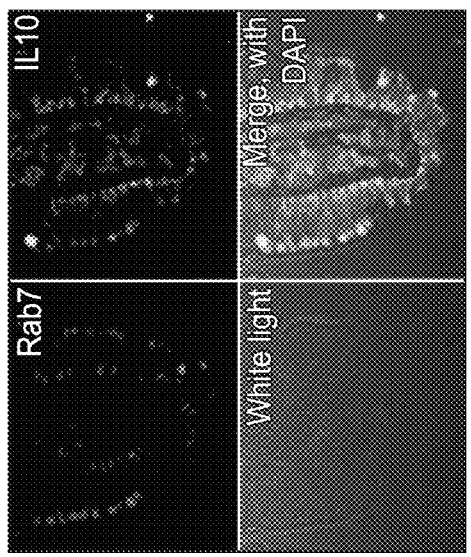

FIG. 21B show that the M+Cholix$^{386}$-IL-10 (SEQ ID NO: 154) delivery construct (top right) strongly co-localizes with the Rab7 (top left) predominantly in the apical compartment of enterocytes, but with only limited co-localization in cells within the Lamina propria, suggesting the presence of the Cholix derived delivery constructs in late endosome compartments (bottom left shows white light image, and bottom right shows merged staining with DAPI).

Figure 21C:
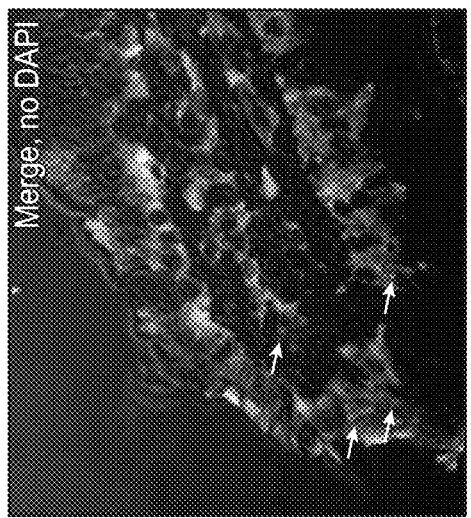

FIG. 21C shows that LAMP1 was identified in large, specific vesicles consistent with mature lysosomes that were devoid of M+Cholix$^{386}$-IL-10 (SEQ ID NO: 154) delivery constructs (white arrows). M+Cholix$^{386}$-IL-10 (SEQ ID NO: 154), however, also co-localizes with the LAMP1 antigen in cellular locations other than lysosome-like structures, consistent with vesicle trafficking at both the apical and basal domains of enterocytes, suggesting the presence of the Cholix derived delivery constructs in late endosomal compartments.

Figure 21D:
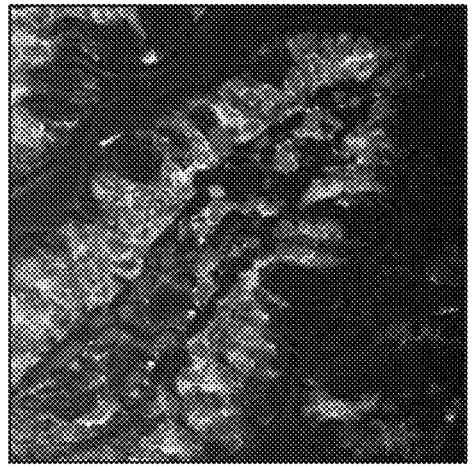

FIG. 21D shows that M+Cholix$^{386}$-IL-10 (SEQ ID NO: 154) chimera also strongly co-localized with clathrin-coated vesicles, particularly in areas adjacent to the nucleus and in the Rab1 1 predominantly in the basal compartment of enterocytes as well as in selected cells within the Lamina propria.

Figure 21E:
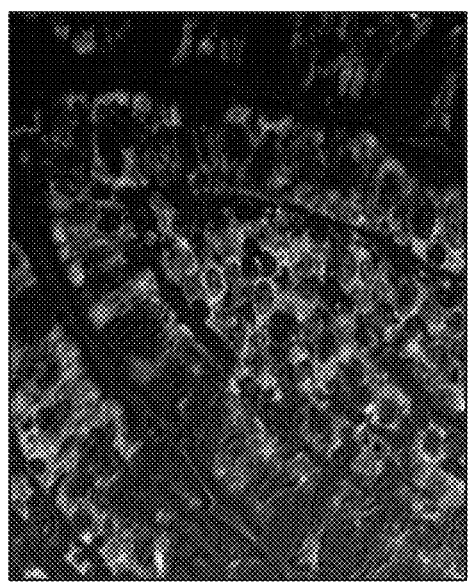

FIG. 21E shows that M+Cholix$^{386}$-IL-10 (SEQ ID NO: 154) delivery construct co-localizes with the endoplasmic reticulum as demonstrated by calnexin in a pattern adjacent to the nucleus in enterocytes and in a large fraction of cells with in the Lamina propria. The M+Cholix$^{386}$-IL-10 (SEQ ID NO: 154) delivery construct strongly co-localizes with the endoplasmatic reticulum Golgi intermediate compartment (ERGIC) and the LAMN1 antigen appeared to re-distribute in response to carrier endocytosis and transcytosis, as shown for 1 (FIG. 21F), 5 (FIG. 21G), 10 (FIG. 21H), and 15 minutes after injection (FIG. 21I).

Figure 21F:
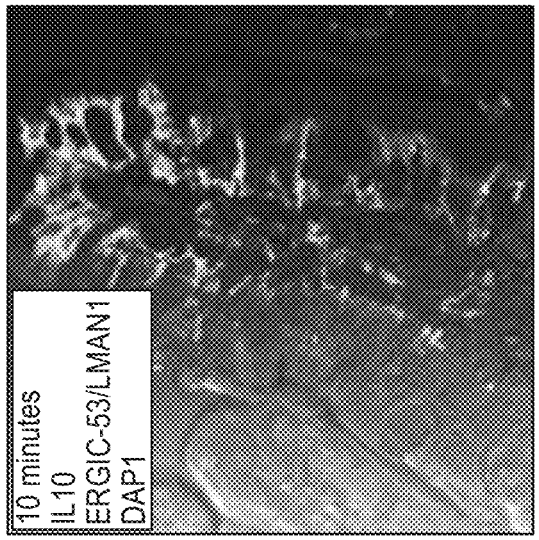

FIG. 21F shows that the M+Cholix$^{386}$-IL-10 (SEQ ID NO: 154) delivery construct strongly co-localizes with the endoplasmatic reticulum Golgi intermediate compartment (ERGIC) and the LAMN1 antigen appeared to re-distribute in response to carrier endocytosis and transcytosis, as shown for 1 minute after injection (white arrow #1 highlights the apical surface, and white arrow #2 highlights the basal surface).

Figure 21G:
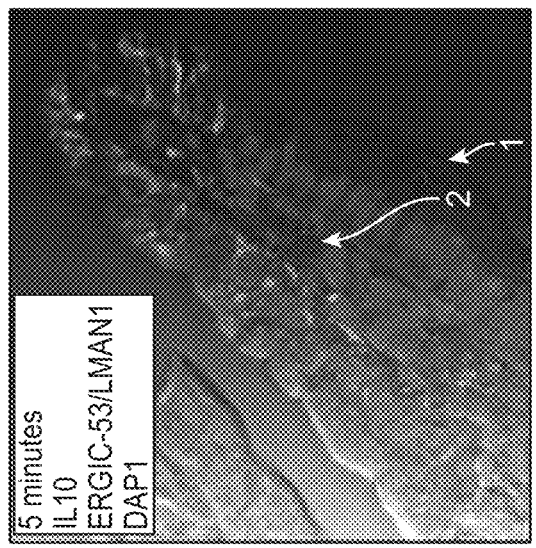

FIG. 21G shows M+Cholix$^{386}$-IL-10 (SEQ ID NO: 154) delivery construct co-localization with LAMN1 antigen 5 minutes after injection (white arrow #1 highlights the apical surface, and white arrow #2 highlights the basal surface).

Figure 21H:
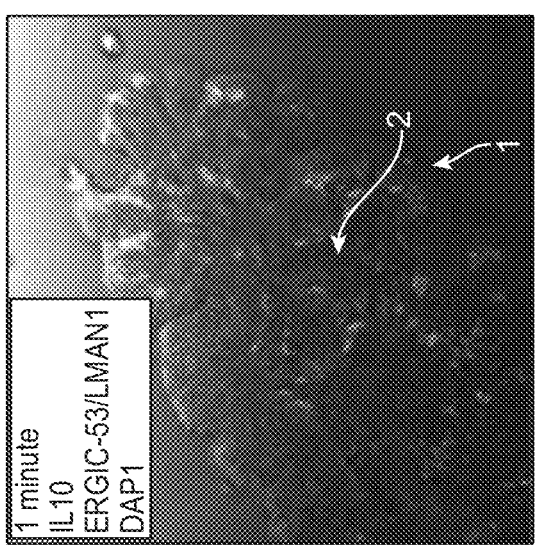
Figure 21I:
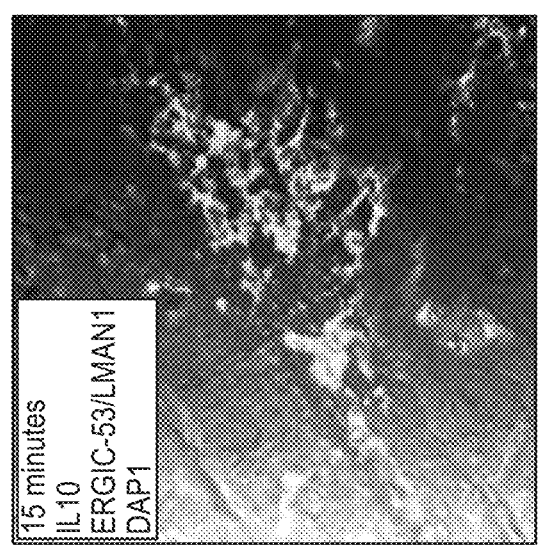

FIG. 21H shows M+Cholix$^{386}$-IL-10 (SEQ ID NO: 154) delivery construct co-localization with LAMN1 antigen 10 minutes after injection.

FIG. 21I shows M+Cholix$^{386}$-IL-10 (SEQ ID NO: 154) delivery construct co-localization with LAMN1 antigen 15 minutes after injection.

Figure 21J:
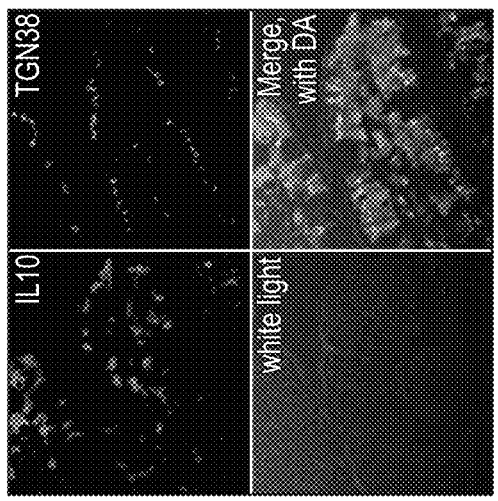

FIG. 21J shows that M+Cholix$^{386}$-IL-10 (SEQ ID NO: 154) delivery construct does not co-localize with the low levels of giantin present in enterocytes. Some giantin co-localized with the chimera in a subset of cells present in the Lamina propria, suggesting that the Cholix derived carrier does not locate with the Golgi compartment (white arrow #1 highlights the apical surface, and white arrow #2 highlights the basal surface).

Figure 21K:
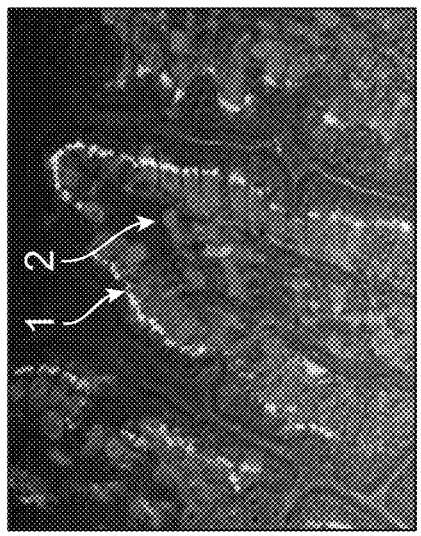

FIG. 21K shows that the 58K antigen localizes in enterocytes at a site apical to the nucleus and the M+Cholix$^{386}$-IL-10 (SEQ ID NO: 154) delivery construct shows some co-localization with this antigen in a manner that suggests a brief movement through this compartment. No 58K antigen was observed in cells within the Lamina propria (white arrow #1 highlights the apical surface, and white arrow #2 highlights the basal surface).

Figure 21L:
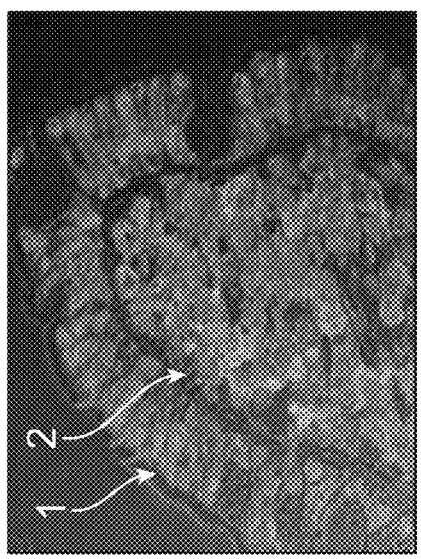

FIG. 21L shows that the M+Cholix$^{386}$-IL-10 (SEQ ID NO: 154) delivery construct showed some level of co-localization with the TGN38 antigen (top right), which showed a cellular distribution that was restricted to the apical side of nuclei in enterocytes and adjacent to the nucleus in a few cells within the Lamina propria (white light and merge images shown bottom left and bottom right, respectively).

Figure 21M:
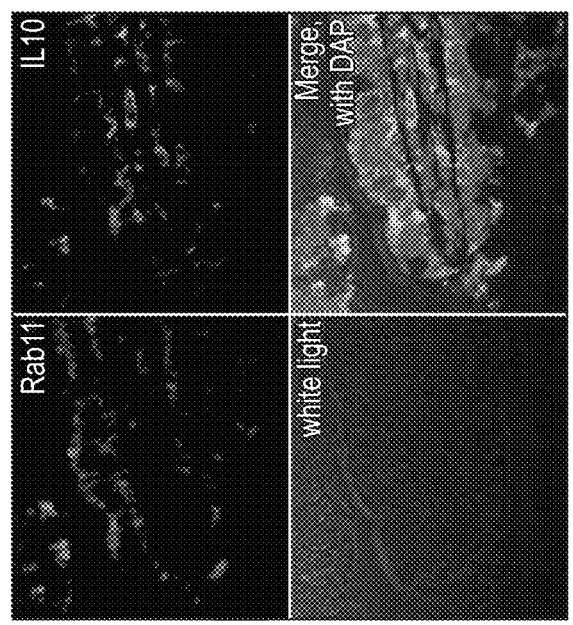

FIG. 21M shows that the M+Cholix$^{386}$-IL-10 (SEQ ID NO: 154) delivery construct (staining shown in green, top right) strongly co-localizes with Rab1 1 (top left) predominantly in the basal compartment of enterocytes and in selected cells within the Lamina propria (white light and merge images shown bottom left and bottom right, respectively).

Figure 22:
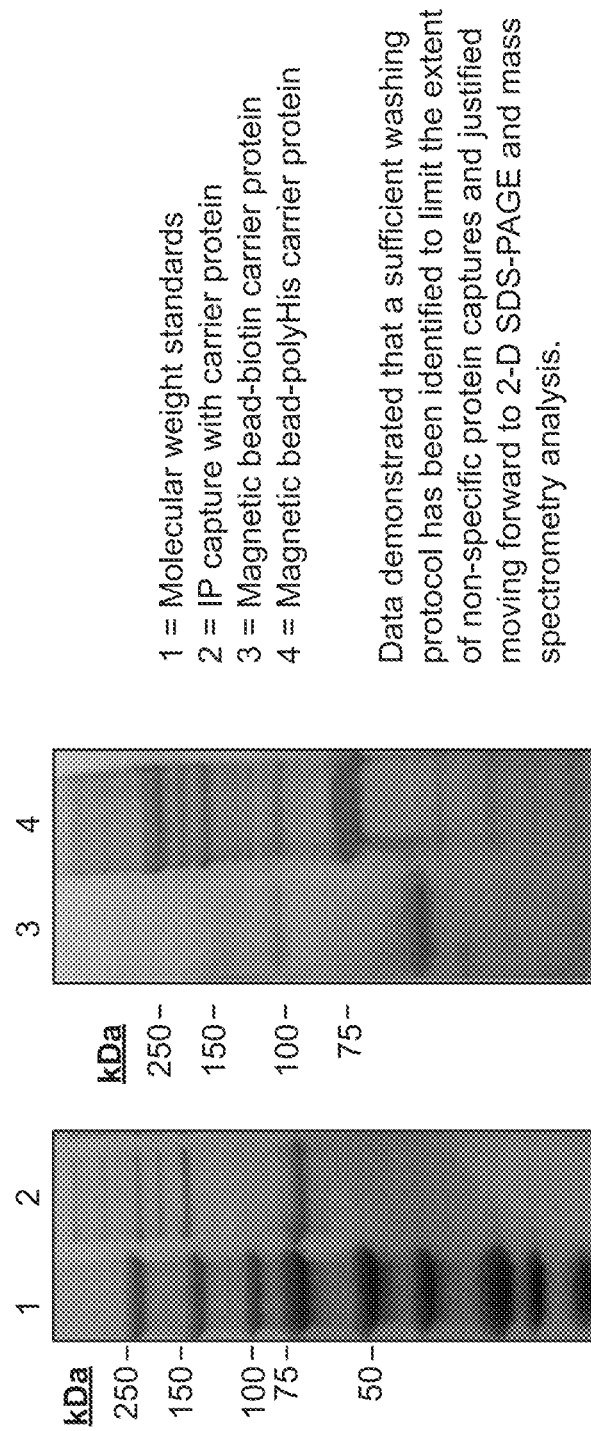

FIG. 22 illustrates a 1D SDS-PAGE showing that an efficient protocol using nano-sized magnetic beads (25 nm or 100 nm diameter) decorated with non-toxic Cholix derived carrier elements can be used for specific protein capture to analyze proteins that interact with Cholix or carriers derived therefrom.

Figure 23:
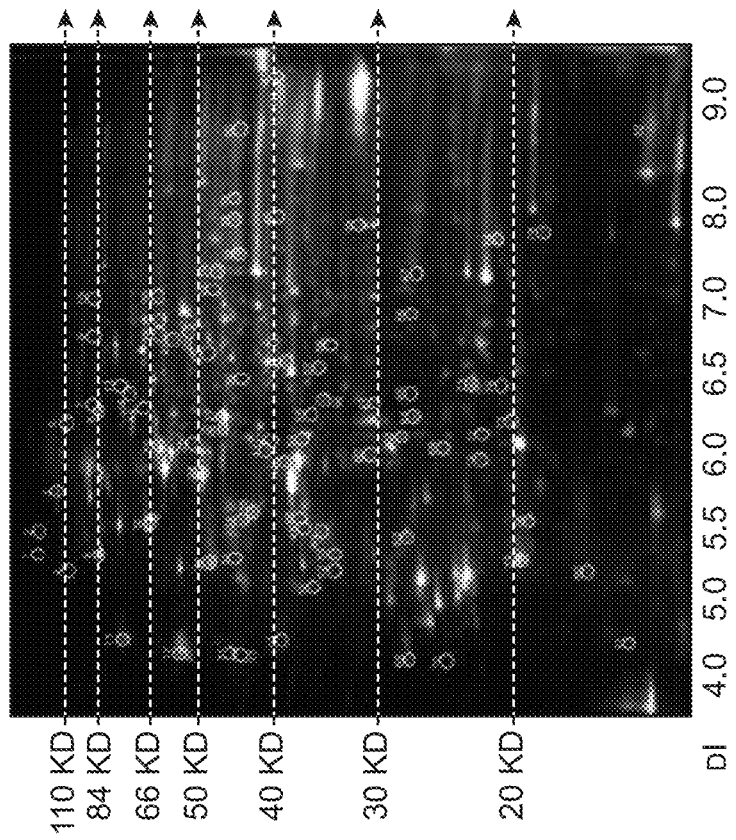

FIG. 23 illustrates that, after multiple washings, the magnetic bead-enriched vesicles can be solubilized in lysis buffer and the protein components present can be separated by 2-D SDS-PAGE for analysis.

Figure 24:
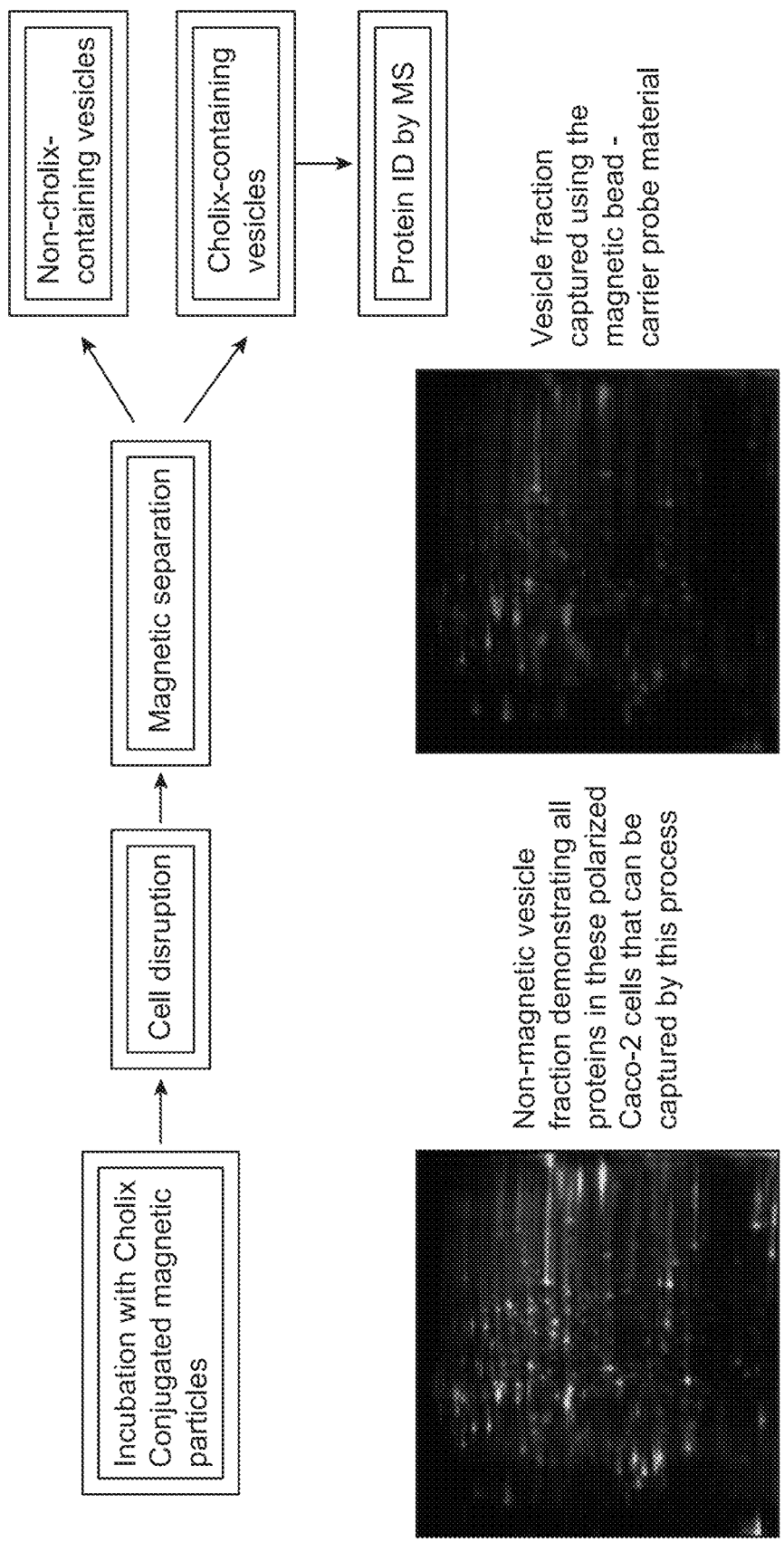

FIG. 24 shows that patterns of these proteins can be compared to the total protein content of the cells and that mass spectrometry can be used to identify specific elements associated with vesicular structures accessed by the Cholix derived delivery constructs.

FIG. 25 shows a comparison of outcomes from repeats of the above described protocol used to identify a set of interaction candidates. The interacting proteins can then examined for their content in Caco-2 cells and in rat small intestine. Interaction of Cholix with the identified candidate proteins can be confirmed using Cholix carrier-coated magnetic beads and purified candidate protein.

Figure 26:
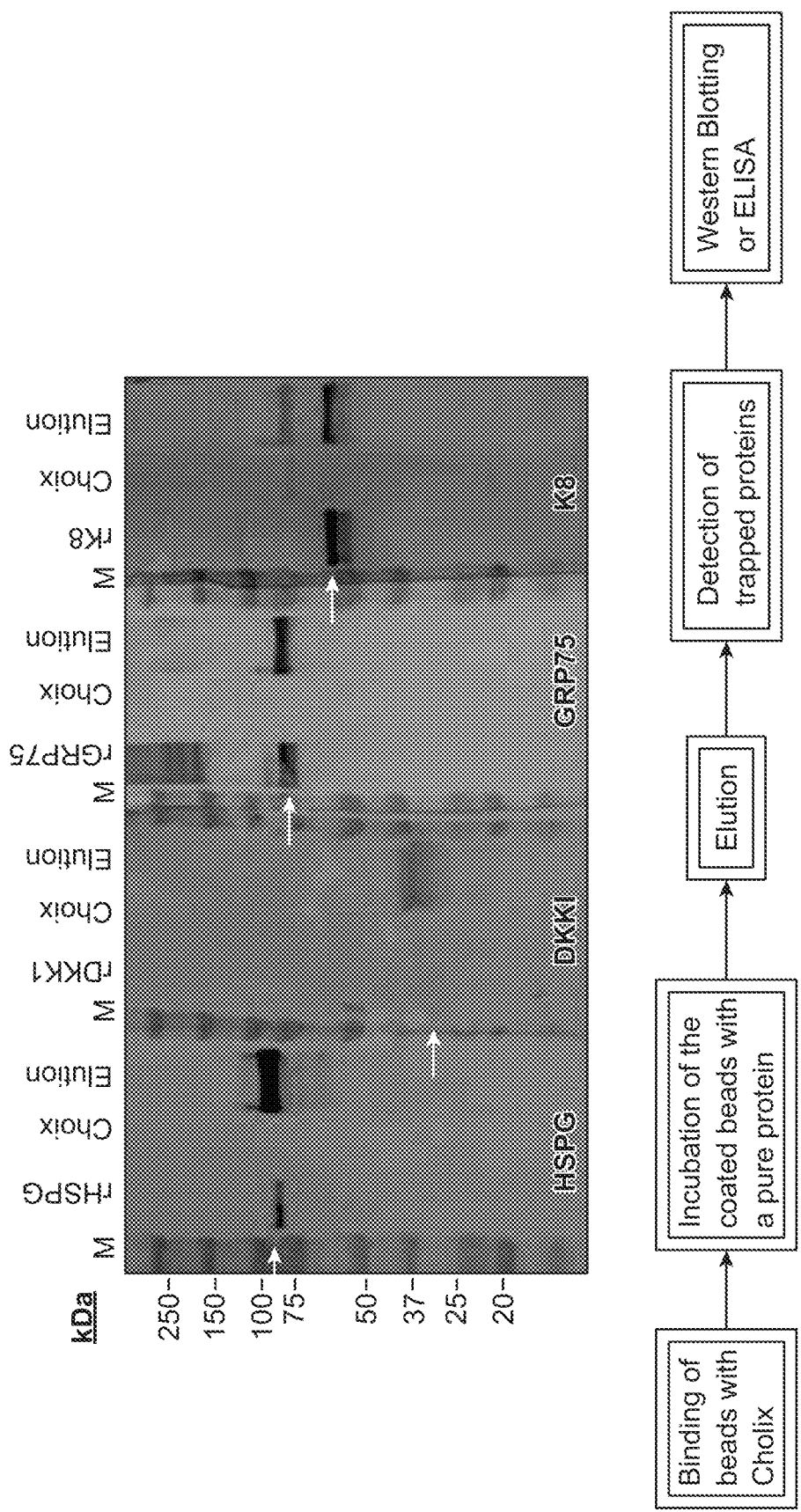

FIG. 26 shows that incubation of the Cholix carrier (having the amino acid set forth in SEQ ID NO: 154)-coated beads with the pure proteins and subsequent Western Blots or ELISA can enable detection of Cholix-protein interaction. For example, this figure shows interaction of Cholix carrier with heparan sulfate proteoglycan (HSPG), Dickkopf-related protein 1 (DKK1), the chaperone glucose-regulated protein 75 (GRP75), and cytokeratin-8 (K8 or CK8).

FIG. 27 shows microscopic co-localization of candidate proteins and Cholix derived delivery construct in rat jejunum. Co-localization of a delivery construct comprising a Cholix carrier protein coupled to IL-10 (SEQ ID NO: 154, M+Cholix$^{386}$-GGGGSGGGGSGGGGS (SEQ ID NO: 210)-IL-10) with CK8 was shown in vivo.

FIG. 27A shows co-localization after rat jejunum was treated with a luminal application of M+Cholix$^{386}$-IL-10 (SEQ ID NO: 154) delivery construct for 1 minute (white arrow #1 highlights the apical surface, and white arrow #2 highlights the basal surface).

FIG. 27B shows co-localization after rat jejunum was treated with a luminal application of M+Cholix$^{386}$-IL-10 (SEQ ID NO: 154) delivery construct for 5 minute.

FIG. 27C shows co-localization after rat jejunum was treated with a luminal application of M+Cholix$^{386}$-IL-10 (SEQ ID NO: 154) delivery construct for 10 minutes. Thus, co-localization in the supra-nuclear region was shown to increase over time.

FIG. 28 shows a comparison of results obtained in an IHC study with the human atlas to ensure that the receptor distribution is consistent between rat in vivo studies and human intestine. Here, two of the receptors identified by mass spectrometry and verified in rat jejunum are examined.

Figure 28A:

FIG. 28A shows that the intestinal localization of GRP75 is consistent between rat and human intestine.

Figure 28B:
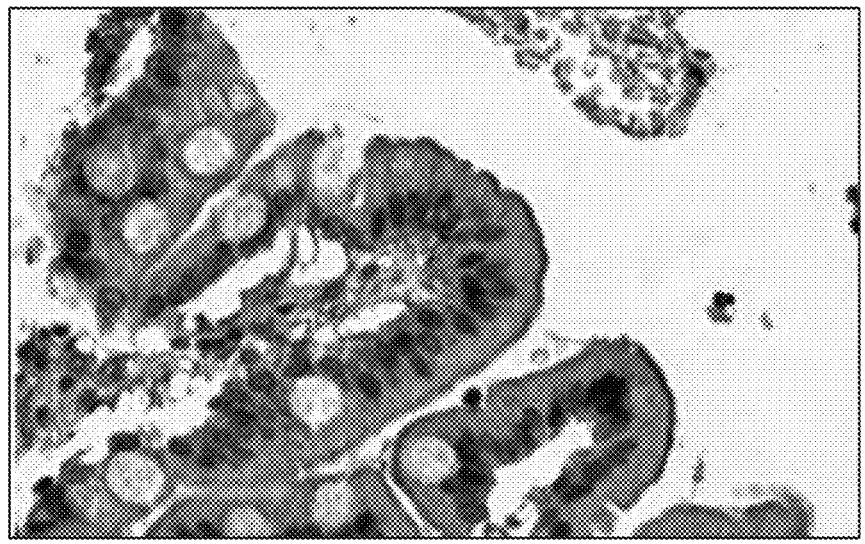

FIG. 28B shows that the intestinal localization of HSPC is consistent between rat and human intestine.

Figure 29:
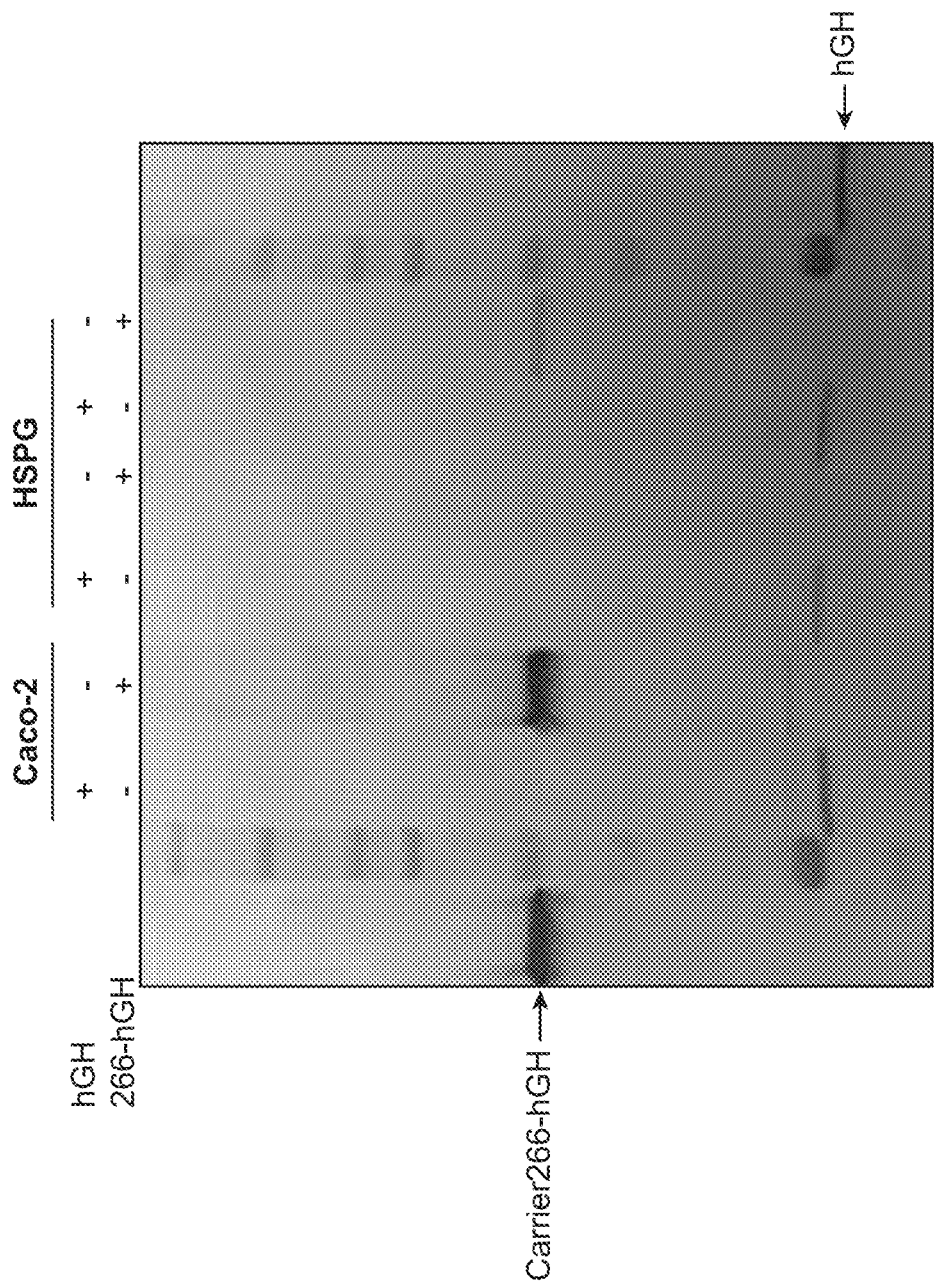

FIG. 29 shows effects of HSPG knockout by CRISPR on transport function of the delivery construct (SEQ ID NO: 164) comprising Cholix domain I (SEQ ID NO: 5) coupled to HGH (SEQ ID NO: 214) via a polyglycine-serine spacer (SEQ ID NO: 210) and HGH alone as internal control of non-selective transport. Cells were seeded at 1.5×10$^5$ cells/mL in transwells. On day 18, transepithelial/transendothelial electrical resistance (TEER) was measured and PBS containing 20 ug/mL of the delivery construct was added to the apical chambers. After 3 h, basolateral samples were collected and concentrated. The extent of protein transport was analyzed by Western blotting using anti-HGH antibody. The results shown in FIG. 29 demonstrate that transcytosis and active, selective transport of Cholix derived carrier proteins is HSPG-dependent, as the Cholix carrier showed significantly less transcytosis function in HSPC-knock-down cells compared to normal, HSPG-positive Caco-2 cells.

Figure 30:
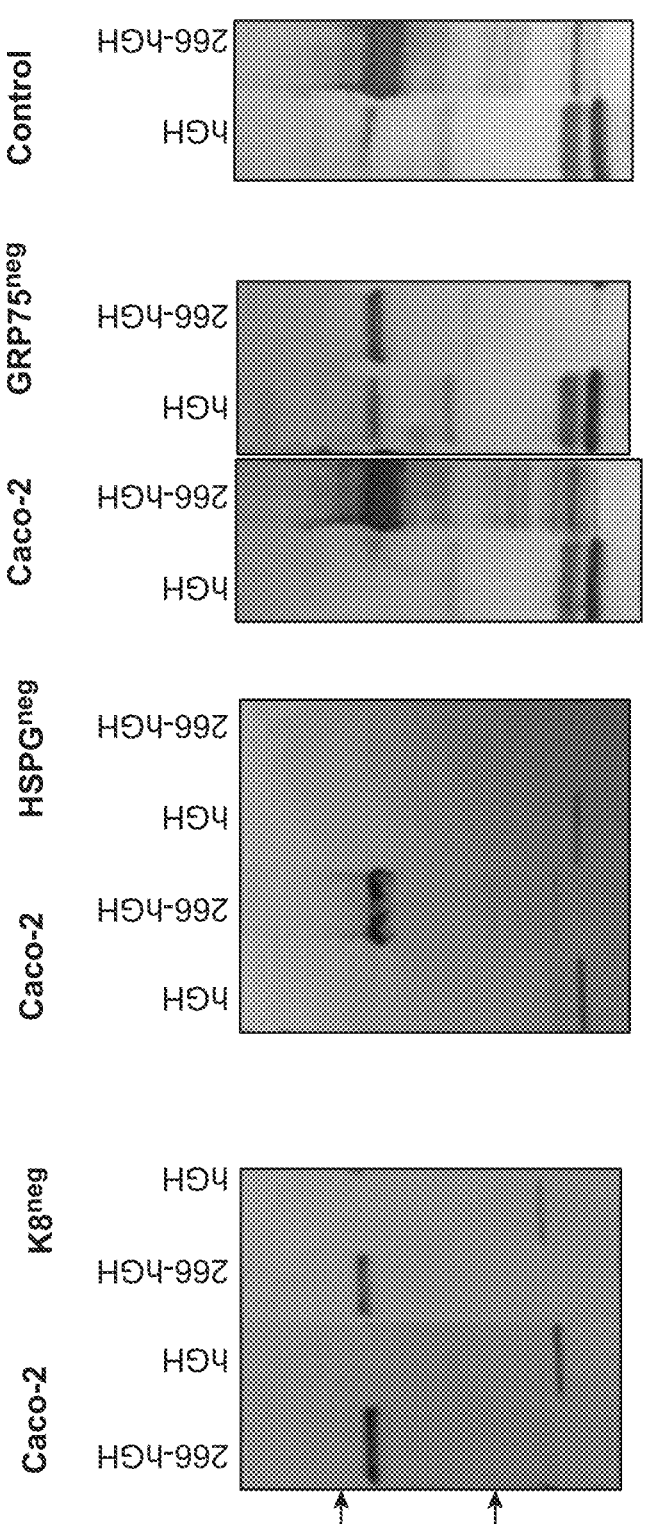

FIG. 30 shows knockout effects of K8, HSPC, and GRP75 on the transcytosis function of Cholix domain I derived delivery constructs. Stable cell lines of Caco-2 cells lacking the expression of specific candidate proteins were used as monolayers in vitro to verify their requirement for carrier transcytosis using active and selective endogenous transport mechanisms. The specific transport of the HGH-containing delivery construct vs non-selective transport of HGH alone was reduced in HSPG and GRP75 knockouts, but not the K8 knockout.

FIG. 30A shows knockout effects of K8.

FIG. 30B shows knockout effects of HSPC.

FIG. 30C shows knockout effects of GRP75.

FIG. 30D shows the control experiment.

Figure 31:
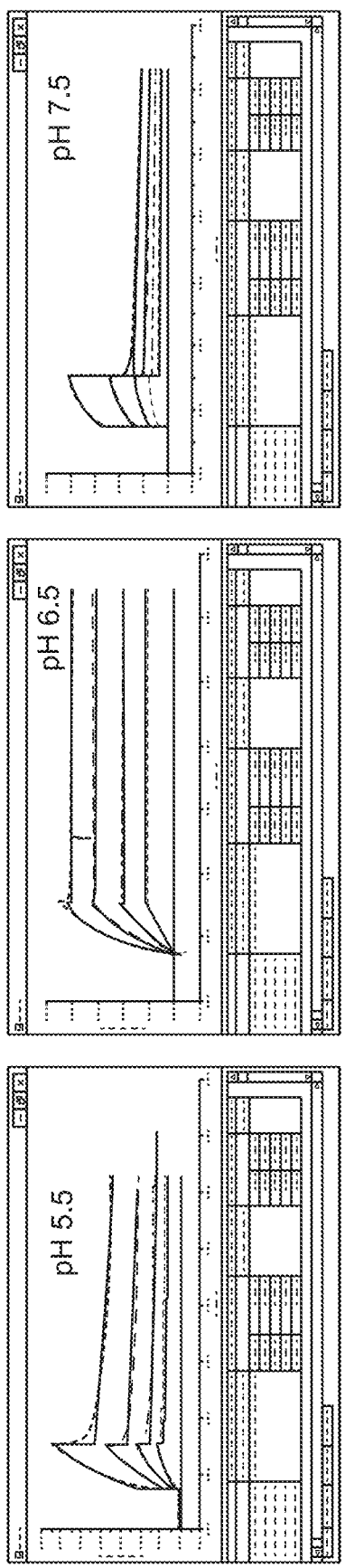

FIG. 31 shows Biacore binding interactions used to examine the pH-dependency of Cholix carrier-GRP75 interactions. Cholix carrier proteins were attached to magnetic beads using the biotin-streptavidin bioconjugation and incubated with purified GRP75 protein in buffer solutions with pH 5.5, 6.5, and 7.5, respectively. Highest binding affinity was shown at pH 6.5.

FIG. 32 shows an exemplary surface model of Cholix domain I (SEQ ID NO: 5) was used to highlight selected areas of potential interest in this transcytosis process due to their projection from the protein surface. It is interesting to note that two amino acids regions between M$^1$ and G$^{40}$ are adjacent to surface exposed amino acids D$^{151}$-A$^{187}$ and A$^{187}$-L$^{206}$. Specifically, L$^{18}$-I$^{26}$ (domain X1) and T$^{171}$-I$^{176}$ (domain X2) coordinate to form a pocket surrounded by several negative charges. Similarly, K$^{187}$-H$^{203}$ (domain X3) coordinates with I$^{32}$-E$^{40}$ (domain X4) to form a continuous ridge structure FIG. 32A shows the proximity of domains X3 and X4.

Figure 32B:
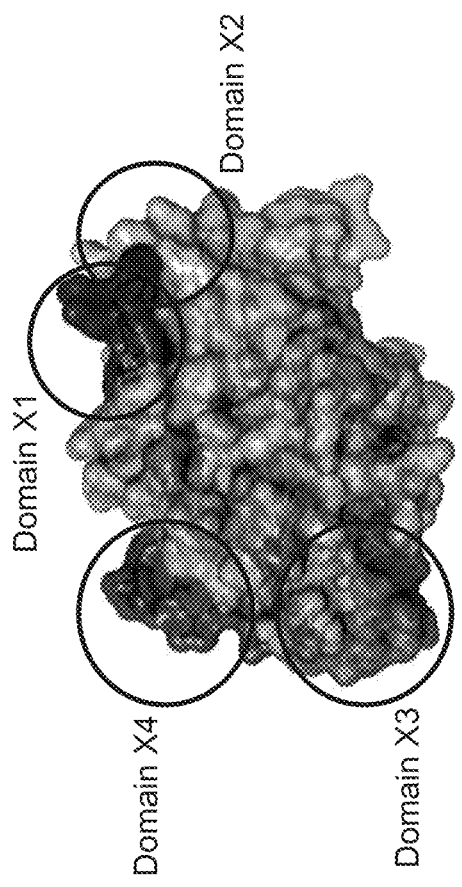

FIG. 32B shows the proximity of domains X1 and X2, as well as X3 and X4.

Figure 32D:
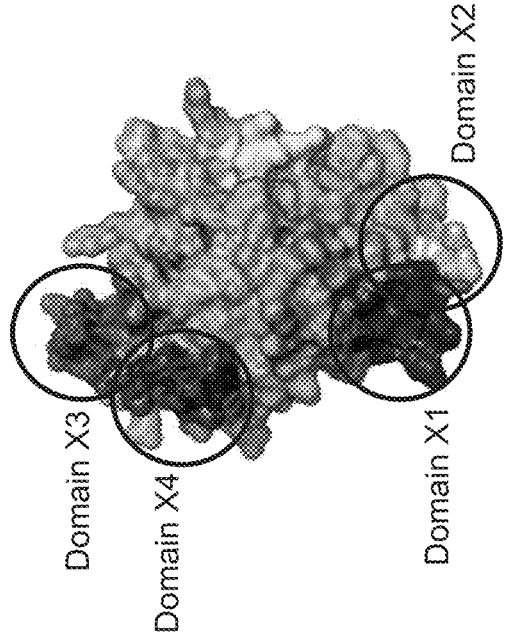
Figure 32A:
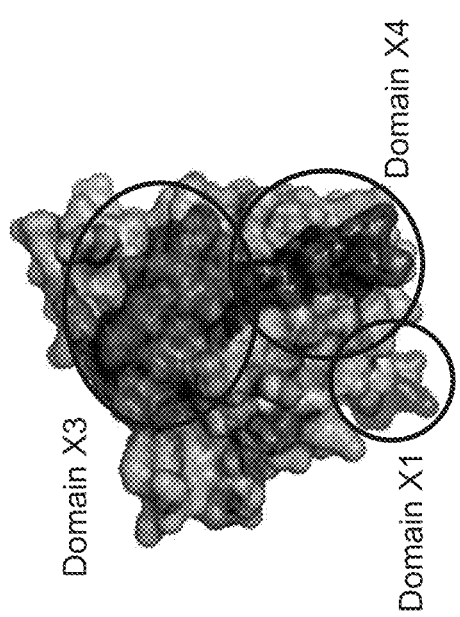
Figure 32C:
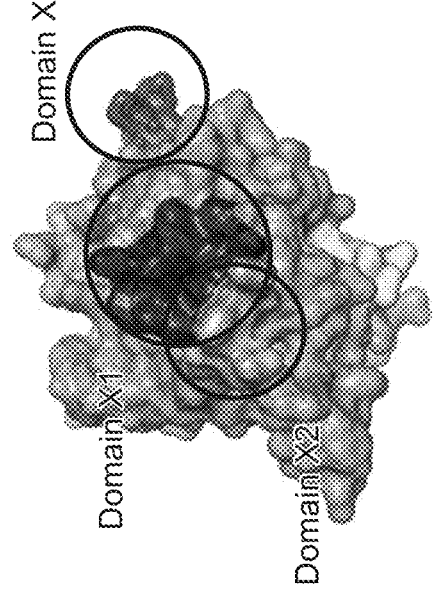

FIG. 32C shows the proximity of domains X1 and X2.

FIG. 32D shows the proximity of domains X1 and X2, as well as X3 and X4.

DETAILED DESCRIPTION

Introduction

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The present disclosure provides methods and compositions for transport and/or delivery of a cargo molecule to certain location(s) within a cell (e.g., a supranuclear location) or across a cell (e.g., epithelial cell), either in vitro or in vivo (e.g., in a rodent or a human). Such cargo can be directed to a set of location(s) by coupling it to a carrier molecule. Such carrier molecule can interact with unique receptors both on the cell surface and intracellularly for the targeted delivery of the cargo. Various such carrier, cargos, and uses thereof are described herein.

Unless otherwise defined herein, scientific and technical terms used in connection with the present disclosure shall have the meanings that are commonly understood by those of ordinary skill in the art. Further, unless otherwise required by context, singular terms shall include pluralities and plural terms shall include the singular. Generally, nomenclatures used in connection with, and techniques of, cell and tissue culture, molecular biology, immunology, microbiology, genetics, protein and nucleic acid chemistry, and hybridization described herein are those commonly used and well known in the art. The methods and techniques of the present disclosure are generally performed according to conventional methods well known in the art and as described in various general and more specific references that are cited and discussed throughout the present specification unless otherwise indicated. See, e.g., Green and Sambrook, Molecular Cloning: A Laboratory Manual, 4th ed., Cold Spring Harbor Laboratory Press, Cold Spring Harbor, N.Y. (2012) and Ausubel et al., Current Protocols in Molecular Biology, Greene Publishing Associates (1992), each incorporated herein by reference. Enzymatic reactions and purification techniques are performed according to manufacturer's specifications, as commonly accomplished in the art or as described herein. The nomenclature used in connection with, and the laboratory procedures and techniques of, analytical chemistry, synthetic organic chemistry, and medicinal and pharmaceutical chemistry described herein are those commonly used and well known in the art. Standard techniques are used for chemical syntheses, chemical analyses, pharmaceutical preparation, formulation, and delivery, and treatment of patients.

As described herein, an amino acid sequence can comprise one or more modification to the amino acid sequences at the N-terminus. An amino acid sequence as disclosed herein can comprise an "N-cap." Generally, an N-cap as disclosed herein can refer to a modification of an N-terminus of a peptide or polypeptide in a variety of ways, and particularly can refer to (i) the addition of one or more amino acid sequences or other moieties (e.g., affinity handles, cell-penetrating peptide sequences, etc.), and (ii) a modification of one or more amino acid residues within the first 1-10 N-terminal amino acids of a peptide or polypeptide, wherein the amino acid modification is relative to a reference sequence or a consensus sequence (see e.g., comparison of the first 4 N-terminal amino acid residues of polypeptide sequences set forth in SEQ ID NO: 4 and SEQ ID NO: 5, or SEQ ID NO: 1 and SEQ ID NO: 2 as described herein). An N-cap can comprise an additional 1, 2, 3, 4, 5, 6, 7, 8, 9, 10, or 15 or 100 additional amino acid residues that are attached to (e.g., chemically coupled to) to the N-terminus of an amino acid sequence, such as a Cholix derived carrier molecule. An N-cap can further comprise one or more variations in the amino acid sequence at the N-terminus. For example, a Cholix domain I derived carrier can comprise an N-cap. The N-cap can comprise substituting one or more N-terminal amino acid residues with other amino acid residues. An N-cap can further comprise an N-terminal methionine residue. One or more of these modifications can be a result of producing the Cholix domain I amino acid sequence in a bacterial production system (e.g., E. coli). As an example, Cholix domain I can comprise amino acid residues 1-265 of SEQ ID NO: 1 which is set forth in SEQ ID NO: 4. A bacterially expressed Cholix domain can comprise an amino acid sequence set forth in SEQ ID NO: 5, which as SEQ ID NO: 4 plus an N-terminal methionine residues, which can also be referred to herein as M+Cholix$^{1-265}$ or M+Cholix$^{265}$.

As described herein, the term "lacks a domain" or "lacking a domain" generally refers to not comprising a complete domain, but optionally comprising a portion or fragment thereof. For example, a carrier that is derived from a domain I of an exotoxin but lacks a domain II, a domain Ib, and a domain III of said exotoxin generally refers to a carrier that does not comprise the full amino acid sequences of (e.g., 100% sequence identity to) any one of the domains II, Ib, and III, but which can optionally comprise portions or fragments thereof. Thus, a carrier derived from a Cholix domain and lacking a Cholix domain II as described herein can comprise Cholix domain I having an amino acid sequence set forth in SEQ ID NO: 4 or SEQ ID NO: 5 and an additional 50-80 amino acid residues of Cholix domain II (e.g., amino acids 1-50 or 1-80 of SEQ ID NO: 126), and or an additional 50-80 amino acid residues of Cholix domain III (e.g., amino acids 1-50 or 1-80 of SEQ ID NO: 128).

As described herein, the terms "attached to", "coupled to", "linked to", "conjugated to" and "fused to" can be used interchangeably and generally mean that a first molecule (e.g., a polypeptide) is associated with a second molecule (e.g., a polypeptide, small molecule, etc.). The association can be via a chemical linkage, wherein the chemical linkage can be covalently or non-covalently. A covalent chemical linkage between a first polypeptide and a second polypeptide can be produced by synthetically coupling the first polypeptide to the second polypeptide, or it can be produced by recombinant fusion of the first polypeptide to the second polypeptide. Thus, a first (e.g., a first polypeptide) molecule can be chemically (e.g., synthetically) or recombinantly coupled to a second molecule (e.g., a second polypeptide).

The terms "polypeptide", "peptide" and "protein" are used interchangeably herein to refer to a polymer of amino acid residues. In addition, the terms "toxin", "carrier", "delivery construct", "chimeric construct", "protein", and "polypeptide" can be used interchangeably and generally refer to a molecule that can be coupled to a heterologous cargo. Generally, "delivery constructs" and "chimeric constructs" are "peptides", "polypeptides", or "proteins", are described herein as chains of amino acids whose alpha carbons are linked through peptide bonds. The terminal amino acid at one end of the chain (amino terminal) therefore has a free amino group, while the terminal amino acid at the other end of the chain (carboxy terminal) has a free carboxyl group. As used herein, the term "amino terminus" (abbreviated N-terminus) refers to the free α-amino group on an amino acid at the amino terminal of a peptide or to the α-amino group (imino group when participating in a peptide bond) of an amino acid at any other location within the peptide. Similarly, the term "carboxy terminus" refers to the free carboxyl group on the carboxy terminus of a peptide or the carboxyl group of an amino acid at any other location within the peptide. Peptides also include essentially any polyamino acid including, but not limited to, peptide mimetics such as amino acids joined by an ether bond as opposed to an amide bond. Generally, peptides, polypeptide, and proteins as described herein can be recombinantly produced or chemically synthesized (e.g., using solid-phase synthesis), or a combination thereof.

As disclosed herein, the term "delivery" generally refers to the presence of a molecule (e.g., a heterologous cargo) at a location (e.g., an intracellular compartment or a supranuclear region) for a certain period of time. The term "delivery" can refer to the presence of a molecule (e.g., a heterologous cargo) at a location (e.g., an intracellular compartment or a supranuclear region) for a time that is sufficient to elicit a certain biological effect, such as an interaction (e.g., binding) with a protein (e.g., an enzyme or a receptor) at that location. The delivery of a molecule (e.g., a heterologous cargo) to a location (e.g., an intracellular compartment or a supranuclear region) can refer to the retention of the molecule at that location. Retention of a molecule at a certain intracellular or extracellular region or compartment can be for a certain amount of time, e.g., at least 2 minutes, at least 5 minutes, at least 10 minutes, at least 15 minutes, at 30 minutes, or at least 60 minutes. Retention of a molecule can depend on various factors such as the location where the molecule is retained and/or the types of molecular interactions that occur between the molecule (e.g., a carrier, a delivery construct, and/or a heterologous cargo). For example, delivery of a heterologous cargo to a basolateral compartment via transcytosis across a polarized epithelial cell can comprise retaining the heterologous cargo at the basolateral location for a time sufficient to elicit a certain effect, such as a therapeutic effect in case of a therapeutic and/or biologically active cargo.

Polypeptides of the disclosure include polypeptides that have been modified in any way and for any reason, for example, to: (1) reduce susceptibility to proteolysis, (2) reduce susceptibility to oxidation, (3) alter binding affinity for forming protein complexes, (4) alter binding affinities, and (5) confer or modify other physicochemical or functional properties. For example, single or multiple amino acid substitutions (e.g., conservative amino acid substitutions) can be made in the naturally occurring sequence (e.g., in the portion of the polypeptide outside the domain(s) forming intermolecular contacts). A "conservative amino acid substitution" refers to the substitution in a polypeptide of an amino acid with a functionally similar amino acid. The following six groups each contain amino acids that are conservative substitutions for one another:

1) Alanine (A), Serine (S), and Threonine (T)
2) Aspartic acid (D) and Glutamic acid (E)
3) Asparagine (N) and Glutamine (Q)
4) Arginine (R) and Lysine (K)
5) Isoleucine (I), Leucine (L), Methionine (M), and Valine (V)
6) Phenylalanine (F), Tyrosine (Y), and Tryptophan (W)

A "non-conservative amino acid substitution" refers to the substitution of a member of one of these classes for a member from another class. In making such changes, according to various embodiments, the hydropathic index of amino acids can be considered. Each amino acid has been assigned a hydropathic index on the basis of its hydrophobicity and charge characteristics. They are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). In other embodiments, the carrier of a delivery constructs is a chimeric carrier comprising a peptide, polypeptide, small molecule, aptamer, fragments thereof, or any combination thereof.

The importance of the hydropathic amino acid index in conferring interactive biological function on a protein is understood in the art (see, for example, Kyte et al., 1982, J. Mol. Biol. 157:105-131). It is known that certain amino acids can be substituted for other amino acids having a similar hydropathic index or score and still retain a similar biological activity. In making changes based upon the hydropathic index, in various embodiments, the substitution of amino acids whose hydropathic indices are within +2 is included. In various embodiments, those that are within +1 are included, and in various embodiments, those within +0.5 are included.

It is also understood in the art that the substitution of like amino acids can be made effectively on the basis of hydrophilicity, particularly where the biologically functional protein or peptide thereby created is intended for use in immunological applications, as disclosed herein. In various embodiments, the greatest local average hydrophilicity of a protein, as governed by the hydrophilicity of its adjacent amino acids, correlates with its immunogenicity and antigenicity, i.e., with a biological property of the protein.

The following hydrophilicity values have been assigned to these amino acid residues: arginine (+3.0); lysine (+3.0); aspartate (+3.0+/−0.1); glutamate (+3.0+/−0.1); serine (+0.3); asparagine (+0.2); glutamine (+0.2); glycine (0); threonine (−0.4); proline (−0.5+/−0.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5) and tryptophan (−3.4). In making changes based upon similar hydrophilicity values, in various embodiments, the substitution of amino acids whose hydrophilicity values are within ±2 is included, in various embodiments, those that are within ±1 are included, and in various embodiments, those within ±0.5 are included.

Exemplary amino acid substitutions are set forth in TABLE 1.

TABLE 1

Exemplary Amino Acid Substitutions

| Original Residues | Exemplary Substitutions | Preferred Substitutions |
|---|---|---|
| Ala | Val, Leu, Ile | Val |
| Arg | Lys, Gln, Asn | Lys |
| Asn | Gln | Gln |
| Asp | Glu | Glu |
| Cys | Ser, Ala | Ser |
| Gln | Asn | Asn |
| Glu | Asp | Asp |
| Gly | Pro, Ala | Ala |
| His | Asn, Gln, Lys, Arg | Arg |
| Ile | Leu, Val, Met, Ala, Phe, Norleucine | Leu |
| Leu | Norleucine, Ile, Val, Met, Ala, Phe | Ile |
| Lys | Arg, 1,4-diamino-butyric acid, Gln, Asn | Arg |
| Met | Leu, Phe, Ile | Leu |
| Phe | Leu, Val, Ile, Ala, Tyr | Leu |
| Pro | Ala | Gly |
| Ser | Thr, Ala, Cys | Thr |
| Thr | Ser | Ser |
| Trp | Tyr, Phe | Tyr |
| Tyr | Trp, Phe, Thr, Ser | Phe |
| Val | Ile, Met, Leu, Phe, Ala, Norleucine | Leu |

A skilled artisan will be able to determine suitable variants of polypeptides as set forth herein using well-known techniques. One skilled in the art can identify suitable areas of the molecule that can be changed without destroying activity by targeting regions not believed to be important for activity. The skilled artisan can identify residues and portions of the molecules that are conserved among similar polypeptides. Areas of these materials that can be important for biological activity or for structure could be subjected to conservative amino acid substitutions without destroying the biological activity or without adversely affecting the polypeptide structure.

Additionally, one skilled in the art can review structure-function studies identifying residues in similar polypeptides that are important for activity or structure. In view of such a comparison, the skilled artisan can predict the importance of amino acid residues in a polypeptide that correspond to amino acid residues important for activity or structure in similar polypeptides. One skilled in the art can opt for chemically similar amino acid substitutions for such predicted important amino acid residues.

One skilled in the art can also analyze the three-dimensional structure and amino acid sequence in relation to that structure in similar polypeptides. In view of such information, one skilled in the art can predict the alignment of amino acid residues of a polypeptide with respect to its three-dimensional structure. One skilled in the art can choose to not make radical changes to amino acid residues predicted to be on the surface of the polypeptide, since such residues can be involved in important interactions with other molecules. Moreover, one skilled in the art can generate test variants containing a single amino acid substitution at each desired amino acid residue. The variants can then be screened using activity assays known to those skilled in the art. Such variants could be used to gather information about suitable variants. For example, if one discovered that a change to a particular amino acid residue resulted in destroyed, undesirably reduced, or unsuitable activity, variants with such a change in the amino acid sequence can be avoided. In other words, based on information gathered from such routine experiments, one skilled in the art can readily determine the amino acids where further substitutions should be avoided either alone or in combination with other mutations.

The term "polypeptide fragment" and "truncated polypeptide" as used herein refers to a polypeptide that has an amino-terminal and/or carboxy-terminal deletion as compared to a corresponding full-length protein. In various embodiments, fragments can be, e.g., at least 5, at least 10, at least 25, at least 50, at least 100, at least 150, at least 200, at least 250, at least 300, at least 350, at least 400, at least 450, at least 500, at least 600, at least 700, at least 800, at least 900 or at least 1000 amino acids in length. In various embodiments, fragments can also be, e.g., at most 1000, at most 900, at most 800, at most 700, at most 600, at most 500, at most 450, at most 400, at most 350, at most 300, at most 250, at most 200, at most 150, at most 100, at most 50, at most 25, at most 10, or at most 5 amino acids in length. A fragment can further comprise, at either or both of its ends, one or more additional amino acids, for example, a sequence of amino acids from a different naturally-occurring protein (e.g., an Fc or leucine zipper domain) or an artificial amino acid sequence (e.g., an artificial spacer sequence).

The terms "polypeptide variant" and "polypeptide mutant" as used herein refer to a polypeptide that comprises an amino acid sequence wherein one or more amino acid residues are inserted into, deleted from and/or substituted into the amino acid sequence relative to another polypeptide sequence. The number of amino acid residues to be inserted, deleted, or substituted can be, e.g., at least 1, at least 2, at least 3, at least 4, at least 5, at least 10, at least 25, at least 50, at least 75, at least 100, at least 125, at least 150, at least 175, at least 200, at least 225, at least 250, at least 275, at least 300, at least 350, at least 400, at least 450 or at least 500 amino acids in length. Variants of the present disclosure include fusion proteins.

A "derivative" of a polypeptide is a polypeptide that has been chemically modified, e.g., conjugation to another chemical moiety such as, for example, polyethylene glycol, albumin (e.g., human serum albumin), phosphorylation, and glycosylation.

The term "% sequence identity" is used interchangeably herein with the term "% identity" and refers to the level of amino acid sequence identity between two or more peptide sequences or the level of nucleotide sequence identity between two or more nucleotide sequences, when aligned using a sequence alignment program. For example, as used herein, 80% identity means the same thing as 80% sequence identity determined by a defined algorithm, and means that a given sequence is at least 80% identical to another length of another sequence. In various embodiments, the % identity is selected from, e.g., at least 60%, at least 65%, at least 70%, at least 75%, at least 80%, at least 85%, at least 90%, at least 95%, or at least 99% or more sequence identity to a given sequence. In various embodiments, the % identity is in the range of, e.g., about 60% to about 70%, about 70% to about 80%, about 80% to about 85%, about 85% to about 90%, about 90% to about 95%, or about 95% to about 99%.

The term "% sequence homology" is used interchangeably herein with the term "% homology" and refers to the level of amino acid sequence homology between two or more peptide sequences or the level of nucleotide sequence homology between two or more nucleotide sequences, when aligned using a sequence alignment program. For example, as used herein, 80% homology means the same thing as 80% sequence homology determined by a defined algorithm, and accordingly a homologue of a given sequence has greater than 80% sequence homology over a length of the given sequence. In various embodiments, the % homology is selected from, e.g., at least 60%, at least 65%, at least 70%, at least 75%, at least 80%, at least 85%, at least 90%, at least 95%, or at least 99% or more sequence homology to a given sequence. In various embodiments, the % homology is in the range of, e.g., about 60% to about 70%, about 70% to about 80%, about 80% to about 85%, about 85% to about 90%, about 90% to about 95%, or about 95% to about 99%.

Exemplary computer programs which can be used to determine identity between two sequences include, but are not limited to, the suite of BLAST programs, e.g., BLASTN, BLASTX, TBLASTX, BLASTP, and TBLASTN, publicly available on the Internet at the NCBI website. See also Altschul et al., 1990, J. Mol. Biol. 215:403-10 (with special reference to the published default setting, i.e., parameters w=4, t=17) and Altschul et al., 1997, Nucleic Acids Res., 25:3389-3402. Sequence searches are typically carried out using the BLASTP program when evaluating a given amino acid sequence relative to amino acid sequences in the GenBank Protein Sequences and other public databases. The BLASTX program is preferred for searching nucleic acid sequences that have been translated in all reading frames against amino acid sequences in the GenBank Protein Sequences and other public databases. Both BLASTP and BLASTX are run using default parameters of an open gap penalty of 11.0, and an extended gap penalty of 1.0, and utilize the BLOSUM-62 matrix. See id.

In addition to calculating percent sequence identity, the BLAST algorithm also performs a statistical analysis of the similarity between two sequences (see, e.g., Karlin & Altschul, Proc. Nat'l. Acad. Sci. USA, 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is, e.g., at most 0.1, at most 0.01, or at most 0.001.

"Polynucleotide" refers to a polymer composed of nucleotide units. Polynucleotides include naturally occurring nucleic acids, such as deoxyribonucleic acid ("DNA") and ribonucleic acid ("RNA") as well as nucleic acid analogs. Nucleic acid analogs include those which include non-naturally occurring bases, nucleotides that engage in linkages with other nucleotides other than the naturally occurring phosphodiester bond or which include bases attached through linkages other than phosphodiester bonds. Thus, nucleotide analogs include, for example and without limitation, phosphorothioates, phosphorodithioates, phosphorotriesters, phosphoramidates, boranophosphates, methylphosphonates, chiral-methyl phosphonates, 2-O-methyl ribonucleotides, peptide-nucleic acids (PNAs), and the like. Such polynucleotides can be synthesized, for example, using an automated DNA synthesizer. The term "nucleic acid" typically refers to large polynucleotides. The term "oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

Conventional notation is used herein to describe polynucleotide sequences: the left-hand end of a single-stranded polynucleotide sequence is the 5'-end; the left-hand direction of a double-stranded polynucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand"; sequences on the DNA strand having the same sequence as an mRNA transcribed from that DNA and which are located 5' to the 5'-end of the RNA transcript are referred to as "upstream sequences"; sequences on the DNA strand having the same sequence as the RNA and which are 3' to the 3' end of the coding RNA transcript are referred to as "downstream sequences."

"Complementary" refers to the topological compatibility or matching together of interacting surfaces of two polynucleotides. Thus, the two molecules can be described as complementary, and furthermore, the contact surface characteristics are complementary to each other. A first polynucleotide is complementary to a second polynucleotide if the nucleotide sequence of the first polynucleotide is substantially identical to the nucleotide sequence of the polynucleotide binding partner of the second polynucleotide, or if the first polynucleotide can hybridize to the second polynucleotide under stringent hybridization conditions.

"Hybridizing specifically to" or "specific hybridization" or "selectively hybridize to", refers to the binding, duplexing, or hybridizing of a nucleic acid molecule preferentially to a particular nucleotide sequence under stringent conditions when that sequence is present in a complex mixture (e.g., total cellular) DNA or RNA. The term "stringent conditions" refers to conditions under which a probe will hybridize preferentially to its target subsequence, and to a lesser extent to, or not at all to, other sequences. "Stringent hybridization" and "stringent hybridization wash conditions" in the context of nucleic acid hybridization experiments such as Southern and northern hybridizations are sequence-dependent, and are different under different environmental parameters. An extensive guide to the hybridization of nucleic acids can be found in Tijssen, 1993, Laboratory Techniques in Biochemistry and Molecular Biology—Hybridization with Nucleic Acid Probes, part I, chapter 2, "Overview of principles of hybridization and the strategy of nucleic acid probe assays", Elsevier, N.Y.; Sambrook et al., 2001, Molecular Cloning: A Laboratory Manual, Cold Spring Harbor Laboratory, 3.sup.rd ed., NY; and Ausubel et al., eds., Current Edition, Current Protocols in Molecular Biology, Greene Publishing Associates and Wiley Interscience, NY.

Generally, highly stringent hybridization and wash conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Very stringent conditions are selected to be equal to the Tm for a particular probe. An example of stringent hybridization conditions for hybridization of complementary nucleic acids which have more than about 100 complementary residues on a filter in a Southern or northern blot is 50% formalin with 1 mg of heparin at 42° C., with the hybridization being carried out overnight. An example of highly stringent wash conditions is 0.15 M NaCl at 72° C. for about 15 minutes. An example of stringent wash conditions is a 0.2×SSC wash at 65° C. for 15 minutes. See Sambrook et al. for a description of SSC buffer. A high stringency wash can be preceded by a low stringency wash to remove background probe signal. An exemplary medium stringency wash for a duplex of, e.g., more than about 100 nucleotides, is 1×SSC at 45° C. for 15 minutes. An exemplary low stringency wash for a duplex of, e.g., more than about 100 nucleotides, is 4-6×SSC at 40° C. for 15 minutes. In general, a signal to noise ratio of 2× (or higher) than that observed for an unrelated probe in the particular hybridization assay indicates detection of a specific hybridization.

"Primer" refers to a polynucleotide that is capable of specifically hybridizing to a designated polynucleotide template and providing a point of initiation for synthesis of a complementary polynucleotide. Such synthesis occurs when the polynucleotide primer is placed under conditions in which synthesis is induced, i.e., in the presence of nucleotides, a complementary polynucleotide template, and an agent for polymerization such as DNA polymerase. A primer is typically single-stranded, but can be double-stranded. Primers are typically deoxyribonucleic acids, but a wide variety of synthetic and naturally occurring primers are useful for many applications. A primer is complementary to the template to which it is designed to hybridize to serve as a site for the initiation of synthesis, but need not reflect the exact sequence of the template. In such a case, specific hybridization of the primer to the template depends on the stringency of the hybridization conditions. Primers can be labeled with, e.g., chromogenic, radioactive, or fluorescent moieties and used as detectable moieties.

"Probe," when used in reference to a polynucleotide, refers to a polynucleotide that is capable of specifically hybridizing to a designated sequence of another polynucleotide. A probe specifically hybridizes to a target complementary polynucleotide, but need not reflect the exact complementary sequence of the template. In such a case, specific hybridization of the probe to the target depends on the stringency of the hybridization conditions. Probes can be labeled with, e.g., chromogenic, radioactive, or fluorescent moieties and used as detectable moieties. In instances where a probe provides a point of initiation for synthesis of a complementary polynucleotide, a probe can also be a primer.

A "vector" is a polynucleotide that can be used to introduce other nucleic acids linked to it into a cell. One type of vector is a "plasmid," which refers to a linear or circular double stranded DNA molecule into which additional nucleic acid segments can be ligated. Another type of vector is a viral vector (e.g., replication defective retroviruses, adenoviruses and adeno-associated viruses), wherein additional DNA segments can be introduced into the viral genome. Certain vectors are capable of autonomous replication in a host cell into which they are introduced (e.g., bacterial vectors comprising a bacterial origin of replication and episomal mammalian vectors). Other vectors (e.g., non-episomal mammalian vectors) are integrated into the genome of a host cell upon introduction into the host cell, and thereby are replicated along with the host genome. An "expression vector" is a type of vector that can direct the expression of a chosen polynucleotide.

A "regulatory sequence" is a nucleic acid that affects the expression (e.g., the level, timing, or location of expression) of a nucleic acid to which it is operably linked. The regulatory sequence can, for example, exert its effects directly on the regulated nucleic acid, or through the action of one or more other molecules (e.g., polypeptides that bind to the regulatory sequence and/or the nucleic acid). Examples of regulatory sequences include promoters, enhancers and other expression control elements (e.g., polyadenylation signals). Further examples of regulatory sequences are described in, for example, Goeddel, 1990, Gene Expression Technology: Methods in Enzymology 185, Academic Press, San Diego, Calif. and Baron et al., 1995, Nucleic Acids Res. 23:3605-06. A nucleotide sequence is "operably linked" to a regulatory sequence if the regulatory sequence affects the expression (e.g., the level, timing, or location of expression) of the nucleotide sequence.

Generally, a cell of the present disclosure can be a eukaryotic cell or a prokaryotic cell. A cell can be an epithelial cell. An epithelial cell can be a polarized epithelial cell (e.g., a Caco-2 cell or a Chinese Hamster Ovary (CHO) cell). A cell can be an animal cell or a plant cell. An animal cell can include a cell from a marine invertebrate, fish, insects, amphibian, reptile, or mammal. A mammalian cell can be obtained from a primate, ape, equine, bovine, porcine, canine, feline, or rodent. A mammal can be a primate, ape, dog, cat, rabbit, ferret, or the like. A rodent can be a mouse, rat, hamster, gerbil, hamster, chinchilla, or guinea pig. A bird cell can be from a canary, parakeet or parrots. A reptile cell can be from a turtles, lizard or snake. A fish cell can be from a tropical fish. For example, the fish cell can be from a zebrafish (e.g., *Danino rerio*). A worm cell can be from a nematode (e.g., *C. elegans*). An amphibian cell can be from a frog. An arthropod cell can be from a tarantula or hermit crab.

A mammalian cell can also include cells obtained from a primate (e.g., a human or a non-human primate). A mammalian cell can include a blood cell, a stem cell, an epithelial cell, connective tissue cell, hormone secreting cell, a nerve cell, a skeletal muscle cell, or an immune system cell. In preferred embodiments, the methods and compositions of the present disclosure are used in combination with one or more mammalian blood cells.

A "host cell" is a cell that can be used to express a polynucleotide of the disclosure. A host cell can be a prokaryote, for example, *E. coli*, or it can be a eukaryote, for example, a single-celled eukaryote (e.g., a yeast or other fungus), a plant cell (e.g., a tobacco or tomato plant cell), an animal cell (e.g., a human cell, a monkey cell, a hamster cell, a rat cell, a mouse cell, or an insect cell) or a hybridoma. Typically, a host cell is a cultured cell that can be transformed or transfected with a polypeptide-encoding series of nucleic acids, which can then be expressed in the host cell. The phrase "recombinant host cell" can be used to denote a host cell that has been transformed or transfected with a polypeptide-encoding series of nucleic acids to be expressed. A host cell also can be a cell that comprises series of nucleic acids but does not express these at a desired level unless a regulatory sequence is introduced into the host cell such that it becomes operably linked with the nucleic acid. It is understood that the term host cell refers not only to the particular subject cell but to the progeny or potential progeny of such a cell. Because certain modifications can occur in succeeding generations due to, e.g., mutation or environmental influence, such progeny may not, in fact, be identical to the parent cell, but are still included within the scope of the term as used herein.

The term "isolated molecule" (where the molecule is, for example, a polypeptide such as a carrier or a delivery construct, or a polynucleotide) is a molecule that by virtue of its origin or source of derivation (1) is not associated with naturally associated components that accompany it in its native state, (2) is substantially free of other molecules from the same species (3) is expressed by a cell from a different species, or (4) does not occur in nature. Thus, a molecule that is chemically synthesized, or expressed in a cellular system different from the cell from which it naturally originates, will be "isolated" from its naturally associated components. A molecule also can be rendered substantially free of naturally associated components by isolation, using purification techniques well known in the art. Molecule purity or homogeneity can be assayed by a number of means well known in the art. For example, the purity of a polypeptide sample can be assayed using polyacrylamide gel electrophoresis and staining of the gel to visualize the polypeptide using techniques well known in the art. For certain purposes, higher resolution separation techniques can be provided by using HPLC or other means well known in the art for purification.

As disclosed herein, the terms "complete transcytosis", "efficient transcytosis", or "transcytosis", or "transport" can be used interchangeably and can refer to the transport of toxin-derived delivery constructs across epithelial layers such as the gut epithelium. These terms can refer to a complete transport of these construct as determined in the respective experiment using various techniques to assess transcytosis efficiency, such as fluorescence microscopy.

As used herein, the terms "comprising" and "having" can be used interchangeably. For example, the terms "a polypeptide comprising an amino acid sequence of SEQ ID NO: 1" and "a polypeptide having an amino acid sequence of SEQ ID NO: 1" can be used interchangeably.

A protein or polypeptide is "substantially pure," "substantially homogeneous," or "substantially purified" when at least about 60% to 75% of a sample exhibits a single species of polypeptide. The polypeptide or protein can be monomeric or multimeric. A substantially pure polypeptide or protein will typically comprise about 50%, 60%, 70%, 80% or 90% W/W of a protein sample, more usually about 95%, and e.g., will be over 99% pure. Protein purity or homogeneity can be indicated by a number of means well known in the art, such as polyacrylamide gel electrophoresis of a protein sample, followed by visualizing a single polypeptide band upon staining the gel with a stain well known in the art. For certain purposes, higher resolution separation techniques can be provided by using HPLC or other means well known in the art for purification.

As disclosed herein, a "spacer" refers to a molecule that joins two other molecules, either covalently, or through ionic, van der Waals or hydrogen bonds, e.g., a nucleic acid molecule that hybridizes to one complementary sequence at the 5' end and to another complementary sequence at the 3' end, thus joining two non-complementary sequences. A "cleavable spacer" refers to a spacer that can be degraded or otherwise severed to separate the two components connected by the cleavable spacer. Cleavable spacers are generally cleaved by enzymes, typically peptidases, proteases, nucleases, lipases, and the like. Cleavable spacers can also be cleaved by environmental cues, such as, for example, specific enzymatic activities, changes in temperature, pH, salt concentration, etc. when there is such a change in environment following transcytosis of the delivery constructs across a polarized epithelial membrane. Thus, a heterologous cargo (e.g., a biologically active cargo) can be released from the carrier in a pH-dependent and/or enzyme-dependent manner.

"Pharmaceutical composition" refers to a composition suitable for pharmaceutical use in an animal. A pharmaceutical composition comprises a pharmacologically effective amount of an active agent and a pharmaceutically acceptable carrier. "Pharmacologically effective amount" refers to that amount of an agent effective to produce the intended pharmacological result.

"Pharmaceutically acceptable carrier" refers to any of the standard pharmaceutical carriers, vehicles, buffers, and excipients, such as a phosphate buffered saline solution, 5% aqueous solution of dextrose, and emulsions, such as an oil/water or water/oil emulsion, and various types of wetting agents and/or adjuvants. Suitable pharmaceutical carriers and formulations are described in Remington's Pharmaceutical Sciences, 21st Ed. 2005, Mack Publishing Co, Easton. A "pharmaceutically acceptable salt" is a salt that can be formulated into a compound for pharmaceutical use including, e.g., metal salts (sodium, potassium, magnesium, calcium, etc.) and salts of ammonia or organic amines.

The terms "treat", "treating" and "treatment" refer to a method of alleviating or abrogating a biological disorder and/or at least one of its attendant symptoms. As used herein, to "alleviate" a disease, disorder or condition means reducing the severity and/or occurrence frequency of the symptoms of the disease, disorder, or condition. Further, references herein to "treatment" include references to curative, palliative and prophylactic treatment.

As used herein, the term "subject," generally refers to a human or to another animal. A subject can be of any age, for example, a subject can be an infant, a toddler, a child, a pre-adolescent, an adolescent, an adult, or an elderly individual.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are in relation to the other endpoint, and independently of the other endpoint. The term "about" as used herein refers to a range that is 15% plus or minus from a stated numerical value within the context of the particular usage. For example, about 10 can include a range from 8.5 to 11.5.

Carriers

Contemplated herein are various carriers that can be used to deliver a cargo to a location within a cell (e.g., epithelial cell) or across a cell (e.g., epithelial cell). Such carriers can be a small molecule, a polypeptide, an aptamer, an antibody, a nucleic acid a fragment of any of the above, or a combination of any of the above.

Examples of a polypeptide contemplated herein include any polypeptide that is derived from a domain I of an exotoxin and lacking a domain II, a domain Ib and a domain III of the exotoxin. Such domain I's include but are not limited to amino acid sequences set forth in SEQ ID NO: 4, SEQ ID NO: 5, and SEQ ID NO: 137. Polypeptides that are derived from any of the above sequences include those that have a high sequence homology to the above sequences (e.g., greater than 80, 85, 90, 95, 96, 97, 98, or 99% sequence identity as defined in more detail herein). Polypeptides that are derived from any of the above sequences include those that are fragments of the above which function to deliver a cargo to a defined location within a cell or across a cell (e.g., epithelial cell).

Examples of small molecules contemplated herein include those that are rationally designed to interact with one or more of the following receptors ribophilin 1, SEC24, CK-8, TMEM132, GRP75, ERGIC-53, and/or perlecan and/or to have a similar or the same 3D structure of a domain I of an exotoxin (e.g., Cholix or PE), or a functional fragment of a domain I of an exotoxin.

Examples of antibodies, or functional binding fragments thereof, that are contemplated include those that are rationally designed to interact with one or more of the following receptors ribophilin 1, SEC24, CK-8, TMEM132, GRP75, ERGIC-53, and/or perlecan and/or to have a similar or the same 3D structure of a domain I of an exotoxin (e.g., Cholix or PE), or a functional fragment of a domain I of an exotoxin.

Examples of nucleic acids that are contemplated herein include those that are rationally designed to interact with one or more of the following receptors ribophilin 1, SEC24, CK-8, TMEM132, GRP75, ERGIC-53, and/or perlecan and/or to have a similar or the same 3D structure of a domain I of an exotoxin (e.g., Cholix or PE), or a functional fragment of a domain I of an exotoxin. The nucleic acid can be a mRNA, a siRNA, shRNA, or a cDNA.

The methods and compositions of the present disclosure are based on the inventors' surprising finding that a carrier capable of interacting with one or more endogenous receptors (e.g., ribophilin 1, SEC24, CK-8, TMEM132, GRP75, ERGIC-53, and/or perlecan) can provide rapid and efficient delivery of cargo into and/or across a cell such an epithelial cell.

The methods and compositions described herein allow rapid and efficient transport and/or delivery of cargo molecules across epithelial cells and/or to the interior (e.g., to the intracellular vesicle or compartment or the cytosol) of epithelial cells (e.g., polarized gut epithelial cells). The present disclosure provides constructs (e.g., isolated delivery constructs) that can comprise a carrier coupled to a heterologous cargo. A carrier as disclosed herein can vary in molecular size and composition as well as other physicochemical parameters such as isoelectric point, overall molecular net charge, etc. Generally, and as further described herein, a carrier can be a small molecule, a polypeptide, an aptamer, a nucleic acid, a fragment and/or any combination thereof.

A carrier can be derived from an exotoxin, e.g., any exotoxin described herein. For example, a carrier can be a non-naturally occurring form of Cholix exotoxin (Cholix) or *Pseudomonas* exotoxin A (PE) comprising only a domain I (i.e., lacking a domain II (sometimes referred to as translocation domain), a domain Ib and a domain III (sometimes referred to as cytotoxic domain)) and can be capable of transporting and/or delivering a cargo (e.g., a heterologous cargo such as biological, therapeutic, or diagnostic molecules) across intact epithelial cells (e.g., polarized gut epithelial cells) and epithelial cell barriers (e.g., Caco-2 cell monolayers or the gut epithelium of a subject) via transcytosis and/or to the interior of an epithelial cell (e.g., via apical endocytosis and subsequent endosomal sorting and trafficking).

The present disclosure provides methods and compositions comprising a carrier, wherein the carrier can be coupled to a cargo, and as such, can deliver the cargo into or across epithelial cells. The carrier can be a polypeptide, wherein the polypeptide can be derived from an exotoxin. The exotoxin can be Cholix or PE, or any combination thereof (e.g., a carrier comprising one or more domains Cholix and PE, or truncated versions thereof). Thus, a carrier as described herein can comprise elements or portions derived from both Cholix and PE, which can be referred to a chimeric carrier. As further described herein, it was surprisingly found that a Cholix domain I or a PE domain I (e.g., SEQ ID NO: 4, SEQ ID NO: 5, SEQ ID NO: 137), or a combination thereof, can be sufficient for rapid and efficient transport and delivery of cargo across an epithelial cell. Such transport and delivery may even be superior to the transcytosis function of the respective full-length Cholix or PE exotoxins (e.g., SEQ ID NO: 1, SEQ ID NO: 2 or SEQ ID NO: 135, respectively). The exotoxin-derived carrier polypeptides described herein can utilize endogenous trafficking pathways, including endogenous receptors and receptor complexes, to achieve apical-to-basal transcytosis and/or uptake into the interior of a cell, such as an epithelial cell (e.g., enterocytes). The delivery carriers of the present disclosure can access a basolateral compartment (e.g., *Lamina propria*) and/or the interior of an epithelial cell without damaging the cell or cell layer and without being altered, degraded or modified (e.g., chemically or enzymatically altered or modified). The carrier constructs (e.g., isolated delivery constructs) of the present disclosure can further utilize specific intracellular compartments during transcytosis and/or intracellular delivery to achieve the described transport efficiency.

The present disclosure provides methods and compositions that can comprise carriers that use (or interaction with) a set of endogenous proteins and receptors involved in the apical-to-basal transcytosis process across epithelial cells, such as polarized intestinal epithelial cells (e.g., enterocytes), to mediate transcytosis of a carrier coupled to a cargo from a lumen bordering the apical surface of a mucous membrane to the basolateral side of a mucous membrane. The delivery constructs disclosed herein can engage in interactions with such proteins and receptors to provide efficient transport and delivery of various cargo molecules to locations within an epithelial cell and/or across an epithelial cell to the basal side of an epithelium (e.g., a gut epithelium of a subject). The constructs described herein, such as delivery constructs, can comprise a carrier coupled to a heterologous cargo, wherein the carrier and/or the heterologous cargo can interact with proteins and/or receptors during intracellular delivery (e.g., to a supranuclear region or to a compartment located at the basal side within the epithelial cell) or during transcytosis (e.g., vesicular transcytosis). The carrier can interact with one or more proteins (e.g., receptors or enzymes). These interactions can be dynamical and/or pH-dependent. It is pointed out that the herein described interactions are examples only and are not limiting the methods and compositions of this disclosure to other interactions (e.g., with other proteins or receptors).

The compositions and methods disclosed herein provide efficient delivery and transport of various cargo molecules (e.g., small molecules as well as macromolecules) across epithelial cells and/or into epithelial cells. The carriers described herein achieve such efficient delivery of cargo in a manner that does not impair the epithelial cell barrier nor the delivery construct itself. Thus, the functional properties of the delivery constructs (e.g., those of the carrier as well as the functions of the cargo) can be retained during transport, allowing a fast and efficient delivery of such cargo. The presently described carriers utilize endogenous trafficking pathways to deliver exogenous or endogenous cargo molecules to specific locations. Those locations can be inside an epithelial cell and/or in basolateral compartments outside epithelial cells on the basal side, e.g., the *Lamina propria*.

The carriers of the present disclosure comprise can be derived from an exotoxin. Bacterial protein toxins are well known in the art, and are discussed in such sources as Burns, D., et al., eds., BACTERIAL PROTEIN TOXINS, ASM Press, Herndon Va. (2003), Aktories, K. and Just, I., eds., BACTERIAL PROTEIN TOXINS (HANDBOOK OF EXPERIMENTAL PHARMACOLOGY), Springer-Verlag, Berlin, Germany (2000), and Alouf, J. and Popoff, M., eds., THE COMPREHENSIVE SOURCEBOOK OF BACTERIAL PROTEIN TOXINS, Academic Press, Inc., San Diego, Calif. (3rd Ed., 2006).

As further described herein, an exotoxin can comprise one or more domains. As disclosed herein, an exotoxin can be Cholix or PE. For Cholix, the following nomenclature is used herein to describe its various domains (N- to C-terminus) and using the functional Cholix variant having the amino acid sequence set forth in SEQ ID NO: 1 as a reference sequence: (i) domain I (amino acid residues 1-265, SEQ ID NO: 4), (ii) domain II (amino acid residues 266-386, SEQ ID NO: 126), (iii) domain Ib (amino acid residues 387-425, SEQ ID NO: 127), and (iv) domain III (amino acid residues 426-634, SEQ ID NO: 128). For PE, the following nomenclature is used herein to describe its various domains (N- to C-terminus) and using the functional PE variant having the amino acid sequence set forth in SEQ ID NO: 135 as a reference sequence: (i) domain I (amino acid residues 1-252, SEQ ID NO: 137), (ii) domain II (amino acid residues 253-364, SEQ ID NO: 138), (iii) domain Ib (amino acid residues 365-404, SEQ ID NO: 139), and (iv) domain III (amino acid residues 405-613, SEQ ID NO: 140). Moreover, the ranges of amino acid residues defining these domains can be flexible and variations of about 5-10 amino acid residues may still fall within the scope of this disclosure, e.g., describing an amino acid sequence comprising the amino acid residues 5-265 or 5-270, or 1-260, or 5-260 of full-length Cholix may still be understood as a Cholix domain I and so forth. As disclosed herein, the terms "domain I" and "receptor binding domain" of an exotoxin can be used interchangeably. As disclosed herein, the terms "domain II" and "translocation domain" of an exotoxin can be used interchangeably. As disclosed herein, the terms "domain III", "catalytic domain" and "cytotoxic domain" of an exotoxin can be used interchangeably.

*Pseudomonas aeruginosa* exotoxin A (PE), *Corynebacterium diphtheria* Diphtheria carrier (DT), and *Vibrio cholera* Cholix make up a family of bacterial protein toxins that act as ADP-ribosyltransferases. Thus, the carrier can be derived from a Cholix toxin. The carrier can be derived from a PE.

A Cholix polypeptide as described herein may be rendered non-toxic by one or more amino acid substitutions. A Cholix derived polypeptide or carrier as described herein may be rendered non-toxic by substituting a glutamic acid residue at position 581 of the amino acid sequence set forth in SEQ ID NO: 2 with alanine, resulting in a Cholix construct comprising an amino acid sequence set forth in SEQ ID NO: 3.

As further described herein, Cholix and PE are organized into distinct domains (I, II, Ib, and III) that are denoted based upon their structural relationships. Domain I appears to facilitate exotoxin internalization and transcytosis, whereas domains II, Ib, and III provide other functions as, for example, enzymatic activity in case of domain III that can ADP-ribosylate elongation factor 2 to induce cell apoptosis via blockade of protein synthesis. It has previously been unknown what components of PE and Cholix proteins are involved in the trans-epithelial transcytosis process.

Cholix is secreted by *Vibrio cholera* as a 70.7 kDa protein composed of three prominent globular domains (Ia, II, and III) and one small subdomain (Ib) connecting domains II and III similar to the structure of PE (Jorgensen, R. et al., J Biol Chem 283(16):10671-10678, 2008). Mature Cholix comprises a genus of functional variants, wherein each variant can differ in one or more amino acid residues compared to another variant. However, all Cholix variants disclosed herein and encompassed in this disclosure are functional Cholix variants. As used herein, Cholix is a 634-residue protein, and two functional variants are specifically included herein, which are those having the amino acid sequences set forth in SEQ ID NO: 1 and SEQ ID NO: 1. A nucleic acid encoding the mature Cholix as used herein is set forth in SEQ ID NO: 134.

*Pseudomonas* exotoxin A or "PE" is secreted by *Pseudomonas aeruginosa* as a 67 kDa protein composed of three prominent globular domains (Ia, II, and III) and one small subdomain (Ib) connecting domains II and III (see Allured et. al., Proc. Natl. Acad. Sci. 83:1320 1324, 1986). Mature PE as used herein is a 613-residue protein, whose sequence is set forth in SEQ ID NO: 134. A nucleic acid encoding mature PE as used herein is set forth in SEQ ID NO: 135.

The amino acid sequence of the mature Cholix toxin is set forth in SEQ ID NO: 1 and is used as the reference sequence, unless specified otherwise. For example, the amino acid sequence set forth in SEQ ID NO: 4 contains the amino acid residues 1-265 of the amino acid sequence of mature Cholix toxin set forth in SEQ ID NO: 1 and is defined as Cholix domain I. Thus, the polypeptide having the amino acid sequence set forth in SEQ ID NO: 4 can also be described as "$Chx^{1-265}$" (or "$Cholix^{1-265}$" or "$Cholix^{265}$" or "Cholix domain I"). In addition to the Cholix reference sequence set forth in SEQ ID NO: 1, any other, functionally active, Cholix exotoxin variants are encompassed in the present disclosure, e.g., those that comprise a consensus sequence defining the functional activity of the Cholix exotoxins. (See e.g., Awasthi et al. Novel Cholix toxin variants, ADP-ribosylating toxins in *Vibrio Cholerae* Non-O1/Non-O139 strains, and their pathogenicity, Infection and Immunity, 81(2), p. 531-541 (2013)). As an example, the polypeptide having the amino acid sequence set forth in SEQ ID NO: 2 is a functional variant of SEQ ID NO: 1. As such, a domain I derived from that Cholix exotoxin sequence, or a truncated version thereof, can be used as a carrier for the rapid and efficient delivery of cargo. Using the nomenclature described herein with the reference sequence being SEQ ID NO: 1, a domain I polypeptide of the Cholix exotoxin with SEQ ID NO: 2 can also be described as amino acid residues 14 of SEQ ID NO: 2+$Cholix^{5-265}$.

In other cases, and as described herein, a first carrier and a second carrier are produced in a different expression system (e.g., a bacterial or a mammalian expression system). Bacterial expression systems include *E. coli*, and mammalian expression systems include CHO cells, for example. A bacterially produced polypeptide can comprise an N-cap, wherein the N-cap can comprise one more modifications at the N-terminal of the polypeptide. An N-cap can comprise an N-terminal methionine residue. Examples of Cholix domain I derived carrier polypeptides that can be bacterially produced and that comprise such N-terminal methionine include those comprising the amino acid sequences set forth in SEQ ID NO: 5, SEQ ID NO: 7, SEQ ID NO: 9, SEQ ID NO: 11, SEQ ID NO: 31, SEQ ID NO: 107, and SEQ ID NO: 125.

The present disclosure contemplates isolated non-naturally occurring and bacterial toxin derived carriers (e.g., an exotoxin derived) that can be coupled to a cargo (e.g., a biologically active); wherein the carrier is capable of delivering the cargo (e.g., a biologically active) via transcytosis transport across the intestinal epithelium. The carrier can be derived from a domain I of an exotoxin (e.g., Cholix or PE). A carrier that is derived form a domain I of an exotoxin can lack a domain II (e.g., SEQ ID NO: 126 or SEQ ID NO: 138), a domain Ib (e.g., SEQ ID NO: 127 or SEQ ID NO: 139), or a domain III (e.g., SEQ ID NO: 128 or SEQ ID NO: 140) of an exotoxin (e.g., Cholix or PE).

As described herein, a carrier that "lacks" a domain II, domain Ib, and a domain III of an exotoxin (e.g., Cholix and/or PE) can still comprise a portion of the domain II, a domain Ib, or the domain III of the exotoxin, or a combination thereof. Thus, the term "lacking" as referred to herein means that a carrier does not comprise a complete domain II, a complete domain Ib, or a complete domain III. A carrier can comprise no more than 70% of the amino acid residues of a domain II, a domain Ib, or a domain III of an exotoxin. For example, a carrier can comprise a Cholix domain I (e.g., SEQ ID NO: 4 or SEQ ID NO: 5) or a truncated version thereof, and further comprise the amino acid residues 1-82 of Cholix domain II (SEQ ID NO: 126). A carrier can comprise no more than 60% of the amino acid residues of a domain II, a domain Ib, or a domain III of an exotoxin. A carrier can comprise no more than 50% of the amino acid residues of a domain II, a domain Ib, or a domain III of an exotoxin. A carrier can comprise no more than 25% of the amino acid residues of a domain II, a domain Ib, or a domain III of an exotoxin. A carrier can comprise no more than 10% of the amino acid residues of a domain II, a domain Ib, or a domain III of an exotoxin.

The present disclosure contemplates isolated non-naturally occurring and bacterial toxin derived carriers (e.g., an exotoxin derived) that can be coupled to a cargo (e.g., a biologically active); wherein the carrier is capable of delivering the cargo (e.g., a biologically active) to the interior of an epithelial cell, such as an intracellular vesicle or compartment or the cytosol. Regions and/or compartments in the interior of an epithelial cell can include regions and/or compartments on the apical side of the interior of an epithelial cell, regions and/or compartments on the basal side of the interior of an epithelial cell, supranuclear regions of an epithelial cell, or any combination thereof. The epithelial cell can be a polarized gut epithelial cell. The polarized gut epithelial cell can be part of a polarized epithelial cell monolayer (e.g., comprising Caco-2 cells) or it can be part of a gut epithelium of a subject (e.g., a rodent or a human).

A carrier can be derived from a bacterial carrier such as an exotoxin (e.g., Cholix and/or PE) and can be derived from a domain I of said exotoxin and can lack a domain II (e.g., SEQ ID NO: 126 or SEQ ID NO: 138), a domain Ib (e.g., SEQ ID NO: 127 or SEQ ID NO: 139), or a domain III (e.g., SEQ ID NO: 128 or SEQ ID NO: 140) of an exotoxin (e.g., Cholix or PE). The carrier can comprise a receptor binding domain or binding fragment, which can be a domain, region, or fragment within the exotoxin derived domain I, and which allows binding of the delivery construct to one or more selective or non-selective receptors on the luminal surface of an epithelial cell. A receptor can be a selective receptor or a non-selective receptor, such as a non-selective scavenger receptor on the luminal surface of intestinal epithelial cells. The one or more receptors that a carrier can interact with on the surface of an epithelial cell and/or during endocytosis can include a low density lipoprotein receptor-related protein 1 (LRP1) or a transmembrane protein 132 (TMEM132). Thus, the delivery construct can bind to one or more cell surface receptor that can be present on the apical membrane of an epithelial cell with sufficient affinity to allow endocytosis. The delivery construct can bind to any receptor known to be present on the apical membrane of an epithelial cell by one of skill in the art without limitation. The carrier can bind to LRP1. The carrier can bind to TMEM132. Alternatively, the carrier can bind to LRP1 and TMEM132.

A carrier can be derived from a domain I of an exotoxin. The exotoxin is selected from the group consisting of Cholix and PE. A carrier as described herein is derived from a domain I of an exotoxin, wherein the exotoxin is Cholix. Thus, a carrier as described herein can comprise an amino acid sequence that is derived from that of Cholix domain I (e.g., SEQ ID NO: 4 or SEQ ID NO: 5). A Cholix Domain I (e.g., SEQ ID NO: 4) can comprise amino acids 1-265 of SEQ ID NO: 1 or it can comprise amino acid sequence set forth in SEQ ID NO: 5 (e.g., when bacterially produced comprising an N-terminal methionine residue) and can be described as a "receptor binding domain" that functions as a ligand for a cell surface receptor and mediates Cholix binding and endocytosis. A carrier can comprise an amino acid sequence with greater than 50% homology to any one of SEQ ID NO: 4-SEQ ID NO: 125. A carrier can comprise an amino acid sequence with greater than 60% homology to any one of SEQ ID NO: 4-SEQ ID NO: 125. A carrier can comprise an amino acid sequence with greater than 70% homology to any one of SEQ ID NO: 4-SEQ ID NO: 125. A carrier can comprise an amino acid sequence with greater than 80% homology to any one of SEQ ID NO: 4-SEQ ID NO: 125. A carrier can comprise an amino acid sequence with greater than 90% homology to any one of SEQ ID NO: 4-SEQ ID NO: 125. A carrier can comprise an amino acid sequence with greater than 95% homology to any one of SEQ ID NO: 4-SEQ ID NO: 125. Conservative or non-conservative substitutions can be made to an amino acid sequence of any one of SEQ ID NO: 4-SEQ ID NO: 125. As described herein, an amino acid residue substitution will be identified by reference to the particular amino acid substitution at a specific amino acid residue. Thus, e.g., the term "S30A" indicates that the "S" (serine, in standard single letter code) residue at position 30 in SEQ ID NO: 4 has been substituted with an "A" (alanine, in standard single letter code), and the modified carrier will be identified as "Cholix$^{S30A}$". A carrier can be a truncated version of a Cholix domain I sequence set forth in SEQ ID NO: 4 or SEQ ID NO: 5. Thus, a carrier comprising a truncated version of a Cholix domain I can comprise an amino acid sequence set forth in any one of SEQ ID NO: 6-SEQ ID NO: 125. A carrier can comprise an amino acid sequence of any one of SEQ ID NO: 4-SEQ ID NO: 125, wherein one or more amino residues of such sequence is deleted. A carrier can comprise an amino acid sequence of any one of SEQ ID NO: 4-SEQ ID NO: 125, wherein one or more amino acid residues can be substituted with another amino acid. As described herein, a truncated carrier can be identified by reference to the amino acid residues comprising the truncated toxin, e.g., a truncated Cholix carrier consisting of amino acid residues 1-260 of SEQ ID NO: 4 will be identified as Cholix$^{260}$ and so forth, according to nomenclature described herein.

Exemplary nucleotide and amino acid sequences of carriers as described herein are shown below in TABLE 2. In various embodiments, a carrier comprises any of the amino acid sequences shown in TABLE 2, or fragment, or a combination thereof.

TABLE 2

Exemplary Nucleotide and Amino Acid Sequences of Carriers

| SEQ ID NO | Sequence |
| --- | --- |
| SEQ ID NO: 1 | VEEALNIFDECRSPCSLTPEPGKPIQSKLSIPSDVVLDEGVLYYS<br>MTINDEQNDIKDEDKGESIITIGEFATVRATRHYVNQDAPFGVI<br>HLDITTENGTKTYSYNRKEGEFAINWLVPIGEDSPASIKISVDEL<br>DQQRNIIEVPKLYSIDLDNQTLEQWKTQGNVSFSVTRPEHNIAI<br>SWPSVSYKAAQKEGSRHKRWAHWHTGLALCWLVPMDAIYN<br>YITQQNCTLGDNWFGGSYETVAGTPKVITVKQGIEQKPVEQRI<br>HFSKGNAMSALAAHRVCGVPLETLARSRKPRDLTDDLSCAYQ<br>AQNIVSLFVATRILFSHLDSVFTLNLDEQEPEVAERLSDLRRINE<br>NNPGMVTQVLTVARQIYNDYVTHHPGLTPEQTSAGAQAADIL<br>SLFCPDADKSCVASNNDQANINIESRSGRSYLPENRAVITPQGV<br>TNWTYQELEATHQALTREGYVFVGYHGTNHVAAQTIVNRIAP<br>VPRGNNTENEEKWGGLYVATHAEVAHGYARIKEGTGEYGLP<br>TRAERDARGVMLRVYIPRASLERFYRTNTPLENAEEHITQVIG<br>HSLPLRNEAFTGPESAGGEDETVIGWDMAIHAVAIPSTIPGNAY<br>EELAIDEEAVAKEQSISTKPPYKERKDELK |
| SEQ ID NO: 2 | VEDELNIFDECRSPCSLTPEPGKPIQSKLSIPSDVVLDEGVLYYS<br>MTINDEQNDIKDEDKGESIITIGEFATVRATRHYVNQDAPFGVI<br>HLDITTENGTKTYSYNRKEGEFAINWLVPIGEDSPASIKISVDEL<br>DQQRNIIEVPKLYSIDLDNQTLEQWKTQGNVSFSVTRPEHNIAI<br>SWPSVSYKAAQKEGSRHKRWAHWHTGLALCWLVPMDAIYN<br>YITQQNCTLGDNWFGGSYETVAGTPKVITVKQGIEQKPVEQRI<br>HFSKGNAMSALAAHRVCGVPLETLARSRKPRDLTDDLSCAYQ<br>AQNIVSLFVATRILFSHLDSVFTLNLDEQEPEVAERLSDLRRINE<br>NNPGMVTQVLTVARQIYNDYVTHHPGLTPEQTSAGAQAADIL<br>SLFCPDADKSCVASNNDQANINIESRSGRSYLPENRAVITPQGV<br>TNWTYQELEATHQALTREGYVFVGYHGTNHVAAQTIVNRIAP<br>VPRGNNTENEEKWGGLYVATHAEVAHGYARIKEGTGEYGLP<br>TRAERDARGVMLRVYIPRASLERFYRTNTPLENAEEHITQVIG<br>HSLPLRNEAFTGPESAGGEDETVIGWDMAIHAVAIPSTIPGNAY<br>EELAIDEEAVAKEQSISTKPPYKERKDELK |
| SEQ ID NO: 3 | VEDELNIFDECRSPCSLTPEPGKPIQSKLSIPSDVVLDEGVLYYS<br>MTINDEQNDIKDEDKGESIITIGEFATVRATRHYVNQDAPFGVI<br>HLDITTENGTKTYSYNRKEGEFAINWLVPIGEDSPASIKISVDEL<br>DQQRNIIEVPKLYSIDLDNQTLEQWKTQGNVSFSVTRPEHNIAI<br>SWPSVSYKAAQKEGSRHKRWAHWHTGLALCWLVPMDAIYN<br>YITQQNCTLGDNWFGGSYETVAGTPKVITVKQGIEQKPVEQRI<br>HFSKGNAMSALAAHRVCGVPLETLARSRKPRDLTDDLSCAYQ<br>AQNIVSLFVATRILFSHLDSVFTLNLDEQEPEVAERLSDLRRINE |

TABLE 2-continued

Exemplary Nucleotide and Amino Acid Sequences of Carriers

| SEQ ID NO | Sequence |
|---|---|
| | NNPGMVTQVLTVARQIYNDYVTHHPGLTPEQTSAGAQAADIL<br>SLFCPDADKSCVASNNDQANINIESRSGRSYLPENRAVITPQGV<br>TNWTYQELEATHQALTREGYVFVGYHGTNHVAAQTIVNRIAP<br>VPRGNNTENEEKWGGLYVATHAEVAHGYARIKEGTGEYGLP<br>TRAERDARGVMLRVYIPRASLERFYRTNTPLENAEEHITQVIG<br>HSLPLRNEAFTGPESAGGEDATVIGWDMAIHAVAIPSTIPGNA<br>YEELAIDEEAVAKEQSISTKPPYKERKDELK |
| SEQ ID NO: 4 | VEEALNIFDECRSPCSLTPEPGKPIQSKLSIPSDVVLDEGVLYYS<br>MTINDEQNDIKDEDKGESIITIGEFATVRATRHYVNQDAPFGVI<br>HLDITTENGTKTYSYNRKEGEFAINWLVPIGEDSPASIKISVDEL<br>DQQRNIIEVPKLYSIDLDNQTLEQWKTQGNVSFSVTRPEHNIAI<br>SWPSVSYKAAQKEGSRHKRWAHWHTGLALCWLVPMDAIYN<br>YITQQNCTLGDNWFGGSYETVAGTPKVITVKQGIEQKPVEQRI<br>HFSK |
| SEQ ID NO: 5 | MVEEALNIFDECRSPCSLTPEPGKPIQSKLSIPSDVVLDEGVLYY<br>SMTINDEQNDIKDEDKGESIITIGEFATVRATRHYVNQDAPFGV<br>IHLDITTENGTKTYSYNRKEGEFAINWLVPIGEDSPASIKISVDE<br>LDQQRNIIEVPKLYSIDLDNQTLEQWKTQGNVSFSVTRPEHNIA<br>ISWPSVSYKAAQKEGSRHKRWAHWHTGLALCWLVPMDAIYN<br>YITQQNCTLGDNWFGGSYETVAGTPKVITVKQGIEQKPVEQRI<br>HFSK |
| SEQ ID NO: 6 | VEEALNIFDECRSPCSLTPEPGKPIQSKLSIPSDVVLDEGVLYYS<br>MTINDEQNDIKDEDKGESIITIGEFATVRATRHYVNQDAPFGVI<br>HLDITTENGTKTYSYNRKEGEFAINWLVPIGEDSPASIKISVDEL<br>DQQRNIIEVPKLYSIDLDNQTLEQWKTQGNVSFSVTRPEHNIAI<br>SWPSVSYKAAQKEGSRHKRWAHWHTGLALCWLVPMDAIYN<br>YITQQNCTLGDNWFGGSYETVAGTPKVITVKQ |
| SEQ ID NO: 7 | MVEEALNIFDECRSPCSLTPEPGKPIQSKLSIPSDVVLDEGVLYY<br>SMTINDEQNDIKDEDKGESIITIGEFATVRATRHYVNQDAPFGV<br>IHLDITTENGTKTYSYNRKEGEFAINWLVPIGEDSPASIKISVDE<br>LDQQRNIIEVPKLYSIDLDNQTLEQWKTQGNVSFSVTRPEHNIA<br>ISWPSVSYKAAQKEGSRHKRWAHWHTGLALCWLVPMDAIYN<br>YITQQNCTLGDNWFGGSYETVAGTPKVITVKQ |
| SEQ ID NO: 8 | VEEALNIFDECRSPCSLTPEPGKPIQSKLSIPSDVVLDEGVLYYS<br>MTINDEQNDIKDEDKGESIITIGEFATVRATRHYVNQDAPFGVI<br>HLDITTENGTKTYSYNRKEGEFAINWLVPIGEDSPASIKISVDEL<br>DQQRNIIEVPKLYSIDLDNQTLEQWKTQGNVSFSVTRPEHNIAI<br>SWPSVSYKAAQKEGSRHKRWAHWHTGLALCWLVPMDAIYN<br>YITQQNCTLGDNWFGGSYETVAGTPK |
| SEQ ID NO: 9 | MVEEALNIFDECRSPCSLTPEPGKPIQSKLSIPSDVVLDEGVLYY<br>SMTINDEQNDIKDEDKGESIITIGEFATVRATRHYVNQDAPFGV<br>IHLDITTENGTKTYSYNRKEGEFAINWLVPIGEDSPASIKISVDE<br>LDQQRNIIEVPKLYSIDLDNQTLEQWKTQGNVSFSVTRPEHNIA<br>ISWPSVSYKAAQKEGSRHKRWAHWHTGLALCWLVPMDAIYN<br>YITQQNCTLGDNWFGGSYETVAGTPK |
| SEQ ID NO: 10 | VEEALNIFDECRSPCSLTPEPGKPIQSKLSIPSDVVLDEGVLYYS<br>MTINDEQNDIKDEDKGESIITIGEFATVRATRHYVNQDAPFGVI<br>HLDITTENGTKTYSYNRKEGEFAINWLVPIGEDSPASIKISVDEL<br>DQQRNIIEVPKLYSIDLDNQTLEQWKTQGNVSFSVTRPEHNIAI<br>SWPSVSYKAAQKEGSRHKRWAHWHTGL |
| SEQ ID NO: 11 | MVEEALNIFDECRSPCSLTPEPGKPIQSKLSIPSDVVLDEGVLYY<br>SMTINDEQNDIKDEDKGESIITIGEFATVRATRHYVNQDAPFGV<br>IHLDITTENGTKTYSYNRKEGEFAINWLVPIGEDSPASIKISVDE<br>LDQQRNIIEVPKLYSIDLDNQTLEQWKTQGNVSFSVTRPEHNIA<br>ISWPSVSYKAAQKEGSRHKRWAHWHTGL |
| SEQ ID NO: 12 | VEEALNIFDECRSPCSLTPEPGKPIQSKLSIPSDVVLDEGVLYYS<br>MTINDEQNDIKDEDKGESIITIGEFATVRATRHYVNQDAPFGVI<br>HLDITTENGTKTYSYNRKEGEFAINWLVPIGEDSPASIKISVDEL<br>DQQRNIIEVPKLYSIDLDNQTLEQWKTQGNVSFSVTRPEHNIAI<br>SWPSVSYKAAQKEGSRHKRWAHWHTG |
| SEQ ID NO: 13 | VEEALNIFDECRSPCSLTPEPGKPIQSKLSIPSDVVLDEGVLYYS<br>MTINDEQNDIKDEDKGESIITIGEFATVRATRHYVNQDAPFGVI<br>HLDITTENGTKTYSYNRKEGEFAINWLVPIGEDSPASIKISVDEL<br>DQQRNIIEVPKLYSIDLDNQTLEQWKTQGNVSFSVTRPEHNIAI<br>SWPSVSYKAAQKEGSRHKRWAHWHT |

TABLE 2-continued

Exemplary Nucleotide and Amino Acid Sequences of Carriers

| SEQ ID NO | Sequence |
| --- | --- |
| SEQ ID NO: 14 | VEEALNIFDECRSPCSLTPEPGKPIQSKLSIPSDVVLDEGVLYYS<br>MTINDEQNDIKDEDKGESIITIGEFATVRATRHYVNQDAPFGVI<br>HLDITTENGTKTYSYNRKEGEFAINWLVPIGEDSPASIKISVDEL<br>DQQRNIIEVPKLYSIDLDNQTLEQWKTQGNVSFSVTRPEHNIAI<br>SWPSVSYKAAQKEGSRHKRWAHWH |
| SEQ ID NO: 15 | VEEALNIFDECRSPCSLTPEPGKPIQSKLSIPSDVVLDEGVLYYS<br>MTINDEQNDIKDEDKGESIITIGEFATVRATRHYVNQDAPFGVI<br>HLDITTENGTKTYSYNRKEGEFAINWLVPIGEDSPASIKISVDEL<br>DQQRNIIEVPKLYSIDLDNQTLEQWKTQGNVSFSVTRPEHNIAI<br>SWPSVSYKAAQKEGSRHKRWAHW |
| SEQ ID NO: 16 | VEEALNIFDECRSPCSLTPEPGKPIQSKLSIPSDVVLDEGVLYYS<br>MTINDEQNDIKDEDKGESIITIGEFATVRATRHYVNQDAPFGVI<br>HLDITTENGTKTYSYNRKEGEFAINWLVPIGEDSPASIKISVDEL<br>DQQRNIIEVPKLYSIDLDNQTLEQWKTQGNVSFSVTRPEHNIAI<br>SWPSVSYKAAQKEGSRHKRWAH |
| SEQ ID NO: 17 | VEEALNIFDECRSPCSLTPEPGKPIQSKLSIPSDVVLDEGVLYYS<br>MTINDEQNDIKDEDKGESIITIGEFATVRATRHYVNQDAPFGVI<br>HLDITTENGTKTYSYNRKEGEFAINWLVPIGEDSPASIKISVDEL<br>DQQRNIIEVPKLYSIDLDNQTLEQWKTQGNVSFSVTRPEHNIAI<br>SWPSVSYKAAQKEGSRHKRWA |
| SEQ ID NO: 18 | VEEALNIFDECRSPCSLTPEPGKPIQSKLSIPSDVVLDEGVLYYS<br>MTINDEQNDIKDEDKGESIITIGEFATVRATRHYVNQDAPFGVI<br>HLDITTENGTKTYSYNRKEGEFAINWLVPIGEDSPASIKISVDEL<br>DQQRNIIEVPKLYSIDLDNQTLEQWKTQGNVSFSVTRPEHNIAI<br>SWPSVSYKAAQKEGSRHKRW |
| SEQ ID NO: 19 | VEEALNIFDECRSPCSLTPEPGKPIQSKLSIPSDVVLDEGVLYYS<br>MTINDEQNDIKDEDKGESIITIGEFATVRATRHYVNQDAPFGVI<br>HLDITTENGTKTYSYNRKEGEFAINWLVPIGEDSPASIKISVDEL<br>DQQRNIIEVPKLYSIDLDNQTLEQWKTQGNVSFSVTRPEHNIAI<br>SWPSVSYKAAQKEGSRHKR |
| SEQ ID NO: 20 | VEEALNIFDECRSPCSLTPEPGKPIQSKLSIPSDVVLDEGVLYYS<br>MTINDEQNDIKDEDKGESIITIGEFATVRATRHYVNQDAPFGVI<br>HLDITTENGTKTYSYNRKEGEFAINWLVPIGEDSPASIKISVDEL<br>DQQRNIIEVPKLYSIDLDNQTLEQWKTQGNVSFSVTRPEHNIAI<br>SWPSVSYKAAQKEGSRHK |
| SEQ ID NO: 21 | VEEALNIFDECRSPCSLTPEPGKPIQSKLSIPSDVVLDEGVLYYS<br>MTINDEQNDIKDEDKGESIITIGEFATVRATRHYVNQDAPFGVI<br>HLDITTENGTKTYSYNRKEGEFAINWLVPIGEDSPASIKISVDEL<br>DQQRNIIEVPKLYSIDLDNQTLEQWKTQGNVSFSVTRPEHNIAI<br>SWPSVSYKAAQKEGSRH |
| SEQ ID NO: 22 | VEEALNIFDECRSPCSLTPEPGKPIQSKLSIPSDVVLDEGVLYYS<br>MTINDEQNDIKDEDKGESIITIGEFATVRATRHYVNQDAPFGVI<br>HLDITTENGTKTYSYNRKEGEFAINWLVPIGEDSPASIKISVDEL<br>DQQRNIIEVPKLYSIDLDNQTLEQWKTQGNVSFSVTRPEHNIAI<br>SWPSVSYKAAQKEGSR |
| SEQ ID NO: 23 | VEEALNIFDECRSPCSLTPEPGKPIQSKLSIPSDVVLDEGVLYYS<br>MTINDEQNDIKDEDKGESIITIGEFATVRATRHYVNQDAPFGVI<br>HLDITTENGTKTYSYNRKEGEFAINWLVPIGEDSPASIKISVDEL<br>DQQRNIIEVPKLYSIDLDNQTLEQWKTQGNVSFSVTRPEHNIAI<br>SWPSVSYKAAQKEGS |
| SEQ ID NO: 24 | VEEALNIFDECRSPCSLTPEPGKPIQSKLSIPSDVVLDEGVLYYS<br>MTINDEQNDIKDEDKGESIITIGEFATVRATRHYVNQDAPFGVI<br>HLDITTENGTKTYSYNRKEGEFAINWLVPIGEDSPASIKISVDEL<br>DQQRNIIEVPKLYSIDLDNQTLEQWKTQGNVSFSVTRPEHNIAI<br>SWPSVSYKAAQKEG |
| SEQ ID NO: 25 | VEEALNIFDECRSPCSLTPEPGKPIQSKLSIPSDVVLDEGVLYYS<br>MTINDEQNDIKDEDKGESIITIGEFATVRATRHYVNQDAPFGVI<br>HLDITTENGTKTYSYNRKEGEFAINWLVPIGEDSPASIKISVDEL<br>DQQRNIIEVPKLYSIDLDNQTLEQWKTQGNVSFSVTRPEHNIAI<br>SWPSVSYKAAQKE |

TABLE 2-continued

Exemplary Nucleotide and Amino Acid Sequences of Carriers

| SEQ ID NO | Sequence |
| --- | --- |
| SEQ ID NO: 26 | VEEALNIFDECRSPCSLTPEPGKPIQSKLSIPSDVVLDEGVLYYS<br>MTINDEQNDIKDEDKGESIITIGEFATVRATRHYVNQDAPFGVI<br>HLDITTENGTKTYSYNRKEGEFAINWLVPIGEDSPASIKISVDEL<br>DQQRNIIEVPKLYSIDLDNQTLEQWKTQGNVSFSVTRPEHNIAI<br>SWPSVSYKAAQK |
| SEQ ID NO: 27 | VEEALNIFDECRSPCSLTPEPGKPIQSKLSIPSDVVLDEGVLYYS<br>MTINDEQNDIKDEDKGESIITIGEFATVRATRHYVNQDAPFGVI<br>HLDITTENGTKTYSYNRKEGEFAINWLVPIGEDSPASIKISVDEL<br>DQQRNIIEVPKLYSIDLDNQTLEQWKTQGNVSFSVTRPEHNIAI<br>SWPSVSYKAAQ |
| SEQ ID NO: 28 | VEEALNIFDECRSPCSLTPEPGKPIQSKLSIPSDVVLDEGVLYYS<br>MTINDEQNDIKDEDKGESIITIGEFATVRATRHYVNQDAPFGVI<br>HLDITTENGTKTYSYNRKEGEFAINWLVPIGEDSPASIKISVDEL<br>DQQRNIIEVPKLYSIDLDNQTLEQWKTQGNVSFSVTRPEHNIAI<br>SWPSVSYKAA |
| SEQ ID NO: 29 | VEEALNIFDECRSPCSLTPEPGKPIQSKLSIPSDVVLDEGVLYYS<br>MTINDEQNDIKDEDKGESIITIGEFATVRATRHYVNQDAPFGVI<br>HLDITTENGTKTYSYNRKEGEFAINWLVPIGEDSPASIKISVDEL<br>DQQRNIIEVPKLYSIDLDNQTLEQWKTQGNVSFSVTRPEHNIAI<br>SWPSVSYKA |
| SEQ ID NO: 30 | VEEALNIFDECRSPCSLTPEPGKPIQSKLSIPSDVVLDEGVLYYS<br>MTINDEQNDIKDEDKGESIITIGEFATVRATRHYVNQDAPFGVI<br>HLDITTENGTKTYSYNRKEGEFAINWLVPIGEDSPASIKISVDEL<br>DQQRNIIEVPKLYSIDLDNQTLEQWKTQGNVSFSVTRPEHNIAI<br>SWPSVSYK |
| SEQ ID NO: 31 | MVEEALNIFDECRSPCSLTPEPGKPIQSKLSIPSDVVLDEGVLYY<br>SMTINDEQNDIKDEDKGESIITIGEFATVRATRHYVNQDAPFGV<br>IHLDITTENGTKTYSYNRKEGEFAINWLVPIGEDSPASIKISVDE<br>LDQQRNIIEVPKLYSIDLDNQTLEQWKTQGNVSFSVTRPEHNIA<br>ISWPSVSYK |
| SEQ ID NO: 32 | EEALNIFDECRSPCSLTPEPGKPIQSKLSIPSDVVLDEGVLYYSM<br>TINDEQNDIKDEDKGESIITIGEFATVRATRHYVNQDAPFGVIH<br>LDITTENGTKTYSYNRKEGEFAINWLVPIGEDSPASIKISVDELD<br>QQRNIIEVPKLYSIDLDNQTLEQWKTQGNVSFSVTRPEHNIAIS<br>WPSVSYK |
| SEQ ID NO: 33 | EALNIFDECRSPCSLTPEPGKPIQSKLSIPSDVVLDEGVLYYSMT<br>INDEQNDIKDEDKGESIITIGEFATVRATRHYVNQDAPFGVIHL<br>DITTENGTKTYSYNRKEGEFAINWLVPIGEDSPASIKISVDELD<br>QQRNIIEVPKLYSIDLDNQTLEQWKTQGNVSFSVTRPEHNIAIS<br>WPSVSYK |
| SEQ ID NO: 34 | ALNIFDECRSPCSLTPEPGKPIQSKLSIPSDVVLDEGVLYYSMTI<br>NDEQNDIKDEDKGESIITIGEFATVRATRHYVNQDAPFGVIHLD<br>ITTENGTKTYSYNRKEGEFAINWLVPIGEDSPASIKISVDELDQ<br>QRNIIEVPKLYSIDLDNQTLEQWKTQGNVSFSVTRPEHNIAISW<br>PSVSYK |
| SEQ ID NO: 35 | LNIFDECRSPCSLTPEPGKPIQSKLSIPSDVVLDEGVLYYSMTIN<br>DEQNDIKDEDKGESIITIGEFATVRATRHYVNQDAPFGVIHLDI<br>TTENGTKTYSYNRKEGEFAINWLVPIGEDSPASIKISVDELDQQ<br>RNIIEVPKLYSIDLDNQTLEQWKTQGNVSFSVTRPEHNIAISWP<br>SVSYK |
| SEQ ID NO: 36 | NIFDECRSPCSLTPEPGKPIQSKLSIPSDVVLDEGVLYYSMTIND<br>EQNDIKDEDKGESIITIGEFATVRATRHYVNQDAPFGVIHLDITT<br>ENGTKTYSYNRKEGEFAINWLVPIGEDSPASIKISVDELDQQRN<br>IIEVPKLYSIDLDNQTLEQWKTQGNVSFSVTRPEHNIAISWPSVS<br>YK |
| SEQ ID NO: 37 | IFDECRSPCSLTPEPGKPIQSKLSIPSDVVLDEGVLYYSMTINDE<br>QNDIKDEDKGESIITIGEFATVRATRHYVNQDAPFGVIHLDITTE<br>NGTKTYSYNRKEGEFAINWLVPIGEDSPASIKISVDELDQQRNII<br>EVPKLYSIDLDNQTLEQWKTQGNVSFSVTRPEHNIAISWPSVS<br>YK |
| SEQ ID NO: 38 | FDECRSPCSLTPEPGKPIQSKLSIPSDVVLDEGVLYYSMTINDEQ<br>NDIKDEDKGESIITIGEFATVRATRHYVNQDAPFGVIHLDITTEN<br>GTKTYSYNRKEGEFAINWLVPIGEDSPASIKISVDELDQQRNIIE |

TABLE 2-continued

Exemplary Nucleotide and Amino Acid Sequences of Carriers

| SEQ ID NO | Sequence |
| --- | --- |
| | VPKLYSIDLDNQTLEQWKTQGNVSFSVTRPEHNIAISWPSVSY<br>K |
| SEQ ID NO: 39 | DECRSPCSLTPEPGKPIQSKLSIPSDVVLDEGVLYYSMTINDEQ<br>NDIKDEDKGESIITIGEFATVRATRHYVNQDAPFGVIHLDITTEN<br>GTKTYSYNRKEGEFAINWLVPIGEDSPASIKISVDELDQQRNIIE<br>VPKLYSIDLDNQTLEQWKTQGNVSFSVTRPEHNIAISWPSVSY<br>K |
| SEQ ID NO: 40 | ECRSPCSLTPEPGKPIQSKLSIPSDVVLDEGVLYYSMTINDEQN<br>DIKDEDKGESIITIGEFATVRATRHYVNQDAPFGVIHLDITTENG<br>TKTYSYNRKEGEFAINWLVPIGEDSPASIKISVDELDQQRNIIEV<br>PKLYSIDLDNQTLEQWKTQGNVSFSVTRPEHNIAISWPSVSYK |
| SEQ ID NO: 41 | CRSPCSLTPEPGKPIQSKLSIPSDVVLDEGVLYYSMTINDEQNDI<br>KDEDKGESIITIGEFATVRATRHYVNQDAPFGVIHLDITTENGT<br>KTYSYNRKEGEFAINWLVPIGEDSPASIKISVDELDQQRNIIEVP<br>KLYSIDLDNQTLEQWKTQGNVSFSVTRPEHNIAISWPSVSYK |
| SEQ ID NO: 42 | RSPCSLTPEPGKPIQSKLSIPSDVVLDEGVLYYSMTINDEQNDIK<br>DEDKGESIITIGEFATVRATRHYVNQDAPFGVIHLDITTENGTK<br>TYSYNRKEGEFAINWLVPIGEDSPASIKISVDELDQQRNIIEVPK<br>LYSIDLDNQTLEQWKTQGNVSFSVTRPEHNIAISWPSVSYK |
| SEQ ID NO: 43 | SPCSLTPEPGKPIQSKLSIPSDVVLDEGVLYYSMTINDEQNDIKD<br>EDKGESIITIGEFATVRATRHYVNQDAPFGVIHLDITTENGTKT<br>YSYNRKEGEFAINWLVPIGEDSPASIKISVDELDQQRNIIEVPKL<br>YSIDLDNQTLEQWKTQGNVSFSVTRPEHNIAISWPSVSYK |
| SEQ ID NO: 44 | PCSLTPEPGKPIQSKLSIPSDVVLDEGVLYYSMTINDEQNDIKDE<br>DKGESIITIGEFATVRATRHYVNQDAPFGVIHLDITTENGTKTY<br>SYNRKEGEFAINWLVPIGEDSPASIKISVDELDQQRNIIEVPKLY<br>SIDLDNQTLEQWKTQGNVSFSVTRPEHNIAISWPSVSYK |
| SEQ ID NO: 45 | CSLTPEPGKPIQSKLSIPSDVVLDEGVLYYSMTINDEQNDIKDE<br>DKGESIITIGEFATVRATRHYVNQDAPFGVIHLDITTENGTKTY<br>SYNRKEGEFAINWLVPIGEDSPASIKISVDELDQQRNIIEVPKLY<br>SIDLDNQTLEQWKTQGNVSFSVTRPEHNIAISWPSVSYK |
| SEQ ID NO: 46 | SLTPEPGKPIQSKLSIPSDVVLDEGVLYYSMTINDEQNDIKDED<br>KGESIITIGEFATVRATRHYVNQDAPFGVIHLDITTENGTKTYS<br>YNRKEGEFAINWLVPIGEDSPASIKISVDELDQQRNIIEVPKLYS<br>IDLDNQTLEQWKTQGNVSFSVTRPEHNIAISWPSVSYK |
| SEQ ID NO: 47 | LTPEPGKPIQSKLSIPSDVVLDEGVLYYSMTINDEQNDIKDEDK<br>GESIITIGEFATVRATRHYVNQDAPFGVIHLDITTENGTKTYSY<br>NRKEGEFAINWLVPIGEDSPASIKISVDELDQQRNIIEVPKLYSI<br>DLDNQTLEQWKTQGNVSFSVTRPEHNIAISWPSVSYK |
| SEQ ID NO: 48 | TPEPGKPIQSKLSIPSDVVLDEGVLYYSMTINDEQNDIKDEDKG<br>ESIITIGEFATVRATRHYVNQDAPFGVIHLDITTENGTKTYSYN<br>RKEGEFAINWLVPIGEDSPASIKISVDELDQQRNIIEVPKLYSIDL<br>DNQTLEQWKTQGNVSFSVTRPEHNIAISWPSVSYK |
| SEQ ID NO: 49 | PEPGKPIQSKLSIPSDVVLDEGVLYYSMTINDEQNDIKDEDKGE<br>SIITIGEFATVRATRHYVNQDAPFGVIHLDITTENGTKTYSYNR<br>KEGEFAINWLVPIGEDSPASIKISVDELDQQRNIIEVPKLYSIDL<br>DNQTLEQWKTQGNVSFSVTRPEHNIAISWPSVSYK |
| SEQ ID NO: 50 | EPGKPIQSKLSIPSDVVLDEGVLYYSMTINDEQNDIKDEDKGES<br>IITIGEFATVRATRHYVNQDAPFGVIHLDITTENGTKTYSYNRK<br>EGEFAINWLVPIGEDSPASIKISVDELDQQRNIIEVPKLYSIDLD<br>NQTLEQWKTQGNVSFSVTRPEHNIAISWPSVSYK |
| SEQ ID NO: 51 | PGKPIQSKLSIPSDVVLDEGVLYYSMTINDEQNDIKDEDKGESII<br>TIGEFATVRATRHYVNQDAPFGVIHLDITTENGTKTYSYNRKE<br>GEFAINWLVPIGEDSPASIKISVDELDQQRNIIEVPKLYSIDLDN<br>QTLEQWKTQGNVSFSVTRPEHNIAISWPSVSYK |
| SEQ ID NO: 52 | GKPIQSKLSIPSDVVLDEGVLYYSMTINDEQNDIKDEDKGESIIT<br>IGEFATVRATRHYVNQDAPFGVIHLDITTENGTKTYSYNRKEG<br>EFAINWLVPIGEDSPASIKISVDELDQQRNIIEVPKLYSIDLDNQ<br>TLEQWKTQGNVSFSVTRPEHNIAISWPSVSYK |
| SEQ ID NO: 53 | KPIQSKLSIPSDVVLDEGVLYYSMTINDEQNDIKDEDKGESIITI<br>GEFATVRATRHYVNQDAPFGVIHLDITTENGTKTYSYNRKEGE |

TABLE 2-continued

Exemplary Nucleotide and Amino Acid Sequences of Carriers

| SEQ ID NO | Sequence |
|---|---|
| | FAINWLVPIGEDSPASIKISVDELDQQRNIIEVPKLYSIDLDNQT<br>LEQWKTQGNVSFSVTRPEHNIAISWPSVSYK |
| SEQ ID NO: 54 | PIQSKLSIPSDVVLDEGVLYYSMTINDEQNDIKDEDKGESIITIG<br>EFATVRATRHYVNQDAPFGVIHLDITTENGTKTYSYNRKEGEF<br>AINWLVPIGEDSPASIKISVDELDQQRNIIEVPKLYSIDLDNQTL<br>EQWKTQGNVSFSVTRPEHNIAISWPSVSYK |
| SEQ ID NO: 55 | IQSKLSIPSDVVLDEGVLYYSMTINDEQNDIKDEDKGESIITIGE<br>FATVRATRHYVNQDAPFGVIELDITTENGTKTYSYNRKEGEFA<br>INWLVPIGEDSPASIKISVDELDQQRNIIEVPKLYSIDLDNQTLE<br>QWKTQGNVSFSVTRPEHNIAISWPSVSYK |
| SEQ ID NO: 56 | QSKLSIPSDVVLDEGVLYYSMTINDEQNDIKDEDKGESIITIGEF<br>ATVRATRHYVNQDAPFGVIHLDITTENGTKTYSYNRKEGEFAI<br>NWLVPIGEDSPASIKISVDELDQQRNIIEVPKLYSIDLDNQTLEQ<br>WKTQGNVSFSVTRPEHNIAISWPSVSYK |
| SEQ ID NO: 57 | SKLSIPSDVVLDEGVLYYSMTINDEQNDIKDEDKGESIITIGEFA<br>TVRATRHYVNQDAPFGVIHLDITTENGTKTYSYNRKEGEFAIN<br>WLVPIGEDSPASIKISVDELDQQRNIIEVPKLYSIDLDNQTLEQW<br>KTQGNVSFSVTRPEHNIAISWPSVSYK |
| SEQ ID NO: 58 | KLSIPSDVVLDEGVLYYSMTINDEQNDIKDEDKGESIITIGEFAT<br>VRATRHYVNQDAPFGVIHLDITTENGTKTYSYNRKEGEFAINW<br>LVPIGEDSPASIKISVDELDQQRNIIEVPKLYSIDLDNQTLEQWK<br>TQGNVSFSVTRPEHNIAISWPSVSYK |
| SEQ ID NO: 59 | LSIPSDVVLDEGVLYYSMTINDEQNDIKDEDKGESIITIGEFATV<br>RATRHYVNQDAPFGVIHLDITTENGTKTYSYNRKEGEFAINWL<br>VPIGEDSPASIKISVDELDQQRNIIEVPKLYSIDLDNQTLEQWKT<br>QGNVSFSVTRPEHNIAISWPSVSYK |
| SEQ ID NO: 60 | SIPSDVVLDEGVLYYSMTINDEQNDIKDEDKGESIITIGEFATVR<br>ATRHYVNQDAPFGVIEILDITTENGTKTYSYNRKEGEFAINWLV<br>PIGEDSPASIKISVDELDQQRNIIEVPKLYSIDLDNQTLEQWKTQ<br>GNVSFSVTRPEHNIAISWPSVSYK |
| SEQ ID NO: 61 | IPSDVVLDEGVLYYSMTINDEQNDIKDEDKGESIITIGEFATVR<br>ATRHYVNQDAPFGVIEILDITTENGTKTYSYNRKEGEFAINWLV<br>PIGEDSPASIKISVDELDQQRNIIEVPKLYSIDLDNQTLEQWKTQ<br>GNVSFSVTRPEHNIAISWPSVSYK |
| SEQ ID NO: 62 | PSDVVLDEGVLYYSMTINDEQNDIKDEDKGESIITIGEFATVRA<br>TRHYVNQDAPFGVIEILDITTENGTKTYSYNRKEGEFAINWLVP<br>IGEDSPASIKISVDELDQQRNIIEVPKLYSIDLDNQTLEQWKTQG<br>NVSFSVTRPEHNIAISWPSVSYK |
| SEQ ID NO: 63 | SDVVLDEGVLYYSMTINDEQNDIKDEDKGESIITIGEFATVRAT<br>RHYVNQDAPFGVIHLDITTENGTKTYSYNRKEGEFAINWLVPI<br>GEDSPASIKISVDELDQQRNIIEVPKLYSIDLDNQTLEQWKTQG<br>NVSFSVTRPEHNIAISWPSVSYK |
| SEQ ID NO: 64 | DVVLDEGVLYYSMTINDEQNDIKDEDKGESIITIGEFATVRATR<br>HYVNQDAPFGVIEILDITTENGTKTYSYNRKEGEFAINWLVPIG<br>EDSPASIKISVDELDQQRNIIEVPKLYSIDLDNQTLEQWKTQGN<br>VSFSVTRPEHNIAISWPSVSYK |
| SEQ ID NO: 65 | VVLDEGVLYYSMTINDEQNDIKDEDKGESIITIGEFATVRATRH<br>YVNQDAPFGVIHLDITTENGTKTYSYNRKEGEFAINWLVPIGE<br>DSPASIKISVDELDQQRNIIEVPKLYSIDLDNQTLEQWKTQGNV<br>SFSVTRPEHNIAISWPSVSYK |
| SEQ ID NO: 66 | VLDEGVLYYSMTINDEQNDIKDEDKGESIITIGEFATVRATRHY<br>VNQDAPFGVIHLDITTENGTKTYSYNRKEGEFAINWLVPIGEDS<br>PASIKISVDELDQQRNIIEVPKLYSIDLDNQTLEQWKTQGNVSF<br>SVTRPEHNIAISWPSVSYK |
| SEQ ID NO: 67 | LDEGVLYYSMTINDEQNDIKDEDKGESIITIGEFATVRATRHYV<br>NQDAPFGVIHLDITTENGTKTYSYNRKEGEFAINWLVPIGEDSP<br>ASIKISVDELDQQRNIIEVPKLYSIDLDNQTLEQWKTQGNVSFS<br>VTRPEHNIAISWPSVSYK |

TABLE 2-continued

Exemplary Nucleotide and Amino Acid Sequences of Carriers

| SEQ ID NO | Sequence |
|---|---|
| SEQ ID NO: 68 | DEGVLYYSMTINDEQNDIKDEDKGESIITIGEFATVRATRHYVN<br>QDAPFGVIHLDITTENGTKTYSYNRKEGEFAINWLVPIGEDSPA<br>SIKISVDELDQQRNIIEVPKLYSIDLDNQTLEQWKTQGNVSFSV<br>TRPEHNIAISWPSVSYK |
| SEQ ID NO: 69 | EGVLYYSMTINDEQNDIKDEDKGESIITIGEFATVRATRHYVNQ<br>DAPFGVIHLDITTENGTKTYSYNRKEGEFAINWLVPIGEDSPASI<br>KISVDELDQQRNIIEVPKLYSIDLDNQTLEQWKTQGNVSFSVTR<br>PEHNIAISWPSVSYK |
| SEQ ID NO: 70 | GVLYYSMTINDEQNDIKDEDKGESIITIGEFATVRATRHYVNQ<br>DAPFGVIHLDITTENGTKTYSYNRKEGEFAINWLVPIGEDSPASI<br>KISVDELDQQRNIIEVPKLYSIDLDNQTLEQWKTQGNVSFSVTR<br>PEHNIAISWPSVSYK |
| SEQ ID NO: 71 | VEEALNIFDECRSPCSLTPEPGKPIQSKLSIPSDVVLDEGVLYYS<br>MTINDEQNDIKDEDKGESIITIGEFATVRATRHYVNQDAPFGVI<br>HLDITTENGTKTYSYNRKEGEFAINWLVPIGEDSPASIKISVDEL<br>DQQRNIIEVPKLYSIDLDNQTLEQWKTQGNVSFSVTRPEHNIAI<br>SWPSVSY |
| SEQ ID NO: 72 | VEEALNIFDECRSPCSLTPEPGKPIQSKLSIPSDVVLDEGVLYYS<br>MTINDEQNDIKDEDKGESIITIGEFATVRATRHYVNQDAPFGVI<br>HLDITTENGTKTYSYNRKEGEFAINWLVPIGEDSPASIKISVDEL<br>DQQRNIIEVPKLYSIDLDNQTLEQWKTQGNVSFSVTRPEHNIAI<br>SWPSVS |
| SEQ ID NO: 73 | VEEALNIFDECRSPCSLTPEPGKPIQSKLSIPSDVVLDEGVLYYS<br>MTINDEQNDIKDEDKGESIITIGEFATVRATRHYVNQDAPFGVI<br>HLDITTENGTKTYSYNRKEGEFAINWLVPIGEDSPASIKISVDEL<br>DQQRNIIEVPKLYSIDLDNQTLEQWKTQGNVSFSVTRPEHNIAI<br>SWPSV |
| SEQ ID NO: 74 | VEEALNIFDECRSPCSLTPEPGKPIQSKLSIPSDVVLDEGVLYYS<br>MTINDEQNDIKDEDKGESIITIGEFATVRATRHYVNQDAPFGVI<br>HLDITTENGTKTYSYNRKEGEFAINWLVPIGEDSPASIKISVDEL<br>DQQRNIIEVPKLYSIDLDNQTLEQWKTQGNVSFSVTRPEHNIAI<br>SWPS |
| SEQ ID NO: 75 | VEEALNIFDECRSPCSLTPEPGKPIQSKLSIPSDVVLDEGVLYYS<br>MTINDEQNDIKDEDKGESIITIGEFATVRATRHYVNQDAPFGVI<br>HLDITTENGTKTYSYNRKEGEFAINWLVPIGEDSPASIKISVDEL<br>DQQRNIIEVPKLYSIDLDNQTLEQWKTQGNVSFSVTRPEHNIAI<br>SWP |
| SEQ ID NO: 76 | VEEALNIFDECRSPCSLTPEPGKPIQSKLSIPSDVVLDEGVLYYS<br>MTINDEQNDIKDEDKGESIITIGEFATVRATRHYVNQDAPFGVI<br>HLDITTENGTKTYSYNRKEGEFAINWLVPIGEDSPASIKISVDEL<br>DQQRNIIEVPKLYSIDLDNQTLEQWKTQGNVSFSVTRPEHNIAI<br>SW |
| SEQ ID NO: 77 | VEEALNIFDECRSPCSLTPEPGKPIQSKLSIPSDVVLDEGVLYYS<br>MTINDEQNDIKDEDKGESIITIGEFATVRATRHYVNQDAPFGVI<br>HLDITTENGTKTYSYNRKEGEFAINWLVPIGEDSPASIKISVDEL<br>DQQRNIIEVPKLYSIDLDNQTLEQWKTQGNVSFSVTRPEHNIAI<br>S |
| SEQ ID NO: 78 | VEEALNIFDECRSPCSLTPEPGKPIQSKLSIPSDVVLDEGVLYYS<br>MTINDEQNDIKDEDKGESIITIGEFATVRATRHYVNQDAPFGVI<br>HLDITTENGTKTYSYNRKEGEFAINWLVPIGEDSPASIKISVDEL<br>DQQRNIIEVPKLYSIDLDNQTLEQWKTQGNVSFSVTRPEHNIAI |
| SEQ ID NO: 79 | VEEALNIFDECRSPCSLTPEPGKPIQSKLSIPSDVVLDEGVLYYS<br>MTINDEQNDIKDEDKGESIITIGEFATVRATRHYVNQDAPFGVI<br>HLDITTENGTKTYSYNRKEGEFAINWLVPIGEDSPASIKISVDEL<br>DQQRNIIEVPKLYSIDLDNQTLEQWKTQGNVSFSVTRPEHNIA |
| SEQ ID NO: 80 | VEEALNIFDECRSPCSLTPEPGKPIQSKLSIPSDVVLDEGVLYYS<br>MTINDEQNDIKDEDKGESIITIGEFATVRATRHYVNQDAPFGVI<br>HLDITTENGTKTYSYNRKEGEFAINWLVPIGEDSPASIKISVDEL<br>DQQRNIIEVPKLYSIDLDNQTLEQWKTQGNVSFSVTRPEHNI |
| SEQ ID NO: 81 | VEEALNIFDECRSPCSLTPEPGKPIQSKLSIPSDVVLDEGVLYYS<br>MTINDEQNDIKDEDKGESIITIGEFATVRATRHYVNQDAPFGVI |

TABLE 2-continued

Exemplary Nucleotide and Amino Acid Sequences of Carriers

| SEQ ID NO | Sequence |
|---|---|
| | HLDITTENGTKTYSYNRKEGEFAINWLVPIGEDSPASIKISVDEL<br>DQQRNIIEVPKLYSIDLDNQTLEQWKTQGNVSFSVTRPEHN |
| SEQ ID NO: 82 | VEEALNIFDECRSPCSLTPEPGKPIQSKLSIPSDVVLDEGVLYYS<br>MTINDEQNDIKDEDKGESIITIGEFATVRATRHYVNQDAPFGVI<br>HLDITTENGTKTYSYNRKEGEFAINWLVPIGEDSPASIKISVDEL<br>DQQRNIIEVPKLYSIDLDNQTLEQWKTQGNVSFSVTRPEH |
| SEQ ID NO: 83 | VEEALNIFDECRSPCSLTPEPGKPIQSKLSIPSDVVLDEGVLYYS<br>MTINDEQNDIKDEDKGESIITIGEFATVRATRHYVNQDAPFGVI<br>HLDITTENGTKTYSYNRKEGEFAINWLVPIGEDSPASIKISVDEL<br>DQQRNIIEVPKLYSIDLDNQTLEQWKTQGNVSFSVTRPE |
| SEQ ID NO: 84 | VEEALNIFDECRSPCSLTPEPGKPIQSKLSIPSDVVLDEGVLYYS<br>MTINDEQNDIKDEDKGESIITIGEFATVRATRHYVNQDAPFGVI<br>HLDITTENGTKTYSYNRKEGEFAINWLVPIGEDSPASIKISVDEL<br>DQQRNIIEVPKLYSIDLDNQTLEQWKTQGNVSFSVTRP |
| SEQ ID NO: 85 | VEEALNIFDECRSPCSLTPEPGKPIQSKLSIPSDVVLDEGVLYYS<br>MTINDEQNDIKDEDKGESIITIGEFATVRATRHYVNQDAPFGVI<br>HLDITTENGTKTYSYNRKEGEFAINWLVPIGEDSPASIKISVDEL<br>DQQRNIIEVPKLYSIDLDNQTLEQWKTQGNVSFSVTR |
| SEQ ID NO: 86 | VEEALNIFDECRSPCSLTPEPGKPIQSKLSIPSDVVLDEGVLYYS<br>MTINDEQNDIKDEDKGESIITIGEFATVRATRHYVNQDAPFGVI<br>HLDITTENGTKTYSYNRKEGEFAINWLVPIGEDSPASIKISVDEL<br>DQQRNIIEVPKLYSIDLDNQTLEQWKTQGNVSFSVT |
| SEQ ID NO: 87 | VEEALNIFDECRSPCSLTPEPGKPIQSKLSIPSDVVLDEGVLYYS<br>MTINDEQNDIKDEDKGESIITIGEFATVRATRHYVNQDAPFGVI<br>HLDITTENGTKTYSYNRKEGEFAINWLVPIGEDSPASIKISVDEL<br>DQQRNIIEVPKLYSIDLDNQTLEQWKTQGNVSFSV |
| SEQ ID NO: 88 | VEEALNIFDECRSPCSLTPEPGKPIQSKLSIPSDVVLDEGVLYYS<br>MTINDEQNDIKDEDKGESIITIGEFATVRATRHYVNQDAPFGVI<br>HLDITTENGTKTYSYNRKEGEFAINWLVPIGEDSPASIKISVDEL<br>DQQRNIIEVPKLYSIDLDNQTLEQWKTQGNVSFS |
| SEQ ID NO: 89 | VEEALNIFDECRSPCSLTPEPGKPIQSKLSIPSDVVLDEGVLYYS<br>MTINDEQNDIKDEDKGESIITIGEFATVRATRHYVNQDAPFGVI<br>HLDITTENGTKTYSYNRKEGEFAINWLVPIGEDSPASIKISVDEL<br>DQQRNIIEVPKLYSIDLDNQTLEQWKTQGNVSF |
| SEQ ID NO: 90 | VEEALNIFDECRSPCSLTPEPGKPIQSKLSIPSDVVLDEGVLYYS<br>MTINDEQNDIKDEDKGESIITIGEFATVRATRHYVNQDAPFGVI<br>HLDITTENGTKTYSYNRKEGEFAINWLVPIGEDSPASIKISVDEL<br>DQQRNIIEVPKLYSIDLDNQTLEQWKTQGNVS |
| SEQ ID NO: 91 | VEEALNIFDECRSPCSLTPEPGKPIQSKLSIPSDVVLDEGVLYYS<br>MTINDEQNDIKDEDKGESIITIGEFATVRATRHYVNQDAPFGVI<br>HLDITTENGTKTYSYNRKEGEFAINWLVPIGEDSPASIKISVDEL<br>DQQRNIIEVPKLYSIDLDNQTLEQWKTQGNV |
| SEQ ID NO: 92 | VEEALNIFDECRSPCSLTPEPGKPIQSKLSIPSDVVLDEGVLYYS<br>MTINDEQNDIKDEDKGESIITIGEFATVRATRHYVNQDAPFGVI<br>HLDITTENGTKTYSYNRKEGEFAINWLVPIGEDSPASIKISVDEL<br>DQQRNIIEVPKLYSIDLDNQTLEQWKTQGN |
| SEQ ID NO: 93 | VEEALNIFDECRSPCSLTPEPGKPIQSKLSIPSDVVLDEGVLYYS<br>MTINDEQNDIKDEDKGESIITIGEFATVRATRHYVNQDAPFGVI<br>HLDITTENGTKTYSYNRKEGEFAINWLVPIGEDSPASIKISVDEL<br>DQQRNIIEVPKLYSIDLDNQTLEQWKTQG |
| SEQ ID NO: 94 | VEEALNIFDECRSPCSLTPEPGKPIQSKLSIPSDVVLDEGVLYYS<br>MTINDEQNDIKDEDKGESIITIGEFATVRATRHYVNQDAPFGVI<br>HLDITTENGTKTYSYNRKEGEFAINWLVPIGEDSPASIKISVDEL<br>DQQRNIIEVPKLYSIDLDNQTLEQWKTQ |
| SEQ ID NO: 95 | VEEALNIFDECRSPCSLTPEPGKPIQSKLSIPSDVVLDEGVLYYS<br>MTINDEQNDIKDEDKGESIITIGEFATVRATRHYVNQDAPFGVI<br>HLDITTENGTKTYSYNRKEGEFAINWLVPIGEDSPASIKISVDEL<br>DQQRNIIEVPKLYSIDLDNQTLEQWKT |
| SEQ ID NO: 96 | VEEALNIFDECRSPCSLTPEPGKPIQSKLSIPSDVVLDEGVLYYS<br>MTINDEQNDIKDEDKGESIITIGEFATVRATRHYVNQDAPFGVI |

TABLE 2-continued

Exemplary Nucleotide and Amino Acid Sequences of Carriers

| SEQ ID NO | Sequence |
|---|---|
| | HLDITTENGTKTYSYNRKEGEFAINWLVPIGEDSPASIKISVDEL<br>DQQRNIIEVPKLYSIDLDNQTLEQWK |
| SEQ ID NO: 97 | VEEALNIFDECRSPCSLTPEPGKPIQSKLSIPSDVVLDEGVLYYS<br>MTINDEQNDIKDEDKGESIITIGEFATVRATRHYVNQDAPFGVI<br>HLDITTENGTKTYSYNRKEGEFAINWLVPIGEDSPASIKISVDEL<br>DQQRNIIEVPKLYSIDLDNQTLEQW |
| SEQ ID NO: 98 | VEEALNIFDECRSPCSLTPEPGKPIQSKLSIPSDVVLDEGVLYYS<br>MTINDEQNDIKDEDKGESIITIGEFATVRATRHYVNQDAPFGVI<br>HLDITTENGTKTYSYNRKEGEFAINWLVPIGEDSPASIKISVDEL<br>DQQRNIIEVPKLYSIDLDNQTLEQ |
| SEQ ID NO: 99 | VEEALNIFDECRSPCSLTPEPGKPIQSKLSIPSDVVLDEGVLYYS<br>MTINDEQNDIKDEDKGESIITIGEFATVRATRHYVNQDAPFGVI<br>HLDITTENGTKTYSYNRKEGEFAINWLVPIGEDSPASIKISVDEL<br>DQQRNIIEVPKLYSIDLDNQTLE |
| SEQ ID NO: 100 | VEEALNIFDECRSPCSLTPEPGKPIQSKLSIPSDVVLDEGVLYYS<br>MTINDEQNDIKDEDKGESIITIGEFATVRATRHYVNQDAPFGVI<br>HLDITTENGTKTYSYNRKEGEFAINWLVPIGEDSPASIKISVDEL<br>DQQRNIIEVPKLYSIDLDNQTL |
| SEQ ID NO: 101 | VEEALNIFDECRSPCSLTPEPGKPIQSKLSIPSDVVLDEGVLYYS<br>MTINDEQNDIKDEDKGESIITIGEFATVRATRHYVNQDAPFGVI<br>HLDITTENGTKTYSYNRKEGEFAINWLVPIGEDSPASIKISVDEL<br>DQQRNIIEVPKLYSIDLDNQT |
| SEQ ID NO: 102 | VEEALNIFDECRSPCSLTPEPGKPIQSKLSIPSDVVLDEGVLYYS<br>MTINDEQNDIKDEDKGESIITIGEFATVRATRHYVNQDAPFGVI<br>HLDITTENGTKTYSYNRKEGEFAINWLVPIGEDSPASIKISVDEL<br>DQQRNIIEVPKLYSIDLDNQ |
| SEQ ID NO: 103 | VEEALNIFDECRSPCSLTPEPGKPIQSKLSIPSDVVLDEGVLYYS<br>MTINDEQNDIKDEDKGESIITIGEFATVRATRHYVNQDAPFGVI<br>HLDITTENGTKTYSYNRKEGEFAINWLVPIGEDSPASIKISVDEL<br>DQQRNIIEVPKLYSIDLDN |
| SEQ ID NO: 104 | VEEALNIFDECRSPCSLTPEPGKPIQSKLSIPSDVVLDEGVLYYS<br>MTINDEQNDIKDEDKGESIITIGEFATVRATRHYVNQDAPFGVI<br>HLDITTENGTKTYSYNRKEGEFAINWLVPIGEDSPASIKISVDEL<br>DQQRNIIEVPKLYSIDLD |
| SEQ ID NO: 105 | VEEALNIFDECRSPCSLTPEPGKPIQSKLSIPSDVVLDEGVLYYS<br>MTINDEQNDIKDEDKGESIITIGEFATVRATRHYVNQDAPFGVI<br>HLDITTENGTKTYSYNRKEGEFAINWLVPIGEDSPASIKISVDEL<br>DQQRNIIEVPKLYSIDL |
| SEQ ID NO: 106 | VEEALNIFDECRSPCSLTPEPGKPIQSKLSIPSDVVLDEGVLYYS<br>MTINDEQNDIKDEDKGESIITIGEFATVRATRHYVNQDAPFGVI<br>HLDITTENGTKTYSYNRKEGEFAINWLVPIGEDSPASIKISVDEL<br>DQQRNIIEVPKLYSID |
| SEQ ID NO: 107 | MVEEALNIFDECRSPCSLTPEPGKPIQSKLSIPSDVVLDEGVLYY<br>SMTINDEQNDIKDEDKGESIITIGEFATVRATRHYVNQDAPFGV<br>IHLDITTENGTKTYSYNRKEGEFAINWLVPIGEDSPASIKISVDE<br>LDQQRNIIEVPKLYSID |
| SEQ ID NO: 108 | VEEALNIFDECRSPCSLTPEPGKPIQSKLSIPSDVVLDEGVLYYS<br>MTINDEQNDIKDEDKGESIITIGEFATVRATRHYVNQDAPFGVI<br>HLDITTENGTKTYSYNRKEGEFAINWLVPIGEDSPASIKISVDEL<br>DQQRNIIEVPKLYSI |
| SEQ ID NO: 109 | VEEALNIFDECRSPCSLTPEPGKPIQSKLSIPSDVVLDEGVLYYS<br>MTINDEQNDIKDEDKGESIITIGEFATVRATRHYVNQDAPFGVI<br>HLDITTENGTKTYSYNRKEGEFAINWLVPIGEDSPASIKISVDEL<br>DQQRNIIEVPKLYS |
| SEQ ID NO: 110 | VEEALNIFDECRSPCSLTPEPGKPIQSKLSIPSDVVLDEGVLYYS<br>MTINDEQNDIKDEDKGESIITIGEFATVRATRHYVNQDAPFGVI<br>HLDITTENGTKTYSYNRKEGEFAINWLVPIGEDSPASIKISVDEL<br>DQQRNIIEVPKLY |
| SEQ ID NO: 111 | VEEALNIFDECRSPCSLTPEPGKPIQSKLSIPSDVVLDEGVLYYS<br>MTINDEQNDIKDEDKGESIITIGEFATVRATRHYVNQDAPFGVI |

TABLE 2-continued

Exemplary Nucleotide and Amino Acid Sequences of Carriers

| SEQ ID NO | Sequence |
| --- | --- |
| | HLDITTENGTKTYSYNRKEGEFAINWLVPIGEDSPASIKISVDEL<br>DQQRNIIEVPKL |
| SEQ ID NO: 112 | VEEALNIFDECRSPCSLTPEPGKPIQSKLSIPSDVVLDEGVLYYS<br>MTINDEQNDIKDEDKGESIITIGEFATVRATRHYVNQDAPFGVI<br>HLDITTENGTKTYSYNRKEGEFAINWLVPIGEDSPASIKISVDEL<br>DQQRNIIEVPK |
| SEQ ID NO: 113 | VEEALNIFDECRSPCSLTPEPGKPIQSKLSIPSDVVLDEGVLYYS<br>MTINDEQNDIKDEDKGESIITIGEFATVRATRHYVNQDAPFGVI<br>HLDITTENGTKTYSYNRKEGEFAINWLVPIGEDSPASIKISVDEL<br>DQQRNIIEVP |
| SEQ ID NO: 114 | VEEALNIFDECRSPCSLTPEPGKPIQSKLSIPSDVVLDEGVLYYS<br>MTINDEQNDIKDEDKGESIITIGEFATVRATRHYVNQDAPFGVI<br>HLDITTENGTKTYSYNRKEGEFAINWLVPIGEDSPASIKISVDEL<br>DQQRNIIEV |
| SEQ ID NO: 115 | VEEALNIFDECRSPCSLTPEPGKPIQSKLSIPSDVVLDEGVLYYS<br>MTINDEQNDIKDEDKGESIITIGEFATVRATRHYVNQDAPFGVI<br>HLDITTENGTKTYSYNRKEGEFAINWLVPIGEDSPASIKISVDEL<br>DQQRNIIE |
| SEQ ID NO: 116 | VEEALNIFDECRSPCSLTPEPGKPIQSKLSIPSDVVLDEGVLYYS<br>MTINDEQNDIKDEDKGESIITIGEFATVRATRHYVNQDAPFGVI<br>HLDITTENGTKTYSYNRKEGEFAINWLVPIGEDSPASIKISVDEL<br>DQQRNII |
| SEQ ID NO: 117 | VEEALNIFDECRSPCSLTPEPGKPIQSKLSIPSDVVLDEGVLYYS<br>MTINDEQNDIKDEDKGESIITIGEFATVRATRHYVNQDAPFGVI<br>HLDITTENGTKTYSYNRKEGEFAINWLVPIGEDSPASIKISVDEL<br>DQQRNI |
| SEQ ID NO: 118 | VEEALNIFDECRSPCSLTPEPGKPIQSKLSIPSDVVLDEGVLYYS<br>MTINDEQNDIKDEDKGESIITIGEFATVRATRHYVNQDAPFGVI<br>HLDITTENGTKTYSYNRKEGEFAINWLVPIGEDSPASIKISVDEL<br>DQQRN |
| SEQ ID NO: 119 | VEEALNIFDECRSPCSLTPEPGKPIQSKLSIPSDVVLDEGVLYYS<br>MTINDEQNDIKDEDKGESIITIGEFATVRATRHYVNQDAPFGVI<br>HLDITTENGTKTYSYNRKEGEFAINWLVPIGEDSPASIKISVDEL<br>DQQR |
| SEQ ID NO: 120 | VEEALNIFDECRSPCSLTPEPGKPIQSKLSIPSDVVLDEGVLYYS<br>MTINDEQNDIKDEDKGESIITIGEFATVRATRHYVNQDAPFGVI<br>HLDITTENGTKTYSYNRKEGEFAINWLVPIGEDSPASIKISVDEL<br>DQQ |
| SEQ ID NO: 121 | VEEALNIFDECRSPCSLTPEPGKPIQSKLSIPSDVVLDEGVLYYS<br>MTINDEQNDIKDEDKGESIITIGEFATVRATRHYVNQDAPFGVI<br>HLDITTENGTKTYSYNRKEGEFAINWLVPIGEDSPASIKISVDEL<br>DQ |
| SEQ ID NO: 122 | VEEALNIFDECRSPCSLTPEPGKPIQSKLSIPSDVVLDEGVLYYS<br>MTINDEQNDIKDEDKGESIITIGEFATVRATRHYVNQDAPFGVI<br>HLDITTENGTKTYSYNRKEGEFAINWLVPIGEDSPASIKISVDEL<br>D |
| SEQ ID NO: 123 | VEEALNIFDECRSPCSLTPEPGKPIQSKLSIPSDVVLDEGVLYYS<br>MTINDEQNDIKDEDKGESIITIGEFATVRATRHYVNQDAPFGVI<br>HLDITTENGTKTYSYNRKEGEFAINWLVPIGEDSPASIKISVDEL |
| SEQ ID NO: 124 | VEEALNIFDECRSPCSLTPEPGKPIQSKLSIPSDVVLDEGVLYYS<br>MTINDEQNDIKDEDKGESIITIGEFATVRATRHYVNQDAPFGVI<br>HLDITTENGTKTYSYNRKEGEFAINWLVPIGEDSPASIKISVDE |
| SEQ ID NO: 125 | MVEEALNIFDECRSPCSLTPEPGKPIQSKLSIPSDVVLDEGVLYY<br>SMTINDEQNDIKDEDKGESIITIGEFATVRATRHYVNQDAPFGV<br>IHLDITTENGTKTYSYNRKEGEFAINWLVPIGEDSPASIKISVDE |
| SEQ ID NO: 126 | GNAMSALAAHRVCGVPLETLARSRKPRDLTDDLSCAYQAQNI<br>VSLFVATRILFSHLDSVFTLNLDEQEPEVAERLSDLRRINENNP<br>GMVTQVLTVARQIYNDYVTHHPGLTPEQTSAGAQA |
| SEQ ID NO: 127 | ADILSLFCPDADKSCVASNNDQANINIESRSGRSYLPEN |

TABLE 2-continued

Exemplary Nucleotide and Amino Acid Sequences of Carriers

| SEQ ID NO | Sequence |
| --- | --- |
| SEQ ID NO: 128 | RAVITPQGVTNWTYQELEATHQALTREGYVFVGYHGTNHVA<br>AQTIVNRIAPVPRGNNTENEEKWGGLYVATHAEVAHGYARIK<br>EGTGEYGLPTRAERDARGVMLRVYIPRASLERFYRTNTPLENA<br>EEHITQVIGHSLPLRNEAFTGPESAGGEDETVIGWDMAIHAVAI<br>PSTIPGNAYEELAIDEEAVAKEQSISTKPPYKERKDELK |
| SEQ ID NO: 129 | VEEALNIFDECRSPCSLTPEPGKPIQSKLSIPSDVVLDEGVLYYS<br>MTINDEQNDIKDEDKGESIITIGEFATVRATRHYVNQDAPFGVI<br>HLDITTENGTKTYSYNRKEGEFAINWLVPIGEDSPASIKISVDEL<br>DQQRNIIEVPKLYSIDLDNQTLEQWKTQGNVSFSVTRPEHNIAI<br>SWPSVSYKAAQKEGSRHKRWAHWHTGLALCWLVPMDAIYN<br>YITQQNCTLGDNWFGGSYETVAGTPKVITVKQGIEQKPVEQRI<br>HFSKGNAMSALAAHRVCGVPLETLARSRKPRDLTDDLSCAYQ<br>AQNIVSLFVATRILFSHLDSVFTLNLDEQEPEVAERLSDLRRINE<br>NNPGMVTQVLTVARQIYNDYVTHHPGLTPEQTSAGAQAADIL<br>SLFCPDADKSCVASNNDQANINIESRSGRSYLPEN |
| SEQ ID NO: 130 | VEEALNIFDECRSPCSLTPEPGKPIQSKLSIPSDVVLDEGVLYYS<br>MTINDEQNDIKDEDKGESIITIGEFATVRATRHYVNQDAPFGVI<br>HLDITTENGTKTYSYNRKEGEFAINWLVPIGEDSPASIKISVDEL<br>DQQRNIIEVPKLYSIDLDNQTLEQWKTQGNVSFSVTRPEHNIAI<br>SWPSVSYKAAQKEGSRHKRWAHWHTGLALCWLVPMDAIYN<br>YITQQNCTLGDNWFGGSYETVAGTPKVITVKQGIEQKPVEQRI<br>HFSKGNAMSALAAHRVCGVPLETLARSRKPRDLTDDLSCAYQ<br>AQNIVSLFVATRILFSHLDSVFTLNLDEQEPEVAERLSDLRRINE<br>NNPGMVTQVLTVARQIYNDYVTHHPGLTPEQTSAGAQAADIL<br>SLFCPDADKSCVASNNDQANINIES |
| SEQ ID NO: 131 | VEEALNIFDECRSPCSLTPEPGKPIQSKLSIPSDVVLDEGVLYYS<br>MTINDEQNDIKDEDKGESIITIGEFATVRATRHYVNQDAPFGVI<br>HLDITTENGTKTYSYNRKEGEFAINWLVPIGEDSPASIKISVDEL<br>DQQRNIIEVPKLYSIDLDNQTLEQWKTQGNVSFSVTRPEHNIAI<br>SWPSVSYKAAQKEGSRHKRWAHWHTGLALCWLVPMDAIYN<br>YITQQNCTLGDNWFGGSYETVAGTPKVITVKQGIEQKPVEQRI<br>HFSKGNAMSALAAHRVCGVPLETLARSRKPRDLTDDLSCAYQ<br>AQNIVSLFVATRILFSHLDSVFTLNLDEQEPEVAERLSDLRRINE<br>NNPGMVTQVLTVARQIYNDYVTHHPGLTPEQTSAGAQAADIL<br>SLFCPDA |
| SEQ ID NO: 132 | VEEALNIFDECRSPCSLTPEPGKPIQSKLSIPSDVVLDEGVLYYS<br>MTINDEQNDIKDEDKGESIITIGEFATVRATRHYVNQDAPFGVI<br>HLDITTENGTKTYSYNRKEGEFAINWLVPIGEDSPASIKISVDEL<br>DQQRNIIEVPKLYSIDLDNQTLEQWKTQGNVSFSVTRPEHNIAI<br>SWPSVSYKAAQKEGSRHKRWAHWHTGLALCWLVPMDAIYN<br>YITQQNCTLGDNWFGGSYETVAGTPKVITVKQGIEQKPVEQRI<br>HFSKGNAMSALAAHRVCGVPLETLARSRKPRDLTDDLSCAYQ<br>AQNIVSLFVATRILFSHLDSVFTLNLDEQEPEVAERLSDLRRINE<br>NNPGMVTQVLTVARQIYNDYVTHHPGLTPEQTSAGAQA |
| SEQ ID NO: 133 | VEEALNIFDECRSPCSLTPEPGKPIQSKLSIPSDVVLDEGVLYYS<br>MTINDEQNDIKDEDKGESIITIGEFATVRATRHYVNQDAPFGVI<br>HLDITTENGTKTYSYNRKEGEFAINWLVPIGEDSPASIKISVDEL<br>DQQRNIIEVPKLYSIDLDNQTLEQWKTQGNVSFSVTRPEHNIAI<br>SWPSVSYKAAQKEGSRHKRWAHWHTGLALCWLVPMDAIYN<br>YITQQNCTLGDNWFGGSYETVAGTPKVITVKQGIEQKPVEQRI<br>HFSKGNAMSALAAHRVCGVPLETLARSRKP |
| SEQ ID NO: 134 | GTCGAAGAAGCTTTAAACATCTTTGATGAATGCCGTTCGCC<br>ATGTTCGTTGACCCCGGAACCGGGTAAGCCGATTCAATCAA<br>AACTGTCTATCCCTAGTGATGTTGTTCTGGATGAAGGTGTTC<br>TGTATTACTCGATGACGATTAATGATGAGCAGAATGATATT<br>AAGGATGAGGACAAAGGCGAGTCCATTATCACTATTGGTGA<br>ATTTGCCACAGTACGCGCGACTAGACATTATGTTAATCAAG<br>ATGCGCCTTTTGGTGTCATCCATTTAGATATTACGACAGAA<br>AATGGTACAAAAACGTACTCTTATAACCGCAAAGAGGGTG<br>AATTTGCAATCAATTGGTTAGTGCCTATTGGTGAAGATTCTC<br>CTGCAAGCATCAAAATCTCCGTTGATGAGCTCGATCAGCAA<br>CGCAATATCATCGAGGTGCCTAAACTGTATAGTATTGATCT<br>CGATAACCAAACGTTAGAGCAGTGGAAAACCCAAGGTAAT<br>GTTTCTTTTTCGGTAACGCGTCCTGAACATAATATCGCTATC<br>TCTTGGCCAAGCGTGAGTTACAAAGCAGCGCAGAAAGAGG<br>GTTCACGCCATAAGCGTTGGGCTCATTGGCATACAGGCTTA<br>GCACTGTGTTGGCTTGTGCCAATGGATGCTATCTATAACTAT<br>ATCACCCAGCAAAATTGTACTTTAGGGGATAATTGGTTTGG<br>TGGCTCTTATGAGACTGTTGCAGGCACTCCGAAGGTGATTA<br>CGGTTAAGCAAGGGATTGAACAAAAGCCAGTTGAGCAGCG |

TABLE 2-continued

Exemplary Nucleotide and Amino Acid Sequences of Carriers

| SEQ ID NO | Sequence |
|---|---|
|  | CATCCATTTCTCCAAGGGGAATGCGATGAGCGCACTTGCTG<br>CTCATCGCGTCTGTGGTGTGCCATTAGAAACTTTGGCGCGC<br>AGTCGCAAACCTCGTGATCTGACGGATGATTTATCATGTGC<br>CTATCAAGCGCAGAATATCGTGAGTTTATTTGTCGCGACGC<br>GTATCCTGTTCTCTCATCTGGATAGCGTATTTACTCTGAATC<br>TTGACGAACAAGAACCAGAGGTGGCTGAACGTCTAAGTGA<br>TCTTCGCCGTATCAATGAAAATAACCCGGGCATGGTTACAC<br>AGGTTTTAACCGTTGCTCGTCAGATCTATAACGATTATGTCA<br>CTCACCATCCGGGCTTAACTCCTGAGCAAACCAGTGCGGGT<br>GCACAAGCTGCCGATATCCTCTCTTTATTTTGCCCAGATGCT<br>GATAAGTCTTGTGTGGCTTCAAACAACGATCAAGCCAATAT<br>CAACATCGAGTCTCGTTCTGGCCGTTCATATTTGCCTGAAAA<br>CCGTGCGGTAATCACCCCTCAAGGCGTCACAAATTGGACTT<br>ACCAGGAACTCGAAGCAACACATCAAGCTCTGACTCGTGAG<br>GGTTATGTGTTCGTGGGTTACCATGGTACGAATCATGTCGCT<br>GCGCAAACCATCGTGAATCGCATTGCCCCTGTTCCGCGCGG<br>CAACAACACTGAAAACGAGGAAAAGTGGGGCGGGTTATAT<br>GTTGCAACTCACGCTGAAGTTGCCCATGGTTATGCTCGCAT<br>CAAAGAAGGGACAGGGGAGTATGGCCTTCCGACCCGTGCT<br>GAGCGCGACGCTCGTGGGGTAATGCTGCGCGTGTATATCCC<br>TCGTGCTTCATTAGAACGTTTTTATCGCACGAATACACCTTT<br>GGAAAATGCTGAGGAGCATATCACGCAAGTGATTGGTCATT<br>CTTTGCCATTACGCAATGAAGCATTTACTGGTCCAGAAAGT<br>GCGGGCGGGAAGACGAAACTGTCATTGGCTGGGATATGG<br>CGATTCATGCAGTTGCGATCCCTTCGACTATCCCAGGGAAC<br>GCTTACGAAGAATTGGCGATTGATGAGGAGGCTGTTGCAAA<br>AGAGCAATCGATTAGCACAAAACCACCTTATAAAGAGCGC<br>AAAGATGAACTTAAG |
| SEQ ID NO: 135 | AEEAFDLWNECAKACVLDLKDGVRSSRMSVDPAIADTNGQG<br>VLHYSMVLEGGNDALKLAIDNALSITSDGLTIRLEGGVEPNKP<br>VRYSYTRQARGSWSLNWLVPIGHEKPSNIKVFIHELNAGNQLS<br>HMSPIYTIEMGDELLAKLARDATFFVRAHESNEMQPTLAISHA<br>GVSVVMAQAQPRREKRWSEWASGKVLCLLDPLDGVYNYLA<br>QQRCNLDDTWEGKIYRVLAGNPAKHDLDIKPTVISHRLHFPEG<br>GSLAALTAHQACHLPLETFTRHRQPRGWEQLEQCGYPVQRLV<br>ALYLAARLSWNQVDQVIRNALASPGSGGDLGEAIREQPEQAR<br>LALTLAAAESERFVRQGTGNDEAGAASADVVSLTCPVAAGEC<br>AGPADSGDALLERNYPTGAEFLGDGGDVSFSTRGTQNWTVER<br>LLQAHRQLEERGYVFVGYHGTFLEAAQSIVFGGVRARSQDLD<br>AIWRGFYIAGDPALAYGYAQDQEPDARGRIRNGALLRVYVPR<br>SSLPGFYRTGLTLAAPEAAGEVERLIGHPLPLRLDAITGPEEEG<br>GRLETILGWPLAERTVVIPSAIPTDPRNVGGDLDPSSIPDKEQ<br>AISALPDYASQPGKPPREDLK |
| SEQ ID NO: 136 | GCCGAGGAAGCCTTCGACCTCTGGAACGAATGCGCCAAGG<br>CCTGCGTGCTCGACCTCAAGGACGGCGTGCGTTCCAGCCGC<br>ATGAGCGTCGACCCGGCCATCGCCGACACCAACGGCCAGG<br>GCGTGCTGCACTACTCCATGGTCCTGGAGGGCGGCAACGAC<br>GCGCTCAAGCTGGCCATCGACAACGCCCTCAGCATCACCAG<br>CGACGGCCTGACCATCCGCCTCGAAGGTGGCGTCGAGCCGA<br>ACAAGCCGGTGCGCTACAGCTACACGCGCCAGGCGCGCGG<br>CAGTTGGTCGCTGAACTGGCTGGTGCCGATCGGCCACGAGA<br>AGCCTTCGAACATCAAGGTGTTCATCCACGAACTGAACGCC<br>GGTAACCAGCTCAGCCACATGTCGCCGATCTACACCATCGA<br>GATGGGCGACGAGTTGCTGGCGAAGCTGGCGCGCGATGCC<br>ACCTTCTTCGTCAGGGCGCACGAGAGCAACGAGATGCAGCC<br>GACGCTCGCCATCAGCCATGCCGGGGTCAGCGTGGTCATGG<br>CCCAGGCCCAGCCGCGCGGGAAAAGCGCTGGAGCGAATG<br>GGCCAGCGGCAAGGTGTTGTGCCTGCTCGACCCGCTGGACG<br>GGGTCTACAACTACCTCGCCCAGCAGCGCTGCAACCTCGAC<br>GATACCTGGGAAGGCAAGATCTACCGGGTGCTCGCCGGCA<br>ACCCGGCGAAGCATGACCTGGACATCAAGCCCACGGTCATC<br>AGTCATCGCCTGCATTTCCCCGAGGGCGGCAGCCTGGCCGC<br>GCTGACCGCGCACCAGGCCTGCCACCTGCCGCTGGAGACCT<br>TCACCCGTCATCGCCAGCCGCGCGGCTGGGAACAACTGGAG<br>CAGTCGGCTATCCGGTGCAGCGGCTGGTCGCCCTCTACCT<br>GGCGGCGCGGCTGTCGTGGAACCAGGTCGACCAGGTGATCC<br>GCAACGCCCTGGCCAGCCCCGGCAGCGGCGGCGACCTGGG<br>CGAAGCGATCCGCGAGCAGCCGGAGCAGGCCCGTCTGGCC<br>CTGACCCTGGCCGCCGCCGAGAGCGAGCGCTTCGTCCGGCA<br>GGGCACAGGCAACGACGAGGCCGGCGCGGCCAGCGCCGAC<br>GTGGTGAGCCTGACCTGCCCGGTCGCCGCCGGTGAATGCGC<br>GGGCCCGGCGGACAGCGGCGACGCCCTGCTGGAGCGCAAC<br>TATCCCACTGGCGCGGAGTTCCTCGGCGACGGCGGCGACAT<br>CAGCTTCAGCACCCGCGGCACGCAGAACTGGACGGTGGAG |

TABLE 2-continued

Exemplary Nucleotide and Amino Acid Sequences of Carriers

| SEQ ID NO | Sequence |
|---|---|
| | CGGCTGCTCCAGGCGCACCGCCAACTGGAGGAGCGCGGCT<br>ATGTGTTCGTCGGCTACCACGGCACCTTCCTCGAAGCGGCG<br>CAAAGCATCGTCTTCGGCGGGGTGCGCGCGCGCAGCCAGG<br>ACCTCGACGCGATCTGGCGCGGTTTCTATATCGCCGGCGAT<br>CCGGCGCTGGCCTACGGCTACGCCCAGGACCAGGAACCCG<br>ACGCGCGCGGCCGGATCCGCAACGGTGCCCTGCTGCGGGTC<br>TATGTGCCGCGCTCGAGTCTGCCGGGCTTCTACCGCACCGG<br>CCTGACCCTGGCCGCGCCGGAGGCGGCGGGCGAGGTCGAA<br>CGGCTGATCGGCCATCCGCTGCCGCTGCGCCTGGACGCCAT<br>CACCGGCCCCGAGGAGGAAGGCGGGCGCCTGGAAACCATT<br>CTCGGCTGGCCGCTGGCCGAGCGCACCGTGGTGATTCCCTC<br>GGCGATCCCCACCGACCCGCGCAACGTCGGCGGCGACCTCG<br>ACCCGTCCAGCATCCCCGACAAGGAACAGGCGATCAGCGC<br>CCTGCCGGACTACGCCAGCCAGCCCGGCAAACCGCCGCGCG<br>AGGACCTGAAG |
| SEQ ID NO: 137 | AEEAFDLWNECAKACVLDLKDGVRSSRMSVDPAIADTNGQG<br>VLHYSMVLEGGNDALKLAIDNALSITSDGLTIRLEGGVEPNKP<br>VRYSYTRQARGSWSLNWLVPIGHEKPSNIKVFIHELNAGNQLS<br>HMSPIYTIEMGDELLAKLARDATFFVRAHESNEMQPTLAISHA<br>GVSVVMAQAQPRREKRWSEWASGKVLCLLDPLDGVYNYLA<br>QQRCNLDDTWEGKIYRVLAGNPAKHDLDIKPTVISHRLHFPE |
| SEQ ID NO: 138 | GGSLAALTAHQACHLPLETFTRHRQPRGWEQLEQCGYPVQRL<br>VALYLAARLSWNQVDQVIRNALASPGSGGDLGEAIREQPEQA<br>RLALTLAAAESERFVRQGTGNDEAGAAS |
| SEQ ID NO: 139 | ADVVSLTCPVAAGECAGPADSGDALLERNYPTGAEFLGDG |
| SEQ ID NO: 140 | GDVSFSTRGTQNWTVERLLQAHRQLEERGYVFVGYHGTFLEA<br>AQSIVFGGVRARSQDLDAIWRGFYIAGDPALAYGYAQDQEPD<br>ARGRIRNGALLRVYVPRSSLPGFYRTGLTLAAPEAAGEVERLI<br>GHPLPLRLDAITGPEEEGGRLETILGWPLAERTVVIPSAIPTDPR<br>NVGGDLDPSSIPDKEQAISALPDYASQPGKPPREDLK |
| SEQ ID NO: 141 | AEEAFDLWNECAKACVLDLKDGVRSSRMSVDPAIADTNGQG<br>VLHYSMVLEGGNDALKLAIDNALSITSDGLTIRLEGGVEPNKP<br>VRYSYTRQARGSWSLNWLVPIGHEKPSNIKVFIHELNAGNQLS<br>HMSPIYTIEMGDELLAKLARDATFFVRAHESNEMQPTLAISHA<br>GVSVVMAQAQPRREKRWSEWASGKVLCLLDPLDGVYNYLA<br>QQRCNLDDTWEGKIYRVLAGNPAKHDLDIKPTVISHRLHFPEG<br>GSLAALTAHQACHLPLETFTRHRQPRGWEQLEQCGYPVQRLV<br>ALYLAARLSWNQVDQVIRNALASPGSGGDLGEAIREQPEQAR<br>LALTLAAAESERFVRQGTGNDEAGAASADVVSLTCPVAAGEC<br>AGPADSGDALLERNYPTGAEFLGDG |
| SEQ ID NO: 142 | AEEAFDLWNECAKACVLDLKDGVRSSRMSVDPAIADTNGQG<br>VLHYSMVLEGGNDALKLAIDNALSITSDGLTIRLEGGVEPNKP<br>VRYSYTRQARGSWSLNWLVPIGHEKPSNIKVFIHELNAGNQLS<br>HMSPIYTIEMGDELLAKLARDATFFVRAHESNEMQPTLAISHA<br>GVSVVMAQAQPRREKRWSEWASGKVLCLLDPLDGVYNYLA<br>QQRCNLDDTWEGKIYRVLAGNPAKHDLDIKPTVISHRLHFPEG<br>GSLAALTAHQACHLPLETFTRHRQPRGWEQLEQCGYPVQRLV<br>ALYLAARLSWNQVDQVIRNALASPGSGGDLGEAIREQPEQAR<br>LALTLAAAESERFVRQGTGNDEAGAASADVVSLTCPVAAGEC<br>AGPADSGDALLERNYP |
| SEQ ID NO: 143 | AEEAFDLWNECAKACVLDLKDGVRSSRMSVDPAIADTNGQG<br>VLHYSMVLEGGNDALKLAIDNALSITSDGLTIRLEGGVEPNKP<br>VRYSYTRQARGSWSLNWLVPIGHEKPSNIKVFIHELNAGNQLS<br>HMSPIYTIEMGDELLAKLARDATFFVRAHESNEMQPTLAISHA<br>GVSVVMAQAQPRREKRWSEWASGKVLCLLDPLDGVYNYLA<br>QQRCNLDDTWEGKIYRVLAGNPAKHDLDIKPTVISHRLHFPEG<br>GSLAALTAHQACHLPLETFTRHRQPRGWEQLEQCGYPVQRLV<br>ALYLAARLSWNQVDQVIRNALASPGSGGDLGEAIREQPEQAR<br>LALTLAAAESERFVRQGTGNDEAGAASADVVSLTCPVA |
| SEQ ID NO: 144 | AEEAFDLWNECAKACVLDLKDGVRSSRMSVDPAIADTNGQG<br>VLHYSMVLEGGNDALKLAIDNALSITSDGLTIRLEGGVEPNKP<br>VRYSYTRQARGSWSLNWLVPIGHEKPSNIKVFIHELNAGNQLS<br>HMSPIYTIEMGDELLAKLARDATFFVRAHESNEMQPTLAISHA<br>GVSVVMAQAQPRREKRWSEWASGKVLCLLDPLDGVYNYLA<br>QQRCNLDDTWEGKIYRVLAGNPAKHDLDIKPTVISHRLHFPEG<br>GSLAALTAHQACHLPLETFTRHRQPRGWEQLEQCGYPVQRLV<br>ALYLAARLSWNQVDQVIRNALASPGSGGDLGEAIREQPEQAR<br>LALTLAAAESERFVRQGTGNDEAGAAS |

TABLE 2-continued

Exemplary Nucleotide and Amino Acid Sequences of Carriers

| SEQ ID NO | Sequence |
|---|---|
| SEQ ID NO: 145 | AEEAFDLWNECAKACVLDLKDGVRSSRMSVDPAIADTNGQG<br>VLHYSMVLEGGNDALKLAIDNALSITSDGLTIRLEGGVEPNKP<br>VRYSYTRQARGSWSLNWLVPIGHEKPSNIKVFIHELNAGNQLS<br>HMSPIYTIEMGDELLAKLARDATFFVRAHESNEMQPTLAISHA<br>GVSVVMAQAQPRREKRWSEWASGKVLCLLDPLDGVYNYLA<br>QQRCNLDDTWEGKIYRVLAGNPAKHDLDIKPTVISHRLHFPEG<br>GSLAALTAHQACHLPLETFTRHRQ |
| SEQ ID NO: 146 | MVEEALNIFDECRSPCSLTPEPGKPIQSKLSIPSDVVLDEGVLYY<br>SMTINDEQNDIKDEDKGESIITIGEFATVRATRHYVNQDAPFGV<br>IHLDITTENGTKTYSYNRKEGEFAINWLVPIGEDSPASIKISVD<br>ELDQQRNIIEVPKLYSIDLDNQTLEQWKTQGNVSFSVTRPEHN<br>IAISWPSVSYKAAQKEGSRHKRWAHWHTGLALCWLVPMDAIYN<br>YITQQNCTLGDNWFGGSYETVAGTPKVITVKQGIEQKPVEQRI<br>HFSKGGGSLAALTAHQACHLPLETFTRHRQPRGWEQLEQCGY<br>PVQRLVALYLAARLSWNQVDQVIRNALASPGSGGDLGEAIRE<br>QPEQARLALTLAAAESERFVRQGTGNDEAGAASADVVSLTCP<br>VAAGECAGPADSGDALLERNYPTGAEFLGDGGDVSFSTRGTQ<br>NWTVERLLQAHRQLEERGYVFVGYHGTFLEAAQSIVFGGVRA<br>RSQDLDAIWRGFYIAGDPALAYGYAQDQEPDARGRIRNGALL<br>RVYVPRSSLPGFYRTSLTLAAPEAAGEVERLIGHPLPLRLDAIT<br>GPEEEGGRLTILGWPLAERTVVIPSAIPTDPRNVGGDLDPSSIPD<br>KEQAISALPDYASQPGKPPREDLK |
| SEQ ID NO: 147 | MAEEAFDLWNECAKACVLDLKDGVRSSRMSVDPAIADTNGQ<br>GVLHYSMVLEGGNDALKLAIDNALSITSDGLTIRLEGGVEPNK<br>PVRYSYTRQARGSWSLNWLVPIGHEKPSNIKVFIHELNAGNQL<br>SHMSPIYTIEMGDELLAKLARDATFFVRAHESNEMQPTLAISH<br>AGVSVVMAQTQPRREKRWSEWASGKVLCLLDPLDGVYNYLA<br>QQRCNLDDTWEGKIYRVLAGNPAKHDLDIKPTVISHRLHFPEG<br>GNAMSALAAHRVCGVPLETLARSRKPRDLTDDLSCAYQAQNI<br>VSLFVATRILFSHLDSVFTLNLDEQEPEVAERLSDLRRINENNP<br>GMVTQVLTVARQIYNDYVTHHPGLTPEQTSAGAQAAEILSLFC<br>PDADKSCVATNNDQANINIESRSGRSYLPENRAVITPQGVTNW<br>TYQELEATHQALTREGYVFVGYTNHVAAQTIVNRIAPVPRGN<br>NTENEEKWGGLYVATHAEVAHGYARIKEGTGEYGLPTRAER<br>DARGVMLRVYIPRASLERFYRTNTPLENAEEHITQVIGHSLPLR<br>NEAFTGPESAGGEDTVIGWDMAIHAVAIPSTIPGNAYEELAIDE<br>EAVAKEQSISTKPPYKERKDELK |

A carrier can be a polypeptide that is derived from a Cholix exotoxin and having: at most 5 amino acid residues; at most 10 amino acid residues; at most 15 amino acid residues; at most 20 amino acid residues; at most 30 amino acid residues; at most 40 amino acid residues; at most 50 amino acid residues; at most 60 amino acid residues; at most 70 amino acid residues; at most 80 amino acid residues; at most 90 amino acid residues; at most 100 amino acid residues; at most 110 amino acid residues; at most 120 amino acid residues; at most 130 amino acid residues; at most 140 amino acid residues; at most 150 amino acid residues; at most 160 amino acid residues; at most 170 amino acid residues; at most 180 amino acid residues; at most 190 amino acid residues; at most 200 amino acid residues; at most 210 amino acid residues; at most 220 amino acid residues; at most 230 amino acid residues; at most 240 amino acid residues; at most 250 amino acid residues; at most 260 amino acid residues; and at most 265 amino acid residues of SEQ ID NO: 4 or SEQ ID NO: 5. The bacterial carrier receptor binding domain can be a polypeptide derived from Cholix and having at least 10%, 20%, 30%, 40%, 50%, 60%, 70%, 80%, 90%, 95%, 99%, or more sequence homology with SEQ ID NO: 4 or SEQ ID NO: 5. The carrier can be a polypeptide derived from Cholix and having at most 10%, 20%, 30%, 40%, 50%, 60%, 70%, 80%, 90%, 95%, or 99% sequence homology with any one of SEQ ID NO: 1-SEQ ID NO: 133. The amino acid residues can be consecutive. The amino acid residues are also be non-consecutive. A carrier can be derived from a domain I of a Cholix exotoxin. A carrier that is derived from a domain I of an exotoxin can comprise an amino acid having at least 80% sequence identity to any one of the amino acid sequences set forth in SEQ ID NO: 4-SEQ ID NO: 125, or at least 80% sequence identity to a functional fragment thereof. A carrier that is derived from a domain I of an exotoxin can comprise an amino acid having at least 90% sequence identity to any one of the amino acid sequences set forth in SEQ ID NO: 4-SEQ ID NO: 125, or at least 90% sequence identity to a functional fragment thereof. A carrier that is derived from a domain I of an exotoxin can comprise an amino acid having at least 95% sequence identity to any one of the amino acid sequences set forth in SEQ ID NO: 4-SEQ ID NO: 125, or at least 95% sequence identity to a functional fragment thereof. A carrier that is derived from a domain I of an exotoxin can comprise an amino acid having at least 99% sequence identity to any one of the amino acid sequences set forth in SEQ ID NO: 4-SEQ ID NO: 125, or at least 99% sequence identity to a functional fragment thereof. A carrier that is derived from a domain I of an exotoxin can comprise an amino acid having 100% sequence identity to any one of the amino acid sequences set forth in SEQ ID NO: 4-SEQ ID NO: 125, or 100% sequence identity to a functional fragment thereof.

A carrier can be artificially synthesized. A carrier can be an artificially synthesized polypeptide having at least 10%, 20%, 30%, 40%, 50%, 60%, 70%, 80%, 90%, 95%, 99%, or more amino acid sequence homology to a Cholix domain I (e.g., any one of SEQ ID NO: 4-SEQ ID NO: 125). A carrier can be a synthetic polypeptide having at most 10%, 20%, 30%, 40%, 50%, 60%, 70%, 80%, 90%, 95%, or 99% amino acid sequence homology to a Cholix domain I (e.g., any one of SEQ ID NO: 4-SEQ ID NO: 125). The polypeptide that a carrier can be comprises of can be synthesized using solid-phase synthesis.

A carrier can be a polypeptide derived from Cholix and having at most 10%, 20%, 30%, 40%, 50%, 60%, 70%, 80%, 90%, 95%, or 99% sequence homology with any one of SEQ ID NO: 4-SEQ ID NO: 125. Certain fragments within the amino acid sequence of the carrier can have specific functions that can be related to one or more aspects of the transcytosis process. These functions can comprise crossing a polarized monolayer of primary human small intestinal epithelial cells or an intact gut epithelium, enabling or promoting endocytosis into an epithelial cell, apical-to-basal transport, release of the delivery construct from the basal membrane into a basolateral compartment, delivery into an intracellular vesicle or compartment or the cytosol of an epithelial cell, and/or delivery to a supra-nuclear region of an epithelial cell (e.g., a polarized gut epithelial cell).

Thus, the present disclosure provides carriers that can have various functions (e.g., one or more of endocytosis, transcytosis, intracellular delivery, etc.). Such a carrier can comprise an amino acid sequence having at least 80% sequence identity to the amino acid sequence of SEQ ID NO: 4 or SEQ ID NO: 5 or at least 80% sequence identity to a functional fragment thereof, and no more than 347 contiguous amino acid residues from SEQ ID NO: 1. Such a carrier can comprise a deletion or mutation in one or more of amino acid residues of the amino acid sequence set forth in SEQ ID NO: 4 (e.g., a Cholix domain I expressed in a mammalian cell) or SEQ ID NO: 5 (e.g., a Cholix domain I expressed in a bacterial cell). Such a carrier can comprise an amino acid sequence having at least 90% sequence identity to the amino acid sequence of SEQ ID NO: 4 or SEQ ID NO: 5 or at least 90% sequence identity to a functional fragment thereof, and no more than 347 contiguous amino acid residues from SEQ ID NO: 1. A carrier can comprise an amino acid sequence having at least 95% sequence identity to the amino acid sequence of SEQ ID NO: 4 or SEQ ID NO: 5 or at least 95% sequence identity to a functional fragment thereof, and no more than 347 contiguous amino acid residues from SEQ ID NO: 1. A carrier can comprise an amino acid sequence having at least 99% sequence identity to the amino acid sequence of SEQ ID NO: 4 or SEQ ID NO: 5 or at least 99% sequence identity to a functional fragment thereof, and no more than 347 contiguous amino acid residues from SEQ ID NO: 1. A carrier can comprise an amino acid sequence having 100% sequence identity to the amino acid sequence of SEQ ID NO: 4 or SEQ ID NO: 5 or 100% sequence identity to a functional fragment thereof, and no more than 347 contiguous amino acid residues from SEQ ID NO: 1. A carrier disclosed herein can comprise the amino acid sequence set forth in SEQ ID NO: 4 or SEQ ID NO: 5 or a functional fragment thereof. The carrier can comprises the amino acid sequence set forth in SEQ ID NO: 6 or SEQ ID NO: 7 or a functional fragment thereof. The carrier can comprises the amino acid sequence set forth in SEQ ID NO: 8 or SEQ ID NO: 9 or a functional fragment thereof.

A functional carrier of the present disclosure can comprise an amino acid sequence having at least 80% sequence identity to any one of the amino acid sequences set forth in SEQ ID NO: 148, SEQ ID NO: 149, SEQ ID NO: 150, SEQ ID NO: 151, SEQ ID NO: 152, a functional fragment thereof, or any combination thereof. A carrier can comprise an amino acid sequence having at least 90% sequence identity to any one of the amino acid sequences set forth in SEQ ID NO: 148, SEQ ID NO: 149, SEQ ID NO: 150, SEQ ID NO: 151, SEQ ID NO: 152, a functional fragment thereof, or any combination thereof. A carrier can comprise an amino acid sequence having at least 95% sequence identity to any one of the amino acid sequences set forth in SEQ ID NO: 148, SEQ ID NO: 149, SEQ ID NO: 150, SEQ ID NO: 151, SEQ ID NO: 152, a functional fragment thereof, or any combination thereof. A carrier can comprise comprises an amino acid sequence having at least 99% sequence identity to any one of the amino acid sequences set forth in SEQ ID NO: 148, SEQ ID NO: 149, SEQ ID NO: 150, SEQ ID NO: 151, SEQ ID NO: 152, a functional fragment thereof, or any combination thereof. A carrier can comprise a spatial structure in which one or more amino acid residues of SEQ ID NO: 148 or SEQ ID NO: 149 are in close proximity to one or more amino acid residues of SEQ ID NO: 151, and one or more amino acid residues of SEQ ID NO: 148 or SEQ ID NO: 149 are in close proximity to one or more amino acid residues of SEQ ID NO: 152.

A carrier of the present disclosure can be capable of delivering a cargo across an epithelial cell (e.g., a polarized epithelial cell). Such a carrier can comprise an amino acid sequence having at least 80% sequence identity to the amino acid sequence set forth in SEQ ID NO: 30 or SEQ ID NO: 31 or the amino acid sequence set forth in SEQ ID NO: 10 or SEQ ID NO: 11 or at least 80% sequence identity to a functional fragment thereof. A carrier can comprise an amino acid sequence having at least 90% sequence identity to the amino acid sequence set forth in SEQ ID NO: 30 or SEQ ID NO: 31 or the amino acid sequence set forth in SEQ ID NO: 10 or SEQ ID NO: 11 or at least 90% sequence identity to a functional fragment thereof. A carrier can comprise an amino acid sequence having at least 95% sequence identity to the amino acid sequence set forth in SEQ ID NO: 30 or SEQ ID NO: 31 or the amino acid sequence set forth in SEQ ID NO: 10 or SEQ ID NO: 11 or at least 95% sequence identity to a functional fragment thereof. A carrier can comprise an amino acid sequence having at least 99% sequence identity to the amino acid sequence set forth in SEQ ID NO: 30 or SEQ ID NO: 31 or the amino acid sequence set forth in SEQ ID NO: 10 or SEQ ID NO: 11 or at least 99% sequence identity to a functional fragment thereof. A carrier can further comprise a deletion or mutation in one or more of amino acid residues 1-187 or 1-205 of SEQ ID NO: 10 or 1-186 or 1-206 of SEQ ID NO: 11. A carrier can comprise residues 1-186 of SEQ ID NO: 30 or 1-187 of SEQ ID NO: 31 and no more than 206 contiguous amino acid residues of SEQ ID NO: 1.

The methods and compositions of the present disclosure can comprise a carrier comprising an amino acid sequence having at least 80% sequence identity to the amino acid sequence set forth in any one of SEQ ID NO: 10-SEQ ID NO: 31 or at least 80% sequence identity to a functional fragment thereof. A carrier can comprise an amino acid sequence having at least 90% sequence identity to the amino acid sequence set forth in any one of SEQ ID NO: 10-SEQ ID NO: 31 or at least 90% sequence identity to a functional fragment thereof. In some instances, the carrier comprises an amino acid sequence having at least 95% sequence identity to the amino acid sequence set forth in any one of SEQ ID NO: 10-SEQ ID NO: 31 or at least 95% sequence identity to a functional fragment thereof. A carrier can comprise an amino acid sequence having at least 99% sequence identity to the amino acid sequence set forth in any one of SEQ ID NO: 10-SEQ ID NO: 31 or at least 99% sequence identity to a functional fragment thereof. The carrier can comprises the amino acid sequence set forth in SEQ ID NO: 10 or SEQ ID NO: 11 or a functional fragment thereof.

A carrier can comprise an amino acid sequence having at least 80% sequence identity to the amino acid sequence set forth in SEQ ID NO: 106 or SEQ ID NO: 107 or to the amino acid sequence set forth in SEQ ID NO: 30 or SEQ ID NO: 31 or at least 80% sequence identity to a functional fragment thereof. Such a carrier can be capable of delivering cargo to an intracellular location. Such an intracellular location may be a supranuclear region. Such a carrier can comprise an amino acid sequence having at least 90% sequence identity to the amino acid sequence set forth in SEQ ID NO: 106 or SEQ ID NO: 107 or to the amino acid sequence set forth in SEQ ID NO: 30 or SEQ ID NO: 31 or at least 90% sequence identity to a functional fragment thereof. A carrier can comprise an amino acid sequence having at least 95% sequence identity to the amino acid sequence set forth in SEQ ID NO: 106 or SEQ ID NO: 107 or to the amino acid sequence set forth in SEQ ID NO: 30 or SEQ ID NO: 31 or at least 95% sequence identity to a functional fragment thereof. A carrier can comprise an amino acid sequence having at least 99% sequence identity to the amino acid sequence set forth in SEQ ID NO: 106 or SEQ ID NO: 107 or to the amino acid sequence set forth in SEQ ID NO: 30 or SEQ ID NO: 31 or at least 99% sequence identity to a functional fragment thereof. A carrier can comprise a deletion or mutation in one or more of amino acid residues 1-151 or 1-187 of SEQ ID NO: 4 or SEQ ID NO: 5.

The methods and compositions of the present disclosure provide a carrier that can lack any one or more of the amino acid residues 1-39 of SEQ ID NO: 5 or amino acid residues 1-38 of SEQ ID NO: 4. Such a carrier can be capable of delivering cargo to an intracellular location via endocytosis. Such a location can be an apical region or compartment. A carrier can lack all of the amino acid residues 1-39 of SEQ ID NO: 5 or amino acid residues 1-38 of SEQ ID NO: 4. A carrier can comprises an amino acid sequence having at least 80% sequence identity to the amino acid sequence set forth in SEQ ID NO: 70 or 80% sequence identity to a functional fragment thereof. A carrier can comprises an amino acid sequence having at least 90% sequence identity to the amino acid sequence set forth in SEQ ID NO: 70 or 90% sequence identity to a functional fragment thereof. A carrier can comprises an amino acid sequence having at least 95% sequence identity to the amino acid sequence set forth in SEQ ID NO: 70 or 95% sequence identity to a functional fragment thereof. A carrier can comprises an amino acid sequence having at least 99% sequence identity to the amino acid sequence set forth in SEQ ID NO: 70 or 99% sequence identity to a functional fragment thereof. A carrier can comprises residues 1-151 of SEQ ID NO: 5 or residues 1-150 of SEQ ID NO: 4 and no more than 187 contiguous amino acid residues of SEQ ID NO: 1.

A carrier of the present disclosure can comprise a truncated version of a Cholix domain I. Thus, a carrier can comprise an amino acid sequence having at least 80% sequence identity to the amino acid sequence set forth in any one of SEQ ID NO: 30-SEQ ID NO: 107 or at least 80% sequence identity to a functional fragment thereof. Such a carrier can be capable of delivering cargo to an intracellular location via endocytosis. Such a location can be an apical and/or a basal region or compartment. A carrier can comprise an amino acid sequence having at least 90% sequence identity to the amino acid sequence set forth in any one of SEQ ID NO: 30-SEQ ID NO: 107 or at least 90% sequence identity to a functional fragment thereof. A carrier can comprise an amino acid sequence having at least 95% sequence identity to the amino acid sequence set forth in any one of SEQ ID NO: 30-SEQ ID NO: 107 or at least 95% sequence identity to a functional fragment thereof. A carrier can comprise an amino acid sequence having at least 99% sequence identity to the amino acid sequence set forth in any one of SEQ ID NO: 30-SEQ ID NO: 107 or at least 99% sequence identity to a functional fragment thereof. A carrier can comprise the amino acid sequence set forth in SEQ ID NO: 30 or SEQ ID NO: 31 or a functional fragment thereof.

A carrier of the present disclosure can comprises an amino acid sequence having at least 80% sequence identity to the amino acid sequence set forth in SEQ ID NO: 106 or SEQ ID NO: 107 or the amino acid sequence set forth in SEQ ID NO: 124 or SEQ ID NO: 125 or at least 80% sequence identity to a functional fragment thereof. Such a carrier can be capable of delivering cargo to an intracellular location via endocytosis. Such a location can be an apical region or compartment. A carrier can comprise an amino acid sequence having at least 90% sequence identity to the amino acid sequence set forth in SEQ ID NO: 106 or SEQ ID NO: 107 or the amino acid sequence set forth in SEQ ID NO: 124 or SEQ ID NO: 125 or at least 90% sequence identity to a functional fragment thereof. A carrier can comprise an amino acid sequence having at least 95% sequence identity to the amino acid sequence set forth in SEQ ID NO: 106 or SEQ ID NO: 107 or the amino acid sequence set forth in SEQ ID NO: 124 or SEQ ID NO: 125 or at least 95% sequence identity to a functional fragment thereof. A carrier can comprise an amino acid sequence having at least 99% sequence identity to the amino acid sequence set forth in SEQ ID NO: 106 or SEQ ID NO: 107 or the amino acid sequence set forth in SEQ ID NO: 124 or SEQ ID NO: 125 or at least 99% sequence identity to a functional fragment thereof. A carrier can further comprise a deletion or mutation in one or more of amino acid residues 1-151 of SEQ ID NO: 6 or in one or more of amino acid residues 1-150 of SEQ ID NO: 7. A carrier as described herein can comprise residues 1-134 of SEQ ID NO: 5 or residues 1-133 of SEQ ID NO: 4 and no more than 151 contiguous amino acid residues of SEQ ID NO: 1. A carrier can comprise an amino acid sequence having at least 80% sequence identity to the amino acid sequence set forth in any of SEQ ID NO: 106-SEQ ID NO: 125 or at least 80% sequence identity to a functional fragment thereof. A carrier can comprise an amino acid sequence having at least 90% sequence identity to the amino acid sequence set forth in any of SEQ ID NO: 106-SEQ ID NO: 125 or at least 90% sequence identity to a functional fragment thereof. A carrier can comprise an amino acid sequence having at least 95% sequence identity to the amino acid sequence set forth in any of SEQ ID NO: 106-SEQ ID NO: 125 or at least 95% sequence identity to a functional fragment thereof. A carrier can comprise an amino acid sequence having at least 99% sequence identity to the amino acid sequence set forth in any of SEQ ID NO: 106-SEQ ID NO: 125 or at least 99% sequence identity to a functional fragment thereof. A carrier can comprise the amino acid sequence set forth in SEQ ID NO: 106 or SEQ ID NO: 107 or a functional fragment thereof.

A carrier of the present disclosure can be derived from a domain I of an exotoxin. The exotoxin can be Cholix. A carrier that is derived from a Cholix domain I can comprise at least one but no more than 20 beta strands. A carrier that is derived from a Cholix domain I can comprise at least one but no more than 15 beta strands. A carrier that is derived from a Cholix domain I can comprise between 10 and 15 beta strands. A carrier that is derived from a Cholix domain I can comprise at least one but less than 10 α-helices. A carrier that is derived from a Cholix domain I can comprise between 1 and 5 α-helices.

A carrier of the present disclosure can comprise an amino acid fragment of Cholix domain I that can enable, promote, and/or enhance apical entry of the Cholix derived carrier into epithelial cells such as polarized gut epithelial cells. Such a fragment can comprise the amino acid sequence set forth in SEQ ID NO: 148 and can promote and/or enhance apical entry of the Cholix derived carrier into epithelial cells on the apical epithelial/luminal surface. This may enhance the delivery and/or transport function of the carrier and increase the amount cargo molecules delivered and/or transported into and/or across an epithelial cell.

A carrier of the present disclosure can comprise an amino acid fragment of Cholix domain I that can enable, promote, and/or enhance apical-to-basal transcytosis of a Cholix-derived carrier as described herein. Such an amino acid fragment that enables, promotes, and/or enhances apical-to-basal transcytosis of the delivery construct can comprise an amino acid sequence set forth in SEQ ID NO: 149 or SEQ ID NO: 150. This may enhance the delivery and/or transport function of the carrier and increase the amount cargo molecules delivered and/or transported into and/or across an epithelial cell. For example, a carrier comprising such fragment with SEQ ID NO: 149 or SEQ ID NO: 150 can increase the amount cargo molecules delivered and/or transported to a basal compartment. This may further enhance basal release of the carrier.

A carrier of the present disclosure can comprise an amino acid fragment of Cholix domain I that can enable, promote, and/or enhance early and/or late endosomal sorting, thereby enabling, promoting, and/or enhancing transport of the Cholix-derived carrier to a supranuclear region within an epithelial cell. Such a peptide fragment of Cholix domain I comprising the amino acid sequence set forth in SEQ ID NO: 151 and can enable, promote, and/or enhance early endosomal sorting of a Cholix-derived delivery construct as described herein. Supranuclear regions that may be targeted using such a carrier can include the endoplasmatic reticulum, the Golgi apparatus, and/or endosomes. Thus, a carrier capable of accessing such region can provide efficient delivery of cargo to such regions.

A carrier of the present disclosure can comprise an amino acid fragment of Cholix domain I that can enable, promote, and/or enhance complete transcytosis of the Cholix-derived delivery construct across an intact epithelial layer such as the gut epithelium. Such a fragment comprising the amino acid sequence set forth in SEQ ID NO: 152 can enable, promote, and/or enhance complete transcytosis of the Cholix-derived delivery construct by enabling basal release of the carrier and/or the delivery construct from the epithelial cell. Complete transcytosis of the Cholix-derived delivery construct can be determined, for example, by measuring the presence of the delivery construct in a basolateral compartment or the *Lamina propia*. The ability of such carriers to delivery cargo across intact epithelial cell layers can be of high significance as it allows the oral administration of drugs that would not be able to cross such epithelial layers by themselves.

As described herein, the present disclosure contemplates the surprising finding that a carrier that is derived from a Cholix domain I and that lacks a Cholix domain II, domain Ib, and domain III, is sufficient for rapid and efficient apical-to-basal transcytosis (e.g., and sufficient for rapid and efficient apical-to-basal transport of cargo via transcytosis). Furthermore, it is shown that certain portions of the amino acid sequence of Cholix domain I can have specific functions related to apical-to-basal transcytosis across an epithelial cell, and/or the delivery into the cytosol or interior of an epithelial cell. A carrier of the present disclosure can comprise any one of the amino acid sequences set forth in SEQ ID NO: 4-SEQ ID NO: 125. A carrier of the present disclosure can comprise one or more of the functional amino acid peptide fragments of a Cholix domain I set forth in SEQ ID NO: 148-SEQ ID NO: 152. A carrier of the present disclosure can comprise a Cholix domain I with an amino acid sequence set forth in SEQ ID NO: 4 and/or SEQ ID NO: 5.

The present disclosure further contemplates carriers that comprise one or more functional fragments of a Cholix domain I. The functional fragments can be in the same order as in the mature Cholix amino acid sequence, or the functional fragments can be in a different order without impairing the functions(s) of such functional fragments. Thus, a carrier can comprise one or more of the functional amino acid sequences derived a Cholix domain I and set forth in SEQ ID NO: 148-SEQ ID NO: 152. Such amino acid sequences can be linked together to form a polymeric polypeptide comprising a plurality of Cholix domain I derived peptide fragments. Such a carrier of the present disclosure can comprise one or more amino acid sequences set forth in SEQ ID NO: 148-SEQ ID NO: 152, or any combination thereof, that form a polymeric polypeptide capable of efficient transcytosis across epithelial layers such as the gut epithelium. Such a polymeric peptide can comprise a plurality of amino acid fragment derived from Cholix domain I and such polymeric polypeptide can be used instead of and/or in addition to a Cholix domain I polypeptide or a truncated version thereof. Such a non-naturally occurring synthetic polymeric peptide can possess superior or inferior transcytosis capabilities when used as a delivery construct compared to Cholix domain I or a truncated version thereof. The functionality of such synthetic polypeptides can depend on several factors such spatial structure and geometry, stability, and/or the cargo that may be coupled to such polypeptide.

A carrier of the present disclosure may not be significantly altered in a chemical, structural, and/or conformational manner during the transcytosis process across an epithelial cell. Thus, the Cholix toxin-derived carrier as disclosed herein (including polymeric peptides comprising a plurality of Cholix-derived amino acid fragments) can be used as an efficient delivery vehicle for various cargo molecules (e.g., therapeutic cargo molecules) as described herein. A Cholix-derived carrier as described herein does not contain the domains II and III, but instead is attached to one or more cargo moieties (e.g., therapeutic cargo molecules) without having reduced transport and/or transcytosis capabilities compared to mature ntChx.

Transport of a carrier as described herein across an epithelial layer (e.g., a gut epithelium) can comprise multiple steps. Transport of a delivery construct (e.g., a Cholix-derived delivery construct) can comprise elements of Cholix domain I functioning in a multistep process. For example, transport or transcytosis can include apical endocytosis, vesicular trafficking involving apical, basal, and/or supranuclear regions of enterocytes, and release from the basal membrane to reach the *Lamina propria*. Furthermore, a Cholix-derived delivery construct as described herein can utilize a receptor-mediated-type endocytosis process. Receptor-mediated endocytosis can involve an amino acid sequence having at least 80% sequence identity to the amino acid set forth in SEQ ID NO: 148 or a fragment or derivative thereof, which, can provide access to an early endosomal vesicular compartment in the apical portion of enterocytes, e.g., via endocytosis. An amino acid sequence having at least 80% sequence identity to the amino acid set forth in SEQ ID NO: 151 or a fragment or derivative thereof, can allow, promote, or enhance the movement of a Cholix-derived delivery construct to a supranuclear region consistent with a sorting site in the cell for secretory events. Movement of a delivery construct comprising a Cholix-derived carrier to the basal compartment of the cells can be more efficient when the carrier comprises an amino acid sequence having at least 80% sequence identity to the amino acid set forth in SEQ ID NO: 149 or SEQ ID NO: 150, or a fragment or derivative thereof. An amino acid sequence having at least 80% sequence identity to the amino acid set forth in SEQ ID NO: 149, a fragment or derivative thereof, can provide a mechanism for secretion from the basal membrane that releases an intact and functional delivery construct (e.g., including the cargo moiety) into a basolateral compartment or the *Lamina propria* from where it can reach various other locations (e.g., cells, tissues or organs) within an organism (e.g., in a human or in a rodent).

In addition to leaving the carrier unaltered or unmodified during transcytosis, transport of a delivery construct as disclosed herein across an epithelial barrier (e.g., an intact intestinal epithelium) generally does not involve enterocyte intoxication or disruption. Thus, a delivery construct as disclosed herein can comprise a Cholix domain I, a fragment or truncated version thereof (e.g., any one of SEQ ID NO: 6-SEQ ID NO: 125), or a polymeric peptide comprising a plurality of amino acid fragments derived from a Cholix domain I (e.g., SEQ ID NO: 148-SEQ ID NO: 152), and wherein the other domains (e.g., domains II, domain Ib, and III) can be replaced by various other moieties, such as spacers, heterologous cargos (e.g., therapeutic and/or biologically active cargo), small molecules, nucleic acids (e.g., aptamers or interfering RNAs), or any combination thereof, as further described herein.

A carrier of the present disclosure can be used to deliver various cargo molecules into and/or across epithelial cells in an efficient manner, e.g., when comprising an amino acid sequence having at least 80% sequence identity to an amino acid sequence set forth in any one of SEQ ID NO: 4-SEQ ID NO: 125). Thus, a carrier of the present disclosure can enable efficient endocytosis on the apical site and transport into the interior of an epithelial cell (e.g., an enterocyte and/or a polarized gut epithelial cell) such as an intracellular vesicle or compartment or the cytosol and/or a supranuclear region. Such a carrier can comprise an amino acid sequence set forth in any one of SEQ ID NO: 30-SEQ ID NO: 125. Thus, constructs for delivery of cargo molecules into epithelial cells may comprise a truncated Cholix domain I or fragment of a Cholix domain I that does not comprise the amino acid sequence set forth in SEQ ID NO: 151, and/or the amino acid amino acid sequence set forth in SEQ ID NO: 152, or any combination thereof.

A carrier of the present disclosure can comprise one or more potential glycosylation sites. The one or more glycosylation sites can be located within a Cholix domain I (e.g., SEQ ID NO: 4 or SEQ ID NO: 5). A carrier as described herein can comprise the amino acid sequence set forth in SEQ ID NO: 5, wherein the asparagine residues N98, N154, N165, N224, or any combination thereof, can be potential glycosylation sites. Variation or mutation of one or more of these amino acid residues that can act as glycosylation sites can affect or reduce a function related to transcytosis of a delivery construct. TABLE 3 shows exemplary functional peptide fragments of Cholix domain I that were identified to provide one or more functions related to apical-to-basal transcytosis.

TABLE 3

Exemplary Functional Peptide Fragments Derived from Cholix Domain I

| SEQ ID NO | Amino acid sequence |
| --- | --- |
| SEQ ID NO: 148 | ELDQQRNIIEVPKLYSID |
| SEQ ID NO: 149 | MVEEALNIFDECRSPCSLTPE PGKPIQSKLSIPSDVVLD |
| SEQ ID NO: 150 | VEEALNIFDECRSPCSLTPEP GKPIQSKLSIPSDVVLD |
| SEQ ID NO: 151 | DLDNQTLEQWKTQGNVSFSVTR PEHNIAISWPSVSYK |
| SEQ ID NO: 152 | KAAQKEGSRHKRWAHWHTGLAL |

As further described herein, a carrier of the present disclosure can comprise one or more functional fragments. Such functional fragments can include those listed in TABLE 3. Thus, a carrier can comprise an amino acid sequence having at least 80% sequence identity to one or more of the amino acid sequences set forth in SEQ ID NO: 148-SEQ ID NO: 152. A carrier can comprise an amino acid sequence having at least 90% sequence identity to one or more of the amino acid sequences set forth in SEQ ID NO: 148-SEQ ID NO: 152. A carrier can comprise an amino acid sequence having at least 95% sequence identity to one or more of the amino acid sequences set forth in SEQ ID NO: 148-SEQ ID NO: 152. A carrier can comprise an amino acid sequence having at least 99% sequence identity to one or more of the amino acid sequences set forth in SEQ ID NO: 148-SEQ ID NO: 152. A carrier as described herein can comprise at least one of the amino acid sequences set forth in SEQ ID NO: 148-SEQ ID NO: 152. A carrier as described herein can comprise at least two of the amino acid sequences set forth in SEQ ID NO: 148-SEQ ID NO: 152. A carrier as described herein can comprise at least three of the amino acid sequences set forth in SEQ ID NO: 148-SEQ ID NO: 152. A carrier as described herein can comprise at least four of the amino acid sequences set forth in SEQ ID NO: 148-SEQ ID NO: 152. A carrier as described herein can comprise all of the amino acid sequences set forth in SEQ ID NO: 148-SEQ ID NO: 152. Thus, a carrier as described herein can comprise the amino acid sequence set forth in SEQ ID NO: 4 or SEQ ID NO: 5, or a functional fragment thereof.

As disclosed herein, the PE exotoxin domain I (SEQ ID NO: 137) comprises amino acids 1-252 of SEQ ID NO: 135 and has been described as a "receptor binding domain" that functions as a ligand for a cell surface receptor and mediates binding of PE to a cell. Thus, a carrier of the present disclosure can be derived from PE and can comprise the receptor binding domain polypeptide having the amino acid sequence set forth in SEQ ID NO: 137. A carrier can comprise an amino acid sequence with greater than 50% homology to SEQ ID NO: 137. A carrier can comprise an amino acid sequence with greater than 60% homology to SEQ ID NO: 137. A carrier can comprise an amino acid sequence with greater than 70% homology to SEQ ID NO: 137. A carrier can comprise an amino acid sequence with greater than 80% homology to SEQ ID NO: 137. A carrier can comprise an amino acid sequence with greater than 90% homology to SEQ ID NO: 137. A carrier can comprise an amino acid sequence with greater than 95% homology to SEQ ID NO: 137. Moreover, conservative or non-conservative substitutions can be made to the amino acid sequence of SEQ ID NO: 7, so long as the ability to mediate binding of the delivery construct to a cell is not substantially eliminated. A carrier can comprise a receptor binding domain that is a truncated version of SEQ ID NO: 137. A carrier can comprise a receptor binding domain polypeptide wherein one or more amino residues of SEQ ID NO: 137 are deleted. A carrier can comprise a receptor binding domain polypeptide wherein one or more amino residues of SEQ ID NO: 137 are substituted with another amino acid.

A carrier of the present disclosure that is derived from a PE domain I can comprise an amino acid sequence having at least 80% identity to the amino acid sequence of SEQ ID NO: 137 or at least 80% identity to a functional fragment thereof. A carrier can comprise a deletion or mutation in one or more of amino acid residues 1-252 of SEQ ID NO: 137. A carrier can comprise an amino acid sequence having at least 90% sequence identity to the amino acid sequence of 1-252 of SEQ ID NO: 137 or at least 90% sequence identity to a functional fragment thereof. A carrier can comprise an amino acid sequence having at least 95% sequence identity to the amino acid sequence of 1-252 of SEQ ID NO: 137 or at least 95% sequence identity to a functional fragment thereof. A carrier can comprise an amino acid sequence having at least 99% sequence identity to the amino acid sequence of 1-252 of SEQ ID NO: 137 or at least 99% sequence identity to a functional fragment thereof. A carrier can comprise an amino acid sequence having 100% sequence identity to the amino acid sequence of 1-252 of SEQ ID NO: 137 or 100% sequence identity to a functional fragment thereof.

A carrier (e.g., a bacterial carrier receptor binding domain) of the present disclosure can be a polypeptide derived from PE and having: at most 5 amino acid residues; at most 10 amino acid residues; at most 15 amino acid residues; at most 20 amino acid residues; at most 30 amino acid residues; at most 40 amino acid residues; at most 50 amino acid residues; at most 60 amino acid residues; at most 70 amino acid residues; at most 80 amino acid residues; at most 90 amino acid residues; at most 100 amino acid residues; at most 110 amino acid residues; at most 120 amino acid residues; at most 130 amino acid residues; at most 140 amino acid residues; at most 150 amino acid residues; at most 160 amino acid residues; at most 170 amino acid residues; at most 180 amino acid residues; at most 190 amino acid residues; at most 200 amino acid residues; at most 210 amino acid residues; at most 220 amino acid residues; at most 230 amino acid residues; at most 240 amino acid residues; at most 250 amino acid residues; at most 260 amino acid residues; and at most 265 amino acid residues of SEQ ID NO: 137. The bacterial carrier receptor binding domain can be a polypeptide derived from PE and having at least 10%, 20%, 30%, 40%, 50%, 60%, 70%, 80%, 90%, 95%, 99%, or more sequence homology with SEQ ID NO: 137. The bacterial carrier receptor binding domain can be a polypeptide derived from PE and having at most 10%, 20%, 30%, 40%, 50%, 60%, 70%, 80%, 90%, 95%, or 99% sequence homology with SEQ ID NO: 137. The amino acid residues can be consecutive. The amino acid residues can be non-consecutive.

A carrier of the present disclosure can comprise a binding domain that is an artificially synthesized polypeptide having at least 10%, 20%, 30%, 40%, 50%, 60%, 70%, 80%, 90%, 95%, 99%, or more amino acid sequence homology to PE domain I. The carrier comprising a receptor binding domain can be a synthetic polypeptide having at most 10%, 20%, 30%, 40%, 50%, 60%, 70%, 80%, 90%, 95%, or 99% amino acid sequence homology to PE domain I set forth in SEQ ID NO: 137. The polypeptide can be synthesized using solid-phase synthesis or recombinant expression.

A carrier of the present disclosure capable of delivering cargo across epithelial cells (e.g., polarized epithelial cells) can comprise a receptor binding domain polypeptide (e.g., a domain I or a derivative thereof) wherein one or more amino acid residues of one bacterial carrier receptor binding domain polypeptide is replaced by one or more amino acid residues of a second bacterial carrier receptor binding domain polypeptide (also referred to hereinafter as "a hybrid receptor binding domain polypeptide"). For example, a carrier can comprise an amino acid sequence wherein one or more amino acid residues of SEQ ID NO: 4 are replaced by one or more amino acid residues of SEQ ID NO: 137. Alternatively, a carrier can comprise an amino acid sequence wherein one or more amino acid residues of SEQ ID NO: 137 are replaced by one or more amino acid residues of SEQ ID NO: 4. Furthermore, such a carrier can comprise an amino acid sequence wherein amino acid residues 77-87 of SEQ ID NO: 4 (Cholix) are replaced by amino acid residues of a second bacterial carrier receptor binding domain polypeptide (e.g., a PE domain I). A carrier can comprise an amino acid sequence wherein amino acid residues 188-236 of SEQ ID NO: 4 are replaced by amino acid residues of a second bacterial carrier receptor binding domain polypeptide. A carrier can comprise an amino acid sequence wherein amino acid residues 69-71 of SEQ ID NO: 137 are replaced by amino acid residues of a second bacterial carrier receptor binding domain polypeptide. A carrier can also comprise an amino acid sequence wherein amino acid residues 177-228 of SEQ ID NO: 137 are replaced by amino acid residues of a second bacterial carrier receptor binding domain polypeptide. Thus, a carrier of the present disclosure can comprise an amino acid sequence having at least 10%, 20%, 30%, 40%, 50%, 60%, 70%, 80%, 90%, 95%, 99%, or more sequence homology with SEQ ID NO: 4 and at least 10%, 20%, 30%, 40%, 50%, 60%, 70%, 80%, 90%, 95%, 99%, or more sequence homology with SEQ ID NO: 137.

A carrier of the present disclosure that is derived from a domain I of an exotoxin can further comprise a portion of an exotoxin translocation domain, or modified translocation domain elements. A translocation domain can be a domain II of an exotoxin. A carrier of the present disclosure that is derived from a domain I of an exotoxin can further comprise a portion of a non-toxic catalytic domain or modified non-toxic catalytic domain elements. A non-toxic catalytic domain can be a modified domain III of an exotoxin, e.g., those that comprise one or more amino acid variations and/or a deletion of one or more amino acid residues rendering the domain III non-toxic (e.g., an E581A substitution (e.g., SEQ ID NO: 3) or a ΔE581deletion). A translocation domain, or a modified translocation domain, and a non-toxic catalytic domain, or a modified non-toxic catalytic domain, can be derived from the same bacterial toxin. Alternatively, a translocation domain, or a modified translocation domain, and a non-toxic catalytic domain, or a modified non-toxic catalytic domain can be derived from a bacterial carrier selected from the group consisting of Cholix carrier (Cholix) and *Pseudomonas* exotoxin (PE), botulinum toxin, diptheria toxin, pertussis toxin, cholera toxin, heat-labile *E. coli* entero-toxin, shiga toxin, and shiga-like toxin.

As described herein, Cholix domain II (SEQ ID NO: 126) comprises amino acids 266-386 of SEQ ID NO: 1. A carrier of the present disclosure can comprise a Cholix derived carrier comprising the entire amino acid sequence of SEQ ID NO: 126, or can comprise a portion(s) of SEQ ID NO: 126. Further, conservative or non-conservative substitutions can be made to SEQ ID NO: 126. A representative assay that can routinely be used by one of skill in the art to determine whether a transcytosis domain has transcytosis activity is described herein. A carrier can comprise at least 1%, at least 5%, at least 10%, at least 20%, at least 30%, at least 40%, at least 50%, at least 60%, at least 70%, at least 75%, at least 80%, at least 85%, at least 90%, at least 95%, or at least 99% amino acid residues of the entire amino acid sequence of SEQ ID NO: 126. A carrier of the present disclosure can comprise a truncated Cholix domain II, e.g., those identified as $Cholix^{425}$ (SEQ ID NO: 129), $Cholix^{415}$ (SEQ ID NO: 130), $Cholix^{397}$ (SEQ ID NO: 131), $Cholix^{386}$ (SEQ ID NO: 132), $Cholix^{291}$ (SEQ ID NO: 133), and $Cholix^{265}$ (SEQ ID NO: 4).

As described herein, a PE domain II (SEQ ID NO: 138) comprises amino acids 253-364 of SEQ ID NO: 135). A carrier of the present disclosure can comprise a PE carrier comprising the entire amino acid sequence of SEQ ID NO: 137, or can comprise a portion(s) of SEQ ID NO: 137. For example, it is demonstrated herein that, similar to the Cholix-exotoxin domain I, PE domain I can be sufficient for rapid and efficient apical-to-basal transcytosis. Thus, as described above for Cholix derived carriers, portion(s) of PE domain II can be used as a spacer to attach further payload, such as a heterologous cargo. Further, conservative or non-conservative substitutions can be made to SEQ ID NO: 137. A representative assay that can routinely be used by one of skill in the art to determine whether a transcytosis domain has transcytosis activity is described herein. As used herein, the transcytosis activity is not substantially eliminated so long as the activity is, e.g., at least 1%, at least 5%, at least 10%, at least 20%, at least 30%, at least 40%, at least 50%, at least 60%, at least 70%, at least 75%, at least 80%, at least 85%, at least 90%, at least 95%, or at least 99% as compared to a PE carrier comprising the entire amino acid sequence of SEQ ID NO: 137. Thus, a carrier of the present disclosure can comprise a truncated PE domain II, e.g., those identified as $PE^{404}$ (SEQ ID NO: 141), $PE^{395}$ (SEQ ID NO: 142), $PE^{376}$ (SEQ ID NO: 143), $PE^{364}$ (SEQ ID NO: 144), $PE^{277}$ (SEQ ID NO: 145), and $PE^{252}$ (SEQ ID NO: 137).

A carrier of the present disclosure can comprise a receptor binding domain, and a translocation domain (e.g., a domain II), or a modified translocation domain (e.g., a modified domain II), and can further comprise a non-toxic catalytic domain (e.g., a domain III), or modified non-toxic catalytic domain (e.g., a modified domain III). The non-toxic catalytic domain, or modified non-toxic catalytic domain can be derived from a bacterial carrier selected from the group consisting of Cholix carrier (Cholix) and *Pseudomonas* exotoxin (PE), botulinum toxin, diptheria toxin, pertussis toxin, cholera toxin, heat-labile *E. coli* entero-toxin, shiga toxin, and shiga-like toxin. In various embodiments, the translocation domain, or modified translocation domain, and the non-toxic catalytic domain, or modified non-toxic catalytic domain, are derived from the same bacterial toxin.

As described herein, Cholix domain III (SEQ ID NO: 128) comprises amino acids 426-634 of SEQ ID NO: 1 and has been described as a catalytic domain responsible for cytotoxicity and includes an endoplasmic reticulum retention sequence. Domain III mediates ADP ribosylation of elongation factor 2 ("EF2"), which inactivates protein synthesis. A carrier that "lacks endogenous ADP ribosylation activity" or a "detoxified Cholix" refers to any Cholix derived carrier described herein (including modified variants) that does not comprise the entire amino acid sequence set forth in SEQ ID NO: 128 (e.g., a portion of a domain III). Such a carrier can comprise one or more modifications within SEQ ID NO: 128 in a manner which detoxifies the molecule. For example, deletion of the glutamic acid (Glu) residue at amino acid position 156 of SEQ ID NO: 128 detoxifies the molecule. In various embodiments, the portion of SEQ ID NO: 128 other than the ER retention signal can be replaced by another amino acid sequence. This amino acid sequence can itself be non-immunogenic, slightly immunogenic, or highly immunogenic. A highly immunogenic ER retention domain is preferable for use in eliciting a humoral immune response. For example, Cholix domain III is itself highly immunogenic and can be used in delivery constructs where a robust humoral immune response is desired.

As described herein, PE Domain III (SEQ ID NO: 140) comprises amino acids 405-613 of SEQ ID NO: 3) and has been described as a catalytic domain responsible for cytotoxicity and includes an endoplasmic reticulum retention sequence. Domain III mediates ADP ribosylation of elongation factor 2 ("EF2"), which inactivates protein synthesis. A PE derived carrier that "lacks endogenous ADP ribosylation activity" or a "detoxified PE" refers to any PE described herein (including modified variants or derivatives) that does not comprise SEQ ID NO: 140 and/or which has been modified within SEQ ID NO: 140 in a manner which detoxifies the molecule. For example, deletion of the glutamic acid (Glu) residue at amino acid position 149 of SEQ ID NO: 140 detoxifies the molecule. In various embodiments, the portion of PE domain III other than the ER retention signal can be replaced by another amino acid sequence. This amino acid sequence can itself be non-immunogenic, slightly immunogenic, or highly immunogenic. A highly immunogenic ER retention domain is preferable for use in eliciting a humoral immune response. For example, PE domain III is itself highly immunogenic and can be used in delivery constructs where a robust humoral immune response is desired.

The present disclosure contemplates carriers that can comprise a receptor binding domain polypeptide having the amino acid sequence derived from the sequence set forth in SEQ ID NO: 137, a translocation domain having the amino acid sequence derived from the sequence set forth in SEQ ID NO: 138, and a non-toxic catalytic domain having the amino acid sequence derived from the sequence set forth in SEQ ID NO: 140. The present disclosure contemplates carriers that can comprise a receptor binding domain polypeptide having the amino acid sequence derived from the sequence set forth in SEQ ID NO: 4 or SEQ ID NO: 5, a translocation domain having the amino acid sequence derived from the sequence set forth in SEQ ID NO: 126, and a non-toxic catalytic domain having the amino acid sequence derived from the sequence set forth in SEQ ID NO: 128.

In addition to carriers comprising a domain I and/or portions of a domain II and a domain III of an exotoxin, the present disclosure provides carriers that can comprise a Cholix domain Ib (SEQ ID NO: 127), or a portion thereof. Cholix domain Ib (SEQ ID NO: 127) consists of amino acids 387-425 of SEQ ID NO: 1. Thus, a carrier that is derived from a domain I of an exotoxin, can further comprise the amino acid sequence set forth in SEQ ID NO: 127, or a modified sequence truncated at an amino acid residue within SEQ ID NO: 127. The herein described PE domain Ib (SEQ ID NO: 139) consists of amino acids 365-404 of SEQ ID NO: 135. Thus, a PE derived carrier that comprises a receptor binding domain, and a translocation domain, or a modified translocation domain, and a non-toxic catalytic domain, or modified non-toxic catalytic domain, can further comprise the amino acid sequence set forth in SEQ ID NO: 139, or a modified sequence truncated at an amino acid residue within SEQ ID NO: 139.

A carrier of the present disclosure can comprise portion(s) of one or more of a domain II, a domain Ib, or a domain III, wherein those portions (e.g., certain amino acid sequences thereof) can be part of a spacer as further described herein.

The methods and compositions of the present disclosure contemplate carriers that can comprise a first portion and a second portion, wherein the first portion is derived from a first exotoxin and the second portion is derived from a second exotoxin; and wherein the carrier can be coupled to a cargo (e.g., a heterologous cargo such as a biologically active cargo). The first exotoxin can be Cholix, and the second exotoxin can be PE. The first portion can be derived from a domain I, a domain II, a domain Ib, or a domain III of Cholix, or any combination thereof. The first portion can comprise an amino acid sequence having at least 80% sequence identity to any one of the amino acid sequences set forth in SEQ ID NO: 1-SEQ ID NO: 133, a functional fragment thereof, or any combination thereof. The first portion can comprise an amino acid sequence having at least 80% sequence identity to any one of the amino acid sequences set forth in SEQ ID NO: 148-SEQ ID NO: 152, a functional fragment thereof, or any combination thereof. The first portion can comprise an amino acid sequence having at least 80% sequence identity to any one of the amino acid sequences set forth in SEQ ID NO: 4, SEQ ID NO: 5, SEQ ID NO: 10, or SEQ ID NO: 11, a functional fragment thereof, or any combination thereof. The second portion can be derived from a domain I, a domain II, a domain Ib, or a domain III of PE, or any combination thereof. The second portion can comprise an amino acid sequence having at least 80% sequence identity to any one of the amino acid sequences set forth in SEQ ID NO: 137-SEQ ID NO: 145, a functional fragment thereof, or any combination thereof. The first portion can be chemically coupled or recombinantly coupled to the second portion. The first portion can further be directly or indirectly coupled to the second portion. Such a carrier can comprise an amino acid sequence having at least 80% sequence identity to the amino acid sequence SEQ ID NO: 146 or SEQ ID NO: 147.

Generally, a carrier of the present disclosure can comprise a polypeptide, wherein the polypeptide can comprise at least 110 amino acid residues of a domain I of the exotoxin. A carrier can comprise at least 120 amino acid residues of a domain I of the exotoxin. A carrier can comprise at least 130 amino acid residues of a domain I of the exotoxin. A carrier can comprise at least 140 amino acid residues of a domain I of the exotoxin. A carrier can comprise at least 150 amino acid residues of a domain I of the exotoxin. A carrier can comprise at least 50 contiguous amino acid residues of the domain I of the exotoxin. A carrier can comprise at least 60 contiguous amino acid residues of the domain I of the exotoxin. A carrier can comprise at least 75 contiguous amino acid residues of the domain I of the exotoxin. A carrier can comprise at least 100 contiguous amino acid residues of the domain I of the exotoxin. A carrier can comprise at least 150 contiguous amino acid residues of the domain I of the exotoxin.

The methods and compositions of the present disclosure contemplate carriers that can comprise on or more modifications at the N-terminal. Such a modification can comprise at least one N-terminal methionine residue. The at least one N-terminal methionine residue can be part of an N-cap as described herein. A carrier comprising an N-cap can further comprise one or more amino acid variations in the first 5-10 amino acid residues compared to a reference sequences. Thus, one or more of the first N-terminal amino acid residues of the amino acid sequence set forth in SEQ ID NO: 1 can be substituted with other amino acid residues, as long as the consensus sequence that can define a functional Cholix is not altered. In addition to such amino acid variations, a carrier described herein comprising an N-cap can further comprise an N-terminal methionine residue. An N-cap can also only comprise an addition of an N-terminal methionine residue. Exemplary carriers of the present disclosure that comprise such N-cap (e.g., an additional N-terminal methionine) are set forth in any one of SEQ ID NO: 5, SEQ ID NO: 7, SEQ ID NO: 9, SEQ ID NO: 11, SEQ ID NO: 31, SEQ ID NO: 107, SEQ ID NO: 125. As described herein, functional variants of such carrier can comprise an amino acid sequence having at least 80% sequence identity to an amino acid sequence set forth in any one of SEQ ID NO: 5, SEQ ID NO: 7, SEQ ID NO: 9, SEQ ID NO: 11, SEQ ID NO: 31, SEQ ID NO: 107, SEQ ID NO: 125, or 80% sequence identity to a functional fragment thereof.

Generally, and as further described herein, a "Cholix" (also referred to herein as Cholix toxin or Cholix exotoxin) can encompass a variety of functional variants (e.g., a functional genus), wherein the functional variants can comprise one or more variations is their amino acid sequence relative to SEQ ID NO: 1 as disclosed herein. Thus, in the present disclosure, the Cholix toxin having the amino acid sequence set forth in SEQ ID NO: 1 is used as the reference sequence when referred to Cholix. However, as described herein, the present disclosure is not limited to the Cholix having the amino acid sequence set forth in SEQ ID NO: 1 but instead encompasses all Cholix variants that fall within the functional genus of Cholix. For example, a first Cholix domain I polypeptide (e.g., a first carrier) can comprise the amino acid sequence set forth in SEQ ID NO: 4, and a second Cholix domain I polypeptide (e.g., a second carrier) can comprise the amino acid sequence set forth in SEQ ID NO: 5, wherein both the first polypeptide and the second polypeptide are capable of carrying out the same functions, e.g., transcytosis across an epithelial cell, and interact with the same receptors, such as ribophilin 1, SEC24, CK-8, TMEM132, GRP75, ERGIC-53, and/or perlecan. As described herein, a first carrier and a second carrier can be produced in the same expression system (e.g., a bacterial expression system such as *E. coli* or a mammalian expression system such as a CHO cell). In other cases, and as described herein, a first carrier and a second carrier are produced in a different expression system (e.g., a bacterial or a mammalian expression system).

A carrier of the present disclosure can comprise properties that allow interactions with endogenous receptors and/or accessing an endogenous transport and transcytosis system. Thus, a carrier of the present disclosure that is derived from Cholix domain I and comprises an amino acid sequence set forth in any one of SEQ ID NO: 4-SEQ ID NO: 125 or SEQ ID NO: 148-SEQ ID NO: 152 can interact with one or more endogenous receptors. Such endogenous receptors can include TMEM132A, GPR75, ERGIC-53, and/or perlecan, and any combination thereof. Such interaction(s) can provide for (e.g., apical-to-basal) transcytosis across an epithelial cell and/or transport to the interior of an epithelial cell. These interactions allow rapid and efficient delivery. These interactions further provide transport mechanisms that may not alter the carrier of the cell that a carrier is delivered into or transported across. For example, carriers described herein do not show any chemical modifications upon release from the basal membrane of an epithelial cell, suggesting that the carriers of the present disclosure may harness one or more endogenous transport system to deliver cargo into and/or across epithelial cells. Receptors that a carrier and/or a delivery construct comprising a carrier can interact with include, but are not limited to, any one of ribophilin 1, SEC24, CK-8, TMEM132, GRP75, ERGIC-53, or perlecan, or any combination thereof. For example, the interaction of a carrier and/or a delivery construct comprising a carrier with ERGIC-53 (also referred to as LAMN1) can be an integral part of the endocytosis and/or transcytosis process as this receptor is the only interacting protein that may subvert in its cellular distribution following luminal application of a carrier. Moreover, and as demonstrated herein, ERGIC-53 (LAMN1) has been implicated in an indirect retrograde pathway from the Golgi to the ER, suggesting that this can be a pathway described as both efficient and rapid.

The present disclosure provides methods and compositions comprising carriers that allow rapid and efficient transport and delivery of cargo across cells such as epithelial cells. A carrier as described herein can transport cargo across an epithelial cell with a transport rate of about $10^{-10}$ cm/sec to about $10^{-2}$ cm/sec. A carrier can transport cargo across an epithelial cell with a transport rate of about $10^{-9}$ cm/sec to about $10^{-3}$ cm/sec. A carrier can transport cargo across an epithelial cell with a transport rate of about $10^{-8}$ cm/sec to about $10^{-4}$ cm/sec. A carrier can transport cargo across an epithelial cell with a transport rate of about $10^{-7}$ cm/sec to about $10^{-5}$ cm/sec. A carrier can transport cargo across an epithelial cell with a transport rate of about $10^{-6}$ cm/sec. A carrier can transport cargo across an epithelial cell with a transport rate of at least $10^{-8}$ cm/sec. A carrier can transport cargo across an epithelial cell with a transport rate of at least $10^{-7}$ cm/sec. A carrier can transport cargo across an epithelial cell with a transport rate of at least $10^{-6}$ cm/sec. A carrier can transport cargo across an epithelial cell with a transport rate of at least $10^{-5}$ cm/sec. A carrier can transport cargo across an epithelial cell with a transport rate of at least $10^{-4}$ cm/sec. A carrier can transport cargo across an epithelial cell with a transport rate of at least $10^{-3}$ cm/sec. A carrier can transport cargo across an epithelial cell with a transport rate of at least $10^{-2}$ cm/sec.

Delivery Constructs

The methods and compositions of the present disclosure provide carrier molecules that rapidly and efficiently transport cargo into and/or across epithelial cells. Delivery and/or transport of cargo can be achieved by coupling the cargo to a carrier as described herein. Such a construct can be referred to herein as a "delivery construct." As described herein, the present disclosure contemplates carriers that can comprise a small molecule, a polypeptide, an aptamer, a fragment thereof, or any combination thereof. As described herein, a carrier can be derived from an exotoxin. The exotoxin can be Cholix or PE. A carrier can be coupled directly or indirectly to the cargo. A carrier can be covalently or non-covalently coupled to the cargo. Thus, a delivery construct can further comprise a spacer that links the carrier to the cargo. The spacer can be any molecule that links the carrier to the cargo and can comprise oligomeric or polymeric spacers (e.g., polyethylene glycol, etc.), and amino acids. Moreover, a delivery construct comprising a carrier coupled to a cargo and, optionally, a spacer and/or another functional moiety, can be produced synthetically or recombinantly (e.g., in E. coli or a CHO cell).

As disclosed herein, the terms "delivery constructs", "delivery constructs", "toxin-derived delivery constructs", "chimeric constructs", "proteins" and "fusion proteins" can be used interchangeably and can refer to constructs comprising at least one delivery or carrier domain (e.g., a Cholix or PE domain I derived carrier, a small molecule, an aptamer, or any combination thereof) and at least one heterologous cargo molecule such as a therapeutic cargo molecule. The term "heterologous cargo" can be referred to as unrelated to these exotoxins. As further described herein, toxicity (e.g., intoxication of enterocytes) of the bacterial carrier (e.g., Cholix or PE) may not be a necessary requirement for efficient transport of the carrier across intact epithelial layers such as the gut epithelium. Instead, it is demonstrated herein that a carrier that is derived from a domain I (e.g., a truncated version of a domain I) of an exotoxin such as Cholix and PE is sufficient for rapid and efficient transcytosis across epithelial cell (e.g., polarized epithelial cells of a gut).

Generally, a delivery construct (e.g., an isolated delivery construct) comprises a carrier that provides rapid and efficient delivery and/or transport of a cargo to a certain location, wherein the location can be an organ, a tissue, a cell, or a cellular compartment. The cargo molecule can be directly or indirectly coupled to the carrier. The cargo that is coupled to the carrier can be a heterologous cargo (e.g., not derived from the carrier itself). Thus, a delivery construct described herein can comprise a carrier coupled to a heterologous cargo. The carrier can comprise certain functions that allow repaid and efficient transport of cargo to a location, e.g., a location within an epithelial cell or a location(s) within a basolateral compartment. A carrier contemplated herein can be derived from an exotoxin. The exotoxin can be Cholix or PE. A carrier that is derived from a Cholix can comprise an amino acid sequence having at least 80% sequence identity to SEQ ID NO: 1, or at least 80% sequence identity to a functional fragment thereof. It is noted that a Cholix (also referred to herein as Cholix toxin or Cholix exotoxin) can encompass a variety of functional variants (e.g., a functional genus), wherein the functional variants can comprise one or more variations is their amino acid sequence relative to SEQ ID NO: 1 as disclosed herein. Thus, in the present disclosure, the Cholix toxin having the amino acid sequence set forth in SEQ ID NO: 1 is used as the reference sequence when referred to Cholix. However, as described herein, the present disclosure is not limited to the Cholix having the amino acid sequence set forth in SEQ ID NO: 1 but instead encompasses all Cholix variants that fall within the functional genus of Cholix. For example, a first Cholix domain I polypeptide (e.g., a first carrier) can comprise the amino acid sequence set forth in SEQ ID NO: 4, and a second Cholix domain I polypeptide (e.g., a second carrier) can comprise the amino acid sequence set forth in SEQ ID NO: 5, wherein both the first polypeptide and the second polypeptide are capable of carrying out the same functions, e.g., transcytosis across an epithelial cell, and interact with the same receptors, such as ribophilin 1, SEC24 (can also be referred to as COPII coat complex component), cytokeratin-8 (CK-8), transmembrane protein 132 (TMEM132), glucose regulated protein 75 (GRP75), endoplasmatic reticulum Golgi intermediate compartment 53 (ERGIC-53, the number 53 may refer to its molecular weight of approximately 53 kDa), and/or perlecan (also referred to as basement membrane-specific heparan sulfate proteoglycan core protein or HSPG). As described herein, a first carrier and a second carrier can be produced in the same expression system (e.g., a bacterial expression system such as E. coli or a mammalian expression system such as a CHO cell). As described herein, a first carrier and a second carrier can be produced in a different expression system (e.g., a bacterial or a mammalian expression system).

Importantly, the delivery constructs contemplated herein can provide advantages over conventional delivery modalities. Such advantages can include, but are not limited to: a) aid in the production of the delivery construct; b) aid in the refolding of the chimera construct; c) aid in the formulation of the delivery construct; d) aid in reducing the sensitivity of the cargo to proteolytic destruction; e) improve the stability of the delivery construct during storage; f) in embodiments wherein the bacterial carrier elements of domain I are coupled to the heterologous (e.g., a biologically active) cargo without a spacer, or with a non-cleavable spacer, the bacterial carrier elements of domain I can function to retain the chimera to selected locations in the body following transcytosis that results in greater exposure of a biologically active (or diagnostic) cargo to specific cells to provide improved pharmacodynamics; g) in embodiments wherein the bacterial carrier elements of domain I are coupled to a heterologous (e.g., biologically active) cargo with a spacer that is cleavable by an enzyme present at a basolateral membrane of an epithelial cell, or an enzyme present in the plasma of the subject, such cleavage will allow the heterologous (e.g., biologically active) cargo to be released from the remainder of the construct soon after transcytosis across the epithelial membrane; h) the direct delivery of the heterologous cargo to the interior of an epithelial cell such as an intracellular vesicle or compartment or the cytosol or a supranuclear region of an epithelial cell; i) the direct delivery of the heterologous (e.g., biologically active) cargo to the submucosal-GI space and hepatic-portal system can reduce the systemic toxicity observed when the cargo is administered by parenteral routes, as well as enabling access to the submucosal target biology that would be difficult to target via non-oral or GI routes; j) by using endogenous transport and delivery mechanisms, the delivery constructs disclosed herein do not damage the epithelial layer; k) once transported across the GI epithelium, the delivery construct or the biologically active cargo will exhibit an extended serum half-life compared to the biologically active cargo in its non-fused state; l) oral administration of the delivery construct can deliver an increased effective concentration of the delivered biologically active cargo to the liver of the subject than is observed in the subject's plasma; and m) the ability to deliver the biologically active cargo to a subject without using a needle to puncture the skin of the subject, thus improving such subjects' quality of life by avoiding pain or potential complications associated therewith, in addition to improved patient/care-giver convenience and compliance.

The present disclosure provides methods and compositions for delivery and transport of cargo molecules across an epithelial cell (e.g., via transcytosis) and/or into the interior of an epithelial cell. The methods and compositions disclosed herein can comprise a delivery construct, wherein the delivery construct comprises a carrier coupled to a heterologous cargo (e.g., via a spacer). The transport and delivery processes described herein using the carriers of the present disclosure can comprise endocytosis on the apical side of an epithelial cell. Depending on whether the carrier is configured to deliver cargo into or across an epithelial cell, the transport processes can comprise the release of the delivery construct on the basal side. Furthermore, various mechanisms can be involved in transporting cargo to those various locations. For example, delivery of cargo to an intracellular vesicle or compartment or the cytosol of an epithelial cell can comprise releasing a delivery construct comprising a carrier coupled to that cargo from a vesicle into the an intracellular vesicle or compartment or the cytosol. As another example, transcytosis of a delivery construct can include vesicular transcytosis and, as such, can comprise encapsulating the delivery construct in a vesicle during transcytosis such that the delivery construct may or may not be in contact with the intracellular cytosol.

The methods and compositions of the present disclosure can comprise delivering a cargo to a certain location such that the cargo remains at that location for a certain amount of time. For example, a cargo molecule can be retained at an intracellular or basolateral location that has been targeted using the compositions described herein. Retention can cause the cargo molecule to elicit a certain response or biological effect (e.g., a therapeutic effect). Thus, the present disclosure provides methods and compositions that allow delivery of cargo to a location within across an epithelial cell such the delivery construct (and the cargo) is retained at that location for a specific amount of time. Such retention can be modulated, e.g., by allowing the cargo to be cleaved from the carrier, or by allowing the carrier to reversibly or irreversibly bind a certain protein (e.g., a receptor) that is present at that location.

The delivery constructs of the present disclosure can comprise a carrier, wherein the carrier can be configured to target a certain location inside or across an epithelial cell. Such a location can be an organ, a tissue, a cell, or a cellular compartment. By targeting such locations, the methods and compositions described herein can be used for various applications, e.g., those that include delivery of cargo across an intact epithelial membrane in vitro or in vivo.

As described herein, a carrier can be coupled to a heterologous cargo in any way described herein. A delivery construct comprises a carrier that is coupled to a heterologous cargo via a spacer. The spacer can comprise any moiety recited herein, and can comprise any one of the amino acid sequences set forth in SEQ ID NO: 166-SEQ ID NO: 213. The spacer can be a cleavable spacer. The spacer can be a non-cleavable spacer. A spacer can comprise the amino acid sequence set forth in SEQ ID NO: 210, or a fragment or derivative thereof.

Generally, and as described herein, any carrier disclosed herein (e.g., those listed in TABLE 2 and TABLE 3) can be combined with any one of the cargo molecules described herein (e.g., those listed in TABLE 11 and TABLE 12), and, optionally, with any spacer described herein (e.g., those listed in TABLES 7-10 and those having an amino acid sequence set forth in SEQ ID NO: 207-SEQ ID NO: 213) to form a delivery construct. Thus, a carrier described herein can be derived from an exotoxin. A carrier can be derived from a domain I of an exotoxin. The exotoxin can be Cholix or PE. A delivery construct contemplated herein can comprise a carrier derived from Cholix, wherein the carrier can comprise an amino acid sequence having at least 80% sequence identity to an amino acid sequence set forth in any one of SEQ ID NO: 1-SEQ ID NO: 125, coupled to a heterologous cargo. A carrier can comprise an amino acid sequence having at least 90% sequence identity to an amino acid sequence set forth in any one of SEQ ID NO: 1-SEQ ID NO: 125. A carrier can comprise an amino acid sequence having at least 95% sequence identity to an amino acid sequence set forth in any one of SEQ ID NO: 1-SEQ ID NO: 125. A carrier can comprise an amino acid sequence having at least 99% sequence identity to an amino acid sequence set forth in any one of SEQ ID NO: 1-SEQ ID NO: 125. The exotoxin that a carrier can be derived from can be PE. Thus, a delivery construct comprises a carrier can comprise an amino acid sequence having at least 80% sequence identity to an amino acid sequence set forth in SEQ ID NO: 137, or a functional fragment thereof, coupled to a heterologous cargo.

Exemplary delivery constructs as described in the present disclosure are shown below in TABLE 4.

TABLE 4

Amino Acid Sequences of Exemplary Delivery Constructs

| SEQ ID NO | Amino acid sequence |
|---|---|
| SEQ ID NO: 153 | MVEEALNIFDECRSPCSLTPEPGKPIQSKLSIPSDVVLD EGVLYYSMTINDEQNDIKDEDKGESIITIGEFATVRATR HYVNQDAPFGVIHLDITTENGTKTYSYNRKEGEFAINWL VPIGEDSPASIKISVDELDQQRNIIEVPKLYSIDLDNQT LEQWKTQGNVSFSVTRPEHNIAISWPSVSYKAAQKEGSR MHKRWAHWHTGLALCWLVPDAIYNYITQQNCTLGDNWFG GSYETVAGTPKVITVKQGIEQKPVEQRIHFSKGNAMSAL AAHRVCGVPLETLARSRKPRDLTDDLSCAYQAQNIVSLF VATRILFSHLDSVFTLNLDEQEPEVAERLSDLRRINENN PGMVTQVLTVARQIYNDYVTHHPGLTPEQTSAGAQAGGG GSGGGGSGGGGSFPTIPLSRLFDNAMLRAHRLHQLAFDT YQEFEEAYIPKEQKYSFLQNPQTSLCFSESIPTPSNREE TQQKSNLELLRISLLLIQSWLEPVQFLRSVFANSLVYGA SDSNVYDLLKDLEEGIQTLMGRLEDGSPRTGQIFKQTYS KFDTNSHNDDALLKNYGLLYCFRKDMDKVETFLRIVQCR SVEGSCGF |
| SEQ ID NO: 154 | MVEEALNIFDECRSPCSLTPEPGKPIQSKLSIPSDVVLD EGVLYYSMTINDEQNDIKDEDKGESIITIGEFATVRATR HYVNQDAPFGVIHLDITTENGTKTYSYNRKEGEFAINWL VPIGEDSPASIKISVDELDQQRNIIEVPKLYSIDLDNQT LEQWKTQGNVSFSVTRPEHNIAISWPSVSYKAAQKEGSR HKRWAHWHTGLALCWLVPMDAIYNYITQQNCTLGDNWFG GSYETVAGTPKVITVKQGIEQKPVEQRIHFSKGNAMSAL AAHRVCGVPLETLARSRKPRDLTDDLSCAYQAQNIVSLF VATRILFSHLDSVFTLNLDEQEPEVAERLSDLRRINENN PGMVTQVLTVARQIYNDYVTHHPGLTPEQTSAGAQAGGG GSGGGGSGGGGSMHSSALLCCLVLLTGVRASPGQGTQSE NSCTHFPGNLPNMLRDLRDAFSRVKTFFQMKDQLDNLLL KESLLEDFKGYLGCQALSEMIQFYLEEVMPQAENQDPDI KAHVNSLGENLKTLRLRLRRCHRFLPCENKSKAVEQVKN AFNKLQEKGIYKAMSEFDIFINYIEAYMTMKIRN |
| SEQ ID NO: 155 | MVEEALNIFDECRSPCSLTPEPGKPIQSKLSIPSDVVLD EGVLYYSMTINDEQNDIKDEDKGESIITIGEFATVRATR HYVNQDAPFGVIHLDITTENGTKTYSYNRKEGEFAINWL VPIGEDSPASIKISVDELDQQRNIIEVPKLYSIDLDNQT LEQWKTQGNVSFSVTRPEHNIAISWPSVSYKAAQKEGSR HKRWAHWHTGLALCWLVPMDAIYNYITQQNCTLGDNWFG GSYETVAGTPKVITVKQGIEQKPVEQRIHFSKGGGGSGG GGSGGGGSMAALQKSVSSFLMGTLATSCLLLLALLVQGG AAAPISSHCRLDKSNFQQPYITNRTFMLAKEASLADNNT DVRLIGEKLFHGVSMSERCYLMKQVLNFTLEEVLFPQSD RFQPYMQEVVPFLARLSNRLSTCHIEGDDLHIQRNVQKL KDTVKKLGESGEIKAIGELDLLFMSLRNACI |
| SEQ ID NO: 156 | MVEEALNIFDECRSPCSLTPEPGKPIQSKLSIPSDVVLD EGVLYYSMTINDEQNDIKDEDKGESIITIGEFATVRATR HYVNQDAPFGVIHLDITTENGTKTYSYNRKEGEFAINWL VPIGEDSPASIKISVDELDQQRNIIEVPKLYSIDLDNQT LEQWKTQGNVSFSVTRPEHNIAISWPSVSYKAAQKEGSR HKRWAHWHTGLALCWLVPMDAIYNYITQQNCTLGDNWFG GSYETVAGTPKVITVKQGIEQKPVEQRIHFSKMRSSKNV IKEFMRFKVRMEGTVNGHEFEIEGEGEGRPYEGHNTVKL KVTKGGPLPFAWDILSPQFQYGSKVYVKHPADIPDYKKL SFPEGFKWERVMNFEDGGVVTVTQDSSLQDGCFIYKVKF IGVNFPSDGPVMQKKTMGWEASTERLYPRDGVLKGEIHK ALKLKDGGHYLVEFKSIYMAKKPVQLPGYYYVDSKLDIT SHNEDYTIVEQYERTEGRHHLFL |
| SEQ ID NO: 157 | VEDELNIFDECRSPCSLTPEPGKPIQSKLSIPSDVVLDE GVLYYSMTINDEQNDIKDEDKGESIITIGEFATVRATRH YVNQDAPFGVIHLDITTENGTKTYSYNRKEGEFAINWLV PIGEDSPASIKISVDELDQQRNIIEVPKLYSIDLDNQTL EQWKTQGNVSFSVTRPEHNIAISWPSVSYKAAQKEGSRH KRWAHWHTGLALCWLVPMDAIYNYITQQNCTLGDNWFGG SYETVAGTPKVITVKQGIEQKPVEQRIHFSKGNAMSALA AHRVCGVPLETLARSRKPRDLTDDLSCAYQAQNIVSLFV ATRILFSHLDSVFTLNLDEQEPEVAERLSDLRRINENNP GMVTQVLTVARQIYNDYVTHHPGLTPEQTSAGAQAADIL SLFCPDADKSCVASNNDQANINIESRSGRSYLPENRAVI TPQGVTNWTYQELEATHQALTREGYVFVGYHGTNHVAAQ TIVNRIAPVPRGNNTENEEKWGGLYVATHAEVAHGYARI KEGTGEYGLPTRAERDARGVMLRVYIPRASLERFYRTNT PLENAEEHITQVIGHSLPLRNEAFTGPESAGGEDATVIG WDMAIHAVAIPSTIPGNAYEELAIDEEAVAKEQSISTKP PYKERKDELKMRSSKNVIKEFMRFKVRMEGTVNGHEFEI EGEGEGRPYEGMNTVKLKVTKGGPLPFAWDILSPQFQYG SKVYVKHPADIPDYKKLSFPEGFKWERVMNFFDGGVVTV TQDSSLQDGCFIYKVKFIGVNFPSDGPVMQKKTMGWEAS TERLYPRDGVLKGEIHKALKLKDGGHYLVEFKSIYMAKK PVQLPGYYYVDSKLDITSHNEDYTIVEQYERTEGRHHLF L |
| SEQ ID NO: 158 | MVEEALNIFDECRSPCSLTPEPGKPIQSKLSIPSDVVLD EGVLYYSMTINDEQNDIKDEDKGESIITIGEFATVRATR HYVNQDAPFGVIHLDITTENGTKTYSYNRKEGEFAINWL VPIGEDSPASIKISVDEGGGGSGGGGSGGGGSFPTIPLS RLFDNAMLRAHRLHQLAFDTYQEFEEAYIPKEQKYSFLQ NPQTSLCFSESIPTPSNREETQQKSNLELLRISLLLIQS WLEPVQFLRSVFANSLVYGASDSNVYDLLKDLEEGIQTL MGRLEDGSPRTGQIFKQTYSKFDTNSHNDDALLKNYGLL YCFRKDMDKVETFLRIVQCRSVEGSCGF |
| SEQ ID NO: 159 | MVEEALNIFDECRSPCSLTPEPGKPIQSKLSIPSDVVLD EGVLYYSMTINDEQNDIKDEDKGESIITIGEFATVRATR HYVNQDAPFGVIHLDITTENGTKTYSYNRKEGEFAINWL VPIGEDSPASIKISVDELDQQRNIIEVPKLYSIDGGGGS GGGGSGGGGSFPTIPLSRLFDNAMLRAHRLHQLAFDTYQ EFEEAYIPKEQKYSFLQNPQTSLCFSESIPTPSNREETQ QKSNLELLRISLLLIQSWLEPVQFLRSVFANSLVYGASD SNVYDLLKDLEEGIQTLMGRLEDGSPRTGQIFKQTYSKF DTNSHNDDALLKNYGLLYCFRKDMDKVETFLRIVQCRSV EGSCGF |
| SEQ ID NO: 160 | MVEEALNIFDECRSPCSLTPEPGKPIQSKLSIPSDVVLD EGVLYYSMTINDEQNDIKDEDKGESIITIGEFATVRATR HYVNQDAPFGVIHLDITTENGTKTYSYNRKEGEFAINWL VPIGEDSPASIKISVDELDQQRNIIEVPKLYSIDLDNQT LEQWKTQGNVSFSVTRPEHNIAISWPSVSYKGGGGSGGG GSGGGGSFPTIPLSRLFDNAMLRAHRLHQLAFDTYQEFE EAYIPKEQKYSFLQNPQTSLCFSESIPTPSNREETQQKS NLELLRISLLLIQSWLEPVQFLRSVFANSLVYGASDSNV YDLLKDLEEGIQTLMGRLEDGSPRTGQIFKQTYSKFDTN SHNDDALLKNYGLLYCFRKDMDKVETFLRIVQCRSVEGS CGF |
| SEQ ID NO: 161 | MVEEALNIFDECRSPCSLTPEPGKPIQSKLSIPSDVVLD EGVLYYSMTINDEQNDIKDEDKGESIITIGEFATVRATR HYVNQDAPFGVIHLDITTENGTKTYSYNRKEGEFAINWL VPIGEDSPASIKISVDELDQQRNIIEVPKLYSIDLDNQT LEQWKTQGNVSFSVTRPEHNIAISWPSVSYKAAQKEGSR HKRWAHWHTGLGGGGSGGGGSGGGGSFPTIPLSRLFDNA MLRAHRLHQLAFDTYQEFEEAYIPKEQKYSFLQNPQTSL CFSESIPTPSNREETQQKSNLELLRISLLLIQSWLEPVQ FLRSVFANSLVYGASDSNVYDLLKDLEEGIQTLMGRLED GSPRTGQIFKQTYSKFDTNSHNDDALLKNYGLLYCFRKD MDKVETFLRIVQCRSVEGSCGF |

TABLE 4-continued

Amino Acid Sequences of Exemplary Delivery Constructs

| SEQ ID NO | Amino acid sequence |
|---|---|
| SEQ ID NO: 162 | MVEEALNIFDECRSPCSLTPEPGKPIQSKLSIPSDVVLD EGVLYYSMTINDEQNDIKDEDKGESIITIGEFATVRATR HYVNQDAPFGVIHLDITTENGTKTYSYNRKEGEFAINWL VPIGEDSPASIKISVDELDQQRNIIEVPKLYSIDLDNQT LEQWKTQGNVSFSVTRPEHNIAISWPSVSYKAAQKEGSR HKRWAHWHTGLALCWLVPMDAIYNYITQQNCTLGDNWFG GSYETVAGTPKGGGGSGGGGSGGGGSFPTIPLSRLFDNA MLRAHRLHQLAFDTYQEFEEAYIPKEQKYSFLQNPQTSL CFSESIPTPSNREETQQKSNLELLRISLLLIQSWLEPVQ FLRSVFANSLVYGASDSNVYDLLKDLEEGIQTLMGRLED GSPRTGQIFKQTYSKFDTNSHNDDALLKNYGLLYCFRKD MDKVETFLRIVQCRSVEGSCGF |
| SEQ ID NO: 163 | MVEEALNIFDECRSPCSLTPEPGKPIQSKLSIPSDVVLD EGVLYYSMTINDEQNDIKDEDKGESIITIGEFATVRATR HYVNQDAPFGVIHLDITTENGTKTYSYNRKEGEFAINWL VPIGEDSPASIKISVDELDQQRNIIEVPKLYSIDLDNQT LEQWKTQGNVSFSVTRPEHNIAISWPSVSYKAAQKEGSR HKRWAHWHTGLALCWLVPMDAIYNYITQQNCTLGDNWFG GSYETVAGTPKVITVKQGGGGSGGGGSGGGGSFPTIPLS RLFDNAMLRAHRLHQLAFDTYQEFEEAYIPKEQKYSFLQ LNPQTSLCFSESIPTPSNREETQQKSNLELRISLLLIQS WLEPVQFLRSVFANSLVYGASDSNVYDLLKDLEEGIQTL MGRLEDGSPRTGQIFKQTYSKFDTNSHNDDALLKNYGLL YCFRKDMDKVETFLRIVQCRSVEGSCGF |
| SEQ ID NO: 164 | MVEEALNIFDECRSPCSLTPEPGKPIQSKLSIPSDVVLD EGVLYYSMTINDEQNDIKDEDKGESIITIGEFATVRATR HYVNQDAPFGVIHLDITTENGTKTYSYNRKEGEFAINWL VPIGEDSPASIKISVDELDQQRNIIEVPKLYSIDLDNQT LEQWKTQGNVSFSVTRPEHNIAISWPSVSYKAAQKEGSR HKRWAHWHTGLALCWLVPMDAIYNYITQQNCTLGDNWEG GSYETVAGTPKVITVKQGIEQKPVEQRIHFSKGGGGSGG GGSGGGGSFPTIPLSRLFDNAMLRAHRLHQLAFDTYQEF EEAYIPKEQKYSFLQNPQTSLCFSESIPTPSNREETQQK SNLELLRISLLLIQSWLEPVQFLRSVFANSLVYGASDSN VYDLLKDLEEGIQTLMGRLEDGSPRTGQIFKQTYSKFDT NSHNDDALLKNYGLLYCFRKDMDKVETFLRIVQCRSVEG SCGF |
| SEQ ID NO: 165 | GVLYYSMTINDEQNDIKDEDKGESIITIGEFATVRATRH YVNQDAPFGVIHLDITTENGTKTYSYNRKEGEFAINWLV PIGEDSPASIKISVDELDQQRNIIEVPKLYSIDLDNQTL EQWKTQGNVSFSVTRPEHNIAISWPSVSYKAGGGGSGGG GSGGGGSFPTIPLSRLFDNAMLRAHRLHQLAFDTYQEFE EAYIPKEQKYSFLQNPQTSLCFSESIPTPSNREETQQKS NLELLRISLLLIQSWLEPVQFLRSVFANSLVYGASDSNV YDLLKDLEEGIQTLMGRLEDGSPRTGQIFKQTYSKFDTN SHNDDALLKNYGLLYCFRKDMDKVETFLRIVQCRSVEGS CGF |

The methods and compositions of the present disclosure can comprise a delivery construct comprising an amino acid sequence having at least 80% sequence identity to an amino acid sequence set forth in any one of SEQ ID NO: 153-SEQ ID NO: 165, or having at least 80% sequence identity to a functional fragment thereof. A delivery construct can comprise an amino acid sequence having at least 90% sequence identity to an amino acid sequence set forth in any one of SEQ ID NO: 153-SEQ ID NO: 165, or having at least 90% sequence identity to a functional fragment thereof. A delivery construct can comprise an amino acid sequence having at least 95% sequence identity to an amino acid sequence set forth in any one of SEQ ID NO: 153-SEQ ID NO: 165, or having at least 95% sequence identity to a functional fragment thereof. A delivery construct can comprise an amino acid sequence having at least 99% sequence identity to an amino acid sequence set forth in any one of SEQ ID NO: 153-SEQ ID NO: 165, or having at least 99% sequence identity to a functional fragment thereof. A delivery construct can comprise an amino acid sequence having 100% sequence identity to an amino acid sequence set forth in any one of SEQ ID NO: 153-SEQ ID NO: 165, or having 100% sequence identity to a functional fragment thereof.

Exemplary combinations of various carriers, spacers, and heterologous cargos that can form a delivery construct as described herein are shown below in TABLE 5.

TABLE 5

Exemplary Delivery Constructs

| Carrier (SEQ ID NO) | Spacer (SEQ ID NO) | Biologically Active Cargo (SEQ ID NO) |
|---|---|---|
| SEQ ID NO: 4-5 | No Spacer | SEQ ID NOs: 214-220 |
| SEQ ID NO: 4-5 | SEQ ID NOs: 187-206 | SEQ ID NOs: 214-220 |
| SEQ ID NO: 4-5 | SEQ ID NOs: 207-211 | SEQ ID NOs: 214-220 |
| SEQ ID NO: 137 | No Spacer | SEQ ID NOs: 214-220 |
| SEQ ID NO: 137 | SEQ ID NOs: 187-206 | SEQ ID NOs: 214-220 |
| SEQ ID NO: 137 | SEQ ID NOs: 207-211 | SEQ ID NOs: 214-220 |

A delivery construct of the present disclosure can interact with one or more specific proteins, enzyme, or receptors during transport and/or delivery across an epithelial cell and/or into the interior of an epithelial cell (e.g., a polarized gut epithelial cell). The one or more receptors can be endogenous receptors. Thus, the delivery constructs of the present disclosure can use endogenous receptor systems that provide for rapid efficient transport and delivery of cargo across an epithelial cell or an intact epithelium (e.g., a monolayer of Caco-2 cells and/or an intact gut epithelium of a subject), and/or to the interior of an epithelial cell of an epithelium. Delivery constructs comprising a carrier comprising an amino acid sequence set forth in any one of SEQ ID NO: 30-SEQ ID NO: 125 can enable delivery and transport of a heterologous (e.g., a therapeutically or biologically active) cargo to the interior of an epithelial cell, e.g., to the basal side of an epithelial cell, and/or a supranuclear region (e.g., the endoplasmatic reticulum, the Golgi apparatus, and/or an endosome) of an epithelial cell. The interior of an epithelial cell can be an intracellular vesicle or compartment or the cytosol of the epithelial cell. A cargo (e.g., a heterologous cargo) can be delivered to the basal side of the epithelial cell (e.g., a location or compartment at the basal side). A heterologous cargo can be delivered to a supranuclear region of the epithelial cell. Transport of a delivery construct to the interior of an epithelial cell can comprise releasing the delivery construct from a vesicle that formed during endocytosis of the delivery construct on the apical surface of the epithelial cell. Delivery and/or transport to a location in the interior of a cell can comprise retaining the delivery construct in a vesicle and/or releasing the delivery construct from that vesicle, such that the delivery construct can be in contact with the cytosol of the epithelial cell (e.g., the construct may or may not be in contact with the cytosol of the epithelial cell during transcytosis due to encapsulation in the vesicle). Thus, a carrier comprising a truncated version of Cholix domain I can be released from a vesicle, e.g., those comprising an amino acid sequence set forth in any one of SEQ ID NO: 30-SEQ ID NO: 107, or a functional fragment or derivative thereof.

Delivery constructs of the present disclosure comprising a carrier comprising an amino acid sequence set forth in any one of SEQ ID NO: 4-SEQ ID NO: 29, SEQ ID NO: 129-SEQ ID NO: 133, or SEQ ID NO: 141-SEQ ID NO: 145 can enable delivery and transport of a heterologous (e.g., a therapeutically or biologically active) cargo across an epithelial cell. Transport across an epithelial cell (e.g., a polarized gut epithelial cell) can occur via transcytosis. The transcytosis mechanism utilized by the herein described delivery constructs is an endogenous trafficking system including a variety of distinct receptors that the delivery construct interacts with. A carrier of a delivery construct can comprise the structural elements that allow these receptor interactions. The receptors that a carrier as disclosed herein can interact with include ribophilin 1, SEC24, CK-8, TMEM132, GRP75, ERGIC-53, and perlecan, or any combination thereof. A carrier as described herein may not or may not significantly interact with clathrin or GPR78, or a combination thereof.

Using an endogenous system including those receptors can have several advantages over other transport mechanisms. Using an endogenous transport system can include the following advantages: (i) an intact layer of epithelial cells such as a monolayer or an epithelium in vivo can be crossed without damaging or disrupting the cells or monolayer structure; (ii) rapid and efficient delivery and transport can be achieved; (iii) the interaction of distinct domains or regions of an exotoxin derived construct with specific receptors allows modulation of these interaction in a way that allows to specifically target certain regions or compartments within a cell or within a subject. For example, delivery and transport (e.g., of a heterologous cargo) to the interior of an epithelial cell can be provided by using certain truncated versions of an exotoxin domain I, such as those having an amino acid sequence set forth in any one of SEQ ID NO: 30-SEQ ID NO: 125, or functional fragment thereof. The epithelial cell can be located in the gut of a subject (e.g., a rodent or a human). In various embodiments, delivery and transport (e.g., of a heterologous cargo) across an epithelial layer via transcytosis (e.g., by using an endogenous transcytosis system) can be provided by using certain truncated versions or derivatives of an exotoxin domain I, such as those having an amino acid sequence set forth in any one SEQ ID NO: 4-SEQ ID NO: 29, SEQ ID NO: 129-SEQ ID NO: 133, or SEQ ID NO: 141-SEQ ID NO: 145. The ability of the herein described delivery constructs to rapidly and efficiently deliver therapeutically active and/or diagnostic cargo to those locations enables new options for treatment, prevention, and/or diagnosis of various diseases (e.g., inflammatory disease, autoimmune diseases, hormone-deficiency diseases, obesity and metabolic disorders, and cancer).

Delivery constructs of the present disclosure, in addition to a carrier, a cargo, and, optionally, a spacer, can further comprise one or more functional moieties. A functional moiety can be a detectable agent, an affinity handle (e.g., a clickable functional groups such as an azide), a barcode (e.g., a nucleic acid barcode), cell-penetrating agents, or other functional moieties that modulate the pharmacokinetic (PK) and/or pharmacodynamic (PD) profile of the delivery construct. A delivery construct can comprise a cell-penetrating agent. The cell-penetrating agent can be a peptide. The cell-penetrating agent can comprise polycations, polyorganic acids, endosomal releasing polymers, poly(2-propylacrylic acid), poly(2-ethylacrylic acid), Tat peptide, Arg patch, a knotted peptide, CysTAT, S19-TAT, R8 (SEQ ID NO: 73), pAntp, Pas-TAT, Pas-R8 (SEQ ID NO: 76), Pas-FHV, Pas-pAntP, F2R4 (SEQ ID NO: 79), B55, aurin, IMT-P8, BR2, OMOTAG1, OMOTAG2, pVEC, SynB3, DPV1047, C105Y, Transpotan, MTS, hLF, PFVYLI (SEQ ID NO: 93), maurocalcine, imperatoxin, hadrucalin, hemicalcin, opicalcin-1, opicalcin-2, midkin(62-104), MCoTI-II, or a chlorotoxin. A cell-penetrating agent can be coupled to a delivery construct as described herein via the N- or the C-terminus. A cell-penetrating agent can provide access to a variety of cell types. A cell-penetrating agent can provide additional functionality, e.g., for therapeutic cargo delivery, once the delivery construct has crossed and epithelial layer (e.g., an epithelium of a subject).

The methods and compositions of the present disclosure contemplate delivery constructs that can form a multimer. A multimer comprising multiple delivery constructs can be formed in solution. A multimer can be formed by multimerization of the carrier and/or the heterologous cargo. The multimer can be a heteromer or a homomer. The homomer can be a homodimer. The homodimer can be formed by dimerization of the heterologous cargo. For example, a delivery construct comprising the amino acid sequence set forth in SEQ ID NO: 217 can form a dimer. Dimerization of such a delivery construct can be due to dimerization of the cargo, e.g., IL-10 (e.g., SEQ ID NO: 217) in this case.

Insertion Site for Attachment of the Heterologous Cargo

The methods and compositions of the present disclosure can comprise a delivery construct comprising a carrier coupled to a cargo, such as a heterologous cargo. A heterologous (e.g., biologically active) cargo re can be attached to the carrier (e.g., a small molecule, a polypeptide, an aptamer, or a nucleic acid) by any method known by one of skill in the art without limitation. The heterologous cargo can be introduced into any portion of the carrier that does not disrupt the endocytosis and/or transcytosis activity of the carrier.

The present disclosure provides delivery constructs that comprise a polypeptide carrier. Thus, a heterologous cargo can be directly coupled to the N-terminus or C-terminus of such a polypeptide carrier (e.g., a domain I or a truncated version thereof, e.g., SEQ ID NO: 4-SEQ ID NO: 125). A heterologous cargo can be couple to the carrier via a side chain of an amino acid of the carrier receptor binding domain. A heterologous cargo can be coupled to the carrier with a cleavable spacer such that cleavage at the cleavable spacer(s) separates the heterologous cargo from the remainder of the delivery construct. A heterologous cargo can be also a polypeptide that comprises a short leader peptide that remains attached to the polypeptide following cleavage of the cleavable spacer. For example, the heterologous cargo can comprise a short leader peptide of greater than 1 amino acid, greater than 5 amino acids, greater than 10 amino acids, greater than 15 amino acids, greater than 20 amino acids, greater than 25 amino acids, greater than 30 amino acids, greater than 50 amino acids, or greater than 100 amino acids. A biological active cargo can comprise a short leader peptide of less than 100 amino acids, less than 50 amino acids, less than 30 amino acids, less than 25 amino acids, less than 20 amino acids, less than 15 amino acids, less than 10 amino acids, or less than 5 amino acids. A biological active cargo can comprise a short leader peptide of between 1-100 amino acids, between 5-10 amino acids, between 10 to 50 amino acids, or between 20 to 80 amino acids.

As described herein, the present disclosure provides methods and compositions comprising carrier that are derived from a domain I of an exotoxin, wherein the exotoxin can be Cholix or PE. In native Cholix (e.g., SEQ ID NO: 1 or SEQ ID NO: 2) and PE (e.g., SEQ ID NO: 135) the domain Ib loop is not essential for any known activity of the toxin, including cell binding, translocation, ER retention or ADP ribosylation activity. Accordingly, domain Ib can be deleted entirely, or modified to contain a heterologous cargo, e.g., a biologically active cargo. Thus, the heterologous cargo (e.g., biologically active cargo) can be inserted into Cholix or PE carrier domain Ib. A heterologous cargo (e.g., biologically active cargo), for example, can be inserted into a Cholix derived carrier domain Ib between the cysteines at positions 395 and 402 that are not cross-linked. This can be accomplished by reducing the disulfide linkage between the cysteines, by deleting one or both of the cysteines entirely from the Ib domain, by mutating one or both of the cysteines to other residues, for example, serine, or by other similar techniques. Alternatively, the biologically active cargo can be inserted into the domain Ib loop between the cysteines at positions 395 and 402. In such embodiments, the disulfide linkage between the cysteines can be used to constrain the biologically active cargo domain.

The methods and compositions described herein can comprise delivery constructs that are produced such that a heterologous cargo is expressed together with a carrier (and, optionally, a spacer) as a fusion protein (e.g., the delivery construct). In such cases, the heterologous cargo can be inserted into the delivery construct by any method known to one of skill in the art without limitation. For example, amino acids corresponding to the heterologous cargo can be directly inserted into the receptor binding domain, with or without deletion of native amino acid sequences. Alternatively, a heterologous cargo may not be expressed together with a carrier (and, optionally, a spacer) as a fusion protein, the heterologous cargo can be coupled to the carrier by any suitable method known by one of skill in the art, without limitation, including peptide conjugation chemistry and/or click chemistry.

Spacers

The methods and compositions of the present disclosure can comprise delivery constructs comprising a carrier coupled to a cargo (e.g., a heterologous cargo), wherein the carrier is capable of delivering the heterologous cargo into and/or across an epithelial cell in vitro (e.g., an epithelial cell monolayer) or in vivo (e.g., a gut epithelium of a subject). Such a carrier can be coupled to a cargo in any way described herein. The carrier can be directly or indirectly coupled the cargo. The carrier can also be covalently or non-covalently coupled to the cargo.

The present disclosure provides delivery constructs comprising a carrier coupled to a heterologous cargo via a spacer. A spacer can comprise any moiety recited herein. A spacer can be any molecule that links the carrier to the cargo and can comprise oligomeric or polymeric spacers (e.g., polyethylene glycol, etc.), other small molecule spacer (e.g., those derived from dicarbonic acids such as succinic acid, aspartic acid, etc.) and amino acids (including short peptide sequences etc.). Thus, a "spacer," as described herein, generally refers to a chemical moiety that can be attached to or coupled to a molecule of the present disclosure. A spacer can be located between a first molecule and a second molecule. A spacer can connect, attach, link, or couple a first molecule (e.g., a polypeptide, small molecule, nucleic acid, etc.) to a second molecule (e.g., a polypeptide, small molecule, nucleic acid, etc.). A spacer can reduce steric hindrance between the first molecule and the second molecule. A spacer can be an amino acid sequence coupled to the C-terminus of a peptide or polypeptide. The amino acid sequence of a spacer as disclosed herein can be between 1-100 amino acid residues long. A spacer can be between 5-75 amino acid residues long. A spacer can be between 5-50 amino acid residues long. In some cases, a spacer is between 5-25 amino acid residues long. A carrier can comprise any one of the amino acid sequences set forth in SEQ ID NO: 4-SEQ ID NO: 125 is coupled to a spacer at its C-terminus (and the spacer can be further coupled to a heterologous cargo via its C-terminus). The spacer can be an amino acid spacer. The spacer can comprise any of the amino acid sequences set forth in SEQ ID NO: 166-SEQ ID NO: 213. The spacer can comprise a portion of a domain II, a domain Ib, or a domain III of an exotoxin, or any combination thereof. For example, a delivery construct as described herein can comprise a carrier comprising an amino acid sequence set forth in any one of SEQ ID NO: 4-SEQ ID NO: 125, coupled to a spacer, wherein the spacer comprises amino acid residues 1-82 of SEQ ID NO: 126.

The present disclosure provides delivery constructs that comprise one or more spacer which are further described herein. A spacer can comprise an amino acid sequence. A spacer can comprise at most 82 amino acid residues of any one SEQ ID NO: 126. Thus, a spacer can comprise the first 82 amino acid residues of the amino acid sequence set forth in SEQ ID NO: 126. The amino acid residues of the Cholix domain II can be contiguous amino acid residues (e.g., residues 1-82 of SEQ ID NO: 126).

Other spacer that can be used in combination with the herein described methods and compositions comprise those comprising an amino acid sequences set forth in SEQ ID NO: 207-SEQ ID NO: 211. A spacer comprises the amino acid sequence set forth in SEQ ID NO: 210, or a fragment or derivative thereof.

The methods and compositions of the present disclosure can comprise spacer that can comprise a portion of a domain II, a domain Ib, and/or a domain III of an exotoxin. For example, a carrier comprising an amino acid sequence set forth in any one of SEQ ID NO: 4-SEQ ID NO: 125 can further be coupled (e.g., via the C-terminus) to a spacer, wherein the spacer comprises from about 80 to about 90 amino acid residues from any one of SEQ ID NO: 126-SEQ ID NO: 128 and/or SEQ ID NO: 138-SEQ ID NO: 140. A spacer can comprise at most 85 amino acid residues of any one of SEQ ID NO: 126-SEQ ID NO: 128 and/or SEQ ID NO: 137-SEQ ID NO: 139. A spacer can comprise at most 82 amino acid residues of any one of SEQ ID NO: 126-SEQ ID NO: 128 and/or SEQ ID NO: 137-SEQ ID NO: 139 A spacer can comprise at most 80 amino acid residues of any one of SEQ ID NO: 126-SEQ ID NO: 128 and/or SEQ ID NO: 137-SEQ ID NO: 139. A spacer can comprise at most 50 amino acid residues of any one of SEQ ID NO: 126-SEQ ID NO: 128 and/or SEQ ID NO: 137-SEQ ID NO: 139. A spacer can comprise at most 25 amino acid residues of any one of SEQ ID NO: 126-SEQ ID NO: 128 and/or SEQ ID NO: 137-SEQ ID NO: 139.

A spacer can comprise at most 82 amino acid residues of any one SEQ ID NO: 126. A spacer can comprise the first 82 amino acid residues of the amino acid sequence set forth in SEQ ID NO: 126. The amino acid residues of the Cholix domain II can be contiguous amino acid residues (e.g., residues 1-82 of SEQ ID NO: 126).

A spacer of the present disclosure can be a cleavable spacer. A spacer of the present disclosure can be a non-cleavable spacer.

Cleavable Spacers

The presently described methods and compositions allow for a heterologous cargo (e.g., a biologically or therapeutically active cargo) to be delivered to a location inside or across an epithelial cell, wherein the heterologous cargo can be coupled to the carrier forming a delivery construct as described herein. Such a delivery construct can further comprise a spacer that can indirectly couple a carrier to a cargo (e.g., a heterologous cargo). A spacer as described herein can be a cleavable spacer. The number of cleavable spacers present in a delivery construct depends, at least in part, on the location of the heterologous cargo in relation to the delivery construct and the nature of the heterologous cargo. When the heterologous cargo can be separated from the remainder of the delivery construct with cleavage at a single spacer, the delivery constructs can comprise a single cleavable spacer. Further, where the heterologous cargo is, e.g., a dimer or other multimer, each subunit of the biologically active cargo can be separated from the remainder of the delivery construct and/or the other subunits of the biologically active cargo by cleavage at the cleavable spacer.

A cleavable spacer can be cleaved by a cleaving enzyme that is present at or near the basolateral membrane of an epithelial cell. By selecting the cleavable spacer to be cleaved by such enzymes, the biologically active cargo can be liberated from the remainder of the delivery construct following transcytosis across the mucous membrane and release from the epithelial cell into the cellular matrix on the basolateral side of the membrane. Further, cleaving enzymes could be used that are present inside the epithelial cell, such that the cleavable spacer is cleaved prior to release of the delivery construct from the basolateral membrane, so long as the cleaving enzyme does not cleave the delivery construct before the delivery construct enters the trafficking pathway in the polarized epithelial cell that results in release of the delivery construct and biologically active cargo from the basolateral membrane of the cell.

A carrier of the present disclosure can be cleaved by an enzyme. The enzyme that is present at a basolateral membrane of a polarized epithelial cell can be selected from, e.g., Cathepsin GI, Chymotrypsin I, Elastase I, Subtilisin AI, Subtilisin AII, Thrombin I, or Urokinase I. TABLE 6 presents these enzymes together with an amino acid sequence that is recognized and cleaved by the particular peptidase.

TABLE 6

Peptidases Present Near Basolateral Mucous Membranes or in Latter Aspects of the Transcytosis Pathway

| Peptidase | Amino Acid Sequence Cleaved | SEQ ID NO |
| --- | --- | --- |
| Cathepsin GI | AAPF | SEQ ID NO: 166 |
| Chymotrypsin I | GGF | SEQ ID NO: 167 |
| Elastase I | AAPV | SEQ ID NO: 168 |
| Subtilisin AI | GGL | SEQ ID NO: 169 |
| Subtilisin AII | AAL | SEQ ID NO: 170 |
| Thrombin I | FVR | SEQ ID NO: 171 |
| Urokinase I | VGR | SEQ ID NO: 172 |
| Furin | RQPR | SEQ ID NO: 173 |

A cleavable spacer can exhibit a greater propensity for cleavage than the remainder of the delivery construct. As one skilled in the art is aware, many peptide and polypeptide sequences can be cleaved by peptidases and proteases. The cleavable spacer can be selected so that it will be preferentially cleaved relative to other amino acid sequences present in the delivery construct during administration of the delivery construct. A carrier of a delivery construct can be substantially (e.g., about 99%, about 95%, about 90%, about 85%, about 80, or about 75%) intact following delivery of the delivery construct to the bloodstream of the subject. A cargo of a delivery construct can be substantially (e.g., about 99%, about 95%, about 90%, about 85%, about 80, or about 75%) intact following delivery of the delivery construct to the bloodstream of the subject. A cleavable spacer can be substantially (e.g., about 99%, about 95%, about 90%, about 85%, about 80, or about 75%) cleaved following delivery of the delivery construct to the bloodstream of the subject.

A cleaving enzyme found in the plasma of the subject can be used to cleave the cleavable spacer. Any cleaving enzyme known by one of skill in the art to be present in the plasma of the subject can be used to cleave the cleavable spacer. Uses of such enzymes to cleave the cleavable spacers is less preferred than use of cleaving enzymes found near the basolateral membrane of a polarized epithelial cell because it is believed that more efficient cleavage will occur in near the basolateral membrane. However, if the skilled artisan determines that cleavage mediated by a plasma enzyme is sufficiently efficient to allow cleavage of a sufficient fraction of the delivery constructs to avoid adverse effects; such plasma cleaving enzymes can be used to cleave the delivery constructs. Accordingly, the cleavable spacer can be cleaved with an enzyme that is selected from the group consisting of caspase-1, caspase-3, proprotein convertase 1, proprotein convertase 2, proprotein convertase 4, proprotein convertase 4 PACE 4, prolyl oligopeptidase, endothelin cleaving enzyme, dipeptidyl-peptidase IV, signal peptidase, neprilysin, renin, and esterase (see, e.g., U.S. Pat. No. 6,673,574, incorporated by reference in its entirety herein). TABLE 7 presents these enzymes together with an amino acid sequence(s) recognized by the particular peptidase. The peptidase cleaves a peptide comprising these sequences at the N-terminal side of the amino acid identified with an asterisk.

TABLE 7

Exemplary Plasma Peptidases

| Peptidase | Amino Acid Sequence Cleaved | SEQ ID NO |
| --- | --- | --- |
| Caspase-1 | Tyr-Val-Ala-Asp-Xaa* | SEQ ID NO: 174 |
| Caspase-3 | Asp-Xaa-Xaa-Asp-Xaa* | SEQ ID NO: 175 |
| Proprotein convertase 1 | Arg-(Xaa)$_n$-Arg-Xaa*; n = 0, 2, 4 or 6 | SEQ ID NO: 176 |
| Proprotein convertase 2 | Lys-(Xaa)$_n$-Arg-Xaa*; n = 0, 2, 4 or 6 | SEQ ID NO: 177 |
| Proprotein convertase 4 | Glu-Arg-Thr-Lys-Arg-Xaa* | SEQ ID NO: 178 |
| Proprotein convertase 4 PACE 4 | Arg-Val-Arg-Arg-Xaa* | SEQ ID NO: 179 |
|  | Decanoyl-Arg-Val-Arg-Arg-Xaa* | SEQ ID NO: 180 |
| Prolyloligopeptidase Endothelin cleaving enzyme in combination with dipeptidyl-peptidase IV | Pro-Xaa*-Trp-Val-Pro-Xaa | SEQ ID NO: 181 |
| Signal peptidase | Trp-Val*-Ala-Xaa | SEQ ID NO: 182 |
| Neprilysin in combination with Dipeptideyl-peptidase IV | Xaa-Phe*-Xaa-Xaa | SEQ ID NO: 183 |
|  | Xaa-Tyr*-Xaa-Xaa | SEQ ID NO: 184 |
|  | Xaa-Trp*-Xaa-Xaa | SEQ ID NO: 185 |

TABLE 7-continued

Exemplary Plasma Peptidases

| Peptidase | Amino Acid Sequence Cleaved | SEQ ID NO |
|---|---|---|
| Renin in combination with dipeptidyl-peptidase IV | Asp-Arg-Tyr-Ile-Pro-Phe-His-Leu*-Leu-(Val, Ala or Pro)-Tyr-(Ser, Pro, or Ala) | SEQ ID NO: 186 |

Thus, a cleavable spacer can be any cleavable spacer known by one of skill in the art to be cleavable by an enzyme that is present at the basolateral membrane of an epithelial cell. A cleavable spacer can comprise a peptide. A cleavable spacer can comprise a nucleic acid, such as RNA or DNA. Furthermore, a cleavable spacer can comprise a carbohydrate, such as a disaccharide or a trisaccharide.

Alternatively, a cleavable spacer can be any cleavable spacer known by one of skill in the art to be cleavable by an enzyme that is present in the plasma of the subject to whom the delivery construct is administered. Such a cleavable spacer can comprise a peptide. Such a cleavable spacer can comprise a nucleic acid, such as RNA or DNA. Such a cleavable spacer comprises a carbohydrate, such as a disaccharide or a trisaccharide.

A cleavable spacer can be selected from, or can be derived from the exemplary list presented in TABLE 8.

TABLE 8

Amino Acid Sequences of Exemplary Spacers

| Peptidase | Spacer amino acid sequence | SEQ ID NO |
|---|---|---|
| Subtilisin A | SGGGGSGKAGSRGLT | SEQ ID NO: 187 |
| Furin | SGGGGSGGGGLRQPR | SEQ ID NO: 188 |
| PC5a | SGGGGSGKKVERFRY | SEQ ID NO: 189 |
| Thrombin | SGGGGSGGGGLMTPR | SEQ ID NO: 190 |
| Pro-matripase | SGGGGSGKAGSFSEG | SEQ ID NO: 191 |
| Cathepsin G | SGGGGSGKAGSAAPF | SEQ ID NO: 192 |
| TEV | GGGGSGGGENLYFQS | SEQ ID NO: 193 |

Moreover, a cleavable spacer can be a spacer that comprises an amino acid sequence that is a known substrate for the tobacco etch virus (TEV) protease. Accordingly, a cleavable spacer can comprise the amino acid sequence set in forth in, e.g., GGGGSGGGENLYFQS (SEQ ID NO: 193).

The novel delivery constructs of the present disclosure can comprise a peptide sequence (or like domain), which serves to inhibit, interfere with, or block the ability of the biologically active cargo to bind to receptors at the surface of epithelial cells. Accordingly, depending upon the biologically cargo to be delivered, the peptide sequence (or like domain) which serves to inhibit, interfere with, or block the ability of the biologically active cargo to bind to its receptor at the surface of epithelial cells will be directed specifically to the receptor to which the biologically active binds.

Various biologically active cargos can bind to GM-1-gangliosides found on the surfaces of mammalian cells. Accordingly, a cleavable spacer of the present disclosure can comprise a peptide sequence, which serves to inhibit, interfere with, or block the ability of the biologically active cargo to bind GM-1 at the surface of epithelial cells. U.S. Pat. No. 8,877,161 teach a number of peptides that interfere with the binding of ligands to GM-1. TABLE 9 presents several examples of peptide sequences, which can be incorporated in whole, or in part, into the cleavable spacers to be used in the preparation of the delivery constructs of the present disclosure.

TABLE 9

Exemplary GM-1 Binding Peptides

| Peptide sequence | SEQ ID NO |
|---|---|
| VSWKTWFPNLAV | SEQ ID NO: 194 |
| YSPFHKWFPSMH | SEQ ID NO: 195 |
| IPQVWRDWFKLP | SEQ ID NO: 196 |
| FPAWFTKLYPRT | SEQ ID NO: 197 |
| QINTAKWWKTHF | SEQ ID NO: 198 |
| DASKALRSSGMP | SEQ ID NO: 199 |
| WKTWFP | SEQ ID NO: 200 |

A cleavable spacer used in the preparation of the delivery constructs of the present disclosure can comprise the amino acid sequence of, e.g., SEQ ID NO: 185, SEQ ID NO: 186, SEQ ID NO: 187, SEQ ID NO: 188, SEQ ID NO: 189 and SEQ ID NO: 190, or variants or fragments thereof, as depicted in TABLE 10 below.

TABLE 10

Exemplary Cleavable GM-1 Binding Peptide-Containing Spacers

| Spacer amino acid sequence | SEQ ID NO |
|---|---|
| SGGGGWKTWFPRGLT | SEQ ID NO: 201 |
| SGGGGWKTWFPRQPR | SEQ ID NO: 202 |
| SGGGGWKTWFPRFRY | SEQ ID NO: 203 |
| SGGGGWKTWFPMTPR | SEQ ID NO: 204 |
| SGGGGWKTWFPFSEG | SEQ ID NO: 205 |
| SGGGGWKTWFPAAPF | SEQ ID NO: 206 |

Non-Cleavable Spacers

A delivery construct of the present disclosure can comprise a carrier coupled to a heterologous cargo (e.g., a biologically active cargo), wherein the cargo can be separated from the carrier by a spacer consisting of one or more amino acids (e.g., up to 25 amino acids). The spacer can be a peptide spacer or any other molecular entity that may be used to couple to link a first and a second molecule. Generally, a spacer will have no specific biological activity other than to join the proteins or to preserve some minimum distance or other spatial relationship between them. However, the constituent amino acids of the spacer can be selected to influence some property of the molecule such as the folding, net charge, or hydrophobicity.

The spacer can be capable of forming covalent bonds to both the delivery construct and to the (e.g., biologically active) cargo. Suitable spacers are well known to those of skill in the art and include, but are not limited to, straight or branched-chain carbon spacers, heterocyclic carbon spacers, or peptide spacers. The spacer(s) can be joined to the constituent amino acids of the delivery construct and/or the biologically active cargo through their side groups (e.g., through a disulfide linkage to cysteine). The spacers can be joined to the alpha carbon amino and/or carboxyl groups of the terminal amino acids of the delivery construct and/or the (e.g., biologically active) cargo.

A bifunctional spacer having one functional group capable of reacting with a group on the bacterial carrier and another group reactive on the biologically active cargo can be used to form the desired conjugate. Alternatively, derivatization can involve chemical treatment of the targeting moiety. Procedures for generation of, for example, free sulfhydryl groups on polypeptides, such as antibodies or antibody fragments, are known (See U.S. Pat. No. 4,659,839).

Many procedures and spacer molecules for attachment of various compounds including radionuclide metal chelates, toxins and drugs to proteins such as antibodies are known. See, for example, European Patent Application No. 188,256; U.S. Pat. Nos. 4,671,958, 4,659,839, 4,414,148, 4,699,784; 4,680,338; 4,569,789; and 4,589,071; and Borlinghaus et al. (1987) Cancer Res. 47: 4071-4075.

A cargo (e.g., a biologically active cargo) to be delivered to a location (e.g., a location within a subject such as a human) can be coupled to the carrier using one or more non-cleavable peptide spacers comprising, e.g., the amino acid sequence GTGGS (SEQ ID NO: 207), GGGGS (SEQ ID NO: 208), GGGGSGGGGS (SEQ ID NO: 209), GGGGSGGGGSGGGGS (SEQ ID NO: 210), or GGGGSGGG (SEQ ID NO: 211), wherein the carrier targets said cargo (e.g., biologically active cargo) to specific cells, including but not limited to, cells of the immune system such as macrophages, antigen-presenting cells and dendritic cells (e.g., upon transporting the cargo across an epithelial cell). Generally, a non-cleavable spacer can comprise one or more of $(GGGGS)_x$ (SEQ ID NO: 212), wherein x=1, 2, 3, 4, 5, 6, 7, 8, 9, or 10. A non-cleavable spacer can comprise one or more of $(GS)_x$ (SEQ ID NO: 213), wherein x=1, 2, 3, 4, 5, 6, 7, 8, 9, or 10.

Production of Delivery Constructs

The delivery constructs of the present disclosure can be produced using a variety of methods. The selection of a production method can depend on the molecular structure of the delivery construct and/or its components (e.g., the carrier, cargo, and/or spacer). Thus, for some delivery constructs organic synthetic methods may be advantageous for producing such delivery construct. A delivery construct of the present disclosure can be a polypeptide. Such polypeptides can be produced, for example, using recombinant DNA methodology. Generally, this involves creating a DNA sequence that encodes the delivery construct, placing the DNA in an expression cassette under the control of a particular promoter, expressing the molecule in a host, isolating the expressed molecule and, if required, folding of the molecule into an active conformational form.

DNA encoding the delivery constructs described herein can be prepared by any suitable method, including, for example, cloning and restriction of appropriate sequences or direct chemical synthesis by methods such as the phosphotriester method of Narang et al. (1979) Meth. Enzymol. 68: 90-99; the phosphodiester method of Brown et al. (1979) Meth. Enzymol. 68: 109-151; the diethylphosphoramidite method of Beaucage et al. (1981) Tetra. Lett., 22: 1859-1862); the solid support method of U.S. Pat. No. 4,458,066, and the like.

Chemical synthesis produces a single stranded oligonucleotide. This can be converted into double stranded DNA by hybridization with a complementary sequence or by polymerization with a DNA polymerase using the single strand as a template. One of skill would recognize that while chemical synthesis of DNA is limited to sequences of about 100 bases, longer sequences can be obtained by the ligation of shorter sequences.

Alternatively, subsequences can be cloned and the appropriate subsequences cleaved using appropriate restriction enzymes. The fragments can then be ligated to produce the desired DNA sequence. A DNA encoding a delivery constructs of the present disclosure can be cloned using DNA amplification methods such as polymerase chain reaction (PCR). Thus, for example, the gene for the biologically active cargo is PCR amplified, using a sense primer containing the restriction site for, e.g., NdeI and an antisense primer containing the restriction site for HindIII. This can produce a nucleic acid encoding the biologically active cargo sequence and having terminal restriction sites. A delivery construct having "complementary" restriction sites can similarly be cloned and then ligated to the biologically active cargo and/or to a spacer attached to the biologically active cargo. Ligation of the nucleic acid sequences and insertion into a vector produces a vector encoding the biologically active cargo joined to the bacterial carrier receptor binding domain. In various embodiments, DNA encoding delivery constructs of the present disclosure is artificially synthesized by, for example, solid-phase DNA synthesis.

The production methods described herein can be used to produce the delivery constructs of the present disclosure, or (functional) variants thereof. For example, a "Cholix" (also referred to herein as Cholix toxin or Cholix exotoxin) can encompass a variety of functional variants (e.g., a functional genus), wherein the functional variants can comprise one or more variations is their amino acid sequence relative to SEQ ID NO: 1 as disclosed herein. Thus, in the present disclosure, the Cholix toxin having the amino acid sequence set forth in SEQ ID NO: 1 is used as the reference sequence when referred to Cholix. However, as described herein, the present disclosure is not limited to the Cholix having the amino acid sequence set forth in SEQ ID NO: 1 but instead encompasses all Cholix variants that fall within the functional genus of Cholix. For example, a variant of the Cholix exotoxin with the amino acid sequence set forth in SEQ ID NI: 1 can be a Cholix exotoxin which amino acid sequence is set forth in SEQ ID NO: 2, wherein both variants are capable of carrying out the same functions, e.g., transcytosis across an epithelial cell, and interact with the same receptors, such as ribophilin 1, SEC24, CK-8, TMEM132, GRP75, ERGIC-53, and/or perlecan.

Moreover, the production method of a polypeptide can affect, to some degree, the amino acid sequence of such polypeptide (e.g., due to post-translational modifications). For example, a first carrier and a second carrier are produced in the same expression system (e.g., a bacterial expression system such as E. coli or a mammalian expression system such as a CHO cell). In other cases, and as described herein, a first carrier and a second carrier are produced in a different expression system (e.g., a bacterial or a mammalian expression system). Bacterial expression systems include E. coli, and mammalian expression systems include CHO cells, for example. A bacterially produced polypeptide can comprise an N-cap, wherein the N-cap can comprise one more modifications at the N-terminal of the polypeptide. An N-cap can comprise an N-terminal methionine residue. Examples of Cholix domain I derived carrier polypeptides that can be bacterially produced and that comprise such N-terminal methionine include those comprising the amino acid sequences set forth in SEQ ID NO: 5, SEQ ID NO: 7, SEQ ID NO: 9, SEQ ID NO: 11, SEQ ID NO: 31, SEQ ID NO: 107, and SEQ ID NO: 135.

Cargo

The present disclosure provides methods and compositions that allow for the rapid and efficient delivery of cargo into and/or across epithelial cells (e.g., polarized epithelial cells) in vitro (e.g., a Caco-2 cell monolayer) and in vivo (e.g., a gut epithelium of a subject). Such rapid and efficient delivery can be achieved by coupling the cargo (e.g., a biologically active cargo) to a carrier to form a delivery construct. Such delivery constructs can be modified to target certain locations within an epithelial cell or to transport cargo across an epithelial cell such as an intact epithelial membrane.

In various embodiments, the compositions and methods of the present disclosure provide efficient transport and delivery of various cargo molecules to different locations (e.g., organs, tissues, or cells) of a subject (e.g., a rodent or a human). The delivery constructs of the present disclosure can allow for delivery into epithelial cells and/or for rapid transcytosis (e.g., vesicular transcytosis) across an epithelial cell layer such as a gut epithelium of a subject. The presently described delivery mechanisms allow for transport and delivery of various cargo molecules. The herein described delivery constructs can be coupled to at least one, at least two, at least three, at least five or at least 10 cargo molecules. The cargo can be a heterologous cargo, e.g., heterologous to the carrier. For example, a delivery construct described herein comprises a Cholix domain I derived carrier (e.g., those having the amino acid sequences set forth in SEQ ID NO: 1-SEQ ID NO: 125) coupled to a heterologous cargo, wherein the heterologous cargo is a non-Cholix derived cargo molecule (e.g., is not derived or does not contain fragments of a Cholix toxin domain I, II, Ib, and III).

A heterologous cargo can be a biologically active cargo. A biologically active cargo can include therapeutic and/or diagnostic molecules. Thus, the delivery constructs of the present disclosure can be used to deliver a biologically active cargo to a subject (e.g., a rodent or a human). A "biologically active cargo" as used herein includes, but is not limited to: a macromolecule, small molecule, peptide, polypeptide, nucleic acid, mRNA, miRNA, shRNA, siRNA, antisense molecule, antibody, DNA, plasmid, vaccine, polymer nanoparticle, or catalytically-active material.

A biologically active cargo of the present disclosure can be a macromolecule that can perform a desirable biological activity when introduced to the bloodstream of the subject. For example, the biologically active cargo can have receptor binding activity, enzymatic activity, messenger activity (i.e., act as a hormone, cytokine, neurotransmitter, or other signaling molecule), luminescent or other detectable activity, or regulatory activity, or any combination thereof. For certain diagnostic purposes, a biologically active cargo can be conjugated to or can itself be a pharmaceutically acceptable gamma-emitting moiety, including but not limited to, indium and technetium, magnetic particles, radiopaque materials such as air or barium and fluorescent compounds.

A heterologous cargo as described herein can be a biologically active cargo. A biologically active cargo that is part of a delivery construct can exert its effects in biological compartments of the subject other than the subject's blood. For example, in various embodiments, the biologically active cargo can exert its effects in the lymphatic system. In other cases, the biologically active cargo can exert its effects in an organ or tissue, such as, for example, the subject's liver, heart, lungs, pancreas, kidney, brain, bone marrow, etc. As such, the biologically active cargo can or cannot be present in the blood, lymph, or other biological fluid at detectable concentrations, yet can still accumulate at sufficient concentrations at its site of action to exert a biological effect.

A biologically active cargo can be a protein that comprises more than one polypeptide subunit. For example, the protein can be a dimer, trimer, or higher order multimer. In various embodiments, two or more subunits of the protein can be connected with a covalent bond, such as, for example, a disulfide bond. The subunits of the protein can be held together with non-covalent interactions. One of skill in the art can routinely identify such proteins and determine whether the subunits are properly associated using, for example, an immunoassay.

A biologically active cargo to be delivered to a certain location (e.g., in a subject) can be selected from, e.g., cytokines and cytokine receptors such as Interleukin-1 (IL-1), IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, lymphokine inhibitory factor, macrophage colony stimulating factor, platelet derived growth factor, stem cell factor, tumor growth factor-β, tumor necrosis factor, lymphotoxin, Fas, granulocyte colony stimulating factor, granulocyte macrophage colony stimulating factor, interferon-α, interferon-β, interferon-γ, growth factors and protein hormones such as erythropoietin, angiogenin, hepatocyte growth factor, fibroblast growth factor, keratinocyte growth factor, nerve growth factor, tumor growth factor-a, thrombopoietin, thyroid stimulating factor, thyroid releasing hormone, neurotrophin, epidermal growth factor, VEGF, ciliary neurotrophic factor, LDL, somatomedin, insulin growth factor, insulin-like growth factor I and II, chemokines such as ENA-78, ELC, GRO-α, GRO-β, GRO-γ, HRG, LEF, IP-10, MCP-1, MCP-2, MCP-3, MCP-4, MIP-1-α, MIP-1-β, MG, MDC, NT-3, NT-4, SCF, LIF, leptin, RANTES, lymphotactin, eotaxin-1, eotaxin-2, TARC, TECK, WAP-1, WAP-2, GCP-1, GCP-2; α-chemokine receptors, e.g., CXCR1, CXCR2, CXCR3, CXCR4, CXCR5, CXCR6, CXCR7; and β-chemokine receptors, e.g., CCR1, CCR2, CCR3, CCR4, CCR5, CCR6, CCR7.

An illustrative, but not limiting, list of suitable biologically active cargo to be used in the constructs and methods of the present invention is provided in TABLE 11.

TABLE 11

| Exemplary Biologically Active Cargo | |
|---|---|
| Cargo | RefSeq (NCBI/Uniprot) |
| Interleukins | |
| IL-10 | NP_000563 |
| IL-19 | NP_037503 |
| IL-20 | NP_061194 |
| IL-22 | NP_065386 |
| IL-24 | NP_006841 |
| IL-26 | NP_060872 |

TABLE 11-continued

Exemplary Biologically Active Cargo

| Cargo | RefSeq (NCBI/Uniprot) |
|---|---|
| TNFSF Ligands | |
| Tumor necrosis factor-α ("TNF-α") | NP_000585.2 |
| lymphotoxin-α ("LT-α") | NP_000586.2 |
| lymphotoxin-β ("LT-β") | NP_002332.1 |
| CD30 ligand | NP_001235.1 |
| CD40 ligand | NP_000065.1 |
| CD70 ligand | NP_001243.1 |
| OX40 ligand | NP_001284491.1 |
| 41BB ligand | NP_001552.2 |
| Apo1 ligand (or FasL or CD95L) | NP_000630.1 |
| Apo2 ligand (or TRAIL, AIM-1 or AGP-1) | NP_001177871.1 |
| Apo3 ligand (or TWEAK) | NP_003800.1 |
| APRIL | NP_001185551.1 |
| LIGHT | NP_003798.2 |
| OPG ligand (or RANK ligand) | NP_003692.1 |
| BlyS (or THANK) | NP_001139117.1 |
| BCMA | NP_001183.2 |
| TACI | NP_036584.1 |
| TNFSFRs | |
| TNFR1 | NP_001056.1 |
| TNFR2 | NP_001057.1 |
| lymphotoxin-βR | NP_001257916.1 |
| CD40 | NP_001241.1 |
| CD95 (or FAS or APO-1) | NP_000034.1 |
| OPG | NP_002537.3 |
| RANK | NP_001257878.1 |
| CD30 | NP_001234.3 |
| CD27 | NP_001233.1 |
| OX40 (or CD134) | NP_003318.1 |
| 41BB | NP_001552.2 |
| NGFR | NP_002498.1 |
| BCMA | NP_001183.2 |
| TAC1 | NP_036584.1 |
| EDA2R | NP_001186616.1 |
| TROY | NP_001191387.1 |
| DR6 | NP_055267.1 |
| DR5 (or TRAILR2) | NP_003833.4 |
| DR4 | NP_003835.3 |
| DR3 | NP_001034753.1 |
| HVEM | NP_001284534.1 |
| LTβR | NP_001257916.1 |
| GITR | NP_004186.1 |
| DcR3 | NP_003814 |
| Fn14 (or TWEAKR) | NP_057723.1 |
| BAFF | NP_443177.1 |
| Glucose metabolism-related proteins | |
| Glucagon proprotein | NP_002045.1 |
| Glucagon peptide | NP_002045.1 (aa 53-81) |
| Glucagon-like peptide 1 | NP_002045.1 (aa 98-128) |
| Glucagon-like peptide 2 | NP_002045.1 (aa 146-178) |
| Glicentin | P01275 (aa 21-89) |
| Glicentin-related polypeptide | P01275 (aa 21-50) |
| Gastric inhibitory polypeptide preprotein | NP_004114.1 |
| Gastric inhibitory polypeptide | NP_004114.1 (aa 52-93) |
| Dipeptidyl peptidase 4 | P27487 |
| Glucose transporter member 4 | NP_001033.1 |
| Preproglucagon | AAA52567.1 |
| Insulin receptor substrate 1 | NP_005535.1 |
| Insulin | P01308 |
| Apolipoprotein A-II | P02652 |
| Solute carrier family 2, facilitated glucose transporter member 1 | P11166 |
| Glycogen synthase 1 | P13807 |
| Glycogen synthase 2 | P54840 |
| Tyrosine-protein phosphatase non-receptor type 1 | P18031 |
| RAC-alpha serine/threonine-protein kinase | P31749 |
| Peroxisome proliferator-activated receptor gamma | P37231 |
| Hexokinase 3 | P52790 |

TABLE 11-continued

Exemplary Biologically Active Cargo

| Cargo | RefSeq (NCBI/Uniprot) |
|---|---|
| Phosphatidylinositol-3,4,5-triphosphate 3-phosphatase and dual-specificty protein | P60484 |
| Pyruvate dehydrogenase kinase 1 | Q15118 |
| Calcium-binding and coiled-coil domain-containing protein 1 | Q9P1Z2 |
| Max-like protein X | Q9UH92 |
| Fructose-bisphosphate aldolase A | P04075 |
| Glucagon-like peptide 1 receptor | P43220 |
| Glucagon-like peptide 2 receptor | O95838 |
| Gastric inhibitory polypeptide receptor | P48546 |
| Insulin-like growth factor 1 receptor | P08069.1 |
| Insulin-like growth factor 2 receptor | P11717.3 |
| Insulin Receptor | P06213 |
| GLP-1 agonist-Exenatide | DB01276 |
| GLP-1 agonist-Liraglutide | DB06655 |
| Growth Hormone Related Proteins | |
| Somatotropin | P01241 |
| Synthetic Human Growth Hormone | AAA72260.1 |
| Synthetic Human Growth Hormone Partial | CAA01435 |
| Synthetic Human Growth Hormone Partial | CAA00380 |
| Human Growth Hormone 2 | P01242 |
| Somatoliberin | P01286.1 |
| Appetite-regulating Hormone | Q9UBU3 |
| Leptin | P41159 |
| Growth Hormone Receptor Proteins | |
| Growth Hormone Receptor | P10912 |
| Growth Hormone-Releasing Hormone Receptor | Q02643 |
| Growth Hormone Secretagogue Receptor | Q92847 |
| Growth Hormone-Releasing Hormone Receptor form a | P78470 |
| Growth Hormone Receptor | E9PCN7 |

A biologically active cargo as described herein can be a hormone. Such a hormone can be a growth hormone. The hormone can be a human growth hormone having, for example, the amino acid sequence set forth in SEQ ID NO: 214.

A biologically active cargo can be a molecule affects and/or interacts with a metabolism of a subject. Thus, a biologically active cargo as described herein can be a drug that can be used to prevent, treat and/or diagnose a metabolic disease or condition. Thus, a biologically active cargo as described herein can be a glucagon-like peptide (GLP). The GLP can be GLP-1 having the amino acid sequence set forth in SEQ ID NO: 215. A hormone that can be used in combination with the methods and compositions described herein can be insulin (with c-peptide element removed from mature protein), or a derivative thereof. An Insulin peptide can comprise the amino acid sequence set forth in SEQ ID NO: 216.

A biologically active cargo can be an interleukin. Specifically, interleukins that can be used with the methods and compositions described herein can include IL-10 and IL-22, having the amino acid sequence set forth in SEQ ID NO: 217 and SEQ ID NO: 218, respectively.

The biologically active cargo disclosed herein can modulate the spatial orientation of a delivery construct. For example, a cargo molecule can induce multimerization of two or more delivery constructs. Such multimers can be homomers or heteromers. The multimer can be a homodimer. For example, a delivery construct comprising the amino acid sequence set forth in SEQ ID NO: 217 can form a dimer. Such dimerization can be induced by IL-10 (as IL-10 can form a natural dimer and thus promote dimerization of a delivery construct comprising an IL-10 as cargo).

A biologically active cargo can also comprise toxin, such as endotoxins, enterotoxins or exotoxins. For example, a biologically active cargo can be an ExtB polypeptide (which will form a natural pentamer) having the amino acid sequence set forth in SEQ ID NO: 219.

Other examples of biologically active cargo that can be delivered according to the present disclosure include, but are not limited to, antineoplastic compounds, such as nitrosoureas, e.g., carmustine, lomustine, semustine, strepzotocin; methylhydrazines, e.g., procarbazine, dacarbazine; steroid hormones, e.g., glucocorticoids, estrogens, progestins, androgens, tetrahydrodesoxycaricosterone; immunoactive compounds such as immunosuppressives, e.g., pyrimethamine, trimethopterin, penicillamine, cyclosporine, azathioprine; and immunostimulants, e.g., levamisole, diethyl dithiocarbamate, enkephalins, endorphins; antimicrobial compounds such as antibiotics, e.g., β-lactam, penicillin, cephalosporins, carbapenims and monobactams, β-lactamase inhibitors, aminoglycosides, macrolides, tetracyclins, spectinomycin; antimalarials, amebicides; antiprotazoals; antifungals, e.g., amphotericin β, antivirals, e.g., acyclovir, idoxuridine, ribavirin, trifluridine, vidarbine, gancyclovir; parasiticides; antihalmintics; radiopharmaceutics; gastrointestinal drugs; hematologic compounds; immunoglobulins; blood clotting proteins, e.g., antihemophilic factor, factor IX complex; anticoagulants, e.g., dicumarol, heparin Na; fibrolysin inhibitors, e.g., tranexamic acid; cardiovascular drugs; peripheral anti-adrenergic drugs; centrally acting antihypertensive drugs, e.g., methyldopa, methyldopa HCl; antihypertensive direct vasodilators, e.g., diazoxide, hydralazine HCl; drugs affecting renin-angiotensin system; peripheral vasodilators, e.g., phentolamine; antianginal drugs; cardiac glycosides; inodilators, e.g., amrinone, milrinone, enoximone, fenoximone, imazodan, sulmazole; antidysrhythmics; calcium entry blockers; drugs affecting blood lipids, e.g., ranitidine, bosentan, rezulin; respiratory drugs; sypathomimetic drugs, e.g., albuterol, bitolterol mesylate, dobutamine HCl, dopamine HCl, ephedrine So, epinephrine, fenfluramine HCl, isoproterenol HCl, methoxamine HCl, norepinephrine bitartrate, phenylephrine HCl, ritodrine HCl; cholinomimetic drugs, e.g., acetylcholine Cl; anticholinesterases, e.g., edrophonium Cl; cholinesterase reactivators; adrenergic blocking drugs, e.g., acebutolol HCl, atenolol, esmolol HCl, labetalol HCl, metoprolol, nadolol, phentolamine mesylate, propanolol HCl; antimuscarinic drugs, e.g., anisotropine methylbromide, atropine $SO_4$, clinidium Br, glycopyrrolate, ipratropium Br, scopolamine HBr; neuromuscular blocking drugs; depolarizing drugs, e.g., atracurium besylate, hexafluorenium Br, metocurine iodide, succinylcholine Cl, tubocurarine Cl, vecuronium Br; centrally acting muscle relaxants, e.g., baclofen; neurotransmitters and neurotransmitter agents, e.g., acetylcholine, adenosine, adenosine triphosphate; amino acid neurotransmitters, e.g., excitatory amino acids, GABA, glycine; biogenic amine neurotransmitters, e.g., dopamine, epinephrine, histamine, norepinephrine, octopamine, serotonin, tyramine; neuropeptides, nitric oxide, $K^+$ channel toxins; antiparkinson drugs, e.g., amaltidine HCl, benztropine mesylate, carbidopa; diuretic drugs, e.g., dichlorphenamide, methazolamide, bendroflumethiazide, polythiazide; antimigraine drugs, e.g, carboprost tromethamine mesylate, methysergide maleate.

Still other examples of biologically active cargo that can be delivered according to the present disclosure include, but are not limited to, hormones such as pituitary hormones, e.g., chorionic gonadotropin, cosyntropin, menotropins, somatotropin, iorticotropin, protirelin, thyrotropin, vasopressin, lypressin; adrenal hormones, e.g., beclomethasone dipropionate, betamethasone, dexamethasone, triamcinolone; pancreatic hormones, e.g., glucagon, insulin; parathyroid hormone, e.g., dihydrochysterol; thyroid hormones, e.g., calcitonin etidronate disodium, levothyroxine Na, liothyronine Na, liotrix, thyroglobulin, teriparatide acetate; antithyroid drugs; estrogenic hormones; progestins and antagonists; hormonal contraceptives; testicular hormones; gastrointestinal hormones, e.g., cholecystokinin, enteroglycan, galanin, gastric inhibitory polypeptide, epidermal growth factor-urogastrone, gastric inhibitory polypeptide, gastrin-releasing peptide, gastrins, pentagastrin, tetragastrin, motilin, peptide YY, secretin, vasoactive intestinal peptide, or sincalide.

Still other examples of biologically active cargo that can be delivered according to the present disclosure include, but are not limited to, enzymes such as hyaluronidase, streptokinase, tissue plasminogen activator, urokinase, PGE-adenosine deaminase; intravenous anesthetics such as droperidol, etomidate, fetanyl citrate/droperidol, hexobarbital, ketamine HCl, methohexital Na, thiamylal Na, thiopental Na; antiepileptics, e.g., carbamazepine, clonazepam, divalproex Na, ethosuximide, mephenyloin, paramethadione, phenyloin, primidone. In various embodiments, the biologically active cargo is an enzyme selected from hyaluronidase, streptokinase, tissue plasminogen activator, urokinase, PGE-adenosine deaminase.

A biologically active cargo as described herein can also include a therapeutic and/or diagnostic antibody, an antibody fragment, a diabody, a minibody, or a single-chain variable fragment (e.g., scFv), or a combination thereof. For example, a biologically active cargo as described herein can be an anti-tumor necrosis factor alpha (anti-TNFa) agent. An anti-TNFa agent is an anti-TNFa antibody or a functional fragment thereof. An Anti-TNFa antibody can be adalimumab (Abbvie HUMIRA®, Drug Bank DB 00051) or infliximab (Centocor REMICADE®, Drug Bank DB 00065), or functional fragment (e.g., a binding fragment thereof).

Yet other examples of biologically active cargo that can be delivered according to the present disclosure include, but are not limited to, chemotherapeutics, such as chemotherapy or anti-tumor agents which are effective against various types of human cancers, including leukemia, lymphomas, carcinomas, sarcomas, myelomas etc., such as, for example, doxorubicin, mitomycin, cisplatin, daunorubicin, bleomycin, actinomycin D, and neocarzinostatin.

Yet other examples of biologically active cargo that can be delivered according to the present disclosure include inhibitors of regulatory T cells (Tregs) such as Tregs that express CD4, CD25 and Foxp3, and Tregs such as Tr1, Th3, CD8+ CD28−, Qa-1 restricted T cells, and IL-17 Treg cells. Such Treg inhibitors have been extensively studied and described in the art (see, e.g., Casares et al, Journal of Immunology, 185(9): 5150-5159, 2010, and references cited therein).

TABLE 12 shows exemplary amino acid sequences of various heterologous cargos that can be used in combination with the herein disclosed methods and compositions. For example, any of the heterologous cargo molecules shown in TABLE 12 below can be combined with any carrier disclosed herein, e.g., those carrier listed in TABLE 2 and/or TABLE 3 above.

TABLE 12

Exemplary Heterologous
Cargo Amino Acid Sequences

| SEQ ID NO | Sequence |
|---|---|
| SEQ ID NO: 214 | FPTIPLSRLFDNAMLRAHRLHQLAFDTYQEFEEAYI PKEQKYSFLQNPQTSLCFSESIPTPSNREETQQKSN LELLRISLLLIQSWLEPVQFLRSVFANSLVYGASDS NVYDLLKDLEEGIQTLMGRLEDGSPRTGQIFKQTYS KFDTNSHNDDALLKNYGLLYCFRKDMDKVETFLRIV QCRSVEGSCGF |
| SEQ ID NO: 215 | MKIILWLCVFGLFLATLFPISWQMPVESGLSSEDSA SSESFASKIKRHGEGTFTSDLSKQMEEEAVRLFIEW LKNGGPSSGAPPPSG |
| SEQ ID NO: 216 | MALWMRLLPLLALLALWGPDPAAAFVNQHLCGSHLV EALYLVCGERGFFYTPKTRREAEDLQVGQVELGGGP GAGSLQPLALEGSLQKRGIVEQCCTSICSLYQLENY CN |
| SEQ ID NO: 217 | MHSSALLCCLVLLTGVRASPGQGTQSENSCTHFPGN LPNMLRDLRDAFSRVKTFFQMKDQLDNLLLKESLLE DFKGYLGCQALSEMIQFYLEEVMPQAENQDPDIKAH VNSLGENLKTLRLRLRRCHRFLPCENKSKAVEQVKN AFNKLQEKGIYKAMSEFDIFINYIEAYMTMKIRN |
| SEQ ID NO: 218 | MAALQKSVSSFLMGTLATSCLLLLALLVQGGAAAPI SSHCRLDKSNFQQPYITNRTFMLAKEASLADNNTDV RLIGEKLFHGVSMSERCYLMKQVLNFTLEEVLFPQS DRFQPYMQEVVPFLARLSNRLSTCHIEGDDLHIQRN VQKLKDTVKKLGESGEIKAIGELDLLFMSLRNACI |
| SEQ ID NO: 219 | MKKNIAFLLASMFVFSIATNAYASTQSNKKDLCEHY RQIAKESCKKGFLGVRDGTAGACFGAQIIVIVAAKG C |
| SEQ ID NO: 220 | MRSSKNVIKEFMRFKVRMEGTVNGHEFEIEGEGEGR PYEGHNTVKLKVTKGGPLPFAWDILSPQFQYGSKVY VKHPADIPDYKKLSFPEGFKWERVMNFEDGGVVTVT QDSSLQDGCFIYKVKFIGVNFPSDGPVMQKKTMGWE ASTERLYPRDGVLKGEIHKALKLKDGGHYLVEFKSI YMAKKPVQLPGYYYVDSKLDITSHNEDYTIVEQYER TEGRHHLFL |

A cargo molecule of the present disclosure can comprise an amino acid sequence having at least 80% sequence identity to any one of the amino acid sequences set forth in SEQ ID NO: 214-SEQ ID NO: 220, at least 80% sequence identity to a functional fragment thereof, and/or any combination of thereof. A cargo molecule of the present disclosure can comprise an amino acid sequence having at least 90% sequence identity to any one of the amino acid sequences set forth in SEQ ID NO: 214-SEQ ID NO: 220, at least 80% sequence identity to a functional fragment thereof, and/or any combination of thereof. A cargo molecule of the present disclosure can comprise an amino acid sequence having at least 95% sequence identity to any one of the amino acid sequences set forth in SEQ ID NO: 214-SEQ ID NO: 220, at least 80% sequence identity to a functional fragment thereof, and/or any combination of thereof. A cargo molecule of the present disclosure can comprise an amino acid sequence having at least 99% sequence identity to any one of the amino acid sequences set forth in SEQ ID NO: 214-SEQ ID NO: 220, at least 80% sequence identity to a functional fragment thereof, and/or any combination of thereof. A cargo molecule of the present disclosure can comprise any one of the amino acid sequences set forth in SEQ ID NO: 214-SEQ ID NO: 220, a functional fragment thereof, and/or any combination of thereof.

Generally, a cargo described and disclosed herein can be retained at a location that has been targeted using the compositions described herein. Retention can cause the cargo molecule to elicit a certain response or biological effect (e.g., a therapeutic effect). The delivery of a molecule (e.g., a heterologous cargo) to a location (e.g., an intracellular compartment or a supranuclear region) can refer to the retention of the molecule at that location. Retention of a molecule at a certain intracellular or extracellular region or compartment can be for a certain amount of time, e.g., at least 2 minutes, at least 5 minutes, at least 10 minutes, at least 15 minutes, at 30 minutes, or at least 60 minutes. Retention of a molecule can depend on various factors such as the location where the molecule is retained and/or the types of molecular interactions that occur between the molecule (e.g., a carrier, a delivery construct, and/or a heterologous cargo). For example, delivery of a heterologous cargo to a basolateral compartment via transcytosis across a polarized epithelial cell can comprise retaining the heterologous cargo at the basolateral location for a time sufficient to elicit a certain effect, such as a therapeutic effect in case of a therapeutic and/or biologically active cargo. A delivery construct can be configured to release a cargo at a specific location, e.g., by using pH-dependent and/or enzyme-dependent spacer. Upon release of a cargo from a carrier, the cargo molecule can elicit a certain effect and/or response. For example, and in the case of biologically and/or therapeutically active cargos, such cargos can elicit their therapeutic effects in vitro or in vivo upon release from the carrier. A cargo may also be capable of eliciting a response when still bound to the carrier. This may depend on the cargo and/or the delivery construct.

A heterologous cargo can be a detectable agent such as a fluorescent molecule or a radioactive moiety. A detectable agent as described herein can be used to detect the molecule that the detectable agent is coupled to in various locations, e.g., inside a subject or inside a cell. A detectable agent can also have additional features and functions, such as therapeutic or other biological properties. For example, a radionuclide coupled to a carrier as described herein can allow the detection of the carrier but can also have therapeutic properties, e.g., as a therapeutic radionuclide. Generally, a carrier can conjugated to, linked to, or fused with detectable agents, such as a fluorophore, a near-infrared dye, a contrast agent, a nanoparticle, a metal-containing nanoparticle, a metal chelate, an X-ray contrast agent, a PET agent, a metal, a radioisotope, a dye, radionuclide chelator, or another suitable material that may be used in imaging.

A delivery construct can comprise about 1, 2, 3, 4, 5, 6, 7, 8, 9, or 10 detectable agents. Non-limiting examples of radioisotopes that may be used as detectable agents include alpha emitters, beta emitters, positron emitters, and gamma emitters. The metal or radioisotope may be selected from the group consisting of actinium, americium, bismuth, cadmium, cesium, cobalt, europium, gadolinium, iridium, lead, lutetium, manganese, palladium, polonium, radium, ruthenium, samarium, strontium, technetium, thallium, and yttrium. The metal may be actinium, bismuth, lead, radium, strontium, samarium, or yttrium. The radioisotope may be actinium-225 or lead-212. The near-infrared dyes that may be used in combination with the herein described chimeric binding agents may not be easily quenched by biological tissues and fluids. The fluorophore may be a fluorescent agent emitting electromagnetic radiation at a wavelength between 650 nm and 4000 nm, such emissions being used to detect such agent. Non-limiting examples of fluorescent dyes that may be used as a conjugating molecule in the present disclosure include DyLight-680, DyLight-750, VivoTag-750, DyLight-800, IRDye-800, VivoTag-680, Cy5.5, or indocyanine green (ICG). Near infrared dyes may include cyanine dyes (e.g., Cy7, Cy5.5, and Cy5). Additional non-limiting examples of fluorescent dyes for use as a conjugating molecule in the present disclosure may include acradine orange or yellow, Alexa Fluors (e.g., Alexa Fluor 790, 750, 700, 680, 660, and 647) and any derivative thereof, 7-actinomycin D, 8-anilinonaphthalene-1-sulfonic acid, ATTO dye and any derivative thereof, auramine-rhodamine stain and any derivative thereof, bensantrhone, bimane, 9-10-bis(phenylethynyl)anthracene, 5,12-bis(phenylethynyl)naththacene, bisbenzimide, brainbow, calcein, carbodyfluorescein and any derivative thereof, 1-chloro-9,10-bis(phenylethynyl)anthracene and any derivative thereof, DAPI, DiOC6, DyLight Fluors and any derivative thereof, epicocconone, ethidium bromide, FlAsH-EDT2, Fluo dye and any derivative thereof, FluoProbe and any derivative thereof, Fluorescein and any derivative thereof, Fura and any derivative thereof, GelGreen and any derivative thereof, GelRed and any derivative thereof, fluorescent proteins and any derivative thereof, m isoform proteins and any derivative thereof such as mCherry, hetamethine dye and any derivative thereof, hoeschst stain, iminocoumarin, indian yellow, indo-1 and any derivative thereof, laurdan, lucifer yellow and any derivative thereof, luciferin and any derivative thereof, luciferase and any derivative thereof, merocyanine and any derivative thereof, nile dyes and any derivative thereof, perylene, phloxine, phyco dye and any derivative thereof, propium iodide, pyranine, rhodamine and any derivative thereof, ribogreen, RoGFP, rubrene, stilbene and any derivative thereof, sulforhodamine and any derivative thereof, SYBR and any derivative thereof, synapto-pHluorin, tetraphenyl butadiene, tetrasodium tris, Texas Red, Titan Yellow, TSQ, umbelliferone, violanthrone, yellow fluorescent protein and YOYO-1. Other Suitable fluorescent dyes may include, but are not limited to, fluorescein and fluorescein dyes (e.g., fluorescein isothiocyanine or FITC, naphthofluorescein, 4', 5'-dichloro-2',7'-dimethoxyfluorescein, 6-carboxyfluorescein or FAM, etc.), carbocyanine, merocyanine, styryl dyes, oxonol dyes, phycoerythrin, erythrosin, eosin, rhodamine dyes (e.g., carboxytetramethyl-rhodamine or TAMRA, carboxyrhodamine 6G, carboxy-X-rhodamine (ROX), lissamine rhodamine B, rhodamine 6G, rhodamine Green, rhodamine Red, tetramethylrhodamine (TMR), etc.), coumarin and coumarin dyes (e.g., methoxycoumarin, dialkylaminocoumarin, hydroxycoumarin, aminomethylcoumarin (AMCA), etc.), Oregon Green Dyes (e.g., Oregon Green 488, Oregon Green 500, Oregon Green 514, etc.), Texas Red, Texas Red-X, SPECTRUM RED, SPECTRUM GREEN, cyanine dyes (e.g., CY-3, Cy-5, CY-3.5, CY-5.5, etc.), ALEXA FLUOR dyes (e.g., ALEXA FLUOR 350, ALEXA FLUOR 488, ALEXA FLUOR 532, ALEXA FLUOR 546, ALEXA FLUOR 568, ALEXA FLUOR 594, ALEXA FLUOR 633, ALEXA FLUOR 660, ALEXA FLUOR 680, etc.), BODIPY dyes (e.g., BODIPY FL, BODIPY R6G, BODIPY TMR, BODIPY TR, BODIPY 530/550, BODIPY 558/568, BODIPY 564/570, BODIPY 576/589, BODIPY 581/591, BODIPY 630/650, BODIPY 650/665, etc.), IRDyes (e.g., IRD40, IRD 700, IRD 800, etc.), and the like. Additional suitable detectable agents are described in PCT/US14/56177. Non-limiting examples of radioisotopes include alpha emitters, beta emitters, positron emitters, and gamma emitters. The metal or radioisotope may be selected from the group consisting of actinium, americium, bismuth, cadmium, cesium, cobalt, europium, gadolinium, iridium, lead, lutetium, manganese, palladium, polonium, radium, ruthenium, samarium, strontium, technetium, thallium, and yttrium. The metal may be actinium, bismuth, lead, radium, strontium, samarium, or yttrium. The radioisotope may be actinium-225 or lead-212. Additionally, the following radionuclides may be used for diagnosis and/or therapy: carbon (e.g., $^{11}C$ or $^{14}C$), nitrogen (e.g., $^{13}N$), fluorine (e.g., $^{18}F$), gallium (e.g., $^{67}Ga$ or $^{68}Ga$), copper (e.g., $^{64}Cu$ or $^{67}Cu$), zirconium (e.g., $^{89}Zr$), lutetium (e.g., $^{177}Lu$).

A delivery construct as disclosed herein can be conjugated to, coupled to, or fused to a radiosensitizer or photosensitizer. Examples of radiosensitizers may include but are not limited to: ABT-263, ABT-199, WEHI-539, paclitaxel, carboplatin, cisplatin, oxaliplatin, gemcitabine, etanidazole, misonidazole, tirapazamine, and nucleic acid base derivatives (e.g., halogenated purines or pyrimidines, such as 5-fluorodeoxyuridine). Examples of photosensitizers may include but are not limited to: fluorescent molecules or beads that generate heat when illuminated, nanoparticles, porphyrins and porphyrin derivatives (e.g., chlorins, bacteriochlorins, isobacteriochlorins, phthalocyanines, and naphthalocyanines), metalloporphyrins, metallophthalocyanines, angelicins, chalcogenapyrrillium dyes, chlorophylls, coumarins, flavins and related compounds such as alloxazine and riboflavin, fullerenes, pheophorbides, pyropheophorbides, cyanines (e.g., merocyanine 540), pheophytins, sapphyrins, texaphyrins, purpurins, porphycenes, phenothiaziniums, methylene blue derivatives, naphthalimides, nile blue derivatives, quinones, perylenequinones (e.g., hypericins, hypocrellins, and cercosporins), psoralens, quinones, retinoids, rhodamines, thiophenes, verdins, xanthene dyes (e.g., eosins, erythrosins, rose bengals), dimeric and oligomeric forms of porphyrins, and prodrugs such as 5-aminolevulinic acid. Advantageously, this approach may allow for highly specific targeting of diseased cells (e.g., cancer cells) using both a therapeutic agent (e.g., drug) and electromagnetic energy (e.g., radiation or light) concurrently. The proteins of the present disclosure can be conjugated to, coupled to, fused with, or covalently or non-covalently coupled to the agent, e.g., directly or via a spacer.

A radionuclide may be attached to a carrier or delivery construct as described herein using a chelator. Exemplary chelator moieties may include 2,2',2"-(3-(4-(3-(1-(4-(1,2,4,5-tetrazin-3-yl)phenyl)-1-oxo-5,8,11,14,17,20,23-heptaoxa-2-azapentacosan-25-yl)thioureido)benzyl)-1,4,7-triazonane-2,5,8-triyl)triacetic acid; 2,2',2"-(3-(4-(3-(1-(4-(1,2,4,5-tetrazin-3-yl)phenyl)-1-oxo-5,8,11,14,17,20,23,26,29,32,35-undecaoxa-2-azaheptatriacontan-37-yl)thioureido)benzyl)-1,4,7-triazonane-2,5,8-triyl)triacetic acid; 2,2'-(7-(4-(3-(1-(4-(1,2,4,5-tetrazin-3-yl)phenyl)-1-oxo-5,8,11,14,17,20,23,26,29,32,35-undecaoxa-2-azaheptatriacontan-37-yl)thioureido)benzyl)-1,4,7-triazonane-1,4-diyl)diacetic acid; 2,2',2"-(3-(4-(3-(1-(4-(1,2,4,5-tetrazin-3-yl)phenyl)-3,7-dioxo-11,14,17,20,23,26,29-heptaoxa-2,8-diazahentriacontan-31-yl)thioureido)benzyl)-1,4,7-triazonane-2,5,8-triyl)triacetic acid; 2,2',2"-(3-(4-(3-(1-(4-(1,2,4,5-tetrazin-3-yl)phenyl)-3,7-dioxo-11,14,17,20,23,26,29,32,35,38,41-undecaoxa-2,8-diazatritetracontan-43-yl)thioureido)benzyl)-1,4,7-triazonane-2,5,8-triyl)triacetic acid; 2,2',2"-(3-(4-(3-(25,28-dioxo-28-((6-(6-(pyridin-2-yl)-1,2,4,5-tetrazin-3-yl)pyridin-3-yl)amino)-3,6,9,12,15,18,21-heptaoxa-24-azaoctacosyl)thioureido)benzyl)-1,4,7-triazonane-2,5,8-triyl)triacetic acid; 2,2',2"-(3-(4-(3-(37,40-dioxo-40-((6-(6-(pyridin-2-yl)-1,2,4,5-tetrazin-3-yl)pyridin-3-yl)amino)-3,6,9,12,15,18,21,24,27,30,33-undecaoxa-36-azatetracontyl)thioureido)benzyl)-1,4,7-triazonane-2,5,8-triyl)triacetic acid; 2,2',2"-(3-(4-(1-(4-(6-methyl-1,2,4,5-tetrazin-3-yl)phenyl)-3-oxo-6,9,12,15,18,21,24-heptaoxa-2-azaheptacosan-27-amido)benzyl)-1,4,7- triazonane-2,5,8-triyl)triacetic acid; 2,2',2''-(2-(4-(1-(4-(6-methyl-1,2,4,5-tetrazin-3-yl)phenoxy)-3,6,9,12,15,18,21,24,27,30,33-undecaoxahexatriacontan-36-amido)benzyl)-1,4,7-triazonane-1,4,7-triyl)triacetic acid; 2,2',2''-(3-(4-(3-(5-amino-6-((4-(6-methyl-1,2,4,5-tetrazin-3-yl)benzyl)amino)-6-oxohexyl)thioureido)benzyl)-1,4,7-triazonane-2,5,8-triyl)triacetic acid; 2,2'-(7-(4-(3-(5-amino-6-((4-6-methyl-1,2,4,5-tetrazin-3-yl)benzyl)amino)-6-oxohexyl)thioureido)benzyl)-1,4,7-triazonane-1,4-diyl)diacetic acid; 2,2',2''-(3-(4-(3-(5-amino-6-((5-amino-6-((4-(6-methyl-1,2,4,5-tetrazin-3-yl)benzyl)amino)-6-oxohexyl)amino)-6-oxohexyl)thioureido)benzyl)-1,4,7-triazonane-2,5,8-triyl)triacetic acid; and 2,2',2''-(3-(4-(3-(5-amino-6-((5-amino-6-((5-amino-6-((4-(6-methyl-1,2,4,5-tetrazin-3-yl)benzyl)amino)-6-oxohexyl)amino)-6-oxohexyl)amino)-6-oxohexyl)thioureido)benzyl)-1,4,7-triazonane-2,5,8-triyl)triacetic acid.

Uses

The present disclosure provides methods and compositions for transport and/or delivery of a cargo molecule to certain location(s) within a cell (e.g., a supranuclear location) or across a cell (e.g., epithelial cell), either in vitro or in vivo (e.g., in a rodent or a human). Such cargo can be directed to a set of location(s) by coupling it to a carrier molecule. Such carrier molecule can interact with unique receptors both on the cell surface and intracellularly for the targeted delivery of the cargo. Various such carrier, cargos, and uses thereof are described herein.

Contemplated herein are delivery constructs that can be used to deliver a cargo to a location within a cell (e.g., epithelial cell) or across a cell (e.g., epithelial cell). Such carriers can be a small molecule, a polypeptide, an aptamer, an antibody, a nucleic acid a fragment of any of the above, or a combination of any of the above. The delivery constructs described herein can be used for various applications, including but not limited to, therapeutic, preventative, and/or diagnostic applications. Such therapeutic, preventative, and/or diagnostic applications can be provided if, for example, therapeutically active cargo molecules are coupled to carriers described herein that enable targeted delivery to various locations (e.g., in a subject such as a human).

Pharmaceutical Compositions and Delivery Methods

The pharmaceutical compositions of the present disclosure relate to compositions for administration to a human subject. The pharmaceutical compositions comprise the non-naturally occurring delivery constructs recited herein, alone or in combination. The pharmaceutical compositions can comprise additional molecules capable of altering the characteristics of the non-naturally occurring delivery constructs, for example, stabilizing, modulating and/or activating their function. The composition may, e.g., be in solid or liquid form and can be, inter alia, in the form of (a) powder(s), (a) tablet(s), (a) solution(s) or (an) aerosol(s). The pharmaceutical composition of the present disclosure may, optionally and additionally, comprise a pharmaceutically acceptable carrier. "Pharmaceutically acceptable carrier" refers to a non-toxic solid, semisolid or liquid filler, diluent, encapsulating material and any of the standard pharmaceutical carriers, vehicles, buffers, and excipients, such as a phosphate buffered saline solution, 5% aqueous solution of dextrose, and emulsions, such as an oil/water or water/oil emulsion, and various types of wetting agents and/or adjuvants.

The pharmaceutical compositions are generally formulated appropriately for the immediate use intended for the delivery construct. For example, if the delivery construct is not to be administered immediately, the delivery construct can be formulated in a composition suitable for storage. One such composition is a lyophilized preparation of the delivery construct together with a suitable stabilizer. Alternatively, the delivery construct composition can be formulated for storage in a solution with one or more suitable stabilizers. Any such stabilizer known to one of skill in the art without limitation can be used. For example, stabilizers suitable for lyophilized preparations include, but are not limited to, sugars, salts, surfactants, proteins, chaotropic agents, lipids, and amino acids. Stabilizers suitable for liquid preparations include, but are not limited to, sugars, salts, surfactants, proteins, chaotropic agents, lipids, and amino acids. Specific stabilizers than can be used in the compositions include, but are not limited to, trehalose, serum albumin, phosphatidylcholine, lecithin, and arginine. Other compounds, compositions, and methods for stabilizing a lyophilized or liquid preparation of the delivery constructs can be found, for example, in U.S. Pat. Nos. 6,573,237, 6,525,102, 6,391,296, 6,255,284, 6,133,229, 6,007,791, 5,997,856, and 5,917,021.

In various embodiments, the pharmaceutical compositions of the present disclosure are formulated for oral delivery. The pharmaceutical compositions formulated for oral administration take advantage of the bacterial toxin's ability to mediate transcytosis across the gastrointestinal (GI) epithelium and/or delivery to the interior of a cell of the GI epithelium (e.g., gut). It is anticipated that oral administration of these pharmaceutical compositions will result in absorption of the delivery construct through polarized epithelial cells of the digestive mucosa, e.g., the intestinal mucosa, followed by release of the biologically active cargo at the basolateral side of the mucous membrane. In various embodiments, the epithelial cell is selected from the group consisting of nasal epithelial cells, oral epithelial cells, intestinal epithelial cells, rectal epithelial cells, vaginal epithelial cells, and pulmonary epithelial cells. Pharmaceutical compositions of the disclosure can include the addition of a transcytosis enhancer to facilitate transfer of the fusion protein across the GI epithelium. Such enhancers are known in the art. See Xia et al., (2000) J. Pharmacol. Experiment. Therap., 295:594-600; and Xia et al. (2001) Pharmaceutical Res., 18(2):191-195, each incorporated by reference in its entirety herein.

Without being bound to any theory, it is assumed that once transported across the GI epithelium, the delivery constructs of the disclosure will exhibit extended half-life in serum, that is, the biologically active cargo of the delivery constructs will exhibit an extended serum half-life compared to the biologically active cargo in its non-fused state. As such, the oral formulations of the pharmaceutical compositions of the present disclosure are prepared so that they are suitable for transport to the GI epithelium and protection of the delivery construct in the stomach. Such formulations can include carrier and dispersant components and can be in any suitable form, including aerosols (for oral or pulmonary delivery), syrups, elixirs, tablets, including chewable tablets, hard or soft capsules, troches, lozenges, aqueous or oily suspensions, emulsions, cachets or pellets granulates, and dispersible powders. In various embodiments, the pharmaceutical compositions are employed in solid dosage forms, e.g., tablets, capsules, or the like, suitable for simple oral administration of precise dosages.

The oral formulation can comprise a delivery construct and one or more compounds that can protect the delivery construct while it is in the stomach. For example, the protective compound should be able to prevent acid and/or enzymatic hydrolysis of the delivery construct. In various embodiments, the oral formulation comprises a delivery construct and one or more compounds that can facilitate transit of the construct from the stomach to the small intestine. The one or more compounds that can protect the delivery construct from degradation in the stomach can also facilitate transit of the construct from the stomach to the small intestine. For example, inclusion of sodium bicarbonate can be useful for facilitating the rapid movement of intra-gastric delivered materials from the stomach to the duodenum as described in Mrsny et al., Vaccine 17:1425-1433, 1999. Other methods for formulating compositions so that the delivery constructs can pass through the stomach and contact polarized epithelial membranes in the small intestine include, but are not limited to, enteric-coating technologies as described in DeYoung, Int J Pancreatol, 5 Suppl: 31-6, 1989 and the methods provided in U.S. Pat. Nos. 6,613,332, 6,174,529, 6,086,918, 5,922,680, and 5,807,832, each incorporated by reference in its entirety herein.

Pharmaceutical compositions intended for oral use can be prepared according to any method known to the art for the manufacture of pharmaceutical compositions and such compositions can contain one or more agents selected from the group consisting of sweetening agents in order to provide a pharmaceutically elegant and palatable preparation. For example, to prepare orally deliverable tablets, the delivery construct is mixed with at least one pharmaceutical excipient, and the solid formulation is compressed to form a tablet according to known methods, for delivery to the gastrointestinal tract. The tablet composition is typically formulated with additives, e.g. a saccharide or cellulose carrier, a binder such as starch paste or methyl cellulose, a filler, a disintegrator, or other additives typically usually used in the manufacture of medical preparations. To prepare orally deliverable capsules, DHEA is mixed with at least one pharmaceutical excipient, and the solid formulation is placed in a capsular container suitable for delivery to the gastrointestinal tract. Compositions comprising delivery constructs can be prepared as described generally in Remington's Pharmaceutical Sciences, 18th Ed. 1990 (Mack Publishing Co. Easton Pa. 18042) at Chapter 89, which is herein incorporated by reference.

The pharmaceutical compositions can be formulated as orally deliverable tablets containing delivery constructs in admixture with non-toxic pharmaceutically acceptable excipients, which are suitable for manufacture of tablets. These excipients can be inert diluents, such as calcium carbonate, sodium carbonate, lactose, calcium phosphate or sodium phosphate; granulating and disintegrating agents, for example, maize starch, gelatin or acacia, and lubricating agents, for example, magnesium stearate, stearic acid, or talc. The tablets can be uncoated or they can be coated with known techniques to delay disintegration and absorption in the gastrointestinal track and thereby provide a sustained action over a longer period of time. For example, a time delay material such as glyceryl monostearate or glyceryl distearate alone or with a wax can be employed.

The pharmaceutical compositions can be formulated as hard gelatin capsules wherein the delivery construct is mixed with an inert solid diluent, for example, calcium carbonate, calcium phosphate, or kaolin or as soft gelatin capsules wherein the delivery construct is mixed with an aqueous or an oil medium, for example, *arachis* oil, peanut oil, liquid paraffin or olive oil.

Aqueous suspensions can contain a delivery construct in the admixture with excipients suitable for the manufacture of aqueous suspensions. Such excipients are suspending agents, for example, sodium carboxymethylcellulose, methylcellulose, hydroxypropylmethylcellulose, sodium alginate, polyvinylpyrrolidone, gum tragacanth and gum acacia; dispersing or wetting agents can be a naturally occurring phosphatide, for example, lecithin, or condensation products of an alkylene oxide with fatty acids, for example, polyoxyethylene stearate, or condensation products of ethylene oxide with long chain aliphatic alcohols, for example, heptadecylethyloxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyoxyethylene sorbitan monooleate. The aqueous suspensions can also contain one or more preservatives for example, ethyl or n-propyl p-hydroxybenzoate, one or more coloring agents, one or more flavoring agents and one or more sweetening agents such as sucrose or saccharin.

Oily suspensions can be formulated by suspending the delivery construct in a vegetable oil, for example, arachis oil, olive oil, sesame oil or coconut oil, or in a mineral oil such as liquid paraffin. The oil suspensions can contain a thickening agent, for example, beeswax, hard paraffin or cetyl alcohol. Sweetening agents, such as those set forth above, and flavoring agents can be added to provide a palatable oral preparation. These compositions can be preserved by the addition of an antioxidant such as ascorbic acid.

The pharmaceutical compositions can be in the form of oil-in-water emulsions. The oil phase can be a vegetable oil, for example, olive oil or arachis oil, or a mineral oil for example, gum acacia or gum tragacanth, naturally-occurring phosphatides, for example soybean lecithin, and esters or partial esters derived from fatty acids and hexitol anhydrides, for example, sorbitan monooleate, and condensation products of the same partial esters with ethylene oxide, for example, polyoxyethylene sorbitan monooleate. The emulsions can also contain sweetening and flavoring agents.

The pharmaceutical composition can be in the form of a tablet or capsule, and the tablet or capsule can be coated or encapsulated to protect a therapeutically or biologically active cargo from enzymatic action in the stomach and to ensure that there is sufficient biologically active cargo to be absorbed by the subject to produce an effective response. Such coating or encapsulation methods include, e.g., encapsulation in nanoparticles composed of polymers with a hydrophobic backbone and hydrophilic branches as drug carriers, encapsulation in microparticles, insertion into liposomes in emulsions, and conjugation to other molecules. In some cases, the capsule or tablet releases the delivery construct in a pH-dependent manner. Capsules or tablets used for administering a delivery construct as described herein can comprise one or more enteric coatings.

Examples of nanoparticles include mucoadhesive nanoparticles coated with chitosan and Carbopol (Takeuchi et al., Adv. Drug Deliv. Rev. 47(1):39-54, 2001) and nanoparticles containing charged combination polyesters, poly(2-sulfobutyl-vinyl alcohol) and poly(D,L-lactic-co-glycolic acid) (Jung et al., Eur. J. Pharm. Biopharm. 50(1):147-160, 2000).

Encapsulated or coated tablets can be used that release a biologically active cargo in a layer-by-layer manner, thereby releasing biologically active cargo over a pre-determined time frame while moving along the gastrointestinal tract. In addition, tablets comprising the biologically active cargo can be placed within a larger tablet, thereby protecting the inner tablet from environmental and processing conditions, such as temperature, chemical agents (e.g., solvents), pH, and moisture. The outer tablet and coatings further serve to protect the biologically active cargo in the gastric environment.

Pharmaceutical compositions described herein can be formulated for oral delivery using polyester microspheres, zein microspheres, proteinoid microspheres, polycyanoacrylate microspheres, and lipid-based systems (see, for example, DiBase and Morrel, Oral Delivery of Microencapsulated Proteins, in Protein Delivery: Physical Systems, Sanders and Hendren (eds.), pages 255-288 (Plenum Press 1997)).

Surface-active agents or surfactants promote absorption of polypeptides through mucosal membrane or lining. Useful surface-active agents or surfactants include fatty acids and salts thereof, bile salts, phospholipid, or an alkyl saccharide. Examples of fatty acids and salts thereof include sodium, potassium and lysine salts of caprylate ($C_8$), caprate ($C_{10}$), laurate ($C_{12}$) and myristate ($C_{14}$). Examples of bile salts include cholic acid, chenodeoxycholic acid, glycocholic acid, taurocholic acid, glycochenodeoxycholic acid, taurochenodeoxycholic acid, deoxycholic acid, glycodeoxycholic acid, taurodeoxycholic acid, lithocholic acid, and ursodeoxycholic acid. Examples of phospholipids include single-chain phospholipids, such as lysophosphatidylcholine, lysophosphatidylglycerol, lysophosphatidylethanolamine, lysophosphatidylinositol and lysophosphatidylserine; or double-chain phospholipids, such as diacylphosphatidylcholines, diacylphosphatidylglycerols, diacylphosphatidylethanolamines, diacylphosphatidylinositols and diacylphosphatidylserines. Examples of alkyl saccharides include alkyl glucosides or alkyl maltosides, such as decyl glucoside and dodecyl maltoside.

The present disclosure relates to methods and compositions that allow orally administering the pharmaceutical compositions of the disclosure. Without intending to be bound to any particular theory or mechanism of action, it is believed that oral administration of the delivery constructs results in absorption of the delivery construct through polarized epithelial cells of the digestive mucosa, e.g., the intestinal mucosa, followed by cleavage of the delivery construct and release of the biologically active cargo at the basolateral side of the mucous membrane. Thus, when the biologically active cargo exerts a biological activity in the liver, such as, for example, activities mediated by IL-10 binding to its cognate receptor, the biologically active cargo is believed to exert an effect in excess of what would be expected based on the plasma concentrations observed in the subject, i.e., oral administration of the delivery construct can deliver a higher effective concentration of the delivered biologically active cargo to the liver of the subject than is observed in the subject's plasma.

The present disclosure relates to methods of orally administering the pharmaceutical compositions of the disclosure. Such methods can include, but are not limited to, steps of orally administering the compositions by the patient or a caregiver. Such administration steps can include administration on intervals such as once or twice per day depending on the delivery construct, disease or patient condition or individual patient. Such methods also include the administration of various dosages of the individual delivery construct. For instance, the initial dosage of a pharmaceutical composition can be at a higher level to induce a desired effect, such as reduction in blood glucose levels. Subsequent dosages can then be decreased once a desired effect is achieved. Such changes or modifications to administration protocols can be performed by the attending physician or health care worker.

These pharmaceutical compositions can be administered to the subject at a suitable dose. The dosage regimen can be determined by the attending physician based upon specific clinical factors. As is well known in the medical arts, dosages for any one patient depend upon many factors, including the patient's size, body surface area, age, the particular compound to be administered, sex, time and route of administration, general health, and other drugs being administered concurrently. The therapeutically effective amount for a given situation will readily be determined by routine experimentation and is within the skills and judgment of the ordinary clinician or physician. The skilled person knows that the effective amount of a pharmaceutical composition administered to an individual will, inter alia, depend on the nature of the biologically active cargo. The length of treatment needed to observe changes and the interval following treatment for responses to occur vary depending on the desired effect. The particular amounts can be determined by conventional tests, which are well known to the person skilled in the art.

The amount of biologically active cargo is an amount effective to accomplish the purpose of the particular active agent. The amount in the composition typically is a pharmacologically, biologically, therapeutically, or chemically effective amount. However, the amount can be less than a pharmacologically, biologically, therapeutically, or chemically effective amount when the composition is used in a dosage unit form, such as a capsule, a tablet or a liquid, because the dosage unit form can contain a multiplicity of carrier/biologically or chemically active agent compositions or can contain a divided pharmacologically, biologically, therapeutically, or chemically effective amount. The total effective amounts can then be administered in cumulative units containing, in total, pharmacologically, biologically, therapeutically or chemically active amounts of biologically active cargo.

As used herein, the terms "co-administration", "co-administered" and "in combination with", referring to the delivery constructs of the disclosure and one or more other therapeutic agents, is intended to mean, and does refer to and include the following: simultaneous administration of such combination of delivery constructs of the disclosure and therapeutic agent(s) to a patient in need of treatment, when such components are formulated together into a single dosage form which releases said components at substantially the same time to said patient; substantially simultaneous administration of such combination of delivery constructs of the disclosure and therapeutic agent(s) to a patient in need of treatment, when such components are formulated apart from each other into separate dosage forms which are taken at substantially the same time by said patient, whereupon said components are released at substantially the same time to said patient; sequential administration of such combination of delivery constructs of the disclosure and therapeutic agent(s) to a patient in need of treatment, when such components are formulated apart from each other into separate dosage forms which are taken at consecutive times by said patient with a significant time interval between each administration, whereupon said components are released at substantially different times to said patient; and sequential administration of such combination of delivery constructs of the disclosure and therapeutic agent(s) to a patient in need of treatment, when such components are formulated together into a single dosage form which releases said components in a controlled manner whereupon they are released in a concurrent, consecutive, and/or overlapping manner at the same and/or different times to said patient, where each part can be administered by either the same or a different route.

A combination therapy can comprise administering the isolated delivery construct composition and the second agent composition simultaneously, either in the same pharmaceutical composition or in separate pharmaceutical compositions. In various embodiments, isolated delivery construct composition and the second agent composition are administered sequentially, i.e., the isolated delivery construct composition is administered either prior to or after the administration of the second agent composition.

An administration of the isolated delivery construct composition and the second agent composition can be concurrent, i.e., the administration period of the isolated delivery construct composition and the second agent composition overlap with each other.

An administration of the isolated delivery construct composition and the second agent composition can be non-concurrent. For example, in various embodiments, the administration of the isolated delivery construct composition is terminated before the second agent composition is administered. The administration second agent composition can be terminated before the isolated delivery construct composition is administered.

Methods of Treatment

The pharmaceutical compositions formulated for oral delivery can be used to treat certain classes of diseases or medical conditions that are particularly amenable for oral formulation and delivery. Such classes of diseases or conditions include, e.g., viral disease or infections, cancer, a metabolic disease, obesity, autoimmune diseases, inflammatory diseases, allergy, graft-vs-host disease, systemic microbial infection, anemia, cardiovascular disease, psychosis, genetic diseases, neurodegenerative diseases, disorders of hematopoietic cells, diseases of the endocrine system or reproductive systems, gastrointestinal diseases. In many chronic diseases, oral formulations of the delivery constructs of the disclosure are particularly useful because they allow long-term patient care and therapy via home oral administration without reliance on injectable treatment or drug protocols.

A pharmaceutical composition of the present disclosure can comprise any of the delivery constructs described herein, which includes any combination of carrier, cargo, and/or spacer described herein. Specifically, the delivery constructs described herein allow for oral administration, which can be followed by transport of the delivery construct across or into a cell of an epithelium of a subject. A delivery construct that has been transported across such an epithelial layer can subsequently reach various parts and/or organs and/or tissues within the subject. A delivery construct, and in various cases the cargo that a delivery construct comprises, can elicit an effect upon reaching a submucosal compartment. For example, a biologically active cargo can be a cargo capable of eliciting an immune response, and thus a delivery construct can present such cargo to immune cell once it has reached a submucosal compartment.

The present disclosure relates to methods for treatment, prophylaxis and/or prevention of an inflammatory disease in a subject, comprising administering a pharmaceutical composition of the present disclosure to the subject. "Inflammatory diseases" include all diseases associated with acute or chronic inflammation. Acute inflammation is the initial response of the body to harmful stimuli and results from an increased movement of plasma and leukocytes (such as e.g. granulocytes) from the blood into the injured tissues. A number of biochemical events propagates and matures the inflammatory response, involving the local vascular system, the immune system, and various cells within the injured tissue. Prolonged inflammation is referred to as chronic inflammation, which leads to a progressive shift in the type of cells present at the site of inflammation and is characterized by simultaneous destruction and healing of the tissue from the inflammatory process. Inflammatory diseases can be caused by e.g. burns, chemical irritants, frostbite, toxins, infection by pathogens, physical injury, immune reactions due to hypersensitivity, ionizing radiation, or foreign bodies, such as e.g. splinters, dirt and debris. Examples of inflammatory diseases are well known in the art.

An inflammatory disease can be selected from the group consisting of inflammatory bowel disease, psoriasis and bacterial sepsis. The term "inflammatory bowel disease", as used herein, refers to a group of inflammatory conditions of the colon and small intestine including, for example, Crohn's disease, ulcerative colitis, collagenous colitis, lymphocytic colitis, ischemic colitis, diversion colitis, Behcet's syndrome and indeterminate colitis. Delivery constructs that can be used to prevent and/or treat such inflammatory disease include those comprising the amino acid sequence set forth in SEQ ID NO: 154 and/or SEQ ID NO: 155.

"Crohn's disease", in accordance with the present disclosure, is a T-helper Type 1 (Th1) inflammatory bowel disease, which has an immune response pattern that includes an increased production of interleukin-12, tumor necrosis factor (TNF), and interferon-γ (Romagnani. Inflamm Bowel Dis 1999; 5:285-94), and which can have a devastating impact on the lifestyle of a patient afflicted therewith. Common symptoms of Crohn's disease include diarrhea, cramping, abdominal pain, fever, and even rectal bleeding. Crohn's disease and complications associated with it often results in the patient requiring surgery, often more than once. There is no known cure for Crohn's disease, and long-term, effective treatment options are limited. The goals of treatment are to control inflammation, correct nutritional deficiencies, and relieve symptoms like abdominal pain, diarrhea, and rectal to bleeding. While treatment can help control the disease by lowering the number of times a person experiences a recurrence, there is no cure. Treatment can include drugs, nutrition supplements, surgery, or a combination of these options. Common treatments which can be administered for treatment include anti-inflammation drugs, including sulfasalazine, cortisone or steroids, including prednisone, immune system suppressors, such as 6-mercaptopurine or azathioprine, and antibiotics.

"Psoriasis", in accordance with the present disclosure, is a disease, which affects the skin and joints. It commonly causes red scaly patches to appear on the skin. The scaly patches caused by psoriasis, called psoriatic plaques, are areas of inflammation and excessive skin production. Skin rapidly accumulates at these sites and takes a silvery-white appearance. Plaques frequently occur on the skin of the elbows and knees, but can affect any area including the scalp and genitals. Psoriasis is hypothesized to be immune-mediated and is not contagious. The disorder is a chronic recurring condition, which varies in severity from minor localized patches to complete body coverage. Fingernails and toenails are frequently affected (psoriatic nail dystrophy)—and can be seen as an isolated finding. Psoriasis can also cause inflammation of the joints, which is known as psoriatic arthritis. Ten to fifteen percent of people with psoriasis have psoriatic arthritis.

The term "bacterial sepsis", as used herein, refers to life-threatening conditions resulting from the circulation of bacteria in the blood stream. Sepsis results in generalized systemic production of pro-inflammatory cytokines that results in tissue damage and ultimately septic shock due to failure of the microcirculation.

The present disclosure relates to methods for treatment, prophylaxis and/or prevention of an autoimmune disease in a subject, comprising administering a pharmaceutical composition of the present disclosure to the subject. An autoimmune disease, as pertains to the present disclosure, is a disease or disorder arising from and directed against an individual's own tissues or a co-segregate or manifestation thereof or resulting condition therefrom. In various embodiments. the autoimmune disease is selected from the group consisting of systemic lupus erythematosus (SLE), pemphigus vulgaris, myasthenia gravis, hemolytic anemia, thrombocytopenia purpura, Grave's disease, Sjogren's disease, dermatomyositis, Hashimoto's disease, polymyositis, inflammatory bowel disease, multiple sclerosis (MS), diabetes mellitus, rheumatoid arthritis, and scleroderma. Exemplary delivery constructs that can be used to treat those disease can include those comprising any carrier set forth in SEQ ID NO: 4-SEQ ID NO: 125 coupled to, for example, an anti-TNFa antibody, or a functional binding fragment thereof.

"Rheumatoid arthritis", in accordance with the present disclosure, is an autoimmune disorder that causes the body's immune system to attack the bone joints (Muller B et al., Springer Semin. Immunopathol., 20:181-96, 1998). Rheumatoid arthritis is a chronic, systemic inflammatory disorder that can affect many tissues and organs, but principally attacks synovial joints. The process produces an inflammatory response of the synovium (synovitis) secondary to hyperplasia of synovial cells, excess synovial fluid, and the development of pannus in the synovium. The pathology of the disease process often leads to the destruction of articular cartilage and ankylosis of the joints. Rheumatoid arthritis can also produce diffuse inflammation in the lungs, pericardium, pleura, and sclera, and also nodular lesions, most common in subcutaneous tissue under the skin.

The present disclosure relates to methods and compositions for treatment, prophylaxis and/or prevention of a cancer in a subject, comprising administering a pharmaceutical composition of the present disclosure to the subject. Cancers to be treated include, but are not limited to, non-Hodgkin's lymphomas, Hodgkin's lymphoma, chronic lymphocytic leukemia, hairy cell leukemia, acute lymphoblastic leukemia, multiple myeloma, carcinomas of the pancreas, colon, gastric intestine, prostate, bladder, kidney ovary, cervix, breast, lung, nasopharynx, malignant melanoma and rituximab resistant NHL and leukemia.

The therapeutically effective amount of a pharmaceutical composition of the present disclosure will be administered in combination with one or more other therapeutic agents. Such therapeutic agents can be accepted in the art as a standard treatment for a particular disease state as described herein, such as inflammatory disease, autoimmune disease, or cancer. Exemplary therapeutic agents contemplated include, but are not limited to, cytokines, growth factors, steroids, NSAIDs, DMARDs, anti-inflammatories, chemotherapeutics, radiotherapeutics, or other active and ancillary agents.

The present disclosure relates to methods for treatment, prophylaxis and/or prevention of a metabolic disorder in a subject, comprising administering a pharmaceutical composition of the present disclosure to the subject. In various embodiments, the metabolic disorder is selected from the group consisting of: diabetes, obesity, diabetes as a consequence of obesity, hyperglycemia, dyslipidemia, hypertriglyceridemia, syndrome X, insulin resistance, impaired glucose tolerance (IGT), diabetic dyslipidemia, and hyperlipidemia.

The present disclosure relates to methods for treatment, prophylaxis and/or prevention of a fatty liver disease (e.g., nonalcoholic fatty liver disease (NAFLD); nonalcoholic steatohepatitis (NASH)), a gastrointestinal disease, or a neurodegenerative disease in a subject, comprising administering a pharmaceutical composition of the present disclosure to the subject.

The present disclosure relates to methods and compositions for treatment, prophylaxis and/or prevention of a GH deficient growth disorder in a subject, said method comprising administering a pharmaceutical composition of the present disclosure to the subject. In various embodiments, the disorder is selected from the group consisting of: growth hormone deficiency (GHD), Turner syndrome (TS), Noonan syndrome, Prader-Willi syndrome, short stature homeobox-containing gene (SHOX) deficiency, chronic renal insufficiency, and idiopathic short stature short bowel syndrome, GH deficiency due to rare pituitary tumors or their treatment, and muscle-wasting disease associated with HIV/AIDS.

A subject of the present disclosure can be a human or a rodent. The subject can be a human. A subject can be affected by one or more of the following: inflammatory bowel disease, psoriasis, bacterial sepsis, systemic lupus erythematosus (SLE), pemphigus vulgaris, myasthenia gravis, hemolytic anemia, thrombocytopenia purpura, Grave's disease, Sjogren's disease, dermatomyositis, Hashimoto's disease, polymyositis, inflammatory bowel disease, multiple sclerosis (MS), diabetes mellitus, rheumatoid arthritis, scleroderma, non-Hodgkin's lymphomas, Hodgkin's lymphoma, chronic lymphocytic leukemia, hairy cell leukemia, acute lymphoblastic leukemia, multiple myeloma, carcinomas of the bladder, kidney ovary, cervix, breast, lung, nasopharynx, malignant melanoma, rituximab resistant NHL or leukemia, diabetes, obesity, diabetes as a consequence of obesity, hyperglycemia, dyslipidemia, hypertriglyceridemia, syndrome X, insulin resistance, impaired glucose tolerance (IGT), diabetic dyslipidemia, hyperlipidemia, growth hormone deficiency (GHD), Turner syndrome (TS), Noonan syndrome, Prader-Willi syndrome, short stature homeobox-containing gene (SHOX) deficiency, chronic renal insufficiency, or idiopathic short stature short bowel syndrome.

The methods and compositions described herein can also be used to diagnose disease or condition. Diagnosing a disease or condition can include invasive and non-invasive diagnostic modalities. Specifically, the compositions described herein can be used to non-invasively diagnose a disease, e.g., by measuring the expression of a certain marker (e.g., a biomarker) or antigen. Such diagnoses can be conducted by coupling a cargo to a carrier, wherein the cargo can have a binding affinity for a certain marker (e.g., a biomolecule representative which presence or concentration in a certain organ, tissue, or cell is representative of a certain disease or condition). Diagnoses as described herein can further comprise monitoring a response to a treatment (e.g., the treatment of a subject). For example, if response to a treatment correlates with a reduction of a certain marker (e.g., a biomarker), the delivery constructs of the present disclosure can be used to measure such marker at a certain location (e.g., a certain immune cell population in a submucosal compartment). In addition to non-invasive diagnoses, the methods and compositions described herein can be used to provide biologically and/or therapeutically relevant information, e.g., upon a biopsy sample has been taken from a subject, which can be followed by immunohistochemistry, e.g., the detection of accumulation of a delivery constructs in a certain tissue etc.

Non-invasive diagnosis can comprise molecular and/or nuclear imaging. For example, a delivery construct can comprise cargo that is labeled with a fluorescent and/or radioactive compound such that the location and/or concentration of such a delivery construct can be determined in a subject after administration. Any moiety with diagnostic applicability as described herein can be used to provide diagnostic and/or theranostic (therapeutic and diagnostic) agents.

Polynucleotides Encoding Delivery constructs

The methods and compositions of the present disclosure provides polynucleotides comprising a nucleotide sequence encoding non-naturally occurring delivery constructs and/or hybrid delivery construct polypeptides. These polynucleotides are useful, for example, for making the delivery constructs and/or hybrid delivery construct polypeptides. The disclosure provides an expression system that comprises a recombinant polynucleotide sequence encoding a bacterial carrier receptor binding domain, and a polyspacer insertion site for a polynucleotide sequence encoding a biologically active cargo. The polyspacer insertion site can be anywhere in the polynucleotide sequence so long as the polyspacer insertion does not disrupt the delivery construct of the bacterial toxin. The expression system can comprise a polynucleotide sequence that encodes a cleavable spacer so that cleavage at the cleavable spacer separates a biologically active cargo encoded by a nucleic acid inserted into the polyspacer insertion site from the remainder of the encoded delivery construct. Thus, in embodiments where the polyspacer insertion site is at an end of the encoded construct, the polynucleotide comprises one nucleotide sequence encoding a cleavable spacer between the polyspacer insertion site and the remainder of the polynucleotide. In embodiments where the polyspacer insertion site is not at the end of the encoded construct, the polyspacer insertion site can be flanked by nucleotide sequences that each encode a cleavable spacer.

Various in vitro methods that can be used to prepare a polynucleotide encoding a delivery construct useful in the delivery constructs of the disclosure include, but are not limited to, reverse transcription, the polymerase chain reaction (PCR), the ligase chain reaction (LCR), the transcription-based amplification system (TAS), the self-sustained sequence replication system (3 SR) and the QP replicase amplification system (QB). Any such technique known by one of skill in the art to be useful in construction of recombinant nucleic acids can be used. For example, a polynucleotide encoding the protein or a portion thereof can be isolated by polymerase chain reaction of cDNA using primers based on the DNA sequence of a delivery construct or a nucleotide encoding the receptor binding domain.

Guidance for using these cloning and in vitro amplification methodologies are described in, for example, U.S. Pat. No. 4,683,195; Mullis et al., 1987, Cold Spring Harbor Symp. Quant. Biol. 51:263; and Erlich, ed., 1989, PCR Technology, Stockton Press, NY. Polynucleotides encoding a delivery construct, or a portion thereof, also can be isolated by screening genomic of cDNA libraries using probes selected from the sequences of the desired polynucleotide under stringent, moderately stringent, or highly stringent hybridization conditions.

Further, the polynucleotides can also encode a secretory sequence at the amino terminus of the encoded delivery construct. Such constructs are useful for producing the delivery constructs in mammalian cells as they simplify isolation of the delivery construct and/or hybrid delivery construct polypeptides.

Furthermore, the polynucleotides of the disclosure also encompass derivative versions of polynucleotides encoding a delivery construct. Such derivatives can be made by any method known by one of skill in the art without limitation. For example, derivatives can be made by site-specific mutagenesis, including substitution, insertion, or deletion of one, two, three, five, ten or more nucleotides, of polynucleotides encoding the delivery construct. Alternatively, derivatives can be made by random mutagenesis. One method for randomly mutagenizing a nucleic acid comprises amplifying the nucleic acid in a PCR reaction in the presence of 0.1 mM $MnCl_2$ and unbalanced nucleotide concentrations. These conditions increase the inaccuracy incorporation rate of the polymerase used in the PCR reaction and result in random mutagenesis of the amplified nucleic acid.

Accordingly, the disclosure provides a polynucleotide that can encode one or more delivery constructs. A delivery construct comprises a bacterial carrier and a biologically active cargo to be delivered to a subject; and, optionally, a non-cleavable or cleavable spacer. Cleavage at the cleavable spacer can separate the biologically active cargo from the remainder of the delivery construct. The cleavable spacer can be cleaved by an enzyme that is present at a basolateral membrane of a polarized epithelial cell of the subject or in the plasma of the subject.

The polynucleotide can hybridize under stringent hybridization conditions to any polynucleotide of this disclosure. The polynucleotide can hybridize under stringent conditions to a nucleic acid that encodes any delivery construct of the disclosure.

The disclosure provides expression vectors for expressing the delivery constructs and/or hybrid delivery construct polypeptides. Generally, expression vectors are recombinant polynucleotide molecules comprising expression control sequences operatively linked to a nucleotide sequence encoding a polypeptide. Expression vectors can readily be adapted for function in prokaryotes or eukaryotes by inclusion of appropriate promoters, replication sequences, selectable markers, etc. to result in stable transcription and translation or mRNA. Techniques for construction of expression vectors and expression of genes in cells comprising the expression vectors are well known in the art. See, e.g., Sambrook et al., 2001, Molecular Cloning—A Laboratory Manual, 3rd edition, Cold Spring Harbor Laboratory, Cold Spring Harbor, N.Y., and Ausubel et al., eds., Current Edition, Current Protocols in Molecular Biology, Greene Publishing Associates and Wiley Interscience, NY.

Useful promoters for use in expression vectors include, but are not limited to, a metallothionein promoter, a constitutive adenovirus major late promoter, a dexamethasone-inducible MMTV promoter, a SV40 promoter, a MRP pol III promoter, a constitutive MPSV promoter, a tetracycline-inducible CMV promoter (such as the human immediate-early CMV promoter), and a constitutive CMV promoter.

The expression vectors should contain expression and replication signals compatible with the cell in which the delivery constructs are expressed. Expression vectors useful for expressing delivery constructs include viral vectors such as retroviruses, adenoviruses and adeno-associated viruses, plasmid vectors, cosmids, and the like. Viral and plasmid vectors are preferred for transfecting the expression vectors into mammalian cells. For example, the expression vector pcDNA1 (Invitrogen, San Diego, Calif.), in which the expression control sequence comprises the CMV promoter, provides good rates of transfection and expression into such cells.

The expression vectors can be introduced into the cell for expression of the delivery constructs by any method known to one of skill in the art without limitation. Such methods include, but are not limited to, e.g., direct uptake of the molecule by a cell from solution; facilitated uptake through lipofection using, e.g., liposomes or immunoliposomes; particle-mediated transfection; etc. See, e.g., U.S. Pat. No. 5,272,065; Goeddel et al., eds, 1990, Methods in Enzymology, vol. 185, Academic Press, Inc., CA; Krieger, 1990, Gene Transfer and Expression—A Laboratory Manual, Stockton Press, NY; Sambrook et al., 1989, Molecular Cloning—A Laboratory Manual, Cold Spring Harbor Laboratory, NY; and Ausubel et al., eds., Current Edition, Current Protocols in Molecular Biology, Greene Publishing Associates and Wiley Interscience, NY.

The expression vectors can also contain a purification moiety that simplifies isolation of the delivery construct and/or hybrid delivery construct polypeptides. For example, a polyhistidine moiety of, e.g., six histidine residues, can be incorporated at the amino terminal end of the protein. The polyhistidine moiety allows convenient isolation of the protein in a single step by nickel-chelate chromatography. In various embodiments, the purification moiety can be cleaved from the remainder of the delivery construct following purification. In other embodiments, the moiety does not interfere with the function of the functional domains of the delivery construct and thus need not be cleaved.

The present disclosure provides a cell that can comprise an expression vector for expression of the delivery constructs and/or hybrid delivery construct polypeptides, or portions thereof. The cell can be selected for its ability to express high concentrations of the delivery construct to facilitate purification of the protein. In various embodiments, the cell is a prokaryotic cell, for example, E. coli. As described in the examples, the delivery constructs are properly folded and comprise the appropriate disulfide linkages when expressed in E. coli. The cell is a eukaryotic cell. Useful eukaryotic cells include yeast and mammalian cells. Any mammalian cell known by one of skill in the art to be useful for expressing a recombinant polypeptide, without limitation, can be used to express the delivery constructs. For example, Chinese hamster ovary (CHO) cells can be used to express the delivery constructs. The delivery constructs and/or hybrid delivery construct polypeptides of the disclosure can be produced by recombination, as described below. However, the delivery constructs can also be produced by chemical synthesis using methods known to those of skill in the art.

The delivery constructs of the present disclosure can be produced using a variety of methods. The selection of a production method can depend on the molecular structure of the delivery construct and/or its components (e.g., the carrier, cargo, and/or spacer). Thus, for some delivery constructs organic synthetic methods may be advantageous for producing such delivery construct. A delivery construct of the present disclosure can be a polypeptide. Such polypeptides can be produced, for example, using recombinant DNA methodology. Generally, this involves creating a DNA sequence that encodes the delivery construct, placing the DNA in an expression cassette under the control of a particular promoter, expressing the molecule in a host, isolating the expressed molecule and, if required, folding of the molecule into an active conformational form.

DNA encoding the delivery constructs described herein can be prepared by any suitable method, including, for example, cloning and restriction of appropriate sequences or direct chemical synthesis by methods such as the phosphotriester method of Narang et al. (1979) Meth. Enzymol. 68: 90-99; the phosphodiester method of Brown et al. (1979) Meth. Enzymol. 68: 109-151; the diethylphosphoramidite method of Beaucage et al. (1981) Tetra. Lett., 22: 1859-1862); the solid support method of U.S. Pat. No. 4,458,066, and the like.

Chemical synthesis produces a single stranded oligonucleotide. This can be converted into double stranded DNA by hybridization with a complementary sequence or by polymerization with a DNA polymerase using the single strand as a template. One of skill would recognize that while chemical synthesis of DNA is limited to sequences of about 100 bases, longer sequences can be obtained by the ligation of shorter sequences.

Alternatively, subsequences can be cloned and the appropriate subsequences cleaved using appropriate restriction enzymes. The fragments can then be ligated to produce the desired DNA sequence. A DNA encoding a delivery constructs of the present disclosure can be cloned using DNA amplification methods such as polymerase chain reaction (PCR). Thus, for example, the gene for the biologically active cargo is PCR amplified, using a sense primer containing the restriction site for, e.g., NdeI and an antisense primer containing the restriction site for HindIII. This can produce a nucleic acid encoding the biologically active cargo sequence and having terminal restriction sites. A delivery construct having "complementary" restriction sites can similarly be cloned and then ligated to the biologically active cargo and/or to a spacer attached to the biologically active cargo. Ligation of the nucleic acid sequences and insertion into a vector produces a vector encoding the biologically active cargo joined to the bacterial carrier receptor binding domain. In various embodiments, DNA encoding delivery constructs of the present disclosure is artificially synthesized by, for example, solid-phase DNA synthesis.

The production methods described herein can be used to produce the delivery constructs of the present disclosure, or (functional) variants thereof. For example, a "Cholix" (also referred to herein as Cholix toxin or Cholix exotoxin) can encompass a variety of functional variants (e.g., a functional genus), wherein the functional variants can comprise one or more variations is their amino acid sequence relative to SEQ ID NO: 1 as disclosed herein. Thus, in the present disclosure, the Cholix toxin having the amino acid sequence set forth in SEQ ID NO: 1 is used as the reference sequence when referred to Cholix. However, as described herein, the present disclosure is not limited to the Cholix having the amino acid sequence set forth in SEQ ID NO: 1 but instead encompasses all Cholix variants that fall within the functional genus of Cholix. For example, a variant of the Cholix exotoxin with the amino acid sequence set forth in SEQ ID NI: 1 can be a Cholix exotoxin which amino acid sequence is set forth in SEQ ID NO: 2, wherein both variants are capable of carrying out the same functions, e.g., transcytosis across an epithelial cell, and interact with the same receptors, such as ribophilin 1, SEC24, CK-8, TMEM132, GRP75, ERGIC-53, and/or perlecan.

Moreover, the production method of a polypeptide can affect, to some degree, the amino acid sequence of such polypeptide (e.g., due to post-translational modifications). For example, a first carrier and a second carrier are produced in the same expression system (e.g., a bacterial expression system such as *E. coli* or a mammalian expression system such as a CHO cell). In other cases, and as described herein, a first carrier and a second carrier are produced in a different expression system (e.g., a bacterial or a mammalian expression system). Bacterial expression systems include *E. coli*, and mammalian expression systems include CHO cells, for example. A bacterially produced polypeptide can comprise an N-cap, wherein the N-cap can comprise one more modifications at the N-terminal of the polypeptide. An N-cap can comprise an N-terminal methionine residue. Examples of Cholix domain I derived carrier polypeptides that can be bacterially produced and that comprise such N-terminal methionine include those comprising the amino acid sequences set forth in SEQ ID NO: 5, SEQ ID NO: 7, SEQ ID NO: 9, SEQ ID NO: 11, SEQ ID NO: 31, SEQ ID NO: 107, and SEQ ID NO: 135.

Experimental Methods

Transcytosis Testing. The transcytosis function of the isolated delivery constructs can be tested as a function of the delivery construct's ability to pass through an epithelial membrane. Because transcytosis first requires binding to the epithelial cell, these assays can also be used to assess the function of the delivery construct of the delivery construct.

The delivery construct's transcytosis activity can be tested by any method known by one of skill in the art, without limitation. In various embodiments, transcytosis activity can be tested by assessing the ability of a delivery construct to enter a non-polarized cell to which it binds. In case of Cholix derived carrier, and without intending to be bound to any particular theory or mechanism of action, it is described herein that the transcytosis function that allows a delivery construct to pass through a polarized epithelial cell and the function to enter non-polarized cells resides in the same domain, i.e. the domain described herein as domain I. Thus, the delivery construct's ability to enter the cell can be assessed, for example, by detecting the physical presence of the construct in the interior of the cell. For example, the delivery construct can be labeled with, for example, a fluorescent marker, and the delivery construct exposed to the cell. Then, the cells can be washed, removing any delivery construct that has not entered the cell, and the amount of label remaining determined. Detecting the label in this traction indicates that the delivery construct has entered the cell.

The delivery construct's transcytosis ability can be tested by assessing the delivery construct's ability to pass through a polarized epithelial cell. For example, the delivery construct can be labeled with, for example, a fluorescent marker (e.g., RFP) and contacted to the apical membranes of a layer of epithelial cells. Fluorescence detected on the basolateral side of the membrane formed by the epithelial cells indicates that the transcytosis domain is functioning properly.

In vivo transcytosis can be tested using male Wistar rats. Male Wistar rats can be housed 3-5 per cage with a 12/12 h light/dark cycle and can be 225-275 g (approximately 6-8 weeks old) when placed on study. Experiments can be conducted during the light phase using a non-recovery protocol that uses continuous isoflurane anesthesia. A 4-5 cm midline abdominal incision that exposes mid-jejunum regions can be conducted. Stock solutions at $3.86 \times 10^{-5}$ M of test articles can be prepared in phosphate buffered saline (PBS), with 50 μL (per 250 g rat) being administered by intraluminal injection (ILI) using a 29-gauge needle. The injection site mesentery can then be marked with a permanent marker. At study termination, a 3-5 mm region that captured the marked intestine segment can be isolated and processed for microscopic assessment. In vivo experiments are performed in accordance with the U.K. Animals (Scientific Procedures) Act of 1986, the European Communities Council Directive of 1986 (86/609/EEC), and the University of Bath's ethical review procedures.

Cleavable Spacer Cleavage Testing. The function of the cleavable spacer can generally be tested in a cleavage assay. Any suitable cleavage assay known by one of skill in the art, without limitation, can be used to test the cleavable spacers. Both cell-based and cell-free assays can be used to test the ability of an enzyme to cleave the cleavable spacers.

An exemplary cell-free assay for testing cleavage of cleavable spacers comprises preparing extracts of polarized epithelial cells and exposing a labeled delivery construct bearing a cleavable spacer to the fraction of the extract that corresponds to membrane-associated enzymes. In such assays, the label can be attached to either the biologically active cargo to be delivered or to the remainder of the delivery construct. Among these enzymes are cleavage enzymes found near the basolateral membrane of a polarized epithelial cell, as described above. Cleavage can be detected, for example, by binding the delivery construct with, for example, an antibody and washing off unbound molecules. If label is attached to the biologically active cargo to be delivered, then little or no label should be observed on the molecule bound to the antibodies. Alternatively, the binding agent used in the assay can be specific for the biologically active cargo, and the remainder of the construct can be labeled. In either case, cleavage can be assessed.

Cleavage can also be tested using cell-based assays that test cleavage by polarized epithelial cells assembled on semi-permeable membranes. For example, a labeled delivery construct, or portion of a delivery construct comprising the cleavable spacer, can be contacted to either the apical or basolateral side of a monolayer of suitable epithelial cells, such as, for example, Caco-2 cells, under conditions that permit cleavage of the spacer. Cleavage can be detected by detecting the presence or absence of the label using a reagent that specifically binds the delivery construct, or portion thereof. For example, an antibody specific for the delivery construct can be used to bind a delivery construct comprising a label distal to the cleavable spacer in relation to the portion of the delivery construct bound by the antibody. Cleavage can then be assessed by detecting the presence of the label on molecules bound to the antibody. If cleavage has occurred, little or no label should be observed on the molecules bound to the antibody. By performing such experiments, enzymes that preferentially cleave at the basolateral membrane rather than the apical membrane can be identified, and, further, the ability of such enzymes to cleave the cleavable spacer in a delivery construct can be confirmed.

Further, cleavage can also be tested using a fluorescence reporter assay as described in U.S. Pat. No. 6,759,207. Briefly, in such assays, the fluorescence reporter is contacted to the basolateral side of a monolayer of suitable epithelial cells under conditions that allow the cleaving enzyme to cleave the reporter. Cleavage of the reporter changes the structure of the fluorescence reporter, changing it from a non-fluorescent configuration to a fluorescent configuration. The amount of fluorescence observed indicates the activity of the cleaving enzyme present at the basolateral membrane.

Further, cleavage can also be tested using an intra-molecularly quenched molecular probe, such as those described in U.S. Pat. No. 6,592,847. Such probes generally comprise a fluorescent moiety that emits photons when excited with light of appropriate wavelength and a quencher moiety that absorbs such photons when in close proximity to the fluorescent moiety. Cleavage of the probe separates the quenching moiety from the fluorescent moiety, such that fluorescence can be detected, thereby indicating that cleavage has occurred. Thus, such probes can be used to identify and assess cleavage by particular cleaving enzymes by contacting the basolateral side of a monolayer of suitable epithelial cells with the probe under conditions that allow the cleaving enzyme to cleave the probe. The amount of fluorescence observed indicates the activity of the cleaving enzyme being tested.

In Vivo Studies. Male Wistar rats, housed in groups of 3-5 per cage with a 12/12 h light/dark cycle, were 225-275 g (approximately 6-8 weeks old) when placed on study after an overnight fast. All experiments were conducted during the light phase and carried out using a non-recovery protocol that used continuous isoflurane anesthesia. A 4-5 cm midline abdominal incision was made to expose the small intestine (mid-jejunum to proximal ileum regions). Equimolar stock solutions of Exotoxin A (PE)-RPF or Cholix-RFP truncation chimeras prepared in phosphate buffered saline were injected intra-lumenally using a 29-gauge hypodermic needle in a volume of 200 μL/kg (or ~50 μL per 250 g rat). The adjacent mesentery of each intra-lumenal injection site was marked with a permanent ink pen. At selected time internals, the animal was euthanized and a 3-5 mm region that captured the marked intestine segment was isolated. All experiments were performed in accordance with the U.K. Animals (Scientific Procedures) Act of 1986, the European Communities Council Directive of 1986 (86/609/EEC), and the University of Bath's ethical review procedures.

Microscopy. Isolated tissues were rinse briefly in ice-cold PBS and then fixed with 4% paraformaldehyde on ice prior to labeling with primary antibodies to Exotoxin A (PE), Cholix, or RFP. Tissue distribution of a fluorescent-labeled secondary antibody that recognized these primary antibodies was assessed using a Zeiss LSM 510 fluorescence microscope. DAPI (4',6-diamidino-2-phenylindole) was used as a nuclear stain.

Immunohistochemistry. Rehydrate tissue slides in decreasing concentrations of ethanol. Slides are immersed in histoclear (x2), 100% ethanol, 90% ethanol, 80% ethanol, 70% ethanol and PBS for 5 minutes each. Boil slides in 10 mM sodium citrate (pH 6) for 10 minutes. Remove from boil and allow to cool for 20 minutes. Dry slide and add a wax border around each tissue section using an ImmEdge hydrophobic pen. Wash tissue sections by pipetting PBS directly onto tissue. Perform 3×5 minute washes. Permeabilise tissue by pipetting 0.2% Triton x-100 in PBS onto sections. Incubate at room temperature for 45 minutes. Wash 3×5 minutes with PBS. Block tissue sections by pipetting 2% BSA and 2% donkey serum in 0.1% Triton x-100 in PBS onto sections. Incubate for 2 hours at room temperature. Remove blocking solution and add primary antibodies. Dilute antibodies to required concentration in 0.05% Triton x-100 and 1% BSA in PBS. Incubate overnight at 4° C. Wash 3×5 minutes with PBS. Incubate with secondary antibodies. Dilute antibodies to required concentration in 0.05% Triton x-100 and 1% BSA in PBS. Incubate for 2 hours at room temperature. Wash 3×5 minutes with PBS. Incubate with 200 nM DAPI at room temperature for 45 minutes. Wash 3×5 minutes with PBS. Dehydrate tissue sections by immersing in 70% ethanol, 100% ethanol, histoclear and 100% ethanol for 5 minutes each. Place a drop of fluorshield mounting media on each tissue section and cover with a glass coverslip. Gently apply pressure to the coverslip to remove air bubbles. Allow mounting media to dry for 4 hours. Store slides at 4° C. and image using confocal fluorescent microscope.

Evaluation of Cholix Domain I Interacting Proteins. In order to identify Cholix and/or PE interacting partners (e.g., receptors, enzymes, etc.) and establish the vesicular compartments where they interact with Cholix or PE exotoxins (e.g., a domain I of those exotoxins or a truncated version thereof), a series of pull-downs can be performed to identify potential interaction partners that can be followed by in silico associations using surface plasmon resonance, in vitro transcytosis studies using polarized Caco-2 human intestinal epithelial cells where genetic knockdown of specific targets can be achieved, and in vivo transcytosis studies where Cholix elements and specific receptors can be co-localized in established vesicular structures. Without being bound to any theory, it is assumed that a transcytosis process can involve elements that are normally restricted within specific vesicular elements of polarized intestinal epithelial cells but can be recruited or "hijacked" by, e.g., Cholix domain I or truncated versions thereof, to leave the late endosome and avoid lysosomal degradation following apical receptor-mediated endocytosis.

EXAMPLES

The following examples merely illustrate the disclosure, and are not intended to limit the disclosure in any way.

Example 1

Preparation of Cholix and PE Derived Delivery Constructs

This Example describes the exemplary preparation of delivery constructs comprising truncated Cholix carriers (truncation in domains II and/or Ib) and truncated PE carriers (truncation in domains II and/or Ib) conjoined to heterologous cargos. In this Example, various non-naturally occurring delivery constructs were prepared as a single amino acid sequence and comprising a modified Cholix carrier sequence and/or a modified PE carrier sequence, a polyglycine-serine peptide spacer sequence, and a heterologous cargo.

The following modified Cholix and/or PE carriers were prepared and used to prepare Constructs 1-12: 1) a modified Cholix carrier truncated at amino acid residue 425 of SEQ ID NO: 1 (Cholix$^{425}$, SEQ ID NO: 129); 2) a modified Cholix carrier truncated at amino acid residue 415 of SEQ ID NO: 1 (Cholix$^{415}$, SEQ ID NO: 130); 3) a modified Cholix carrier truncated at amino acid residue 397 of SEQ ID NO: 1 (Cholix$^{397}$, SEQ ID NO: 131); 4) a modified Cholix carrier truncated at amino acid residue 386 of SEQ ID NO: 1 (Cholix$^{386}$, SEQ ID NO: 132); 5) a modified Cholix carrier truncated at amino acid residue 291 of SEQ ID NO: 1 (Cholix$^{291}$, SEQ ID NO: 133); 6) a modified Cholix carrier truncated at amino acid residue 265 of SEQ ID NO: 1 (Cholix$^{265}$, SEQ ID NO: 4); 7) a modified PE carrier truncated at amino acid residue 404 of SEQ ID NO: 135 (PE$^{404}$, SEQ ID NO: 141); 8) a modified PE carrier truncated at amino acid residue 395 of SEQ ID NO: 135 (PE$^{395}$, SEQ ID NO: 142); 9) a modified PE carrier truncated at amino acid residue 375 of SEQ ID NO: 135 (PE$^{375}$, SEQ ID NO: 143); 10) a modified PE carrier truncated at amino acid residue 364 of SEQ ID NO: 135 (PE$^{364}$, SEQ ID NO: 144); 11) a modified PE carrier truncated at amino acid residue 277 of SEQ ID NO: 135 (PE$^{277}$, SEQ ID NO: 145);

and 12) a modified PE carrier truncated at amino acid residue 252 of SEQ ID NO: 135 ($PE^{252}$, SEQ ID NO: 137). In each Construct 1-12, the polyglycine-serine peptide spacer GTGGS (SEQ ID NO: 201) was used to conjoin red fluorescent protein (RFP, SEQ ID NO: 220) at the C-terminus of each modified toxin. The RFP emulated the presence of a biologically active cargo.

Codon-optimized genes were obtained from a commercial source and cloned into the pET26(+) expression vector that was used to transform BL21(DE3) component *E. coli* cells using the manufacturer's suggested protocol. Clones were selected using Kanamycin/Agar plates incubate overnight at 37° C. Protein expression in fermented cultures of selected clones was achieved by 1 mM IPTG induction. Pelleted bacteria were lysed to collect inclusion bodies that were extensively washed in 50 mM Tris, 20 mM EDTA, 2.5% Triton X-100, 0.5 M NaCl, pH 8 prior to solubilization facilitated by sonication in 100 mM Tris, pH 8, 7 M Guanidine HCl. After centrifugation to pellet insoluble materials and the addition of dithiothreitol, proteins in the supernatant were refolded using a shuffle buffer containing 100 mM Tris, pH 8, 0.5 M L-Arginine, 1 M Urea, 2 mM EDTA, 1 mM oxidized glutathione (fresh made), and 1 mM Reduced glutathione (fresh made) that was dialyzed at 4° C. against 25 mM Tris, pH 8, 0.1 M Urea, and 1 mM EDTA. Following 0.45 μm filtration, desired proteins were purified using ion exchange and size exclusion chromatography. Final protein samples were analyzed by SDS-polyacrylamide gel electrophoresis and stored at −80° C.

Example 2

In Vivo Experiments Assessing Delivery Functions of Exotoxin Derived Carrier Molecules This Example describes an exemplary in vivo study to evaluate epithelial trafficking and delivery functions of the exotoxin derived carrier molecules described herein.

The in vivo studies used 7-8 weeks old male adult Wistar rats with an average weight of about 250 g. Where required, experiments were performed using a non-recovery protocol. Generally, rats were anesthetized using inhaled isoflurane and euthanized, when required, by inhaled $CO_2$. Experiments were initiated by making an about 4 cm long abdominal incision to access the mid-jejunum region of the small intestine. Upon making the incision, approximately 50 μL of a prepared solution containing the delivery construct or multiple delivery constructs in a concentration of about 1-1.5 mg/mL was injected into the intestinal lumen of an area devoid of foodstuffs through a 27-gauge needle using a 1 mL syringe. The mesentery adjacent to the site of injection was labeled with a marker and the intestine was returned to the abdominal cavity, with the incision being closed with clamps At specific time points, the injected intestine was retrieved, surgically isolated and flushed with a 4° C. isotonic PBS solution.

Washed, excised samples were fixed (4% paraformaldehyde in PBS) overnight at 4° C. before dehydration through graded series of ethanol/water solutions and overnight incubation in chloroform. Dehydrated tissues were immersed in wax, sectioned, and mounted on polylysine slides and processed for antigen retrieval using sodium citrate. Afterward, sections were permeabilized with 0.2% Triton-X100 in PBS prior to thrice washing in PBS and blocking with 2% BSA+2% serum of the animal the secondary antibodies have been raised. Primary antibodies were diluted in 1% BSA, 0.1% Triton-X100 in PBS and incubate overnight at 4° C. in humidified air. Fluorescent secondary antibodies were diluted in 1% BSA, 0.1% Triton-X100 in PBS and incubated for 2 hours at room temperature prior to processing for confocal microscopy. On occasion, an approximately 1 cm section of intestine at the injection site was collected for biochemical studies.

Example 3

Evaluation of Specific Marker Proteins for Interactions with Cholix Derived Delivery Constructs During Transcytosis and Intracellular Delivery This Example shows an exemplary list of proteins or markers for specific cell compartments that were analyzed using immunohistochemical (IHC) staining and immunofluorescence confocal microscopy and when evaluating the delivery constructs of the present disclosure.

The following TABLE 13 shows exemplary Cell compartment specific protein markers used herein. For example, Cholix derived delivery constructs comprising an IL-10 as the heterologous cargo were followed during experiments using either a monoclonal antibody (mAb) against IL-10 and/or a polyclonal antibody (pAb) raised against the Cholix carrier (e.g., a truncated domain I).

TABLE 13

Cell Compartment Specific Protein Markers

| Target | pAb/mAb | Species reactivity | Host | Dilution for IHC (P) | Notes | Storage | Cat. # |
|---|---|---|---|---|---|---|---|
| $Cholix^{386}$ carrier | pAb | | Rabbit | 1/500 | Whole antiserum | −20° C. | |
| IL-10 | mAb; pAb | Human | Mouse, Goat | 1/25 | | −20° C. | |
| EEA1 | pAb | Mouse, rat, human | Rabbit | 1/200 | Early endosome | −20° C. | Ab2900 |
| Rab7 | mAb | Mouse, rat, human | Rabbit | 1/100 | Late endosome | −20° C. | Ab1267712 |
| Rab11 | pAb | Mouse, rat, human, rabbit, dog | Rabbit | 1/500 | Recycling endosome | −20° C. | Fisher71-5300 |
| LAMP1 | pAb | Mouse, rat, human | Rabbit | 1/500 | Lysosome marker | −20° C. | Ab24170 |
| GM130 | pAb | Mouse, rat, human | Rabbit | 1/500 | Cis-Golgi | −20° C. | |

TABLE 13-continued Cell Compartment Specific Protein Markers

| Target | pAb/mAb | Species reactivity | Host | Dilution for IHC (P) | Notes | Storage | Cat. # |
|---|---|---|---|---|---|---|---|
| Glantin | mAb | Rat, human | Mouse | 1/20 | Golgi | −20° C. | Ab37266 |
| 58K Golgi protein | mAb | Mouse, rat, human | Mouse | 1/100 | Golgi | −20° C. | Nb600-4512 |
| TGN38 | mAb | Mouse, rat, human | Mouse | 1/1000 | Trans-Golgi | −20° C. | Nb300-575 |
| Calnexin | pAb | Mouse, rat, human | Rabbit | 1/500 | Endoplasmatic reticulum | −20° C. | Ab22595 |
| Clathrin | mAb | Mouse, rat, human | Mouse | 1/500 | Clathrin-mediated endocytosis | −20° C. | Ab2731 |

Example 4

Trans-Epithelial In Vivo Delivery of Cholix and PE Derived Carriers Truncated within Domain II or Domain Ib This example describes trans-epithelial transport of delivery constructs comprising truncated Cholix carriers (e.g., truncation in domains II and/or Ib) and truncated PE carriers (e.g., truncation in domain II and/or Ib) conjoined to biologically active cargos across polarized intestinal epithelium occurred (e.g., via apical-to-basolateral transcytosis).

Using the purified isolated monomeric forms of the various delivery constructs prepared as described in EXAMPLE 1, a series of in vivo transport studies were performed using the rat intra-luminal injection model (see additional methods section below). In this analysis, a rat is maintained under isoflurane anesthesia for the duration of this non-recovery study. During this time, the small intestine is exposed following a midline abdominal incision and a mid-jejunum region is selected with the adjacent mesentery being identified using an indelible marking pen. At the location, a 50 μL injection volume was used to administer ~5 μg of Constructs 7-12. The test protein was dissolved in phosphate buffered saline (PBS) and injected using a 28-gauge needle. After intra-luminal injection, the small intestine segment was returned to the abdominal cavity and retrieved at set periods of time.

Once retrieved, the tissue segment exposed to Constructs 7-12 was flushed with PBS, lightly fixed in paraformaldehyde, and prepared for fluorescence microscopy (see additional methods section below) where the delivery construct was detected using a polyclonal raised against the PE or Cholix that was recognized using a secondary antibody labelled with a red fluorescent dye. The presence or absence of transport for Constructs 7-12 is depicted in FIG. 1 (Constructs 12 (FIG. 1A-FIG. 1C), 11 (FIG. 1D-FIG. 1F) and 10 (FIG. 1G-FIG. 1I)) and FIG. 2 (Constructs 9 (FIG. 2A-FIG. 2C), 8 (FIG. 2D-FIG. 2F) and 7 (FIG. 2G-FIG. 2I)).

Uptake of each of Constructs 7-12 into a limited population of cells within the *Lamina propria* was consistent with that observed previously for full-length PE. The finding that efficient trans-epithelial transport of PE across polarized intestinal epithelium occurred even for Construct 12 ($PE^{252}$-RFP, e.g., amino acid with SEQ ID NO: 137 coupled to amino acid with SEQ ID NO: 220) was surprising and remarkable, suggesting that not only trans-epithelial transport across polarized intestinal epithelial cells, but also targeting to specific cells within the submucosal compartment can be achieved by elements found within domain I (SEQ ID NO: 137) of PE.

Based upon the surprising findings using the PE Constructs 7-12, Construct 6 ($Cholix^{265}$-RFP), which comprises only domain I of Cholix (SEQ ID NO: 4) was evaluated. Immunofluorescence assessment of $Cholix^{265}$-RFP (e.g., amino acid of SEQ ID NO: 4 or 5 coupled to SEQ ID NO: 220) transport across rat small intestine in vivo produced a similar outcome as observed with PE Construct 12. Evaluation using an antibody to both the Cholix and the RFP component was used to demonstrate that both elements of the chimera were being transported (see e.g., FIG. 3). The observed staining pattern for these two antibodies was similar, showing that both elements moved across the epithelium and ended up in the same population of cells within the *Lamina propria*. This data suggests that domain I (SEQ ID NO: 4) of Cholix may be sufficient to transport a protein cargo (26.9 kDa) and deliver it to a selected cell population (FIG. 3A-FIG. 3F).

Example 5

Transport Across Rat Jejunum of Chimeric Cholix-PE Constructs

In this example, delivery constructs comprising the amino acid sequences set forth in SEQ ID NO: 146 (Construct 13) and SEQ ID NO: 146 (Construct 14) were prepared, and evaluated as described above in EXAMPLE 2. The chimeric Cholix-PE constructs of this example comprise mixed domains I, II, Ib, and III from either the Cholix exotoxin or the PE exotoxin as described herein.

The chimeric carrier construct 13 (SEQ ID NO: 146) comprises a Cholix domain I derived from the sequence set forth in SEQ ID NO: 1 (amino acid residues 1-265 of SEQ ID NO: 2), a PE translocation domain II derived from the sequence set forth in SEQ ID NO: 138, a PE domain Ib derived from the sequence set forth in SEQ ID NO: 139, and a non-toxic PE catalytic domain III derived from the sequence set forth in SEQ ID NO: 140. The chimeric carrier construct 14 (SEQ ID NO: 147) comprises a PE domain I derived from the sequence set forth in SEQ ID NO: 137, a Cholix carrier translocation domain II derived from the sequence set forth in SEQ ID NO: 126, a Cholix carrier domain Ib derived from the sequence set forth in SEQ ID NO: 127, and a non-toxic Cholix carrier catalytic domain III derived from the sequence set forth in SEQ ID NO: 128.

As shown in FIG. 4 (after 1 minute, FIG. 4A-FIG. 4E) and FIG. 5 (after 20 minute, FIG. 5A-FIG. 5E) for construct 13 and FIG. 6 (after 1 minute, FIG. 6A-FIG. 6E) and FIG. 7 (after 20 minute, FIG. 7A-FIG. 7E) for construct 14, the chimeric carrier constructs are capable of transport across rat jejunum and target cells in the *Lamina propria* in vivo. Thus, it is demonstrated herein that also chimeric delivery constructs comprising portions or domains from two or more different exotoxins (e.g., Cholix and PE) can efficiently deliver cargo into and across epithelial cells.

Example 6

Production and First In Vivo Transport Studies of Truncated Cholix Domain I Delivery Constructs This example demonstrates the transcytosis function of truncated Cholix derived carrier polypeptides, wherein, importantly, the truncation occurred at various locations within the domain I of the Cholix exotoxin.

The non-cleavable polyglycine-serine peptide spacer GGGGSGGGGSGGGGS (SEQ ID NO: 210) was used to couple human growth hormone (HGH) (SEQ ID NO: 214) to the C-terminus of various modified Cholix carrier polypeptides to prepare the following delivery constructs for evaluation according to the protein production procedure described in EXAMPLE 1 above (in this bacterially produced): 1) SEQ ID NO: 160, which comprises a modified Cholix carrier truncated at amino acid residue 187 of SEQ ID NO: 5; 2) SEQ ID NO: 159, which comprises a modified Cholix carrier truncated at amino acid residue 151 of SEQ ID NO: 5; 3) SEQ ID NO: 158, which comprises a modified Cholix carrier truncated at amino acid residue 134 of SEQ ID NO: 5; 4) SEQ ID NO: 161, which comprises a modified Cholix carrier truncated at amino acid residue 206 of SEQ ID NO: 5; 5) SEQ ID NO: 162, which comprises a modified Cholix carrier truncated at amino acid residue 245 of SEQ ID NO: 5; 6) SEQ ID NO: 163, which comprises a modified Cholix carrier truncated at amino acid residue 251 of SEQ ID NO: 5; and 8) SEQ ID NO: 165, which comprises a modified Cholix carrier comprising amino acid residues 40-187 of SEQ ID NO: 5.

In order to analyze the produced fusion proteins, constructs were injected into the lumen of the small intestine of rats and the injection site was collected 5, 10 or 15 minutes after injection. The tissue was fixed and sectioned then stained with anti-Cholix and anti-HGH antibodies. Fluorescent secondary antibodies were used to visualize the protein location using confocal microscopy. As depicted in FIG. 8A-FIG. 8C, the construct comprising the amino acid sequence of SEQ ID NO: 165 was visualized in the epithelial cells and limited to an area near the membrane in the apical side of the cells at 5, 10 and 15 minutes. There was no significant movement of the protein through the cells away from this compartment and no protein appearing in the *Lamina propria*. This suggests that the polypeptide carrier with the amino acid sequence of SEQ ID NO: 165 is sufficient for uptake into the epithelial cells, e.g., via its receptor binding site and/or via interactions with TMEM132 and/or LRP1, but lacks the part of the sequence for transcytosis, resulting in accumulation in the epithelial cells. In comparison, constructs comprising the amino acid sequences of SEQ ID NO: 161-SEQ ID NO: 164 were shown to rapidly move across the epithelial cells following uptake and transport out of the cells into the *Lamina propria*. As depicted in FIG. 9, the Cholix derived construct with SEQ ID NO: 160 was also visualized in the apical compartment of the epithelial cells at 5 minutes. At 10 and 15 minutes, small amounts of the protein moved to the basal side of the cell, but did not appear in the *Lamina propria*.

This suggests that the N-terminal can be involved in the transport pathway but is not sufficient for complete transcytosis through the cell. The surprising findings depicted in FIG. 8A-FIG. 8C and FIG. 9 represent a potential method of specifically delivering a cargo attached to these truncations to the epithelial cells, as they are taken up into the cells but cannot transport out and so accumulate inside.

Example 7

In Vitro Apical-to-Basal Transcytosis of Non-Toxic Full-Length Cholix Constructs This example demonstrates apical-to-basolateral transcytosis of a modified, non-toxic Cholix (ntChx) across polarized intestinal epithelial cells in vitro.

In this example, the Cholix construct was rendered non-toxic through an amino acid variation of a specific glutamic acid residue (substituted with alanine) within the enzymatic pocket for ADP-ribosylation, resulting in the E581A substitution and a polypeptide with the amino acid sequence set forth in SEQ ID NO: 3 (ntChx).

transport at 37° C. of non-toxic E581A Cholix (ntChx) was measured across confluent sheets (0.6 cm$^2$ filter surface area) of primary human intestinal epithelium in vitro, with concentrations of 2.5-200 µg/mL being applied to the apical surface and the amount of ntChx in the basal compartment after 2 h being measured by ELISA (FIG. 10A). The concentration range tested demonstrated an apparent permeability for apical ntChx concentrations of 2.5-20 µg/mL that was roughly 2-fold greater than for apical concentrations above 20 µg/mL, although all concentrations demonstrated significant efficiencies for transport of this ~70 kDa protein. The break in permeability rates may be consistent with a receptor-mediated transport mechanism that saturated at ~20 µg/mL for the 0.6 cm$^2$ filter surface area systems of primary human intestinal epithelium used for this in vitro study. Importantly, transported ntChx did not appear to be significantly modified (e.g., chemically modified) in its apparent size when assessed by Western blot analysis (FIG. 10B).

A time-course assessing transcytosis of ntChx at concentrations of 5, 10, and 20 µg/mL demonstrated that ntChx transcytosis began to reach a linearity after an approximately 20-25 min lag phase (FIG. 10C). Using these transport values, the permeability for ntChx at 37° C. across primary human intestinal epithelium in vitro was calculated to be ~1.92×10$^{-5}$ cm/sec. This permeability rate was reduced when the same in vitro transport protocol was performed at 4° C. (FIG. 10C). It can be assumed that, at the quantities of ntChx applied apically, the apical concentration of ntChx begins to be depleted after-90 min in this in vitro model. Together, these data suggest that ntChx transported via an energy-requiring, highly-efficient, receptor-mediated transcytosis process. Such a process can be dependent upon the amount of ntChx capable of interacting with apical surface receptors (e.g., low density lipoprotein receptor-related protein 1 (LRP1)) involved in endocytosis that results in accessing a transcytosis pathway that remains privileged from significant catabolism.

The apical membrane surface pH of the small intestinal epithelium can be between 5 and 7 (17). transcytosis across primary human intestinal epithelium in vitro tested for 20 µg/mL and examined after 120 min was observed to be approximately twice as efficient when the apical media was pH 7 compared to pH 5, while the basal pH of 7 or 5 did not seem to have an effect (FIG. 11).

Without being bound to any theory, it was assumed that the greater variability observed for outcomes where the apical pH of 5 was tested on ntChx transport can have been due to efforts by the epithelium to neutralize this apical compartment during the course of the study that can be occurring just at the apical plasma membrane in close proximity to the site of receptor-endocytosis of ntChx. In sum, these data suggest that ntChx as disclosed herein can be capable of efficient, consistent, and continuous transport across human intestinal epithelium through a receptor-mediated process that can not result in significant size modification to the transported protein.

Example 8

Analysis of the Transcytosis Pathway of Full-Length Non-Toxic Cholix Constructs

This example demonstrates apical-to-basolateral transcytosis of ntChx (SEQ ID NO: 3) across polarized intestinal epithelial cells in vivo, examining the ability of ntChx to transport across an intestinal epithelium in vivo by direct intra-luminal injection (ILI) into rat jejunum.

Immunofluorescent microscopic images showed that ntChx, identified using an anti-Cholix polyclonal antisera, entered into epithelial cells rapidly and trafficked through these epithelial cells in vesicular-like structures that involved clatherin co-localizations, with the transcytosis process being completed within minutes (FIG. 12A-FIG. 12C). Time-dependent changes in the location of vesicle-like structures positive for ntChx demonstrated its distribution within compartments localized above and below the enterocyte nucleus as well as within a selected population of cells within the *Lamina propria*. Transcytosis of ntChx appeared to also occur through goblet cells. Transport of ntChx between adjacent epithelial cells, the so-called paracellular route, was not observed in this experiment.

ILI of ntChx into rat jejunum appeared to restrict the exposure to the upper segments and tip of the intestinal villi.

Example 9

Transcytosis of Non-Toxic Cholix Constructs Involves Specific Vesicular Compartments This example demonstrates apical-to-basolateral transcytosis of ntChx (SEQ ID NO: 3) that involves accessing specific vesicular compartments (e.g., FIG. 13A-FIG. 13F).

Transcytosis of ntChx can involve receptor-mediated endocytosis processes and subsequent vesicular trafficking that avoids the typical fate for ligands internalized by this route of lysosomal degradation. A number of obligate and facilitative intracellular pathogens are capable of subverting host cells endocytic and secretory pathways that restrict their exposure to the lysosomal through effector proteins capable or manipulating host cells processes. This example examined ntChx-containing vesicles undergoing transcytosis to determine the identity of associated proteins that can define the trafficking elements and cellular compartments that can be involved in transcytosis of Chx and Chx variants as disclosed herein.

Upon uptake at the apical plasma membrane, ntChx-positive vesicles were observed to co-localize with Ras-related protein Rab 5 and early endosomal antigen 1 (EEA1) (FIG. 13A), demonstrating hallmarks of the early endosome/sorting endosome (EE/SE), suggesting that this exotoxin can enter intestinal epithelial cells through a receptor-mediated endocytosis. Populations of EEA1-positive vesicles were also observed in the basal compartment of enterocytes, but these were less heavily associated with the presence of ntChx (FIG. 13A). Ras-related protein Rab 11a, known to be associated with recycling endosomes, were observed in both apical and basal compartments of enterocytes but Rab 11a co-localization with ntChx-containing vesicles was observed predominantly in the basal compartment (FIG. 13B). Furthermore, the trans-Golgi network (TGN) can be considered to function as a secretory pathway sorting station, directing newly synthesized proteins to different cellular compartments, with TGN-38 being identified as indicative. Remarkably, ntChx was not observed to co-localize with TGN-38 in enterocytes in this experiment, but did co-localize after transcytosis in non-polarized cells with the *Lamina propria* (FIG. 13C). Calnexin is a lectin chaperone located in the endoplasmic reticulum (ER) that can be involved in regulating the free cytosolic Ca' concentration. During transcytosis, it was found that ntChx can co-localize with calnexin primarily in the apical compartment of enterocytes but with distributions that included the basal compartment (FIG. 13D). Furthermore, Ras-related protein Rab 7, a marker late endosomes and vesicles being trafficked to lysosomes, was observed to co-localized in both the apical and basal portions of enterocytes with ntChx (FIG. 13E). LAMP1 (lysosome-associated membrane protein 1), distributed in both late endosomes and lysosomes was observed to similarly co-localize with ntChx in both the apical and basal portions of enterocytes, but did not appear to co-localize with larger vesicular structures that were consistent in size and number with lysosomal structures (FIG. 13F).

Apical application of ntChx-NPs resulted in a transcytosis process consistent with that observed for ntChx alone and without co-localization with LAMP1-positive structures (FIG. 13F). Once across the intestinal epithelial cell layer, ntChx-NPs was observed in LAMP1-positive structures within cells present within the *Lamina propria* (FIG. 13C).

Example 10

Comparison of Transcytosis Function of Non-Toxic Full-Length Cholix Exotoxin Vs. Cholix Domain I Only This example demonstrates the in vivo transport of Cholix domain I (e.g., SEQ ID NO: 4 or SEQ ID NO: 4) truncated carrier proteins as described in EXAMPLE 6 compared to non-toxic full-length Cholix as described in EXAMPLE 7.

Transcytosis of ntChx (SEQ ID NO: 3) in vitro was monitored by Western blot and immunofluorescence microscopy using a polyclonal antibody raised against the full-length protein. To test whether this polyclonal antibody can provide equivalent coverage across all regions of ntChx for the purpose of detecting truncated forms of the exotoxin, the capacity for a truncated form of Cholix to ferry a protein cargo that could be used to assess transcytosis equivalence was investigated.

Genetic chimeras of full-length protein (ntChx) and a version of the protein composed of only domain I were prepared, comprising the amino acid sequence set forth in SEQ NO: 5, and its C-terminus was used to conjugate red fluorescent protein (RFP, SEQ ID NO: 220) via its N-terminus, resulting in the construct having the amino acid sequence set forth in SEQ ID NO: 157). RFP alone, having a molecular weight of 25.9 kDa (225 amino acid residues) was used as a transcytosis control.

The data show that the extent of transcytosis of RFP alone was minimal compared that of ntChx-RFP and Cholix domain I (M+Cholix$^{1-265}$ or residues 1-266 of SEQ ID NO: 5)—RFP (SEQ ID NO: 156) when examined 30 min after ILI in to rat jejunum in vivo (FIG. 14A). Epithelial transcytosis patterns were similar and the extent of RFP detectable in the *Lamina propria* was also comparable for both ntChx-RFP (FIG. 14B) and Cholix domain I-RFP (FIG. 14C) (arrows in these figures illustrate the apical side of the epithelium). These results suggest that elements of Cholix involved in transcytosis reside within domain I and that this domain can be sufficient to ferry a protein cargo replacing domains II and III of Cholix across the intestinal epithelium.

Example 11

In Vitro Transcytosis and Intracellular Delivery Function of Truncated Cholix Domain I Carrier Proteins This example demonstrates the in vitro apical-basolateral transcytosis and intracellular delivery functions of various truncated Cholix domain I carrier proteins conjugated to human growth hormone via a spacer as described above in EXAMPLE 6.

To further explore the function of elements within Cholix domain I involved in transcytosis, a series of chimeras that contained a pharmaceutically-relevant protein, human growth hormone (HGH, SEQ ID NO: 214), were prepared as genetic constructs. Each truncated sequence of the Cholix domain I (SEQ ID NO: 5, bacterially expressed) was conjugated via the C-terminus to the N-terminus of HGH through a $G_4SG_4SG_4S$ spacer sequence (SEQ ID NO: 210), resulting in the chimeras having the amino acid sequences set forth in SEQ ID NO: 158, SEQ ID NO: 159, SEQ ID NO: 160, SEQ ID NO: 161, SEQ ID NO: 162, SEQ ID NO: 163, and SEQ ID NO: 164. In the case of the K187 truncation of Cholix domain I with SEQ ID NO: 5, the first 39 amino acids were also deleted to produce the E40-K187 fragment of Cholix domain I (SEQ ID NO: 5) to yield the construct with the amino acid sequence set forth in SEQ ID NO: 165 (TABLE 14).

TABLE 14

Truncated Cholix Domain I Delivery Constructs for HGH

| SEQ ID NO | Notation (relative to SEQ ID NO: 4) | Mol. Ma | Ca |
|---|---|---|---|
| SEQ ID NO: 158 | M + Cholix$^{1-133}$-HGH | 38.0 | 4.70 |
| SEQ ID NO: 159 | M + Cholix$^{1-150}$-HGH | 40.0 | 4.69 |
| SEQ ID NO: 160 | M + Cholix$^{1-186}$-HGH | 44.2 | 4.76 |
| SEQ ID NO: 161 | M + Cholix$^{1-205}$-HGH | 46.4 | 5.04 |
| SEQ ID NO: 162 | M + Cholix$^{1-244}$-HGH | 50.7 | 4.96 |
| SEQ ID NO. 163 | M + Cholix$^{1-250}$-HGH | 51.4 | 5.01 |
| SEQ ID NO. 164 | M + Cholix$^{1-265}$-HGH | 53.1 | 5.12 |
| SEQ ID NO: 165 | Chx$^{39-186}$-HGH | 40.0 | 4.91 |

Experiments investigating the transport capabilities of these chimeras across human intestinal epithelial monolayers in vitro demonstrated that the delivery constructs with the amino acid sequences set forth in SEQ ID NO: 158, SEQ ID NO: 159, SEQ ID NO: 160, and SEQ ID NO: 165 did not transport, unlike SEQ ID NO: 161, as shown in FIG. 15A. Despite its much lower molecular weight, HGH alone transported to a lesser extent when compared to SEQ ID NO: 164 (FIG. 15A, right part showing presence in basal compartment). Transcytosis of SEQ ID NO: 161 and SEQ ID NO: 162 were comparable to that of SEQ ID NO: 164 at the 2 h time point of assessment in this in vitro model of human small intestine (FIG. 15B). Surprisingly, the delivery construct with the amino acid set forth in SEQ ID NO: 161 was superior in its transport capacity compared to SEQ ID NO: 164 as demonstrated by the higher relative signal of SEQ ID NO: 161 compared to SEQ ID NO: 164.

These results suggest that domain I of Cholix is sufficient for apical-to-basal transport, and that it can function as a transcytosis element to deliver various heterologous cargos across epithelial cells, wherein the heterologous cargo may replace the domains II, Ib, and III of the Cholix exotoxin. Additionally, it has been demonstrated that elements within the first 206 amino acid residues of the bacterially expressed Cholix protein (e.g., SEQ ID NO: 5, or, alternatively the first 205 amino acid residues of SEQ ID NO: 4) can be sufficient for the transcytosis function and thus may be used as an efficient carrier for various heterologous cargos. Remarkably, the results suggest that the transcytosis efficiency of these first 206 amino acids of SEQ ID NO: 5 may even be greater than that of the entire domain I (e.g., SEQ ID NO: 5) or the full-length mature Cholix exotoxin (e.g., SEQ ID NO: 1 or SEQ ID NO: 2). Thus, the herein disclosed truncated Cholix domain I constructs can be used to efficiently shuttle heterologous cargo molecules such as therapeutic and/or diagnostic agents across an epithelial cell layer (e.g., the gut epithelium) enabling oral administration of therapeutic and/or diagnostic agents (e.g., larger polypeptides or proteins such as antibodies) that are otherwise administered via parenteral administration routes (e.g., intravenously of subcutaneously). In addition, these results show that truncated versions of Cholix domain I may be used to deliver various heterologous cargo into epithelial cells using the delivery constructs as described herein.

Example 12

In Vivo Transcytosis and Intracellular Delivery Function of Truncated Cholix Domain I Carrier Proteins This example demonstrates the in vivo transport of a Cholix domain I (e.g., SEQ ID NO: 4 or SEQ ID NO: 5) truncated protein chimeras across gut epithelial cells for delivery of heterologous cargo (in this example: human growth hormone).

Selected truncation chimeras as shown above in TABLE 14 of EXAMPLE 11 were examined for their capacity for transcytosis in vivo following ILI into rat jejunum. The notation indicating the length and residue at which the truncated occurred of the truncated Cholix domain I carriers are relative to SEQ ID NO: 5.

The data obtained in these studies show that while M+Cholix$^{1-133}$-(SEQ ID NO: 10)-HGH (SEQ ID NO: 158) did not enter into rat epithelium by 15 min (FIG. 16A), M+Cholix$^{1-150}$-(SEQ ID NO: 10)-HGH (SEQ ID NO: 159) underwent endocytosis, but did not complete transcytosis as evidenced by a lack of this chimera in the *Lamina propria* (FIG. 16B). The construct with SEQ ID NO: 159 was retained in a vesicular pool restricted to compartments near the apical and basal plasma membranes of enterocytes (FIG. 16B). The truncation mutant M+Cholix$^{1-186}$-(SEQ ID NO: 10)-HGH (SEQ ID NO: 160) resulted in similar outcomes as observed for the construct with SEQ ID NO: 159 with one difference that the construct with SEQ ID NO: 160 appeared to access a supra-nuclear vesicular compartment that was not accessed by the construct with SEQ ID NO: 159 (FIG. 16C). Furthermore, removal of the first 39 amino acids of the Cholix domain I with SEQ ID NO: 5 (resulting in the construct M+Cholix$^{39-186}$-(SEQ ID NO: 210)-HGH, SEQ ID NO: 165) resulted in a protein that could undergo endocytosis, but did not migrate from the apical vesicular compartment to the basal vesicular compartment of the enterocyte by 15 min after ILI (FIG. 16D).

These results suggest that elements of Cholix domain I (SEQ ID NO: 5) between E134 and D151 are essential to apical endocytosis, that elements within the first 39 amino acids of Cholix domain I may be critical for trafficking from the apical vesicular pool to the basal vesicular pool, and that elements between K187 and K206 may be critical for Cholix secretion from the basolateral surface of enterocytes. Thus, these results demonstrate that Cholix domain I and truncated version thereof, e.g., those comprising the first 206 amino acid residues of Cholix domain I (SEQ ID NO: 5), can efficiently deliver various cargo across epithelial cells (e.g., across polarized gut epithelial cells of a subject). Moreover, these results show that truncated versions of Cholix domain I may be used to deliver various heterologous cargo into epithelial cells using the delivery constructs as described herein.

Example 13

Evaluation of Functional Peptide Fragments of Cholix Domain I

This example demonstrates recapitulation of Cholix domain I (SEQ ID NO: 5) transcytosis using functional elements, e.g., functional peptide fragments, of Cholix domain I to generate a synthetic polypeptide that is capable of delivery into epithelial cells and/or across an epithelial cell layer (e.g., an epithelial cell monolayer and/or a gut epithelium of a subject) in vitro (FIG. 17A) and in vivo (FIG. 17B). In addition, FIG. 18, for example, depicts some functional amino acid sequences within Cholix Domain I as colored sequence fragments. Moreover, FIG. 20 illustrates general 3D structures of Cholix domain I with the highlighted functional fragments SEQ ID NO: 148 (FIG. 20A), SEQ ID NO: 151 (FIG. 20B), and SEQ ID NO: 152 (FIG. 20C). All amino acid residues and their positions are shown relative to the bacterially expressed Cholix domain I sequence set forth in SEQ ID NO: 5.

To that end, transcytosis experiments using specific peptides derived from portions of Cholix domain I (SEQ ID NO: 5) that were identified as critical for apical endocytosis were used to model the various steps and aspects such as intracellular trafficking, and basal membrane secretion of transcytosis of full-length ntChx, exemplary peptide fragments of Cholix domain are shown below in TABLE 15 (including the molecular mass and isoelectric point (pI)).

TABLE 15

Identified Exemplary Functional Peptide Domains Within the Amino Acid Sequence of Cholix Domain I (SEQ ID NO: 5)

| SEQ ID NO | Peptide sequence | Designation | Mol. Mass (Da) | pI |
|---|---|---|---|---|
| SEQ ID NO: 148 | $_{134}$ELDQQRNII EVPKLYSID$_{151}$ | Endocytosis (E) | 2173.5 | 4.32 |

TABLE 15-continued

Identified Exemplary Functional Peptide Domains Within the Amino Acid Sequence of Cholix Domain I (SEQ ID NO: 5)

| SEQ ID NO | Peptide sequence | Designation | Mol. Mass (Da) | pI |
|---|---|---|---|---|
| SEQ ID NO: 149 | $_{1}$MVEEALNIFD ECRSPCSLTPE PGKPIQSKLSI PSDVVLD$_{39}$ | Apical-Basal (T) | 4258.9 | 4.20 |
| SEQ ID NO: 151 | $_{151}$DLDNQTLEQ WKTQGNVSFSV TRPEHNIAISW PSVSYK$_{187}$ | Supranuclear (N) | 4276.7 | 5.48 |
| SEQ ID NO: 152 | $_{187}$KAAQKEGSR HKRWAHWHTG LAL$_{206}$ | Basal release (R) | 2568.9 | 11.1 |

For example, the peptide $_{134}$ELDQQRNIIEVPKLY-SID$_{151}$ (SEQ ID NO: 148) was the element that differed between M+Cholix$^{1-150}$-HGH (amino acid sequence set forth in SEQ ID NO: 159) and M+Cholix$^{1-133}$-HGH (amino acid sequence set forth in SEQ ID NO: 158), one chimera that could undergo endocytosis and one that could not. Another peptide of interest is within the first 39 amino acids ($_{1}$MVEEALNIFDECRSPCSLTPEPGKPIQSKL-SIPSDVVLD$_{39}$, SEQ ID NO: 149), which was lacking in the M+Cholix$^{39-186}$ construct (SEQ ID NO: 165) that lacked the ability to traffic from the apical portion of the epithelial cell to the basal domain following endocytosis. The peptide that provided the difference between M+Cholix$^{1-150}$-(SEQ ID NO: 210)-HGH and M+Cholix$^{1-186}$-(SEQ ID NO: 210)-HGH was $_{151}$DLDNQTLEQWKTQGNVSFSVTRPEH-NIAISWPSVSYK$_{187}$ (SEQ ID NO: 151); M+Cholix$^{1-150}$-(SEQ ID NO: 210)-HGH showed the ability to access a supra-nuclear area of the cell that was not accessed by M+Cholix$^{1-150}$-(SEQ ID NO: 210)-HGH. Finally, M+Cholix$^{1-265}$-(SEQ ID NO: 210)-HGH was secreted from the basal surface of intestinal epithelial cells while M+Cholix$^{1-186}$-(SEQ ID NO: 210)-HGH was not; $_{187}$KAAQKEG-SRHKRWAHWHTGLAL$_{206}$ (SEQ ID NO: 152) is the peptide that describes the difference in the sequences of these two chimeras (see e.g., FIG. 17A).

A polymer framework containing peptide sequences of amino acids from positions 1-39, 134-151, 151-178, and 178-206 of Cholix domain I with SEQ ID NO: 5 in various combinations was labeled with different of quantum dot forms.

The in vitro data show that some selected peptide sequences of Cholix domain I peptide elements are sufficient to achieve apical to basal transcytosis in vitro and in vivo (FIG. 17). For example, transcytosis across polarized intestinal epithelium was measure in vitro after 2 h as shown in FIG. 17A. The amount of transported material is reported as the florescence-fold increase relative to polymer-quantum dot preparation lacking any Chx peptides. (N=2; mean±S.E) (FIG. 17A). Subsequently, in vivo transcytosis at 15 min of polymer-quantum dot preparations labeled with quantum dots was conducted (FIG. 17B and FIG. 17C).

The data shows that various Cholix sequence variants as disclosed herein retain efficient endocytosis following uptake from the lumen but lack ability to complete transcytosis, being useful to target apical or apical and basal vesicular structures. From the data presented, it appears that Cholix utilizes a receptor-mediated-type endocytosis process that involves amino acids 134-151, which provides access to an early endosomal vesicular compartment in the apical portion of enterocytes (e.g., gut epithelial cells). Amino acids 151-187 of the Cholix exotoxin domain I (e.g., SEQ ID NO: 5) as described herein appear to allow its movement to a supra-nuclear compartment consistent with a sorting site in the cell for secretory events, and thus allow delivery of various cargos to those locations as well. Movement to the basal compartment of the cells becomes more efficient with the presence of amino acids 1-40. Finally, amino acids 187-206 provide a mechanism for secretion from the basal membrane that releases the entire and intact protein into the Lamina propria where it could provide therapeutically effective concentrations of therapeutic cargo molecules (e.g., interleukins), present antigens to immune cells, and/or allow the cargo to be taken up into systemic circulation for delivery to other target organs/tissues in a subject.

Example 14

Co-Localization of Cholix Domain I Delivery Constructs with Various Marker Proteins Demonstrates Trafficking Using Distinct Compartments This example demonstrates that Cholix domain I derived delivery constructs utilize distinct compartments for trafficking into and across (e.g., via transcytosis) epithelial cells using various marker proteins (see e.g., EXAMPLE 3) that indicate Cholix derived carrier constructs utilize specific and endogenous trafficking pathways. The study described in this example was conducted using the Cholix derived delivery construct having the amino acid sequence set forth in SEQ ID NO: 154 (comprising the M+Cholix$^{386}$ carrier coupled to IL-10 via the spacer with the sequence set forth in SEQ ID NO: 210, M=N-term. methionine).

EEA1 antigen. FIG. 21A shows that the Cholix-IL-10 delivery constructs (SEQ ID NO: 154) strongly co-localized with the EEA1 antigen in cellular locations consistent with trafficking at both the apical and basal domains of enterocytes, suggesting the presence of the Cholix derived delivery constructs in early endosome compartments.

Rab7. Moreover, it was shown that the Cholix-IL-10 delivery constructs (SEQ ID NO: 154, top right) strongly co-localizes with the Rab7 (top left) predominantly in the apical compartment of enterocytes, but with only limited co-localization in cells within the Lamina propria, suggesting the presence of the Cholix derived delivery constructs in late endosome compartments (FIG. 21B, bottom left shows white light image, and bottom right shows merged staining with DAPI).

LAMP1. LAMP1 was identified in large, specific vesicles consistent mature lysosomes that were devoid of Cholix-IL-10 delivery constructs (SEQ ID NO: 154, whitearrows). Cholix-IL-10 chimera, however, also co-localizes with the LAMP1 antigen in cellular locations other than lysosome-like structures, consistent with vesicle trafficking at both the apical and basal domains of enterocytes, suggesting the presence of the Cholix derived delivery constructs in lysosomal compartments (FIG. 21C).

Clathrin. Next, Cholix-IL-10 chimera (SEQ ID NO: 154) also strongly co-localized with clathrin-coated vesicles, particularly in areas adjacent to the nucleus and with Rab 1 predominantly in the basal compartment of enterocytes as well as in selected cells within the Lamina propria (FIG. 21D).

Calnexin. Cholix-IL-10 chimera (SEQ ID NO: 154) co-localized with the endoplasmic reticulum as demonstrated by calnexin in a pattern adjacent to the nucleus in enterocytes and in a large fraction of cells with in the Lamina propria (FIG. 21E).

Endoplasmatic reticulum Golgi intermediate compartment. Cholix-IL-10 chimera (SEQ ID NO: 154) strongly co-localizes with the endoplasmatic reticulum Golgi intermediate compartment (ERGIC) and the LAMN1 antigen appeared to re-distribute in response to carrier endocytosis and transcytosis, as shown for 1 (FIG. 21F), 5 (FIG. 21G), 10 (FIG. 21H), and 15 minutes after injection (FIG. 21I). Transcytosis of the delivery construct was demonstrated to consistently traffic in large quantities across enterocytes. Specific compartments that strongly co-localized with this transcytosis included early endosomes and late endosomes. The Cholix derived carrier appeared to be associated with clathrin-coated vesicles in the vicinity of the ER-Golgi network organized adjacent to enterocyte nuclei. Co-localization of the Cholix derived carrier was observed with the ER and ERGIC, also described as LMAN1 (lectin, mannose binding 1), but limited in its association with elements of the cis-Golgi, Golgi, and trans-Golgi network. The Cholix derived carrier co-localized with recycling endosomes near the basal surface of enterocytes in a manner that might coordinate with ERGIC re-distribution. ERGIC-53 can also function as an intracellular cargo receptor involved in the anterograde transport of a limited number of glycoprotein ligands in the early exocytic pathway and is used by a number of RNA viruses as part of their exocytosis strategy. ELISA-based binding studies demonstrated that Cholix and Cholix-derived delivery constructs can associate with ERGIC-53 at pH 7.4, but this interaction is significantly stronger at pH 5.5. SPR studies further supported this pH-dependent interaction (FIG. 31).

Giantin. Cholix-IL-10 chimera (SEQ ID NO: 154) did not co-localize with the low levels of giantin present in enterocytes (FIG. 21J). Some giantin co-localized with the chimera in a subset of cells present in the Lamina propria, suggesting that the Cholix derived carrier does not locate with the Golgi compartment.

58K antigen. The 58K antigen localized in enterocytes at a site apical to the nucleus and the Cholix-IL10 chimera shows some co-localization with this antigen in a manner that suggests a brief movement through this compartment. No 58K antigen was observed in cells within the Lamina propria (FIG. 21K).

TGN38 antigen. Cholix-IL-10 chimera (SEQ ID NO: 154) showed some level of co-localization with the TGN38 antigen (top right), which showed a cellular distribution that was restricted to the apical side of nuclei in enterocytes and adjacent to the nucleus in a few cells within the Lamina propria (FIG. 21L, white light and merge images shown bottom left and bottom right, respectively).

Rab 1. Cholix-IL-10 chimera (SEQ ID NO: 154, top right) strongly co-localized with Rab 1 (top left) predominantly in the basal compartment of enterocytes and in selected cells within the Lamina propria (FIG. 21M, white light and merge images shown bottom left and bottom right, respectively).

This data demonstrates that the Cholix derived delivery constructs of the present disclosure interact with various endogenous proteins and receptors to harness an endogenous transport system for efficient delivery of cargo across and/or into epithelial cells (e.g., polarized gut epithelial cells).

Example 15

General Protocol for Assessing Cholix Exotoxin Interacting Receptors

Based on the results shown above in EXAMPLE 14, this example demonstrates a protocol for the assessment of Cholix interacting receptors and various additional information regarding those interactions. Various Cholix derived delivery constructs including those having an amino sequence set forth in SEQ ID NO: 154 (M+Cholix$^{386}$-GGGGSGGGGSGGGGS (SEQ ID NO: 210)-IL-10) and a construct comprising the Cholix domain I set forth in SEQ ID NO: 5 coupled to IL-10 (SEQ ID NO: 217) or HGH (SEQ ID NO: 153) via the GGGGSGGGGSGGGGS spacer (SEQ ID NO: 210) were used in this study, e.g., SEQ ID NO: 164. First, a limited set of candidate proteins as carrier protein receptors have been identified through bead capture and mass spectrometry analysis studies. Then, the interactions of the Cholix carrier with these candidate proteins were assessed in vitro (e.g., using Caco-2 cell monolayers) and in vivo (e.g., in the rat jejunum).

Generally, nano-sized magnetic beads (25 nm or 100 nm diameter) were decorated with the non-toxic carrier elements of the Cholix protein using either a biotin-based or poly-histidine-based method of interaction (e.g., using 1D SDS-PAGE, described in e.g., FIG. 22). These decorated beads were allowed to transport across polarized monolayers in vitro of the human colon cancer cell lines Caco2 for set periods of time before gentle cell disruption and capture of vesicles containing these magnetic beads.

After multiple washings, these magnetic bead-enriched vesicles were solubilized in lysis buffer and the protein components present were separated by 2-D SDS-PAGE (FIG. 23). The pattern of these proteins was compared to the total protein content of these cells and mass spectrometry was used to identify specific elements associated with vesicular structures accessed by the Cholix derived delivery construct (FIG. 24).

Comparison of outcomes from repeats of this protocol were used to identify a limited set of most promising candidates that were then examined for their content in Caco-2 cells and in rat small intestine (FIG. 25). Subsequently, interaction of Cholix with the identified candidate proteins was confirmed using Cholix carrier-coated magnetic beads and purified candidate protein. Incubation of the Cholix carrier-coated beads with the pure proteins and subsequent Western Blots or ELISA enabled detection of Cholix-protein interaction as exemplary shown in FIG. 26. This figure shows interaction of Cholix carrier with heparan sulfate proteoglycan (HSPG), Dickkopf-related protein 1 (DKK1), the chaperone glucose-regulated protein 75 (GRP75), and cytokeratin-8 (K8 or CK8).

Microscopic co-localization of candidate proteins and Cholix derived delivery construct was evaluated in rat jejunum in vivo. Here, co-localization of a delivery construct comprising a Cholix carrier protein coupled to IL-10 (SEQ ID NO: 154, M+Cholix$^{386}$-GGGGSGGGGSGGGGS (SEQ ID NO: 210)-IL-10) with CK8 was shown in vivo, after rat jejunum was treated with a luminal application of the construct having the amino acid sequence set forth in SEQ ID NO: 154 for 1 minute (FIG. 27A), 5 minutes (FIG. 27B), and 10 minutes (FIG. 27C). Co-localization in a supra-nuclear region increased over time. Although transcytosis of the delivery construct was observed in most epithelial cells, it interacted with only a discrete population of cells within the Lamina propria.

To ensure that the receptor distribution was consistent between rat in vivo studies and human intestine, information was compared to IHC studies described in the human atlas. Here, two of the receptors identified by mass spectrometry and verified in rat jejunum were examined. FIG. 28A and FIG. 28B show that the intestinal localization of GRP75 and HSPC is consistent between rat and human intestine.

Knock-down in Caco-2 cells using sh-RNA technology were used to establish stable cell lines that were used to validate the involvement of these target proteins in the apical-to-basal transcytosis of the Cholix carrier protein. These studies were then repeated using rat jejunum in vivo to compare to the Caco-2 cell in vitro findings.

Here, transport of Cholix domain I derived delivery construct in CRISPR knockout HSPC stable Caco-2 cells was evaluated. FIG. 29 shows effects of HSPG knockout by CRISPR on transport function of the delivery construct (SEQ ID NO: 164) comprising Cholix domain I coupled to HGH and HGH alone as internal control of non-selective transport. Cells were seeded at $1.5 \times 10^5$ cells/mL in transwells. On day 18, transepithelial/transendothelial electrical resistance (TEER) was measured and PBS containing 20 ug/mL of the carrier with SEQ ID NO: 164 was added to the apical chambers. After 3 h, basolateral samples were collected and concentrated. The extent of protein transport was analyzed by Western blotting using anti-HGH antibody. The results shown in FIG. 29 demonstrate that transcytosis and active, selective transport of Cholix derived carrier proteins is HSPG-dependent, as the Cholix carrier showed significantly less transcytosis function in HSPC-knock-down cells compared to normal, HSPG-positive Caco-2 cells.

Similar studies were conducted for the additional candidate proteins K8 (FIG. 30A), HSPC (FIG. 30B), and GRP75 (FIG. 30C, control run shown in FIG. 30D). Stable cell lines of Caco-2 cells lacking the expression of specific candidate proteins were used as monolayers in vitro to verify their requirement for carrier transcytosis using active and selective endogenous transport mechanisms. The specific transport of delivery construct SEQ ID NO: 164 vs non-selective transport of HGH alone was reduced in HSPG and GRP75 knockouts, but not the K8 knockout. This suggests that HSPG and GRP75 are required to active transport and transcytosis of Cholix derived carrier proteins, and that K8 may not be required for active transport across an epithelial cell.

Rat jejunum ILI studies demonstrated that GRP75 was distributed in enterocytes in distinct apical and basal vesicular populations; SEQ ID NO: 164 co-localized with GRP75 in vesicles within the apical third of enterocytes not immediately adjacent to the apical plasma membrane (FIG. 3D). The construct having the sequence set forth in SEQ ID NO: 164 was observed in this apical GPR75-positive compartment occurred within 5 min of luminal application and was consistent with an early endosomal compartment. At later times, a portion of GPR75-positive vesicles observed near the basal membrane were observed that contained the constructs with SEQ ID NO: TMEM132A is highly similar to the rat GRP78 binding protein. Without being bound by any theory, it was assumed that the similarities between GRP78 and GRP75 may provide a rational for TMEM132A interactions with GRP75 and the potential for their co-localization at the time of Cholix endocytosis.

This data demonstrates that, indeed, Cholix derived carrier and cargo transport and delivery is an active and selective process involving distinct receptors. This may be useful for the targeted delivery and therapeutic and/or diagnostic molecules across and/or to the interior of epithelial cells (e.g., gut epithelial cells) for the treatment and diagnosis of diseases as described herein.

Example 16

Assessment of pH-Dependence of Cholix Carrier-GRP75 Interaction

This example demonstrates the assessment of the pH-dependence of a Cholix derived carrier protein (e.g., SEQ ID NO: 4) and one of its interacting receptors during active transcytosis, GRP75.

For this study, Biacore binding interactions were used to examine the pH-dependency of Cholix carrier-GRP75 interactions. Cholix carrier proteins were attached to magnetic beads using the biotin-streptavidin bioconjugation and incubated with purified GRP75 protein in buffer solutions with pH 5.5, 6.5, and 7.5, respectively (FIG. 31).

Binding affinities at those three pH levels were generally in the low nanomolar range, however, a significantly higher (approximately 20-fold higher) binding affinity of the Cholix carrier to GRP75 was measured at pH 6.5, indicating pH dependency of this interaction.

Example 17

Assessment of Type and Location of Cholix Domain I Interaction Partners

In this example, the type of proteins and their compartmental locations in epithelial cells was examined using a Cholix domain I derived delivery construct (SEQ ID NO: 5) that was shown to possess equal, if not higher, transcytosis function than full-length Cholix exotoxin (SEQ ID NO: 1). All amino acid residues and their positions are shown relative to the bacterially expressed Cholix domain I sequence set forth in SEQ ID NO: 5.

Interaction partners for Cholix domain I ending at K266 of SEQ ID NO: 5, bacterially expressed Cholix carrier comprise an N-terminal methionine) were captured using a magnetic bead and isolation procedure followed separated by 2-D gel electrophoresis separation and identified using mass spectrometry as described above in EXAMPLE 15. Importantly, in this example a number of truncated forms of the full-length Cholix exotoxin were also prepared to examine various aspects of these interactions: truncations at amino acid E134, D151, K187, L206, K245, or Q251, or L206 conjoined to the N-terminus of human growth hormone (HGH) through a $G_4SG_4SG_4S$ sequence with this glycine-serine spacer being identified previously for constructing genetic chimeras. In the case of the K187 truncation, we also deleted the first 39 amino acids to produce the E40-K187 fragment of Chx domain I with SEQ ID NO: 5. As described above, e.g., in EXAMPLE 10, the construct with SEQ ID NO: 158 failed to achieve apical entry into intestinal epithelial cells, the construct with SEQ ID NO: 159 and SEQ ID NO: 160 underwent endocytosis to reach both apical and basal vesicular pools within enterocytes but did not to access the *Lamina propria*, and the construct with SEQ ID NO: 165 underwent endocytosis but failed to migrate from the apical to the basal vesicular compartment of the enterocyte, and, finally, the construct with SEQ ID NO: 164 efficiently and rapidly completes transcytosis. Thus, the first 206 amino acids of Cholix domain I were evaluated for elements that may participate in the events that resulted in apical-to-basal transcytosis.

Example 18

Evaluation of Apical Endocytosis of Cholix Domain I Derived Delivery Constructs

First, the transmembrane protein 123A (TMEM132A) was evaluated. TMEM132A is a single-pass transmembrane protein that contains cohesin and three tandem immunoglobulin domains, thus connecting the extracellular medium with the intracellular cytoskeleton. Interactions between TMEM132A and serine/threonine-protein phosphatase 1 (PP1) have been demonstrated, providing a mechanism to regulate intracellular cytoskeletal events through a RVxF interaction motif.

It was found that Cholix domain I (SEQ ID NO: 5, bacterially expressed) enriched the isolation of TMEM132A along with catalytic and regulatory subunits of the PP1 complex. ELISA-based studies showed that Cholix domain I with SEQ ID NO: 5 interacted with the extracellular domain of TMEM132A; SPR studies showed this interaction to occur at pH 7.5 and less at pH 5.5. Knock-down studies in Caco-2 cells, to generate Caco-$2^{TMEM132A-}$ cells, showed that reduction of TMEM132A dramatically reduced the transport of transcytosis of Cholix domain I with SEQ ID NO: 5.

Intraluminal injection (ILI) studies performed in rat jejunum resulted in co-localization of the Cholix domain I-HGH delivery construct (SEQ ID NO: 164) with TMEM132A that was restricted to the apical plasma membrane of enterocytes. A time course examining transcytosis of SEQ ID NO: 164 suggested that TMEM132A remained at or adjacent to the apical plasma membrane and did not redistribute significantly to other regions of these polarized epithelial cells. While the construct with SEQ ID NO: 158 did not significantly enter into enterocytes following apical application, the construct with SEQ ID NO: 159 did enter, suggesting that a domain of Chx critical for apical cell entry resided with the 17 amino acids that discriminated where two carrier constructs. Once internalized, the internal pH of an early or a recycling endosome can drop from neutrality to ~6.0. Examination of interactions between the construct having sequence set forth in SEQ ID NO: 164 and TMEM132A demonstrated that these occurred to a much greater extent at pH 7.4 compared to pH 5.5, consistent with the theory that release from an internalization receptor, in this case TMEM132A, could be facilitated by decreased vesicle pH that could occur following apical Chx uptake.

Studies examining clathrin distribution in rat enterocytes did not show co-localizations with the construct having sequence set forth in SEQ ID NO: 164 at the apical surface, suggesting that Chx entry may not involve clathrin-mediated uptake. Strikingly, the cellular distribution of TMEM132A following the construct having sequence set forth in SEQ ID NO: 164 application remained at the apical surface, but was found more frequently in apical vesicles following apportion of the construct with SEQ ID NO: 159, suggesting that the lack of other elements within Cholix domain I (SEQ ID NO: 5) were necessary for the handoff to a receptor (or receptors) required for the next step in its trafficking. These results suggest that Chx can engage TMEM132A at the luminal surface and that these interactions are involved in the initial endocytosis process from the intestinal lumen and that subsequent interactions within early endosomes are required for the transcytosis process to continue.

Cytokeratin 8 (CK-8) was one of several proteins in this family identified in the initial screen as a potential Chx interaction partner; CK-8 was previously identified as a cell-surface receptor for the Pet toxin secreted from enteroaggregative *E. coli*. ELISA-based binding studies showed CK-8 to interact with TMEM132A and also Chx. CK-8 distribution in rat enterocytes was restricted to the apical surface and at discrete domains in the apical and basal compartments. A time course examining transcytosis of the construct having sequence set forth in SEQ ID NO: 164 suggested that CK-8 cellular distribution did not change dramatically following apical M+Cholix$^{1-265}$-HGH (SEQ ID NO: 164) application and that some co-localizations were observed in the apical compartment of enterocytes. Knockdown of CK-8 was performed in Caco-2 cells (Caco-2$^{CK8-}$) and evaluated with its impact on transcytosis of the construct having sequence set forth in SEQ ID NO: 164. CK-8 knockdown, as further shown above in EXAMPLE 15, did not affect the transport of the construct having sequence set forth in SEQ ID NO: 164, demonstrating the ability for this in vitro model to determine selective function for interaction partners in the transcytosis process of Chx. These studies point out that proteins identified in Chx pull-downs that co-localize with cellular compartments visited by the construct having sequence set forth in SEQ ID NO: 164 may not be essential for transcytosis.

Example 19

Early Endosomal Sorting of Cholix Domain I Derived Delivery Constructs

This example demonstrates that distinct proteins such as GRP75 are involved in early endosomal sorting of Cholix and Cholix derived delivery constructs (e.g., those having an amino acid sequence set forth in SEQ ID NO: 158-SEQ ID NO: 165).

Transcytosis of the delivery construct was demonstrated to consistently traffic in large quantities across enterocytes. Specific compartments that strongly co-localized with this transcytosis included early endosomes and late endosomes. The Cholix derived carrier appeared to be associated with clathrin-coated vesicles in the vicinity of the ER-Golgi network organized adjacent to enterocyte nuclei. Co-localization of the Cholix derived carrier was observed with the ER and ERGIC, also described as LMAN1 (lectin, mannose binding 1), but limited in its association with elements of the cis-Golgi, Golgi, and trans-Golgi network. The Cholix derived carrier having SEQ ID NO: 164 co-localized with recycling endosomes near the basal surface of enterocytes in a manner that might coordinate with ERGIC re-distribution. ERGIC-53 can also function as an intracellular cargo receptor involved in the anterograde transport of a limited number of glycoprotein ligands in the early exocytic pathway and is used by a number of RNA viruses as part of their exocytosis strategy. ELISA-based binding studies demonstrated that the construct having sequence set forth in SEQ ID NO: 164 can associate with ERGIC-53 at pH 7.4, but this interaction is significantly stronger at pH 5.5. SPR studies further supported this pH-dependent interaction.

The observed distribution of GPR75 in both apical and basal vesicular compartments of enterocytes did not suggest a role for an efficient vectored routing mechanism of the construct having sequence set forth in SEQ ID NO: 164 from an apical to a basal vesicular compartment; rather, GPR75 could play a role in the local vesicular pools in each location. Further, we did not observe any subverted distribution of GPR75 as has been observed for the actions of other bacterial effector proteins. Thus, we conjectured that Chx interactions with GPR75 may provide some function other that routing vesicles from an apical endosomal compartment to a basal endosome compartment and hypothesized that GPR75 interactions could function to minimize routing of this bacterial effector protein from vesicles to lysosomes at both locations.

Additional studies with TMEM132A demonstrated a greater interaction affinity with the construct having sequence set forth in SEQ ID NO: 164 at neutral compared to an acidic pH suggesting that once internalized, the construct having sequence set forth in SEQ ID NO: 164 could find another receptor for trafficking while the internalization receptor cycled back to the apical surface of the cell. In this hypothesis, the trafficking receptor would have a greater interaction affinity for Chx at an acidic pH relative to neutrality. Indeed, examination of GPR75 interactions with the construct having sequence set forth in SEQ ID NO: 164 demonstrated a higher affinity between these two molecules at pH 5.5 compared to pH 7.4.

This data demonstrates that the herein described Cholix derived delivery constructs efficiently access the enterocytes (e.g., polarized gut epithelial cells) and interact with proteins involved in early endosomal sorting, allowing these constructs to avoid intracellular degradation pathways that results in the delivery and transport of intact carrier and cargo, e.g., across epithelial cell via transcytosis and/or to the interior via endocytosis.

Example 20

Intracellular Sorting of Cholix Domain I Derived Delivery Constructs

This example demonstrates that Cholix domain I derived delivery constructs interact with distinct proteins such as ERGIC-53 during intracellular sorting.

Luminal introduction of the delivery constructs with SEQ ID NO: 164 in the rat ILI model provided data to support ERGIC-53 as an element subverted by Cholix constructs of the present disclosure to achieve efficient transcytosis. Prior to and at times immediately following apical application of the construct having sequence set forth in SEQ ID NO: 164, ERGIC-53 was observed in discrete populations in enterocytes that was focused near the apical surface of the cell nucleus, a location where ERGIC is consistently located. Within a few minutes of luminal application of the construct having sequence set forth in SEQ ID NO: 164, ERGIC-53 was observed to move to areas within enterocytes adjacent to the apical plasma membrane and to a basal domain. Thus, Cholix carrier transcytosis and ERGIC-53 redistribution to the basal area of enterocytes was coincident.

Since ERGIC-53 is involved in glycoprotein export from the ER, the cellular distribution of an ER resident protein ribophorin 1 (dolichyl-diphosphooligosaccharide protein glycosyltransferase subunit 1) that mediates N-glycosylation events was examined. Importantly, ribophorin 1 was observed in a pull-down using GRP75. Transcytosis of the construct having sequence set forth in SEQ ID NO: 164 was observed following its ILI into rat jejunum did not affect the intracellular distribution of ribophorin 1, showing it to co-localize to a limited extent in the apical vesicular compartment where ribophorin 1 was present throughout the time course during which ERGIC-53 was subverted to the basal compartment. Additionally, ERGIC-53 interacts with a constellation of proteins, including SEC24, in its role as a soluble cargo receptor. Notably, a pull-down with GRP75 as bait identified SEC24. Similarly, apical application of the construct having sequence set forth in SEQ ID NO: 164 did not induce a gross alteration of intracellular compartment organization.

The ERGIC is involved in sorting soluble molecules destined for secretion from the cell and ERGIC-53 undergoes a process of concentrative sorting that involves the coat protein COPII. Since both COPI and COPII are involved in vesicle trafficking at the ER-Golgi interface, the potential for these coat proteins to co-localized with the construct having sequence set forth in SEQ ID NO: 164 during the transcytosis process was investigated. Rat enterocytes demonstrated a COPI distribution beneath the apical plasma membrane and at a supra-nuclear site consistent with the Golgi apparatus, a distribution that was also observed following the apical application of the construct with SEQ ID NO: 158 that did not enter these cells, and the construct with SEQ ID NO: 165 that underwent endocytosis but remained in an apical vesicular compartment. Similar to that observed for untreated tissues or those exposed to the construct with SEQ ID NO: 158, ERGIC-53 (LMAN1) distribution in enterocytes exposed to an apical application of the construct with SEQ ID NO: 159 or the construct with SEQ ID NO: 165 remained primarily in an apical vesicular compartment, with very little basal vesicular compartment distribution in enterocytes (FIG. 5). Movement of ERGIC-53 (LMAN1) to a basal vesicular compartment was observed sporadically in enterocytes following apical application of the construct with SEQ ID NO: 159, and this movement was much more consistent in enterocytes treated apically with the construct with SEQ ID NO: 160 or the construct with SEQ ID NO: 164. The distribution of COPI in enterocytes treated apically with the construct with SEQ ID NO: 160 was now longer evident in the supra-nuclear region of the cell but was now focused to the apical surface and apical vesicular compartment where it co-localized to some extent with ERGIC-53 (LMAN1).

Apical application of the construct with SEQ ID NO: 159 or the construct with SEQ ID NO: 165 resulted in the co-localization of HGH with COPI beneath the apical membrane and at a supra-nuclear site, with limited co-localization events being observed in the apical vesicular pool region of enterocytes. Apical treatment with the construct with SEQ ID NO: 160 resulted in extensive co-localization of HGH with COPI beneath the apical membrane and some co-localizations within the apical vesicular compartment, and less co-localization events in the supra-nuclear region.

This data demonstrate that Cholix derived delivery constructs such as those having amino acid sequences set forth in SEQ ID NO: 158, SEQ ID NO: 159 and SEQ ID NO: 165 can be used to delivery various cargo molecules to intracellular compartments of an epithelial cell. This may be particularly useful for the targeted delivery of therapeutic and/or biologically active molecules capable of eliciting a therapeutic and/or biological effect at those locations.

Example 21

Basal Secretion of Cholix Domain I Derived Delivery Constructs

This example demonstrates a mechanism that can be harnessed to achieve efficient basal release of Cholix derived delivery constructs, allowing efficient transport of cargo across epithelial layers (e.g., a gut epithelium).

The basement membrane-specific heparan sulfate proteoglycan protein (HSPG, HSPG2 or perlecan), an integral component of basement membranes that support the simple columnar epithelium of the intestine, was identified in initial capture studies (see e.g., FIG. 29, FIG. 30). Perlecan is modulated by tyrosine phosphatase (PTPN6) and interacts with von Willebrand factor A domain-containing protein 1 (VWA1), both of which was also enriched in pull-down captures using the construct with SEQ ID NO: 164.

Stable knock-down of perlecan in Caco-2 cells (Caco-$2^{HSPG2-}$) grown in a polarized format significantly reduced the ability of the construct with SEQ ID NO: 164 to complete transcytosis in vitro. ELISA-based binding studies demonstrated that Chx can associate with perlecan. SPR studies showed that Chx interacts with perlecan at pH 5.5 but not at pH 7.4.

In enterocytes from untreated animals of following apical exposure with the construct with SEQ ID NO: 158, perlecan-positive immunolabeling was observed in vesicles that were distributed in the apical, supra-nuclear, and basal compartments; ERGIC-53 (LAMN1) distribution was restricted to a location between the apical and supra-nuclear compartments (FIG. 9D). Apical application of the construct with SEQ ID NO: 164 resulted in a reduction of relative perlecan labeling observed in the supra-nuclear compartment and a co-localization with ERGIC-53 (LAMN1) in the apical and basal compartments, with an area beneath the luminal plasma membrane that positive for ERGIC-53 (LAMN1) but not perlecan. ERGIC-53 (LAMN1) present in area beneath the luminal plasma membrane was positive for the construct with SEQ ID NO: 164, but devoid of perlecan. Vesicles positive for HGH were also positive for ERGIC-53 (LAMN1) or perlecan or both to varying degrees in the apical and basal compartments. The striking co-localization of the construct with SEQ ID NO: 164, ERGIC-53 (LAMN1) and perlecan in these compartments and suggests that Cholix might traffic to the basal side of the cell with either ERGIC-53 (LAMN1) and/or perlecan (and/or possibly other interacting elements) where it can be released through an exocytosis process.

Notably, the Chx transcytosis pathway described herein suggests that Cholix derived carrier proteins coupled to a heterologous (non-Cholix derived) cargo do not result in cellular disorganization, outside of the subversion of ERGIC-53 (LAMN1), indicating that the cargo (e.g., therapeutic) delivery mechanisms described herein do not impair the epithelial layer or the cell itself. Thus, highly efficient cargo delivery without impairing the epithelium of the delivery construct itself may be an important feature of the herein described delivery constructs and methods. It may allow delivery of various therapeutic and/or diagnostic or other cargo molecules in a non-invasive manner, potentially allowing for standards of safety and therapeutic efficacy.

This data demonstrates that specific proteins (e.g., ERGIC-53, ribophilin 1, SEC24, CK-8, TMEM132A, GPR75, and perlecan) are involved in trafficking a Cholix domain I derived delivery construct across an epithelial cell and allow its release from the basal membrane. The identity of the distinct interaction partners and pH-dependencies of these interactions may be particularly useful for the therapeutic applications as the herein described trafficking pathway allows the delivery of Cholix domain I derived carriers coupled to various cargo molecules to reach the basolateral compartment (e.g., *Lamina propria*) by using endogenous trafficking pathways. However, and demonstrated in EXAMPLE 11 above, specific functional elements of Cholix (and PE) domain I allow the delivery of heterologous cargo to distinct locations within and/or across the epithelium.

Thus, the herein described multi-receptor, multi-compartment pathways used by Cholix derived delivery constructs to efficiently achieve the transcytosis can provide a potential roadmap for the oral delivery of therapeutic molecules (e.g., protein therapeutics such as therapeutic antibodies) that can be coupled to a Cholix domain I carrier or a carrier derived therefrom.

Example 22

Functional Peptide Fragments of Cholix Domain I are Located on the Protein Surface This example shows that portions of the functional sequence elements of Cholix domain I that are described herein to promote transcytosis and apical-to-basal trafficking are located at the protein surface of domain I of the Cholix exotoxin.

Protein structure analyses demonstrated that functional elements required for apical endocytosis, apical-to-basal trafficking and basal release are in proximity to each other on the surface of the Cholix domain I protein.

A surface model of bacterially expressed Cholix domain I (SEQ ID NO: 5) was used to highlight selected areas of potential interest in this transcytosis process due to their projection from the protein surface (FIG. 32). It is interesting to note that two amino acids regions between $M^1$ and $G^{40}$ are adjacent to surface exposed amino acids $D^{151}$-$A^{187}$ and $A^{187}$-$L^{206}$. Specifically, $L^{18}$-$I^{26}$ (domain X1) and $T^{171}$-$I^{76}$ (domain X2) coordinate to form a pocket surrounded by several negative charges. Similarly, $K^{187}$-$H^{203}$ (domain X3) coordinates with $I^{32}$-$E^{40}$ (domain X4) to form a continuous ridge structure (FIG. 32A-FIG. 32D).

This data shows that portions of the amino acid sequence of Cholix domain I that are distant from each other in terms of amino acid position within the sequence can, in fact, be in close proximity to each other in a 3D configuration of the Cholix domain I protein. This data suggests that the 3D structure and surface morphology of Cholix domain I allows interaction with receptors and receptor elements required to efficient endocytosis and/or transport the epithelial cell. This can be useful to design orally administrable therapeutics comprising such Cholix domain I derived carrier molecules to provide therapeutically effective doses basolateral compartments, the *Lamina propria*, etc. to elicit therapeutic effects.

All of the articles and methods disclosed and claimed herein can be made and executed without undue experimentation in light of the present disclosure. While the articles and methods of this disclosure have been described in terms of embodiments, it will be apparent to those of skill in the art that variations can be applied to the articles and methods without departing from the spirit and scope of the disclosure. All such variations and equivalents apparent to those skilled in the art, whether now existing or later developed, are deemed to be within the spirit and scope of the disclosure as defined by the appended claims. All patents, patent applications, and publications mentioned in the specification are indicative of the levels of those of ordinary skill in the art to which the disclosure pertains. All patents, patent applications, and publications are herein incorporated by reference in their entirety for all purposes and to the same extent as if each individual publication was specifically and individually indicated to be incorporated by reference in its entirety for any and all purposes. The disclosure illustratively described herein suitably can be practiced in the absence of any element(s) not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the disclosure claimed. Thus, it should be understood that although the present disclosure has been specifically disclosed by embodiments and optional features, modification and variation of the concepts herein disclosed can be resorted to by those skilled in the art, and that such modifications and variations are considered to be within the scope of this disclosure as defined by the appended claims.

Sequence Listings

SEQ ID NO: 1 is a 634 amino acid sequence of mature *Vibrio cholera* Cholix toxin.

SEQ ID NO: 2 is a 634 amino acid sequence of mature *Vibrio cholera* Cholix toxin.

SEQ ID NO: 3 is a non-toxic (nt) variant of the mature *V. cholera* Cholix toxin.

SEQ ID NO: 4 is a domain I of a Cholix toxin.

SEQ ID NO: 5 is a domain I of a Cholix toxin comprising an N-terminal methionine residue (e.g., due to bacterial expression).

SEQ ID NO: 6-SEQ ID NO: 125 are truncated versions of Cholix domain I.

SEQ ID NO: 126 is an amino acid sequence of the *V. cholera* Cholix carrier translocation domain (domain II).

SEQ ID NO: 127 is an amino acid sequence of the *V. cholera* Cholix carrier domain Ib.

SEQ ID NO: 128 is an amino acid sequence of the *V. cholera* Cholix carrier catalytic domain (domain III).

SEQ ID NO: 129 is the amino acid sequence of $Cholix^{1-425}$.

SEQ ID NO: 130 is the amino acid sequence of $Cholix^{1-415}$.

SEQ ID NO: 131 is the amino acid sequence of $Cholix^{1-397}$.

SEQ ID NO: 132 is the amino acid sequence of $Cholix^{1-386}$.

SEQ ID NO: 133 is the amino acid sequence of $Cholix^{1-291}$.

SEQ ID NO: 134 is a nucleic acid sequence encoding the mature *Vibrio cholera* Cholix toxin set forth in SEQ ID NO: 2.

SEQ ID NO: 135 is a nucleic acid sequence encoding the 613 amino acid sequence of mature *Pseudomonas* exotoxin A (PE).

SEQ ID NO: 136 is a nucleic acid sequence encoding the mature *Pseudomonas* exotoxin A (PE) set forth in SEQ ID NO: 135.

SEQ ID NO: 137 is an amino acid sequence of the *Pseudomonas* exotoxin A (PE) receptor binding domain (Domain I).

SEQ ID NO: 138 is an amino acid sequence of the *Pseudomonas* exotoxin A (PE) translocation domain (Domain II).

SEQ ID NO: 139 is an amino acid sequence of the *Pseudomonas* exotoxin A (PE) Domain Ib.

SEQ ID NO: 140 is an amino acid sequence of the *Pseudomonas* exotoxin A (PE) catalytic domain (Domain III).

SEQ ID NO: 141 is the amino acid sequence of $PE^{1-404}$.
SEQ ID NO: 142 is the amino acid sequence of $PE^{1-395}$.
SEQ ID NO: 143 is the amino acid sequence of $PE^{1-375}$.
SEQ ID NO: 144 is the amino acid sequence of $PE^{1-364}$.
SEQ ID NO: 145 is the amino acid sequence of $PE^{1-277}$.

SEQ ID NO: 146 is the amino acid sequence of a hybrid delivery construct.

SEQ ID NO: 147 is the amino acid sequence of a hybrid delivery construct.

SEQ ID NO: 148 is the amino acid sequence of a functional peptide sequence derived from Cholix domain I (e.g., for endocytosis).

SEQ ID NO: 149 is the amino acid sequence of a functional peptide sequence derived from Cholix domain I (e.g., for apical-to-basal transport).

SEQ ID NO: 150 is the amino acid sequence of a functional peptide sequence derived from Cholix domain I (e.g., for apical-to-basal transport).

SEQ ID NO: 151 is the amino acid sequence of a functional peptide sequence derived from Cholix domain I (e.g., for supranuclear localization).

SEQ ID NO: 152 is the amino acid sequence of a functional peptide sequence derived from Cholix domain I (e.g., for basal release).

SEQ ID NO: 153 is the amino acid sequence of a Cholix derived delivery construct comprising human growth hormone (HGH).

SEQ ID NO: 154 is the amino acid sequence of a Cholix derived delivery construct comprising interleukin-10 (IL-10).

SEQ ID NO: 155 is the amino acid sequence of a Cholix derived delivery construct comprising interleukin-10 (IL-22).

SEQ ID NO: 156 is the amino acid sequence of a Cholix derived delivery construct comprising red fluorescent protein (RFP).

SEQ ID NO: 157 is the amino acid sequence of a Cholix derived (comprising non-toxic mature Cholix) delivery construct comprising red fluorescent protein (RFP).

SEQ ID NO: 158 is the amino acid sequence of a truncated Cholix domain I delivery construct comprising HGH.

SEQ ID NO: 159 is the amino acid sequence of a truncated Cholix domain I delivery construct comprising HGH.

SEQ ID NO: 160 is the amino acid sequence of a truncated Cholix domain I delivery construct comprising HGH.

SEQ ID NO: 161 is the amino acid sequence of a truncated Cholix domain I delivery construct comprising HGH.

SEQ ID NO: 162 is the amino acid sequence of a truncated Cholix domain I delivery construct comprising HGH.

SEQ ID NO: 163 is the amino acid sequence of a truncated Cholix domain I delivery construct comprising HGH.

SEQ ID NO: 164 is the amino acid sequence of a Cholix domain I delivery construct comprising HGH.

SEQ ID NO: 165 is the amino acid sequence of a truncated Cholix domain I delivery construct comprising HGH.

SEQ ID NO: 166-SEQ ID NO: 186 are the amino acid sequences of various peptidase cleavage sites.

SEQ ID NO: 187-SEQ ID NO: 193 are the amino acid sequences of various GM-1 receptor binding peptides.

SEQ ID NO: 194-SEQ ID NO: 206 are the amino acid sequences of various cleavable spacers.

SEQ ID NO: 207-SEQ ID NO: 213 are the amino acid sequences of various non-cleavable spacers.

SEQ ID NO: 214 is the amino acid sequence of a human growth hormone (HGH).

SEQ ID NO: 215 is the amino acid sequence of a GLP-1 agonist peptide.

SEQ ID NO: 216 is the amino acid sequence of an insulin peptide.

SEQ ID NO: 217 is the amino acid sequence of a human interleukin-10 (IL-10).

SEQ ID NO: 218 is the amino acid sequence of a human interleukin-22 (IL-22).

SEQ ID NO: 219 is the amino acid sequence of an ExtB polypeptide.

SEQ ID NO: 220 is the amino acid sequence of a Red Fluorescent Protein (RFP).

SEQ ID NO: 221 is the amino acid sequence of a Cholix domain I derived carrier coupled to a spacer.

What is claimed is:

1. A method for delivering a heterologous cargo across a polarized epithelial cell in a subject via transcytosis, the method comprising administering a carrier to the subject via pulmonary administration, the carrier consisting of domain I of a *Pseudomonas* exotoxin (PE) and optionally an N-terminal methionine, wherein the carrier is coupled to a heterologous cargo.

2. The method of claim 1, wherein the heterologous cargo comprises a respiratory drug.

3. The method of claim 1, wherein the heterologous cargo comprises an antiviral drug.

4. The method of claim 1, wherein the heterologous cargo comprises an interferon.

5. The method of claim 1, wherein the carrier has at least about 80% sequence identity to the amino acid sequence set forth in SEQ ID NO: 137.

6. The method of claim 1, wherein the carrier is covalently coupled to the heterologous cargo.

7. The method of claim 1, wherein the carrier is coupled to the heterologous cargo via a spacer.

8. The method of claim 1, wherein the carrier delivers the heterologous cargo across a polarized pulmonary epithelial cell via transcytosis.

9. The method of claim 1, wherein the subject has an infectious disease.

10. The method of claim 9, wherein the infectious disease is a systemic microbial infection.

11. The method of claim 9, wherein the infectious disease is a viral disease.

12. The method of claim 1, wherein the carrier is in a pharmaceutical composition.

13. The method of claim 12, wherein the pharmaceutical composition is formulated for pulmonary delivery.

14. The method of claim 12, wherein the pharmaceutical composition is formulated into an aerosol.

15. A pharmaceutical composition comprising a carrier for delivery of a heterologous cargo across a polarized epithelial cell in a subject via transcytosis, the carrier consisting of domain I of a *Pseudomonas* exotoxin (PE) and optionally an N-terminal methionine, wherein the carrier is coupled to a heterologous cargo, and wherein the pharmaceutical composition is formulated for pulmonary administration.

16. The pharmaceutical composition of claim 15, wherein the heterologous cargo comprises a respiratory drug.

17. The pharmaceutical composition of claim 15, wherein the heterologous cargo comprises an antiviral drug.

18. The pharmaceutical composition of claim 15, wherein the heterologous cargo comprises an interferon.

19. The pharmaceutical composition of claim 15, wherein the carrier has at least about 80% sequence identity to the amino acid sequence set forth in SEQ ID NO: 137.

20. The pharmaceutical composition of claim 15, wherein the carrier is covalently coupled to the heterologous cargo.

21. The pharmaceutical composition of claim 20, wherein the carrier is coupled to the heterologous cargo via a spacer.

22. The pharmaceutical composition of claim 15, wherein the pharmaceutical composition is formulated into an aerosol.

23. A carrier for delivery of a respiratory drug across a polarized epithelial cell in a subject via transcytosis, the carrier consisting of domain I of a *Pseudomonas* exotoxin (PE) and optionally an N-terminal methionine, wherein the carrier is coupled to a respiratory drug.

24. The carrier of claim 23, wherein the carrier has at least about 80% sequence identity to the amino acid sequence set forth in SEQ ID NO: 137.

25. The carrier of claim 23, wherein the carrier is covalently coupled to the respiratory drug.

26. The carrier of claim 25, wherein the carrier is coupled to the respiratory drug via a spacer.

27. A pharmaceutical composition comprising the carrier of claim 23 and a pharmaceutically acceptable excipient.

28. The pharmaceutical composition of claim 27, wherein the pharmaceutical composition is formulated for pulmonary administration.

29. The pharmaceutical composition of claim 27, wherein the pharmaceutical composition is formulated into an aerosol.

* * * * *